(12) United States Patent
Disis et al.

(10) Patent No.: US 10,293,035 B2
(45) Date of Patent: May 21, 2019

(54) BREAST AND OVARIAN CANCER VACCINES

(71) Applicant: UNIVERSITY OF WASHINGTON THROUGH ITS CENTER FOR COMMERCIALIZATION, Seattle, WA (US)

(72) Inventors: Mary L. Disis, Renton, WA (US); Denise Cecil, Shoreline, WA (US); Meredith Slota, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 33 days.

(21) Appl. No.: 15/300,208

(22) PCT Filed: Mar. 27, 2015

(86) PCT No.: PCT/US2015/023161
§ 371 (c)(1),
(2) Date: Sep. 28, 2016

(87) PCT Pub. No.: WO2015/149016
PCT Pub. Date: Oct. 1, 2015

(65) Prior Publication Data
US 2017/0182137 A1  Jun. 29, 2017

Related U.S. Application Data

(60) Provisional application No. 61/972,176, filed on Mar. 28, 2014.

(51) Int. Cl.
| A61K 39/00 | (2006.01) |
| C07K 14/47 | (2006.01) |
| C07K 14/705 | (2006.01) |
| C07K 14/71 | (2006.01) |
| C12N 9/10 | (2006.01) |
| A61K 48/00 | (2006.01) |

(52) U.S. Cl.
CPC ...... *A61K 39/0011* (2013.01); *C07K 14/4702* (2013.01); *C07K 14/705* (2013.01); *C07K 14/70567* (2013.01); *C07K 14/70596* (2013.01); *C07K 14/71* (2013.01); *C12N 9/104* (2013.01); *C12Y 203/02* (2013.01); *A61K 48/00* (2013.01); *A61K 2039/53* (2013.01); *A61K 2039/54* (2013.01)

(58) Field of Classification Search
None
See application file for complete search history.

(56) References Cited

U.S. PATENT DOCUMENTS

| 5,679,356 | A | 10/1997 | Bonnem et al. |
| 6,020,462 | A | 2/2000 | Semenza |
| 6,495,347 | B1 | 12/2002 | Siegel et al. |
| 7,488,798 | B2 | 2/2009 | Forbes |
| 7,943,138 | B2 | 5/2011 | Ciesielski et al. |
| 8,080,634 | B2 | 12/2011 | Singh et al. |
| 9,060,961 | B2 | 6/2015 | Disis et al. |
| 2007/0083334 | A1 | 4/2007 | Mintz et al. |
| 2009/0162383 | A1 | 6/2009 | Padlan |
| 2009/0170767 | A1 | 7/2009 | Karumanchi et al. |
| 2010/0136620 | A1* | 6/2010 | Taremi ............... C07D 209/20 435/69.1 |
| 2010/0150918 | A1 | 6/2010 | Kufer et al. |
| 2010/0310640 | A1 | 12/2010 | Knutson et al. |
| 2011/0008347 | A1 | 1/2011 | Ullrich et al. |
| 2011/0135617 | A1 | 6/2011 | Kruse |
| 2012/0128584 | A1 | 5/2012 | Togashi et al. |
| 2012/0135033 | A1 | 5/2012 | Wallecha |
| 2012/0263754 | A1 | 10/2012 | Dubensky, Jr. et al. |
| 2013/0034566 | A1 | 2/2013 | Shiba et al. |
| 2017/0266269 | A1 | 9/2017 | Disis et al. |

FOREIGN PATENT DOCUMENTS

| WO | WO-0050590 A1 | 8/2000 |
| WO | WO-0102556 A3 | 8/2001 |
| WO | WO-0182963 A2 | 11/2001 |
| WO | WO-2008073660 A1 | 6/2008 |
| WO | WO2010001585 | * 1/2010 |
| WO | WO2015149010 | * 10/2015 |
| WO | WO-2015149010 A1 | 10/2015 |
| WO | WO-2015149016 A2 | 10/2015 |

OTHER PUBLICATIONS

Fridman, et al., The immune contexture in human tumors: impact on clinical outcome, Apr. 2012, 12:298-306.
Salazar, et al., Immunization of cancer patients with HER-2/neu-derived peptides demonstrating high-affinity binding to multiple class II alleles, Clin Cancer Res, Nov. 15, 2003 9(15):5559-65.
Al-Hajj, et al., Prospective identification of tumorigenic breast cancer cells, Proc Natl Acad. Sci. USA, 2003, 100(7):3983-8.
Amato, et al., Vaccination of Metastatic Renal Cancer Patients with MVA-5T4: A Randomized, Double-Blind, Placebo-Controlled Phase III Study, Cancer Therapy: Clinical, 2010 American Association for Cancer Research, 5539-47.
Santisteban, et al., Immune-induced epithelial to mesenchymal transition in vivo generates breast cancer stem cells. Cancer Res, Apr. 1, 2009 69(7):2887-95.
Aspord, et al., Breast cancer instructs dendritic cellsto prime interleukin 13—secreting CD4+T cells that facilitate tumor development, JEM, May 14, 2007, 204(5):1037-1047.

(Continued)

*Primary Examiner* — Lei Yao
(74) *Attorney, Agent, or Firm* — Wilson Sonsini Goodrich & Rosati

(57) ABSTRACT

The compositions described herein include an epitope of a peptide that may elicit an immune response in a subject following administration. The compositions may comprise nucleic acids. The compositions may comprise peptides. The methods described herein include administering a composition comprising an epitope of a peptide to a subject in need thereof.

12 Claims, 48 Drawing Sheets

Specification includes a Sequence Listing.

(56) References Cited

OTHER PUBLICATIONS

Le Bon, et al., Cross-priming of CD8+ T cells stimulated by virus-induced type I interferon, Nat Immunol, Oct. 2003, 4(10):1009-15.

Brentville, et al., High Avidity Cytotoxic T Lymphocytes Can Be Selected into the Memory Pool but They Are Exquisitely Sensitive to Functional Impairment, PLoS One, 7(7):e41112, 12 pages.

Brooks, et al., IL-10 blockade facilitates DNA vaccine-induced T cell responses and enhances clearance of persistent virus infection, JEM, Mar. 17, 2008,205(3):533-541.

Camacho, et al., A key role for ICAM-1 in generating effector cells mediating inflammatory responses, nature immunology, Jun. 2001, 2(6):523-29.

Caserta, et al., Reduced Functional Avidity Promotes Responses to Tumor-Associated Antigens Central and Effector Memory CD4 T Cell, J Immunol 2010, 185:6545-6554.

Castellino, et al., Cooperation between CD4+ and CD8+ T cells: when, where, and how. Annu Rev Immunol, 2006, 24:519-40.

Cecil, et al., T-helper I immunity, specific for the breast cancer antigen insulin-like growth factor-I receptor (IGF-IR), is associated with increased adiposity, Breast Cancer Res Treat, 2013, 139:657-665.

Cheever, et al., The prioritization of cancer antigens: a national cancer institute pilot project for the acceleration of translational research, Clin Cancer Res, Sep. 1, 2009, 15(17):5323-37.

Schwartzentruber, et al., gp100 peptide vaccine and interleukin-2 in patients with advanced melanoma, N. Engl. J. Med, Jun. 2011, 364(22): 2119-27.

Curtsinger, et al., Inflammatory Cytokines as a Third Signal for T Cell Activation, Curr Opin Immunol. Jun. 2010;22(3): 333-340. doi:10.1016/j.coi.2010.02.013.

Dang, et al., Identification of immunologic biomarkers associated with clinical response after immune-based therapy for cancer, Annals of the New York Academy of Sciences, 2009, 1174:81-7.

Darrah, et al., Il-10 production differentially influences the magnitude, quality, and protective capacity of Th1 responses depending on the vaccine platform, J. Exp. Med., 207(7):1421-1433.

Davis, et al., DNA-mediated immunization to hepatitis B surface antigen: longevity of primary response and effect of boost, Vaccine, 1996, 14(9):910-5.

Disis, et al., A multi-antigen vaccine targeting neu, IGFBP-2 and IGF-IR prevents tumor progression in mice with pre-invasive breast disease, Cancer Prev Res (Phila). , doi:10.1158/1940-6207, Dec. 2013, 6(12):19 pages.

Disis, et al., Concurrent Trastuzumab and HER2/neu-Specific Vaccination in Patients With Metastatic Breast Cancer, American Society of Clinical Oncology, Oct. 1, 2009, 27(28):4685-4692.

Disis, et al., Maximizing the retention of antigen specific lymphocyte function after cryopreservation, Journal of Immunological Methods, 2006, 308:13-18.

Ebert, et al., A Cancer Vaccine Induces Expansion of NY-ESO-1-Specific Regulatory T Cells in Patients with Advanced Melanoma, PLoS One, Oct. 2012, 79(10):e48424, 10 pages.

Galon, et al., Type, Density, and Location of Immune Cells Within Human Colorectal Tumors Predict Clinical Outcome, Science, Sep. 29, 2006, vol. 313, 34 pages.

Goodell, V., et al., Level of HER-2/neu protein expression in breast cancer may affect the development of endogenous HER-2/neu-specific immunity, Molecular Cancer Therapeutics, Mar. 4, 2008 7(3):449-54.

Grange, et al., Sca-1 identifies the tumor-initiating cells in mammary tumors of BALB-neuT transgenic mice, Neoplasia, 2008,10(12):1433-43.

Guenova, et al., Th2 cytokines from malignant cells suppress Th1 responses and enforce a global Th2 bias in leukemic cutaneous T cell lymphoma, Clin. Cancer Res., Jul. 15, 2013 19(14):3755-3763.

Shackleton, et al., Generation of a functional mammary gland from a single stem cell. Nature, Jan. 2006, 439(7072):84-8.

Hansmann, et al., Dominant Th2 Differentiation of Human Regulatory T Cells upon Loss of FOXP3 Expression, J Immunol 2012, 188:1275-1282.

Harper, et al., Interpreting the biological relevance of bioinformatic analyses with T-DNA sequence for protein allergenicity, Regulatory Toxicology and Pharmacology, 2012, 63:426-432.

Herman, et al., Value of eight-amino-acid matches in predicting the allergenicity status of proteins: an empirical bioinformatic investigation, Clinical and Molecular Allergy 2009, 7:9, 7 pages.

Hueber, et al., Autoantibody profiling for the study and treatment of autoimmune disease, Arthritis Res, May 2, 2002 4(5):290-5.

International search report and written opinion dated Jul. 7, 2015 for PCT/US2015/023149.

International search report and written opinion dated Oct. 16, 2015 for PCT/US2015/023161.

Kalinski, Dendritic cells in immunotherapy of established cancer: Roles of signals 1, 2, 3 and 4, Curr Opin Investig Drugs, Jun. 2009, 10(6): 526-535.

Kalli, et al., An HLA-DR-degenerate epitope pool detects insulin-like growth factor binding protein 2-specific immunity in patients with cancer. Cancer Research, Jun. 15, 2008 68(12):4893-901.

Kantoff, et al., Sipuleucel-T immunotherapy for castration-resistant prostate cancer,N Engl. J. Med, 2010, 363(5):411-22.

Kenter, et al., Vaccination against HPV-16 oncoproteins for vulvar intraepithelial neoplasia, N. Engl. J Med, Nov. 5, 2009 361(19):1838-47.

Knutson, et al., Immunoediting of cancers may lead to epithelial to mesenchymal transition. Journal of immunology, 2006,177(3):1526-33.

Knutson, et al., neu Antigen-Negative Variants Can Be Generated after neu-Specific Antibody Therapy in neu Transgenic Mice, Cancer Research, Feb. 1, 2004, 64:1146-1151.

Lawson, et al., Cancer stem cells in breast cancer and metastasis, Breast Cancer Res. Treat, 2009, 118(2): 241-54.

Le, et al., Safety, tolerability and humoral immune responses after intramuscular administration of a malaria DNA vaccine to healthy adult volunteers, Vaccine, 2000, 18(18):1893-901.

Li, et al., Messenger RNA vaccine based on recombinant MS2 virus-like particles against prostate cancer, Int. J. Cancer, 2014, 134,:1683-1694.

Linterman, et al., Signals that influence T follicular helper cell differentiation and function, Published online: Jan. 27, 2010, Semin Immunopathol (2010) 32:183-196.

Lu, et al., Inflammation and Can Be Overcome by Occurs Due to Self-Regulation of Acute Treatment Failure of a TLR-7 Agonist IL-10 Blockade, J Immunol 2010; 184:5360-5367.

Luheshi, et al., Th1 cytokines are more effective than Th2 cytokines at licensing anti-tumour functions in CD40-activated human macrophages in vitro, Eur. J. Immunol. 2014, 44:162-172.

Madan, et al., Clinical Evaluation of TRICOM Vector Therapeutic Cancer Vaccines, Semin Oncol. Jun. 2012, 39(3): 296-304. doi:10.1053/j.seminoncol.2012.02.010.

Maeda, et al., TGF-beta contributes to the shift toward Th2-type responses through direct and IL-10-mediated pathways in tumor-bearing mice, J Immunol 1996; 156:73-78.

Mandapathil, et al., Generation and immunosuppressive functions of p53-induced human adaptive regulatory T cells, Jul. 2013, OncoImmunology, 2(7):e25514, 9 pages.

Mani, et al., The epithelial-mesenchymal transition generates cells with properties of stem cells, Cell, May 16, 2008 133(4):704-15.

Mazzaccara, et.al: Age-Related Reference Intervals of the Main Biochemical and Hematological Parameters in C57BL/6J, 129SV/EV and C3H/HeJ Mouse Strains, PLoS One, 2008,3(11):e3772.

Morel, et al., Generation of breast cancer stem cells through epithelial-mesenchymal transition. PLoS One, Aug. 2008, 3(8):e2888.

Pardal, et al., Applying the principles of stem-cell biology to cancer, Nat Rev Cancer, Dec. 2003, 3(12):895-902.

Park, et al., Insulin-like growth factor binding protein 2 is a target for the immunomodulation of breast cancer, Cancer Res. Oct. 15, 2008 68(20): 8400-09.

Pedroza-Gonzalez, et al., Thymic stromal lymphopoietin fostershuman breast tumor growth by promoting type 2 inflammation, J. Exp. Med., 208(3):479-490.

(56) References Cited

OTHER PUBLICATIONS

Perret, et al., Adjuvants That Improve the Ratio of Antigen-Specific Effector to Regulatory T Cells Enhance Tumor Immunity, Microenvironment and Immunology, Cancer Res, 73(22); 6597-608.

Pfeiffer, et al., Altered Peptide Ligands Can Control CD4 T Lymphocyte Differentiation In Vivo, J. Exp. Med., Apr. 1995, 181:1569-1574.

Salazar-Onfray, et al., Paradoxical effects of cytokines in tumor immune surveillance and tumor immune escape, Cytokine & Growth Factor Reviews, 2007, 18:171-182.

Schmidt, et al., HLA Class II tetramers reveal tissue-specific regulatory T cells that suppress T-cell responses in breast carcinoma patients, OncoImmunology, 2013, 2:e24962, 9 pages.

Seon, et al. Endoglin-targeted cancer therapy. Curr Drug Deliv. Jan. 2011;8(1):135-43.

Sondak, et al., Adjuvant Immunotherapy of Resected, Intermediate-Thickness, Node-Negative Melanoma With an Allogeneic Tumor Vaccine: Overall Results of a Randomized Trial of the Southwest Oncology Group, Journal of Clinical Oncology, Apr. 15, 2002, 20(8):2058-2066.

Stingl, et al., Purification and unique properties of mammary epithelial stem cells, Nature, 2006, 439(7079):993-7.

Vence, et al., Circulating tumor antigen-specific regulatory T cells in patients with metastatic melanoma, PNAS, Dec. 26, 2007,104(52): 20884-20889.

Watson, et al., Persistence of immunologic memory for 13 years in recipients of a recombinant hepatitis B vaccine, Vaccine, 2001, 19:3164-8.

Wood, et al., An adjuvant autologous therapeutic vaccine (HSPPC-96; vitespen) versus observation alone for patients at high risk of recurrence after nephrectomy for renal cell carcinoma: a multicentre, open-label, randomised phase III trial, Lancet, Jul. 12, 2008, 372:145-54.

Zaias, et al., Reference values for serum proteins of common laboratory rodent strains, J. Am Assoc Lab Anim Sci., Jul. 2009, 48(4):387-90.

Zhu, et al., High-Avidity T Cells Are Preferentially Tolerized in the Tumor Microenvironment, Microenvironment and Immunology, Cancer Research, 595-604.

Co-pending U.S. Appl. No. 15/300,257, filed Sep. 28, 2016.

Tarin, et al., The Fallacy of Epithelial Mesenchymal Transition in Neoplasia, Cancer Res, Jul. 15, 2005 65(14):5996-6001.

"EP 15768124.8 Supplementary Partial Search Report and Search Opinion dated Mar. 20, 2018".

EP 15768124.8 Supplementary Partial European Search Report and Search Opinion dated Jan. 9, 2018.

EP 15768124.8 Office action dated Sep. 15, 2017.

Viehl, et al., Generation of mammaglobin-A-specific CD4 T cells and identification of candidate CD4 epitopes for breast cancer vaccine strategies, Breast Cancer Research and Treatment, May 2008, 109(2): pp. 305-314.

\* cited by examiner

| Patient | Antigen | Th1 | | | Th17 |
| --- | --- | --- | --- | --- | --- |
| | | IFN-g | TNF-a | IL-1b | IL-17 |
| 9 | ICD | | | | |
| 10 | ICD | | | | |
| 11 | ICD | | | | |
| 12 | ICD | | | | |
| 14 | ICD | | | | |
| 15 | ICD | | | | |
| 16 | ICD | | | | |
| 17 | ICD | | | | |

FIG. 37

| Antigen Combinations | All BrCA (n=124) | ER+BrCA (n=78) |
|---|---|---|
| HIF1a, Survivin | AUC: 0.580<br>CI: 0.505-0.655<br>p=0.04 | ND |
| HIF1a, CDC25b | ND | AUC: 0.611<br>CI: 0.527-0.695<br>p=0.011 |
| HIF1a, Survivin CDC25b | AUC: 0.584<br>CI: 0.509-0.659<br>p=0.03 | AUC: 0.621<br>CI: 0.538-0.705<br>p=0.005 |
| HIF1a, Survivin CDC25b, c-met | AUC: 0.575<br>CI: 0.499-0.650<br>p=0.054 | AUC: 0.607<br>CI: 0.523-0.691<br>p=0.014 |
| HIF1a, Survivin CDC25b, c-met, MDM2 | AUC: 0.572<br>CI: 0.496-0.647<br>p=0.085 | AUC: 0.610<br>CI: 0.526-0.693<br>p=0.012 |

FIG. 38

| PROTEIN | STEM CELL | EMT | POOR PROGNOSIS | HOMOLOGY TO MOUSE |
|---|---|---|---|---|
| CD105 | | ▓ | ▓ | 72% |
| Cripto | ▓ | ▓ | ▓ | 67% |
| Cyclin B1 | | ▓ | ▓ | 82% |
| GLI1 | ▓ | ▓ | ▓ | 85% |
| HIF-1α | ▓ | ▓ | ▓ | 87% |
| JAG-1 | ▓ | ▓ | ▓ | 96% |
| c-met | | ▓ | ▓ | 88% |
| NRP2 | | ▓ | ▓ | 94% |
| PRAME | ▓ | | ▓ | 50% |
| PRL3 | ▓ | ▓ | ▓ | 96% |
| SATB1 | | ▓ | ▓ | 97% |
| IGF-1R | ▓ | ▓ | ▓ | 95% |

FIG. 39

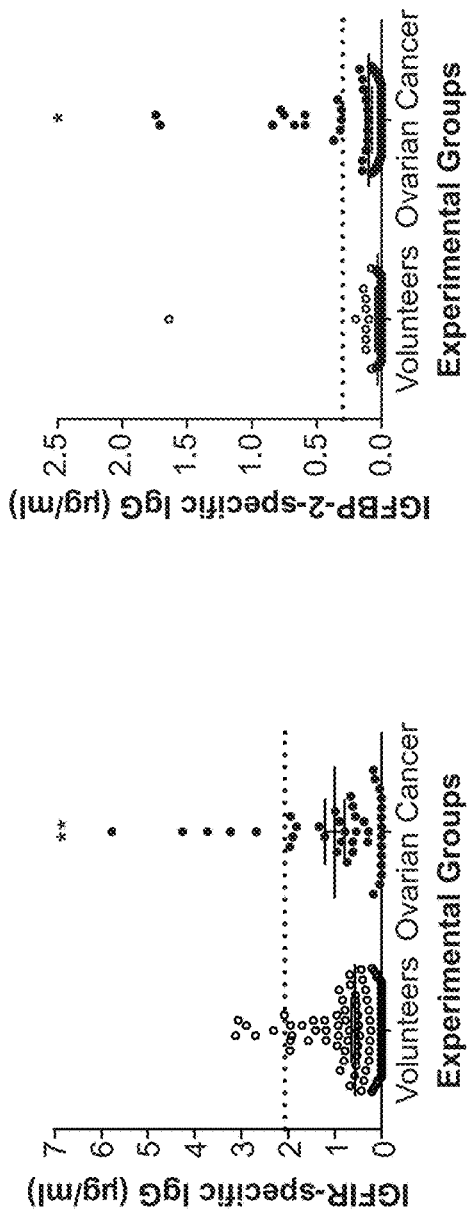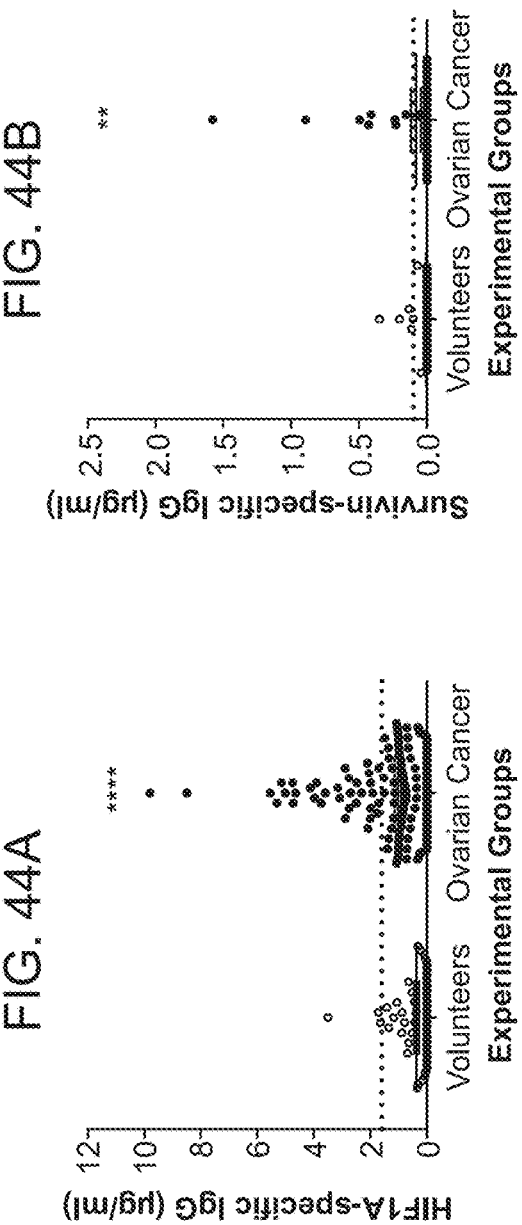
FIG. 44A
FIG. 44B
FIG. 44C
FIG. 44D

BREAST AND OVARIAN CANCER VACCINES

CROSS-REFERENCE

This application is a U.S. National Phase Application under 35 U.S.C. § 371 of International Patent Application No. PCT/US2015/023161, filed Mar. 27, 2015, which claims the benefit of U.S. provisional patent application no. 61/972,176, filed Mar. 28, 2014, which is herein incorporated by reference in its entirety.

STATEMENT AS TO FEDERALLY SPONSORED RESEARCH

This invention was made with the support of the United States government under grant number W81XWH-11-1-0760 by the Department of Defense, grant number P50CA083636 by the National Cancer Institute and grant number R01CA098761 by the National Cancer Institute.

BACKGROUND

Cancer therapy has conventionally been accomplished by surgical reduction of a tumor mass and subsequent chemo- and/or radiotherapy. This strategy can reduce the tumor and, in less advanced stages, often results in complete remission. Unfortunately, the prognosis for more advanced tumors has changed little over the past 50 years and a significant proportion of cancer-related deaths are caused by subsequent metastases. New prophylactic and therapeutic treatments are needed to combat the increasing occurrence of cancer.

Over 1 million people are diagnosed with breast cancer each year worldwide and more than 400,000 people die of breast cancer each year. It is estimated that one in eight women will be diagnosed with breast cancer at some point in her lifetime. Preventing the development of breast cancer could have significant health and economic benefits for all individuals. Billions of dollars would be saved if people did not need to receive expensive cancer-related surveillance and therapeutic interventions. New approaches for the prevention and treatment of breast cancer are needed.

SUMMARY

The compositions described herein include, in some aspects, a composition comprising: a first plasmid comprising a first nucleotide sequence, the first nucleotide sequence encoding a first epitope of a first antigen expressed by cells associated with breast cancer; and a second nucleotide sequence, the second nucleotide sequence encoding a second epitope of a second antigen expressed by cells associated with breast cancer, wherein the first nucleotide sequence and the second nucleotide sequence are located in one or more plasmids.

In other aspects, the disclosure includes a composition comprising: a first plasmid comprising a first nucleotide sequence, the first nucleotide sequence encoding a first epitope of a first antigen, the first epitope is a portion of an HIF-1α peptide, wherein the first nucleotide sequence is located in a plasmid. In yet other aspects, the disclosure includes a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are portions of an HIF-1α peptide, wherein the first nucleotide sequence and the second nucleotide sequence are located in one or more plasmids.

The compositions described herein include, in some aspects, a composition comprising: a first plasmid comprising a first nucleotide sequence, the first nucleotide sequence encoding a first epitope of a first antigen, the first epitope is a portion of a peptide selected from: CD105, Yb-1, SOX-2, CDH3 or MDM2, wherein the first nucleotide sequence is located in a plasmid. In other aspects, the disclosure includes a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CD105, Yb-1, SOX-2, CDH3 or MDM2, wherein the first nucleotide sequence and the second nucleotide sequence are located in one or more plasmids.

The compositions described herein include, in some aspects, a composition comprising: a first plasmid comprising a first nucleotide sequence, the first nucleotide sequence encoding a first epitope of a first antigen, the first epitope is a portion of a peptide selected from: IGFBP-2, HER-2, IGF-1R, wherein the first nucleotide sequence is located in a plasmid. In yet some other aspects, the disclosure includes a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: IGFBP-2, HER-2 or IGF-1R, wherein the first nucleotide sequence and the second nucleotide sequence are located in one or more plasmids.

The compositions described herein include, in some aspects, a composition comprising: a first epitope of a first antigen expressed by cells associated with breast cancer; and a second epitope of a second antigen expressed by cells associated with breast cancer.

In other aspects, the disclosure includes a composition comprising: at least a first epitope of a first antigen, the first epitope is a portion of a peptide from HIF-1α. In yet other aspects, the disclosure includes, a composition comprising: at least a first epitope of a first antigen, at least a second epitope of a second antigen, the first and the second epitopes are from HIF-1α.

In other aspects, the disclosure includes a composition comprising: at least a first epitope of a first antigen, the first epitope is a portion of a peptide selected from: CD105. Yb-1, SOX-2, CDH3 or MDM2. In yet other aspects, the disclosure includes a composition comprising: at least a first epitope of a first antigen, at least a second epitope of a second antigen, the first and the second epitopes are independently selected from: CD105, Yb-1, SOX-2, CDH3 or MDM2.

In some instances, the disclosure includes a composition that comprises an isolated and purified plasmid comprising a nucleotide sequence encoding a polypeptide, wherein the polypeptide comprises a plurality of epitopes; and an excipient. Sometimes, the plurality of epitopes comprises one or more epitopes comprising at least 90% sequence identity to an amino acid sequence selected from SEQ ID NOs: 1, 6, 8-10, 14-16, 20, 25-28, 32-34, 46-56, 60-62, 66-75, 82-85, and 87.

Sometimes, the isolated and purified plasmid may further comprise a first nucleotide sequence encoding a first epitope of a first antigen expressed by cells associated with breast cancer. In some cases, the composition further comprises a second nucleotide sequence encoding a second epitope of a second antigen expressed by cells associated with breast cancer. The first nucleotide sequence and the second nucleotide sequence may be located in one or more isolated and purified plasmids. The first epitope and the second epitope may independently be selected from a portion of an HIF-1α peptide comprising at least 90% sequence identity to an amino acid sequence selected from SEQ ID NOs: 82-84. The first and the second epitopes may independently be selected from: CD105, Yb-1, SOX-2, CDH3 or MDM2, wherein the first nucleotide sequence and the second nucleotide sequence are located in one or more isolated and purified plasmids. The first and the second epitopes may independently be selected from: IGFBP-2, HER-2 or IGF-1R, wherein the first nucleotide sequence and the second nucleotide sequence are located in one or more isolated and purified plasmids. The first and the second nucleic acid sequences may be located on the first isolated and purified plasmid. The second nucleic acid sequence may be located on a second isolated and purified plasmid.

In some cases, the disclosure includes a composition that comprises a first epitope of a first antigen expressed by cells associated with breast cancer or ovarian cancer; and a second epitope of a second antigen expressed by cells associated with breast cancer or ovarian cancer; wherein the first and the second epitopes independently comprise at least 90% sequence identity to an amino acid sequence selected from SEQ ID NOs: 1, 6, 8-10, 14-16, 20, 25-28, 32-34, 46-56, 60-62, 66-75, 82-85, and 87.

In some instances, the disclosure includes a composition that comprises a plasmid comprising at least one nucleotide sequence encoding a polypeptide comprising at least 70% sequence identity to an epitope sequence selected from SEQ ID NOs: 54, 73, 85, and 87; and an excipient.

In some cases, the disclosure includes a composition that comprises a plasmid comprising four nucleotide sequences, wherein each of the four nucleotide sequences independently encodes a polypeptide comprising at least 70% sequence identity to an epitope sequence selected from SEQ ID NOs: 54, 73, 85, and 87; and an excipient.

Sometimes, the disclosure includes a composition that comprises a plasmid comprising a nucleotide sequence encoding a polypeptide comprising at least 80% sequence identity to SEQ ID NO: 89; and an excipient.

Sometimes, the disclosure includes a composition that comprises a polypeptide comprising at least 80% sequence identity to SEQ ID NO: 89.

In some instances, a method of administering one or more of the compositions described herein to a subject is disclosed herein. Sometimes, the subject may be in need thereof of one or more of the composition.

Sometimes, a method of preventing breast cancer or ovarian cancer in a subject is described herein, in which the method comprises administering a composition described herein to the subject. Sometimes, the cancer may be ovarian cancer. The cancer may be breast cancer. A method of preventing breast cancer in a subject is described herein, in which the method comprises administering a composition described herein to the subject.

Sometimes, a method of treating breast cancer or ovarian cancer in a subject is described herein, in which the method comprises administering a composition described herein to the subject. Sometimes, the cancer may be ovarian cancer. The cancer may be breast cancer. A method of treating breast cancer in a subject is described herein, in which the method comprises administering a composition described herein to the subject.

Sometimes, the administering further comprises delivery of at least one dose of a composition described herein to the subject. Sometimes, the administering further comprises delivery of a composition described herein to the subject by subcutaneous injection, intradermal injection, intramuscular injection, intravascular injection, topical application or inhalation.

In some instances, a method of producing an immune response in a subject having a breast cancer or ovarian cancer is described herein, which comprises administering to the subject a composition described herein.

The disclosure further includes an isolated and purified plasmid comprising at least one nucleotide sequence encoding a polypeptide comprising at least 90% sequence identity to an epitope sequence selected from SEQ ID NOs: 82-84. The isolated and purified plasmid may comprise a set of two or more nucleotide sequences in which each of the two or more nucleotide sequences independently encodes a polypeptide comprising at least 90% sequence identity selected from SEQ ID NOs: 82-84. The isolated and purified plasmid may comprise a set of two or more nucleotide sequences in which each of the two or more nucleotide sequences encodes a polypeptide comprising at least 90% sequence identity selected from SEQ ID NOs: 82-84; and each of the nucleotides are not identical within the set of two or more nucleotide sequences.

The disclosure may also include an isolated and purified plasmid comprising at least one nucleotide sequence encoding a polypeptide comprising at least 90% sequence identity to an epitope sequence selected from SEQ ID NOs: 1, 6, 8-10, 14-16, 20, 25-28, and 32-34. The isolated and purified plasmid may comprise a set of two or more nucleotide sequences in which each of the two or more nucleotide sequences independently encodes a polypeptide comprising at least 90% sequence identity selected from SEQ ID NOs: 1, 6, 8-10, 14-16, 20, 25-28, and 32-34. The isolated and purified plasmid may comprise a set of two or more nucleotide sequences in which each of the two or more nucleotide sequences encodes a polypeptide comprising at least 90% sequence identity selected from SEQ ID NOs: 1, 6, 8-10, 14-16, 20, 25-28, and 32-34; and each of the nucleotides are not identical within the set of two or more nucleotide sequences.

The disclosure may include an isolated and purified plasmid comprising at least one nucleotide sequence encoding a polypeptide comprising at least 90% sequence identity to an epitope sequence selected from SEQ ID NOs: 46-56, 60-62, or 66-75. The isolated and purified plasmid may comprise a set of two or more nucleotide sequences in which each of the two or more nucleotide sequences independently encodes a polypeptide comprising at least 90% sequence identity selected from SEQ ID NOs: 46-56, 60-62, or 66-75. The isolated and purified plasmid may comprise a set of two or more nucleotide sequences in which each of the two or more nucleotide sequences encodes a polypeptide comprising at least 90% sequence identity selected from SEQ ID NOs: 46-56, 60-62, or 66-75; and each of the nucleotides are not identical within the set of two or more nucleotide sequences.

Sometimes, the disclosure may further include an isolated and purified plasmid comprising at least one nucleotide sequence encoding a polypeptide comprising at least 70% sequence identity to an epitope sequence selected from SEQ ID NOs: 54, 73, 85, and 87.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 37 shows exemplary cytokine secretion patterns induced by HER2 vaccination.

FIG. 38 depicts a ROC analysis of stem cell/EMT antigens.

FIG. 39 depicts candidate proteins overexpressed in stem cells and/or EMT.

FIG. 43A shows the TH1 response with respect to HIF-1A peptides. FIG. 43B shows the TH1 response with respect to Survivin peptides. Vertical lines show the selected sequences.

FIG. 44A-FIG. 44D show a comparison of IgG antibody expression levels in ovarian cancer patients and volunteers. IgG antibodies specific for candidate antigens are significantly elevated in ovarian cancer patients as compared to volunteer controls. IgG in ug/ml (y-axis) and experimental populations (X-axis) are shown for IGF-IR (FIG. 44A), IGFBP-2 (FIG. 44B), HIF-1A (FIG. 44C), and Survivin (FIG. 44D). Mean and 2 stand dev of volunteer controls (dotted line), *p<0.05; p<0.01; *p<0.001.

DETAILED DESCRIPTION

Figure 1:
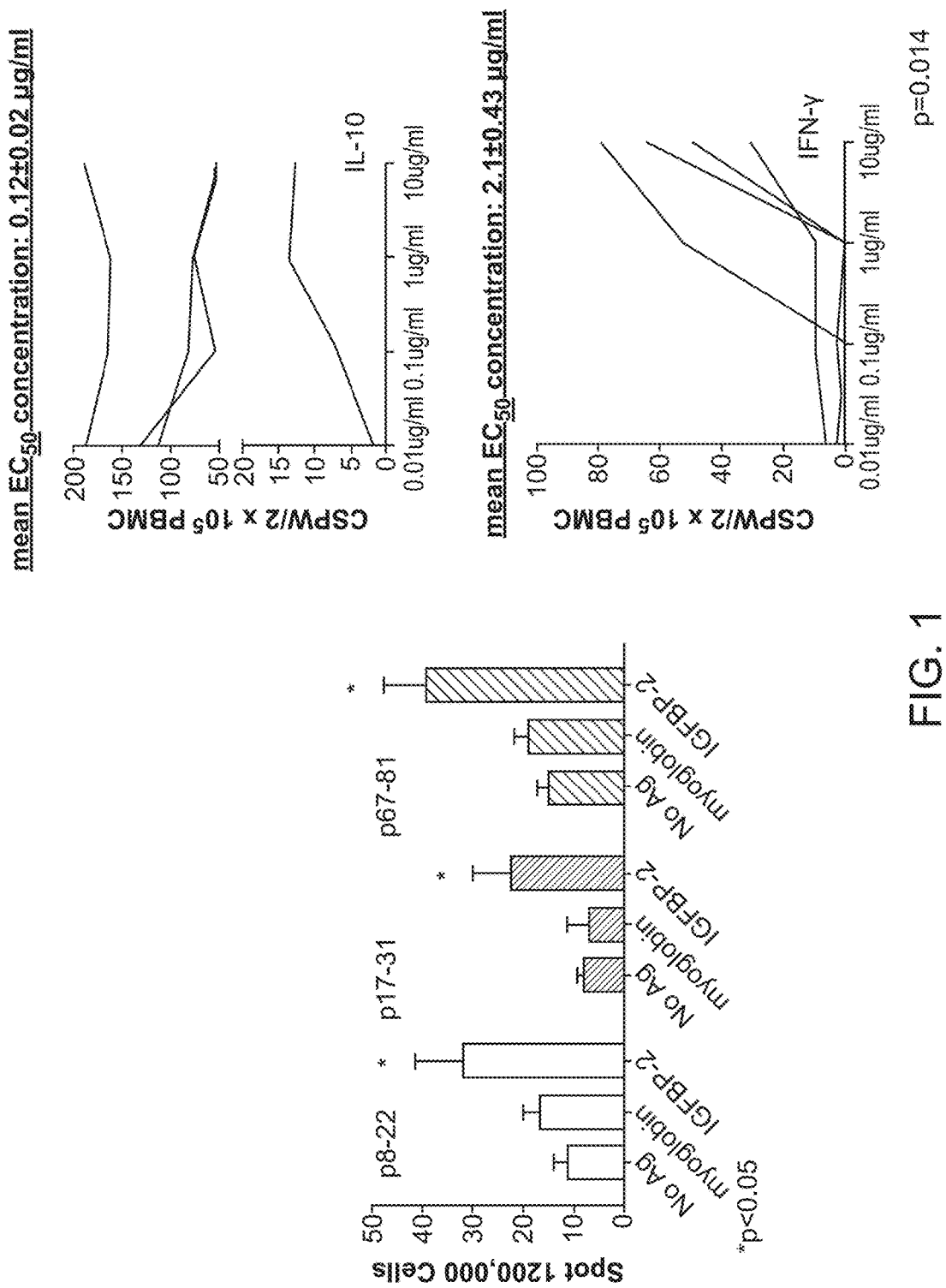
FIG. 1 demonstrates that Th1 and Th2 epitopes vary in functional avidity.

This disclosure provides compositions of breast cancer vaccines and ovarian cancer vaccines, often for the prevention or treatment of breast cancer or ovarian cancer. The disclosure further provides methods of administering breast cancer vaccines or ovarian cancer vaccines to a subject. The compositions provided herein may be used in combination with the methods provided herein for the prevention or treatment of breast cancer or ovarian cancer.

In some cases, the compositions may include; sequences of nucleic acids encoding epitopes of breast cancer or ovarian cancer antigens, the epitopes may elicit an immunogenic response in a subject, plasmids containing the sequences described herein, an adjuvant, a pharmaceutical carrier and, inert chemicals suitable for use with pharmaceutical compositions. The breast cancer or ovarian cancer antigens may be at least one of any antigen expressed in a subject that may have or may develop breast cancer or ovarian cancer. Often, the breast cancer or ovarian cancer antigens are expressed by breast cancer cells, ovarian cancer cells, and/or tissues such as breast cancer or ovarian cancer stem cells (CSC)s. CSCs may exhibit capable of self renewal, unregulated growth, and drug resistance. In some cases, CSCs may express proteins (e.g., antigens) and for example, the level of expression of proteins (e.g., antigens) by CSCs may be upregulated (e.g., increased expression relative to a given amount) or downregulated (e.g., decreased expression relative to a given amount). In some cases, proteins that are upregulated by CSCs compared to normal tissue or cells may be involved in the development and/or progression of breast cancer or ovarian cancer. For example, the proteins may be identified and epitopes of antigens targeted using the compositions and methods described herein.

In some cases, one epitope of a breast cancer or ovarian cancer antigen may be used in the composition. In other cases, more than one epitope of a breast cancer or ovarian cancer antigen may be used in the composition. In other cases, more than two antigens, more than three, more than four, more than five, more than six, more than seven, more than eight, more than nine, more than ten, more than 15, more than 20, more than 25 or more than 30 breast cancer or ovarian cancer antigens may be used in the composition. In some cases, the antigens may be the same. In other cases, the antigens may be different. The compositions of breast cancer or ovarian cancer vaccines described herein could be formulated for the prevention of breast cancer or ovarian cancer. For example, prevention compositions may eliminate cells (e.g., CSCs such as breast CSCs or ovarian CSCs) with abnormal (e.g., upregulated) expression of proteins to prevent breast cancer or ovarian cancer.

In some cases, the epitope and/or epitopes may be on the same breast cancer or ovarian cancer antigen or the epitope and/or epitopes may be on a different breast cancer or ovarian cancer antigen. In some cases, one epitope on a breast cancer or ovarian cancer antigen may be used in the composition. In other cases, more than one epitope on a breast cancer or ovarian cancer antigen, more than two antigens, more than three, more than four, more than five, more than six, more than seven, more than eight, more than nine, more than ten, more than 15, more than 20, more than 25 or more than 30 epitope on a breast cancer or ovarian cancer antigens may be used in the composition.

The compositions and methods described herein may elicit an immune response in a subject. The immune response may be an immune response to the epitopes of the antigens in the composition (e.g., vaccine). Vaccines arm the immune system of the subject such that the immune system may detect and destroy that which contains the antigens of the vaccines in the subject. The compositions and methods described herein may elicit a Type 1 (Th1) immune response in the subject. Th1 immune responses may include secretion of inflammatory cytokines (e.g., IFNγ, TNFα) by a subset of immune cells (e.g., antigen specific T-cells). In some cases, the inflammatory cytokines activate another subtype of immune cells (e.g., cytotoxic T-cells) which may destroy that which contains the antigen in the subject.

Using the screening methods described herein to identify epitopes and binding peptides from tumor antigens, epitopes of a plurality of antigens may be screened for induction of a Th1 immune responses. For example, the methods of screening may identify epitopes from at least one tumor antigen that elicit a Th1 response (e.g., preferentially cause secretion of Th1 cytokines) to breast cancer or ovarian cancer antigens, including CSC (e.g., breast CSC, or ovarian CSC) antigens as described herein.

In some cases, the epitopes and/or antigens used in the compositions and methods described herein may be recognized by the immune system of a subject to elicit a Th1 immune response and release Type I cytokines. The Th1 response may be initiated by the interaction between the epitope and the T-cell, more specifically, the major histocompatibility complex (MHC) expressed by the T-cell. For example, high affinity binding of an epitope to an MHC receptor may stimulate a Th1 response. MHC receptors may be at least one of a plurality of types of MHC receptors. The MHC receptors engaged on a T-cell may vary across individuals in a population.

The compositions described herein may include additional components in addition to nucleic acids encoding epitopes of antigens. In some cases, the compositions may include at least one adjuvant. In some cases, the composition may include at least one pharmaceutical carrier. In some cases, the composition may include at least one inert chemical suitable for use with pharmaceutical compositions. In some cases, the composition may include at least one adjuvant and at least one pharmaceutical carrier. In some cases, the composition may include at least one adjuvant and at least one inert chemical suitable for use with pharmaceutical compositions. In some cases, the composition may include at least one inert chemical suitable for use with pharmaceutical compositions and a pharmaceutical carrier. In some cases, the composition may contain a plurality of adjuvants, a plurality of pharmaceutical carriers and a plurality of inert chemicals suitable for use with pharmaceutical compositions.

In some cases, one adjuvant may be used in the composition. In other cases, more than one adjuvant, more than two adjuvants, more than three adjuvants, more than four adjuvants, more than five adjuvants, more than six adjuvants, more than seven adjuvants, more than eight adjuvants, more than nine adjuvants or more than ten adjuvants may be used in the composition. In some cases, one pharmaceutical carrier may be used in the composition. In other cases, more than one pharmaceutical carrier, more than two pharmaceutical carriers, more than three pharmaceutical carriers, more than four adjuvants, more than five pharmaceutical carriers, more than six pharmaceutical carriers, more than seven pharmaceutical carriers, more than eight pharmaceutical carriers, more than nine pharmaceutical carriers or more than ten pharmaceutical carriers may be used in the composition. In some cases, one chemical may be used in the composition. In other cases, more than one chemical, more than two chemicals, more than three chemicals, more than four chemicals, more than five chemicals, more than six chemicals, more than seven chemicals, more than eight chemicals, more than nine chemicals or more than ten chemicals may be used in the composition.

The disclosure further describes methods administering can breast cancer or ovarian cancer vaccines to a subject. In some cases, the methods may include constructing a plasmid based vaccine that targets those antigens and determining whether administration of the vaccine is safe, immunogenic, and effective to prevent the development of breast cancer. For example, the composition may be a multiantigen Th1 polyepitope plasmid based vaccine. In some cases, the method may include conducting at least one clinical trial to determine the safety and immunogenicity of the plasmid based vaccine in subjects with breast cancer or ovarian cancer. For example, antigens may be expressed by or associated with CSCs (e.g., breast CSCs or ovarian CSCs) and/or the transition of a cell from an epithelial cell to a mesenchymal cell (EMT). In some cases, epitopes of the compositions may be derived from antigens wherein the epitopes may elicit a Th1 immune response in the subject. For example, the Th1 immune response may include immune cells, often CD4+ T-cells. In some cases, the composition may be a nucleic acid (e.g., plasmid based vaccine) that may include nucleic acids encoding more than one antigen or more than one epitope of an antigen. In some cases, the methods may be used to determine if the compositions described herein prevent the development of breast cancer or ovarian cancer in a plurality of organism, for example, in models of cancer (e.g., breast cancer or ovarian cancer) using genetically similar rodents (e.g., mice), using genetically diverse rodents (e.g., mice), and in subjects which may or may not have breast cancer or ovarian cancer. In some instances, the cancer may be a breast cancer. In some cases, breast cancer may be triple negative breast cancer (TNBC).

Identification of Antigens

The compositions and methods described herein include the identification and engineering of breast cancer or ovarian cancer antigens in a pharmaceutical composition (e.g., a vaccine). While any techniques known to one of ordinary skill in the art may be used to identify antigens expressed by a subject with breast cancer or ovarian cancer, in an exemplary case, suitable antigens may be identified using the methods described herein. In some cases, the methods may include by screening sera from subjects. In some cases, the screening may be antibody screening. For example, the antibodies screened may be IgG antibodies. In some cases, the sera may be from a subject with breast cancer or ovarian cancer. In other cases, the sera may be from a subject that does not have breast cancer or ovarian cancer.

Cancer antigens, such as for example breast cancer antigens or ovarian cancer antigens, may be a portion of a protein, a portion of a peptide or a portion of a polyamino acid. In some cases, the portion may be a percentage of a protein, a percentage of a peptide or a percentage of a polyamino acid. In some cases, the percentage may be less than 1%, 5%, 10%, 15%, 20%, 25%, 30%, 35%, 40%, 45%, 50%, 55%, 60%, 65%, 70%, 75%, 80%, 85%, 90%, 95% or 100% of a protein, a peptide or a polyamino acid. In some cases, the portion may be located at the C terminus of a protein, a peptide or a polyamino acid. In other cases, the portion may be located near the C terminus of a protein, a peptide or a polyamino acid. For example, near the C terminus may be within 1%, 5%, 10%, 15%, 20%, 25%, 30%, 35%, 40%, 45%, 50% of the length of the total protein, peptide or polyamino acid from the median. In some cases, the portion may be located at the N terminus of a protein, a peptide or a polyamino acid. In other cases, the portion may be located near the N terminus of a protein, a peptide or a polyamino acid. For example, near the N terminus may be within 1%, 5%, 10%, 15%, 20%, 25%, 30%, 35%, 40%, 45%, 50% of the length of the total protein, peptide or polyamino acid from the median. In some cases, the portion may be located near the middle of a protein, a peptide or a polyamino acid. In other cases, the portion may be located near the middle of a protein a peptide or a polyamino acid. For example, near the middle may be within 1%, 5%, 10%, 15%6, 20%, 25%, 30%, 35%, 40%, 45%, 50% of the length of the total protein, peptide or polyamino acid from the termini.

At least one antigen may identified and screened for suitability as an antigen in a composition described herein (e.g., a vaccine). In some cases, one antigen may be identified and screened. In other cases, more than one antigen may be identified and screened, more than two antigens may be identified and screened, more than three antigens may be identified and screened, more than four antigens may be identified and screened, more than five antigens may be identified and screened, more than six antigens may be identified and screened, more than seven antigens may be identified and screened, more than eight antigens may be identified and screened, more than nine antigens may be identified and screened, more than ten antigens may be identified and screened, more than 1 antigens may be identified and screened, more than 12 antigens may be identified and screened, more than 13 antigens may be identified and screened, more than 14 antigens may be identified and screened, more than 15 antigens may be identified and screened, more than 20 antigens may be identified and screened, more than 25 antigens may be identified and screened, more than 30 antigens may be identified and screened, more than 35 antigens may be identified and screened, more than 40 antigens may be identified and screened, more than 45 antigens may be identified and screened or more than 50 antigens may be identified and screened for suitability in a vaccine. In an exemplary case, five antigens may be identified and screened for suitability in a vaccine.

The antigens screened for suitability in a vaccine may be derived from any protein detected in the sera from a subject with breast cancer or ovarian cancer using the screening techniques known to one of ordinary skill in the art. In some cases, the screening may often be antibody screening. While the proteins may be any protein detected in the sera from a subject with breast cancer or ovarian cancer, in an exemplary case, the proteins from which antigens may be derived may be classified as stem cell proteins and/or EMT proteins. For example, in breast cancer stem cell/EMT proteins may include SOX2, YB1, CD105, MDM2, CDH3+/− and HIF1α. Often, the antigens may be immunogenic in both breast cancer subjects and subjects without breast cancer.

Mapping Epitopes of Antigens

The compositions and methods provided herein include mapping of at least one epitope within antigens, such that the epitopes result in a Th1 immune response when administered to a subject. In some cases, the epitope may be administered as a breast cancer vaccine or ovarian cancer vaccine. While any technique known to one of ordinary skill in the art may be used to identify epitopes which may elicit a Th1 immune response by a subject, the methods described herein may be preferably used. In some cases, the epitope may be a portion of an antigen (e.g., identified above). For example, the epitope may be a peptide of an antigenic protein and/or a portion of an antigenic protein.

In some cases, the epitopes may be human leukocyte antigen (HLA) class I epitopes derived from breast cancer or ovarian cancer antigens. For example, HLA class I epitopes may include epitopes which bind to HLA-A, -B, and -C molecules. In some cases, the epitopes may be class II epitopes derived from breast cancer or ovarian cancer antigens for cancer vaccine (e.g., breast cancer or ovarian cancer) development. For example, HLA class 11 epitopes may include epitopes which bind to HLA-DP, -DM, -DOA, -DOB, -DQ and -DR molecules. In some cases, in addition to the methods described herein, epitopes may be mapped using the steps of, (1) determining if the epitopes bind MHC (e.g., with high affinity) by at least one HLA allele (e.g., HLA-DR, i.e., are universal epitopes), (2) determining if the epitopes stimulate IFNγ rather than IL-10 secretion (e.g., from antigen specific T-cells), and (3) determining whether T-cells may recognize peptides (e.g., epitopes) processed by antigen presenting cells (APCs), i.e., are native epitopes. In some cases, T-cell lines may be used. For example, T-cell lines may be epitope-derived T-cell lines. In some cases, the T-cell may be an exogenous T-cell engineered to express a Chimeric Antigen Receptor construct that binds the epitope with high selectivity and avidity. In some cases, the epitopes may be derived from proteins (e.g., recombinant proteins). In other cases, the proteins may be native proteins. In some cases, the proteins may be processed endogenously. In other cases, the proteins may be processed exogenously. In some cases, the proteins may be processed endogenously by autologous APCs. In other cases, the proteins may be processed exogenously by autologous APCs.

In all cases, the peptides are epitopes mapped from antigens and may be identified using the methods described herein for the selection of peptide epitopes. In some cases, the epitopes may be derived from human proteins that may be used directly in a peptide based vaccine. In other cases, the epitopes may be derived from human proteins and the encoding nucleic acid sequences may be incorporated into a nucleic acid construct designed to induce expression of the epitope in the subject following administration. For example, the nucleic acid construct may allow for the immune response to at least one epitope to be entrained, amplified, attenuated, suppressed, or eliminated to specific sets of self-proteins. In some cases, the peptide or the nucleic acid construct may be optimized into a protein or plasmid-based vaccination to induce, amplify or entrain a Th1 immune response. In some cases, the epitopes may be extended Th1 epitopes. In other cases, the peptide or the nucleic acid construct may be optimized into a protein or plasmid-based vaccination to suppress, attenuate or eliminate a pathological response, in a subject (e.g., human or animal) in need thereof.

In some cases, the peptides are located within portions of a protein, peptide or polyamino acid such that the protein, peptide or polyamino acid stimulates secretion of IFNγ. In some cases, the peptides are located within portions of a protein, peptide or polyamino acid such that the protein, peptide or polyamino acid that inhibits secretion of IFNγ. In some cases, the peptides are located within portions of a protein, peptide or polyamino acid such that the protein, peptide or polyamino acid stimulates secretion of IL-10. In some cases, the peptides are located within portions of a protein, peptide or polyamino acid such that the protein, peptide or polyamino acid that inhibits secretion of IL-10. In some cases, the peptide may stimulate secretion of IFNγ and inhibits secretion of IL-10. In other cases, the peptide may stimulate secretion of IL-10 and inhibits secretion of IFNγ. In some cases, the peptide may stimulate secretion of IFNγ and stimulate secretion of IL-10. In other cases, the peptide may inhibit secretion of IL-10 and inhibits secretion of IFNγ.

In some cases, the amino acids comprising the peptide may be tuned such that the desired effect of the peptide on IFNγ secretion and/or the desired effect of the peptide on IL-10 secretion may be achieved. For example, a peptide which stimulates secretion of both IFNγ and IL-10 may be tuned such that the length of the peptide is shortened to eliminate amino acids which stimulate IL-10 secretion such that the peptide only stimulates secretion of IFNγ.

In some cases, identified epitopes may be included in vaccine compositions of extended epitope vaccines. In some cases, extended epitopes may be 40-80-mer peptides. In an exemplary case, either the nucleic acid sequences or the peptide sequences are juxtaposed for construction of extended epitope sequences. Juxtaposition (e.g., within 10 amino acids of each other) of selected peptides within the parent protein may allow for the construction of in-tandem extended epitopes that may contain tolerizing and/or suppressive epitopes. For example, the in-tandem extended epitopes may contain short intervening, <10 amino acid sequences. Any of these peptides and/or extended epitopes (embodied either as the peptide itself, or as the corresponding nucleic acid construct) singularly, or in any combination, may be optimized into a protein or plasmid-based vaccination that will specifically induce, amplify or entrain a protective immune response, or alternatively, will suppress, attenuate or eliminate a pathological one, in a subject (human or animal) in need thereof.

In some cases, the epitopes may be a length of amino acids. In some cases, the epitopes may be less than five amino acids, less than 10 amino acids, less than 15 amino acids, less than 20 amino acids, less than 25 amino acids, less than 30 amino acids, less than 35 amino acids, less than 40 amino acids, less than 45 amino acids, less than 50 amino acids, less than 55 amino acids, less than 60 amino acids, less than 70 amino acids, less than 75 amino acids, less than 80 amino acids, less than 85 amino acids, less than 90 amino acids, less than 95 amino acids, less than 100 amino acids, less than 110 amino acids, less than 120 amino acids, less than 130 amino acids, less than 140 amino acids, less than 150 amino acids, less than 160 amino acids, less than 170 amino acids, less than 180 amino acids, less than 190 amino acids, less than 200 amino acids, less than 210 amino acids, less than 220 amino acids, less than 230 amino acids, less than 240 amino acids, less than 250 amino acids, less than 260 amino acids, less than 270 amino acids, less than 280 amino acids, less than 290 amino acids, less than 300 amino acids, less than 350 amino acids, less than 400 amino acids, less than 450 amino acids or less than 500 amino acids.

In some instances, the disclosure provides a composition comprising an isolated and purified plasmid comprising a nucleotide sequence encoding a polypeptide, wherein the polypeptide comprises a plurality of epitopes; and an excipient. In some instances, the plurality of epitopes comprises one or more epitopes comprising at least 90% sequence identity to an amino acid sequence selected from SEQ ID NOs: 1, 6, 8-10, 14-16, 20, 25-28, 32-34, 46-56, 60-62, 66-75, 82-85, and 87. In some cases, the plurality of epitopes comprises one or more epitopes comprising at least 90% sequence identity to an amino acid sequence selected from SEQ ID NOs: 82-84. In some cases, the plurality of epitopes comprises one or more epitopes comprising at least 90% sequence identity to an amino acid sequence selected from SEQ ID NOs: 1, 6, 8-10, 14-16, 20, 25-28, or 32-34. In some cases, the plurality of epitopes comprises one or more epitopes comprising at least 90% sequence identity to an amino acid sequence selected from SEQ ID NOs: 46-56, 60-62, or 66-75. In some cases, the plurality of epitopes comprises one or more epitopes comprising at least 90% sequence identity to an amino acid sequence selected from SEQ ID NOs: 54, 73, 85, and 87. In some cases, the plurality of epitopes comprises one or more epitopes selected from SEQ ID NOs: 1, 6, 8-10, 14-16, 20, 25-28, 32-34, 46-56, 60-62, 66-75, 82-85, and 87.

In some cases, the plurality of epitopes is a plurality of contiguous epitopes. In some cases, the contiguous epitopes further comprise a linker between one or more of the epitope sequences. In some cases, the amino acid sequences of the first and the second epitopes are separated by a sequence of linker amino acids. In some cases, the amino acid sequence of the first epitope is adjacent to the amino acid sequence of the second epitope.

In some cases, the composition further comprises an additional isolated and purified plasmid comprising an additional nucleotide sequence encoding an additional polypeptide, wherein the additional polypeptide comprises a plurality of epitopes comprising one or more epitopes comprising at least 90% sequence identity to an amino acid sequence selected from SEQ ID NOs: 1, 6, 8-10, 14-16, 20, 25-28, 32-34, 46-56, 60-62, 66-75, 82-85, and 87. Sometimes, the composition further comprises an additional isolated and purified plasmid comprising an additional nucleotide sequence encoding an additional polypeptide, wherein the additional polypeptide comprises a plurality of epitopes selected from SEQ ID NOs: 1, 6, 8-10, 14-16, 20, 25-28, 32-34, 46-56, 60-62, 66-75, 82-85, and 87. In some cases, the sequences of the polypeptide and the additional polypeptide are different.

In some cases, the immune response is a Type 1 immune response. In some cases, the immune response is characterized by a ratio of Type I cytokine production to Type II cytokine production that is greater than 1. In some cases, the immune response is characterized by a ratio of Type I cytokine production to Type II cytokine production that is less than 1. In some cases, the immune response is characterized by a ratio of IFNγ production to IL-10 production that is greater than 1. In some cases, the immune response is characterized by a ratio of IFNγ production to IL-10 production that is less than 1.

In some cases, the composition is administered to a subject. In some cases, the subject is in need of administration of the composition. In some cases, the composition is effective to elicit an immune response in a subject. In some cases, the composition is effective to eliminate a number of cells associated with breast cancer or ovarian cancer in a subject. In some cases, the composition may be used to prevent the growth of cells associated with breast cancer or ovarian cancer in a subject.

In some cases, the cancer is breast cancer. In some instances, the breast cancer is a relapsed or refractory or metastasized breast cancer. In some instances, the cancer is ovarian cancer. In some cases, the ovarian cancer is a relapsed or refractory or metastasized ovarian cancer.

In some cases, at least the first epitope is contained within a pharmaceutical composition. In some cases, at least the first epitope is contained within a pharmaceutical composition further comprising a pharmaceutical carrier. In some cases, at least the first epitope is contained within a pharmaceutical composition further comprising a pharmaceutical carrier and an adjuvant. In some cases, at least the first epitope is contained within a pharmaceutical composition further comprising an adjuvant. In some cases, the composition further comprises an adjuvant and a pharmaceutical carrier. In some cases, the adjuvant is GM-CSF.

The disclosure also provides for a kit for preparing the compositions described herein, the kit comprising instructions for preparing the composition. The disclosure also provides for a kit for administering the compositions described herein, the kit comprising instructions for administering the composition.

Compositions Comprising Epitopes for a Breast Cancer Vaccine

The compositions described herein include a composition comprising: a first plasmid comprising a first nucleotide sequence, the first nucleotide sequence encoding a first epitope of a first antigen expressed by cells associated with breast cancer; and a second nucleotide sequence, the second nucleotide sequence encoding a second epitope of a second antigen expressed by cells associated with breast cancer, wherein the first nucleotide sequence and the second nucleotide sequence are located in one or more plasmids. In some cases, the composition may include nucleic acids which encode epitopes from the following proteins, CD105, HIF1α, MDM2, Yb1, SOX-2, HER-2, IGFBP2, IGF-1R, CDH3, and Survivin.

In some cases, the compositions may include a composition comprising: a first plasmid comprising a first nucleotide sequence, the first nucleotide sequence encoding a first epitope of a first antigen, the first epitope is a portion of a peptide selected from: CD105, Yb-1, SOX-2. CDH3 or MDM2, wherein the first nucleotide sequence is located in a plasmid. In other cases, the composition may include a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected front CD105, Yb-1, SOX-2, CDH3 or MDM2, wherein the first nucleotide sequence and the second nucleotide sequence are located in one or more plasmids.

In some cases, the composition may include nucleic acids which encode epitopes from the following proteins, CD105, MDM2, Yb-1, SOX-2, and CDH3. In some cases, the composition may include a nucleic acid sequence encoding an epitope of the peptide CD105 is selected from the group consisting of: a nucleotide sequence having at least 90% sequence identity to the nucleotide sequence of CAGAACGGCACCTGGCCCCGCGAGTGCTGCTGT-GCTGTCCGTGAACTCCTCCGT GTTCCTGCACCTA-CAGGCCCTGGGCATCCCCCTGCACCTGGCCTA-CAACTCCTCCCT GGTGACCTTCCAGGAGCCCCCCGGCGTGAACAC-CACCGAGCTG (SEQ ID NO: 2); a nucleotide sequence having at least 90% sequence identity to the nucleotide sequence of ACCGTGTTCATGCGCCTGAACAT-CATCTCCCCCGACCTGTCCGGCTGCACCTCCAAG GGCCTGGTGCTGCCCGCCGTGCTGGGCATCACCT-TCGGCGCCTTCCTGATCGGCGCC CTGCTGACCGC-CGCCCTGTGGTACATCTACTCCCACACCCGCTC-CCCCTCCAAGCGC GAGCCCGTGGTGGCCGTGGCCGCCCCCGCCTC-CTCCGAGTCCTCCTCCACCAACCAC TCCATCG-GCTCCACCCAGTCCACCCCCTGCTCCACCTCCATG-GCC (SEQ ID NO: 3); a nucleotide sequence having at least 90% sequence identity to the nucleotide sequence of ACCGTGTCCATGCGCCTGAACATCGTGTC-CCCCGACCTGTCCGGCAAGGGCCTGGTG CTGC-CCTCCGTGCTGGGCATCACCTTCGGCGCCTTCCT-GATCGGCGCCCTGCTGACC GCCGCCCTGTGGTACATCTACTCCCACACCCGCG-GCCCCTCCAAGCGCGAGCCCGTG GTGGCCGTGGC-CGCCCCCGCCTCCTCCGAGTCCTCCTCCACCAAC-CACTCCATCGGC TCCACCCAGTCCACCCCCTGCTCCACCTCCTC-CATGGCC (SEQ ID NO: 4); a nucleotide sequence having at least 90% sequence identity to the nucleotide sequence of ACCGTGTCCATGCGCCTGAACATCGTGTC-CCCCGACCTGTCCGGCAAGGGCCTGGTG CTGC-CCTCCGTGCTGGGCATCACCTTCGGCGCCTTCCT-GATCGGCGCCCTGCTGACC GCCGCCCTGTGGTACATCTACTCCGCGCACAC-CCCTCCAAGCGCGAGCCCGTG GTGGCCGTGGC-CGCCCCCGCCTCCTCCGAGTCCTCCTCCACCAAC-CACTCCATCGGC TCCACCCAGTCCACCCCCTGCTCCACCTCCTC-CATGGCC (SEQ ID NO: 5); a nucleotide sequence encoding an amino acid sequence, the amino acid sequence having at least 90% sequence identity to the amino acid sequence of EARMLNASIVASFVELPL (SEQ ID NO: 6); a nucleotide sequence encoding an amino acid sequence, the amino acid sequence having at least 90% sequence identity to the amino acid sequence of QNGTWPREVLLVLSVNSSVFL-HLQALGIPLHLAYNSSLVTFQEPPGVNTTEL (SEQ ID NO: 7); a nucleotide sequence encoding an amino acid sequence, the amino acid sequence having at least 90% sequence identity to the amino acid sequence of TVFMRL-NIISPDLSGCTSKGLVLPAVLGITFGAFLIGALLTAAL-WYIYSHTRSPSKREPVV AVAAPASSESSSTNHSIG-STQSTPCSTSSMA (SEQ ID NO: 8); a nucleotide sequence encoding an amino acid sequence, the amino acid sequence having at least 90% sequence identity to the amino acid sequence of TVSMRLNIVSPDLSGKGLVLPSVLGITF-GAFLIGALLTAALWYIYSHTRGPSKREPVVAV AAPASSESSSTNHSIGSTQSTPCSTSSMA (SEQ ID NO: 9); or a nucleotide sequence encoding an amino acid sequence, the amino acid sequence having at least 90% sequence identity to the amino acid sequence of TVSMRL-NIVSPDLSGKGLVLPSVLGITFGAFLIGALLTAALWYI-YSHTRAPSKREPVVAV AAPASSESSSTNHSIGSTQST-PCSTSSMA (SEQ ID NO: 10). In some cases, the composition may include a nucleic acid sequence encoding an epitope of the peptide Yb-1 is selected from the group consisting of: a nucleotide sequence having at least 90% sequence identity to the nucleotide sequence of GGAGT-GCCAGTGCAGGGCTCCAAGTACGCTGCCGACCG-CAACCACTACCGCCGCTA CCCACGCCGTCGCGGC-CCACCCCGCAACTACCAGCAGAAC (SEQ ID NO: 11); a nucleotide sequence having at least 90% sequence identity to the nucleotide sequence of GGCGTGCCCGTGCA-GGGCTCCAAGTACGCCGCCGACCGCAACCACTAC-CGCCGCTA CCCCCGCCGCCGCGGCCCCCCCCG-CAACTACCAGCAGAAC (SEQ ID NO: 12); a nucleotide sequence having at least 90%6 sequence identity to the nucleotide sequence of GGCGTGCCCGTGCAGGGCTC-CAAGTACGCCGCCGACCGCAACCACTACCGC-CGCTA CCCCCGCCGCCGCGGCCCCCCCCGCAAC-TACCAGCAGAAC (SEQ ID NO: 13); a nucleotide sequence encoding an amino acid sequence, the amino acid sequence having at least 90% sequence identity to the amino acid sequence of EDVFVHQTAIKKNNPRK (SEQ ID NO: 14); a nucleotide sequence encoding an amino acid sequence, the amino acid sequence having at least 90% sequence identity to the amino acid sequence of YRRNF-NYRRRRPEN (SEQ ID NO: 15); or a nucleotide sequence encoding an amino acid sequence, the amino acid sequence having at least 90% sequence identity to the amino acid sequence of GVPVQGSKYAADRNHYRRYPRRRGP-PRNYQQN (SEQ ID NO: 16). In some cases, the composition may include a nucleic acid sequence encoding an epitope of the peptide SOX-2 is selected from the group consisting of: a nucleotide sequence having at least 90% sequence identity to the nucleotide sequence of GGCCT-CAATGCGCACGGCGCAGCGCAGATGCAGCCCATG-CACCGCTACGACGTGAG CGCCCTGCAGTA-CAACTCCATGACCAGCTCGCAGACCTACATGAAC-GGCTCGCCCA CCTACAGCATGTCCTACTCGCAGCA-GGGCACCCCTGGCATGGCTCTTGGCTCCATGG GTTCGGTG (SEQ ID NO: 17); a nucleotide sequence having at least 90% sequence identity to the nucleotide sequence of GGCCTGAACGCCCACGGCGCCGCCCA-GATGCAGCCCATGCACCGCTACGACGTGTC CGC-CCTGCAGTACAACTCCATGACCTCCTCCCAGAC-CTACATGAACGGCTCCCCCAC CTACTCCATGTCCTACTCCCAGCAGGGCACCCCCG-GCATGGCCCTGGGCTCCATGGG CTCCGTG (SEQ ID NO: 18); a nucleotide sequence having at least 90% sequence identity to the nucleotide sequence of GGCCT-GAACGCCCACGGCGCCGCCCAGATGCAGCCCATG-CACCGCTACGACGTGTC CGCCCTGCAGTA-CAACTCCATGACCTCCTCCCAGACCTACATGAACG-GCTCCCCCAC CTACTCCATGTCCTACTCCCA-GCAGG GCACCCCGCATGGCCCTGGGCTCCATGGG CTCCGTG (SEQ ID NO: 19); or a nucleotide sequence encoding an amino acid sequence, the amino acid sequence having at least 90% sequence identity to the amino acid sequence of GLNAHGAAQMQPMHRYDVSALQYNS-MTSSQTYMNGSPTYSMSYSQQGTPGMALGSM GSV (SEQ ID NO: 20). In some cases, the composition may include, a nucleic acid sequence encoding an epitope of the peptide CDH3 is selected from the group consisting of: a nucleotide sequence having at least 90% sequence identity to the nucleotide sequence of AGGTCACT-GAAGGAAAGGAATCCATTGAAAATCTTCCCATC-CAAACGTATCTTACG AAGACACAAGAGAGAT-TGGGTGGTTGCTCCAATATCTGTCCCTGAAAATGG-CAAGG GTCCCTTCCCACAGAGACTGAATCAGCT-CAAGTCTAATAAAGATAGAGACACCAAG ATTTTC-TACAGCATCACGGGGCCGGGTGCAGACAGCCCAC-CTGAGGGTGTCTTCGCT GTAGAGAAGGAGACA (SEQ ID NO: 21); a nucleotide sequence having at least 90% sequence identity to the nucleotide sequence of TTGAAAATCTCCCATCCAAACGTATCTTACGAAGA-CACAAGAGAGATGGGTGGT TGCTCCAATATCTGTC-CCTGAAAATGGCAAGGGTCCCTTCCCACAGA-GACTGAATCA GCTCAAGTCTAATAAAGATAGAGACAC-CAAGATTTTCTACAGCATCACGGGGCCGG GTGCA-GACAGCCCACCTGAGGGTGTCTCGCTGTAGA- GAAGGAGACA (SEQ ID NO: 22); a nucleotide sequence having at least 90% sequence identity to the nucleotide sequence of GCCATGCACTCCCCCCCCACCCGCATCCTGCGCCGCCGCAAGCGCGAGTGGGTGATGCCCCCCATCTTCGTGCCCGAGAACGGCAAGGGCCCCTTCCCCCAGCGCCTGAACC AGCTGAAGTCCAACAAGGACCGCGGCACCAAGATCTTCTACTCCATCACCGGCCCC GGCGCCGACTCCCCCCCCGAGGGCGTGTTCACCATCGAGAAGGAGTCC (SEQ ID NO: 23); a nucleotide sequence having at least 90% sequence identity to the nucleotide sequence of GTGATGAACTCCCCCCCCTCCCGCATCCTGCGCCGCCGCAAGCGCGAGTGGGTGAT GCCCCCCATCTCCGTGCCCGAGAACGGCAAGGGCCCCTTCCCCCAGCGCCTGAACC AGCTGAAGTCCAACAAGGACCGCGGCACCAAGCTGTTCTACTCCATCACCGGCCCC GGCGCCGACTCCCCCCCCGAGGGCGTGTTCACCATCGAGAAGGAGACC (SEQ ID NO: 24); a nucleotide sequence encoding an amino acid sequence, the amino acid sequence having at least 90% sequence identity to the amino acid sequence of RSLKERNPLKIFPSKRILRRHKRDWVVAPISVPENGKGPFPQRLNQLKSNKDRDTKIFYSI TGPGADSPPEGVFAVEKET (SEQ ID NO: 25); a nucleotide sequence encoding an amino acid sequence, the amino acid sequence having at least 90% sequence identity to the amino acid sequence of LKIFPSKRILRRHKRDWVVAPISVPENGKGPFPQRLNQLKSNKDRDTKIFYSITGPGADSP PEGVFAVEKET (SEQ ID NO: 26); a nucleotide sequence encoding an amino acid sequence, the amino acid sequence having at least 90% sequence identity to the amino acid sequence of AMHSPPTRILRRRKREWVMPPIFVPENGKGPFPQRLNQLKSNKDRGTKIFYSITGPGADS PPEGVFTIEKES (SEQ ID NO: 27); or a nucleotide sequence encoding an amino acid sequence, the amino acid sequence having at least 90% sequence identity to the amino acid sequence of VMNSPPSRILRRRKREWVMPPISVPENGKGPFPQRLNQLKSNKDRGTKLFYSITGPGADS PPEGVFTIEKET (SEQ ID NO: 28). In some cases, the composition may include, a nucleic acid sequence encoding an epitope of the peptide MDM2 is selected from the group consisting of: a nucleotide sequence having at least 90% sequence identity to the nucleotide sequence of ACCTACACCATGAAGGAGGTGCTGTTCTACCTGGGCCAGTACATCATGACCAAGCG CCTGTACGACGAGAAGCAGCAGCACATCGTGTACTGCTCCAACGACCTGCTGGGCG ACCTGTTCGGCGTGCCCTCCTTCTCCGTGAAGGAGCACCGCAAaATCTACACCATGA TCTACCGCAACCTGGTGGTGGTGAACCAGCAGGAGTCCTCCGACTCCGGCACCTCC GTGTCC (SEQ ID NO: 29); a nucleotide sequence having at least 90% sequence identity to the nucleotide sequence of ACCTACACCATGAAGGAGATCATCTTCTACATCGGCCAGTACATCATGACCAAGCG CCTGTACGACGAGAAGCAGCAGCACATCGTGTACTGCTCCAACGACCTGCTGGGCG ACGTGTTCGGCGTGCCCTCCTTCTCCGTGAAGGAGCACCGCAAGATCTACGCCATGA TCTACCGCAACCTGGTGGCCGTGTCCAGCAGGACTCCGGCACCTCCCTGTCC (SEQ ID NO: 30); a nucleotide sequence having at least 90% sequence identity to the nucleotide sequence of ATCTACACCATGAAGGAGATCATCTTCTACATCGGCCAGTACATCATGACCAAGCG CCTGTACGACGAGAAGCAGCAGCACATCGTGTACTGCTCCAACGACCTGCTGGGCG ACGTGTTCGGCGTGCCCTCCTTCTCCGTGAAGGAGCACCGCAAGATCTACGCCATGA TCTACCGCAACCTGGTGGTGGTGTCCCAGCAGGACTCCGGCACCTCCCCCTCC (SEQ ID NO: 31); a nucleotide sequence encoding an amino acid sequence, the amino acid sequence having at least 90% sequence identity to the amino acid sequence of TYTMKEVLFYLGQYIMTKRLYDEKQQHIVYCSNDLLGDLFGVPSFSVKEHRKIYTMIYR NLVVVNQQESSDSGTSV (SEQ ID NO: 32); a nucleotide sequence encoding an amino acid sequence, the amino acid sequence having at least 90% sequence identity to the amino acid sequence of TYTMKEIIFYIGQYIMTKRLYDEKQQHIVYCSNDLLGDVFGVPSFSVKEHRKIYAMIYRN LVAVSQQDSGTSLS (SEQ ID NO: 33); or a nucleotide sequence encoding an amino acid sequence, the amino acid sequence having at least 90% sequence identity to the amino acid sequence of IYTMKEIIFYIGQYIMTKRLYDEKQQHIVYCSNDLLGDVFGVPSFSVKEHRKIYAMIYRN LVVVSQQDSGTSPS (SEQ ID NO: 34).

In an exemplary case, the compositions may include a nucleic acid sequence encoding a fusion peptide of five epitopes is selected from the group consisting of: a nucleotide sequence having at least 90% sequence identity to the nucleotide sequence of ATGGCGGTACCCATGCAACTGTCCTGCTCTAGACAGAACGGCACCTGGCCCCGCGA GGTGCTGCTGGTGCTGTCCGTGAACTCCTCCGTGTTCCTGCACCTACAGGCCCTGGG CATCCCCCTGCACCTGGCCTACAACTCCTCCCTGGTGACCTTCCAGGAGCCCCCCGG CGTGAACACCACCGAGCTGAGATCCACCGGTGGAGTGCCAGTGCAGGGCTCCAAGT ACGCTGCCGACCGCAACCACTACCGCCGCTACCCACGCCGTCGCGGCCCACCCCGC AACTACCAGCAGAACACGCGTGGCCTCAATGCGCACGGCGCAGCGCAGATGCAGCC CATGCACCGCTACGACGTGAGCGCCCTGCAGTACAACTCCATGACCAGCTCGCAGA CCTACATGAACGGCTCGCCCACCTACAGCATGTCCTACTCGCAGCAGGGCACCCCT GGCATGGCTCTTGGCTCCATGGGTCGGTGAGATCCCAATTGAGGTCACTGAAGGA AAGGAATCCATTGAAAATCTTCCCATCCAAACGTATCTTACGAAGACACAAGAGAG ATTGGGTGGTGCTCCAATATCTGTCCCTGAAAATGGCAAGGGTCCCTrCCCACAGA GACTGAATCAGCTCAAGTCTAATAAAGATAGAGACACCAAGATTTTFCTACAGCATC ACGGGGCCGGGTGCAGACAGCCCACCTGAGGGTGTCTFCGCTGTAGAGAAGGAGAC AAGATCCGCCGGCGAAACCTACACCATGAAGGAGGTGCTGTCTACCTGGGCCAGT ACATCATGACCAAGCGCCTGTACGACGAGAAGCAGCAGCACATCGTGTACTGCTCC AACGACCTGCTGGGCGACCTGTTCGGCGTGCCCTCCTTCTCCGTGAAGGAGCACCGC AAAATCTACACCATGATCTACCGCAACCTGGTGGTGGTGAACCAGCAGGAGTCCTC CGACTCCGCACCTCCGTGTCCAGATCTTAG (SEQ ID NO: 35); a nucleotide sequence having at least 90% sequence identity to the nucleotide sequence of ATGGCGGTACCCATGACCGTGTTCATGCGCCTGAACATCATCTCCCCCGACCTGTCC GGCTGCACCTCCAAGGGCCTGGTGCTGCCGCCGTGCTGGGCATCACCTTCGGCGCC TTCCTGATCGGCGCCCTGCTGACCGCCGCCCTGTGGTACATCTACTCCCACACCCGC TCCCCCTCCAAGCGCGAGCCCGTGGTGGCCGTGGCCGCCCCCGCCTCCTCCGGATCC TCCTCCACCAACCACTCCATCGGCTCCACCCAGTCCACCCCCCTGCTCCACCTCCTCC ATGGCCACCGGTGGAGTGCCAGTGCAGGGCTCCAAGTACGCTGCCGACCGCAACCA CTACCGCCGCTACCCACGCCGTCGCGGCCCCAC CCCGCAACTACCAGCAGAACACGC GTGGCCT-CAATGCGCACGGCGCAGCGCAGATGCAGCCCATG-CACCGCTACGACGTG
AGCGCCCTGCAGTACAACTCCATGACCA-GCTCGCAGACCTACATGAACGGCTCGCC CACCTA-CAGCATGTCCTACTCGCAGCAGGGCACCCTG-GCATGGCTCTGGCTCCAT
GGGTCGGTGAGATCCCAATTGAAAATGAAAATCT-TCCCATCCAAACGTATCTFACGAAG ACACAAGA-GAGATGGGTGGTGCTCCAATATCTGTCCCT-GAAAATGGCAAGGGTC
CCTTCCCACAGAGACTGAATCAGCT-CAAGTCTAATAAAGATAGAGACACCAAGATT TTC-TACAGCATCACGGGGCCGGGTGCAGACAGCCCAC-CTGAGGGTGTCTCGCTGT
AGAGAAGGAGACAAGATCCGCCGGCGAAACCTA-CACCATGAAGGAGGTGCTGTTC TACCTGGGCCAG-TACATCATGACCAAGCGCCTGTACGACGA-GAAGCAGCAGCACAT
CGTGTACTGCTCCAACGACCTGCTGGGCGACCT-GTCGGCGTGCCCTCCTTCTCCGT GAAGGAGCAC-CGCAAAATCTACACCATGATCTACCGCAACCTG-GTGGTGGTGAACC
AGCAGGAGTCCTCCGACTCCGGCACCTCCGTGTC-CAGATCTTAG (SEQ ID NO: 36); a nucleotide sequence having at least 90% sequence identity to the nucleotide sequence of ATGGCGGTACCCATGACCGTGTCCAT-GCGCCTGAACATCGTGTCCCCCGACCTGTCC
GGCAAGGGCCTGGTGCTGCCCTCCGT-GCTGGGCATCACCTCGGCGCCTTCCTGATC
GGCGCCCTGCTGACCGCCGCCCTGTGGTACATC-TACTCCCACACCCGCGGCCCCTCC AAGCGCGAGC-CCGTGGTGGCCGTGGCCGCCCCGCCTCCTC-CGAGTCCTCCTCCACC
AACCACTCCATCGGCTCCACCCAGTCCACCCCCT-GCTCCACCTCCTCCATGGCCACC GGTGGCGTGC-CCGTGCAGGGCTCCAAGTACGCCGCCGACCG-CAACCACTACCGCCG
CTACCCCCGCCGCCGCGGCCCCCCCGCAACTAC-CAGCAGAACACGCGTGGCCTGA ACGCCCACG-GCGCCGCCCAGATGCAGCCCATGCACCGCTAC-GACGTGTCGCCCTG
CAGTACAACTCCATGACCTCCTCCCAGACCTACAT-GAACGGCTCCCCCACCTACTCC ATGTCCTACTC-CCAGCAGGGCACCCCCGGCATGGCCCTGGGCTC-CATGGGCTCCGTG
AGATCCCAATTGGCCATGCACTCCCCCCCCACCCG-CATCCTGCGCCGCCGCAAGCGC GAGTGGGTGAT-GCCCCCCATCTTCGTGCCCGAGAACGGCAAGGGC-CCCTTCCCCCA
GCGCCTGAACCAGCTGAAGTCCAACAAGGAC-CGCGGCACCAAGATCTTCTACTCCA TCACCGGC-CCCGGCGCCGACTCCCCCCCCGAGGGCGTGTCAC-CATCGAGAAGGAG
TCCAGATCCGCCGGCGAAACCTACACCAT-GAAGGAGATCATCTTCTACATCGGCCA GTACAT-CATGACCAAGCGCCTGTACGACGAGAAGCAGCAG-CACATCGTGTACTGCT
CCAACGACCTGCTGGGCGACGTGTTCGGCGTGC-CCTCCTTCTCCGTGAAGGAGCACC GCAAGATC-TACGCCATGATCTACCGCAACCTGGTGGCCGTGTC-CCAGCAGGACTCC
GGCACCTCCCCTGTCCAGATCTTAG (SEQ ID NO: 37); a nucleotide sequence having at least 90% sequence identity to the nucleotide sequence of ATGGCGGTACCCATGAC-CGTGTCCATGCGCCTGAACATCGTGTCCCCCGAC-CTGTCC GGCAAGGGCCTGGTGCTGCCCTCCGT- GCTGGGCATCACCTTCGGCGCCTTCCTGATC
GGCGCCCTGCTGACCGCCGCCCTGTGGTACATC-TACTCCCACACCCGCGCCCCTCC AAGCGCGAGC-CCGTGGTGGCCGTGGCCGCCCCGCCTCCTC-CGAGTCCTCCTCCACC
AACCACTCCATCGGCTCCACCCAGTCCACCCCCT-GCTCCACCTCCTCCATGGCCACC GGTGGCGTGC-CCGTGCAGGGCTCCAAGTACGCCGCCGACCG-CAACCACTACCGCCG
CTACCCCCGCCGCCGCGGCCCCCCCGCAACTAC-CAGCAGAACACGCGTGGCCTGA ACGCCCACG-GCGCCGCCCAGATGCAGCCCATGCACCGCTAC-GACGTGTCCGCCCTG
CAGTACAACTCCATGACCTCCTCCCAGACCTACAT-GAACGGCTCCCCCACCTACTCC ATGTCCTACTC-CCAGCAGGGCACCCCCGGCATGGCCCTGGGCTC-CATGGGCTCCGTG
AGATCCCAATTGGTGATGAACTCCCCCCCCTCCCG-CATCCTGCGCCGCCGCAAGCGC GAGTGGGTGAT-GCCCCCCATCTCCGTGCCCGAGAACGGCAAGGGC-CCCTTCCCCCA
GCGCCTGAACCAGCTGAAGTCCAACAAGGAC-CGCGGCACCAAGCTGTTCTACTCCA TCACCGGC-CCCGGCGCCGACTCCCCCCCCGAGGGCGTGT-CACCATCGAGAAGGAG
ACCAGATCCGCCGGCGAAATCTACACCAT-GAAGGAGATCATCTTCTACATCGGCCA GTACAT-CATGACCAAGCGCCTGTACGACGAGAAGCAGCAG-CACATCGTGTACTGCT
CCAACGACCTGCTGGGCGACGTGTTCGGCGTGC-CCTCCTTCTCCGTGAAGGAGCACC GCAAGATC-TACGCCATGATCTACCGCAACCTGGTGGTGGTGTC-CCAGCAGGACTCC
GGCACCTCCCCCTCCAGATCTTAG (SEQ ID NO: 38); a nucleotide sequence encoding an amino acid sequence, the amino acid sequence having at least 90% sequence identity to the amino acid sequence of MAVPMQLSC-SRQNGTWPREVLLVLSVNSSVFLHLQALGIPL-HLAYNSSLVTFQEPPGVN TTELRSTGGVPVQG-SKYAADRNHYRRYPRRRGPPRNYQQNTRGLNAHGA-AQMQPMH RYDVSALQYNSMTSSQTYMNGSP-TYSMSYSQQGTPGMALGSMGSVRSQLRSLKERNP LKIFPSKRILRRHKRDWVVAPISVPENGKGPFPQRLN-QLKSNKDRDTKIFYSITGPGADSP PEGV-FAVEKETRSAGETYTMKEVLFYLGQYIMT-KRLYDEKQQHIVYCSNDLLGDLFGV PSFSVKEHRKIYTMIYRNLVVVNQQESSDSGTSVSRS (SEQ ID NO: 39); a nucleotide sequence encoding an amino acid sequence, the amino acid sequence having at least 90% sequence identity to the amino acid sequence of MAVPMT-VFMRLNIISPDLSGCTSKGLVLPAVLGITFGAFLI-GALLTAALWYIYSHTRSPS KREPVVA-VAAPASSESSSTNHSIGSTQSTPCSTSSMATGGVPVQ-GSKYAADRNHYRRYP RRRGPPRNYQQNTRGLNAH-GAAQMQPMHRYDVSALQYNSMTSSQTYMNGSP-TYSMS YSQQGTPGMALGSMGSVRSQLLKIFPSKRIL-RRHKRDWVVAPISVPENGKGPFPQRLNQ LKSNKDRDTKIFYSITGPGADSPPEGV-FAVEKETRSAGETYTMKEVLFYLGQYIMTKRL YDEKQQHIVYCSNDLLGDLFGVPSFSVKEHRKIYT-MIYRNLVVVNQQESSDSGTSVSRS (SEQ ID NO: 40); a nucleotide sequence encoding an amino acid sequence, the amino acid sequence having at least 90% sequence identity to the amino acid sequence of MAVPMTVSMRLNIVSP-DLSGKGLVLPSVLGITFGAFLIGALLTAALWYIYSH-TRGPSKRE PVVAVAAPASSESSSTNHSIGSTQSTPCST-SSMATGGVPVQGSKYAADRNHYRRYPRRR GPPRNYQQNTRGLNAHGAAQMQPMHRYD-
VSALQYNSMTSSQTYMNGSPTYSMSYSQ QGTPG-
MALGSMGSVRSQLAMHSPPTRILRRRKREWVMP-
PIFVPENGKGPFPQRLNQLK
SNKDRGTKIFYSITGPGADSPPEGVFTIEKESRSAG-
ETYTMKEIIFYIGQYIMTKRLYDEK QQHIVYC-
SNDLLGDVFGVPSFSVKEHRKIYAMIYRNLVA-
VSQQDSGTSLSRS (SEQ ID NO: 41); or a nucleotide sequence encoding an amino acid sequence, the amino acid sequence having at least 90% sequence identity to the amino acid sequence of MAVPMTVSMRLNIVSPDLSGKGLV-
LPSVLGITFGAFLIGALLTAALWYIYSHTRAPSKRE
PVVAVAAPASSESSSTNHSIGSTQSTPCSTSSMATG-
GVPVQGSKYAADRNHYRRYPRRR GPPRNYQQN-
TRGLNAHGAAQMQPMHRYDVSALQYNSMTSSQ-
TYMNGSPTYSMSYSQ
QGTPGMALGSMGSVRSQLVMNSPPSRILR-
RRKREWVMPPISVPENGKGPFPQRLNQLKS
NKDRGTKLFYSITGPGADSPPEGVFTIEKETRSAGE
IYTMKEIIFYIGQYIMTKRLYDEKQQHIVYCSNDLL-
GDVFGVPSFSVKEHRKIYAMIYRN LVVVSQQDS-
GTSPSRS (SEQ ID NO: 42).

In some cases, the composition may include nucleic acids which encode epitopes from the following proteins, HER-2, IGFBP2 and IGF-1R. In some cases, the composition may comprise a first plasmid comprising a first nucleotide sequence, the first nucleotide sequence encoding a first epitope of a first antigen, the first epitope is a portion of a peptide selected from: IGFBP-2, HER-2, IGF-1R, wherein the first nucleotide sequence is located in a plasmid. In some cases, the composition may comprise: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: IGFBP-2, HER-2 or IGF-1R, wherein the first nucleotide sequence and the second nucleotide sequence are located in one or more plasmids. In some cases, the compositions may comprise a nucleic acid sequence encoding an epitope of the peptide IGFBP-2 is selected from the group consisting of: a nucleotide sequence having at least 90% sequence identity to the nucleotide sequence of ATGCTGC-
CGAGAGTGGGCTGCCCCGCGCTGCCGCTGCCGC-
CGCCGCCGCTGCTGCC GCTGCTGCCGCTGCTGCT-
GCTGCTACTGGGCGCGAGTGGCGGCGGCGGCGGG-
GCGC GCGCGGAGGTGCTGTTCCGCTGCCCGCCCT-
GCACACCCGAGCGCCTGGCCGCCTGC GGGC-
CCCCGCCGGTTGCGCCGCCCGCCGCGGTGGC-
CGCAGTGGCCGGAGGCGCCCG
CATGCCATGCGCGGAGCTCGTCCGGGAGC-
CGGGCTGCGGCTGCTGCTCGGTGTGCG CCCG-
GCTGGAGGGCGAGGCGTGCGGCGTCTACAC-
CCCGCGCTGCGGCCAGGGGCTG
CGCTGCTATCCCCACCCGGGCTCCGAGCTGCCCCT-
GCAGGCGCTGGTCATGGGCGA GGGCACTTGT-
GAGAAGCGCCGGGACGCCGAGTATGGCGCCAGC-
CCGGAGCAGGIT
GCAGACAATGGCGATGACCACTCAGAAGGAGGC-
CTGGTGGAG (SEQ ID NO: 43); a nucleotide sequence having at least 90% sequence identity to the nucleotide sequence of ATGCTGCCCCGCCTGGGCGGCCCCGC-
CCTGCCCCTGCTGCTGCCCTCCCTGCTGCTG
CTGCTGCTGCTGGGCGCCGGGCTGCGGCCCCG-
GCGTGCGCGCCGAGGTGCTGTT CCGCTGC-
CCCCCTGCACCCCGAGCGCCTGGCCGCCTGCG-
GCCCCCCCCCCGACGC
CCCCTGCGCCGAGCTGGTGCGCGAGCCCGGCT-
GCGGCTGCTGCTCCGTGTGCGCCC GCCAG-
GAGGGCGAGGCCTGCGGCGTGTACATCCCCCGCT-
GCGCCCAGACCCTGCGC
TGCTACCCCAACCCCGGCTCCGAGCTGCCCCT-
GAAGGCCCTGGTGACCGGCGCCGG CACCTGCGA-
GAAGCGCCGCGTGGGCACCACCCCCC CAGGTG-
GCCGACTCCGACG
ACGACCACTCCGAGGGCGGCCTGGTGGAG (SEQ ID NO: 44); a nucleotide sequence having at least 90% sequence identity to the nucleotide sequence of ATGCTGC-
CCCGCCTGGGCGGCCCCGCCCTGCCCCTGCTGC-
CCTGCCCC TGCTGCTG CTGCTGCTGCTGGGCGC-
CGGCGGCTGCGGCCCCGGCGTGCGCGCCGAGGTG-
CTGTT CCGCTGCCCCCCCTGCACCCCCGAGCGC-
CTGGCCGCCTGCGGCCCCCCCCCCGACGC CCCCT-
GCGCCGAGCTGGTGCGCGAGCCCGGCTGCGGCT-
GCTGCTCCGTGTGCGCCC
GCCAGGAGGGCGAGGCCTGCGGCGTGTACATC-
CCCCGCTGCGCCCAGACCCTGCGC TGCTAC-
CCCAACCCCGGCTCCGAGCTGCCCCTGAAGGC-
CCTGGTGACCGGCGCCGG
CACCTGCGAGAAGCGCCGCGTGGGCACCAC-
CCCCCAGCAGGTGGCCGACTCCGAGG ACGAC-
CACTCCGAGGGCGGCCTGGTGGAG (SEQ ID NO: 45); a nucleotide sequence encoding an amino acid sequence, the amino acid sequence having at least 90% sequence identity to the amino acid sequence of NHVDST-
MNMLGGGGS (SEQ ID NO: 46); a nucleotide sequence encoding an amino acid sequence, the amino acid sequence having at least 90% sequence identity to the amino acid sequence of ELAVFREKVTEQHRQ (SEQ ID NO: 47), a nucleotide sequence encoding an amino acid sequence, the amino acid sequence having at least 90% sequence identity to the amino acid sequence of LGLEEPKKLRPPPAR (SEQ ID NO: 48); a nucleotide sequence encoding an amino acid sequence, the amino acid sequence having at least 90% sequence identity to the amino acid sequence of DQVLER-
ISTMRLPDE (SEQ ID NO: 49); a nucleotide sequence encoding an amino acid sequence, the amino acid sequence having at least 90% sequence identity to the amino acid sequence of GPLEHLYSLHIPNCD (SEQ ID NO: 50); a nucleotide sequence encoding an amino acid sequence, the amino acid sequence having at least 90% sequence identity to the amino acid sequence of KHGLYNLKQCKMSLN (SEQ ID NO: 51); a nucleotide sequence encoding an amino acid sequence, the amino acid sequence having at least 90% sequence identity to the amino acid sequence of PNTG-
KLIQGAPTIRG (SEQ ID NO: 52); a nucleotide sequence encoding an amino acid sequence, the amino acid sequence having at least 90% sequence identity to the amino acid sequence of PECHLFYNEQQEARG (SEQ ID NO: 53); a nucleotide sequence encoding an amino acid sequence, the amino acid sequence having at least 90% sequence identity to the amino acid sequence of MLPRVGCPALPLPPPPLL-
PLLPLLLLLLGASGGGGGARAEVLFRCPPCTPER-
LAACGPPP VAPPAAVAAVAGGARMPCAEL-
VREPGCGCCSVCARLEGEACGVYTPRCGQGLRCYPH
PGSELPLQALVMGEGTCEKRRDAEYGASPEQ-
VADNGDDHSEGGLVE (SEQ ID NO: 54); a nucleotide sequence encoding an amino acid sequence, the amino acid sequence having at least 90% sequence identity to the amino acid sequence of MLPRLGGPALPLLLPSLLLLLLLGAG-
GCGPGVRAEVLFRCPPCTPERLAACGPPPDAPCA
ELVREPGCGCCSVCARQEGEACGVYIPRCAQTLRCY-
PNPGSELPLKALVTGAGTCEKRR VGTTPQQ-
VADSDDDHSEGGLVE (SEQ ID NO: 55); and a nucleotide sequence encoding an amino acid sequence, the amino acid sequence having at least 90% sequence identity to the amino acid sequence of MLPRLGGPALPLLLPSLLLLLLLGAGGCGPGVRAEVLFRCPPCTPERLAACGPPPDAPCAELVREPGCGCCSVCARQEGEACGVYIPRCAQTLRCYPNPGSELPLKALVTGAGTCEKRR VGATPQQVADSEDDHSEGGLVE (SEQ ID NO: 56). In some cases, the compositions may comprise a nucleic acid sequence encoding an epitope of the peptide HER-2 is selected from the group consisting of: a nucleotide sequence having at least 90% sequence identity to the nucleotide sequence of ACGATGCGGAGACTGCTGCAGGAAACGGAGCTGGTGGAGCCGCTGACACCTAGCG GAGCGATGCCAACCAGGCGCAGATGCGGATCCTGAAAGAGACGGAGCTGAGGAA
GGTGAAGGTGCTTGGATCTGGCGCTTTTGGCACAGTCTACAAGGGCATCTGGATCCC TGATGGGGAGAATGTGAAAATTCCAGTGGCCATCAAAGTGTTGAGGGAAACACAT
CCCCCAAAGCCAACAAAGAAATCTTAGACGAAGCATACGTGATGGCTGGTGTGGGCTCCCCATATGTCTCCCGCCTTCTGGGCATCTGCCTGACATCCACGGTGCAGCTGGTG ACACAGCTTATGCCCTATGGCTGCCTCTTAGACCATGTCCGGGAAAACCGCGGACG
CCTGGGCTCCCAGGACCTGCTGAACTGGTGTATGCAGATTGCCAAGGGGATGAGCT ACCTGGAGGATGTGCGGCTCGTACACAGGGACTTGGCCGCTCGGAACGTGCTGGTC
AAGAGTCCCAACCATGTCAAAATTACAGACTTCGGGCTGGCTCGGCTGCTGGACAT TGACGAGACAGAGTACCATGCAGATGGGGGCAAGGTGCCATCAAGTGGATGGCG
CTGGAGTCCATTCTCCGCCGGCGGTTCACCCACCAGAGTGATGTGTGGAGTTATGGT GTGACTGTGTGGGAGCTGATGACTTTTGGGGCCAAACCTTACGATGGGATCCAGC
CCGGGAGATCCCTGACCTGCTGGAAAAGGGGGAGCGGCTGCCCCAGCCCCCCATCTGCACCATTGATGTCTACATGATCATGGTCAAATGTTGGATGATTGACTCTGAATGTC GGCCAAGATTCCGGGAGTTGGTGTCTGAATTCTCCCGCATGGCCAGGGACCCCCAG
CGCTTTGTGGTCATCCAGAATGAGGACTTGGCTCCCGGAGCTGGCGGCATGGTGCA CCACAGGCACCGCAGCTCATCTCCTCTGCCTGCTGCCCGACCTGCTGGTGCCACTCT
GGAAAGGCCCAAGACTCTCTCCCCAGGGAAGAATGGGiGTCGTCAAAGACGTTG CCTTTGGGGGTGCCGTGGAGAACCCCGAGTACTTG (SEQ ID NO: 57); a nucleotide sequence having at least 90% sequence identity to the nucleotide sequence of ACCATGCGCCGCCTGCTGCAGGAGACCGAGCTGGTGGAGCCCCTGACCCCCTCCGG CGCCGTGCCCAACCAGGCCCAGATGCGCATCCTGAAGGAGACCGAGCTGCGCAAGC TGAAGGTGCTGGGCTCCGGCGCCTTCGGCACCGTGTACAAGGGCATCTGGATCCCC
GACGGCGAGAACGTGAAGATCCCCGTGGCCATCAAGGTGCTGCGCGAGAACACCTC CCCCAAGGCCAACAAGGAGATCCTGGACGAGGCCTACGTGATGGCCGGCGTGGGCT
CCCCCTACGTGTCCCGCCTGCTGGGCATCTGCCTGACCTCCACCGTGCAGCTGGTGA CCCAGCTGATGCCCTACGGCTGCCTGCTGGACCACGTGCGCGAGCACCGCGGCCGC
CTGGGCTCCCAGGACCTGCTGAACTGGTGCGTGCAGATCGCCAAGGGCATGTCCTA CCTGGAGGAG
GTGCGCCTGGTGCACCGCGACCTGGCCGCCCGCAACGTGCTGGTGA
AGTCCCCCAACCACGTGAAGATCACCGACTCGGCCTGGCCCGCCTGCTGGACATC GACGAGACCGAGTACCACGCCGACGGCGGCAAGGTGCCCATCAAGTGGATGGCCCT
GGAGTCCATCCTGCGCCGCCGCTFCACCCACCAGTCCGACGTGTGGTCCTACGGCGT GACCGTGTGGGAGCTGATGACCTCGGCGCCAAGCCCTACGACGGCATCCCCGCCC
GCGAGATCCCCGACCTGCTGGAGAAGGGCGAGCGCCTGCCCCAGCCCCCCATCTGC ACCATCGACGTGTACATGATCATGGTGAAGTGCTGGATGATCGACTCCGAGTGCCG
CCCCCGCTTCCGCGAGCTGGTGTCCGAGTTCTCCCGCATGGCCCGCGACCCCCAGCG CTITCGTGGTGATCCAGAACGAGGACCTGGCCCTGGGCACCGGCTCCACCGCCCACC
GCCGCCACCGCTCCTCCTCCCCCCCCCCCCCATCCGCCCCGCCGGCGCCACCCTGG AGCGCCCAAGACCCTGTCCCCCGGCAAGAACGGCGTGGTGAAGGACGTGTTCGCC
TTCGGCGGCGCCGTGGAGAACCCCGAGTACCTG (SEQ ID NO: 58); a nucleotide sequence having at least 90% sequence identity to the nucleotide sequence of ACCATGCGCCGCCTGCTGCAGGAGACCGAGCTGGTGGAGCCCCTGACCCCCTCCGG CGCCATGCCCAACCAGGCCCAGATGCGCATCCTGAAGGAGACCGAGCTGCGCAAGG TGAAGGTGCTGGGCTCCGGCGCCTTCGGCACCGTGTACAAGGGCATCTGGATCCCC
GACGGCGAGAACGTGAAGATCCCCGTGGCCATCAAGGTGCTGCGCGAGAACACCTC CCCCAAGGCCAACAAGGAGATCCTGGACGAGGCCTACGTGATGGCCGGCGTGGGCT
CCCCCTACGTGTCCCGCCTGCTGGGCATCTGCCTGACCTCCACCGTGCAGCTGGTGA CCCAGCTGATGCCCTACGGCTGCCTGCTGGACCACGTGCGCGAGCACCGCGGCCGC
CTGGGCTCCCAGGACCTGCTGAACTGGTGCGTGCAGATCGCCAAGGGCATGTCCTA CCTGGAGGACGTGCGCCTGGTGCACCGCGACCTGGCCGCCCGCAACGTGCTGGTGA
AGTCCCCCAACCACGTGAAGATCACCGACTTCGGCCTGGCCCGCCTGCTGGACATC GACGAGACCGAGTACCACGCCGACGGCGGCAAGGTGCCCATCAAGTGGATGGCCCT
GGAGTCCATCCTGCGCCGCCGCTTCACCCACCAGTCCGACGTGTGGTCCTACGGCGT GACCGTGTGGGAGCTGATGACCTTCGGCGCCAAGCCCTACGACGGCATCCCCGCCC
GCGAGATCCCCGACCTGCTGGAGAAGGGCGAGCGCCTGCCCCAGCCCCCCATCTGC ACCATCGACGTGTACATGATCATGGTGAAGTGCTGGATGATCGACTCCGAGTGCCG
CCCCCGCTTCCGCGAGCTGGTGTCCGAGTCTCCCGCATGGCCCGCGACCCCCAGCG CTTCGTGGTGATCCAGAACGAGGACCTGACCCCCGGCACCGGCTCCACCGCCCACC
GCCGCCACCGCTCCTCCTCCCCCCTGCCCCCCGTGCGCCCCGCCGGCGCCACCCTGG AGCGCCCAAGACCCTGTCCCCCGGCAAGAACGGCGTGGTGAAGGACGTGTTCGCC
TTCGGCGGCGCCGTGGAGAACCCCGAGTACCTG (SEQ ID NO: 59); a nucleotide sequence encoding an amino acid sequence, the amino acid sequence having at least 90% sequence identity to the amino acid sequence of TMRRLLQETELVEPLTPSGAMPNQAQMRILKETELRKVK- VLGSGAFGTVYKGIWIPDGE NVKIPVAIKVL-RENTSPKANKEILDEAYVMAGVGSPYVSRLLGICLT-STVQLVTQLMPY GCLLDHVRENRGRLGSQDLLNW-CMQIAKGMSYLEDVRLVHRDLAARNVLVKSPNHV KITDFGLARLLDIDETEYHADGGKVPIKWMALESIL-RRRFTHQSDVWSYGVTVWELMT FGAKPYDGIPA-REIPDLLEKGERLPQPPICTIDVYMIMVKCWMIDSE-CRPRFRELVSEFSR MARDPQRFVVIQNEDLAPGAGGMVHHRHRSSSPL-PAARPAGATLERPKTLSPGKNGVV KDVFAFGGAV-ENPEYL (SEQ ID NO: 60); a nucleotide sequence encoding an amino acid sequence, the amino acid sequence having at least 90% sequence identity to the amino acid sequence of TMRRLLQETELVEPLTPSGAVPNQAQMRILKETEL-RKLKVLGSGAFGTVYKGIWIPDGE NVKIPVAIKVL-RENTSPKANKEILDEAYVMAGVGSPYVSRLLGICLT-STVQLVTQLMPY GCLLDHVREHRGRLGSQDLLNWCVQIAKGM-SYLEEVRLVHRDLAARNVLVKSPNHVK ITDF-GLARLLDIDETEYHADGGKVPIKWMALESILR-RRFTHQSDVWSYGVTVWELMTF GAKPYDGIPAREIPDLLEKGERLPQPPICTIDVYMIM-VKCWMIDSECRPRFRELVSEFSR MARDPQRFV-VIQNEDLALGTGSTAHRRHRSSSPPPPIRPAGATLERP-KTLSPGKNGVVK DVFAFGGAVENPEYL (SEQ ID NO: 61); and a nucleotide sequence encoding an amino acid sequence, the amino acid sequence having at least 90% sequence identity to the amino acid sequence of TMR-RLLQETELVEPLTPSGAMPNQAQMRILKETELRKVK-VLGSGAFGTVYKGIWIPDGE NVKIPVAIKVL-RENTSPKANKEILDEAYVMAGVGSPYVSRLLGICLT-STVQLVTQLMPY GCLLDHVREHRGRLGSQDLLNW-CVQIAKGMSYLEDVRLVHRDLAARNVLVKSPNHV KITDFGLARLLDIDETEYHADGGKVPIKWMALESIL-RRRFTHQSDVWSYGVTVWELMT FGAKPYDGIPA-REIPDLLEKGERLPQPPICTIDVYMIMVKCWMIDSE-CRPRFRELVSEFSR MARDPQRFVVIQNEDLTPGTGSTAHRRHRSSSPLP-PVRPAGATLERPKTLSPGKNGVVK DVFAFGGAVEN-PEYL (SEQ ID NO: 62). In some cases, the compositions may comprise a nucleic acid sequence encoding an epitope of the peptide IGF-1R is selected from the group consisting of: a nucleotide sequence having at least 90% sequence identity to the nucleotide sequence of TGGTCCTTCG-GCGTGGTGCTGTGGGAGATCGCCACCCTGGC-CGAGCAGCCCTACCA GGGCCTGTCCAACGAGCAG-GTGCTGCGCTTCGTGATGGAGGGCGGCCTGCTGG-ACA AGCCCGACAACTGCCCCGACATGCTGTTC-GAGCTGATGCGCATGTGCTGGCAGTAC AAC-CCCAAGATGCGCCCCTCCTTCCTGGAGCA-CAAGGCCGAGAACGGCCCCGGCCC CGGCGTGCTGGTGCTGCGCGCCTCCTTCGAC-GAGCGCCAGCCCTACGCCCACATGA ACGGAGGC-CGCAAGAACGAGCGCGCCCTGCCC (SEQ ID NO: 63); a nucleotide sequence having at least 90% sequence identity to the nucleotide sequence of TGGTCCTTCG-GCGTGGTGCTGTGGGAGATCGCCACCCTGGC-CGAGCAGCCCTACCA GGGCCTGTCCAACGAGCAG-GTGCTGCGCTTCGTGATGGAGGGCGGCCTGCTGG-ACA AGCCCGACAACTGCCCCGACATGCTGTTC-GAGCTGATGCGCATGTGCTGGCAGTAC AAC-CCCAAGATGCGCCCCTCCTTCCTGGAGCA-CAAGGCCGAGAACGGCCCCGGCCC CGGCGTGCTGGTGCTGCGCGCCTCCTTCGAC-GAGCGCCAGCCCTACGCCCACATGA ACGGCGGC-CGCGCCAACGAGCGCGCCCTGCCC (SEQ ID NO: 64): a nucleotide sequence having at least 90% sequence identity to the nucleotide sequence of TGGTCCTTCGGCGTGGT-GCTGTGGGAGATCGCCACCCTGGCCGAGCAGC-CCTACCA GGGCCTGTCCAACGAGCAGGTGCT-GCGCTTCGTGATGGAGGGCGGCCTGCTGGACA AGCCCGACAACTGCCCCGACATGCTGTTCGAGCT-GATGCGCATGTGCTGGCAGTAC AACCCCAAGAT-GCGCCCCTCCTTCCTGGAGCACAAGGCCGA-GAACGGCCCCGGCGT GCTGGTGCTGCGCGCCTCCTTCGACGAGCGCCA-GCCCTACGCCCACATGAACGGCG GCCGCGCCAAC-GAGCGCGCCCTGCCC (SEQ ID NO: 65); a nucleotide sequence encoding an amino acid sequence, the amino acid sequence having at least 90% sequence identity to the amino acid sequence of DYRSYRFPKLTVITE (SEQ ID NO: 66); a nucleotide sequence encoding an amino acid sequence, the amino acid sequence having at least 90% sequence identity to the amino acid sequence of IRGWKLFYNYALVIF (SEQ ID NO: 67); a nucleotide sequence encoding an amino acid sequence, the amino acid sequence having at least 90% sequence identity to the amino acid sequence of VVT-GYVKIRHSHALV (SEQ ID NO: 68); a nucleotide sequence encoding an amino acid sequence, the amino acid sequence having at least 90% sequence identity to the amino acid sequence of FFYVQAKTGYENFIH (SEQ ID NO: 69); a nucleotide sequence encoding an amino acid sequence, the amino acid sequence having at least 90% sequence identity to the amino acid sequence of LIIALPVAVLLIVGG (SEQ ID NO: 70); a nucleotide sequence encoding an amino acid sequence, the amino acid sequence having at least 90% sequence identity to the amino acid sequence of LVIMLY-VFHRKRNNS (SEQ ID NO: 71); a nucleotide sequence encoding an amino acid sequence, the amino acid sequence having at least 90% sequence identity to the amino acid sequence of NCHHVVRLLGVVSQG (SEQ ID NO: 72); a nucleotide sequence encoding an amino acid sequence, the amino acid sequence having at least 90% sequence identity to the amino acid sequence of WSFGVVLWEIATLAEQPY-QGLSNEQVLRFVMEGGLLDKPDNCPDMLFELMRM-CWQY NPKMRPSFLEHKAENGPGPGVLVLRASFDER-QPYAHMNGGRKNERALP (SEQ ID NO: 73); a nucleotide sequence encoding an amino acid sequence, the amino acid sequence having at least 90% sequence identity to the amino acid sequence of WSFGVVLWEIATLAEQPY-QGLSNEQVLRFVMEGGLLDKPDNCPDMLFELMRM-CWQY NPKMRPSFLEHKAENGPGPGVLVLRASFDER-QPYAHMNGGRANERALP (SEQ ID NO: 74); and a nucleotide sequence encoding an amino acid sequence, the amino acid sequence having at least 90% sequence identity to the amino acid sequence of WSFGVVLWEIATLAEQPY-QGLSNEQVLRFVMEGGLLDKPDNCPDMLFELMRM-CWQY NPKMRPSFLEHKAENGPGPGVLVLRASFDER-QPYAHMNGGRANERALP (SEQ ID NO: 75). In some cases, the compositions may comprise a nucleic acid sequence encoding a fusion protein of three epitopes is selected from the group consisting of: a nucleotide sequence having at least 90% sequence identity to the nucleotide sequence of ATGGCGGTACCAATGCTGCCGA-GAGTGGGGGCTGCCCCGCCGCC GCCGCTGCTGC-CGCTGCTGCCGCTGCTGCTGCTGCTACTGGGCGC-GAGTGGCGGCG GCGGCGGGGCGCGCGCGGAGGTGCTGTTCCGCT-GCCCGCCCTGCACACCCGAGCGC CTGGCCGCCT-GCGGGCCCCCGCCGGTTGCGCCGCCCGCCGGTG-GCCGCAGTGGC CGGAGGCGCCCGCATGCCATGCGCGGAGCTCGTC-CGGGAGCCGGGCTGCGGCTGCT GCTCGGTGT-GCGCCCGGCTGGAGGGCGAGGCGTGCGGCGTCTA- CACCCCGCGCTGC GGCCAGGGGCTGCGCTGCTATCCCCAC-CCGGGCTCCGAGCTGCCCCTGCAGGCGCT GGT-CATGGGCGAGGGCACTTGTGAGAAGCGC-CGGGACGCCGAGTATGGCGCCAGC CCGGAGCAGGTFGCAGACAATGGCGATGAC-CACTCAGAAGGAGGCCTGGTGGAGC AATTGAC-GATGCGGAGACTGCTGCAGGAAACGGAGCTGGTG-GAGCCGCTGACACCT AGCGGAGCGATGCCCAACCAGGCGCAGATGCG-GATCCTGAAAGAGACGGAGCTGA GGAAGGT-GAAGGTGCTGGATCGGCGCTTGGCACAGTCTA-CAAGGGCATCTGG ATCCCTGATGGGGAGAATGTGAAAATCCAGTGGC-CATCAAAGTGTGAGGGAAAA CACATC-CCCCAAAGCCAACAAAGAAATCTTAGAC-GAAGCATACGTGATGGCTGGTG TGGGCTCCCCATATGTCTCCCGCCTCTGGGCATCT-GCCTGACATCCACGGTGCAGC TGGTGACACAGC-TATGCCCTATGGCTGCCTCTAGACCATGTC-CGGGAAAACCGCG GACGCCTGGGCTCCCAGGACCTGCTGAACTGGTG-TATGCAGATFGCCAAGGGGATG AGCTACCTGGAG-GATGTGCGGCTCGTACACAGGGACTTGGC-CGCTCGGAACGTGCT GGTCAAGAGTCCCAACCATGTCAAAATACA-GACTCGGGCTGGCTCGGCTGCTGG ACATGACGA-GACAGAGTACCATGCAGATGGGGCAAGGTGC-CCATCAAGTGGAT GGCGCTGGAGTCCATCTCCGCCGGCGGTCAC-CCACCAGAGTGATGTGTGGAGTT ATGGTGTGACT-GTGTGGGAGCTGATGACTTTTfGGGGCCAAAC-CTACGATGGGATC CCAGCCCGGGAGATCCCTGACCTGCTG-GAAAAGGGGGAGCGGCTGCCCCAGCCCCC CATCT-GCACCATTGATGTCTACATGATCATGGTCAAATGT-TGGATGATTGACTCTGA ATGTCGGCCAAGATCCGGGAGTGGTGTCTGAAT-TCTCCCGCATGGCCAGGGACC CCCAGCGCTTGTG-GTCATCCAGAATGAGGACTTGGCTCCCGGAGCTG-GCGGCATG GTGCACCACAGGCACCGCAGCTCATCTCCTCTGC-CTGCTGCCCGACCTGCTGGTGCC ACTCTG-GAAAGGCCCAAGACTCTCTCCCCA-GGGAAGAATGGGGTCGTCAAAGACGT TITTGCCTTGGGGGTGCCGTGGAGAACCCCGAG-TACTTGGGCCGGCCGGTACCTTG GTCCTCG-GCGTGGTGCTGTGGGAGATCGCCACCCTGGC-CGAGCAGCCCTACCAGG GCCTGTCCAACGAGCAGGTGCTGCGCTCGTGATG-GAGGGCGGCCTGCTGGACAAG CCCGACAACTGC-CCCGACATGCTGTITCGAGCTGATGCGCATGT-GCTGGCAGTACAA CCCCAAGATGCGCCCTCCTTCCTGGAGCA-CAAGGCCGAGAACGGCCCCGGCCCCG GCGT-GCTGGTGCTGCGCGCCTCCTCGACGAGCGCCAGC-CCTACGCCCACATGAAC GGAGCCGCAAGAACGAGCGCGCCCTGCCCGCG-GCCGCATAG (SEQ ID NO: 76); a nucleotide sequence having at least 90% sequence identity to the nucleotide sequence of ATGGCGGTACCAATGCTGCCCCGC-CTGGCGGCCCCGCCCTGCCCCTGCTGCTGCCC TCCCTGCTGCTGCTGCTGCTGGGCGCGGCG-GCTGCGGCCCCGGCGTGCGCGCC GAGGTGCTGT-TCCGCTGCCCCCCCTGCACCCCGAGCGCCTGGC-CGCCTGCGGCCCC CCCCCCGACGCCCCCTGCGCCGAGCTGGTGCGC-GAGCCCGGCTGCGGCTGCTGCTC CGTGTGCGC-CCGCCAGGAGGGCGAGGCCTGCGGCGTGTACATC-CCCCGCTGCGCCC AGACCCTGCGCTGCTACCCCAACCCCGGCTC-CGAGCTGCCCCTGAAGGCCCTGGTG ACCGGCGC-CGGCACCTGCGAGAAGCGCCGCGTGGGCACCAC-CCCCCAGCAGGTGGC CGACTCCGACGACGACCACTCCGAGGGCGGCCTG-GTGGAGCAATGACCATGCGCC GCCTGCTGCAGGA-GACCGAGCTGGTGGAGCCCTGACCCCTCCG-GCGCCGTGCCC AACCAGGCCCAGATGCGCATCCTGAAGGAGAC-CGAGCTGCGCAAGCTGAAGGTGCT GGGCTCCG-GCGCCTTCGGCACCGTGTACAAGGGCATCTGGATC-CCCGACGGCGAGA ACGTGAAGATCCCCGTGGCCATCAAGGTGCT-GCGCGAGAACACCTCCCCCAAGGCC AACAAGGA-GATCCTGGACGAGGCCTACGTGATGGCCG-GCGTGGGCTCCCCCTACGT GTCCCGCCTGCTGGGCATCTGCCTGACCTCCAC-CGTGCAGCTGGTGACCCAGCTGAT GCCCTACG-GCTGCCTGCTGGACCACGTGCGCGAGCACCGCG GCCGCCTGGGCTCCC AGGACCTGCTGAACTGGTGCGTGCAGATCGC-CAAGGGCATGTCCTACCTGGAGGAG GTGCGCCTG-GTGCACCGCGACCTGGCCGCCCGCAACGTGCTG-GTGAAGTCCCCCAA CCACGTGAAGATCACCGACTTCGGCCTGGCCCGC-CTGCTGGACATCGACGAGACCG AGTACCACGC-CGACGGCGGCAAGGTGCCCATCAAGTGGATGGC-CCTGGAGTCCATC CTGCGCCGCCGCTCACCCACCAGTCCGACGTGTG-GTCCTACGGCGTGACCGTGTGG GAGCTGATGAC-CTTCGGCGCCAAGCCCTACGACGGCATCCCCGC-CCGCGAGATCCC CGACCTGCTGGAGAAGGGCGAGCGCCTGCCCCA-GCCCCCCATCTGCACCATCGACG TGTACATGAT-CATGGTGAAGTGCTGGATGATCGACTCCGAGTGC-CGCCCCGCTCC GCGAGCTGGTGTCCGAGTTCTCCCGCATGGCCCGC-GACCCCCAGCGCTCGTGGJTGA TCCAGAACGAG-GACCTGGCCCTGGGCACCGGCTCCACCGCCCAC-CGCCGCCACCGC TCCTCCTCCCCCCCCCCCCCCATCCGCCCCGCCG-GCGCCACCCTGGAGCGCCCCAAG ACCCTGTC-CCCCGGCAAGAACGGCGTGGTGAAGGACGT-GTCGCCTTCGGCGGCGC CGTGGAGAACCCCGAGTACCTGGGCCGGCCGG-TACCTTGGTCCTTCGGCGTGGTGC TGTGGGA-GATCGCCACCCTGGCCGAGCAGCCCTACCAGGGC-CTUITCCAACGAGCAG GTGCTGCGCTCGTGATGGAGGGGCGGCCTGCTG-GACAAGCCCGACAACTGCCCCGA CATGCTGTC-GAGCTGATGCGCATGTGCTGGCAGTACAAC-CCCAAGATGCGCCCCTC CTTCCTGGAGCACAAGGCCGAGAACGGCCCCGGC-CCCGGCGTGCTGGTGCTGCGCG CCTCCTCGAC-GAGCGCCAGCCCTACGCCCACATGAACGGCGGC-CGCGCCAACGAG CGCGCCCTGCCCGCGGCCGCATAG (SEQ ID NO: 77); a nucleotide sequence having at least 90% sequence identity to the nucleotide sequence of ATGGCGGTACCAATGCT-GCCCCGCCTGGGCGGCCCCGCCCTGCCCCTGCT-GCTGCCC TCCCTGCTGCTGCTGCTGCT-GCTGGGCGCCGGCGGCTGCGGCCCCGGCGTGCGC-GCC GAGGTGCTGTCCGCTGCCCCCCTGCAC-CCCGAGCGCCTGGCCGCCTGCGGCCCC CCCCCCGACGCCCCCTGCGCCGAGCTGGTGCGCGAGCCCGGCTGCGGCTGCTGCTC CGTGTGCGCCCGCCAGGAGGGCGAGGCCTGCGGCGTGTACATCCCCGCTGCGCCC
AGACCCTGCGCTGCTACCCCAACCCCGGCTCCGAGCTGCCCCTGAAGGCCCTGGTG ACCGGCGCCGGCACCTGCGAGAAGCGCCGCGTGGGCGCCACCCCCCAGCAGGTGGC
CGACTCCGAGGACGACCACTCCGAGGGCGGCCTGGTGGAGCAATGACCATGCGCC GCCTGCTGCAGGAGACCGAGCTGGTGGAGCCCCTGACCCCCTCCGGCGCCATGCCC
AACCAGGCCCAGATGCGCATCCTGAAGGAGACCGAGCTGCGCAAGGTGAAGGTGC TGGGCTCCGGCGCCTTCGGCACCGTGTACAAGGGCATCTGGATCCCCGACGGCGAG
AACGTGAAGATCCCCGTGGCCATCAAGGTGCTGCGCGAGAACACCTCCCCCAAGGC CAACAAGGAGATCCTGGACGAGGCCTACGTGATGGCCGGCGTGGGCTCCCCCTACG
TGTCCCGCCTGCTGGGCATCTGCCTGACCTCCACCGTGCAGCTGGTGACCCAGCTGA TGCCCTACGGCTGCCTGCTGGACCACGTGCGCGAGCACCGCGGCGCCTGGGCTCC
CAGGACCTGCTGAACTGGTGCGTGCAGATCGCCAAGGGCATGTCCTACCTGGAGGA CGTGCGCCTGGTGCACCGCGACCTGGCCGCCCGCAACGTGCTGGTGAAGTCCCCA
ACCACGTGAAGATCACCGACTCGGCCTGGCCCGCCTGCTGGACATCGACGAGACC GAGTACC ACGCCGACGGCGGCAAGGTGCCCATCAAGTGGATGGCCTGGAGTCCAT
CCTGCGCCGCCGCTTCACCCACCAGTCCGACGTGTGGTCCTACGGCGTGACCGTGTG GGAGCTGATGACCTCGGCGCCAAGCCCTACGACGGCATCCCCGCCCGCGAGATCC
CCGACCTGCTGGAGAAGGGCGAGCGCCTGCCCCAGCCCCCCATCTGCACCATCGAC GTGTACATGATCATGGTGAAGTGCTGGATGATCGACTCCGAGTGCCGCCCCCGCTFC
CGCGAGCTGGTGTCCGAGTTCTCCCGCATGGCCCGCGACCCCCAGCGCTTCGTGGTG ATCCAGAACGAGGACCTGACCCCCGGCACCGGCTCCACCGCCCACCGCCGCCACCG
CTCCTCCTCCCCCCTGCCCCCCGTGCGCCCCGCCGGCGCC ACCCTGGAGCGCCCCAA GACCCTGTCCCCCGGCAAGAACGGCGTGGTGAAGGACGTGTTCGCCTCGGCGGCG
CCGTGGAGAACCCCGAGTACCTGGGCCGGCCGGTACCTTGGTCCTCGGCGTGGTG CTGTGGGAGATCGCCACCCTGGCCGAGC AGCCCTACCAGGGCCTGTCC AACGAGC A
GGTGCTGCGCTTCGTGATGGAGGGCGGCCTGCTGGACAAGCCCGACAACTGCCCCG ACATGCTGTTCGAGCTGATGCGCATGTGCTGGCAGTACAACCCCAAGATGCGCCCC
TCCTCCTGGAGCACAAGGCCGAGAACGGCCCCGGCGTGCTGGTGCTGCGCGCCTC CTCGACGAGCGCCAGCCCTACGCCCACATGAACGGCGGCCGCGCCAACGAGCGCG CCCTGCCCGCGGCCGCATAG (SEQ ID NO: 78); a nucleotide sequence encoding an amino acid sequence, the amino acid sequence having at least 90% sequence identity to the ammno acid sequence of MAVPMLPRVGCPALPLPPPPLPLLPLLLLLLGASGGGGGARAEVLFRCPPCTPERLAAC GPPPVAPPAAVAAVAGGARMPCAELVREPGCGCCSVCARLEGEACGVYTPRCGQGLR CYPHPGSELPLQALVMGEGTCEKRRDAEY
GASPEQVADNGDDHSEGGLVEQLTMRRL LQETELVEPLTPSGAMPNQAQMRILKETELRVKV LGSGAFGTVYKGIWIPDGENVKIP VAIKVLRENTSPKANKEILDEAYVMAGVGSPYVSRLLGICLTST VQLVTQLMPYGCLLD
HVRENRGRLGSQDLLNWCMQIAKGMSYLEDVR LVHRDLAARNVLVKSPNHVKITDFG LARLLDIDE TEYHADGGKVPIKWMALESILRRRFTHQSD VWSYGVTVWELMTFGAKPY
DGIPAREIPDLLEKGERLPQPPICTIDVYMIMVKCW MIDSECRPRFRELVSEFSRMARDP QRFVVIQNED LAPGAGGMVHHRHRSSSPLPAARPAGATLERPKTL SPGKNGVVKDVFA
FGGAVENPEYLGRPVPWSFGVVLWEIATLAEQPY QGLSNEQVLRFVMEGGLLDKPDNC PDMLFELMRM CWQYNPKMRPSFLEHKAENGPGPGVLVLRASFDER QPYAHMNGGRK NERALPAAA (SEQ ID NO: 79); a nucleotide sequence encoding an amino acid sequence, the amino acid sequence having at least 90% sequence identity to the amino acid sequence of MAVPMLPRLGGPALPLLLPSLLLLLLLGAGGCGPGVRAEVLFRCPPCTPERLAACGPPP DAPCAELVREPGCGCCSVCARQEGEACGVYIPRCAQTLRCYPNPGSELPLKALVTGAGT CEKRRVGTTPQQVADSDDDHSEGGLVEQLTMRRLLQETELVEPLTPSGAVPNQAQMRI LKETELRKLKVLGSGAFGTVYKGIWIPDGENVKIPVAIKVLRENTSPKANKEILDEAYV MAGVGSPYVSRLLGICLTSTVQLVTQLMPYGCLLDHVREHRGRLGSQDLLNWCVQIAK GMSYLEEVRLVHRDLAARNVLVKSPNHVKITDFGLARLLDIDE TEYHADGGKVPIKWM ALESILRRRFTHQSDVWSYGVTVWELMTFGAKPYDGIPAREIPDLLEKGERLPQPPICTI DVYMIMVKCWMIDSECRPRFRELVSEFSRMARDPQRFVVIQNEDLALGTGSTAHRRHR SSSPPPPIRPAGATLERPKTLSPGKNGVVKDVFAFGGAVENPEYLGRPVPWSFGVVLWEI ATLAEQPYQGLSNEQVLRFVMEGGLLDKPDNCPDMLFELMRMCWQYNPKMRPSFLEH KAENGPGPGVLVLRASFDERQPYAHMNGGRANERALPAAA (SEQ ID NO: 80); and a nucleotide sequence encoding an amino acid sequence, the amino acid sequence having at least 90% sequence identity to the amino acid sequence of MAVPMLPRLGGPALPLLLPSLLLLLLL GAGGCGPGVRAEVLFRCPPCTPERLAACGPPP DAPCAELVREPGCGCCSVCARQEGEACGVYIPRCAQTLRCYPNPGSELPLKALVTGAGT CEKRRVGATPQQVADSEDDHSEGGLVEQLTMRRLLQETELVEPLTPSGAMPNQAQMRI LKETELRKVKVLGSGAFGTVYKGIWIPDGENVKIPVAIKVLRENTSPKANKEILDEAYV MAGVGSPYVSRLLGICLTSTVQLVTQLMPYGCLLDHVREHRGRLGSQDLLNWCVQIAK GMSYLEDVRLVHRDLAARNVLVKSPNHVKITDFGLARLLDIDE TEYHADGGKVPIKW MALESILRRRFTHQSDVWSYGVTVWELMTFGAKPYDGIPAREIPDLLEKGERLPQPPICT IDVYMIMVKCWMIDSECRPRFRELVSEFSRMARDPQRFVVIQNEDLTPGTGSTAHRRHR SSSPLPPVRPAGATLERPKTLSPGKNGVVKDVFAFGGAVENPEYLGRPVPWSFGVVLW EIATLAEQPYQGLSNEQVLRFVMEGGLLDKPDNCPDMLFELMRMCWQYNPKMRPSFL EHKAENGPGVLVLRASFDERQPYAHMNGGRANERALPAAA (SEQ ID NO: 81).

In some cases, the compositions may comprise a first and a second epitope independently selected from: CD105, Yb-1, SOX-2, CDH3 or MDM2. In some cases, the compositions may comprise a third epitope, the first, second and third epitopes independently selected from: CD105, Yb-1, SOX-2, CDH3 or MDM2. In some cases, the compositions may comprise a third and a fourth epitope, the first, second, third and fourth epitopes independently selected from: CD105, Yb-1, SOX-2, CDH3 or MDM2. In some cases, the compositions may comprise a third, a fourth and a fifth epitope, the first, second, third, fourth and fifth epitopes independently selected from: CD105, Yb-1, SOX-2, CDH3 or MDM2.

In some cases, the compositions may comprise a first and a second epitope independently selected from: IGFBP2, HER-2 or IGF-1R. In some cases, the compositions may comprise a third epitope, the first, second and third epitopes independently selected from: IGFBP2, HER-2 or IGF-1R.

In some cases, the compositions may be capable of being administered to a subject. In some cases, the subject is in need of administration of the composition. In some cases, the composition is effective to elicit an immune response in a subject. In some cases, the composition is effective to eliminate a number of cells associated with breast cancer in a subject. In some cases, the composition can be used to prevent the growth of cells associated with breast cancer in a subject.

In some cases, the first and the second nucleic acid sequences are located on the first plasmid. In some cases, the second nucleic acid sequence is located on a second plasmid.

In some cases, the cells associated with breast cancer are selected from: breast cells expressing atypical features, pre-neoplastic breast cells, breast cancer cells, pre-invasive breast cancer cells, breast cancer stem cells, epithelial cells, mesenchymal cells, stromal cells, or a combination thereof.

In some cases, the first and the second nucleic acid sequences are purified to at least 70% purity. In some cases, the first and the second nucleic acid sequences are located on the first plasmid and are separated by a sequence of linker nucleic acids. In some cases, the first nucleic acid sequence is adjacent to the second nucleic acid sequence on the first plasmid.

In some cases, at least the first plasmid is contained within a pharmaceutical composition. In some cases, at least the first plasmid is contained within a pharmaceutical composition further comprising a pharmaceutical carrier. In some cases, at least the first plasmid is contained within a pharmaceutical composition further comprising a pharmaceutical carrier and an adjuvant. In some cases, at least the first plasmid is contained within a pharmaceutical composition further comprising an adjuvant. In some cases, the composition further comprises an adjuvant and a pharmaceutically acceptable carrier. In some cases, the adjuvant is GM-CSF.

In some cases, a subject is selected from: a human with breast cancer, a mouse with breast cancer or a rat with breast cancer. In some cases, a subject is selected from: a human without breast cancer, a mouse without breast cancer or a rat without breast cancer.

In some cases, the immune response is a Type 1 immune response. In some cases, the first nucleic acid sequence is a species selected from: human, mouse or rat. In some cases, the second nucleic acid sequence is a species selected from: human, mouse or rat. In some cases, the immune response is characterized by a ratio of Type 1 cytokine production to Type II cytokine production that is greater than 1. In some cases, the immune response is characterized by a ratio of Type I cytokine production to Type II cytokine production that is less than 1. In some cases, the immune response is characterized by a ratio of IFNγ production to IL-10 production that is greater than 1. In some cases, the immune response is characterized by a ratio of IFNγ production to IL-10 production that is less than 1.

In some cases, the compositions include a composition comprising: a first plasmid comprising a first nucleotide sequence, the first nucleotide sequence encoding a first epitope of a first antigen, the first epitope is a portion of an HIF-1α peptide, wherein the first nucleotide sequence is located in a plasmid. In other cases, the compositions include a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are portions of an HIF-1α peptide, wherein the first nucleotide sequence and the second nucleotide sequence are located in one or more plasmids.

The nucleic acid sequences which encode epitopes from the following proteins, CD105, HIF1α, MDM2, Yb1, SOX-2, HER-2, IGFBP2, IGF-1R and CDH3 may differ from those listed herein. In some cases, nucleic acid sequences which are greater than 95%, 90%, 85%, 80%, 75%, 70%, 65%, 60%, 55% or greater than 50% homologous to those disclosed herein may be used in the compositions described herein.

The compositions described herein, in some cases, may include a composition comprising: a first epitope of a first antigen expressed by cells associated with breast cancer; and a second epitope of a second antigen expressed by cells associated with breast cancer.

In some cases, the composition may comprise: at least a first epitope of a first antigen, the first epitope is a portion of a peptide selected from: CD105, Yb-1, SOX-2, CDH3 or MDM2. In some cases, the composition may comprise: at least a first epitope of a first antigen, at least a second epitope of a second antigen, the first and the second epitopes are independently selected from: CD105, Yb-1, SOX-2, CDH3 or MDM2. In some cases, at least a first epitope of the peptide CD105 is selected from the group consisting of: an amino acid sequence, the amino acid sequence having at least 90% sequence identity to the amino acid sequence of EARMLNASIVASFVELPL (SEQ ID NO: 6); an amino acid sequence, the amino acid sequence having at least 90% sequence identity to the amino acid sequence of QNGTWPREVLLVLSVNSSVFLHLQALGIPLHLAYNS-SLVTFQEPPGVNTTEL (SEQ ID NO: 1); an amino acid sequence, the amino acid sequence having at least 90% sequence identity to the amino acid sequence of TVFMRL-NIISPDLSGCTSKGLVLPAVLGITFGAFLIGALLTAAL-WYIYSHTRSPSKREPVV AVAAPASSESSSTNHSIG-STQSTPCSTSSMA (SEQ ID NO: 8); an amino acid sequence, the amino acid sequence having at least 90%6 sequence identity to the amino acid sequence of TVSMRL-NIVSPDLSGKGLVLPSVLGITFGAFLIGALLTAALWYI-YSHTRGPSKREPVVAV AAPASSESSSTNHSIGSTQST-PCSTSSMA (SEQ ID NO: 9); or an amino acid sequence, the amino acid sequence having at least 90% sequence identity to the amino acid sequence of TVSMRLNIVSP-DLSGKGLVLPSVLGITFGAFLIGALLTAALWYIYSH-TRAPSKREPVVAV AAPASSESSSTNHSIGSTQSTPCST-SSMA (SEQ ID NO: 10). In some cases, at least a first epitope of the peptide Yb-1 is selected from the group consisting of: an amino acid sequence, the amino acid sequence having at least 90% sequence identity to the amino acid sequence of EDVFVHQTAIKKNNPRK (SEQ ID NO: 14); an amino acid sequence, the amino acid sequence having at least 90% sequence identity to the amino acid sequence of YRRNFNYRRRRPEN (SEQ ID NO: 15); or an amino acid sequence, the amino acid sequence having at least 90% sequence identity to the amino acid sequence of GVPVQGSKYAADRNHYRRYPRRRGPPRNYQQN (SEQ ID NO: 16). In some cases, at least a first epitope of the peptide SOX-2 is selected from the group consisting of: an amino acid sequence, the amino acid sequence having at least 90% sequence identity to the amino acid sequence of GLNAHGAAQMQPMHRYDVSALQYNSMTSSQ-TYMNGSPTYSMSYSQQGTPGMALGSM GSV (SEQ ID NO: 20). In some cases, at least a first epitope of the peptide CDH3 is selected from the group consisting of: an amino acid sequence, the amino acid sequence having at least 906 sequence identity to the amino acid sequence of RSLKERN-PLKIFPSKRILRRHKRDWVVAPISVPENGKGPFPQRL-NQLKSNKDRDTKIFYSI TGPGADSPPEGVFAVEKET (SEQ ID NO: 25); an amino acid sequence, the amino acid sequence having at least 90% sequence identity to the amino acid sequence of LKIFPSKRILRRHKRDWV-VAPISVPENGKGPFPQRLNQLKSNKDRDTKIFYSITG-PGADSP PEGVFAVEKET (SEQ ID NO: 26); an amino acid sequence, the amino acid sequence having at least 90% sequence identity to the amino acid sequence of AMHSPP-TRILRRRKREWVMPPIFVPENGKGPFPQRLNQLK-SNKDRGTKIFYSITGPGADS PPEGVFTIEKES (SEQ ID NO: 27); or an amino acid sequence, the amino acid sequence having at least 90% sequence identity to the amino acid sequence of VMNSPPSRILRRRKREWVMPPIS-VPENGKGPFPQRLNQLKSNKDRGTKLFYSITGP-GADS PPEGVFTIEKET (SEQ ID NO: 28). In some cases, at least a first epitope of the peptide MDM-2 is selected from the group consisting of an amino acid sequence, the amino acid sequence having at least 90% sequence identity to the amino acid sequence of TYTMKEVLFYLGQYIMT-KRLYDEKQQHIVYCSNDLLGDLFGVPSFSVKEHRKI-YTMIYR NLVVVNQQESSDSGTSV (SEQ ID NO: 32); an amino acid sequence, the amino acid sequence having at least 90% sequence identity to the amino acid sequence of TYTMKEIIFYIGQYIMTKRLYDEKQQHIVYCSNDLL-GDVFGVPSFSVKEHRKIYAMIYRN LVAVSQQDSGT-SLS (SEQ ID NO: 33); or an amino acid sequence, the amino acid sequence having at least 90% sequence identity to the amino acid sequence of IYTMKEIIFYIGQYIMT-KRLYDEKQQHIVYCSNDLLGDVFGVPSFSVKEHRKI-YAMIYRN LVVVSQQDSGTSPS (SEQ ID NO: 34).

In some cases, the compositions described herein include an amino acid sequence of a fusion peptide of five epitopes is selected from the group consisting of: an amino acid sequence, the amino acid sequence having at least 90% sequence identity to the amino acid sequence of MAVP-MQLSCSRQNGTWPREVLLVLSVNSSVFLHLQALGI-PLHLAYNSSLVTFQEPPGVN TTELRSTGGVPVQG-SKYAADRNHYRRYPRRRGPPRNYQQNTRGLNAHG-AAQMQPMH RYDVSALQYNSMTSSQTYMNGSP-TYSMSYSQQGTPGMALGSMGSVRSQLRSLKERNP LKIFPSKRILRRHKRDWVVAPISVPENGKGPFPQRLN-QLKSNKDRDTKIFYSITGPGADSP PEGV-FAVEKETRSAGETYTMKEVLFYLGQYIMT-KRLYDEKQQHIVYCSNDLLGDLFGV PSFSVKEHRKIYTMIYRNLVVVNQQESSDSGTSVSRS (SEQ ID NO: 39); an amino acid sequence, the amino acid sequence having at least 90% sequence identity to the amino acid sequence of MAVPMTVFMRLNIISPDLSGCTSK-GLVLPAVLGITFGAFLIGALLTAALWYIYSHTRSPS KREPVVAVAAPASSESSSTNHSIGSTQSTPCSTSS-MATGGVPVQGSKYAADRNHYRRYP RRRGPPRNY-QQNTRGLNAHGAAQMQPMHRYDVSALQYNS-MTSSQTYMNGSPTYSMS YSQQGTPGMALGSMGSVRSQLLKIFPSKRILRRH-KRDWVVAPISVPENGKGPFPQRLNQ LKSNKDRDT-KIFYSITGPGADSPPEGVFAVEKETRSAGETYTMKEV-LFYLGQYIMTKRL YDEKQQHIVYCSNDLLGDLFGVPSFSVKEHRKIYT-MIYRNLVVVNQQESSDSGTSVSRS (SEQ ID NO: 40); an amino acid sequence, the amino acid sequence having at least 90% sequence identity to the amino acid sequence of MAVPMTVSMRLNIVSPDLSGKGLVLPSVLGITFGA-FLIGALLTAALWYIYSHTRGPSKRE PVVA-VAAPASSESSSTNHSIGSTQSTPCSTSSMATG-GVPVQGSKYAADRNHYRRYPRRR GPPRNYQQNTRGLNAHGAAQMQPMHRYD-VSALQYNSMTSSQTYMNGSPTYSMSYSQ QGTPG-MALGSMGSVRSQLAMHSPPTRILRRRKREWVMP-PIFVPENGKGPFPQRLNQLK SNKDRGTKIFYSITGPGADSPPEGVFTIEKESRSAG-ETYTMKEIIFYIGQYIMTKRLYDEK QQHIVYC-SNDLLGDVFGVPSFSVKEHRKIYAMIYRNLVA-VSQQDSGTSLSRS (SEQ ID NO: 41); or an amino acid sequence, the amino acid sequence having at least 90% sequence identity to the amino acid sequence of MAVPMT-VSMRLNIVSPDLSGKGLVLPSVLGITFGAFLIGALL-TAALWYIYSHTRAPSKRE PVVAVAAPASSESSST-NHSIGSTQSTPCSTSSMATGGVPVQGSKYAADRNHY-RRYPRRR GPPRNYQQNTRGLNAHGAAQMQPMHRY-DVSALQYNSMTSSQTYMNGSPTYSMSYSQ QGTPG-MALGSMGSVRSQLVMNSPPSRILRRRKREWVMPPIS-VPENGKGPFPQRLNQLKS NKDRGTKLFYSITGPGADSPPEGVFTIEKETRSAGEI-YTMKEIIFYIGQYIMTKRLYDEKQ QHIVYCSNDLL-GDVFGVPSFSVKEHRKIYAMIYRNLVVVSQQDS-GTSPSRS (SEQ ID NO: 42).

The compositions described herein may further include a composition comprising: a first plasmid comprising a first nucleotide sequence, the first nucleotide sequence encoding a first epitope of a first antigen, the first epitope is a portion of a peptide selected from: IGFBP-2, HER-2 or IGF-1R, wherein the first nucleotide sequence is located in a plasmid. In some cases, the composition may comprise: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: IGFBP-2, HER-2 or IGF-1R, wherein the first nucleotide sequence and the second nucleotide sequence are located in one or more plasmids. In some cases, at least a first epitope of the peptide IGFBP-2 is selected from the group consisting of: an amino acid sequence, the amino acid sequence having at least 90% sequence identity to the amino acid sequence of NHVDSTMNMLGGGGS (SEQ ID NO: 46); an amino acid sequence, the amino acid sequence having at least 90% sequence identity to the amino acid sequence of ELAVFREKVTEQHRQ (SEQ ID NO: 47); an amino acid sequence, the amino acid sequence having at least 90% sequence identity to the amino acid sequence of LGLEEPKKLRPPPAR (SEQ ID NO: 48); an amino acid sequence, the amino acid sequence having at least 90% sequence identity to the amino acid sequence of DQVLER-ISTMRLPDE (SEQ ID NO: 49); an amino acid sequence, the amino acid sequence having at least 90% sequence identity to the amino acid sequence of GPLEHLYSLHIP-NCD (SEQ ID NO: 50); an amino acid sequence, the amino acid sequence having at least 90% sequence identity to the amino acid sequence of KHGLYNLKQCKMSLN (SEQ ID NO: 51); an amino acid sequence, the amino acid sequence having at least 90% sequence identity to the amino acid sequence of PECHLFYNEQQEARG (SEQ ID NO: 53); an amino acid sequence, the amino acid sequence having at least 90% sequence identity to the amino acid sequence of MLPRVGCPALPLPPPPLLPLLPLLLLLL-GASGGGGGGARAEVLFRCPPCTPERLAACGPPPVAP-PAAVAAVAGGARMPCAELVREPGCGCCSVCAR-LEGEACGVYTPRCGQGLRCYPH PGSELPLQALVMGEGTCEKRRDAEYGASPEQ-VADNGDDHSEGGLVE (SEQ ID NO: 54); an amino acid sequence, the amino acid sequence having at least 90% sequence identity to the amino acid sequence of MLPRLG-GPALPLLLPSLLLLLLLGAGGCGPGVRAEVLFRCP-PCTPERLAACGPPPDAPCA ELVREPGCGCCSVCAR-QEGEACGVYIPRCAQTLRCYPNPGSELPLKALVTGA-GTCEKRR VGTTPQQVADSDDDHSEGGLVE (SEQ ID NO: 55); or an amino acid sequence, the amino acid sequence having at least 90% sequence identity to the amino acid sequence of MLPRLGGPALPLLLPSLLLLLLLGAG-GCGPGVRAEVLFRCPPCTPERLAACGPPPDAPCA ELVREPGCGCCSVCARQEGEACGVYIPRCAQTLRCY-PNPGSELPLKALVTGAGTCEKRR VGATPQQ-VADSEDDHSEGGLVE (SEQ ID NO: 56). In some cases, at least a first epitope of the peptide HER-2 is selected from the group consisting of: a nucleotide sequence encoding an amino acid sequence, the amino acid sequence having at least 90% sequence identity to the amino acid sequence of TMRRLLQETELVEPLTPSGAMPNQAQMRILKETEL-RKVKVLGSGAFGTVYKGIWIPDGE NVKIPVAIKVL-RENTSPKANKEILDEAYVMAGVGSPYVSRLLGICLT-STVQLVTQLMPY GCLLDHVRENRGRLGSQDLLNWCMQIAKGM-SYLEDVRLVHRDLAARNVLVKSPNHV KITDF-GLARLLDIDETEYHADGGKVPIKWMALESILR-RRFTHQSDVWSYGVTVWELMT FGAKPYDGIPAREIPDLLEKGERLPQPPICTIDVYMIM-VKCWMIDSECRPRFRELVSEFSR MARDPQRFV-VIQNEDLAPGAGGMVHHRHRSSSPLPAARPA-GATLERPKTLSPGKNGVV KDVFAFGGAVENPEYL (SEQ ID NO: 60); a nucleotide sequence encoding an amino acid sequence, the amino acid sequence having at least 90% sequence identity to the amino acid sequence of TMR-RLLQETELVEPLTPSGAVPNQAQMRILKETELRKLKV-LGSGAFGTVYKGIWIPDGE NVKIPVAIKVLRENTSP-KANKEILDEAYVMAGVGSPYVSRLLGICLTSTVQLV-TQLMPY GCLLDHVREHRGRLGSQDLLNWCVQIAK-GMSYLEEVRLVHRDLAARNVLVKSPNHVK ITDF-GLARLLDIDETEYHADGGKVPIKWMALESILR-RRFTHQSDVWSYGVTVWELMTF GAKPYDGIPAREIPDLLEKGERLPQPPICTIDVYMIM-VKCWMIDSECRPRFRELVSEFSR MARDPQRFV-VIQNEDLALGTGSTAHRRHRSSSPPPPIRPAGATLERP-KTLSPGKNGVVK DVFAFGGAVENPEYL (SEQ ID NO: 61); or a nucleotide sequence encoding an amino acid sequence, the amino acid sequence having at least 90% sequence identity to the amino acid sequence of TMR-RLLQETELVEPLTPSGAMPNQAQMRILKETELRKVK-VLGSGAFGTVYKGIWIPDGE NVKIPVAIKVL-RENTSPKANKEILDEAYVMAGVGSPYVSRLLGICLT-STVQLVTQLMPY GCLLDHVREHRGRLGSQDLLNW-CVQIAKGMSYLEDVRLVHRDLAARNVLVKSPNHV KITDFGLARLLDIDETEYHADGGKVPIKWMALESIL-RRRFTHQSDVWSYGVTVWELMT FGAKPYDGIPA-REIPDLLEKGERLPQPPICTIDVYMIMVKCWMIDSE-CRPRFRELVSEFSR MARDPQRFVVIQNEDLTPGTGSTAHRRHRSSSPLP-PVRPAGATLERPKTLSPGKNGVVK DVFAFGGAVEN-PEYL (SEQ ID NO: 62). In some cases, a nucleic acid sequence encoding an epitope of the peptide IGF-1R is selected from the group consisting of: an amino acid sequence, the amino acid sequence having at least 90% sequence identity to the amino acid sequence of DYRSYR-FPKLTVITE (SEQ ID NO: 66); an amino acid sequence, the amino acid sequence having at least 90% sequence identity to the amino acid sequence of IRGWKLFYNYALVIF (SEQ ID NO: 67); an amino acid sequence, the amino acid sequence having at least 90% sequence identity to the amino acid sequence of VVTGYVKIRHSHALV (SEQ ID NO: 68); an amino acid sequence, the amino acid sequence having at least 90% sequence identity to the amino acid sequence of FFYVQAKTGYENFIH (SEQ ID NO: 69); an amino acid sequence, the amino acid sequence having at least 90% sequence identity to the amino acid sequence of LIIALPVAVLLIVGG (SEQ ID NO: 70); an amino acid sequence, the amino acid sequence having at least 90% sequence identity to the amino acid sequence of LVIMLY-VFHRKRNNS (SEQ ID NO: 71); an amino acid sequence, the amino acid sequence having at least 90% sequence identity to the amino acid sequence of NCHHVVRLLGV-VSQG (SEQ ID NO: 72); an amino acid sequence, the amino acid sequence having at least 90% sequence identity to the amino acid sequence of WSFGVVLWEIATLAEQPY-QGLSNEQVLRFVMEGGLLDKPDNCPDMLFELMRM-CWQY NPKMRPSFLEHKAENGPGPGVLVLRASFDER-QPYAHMNGGRKNERALP (SEQ ID NO: 73); an amino acid sequence, the amino acid sequence having at least 90% sequence identity to the amino acid sequence of WSFGV-VLWEIATLAEQPYQGLSNEQVLRFVMEGGLLDKP-DNCPDMLFELMRMCWQY NPKMRPSFLEHKAENG-PGPGVLVLRASFDERQPYAHMNGGRANERALP (SEQ ID NO: 74); or an amino acid sequence, the amino acid sequence having at least 90% sequence identity to the amino acid sequence of WSFGVVLWEIATLAEQPYQGL-SNEQVLRFVMEGGLLDKPDNCPDMLFELMRM-CWQY NPKMRPSFLEHKAENGPGVLVLRASFDER-QPYAHMNGGRANERALP (SEQ ID NO: 75).

The compositions described herein may further include a nucleic acid sequence encoding a fusion protein of three epitopes is selected from the group consisting of: an amino acid sequence, the amino acid sequence having at least 90% sequence identity to the amino acid sequence of MAVPM-LPRVGCPALPLPPPPLLPLLPLLLLLLGASGGGGA-RAEVLFRCPPCTPERLAAC GPPPVAPPAAVAAVAG-GARMPCAELVREPGCGCCSVCARLEGEACGVYTPR-CGQGLR CYPHPGSELPLQALVMGEGTCEKRRDAEY-GASPEQVADNGDDHSEGGLVEQLTMRRL LQETELVEPLTPSGAMPNQAQMRILKETELRKVKV-LGSGAFGTVYKGIWIPDGENVKIP VAIKVLRENTSP-KANKEILDEAYVMAGVGSPYVSRLLGICLTST-VQLVTQLMPYGCLLD HVRENRGRLGSQDLLNWCMQIAKGMSYLEDVR-LVHRDLAARNVLVKSPNHVKITDFG LARLLDIDE-TEYHADGGKVPIKWMALESILRRRFTHQSD-VWSYGVTVWELMTFGAKPY DGIPAREIPDLLEKGERLPQPPICTIDVYMIMVKCW-MIDSECRPRFRELVSEFSRMARDP QRFVVIQNED-LAPGAGGMVHHRHRSSSPLPAARPAGATLERPKTL-SPGKNGVVKDVFA FGGAVENPEYLGRPVPWSFGVVLWEIATLAEQPY-QGLSNEQVLRFVMEGGLLDKPDNC PDMLFELMRM-CWQYNPKMRPSFLEHKAENGPGPGVLVL-RASFDERQPYAHMNGGRK NERALPAAA (SEQ ID NO: 79); an amino acid sequence, the amino acid sequence having at least 90% sequence identity to the amino acid sequence of MAVPMLPRLGGPALPLLLPSLLLLLLL-GAGGCGPGVRAEVLFRCPPCTPERLAACGPPP DAP-CAELVREPGCGCCSVCARQEGEACGVYIPRCAQTLR-CYPNPGSELPLKALVTGAGT CEKRRVGTTPQQVADSDDDHSEGGLVEQLTMR-RLLQETELVEPLTPSGAVPNQAQMRI LKETELRKLK-VLGSGAFGTVYKGIWIPDGENVKIPVAIKVLRENTSP-KANKEILDEAYV MAGVGSPYVSRLLGICLTSTVQLVTQLMPYGCLLD-HVREHRGRLGSQDLLNWCVQIAK GMSYLEEVR-LVHRDLAARNVLVKSPNHVKITDFGLARLLDIDE-TEYHADGGKVPIKWM ALESILRRRFTHQSDVWSYGVTVWELMTFGAKPYD-GIPAREIPDLLEKGERLPQPPICTI DVYMIMVKCW-MIDSECRPRFRELVSEFSRMARDPQRFVVIQNEDLA-LGTGSTAHRRHR SSSPPPPIRPAGATLERPKTLSPGKNGVVKDVFAFG-GAVENPEYLGRPVPWSFGVVLWEI ATLAEQPYQGL-SNEQVLRFVMEGGLLDKPDNCPDMLFELMRM-CWQYNPKMRPSFLEH KAENGPGPGVLVLRASFDERQPYAHMNGGRANER-ALPAAA (SEQ ID NO: 80); or an amino acid sequence, the amino acid sequence having at least 90% sequence identity to the amino acid sequence of MAVPMLPRLGGPALPLLL-PSLLLLLLLGAGGCGPGVRAEVLFRCPPCTPER-LAACGPPP DAPCAELVREPGCGCCSVCARQEGE-ACGVYIPRCAQTLRCYPNPGSELPLKALVTGAGT CEKRRVGATPQQVADSEDDHSEGGLVEQLTMR-RLLQETELVEPLTPSGAMPNQAQMRI LKETELRKVK-VLGSGAFGTVYKGIWIPDGENVKIPVAIKVLRENTSP-KANKEILDEAYV MAGVGSPYVSRLLGICLTSTVQLVTQLMPYGCLLD-HVREHRGRLGSQDLLNWCVQIAK GMSYLEDVR-LVHRDLAARNVLVKSPNHVKITDFGLARLLDIDE-TEYHADGGKVPIKW MALESILRRRFTHQSDVWSYGVTVWELMTFGAKPY-DGIPAREIPDLLEKGERLPQPPICT IDVYMIMVKCW-MIDSECRPRFRELVSEFSRMARDPQRFVVIQNEDLT-PGTGSTAHRRHR SSSPLPPVRPAGATLERPKTLSPGKNGVVKDVFAFG-GAVENPEYLGRPVPWSFGVVLW EIATLAEQPYQGL-SNEQVLRFVMEGGLLDKPDNCPDMLFELMRM-CWQYNPKMRPSFL EHKAENGPGVLVLRASFDERQPYAHMNGGRANER-ALPAAA (SEQ ID NO: 81).

In some cases, the composition comprises a first and a second epitope independently selected from: CD105, Yb-1, SOX-2, CDH3 or MDM2. In some cases, the composition further comprises a Third epitope, the first, second and Third epitopes independently selected from: CD105, Yb-1, SOX-2, CDH3 or MDM2. In some cases, the composition further comprises a Third and a fourth epitope, the first, second, Third and fourth epitopes independently selected from: CD105, Yb-1, SOX-2, CDH3 or MDM2. In some cases, the composition further comprises a Third, a fourth and a fifth epitope, the first, second, Third, fourth and fifth epitopes independently selected from: CD105, Yb-1, SOX-2, CDH3 or MDM2.

In some cases, the composition comprises a first and a second epitope independently selected from: IGFBP2, HER-2 or IGF-1R. In some cases, the composition further comprises a Third epitope, the first, second and Third epitopes independently selected from: IGFBP2, HER-2 or IGF-1R.

In some cases, a composition may comprise: at least a first epitope of a first antigen, the first epitope is a portion of a peptide from HIF-1α. In some cases, a composition may comprise: at least a first epitope of a first antigen, at least a second epitope of a second antigen, the first and the second epitopes are from HIF-1α.

In some cases, the compositions may include a nucleic acid sequence encoding an epitope of the peptide HIF-1α is selected from the group consisting of: a nucleotide sequence encoding an amino acid sequence, the amino acid sequence having at least 90% sequence identity to the amino acid sequence of DSKTFLSRHSLDMKFSYCDERITELM-GYEPEELLGRSIYEYYHALDSDHLTKTHHDMFT KGQVTTGQYRMLAKRGGYVWVETQATVIYN (SEQ ID NO: 82); a nucleotide sequence encoding an amino acid sequence, the amino acid sequence having at least 90% sequence identity to the amino acid sequence of SDN-VNKYMGLTQFELTGHSVFDFTHP (SEQ ID NO: 83); and a nucleotide sequence encoding an amino acid sequence, the amino acid sequence having at least 90% sequence identity to the amino acid sequence of GGYVWVETQATVIYNTKNSQ (SEQ ID NO: 84).

In some cases, the composition may include at least a first epitope of the peptide HIF-1α is selected from the group consisting of: an amino acid sequence, the amino acid sequence having at least 90% sequence identity to the amino acid sequence of DSKTFLSRHSLDMKFSYCDERITELM-GYEPEELLGRSIYEYYHALDSDHLTKTHHDMFT KGQVTGQYRMLAKRGGYVWVETQATVIYN (SEQ ID NO: 82); an amino acid sequence, the amino acid sequence having at least 90% sequence identity to the amino acid sequence of SDNVNKYMGLTQFELTGHSVFDFTHP (SEQ ID NO: 83); and an amino acid sequence, the amino acid sequence having at least 90% sequence identity to the amino acid sequence of GGYVWVETQATVIYNTKNSQ (SEQ ID NO: 84).

The amino acid sequences of the epitopes from the following proteins, CD105, HIF1α, MDM2, Yb1, SOX-2, HER-2, IGFBP2, IGF-1R and CDH3 may differ from those listed herein. In some cases, amino acid sequences which are greater than 95%, 90%, 85%, 80%, 75%, 70%, 65%, 60%, 55% or greater than 50% homologous to those disclosed herein may be used in the compositions described herein.

In some cases, the first amino acid sequences are selected from a group of species consisting of, human, mouse and rat. In some cases, the second amino acid sequences are selected from a group of species consisting of, human, mouse and rat.

In some cases, the first and the second nucleic acid sequences are located on the first plasmid. In some cases, the second nucleic acid sequence is located on a second plasmid. In some cases, the amino acid sequences of the first and the second epitopes are separated by a sequence of linker amino acids. In some cases, the amino acid sequence of the first epitope is adjacent to the amino acid sequence of the second epitope.

In some cases, the immune response is a Type 1 immune response. In some cases, the immune response is characterized by a ratio of Type I cytokine production to Type 11 cytokine production that is greater than 1. In some cases, the immune response is characterized by a ratio of Type I cytokine production to Type II cytokine production that is less than 1. In some cases, the immune response is characterized by a ratio of IFNγ production to IL-10 production that is greater than 1. In some cases, the immune response is characterized by a ratio of IFNγ production to IL-10 production that is less than 1.

In some cases, the composition is administered to a subject. In some cases, the subject is in need of administration of the composition. In some cases, the composition is effective to elicit an immune response in a subject. In some cases, the composition is effective to eliminate a number of cells associated with breast cancer in a subject. In some cases, the composition may be used to prevent the growth of cells associated with breast cancer in a subject.

In some cases, a subject is selected from the group consisting of a human with breast cancer, a mouse with breast cancer and a rat with breast cancer. In some cases, a subject is selected from the group consisting of a human without breast cancer, a mouse without breast cancer and a rat without breast cancer.

In some cases, the cells associated with breast cancer are selected from: breast cells expressing atypical features, pre-neoplastic breast cells, breast cancer cells, pre-invasive breast cancer cells, breast cancer stem cells, epithelial cells, mesenchymal cells, stromal cells, or a combination thereof.

In some cases, at least the first epitope is contained within a pharmaceutical composition. In some cases, at least the first epitope is contained within a pharmaceutical composition further comprising a pharmaceutical carrier. In some cases, at least the first epitope is contained within a pharmaceutical composition further comprising a pharmaceutical carrier and an adjuvant. In some cases, at least the first epitope is contained within a pharmaceutical composition further comprising an adjuvant. In some cases, the composition further comprises an adjuvant and a pharmaceutical carrier. In some cases, the adjuvant is GM-CSF.

In some cases, the composition may be administered to a subject. In some cases, the subject is in need thereof. In some cases, methods for preventing breast cancer in a subject are provided herein such that the method comprises administering the compositions described herein to a subject. In some cases, methods for treating breast cancer in a subject are provided herein such that the method comprises administering the compositions described herein to a subject. In some cases, administering further comprises delivery of at least one dose of the composition described herein to the subject. In some cases, the administering further comprises delivery of the compositions described herein to the subject by subcutaneous injection, intradermal injection, intramuscular injection, intravascular injection, topical application or inhalation. In some cases, the subject is selected from the group consisting of a human with breast cancer, a mouse with breast cancer and a rat with breast cancer. In some cases, the subject is selected from the group consisting of a human without breast cancer, a mouse without breast cancer and a rat without breast cancer.

The disclosure also provides for a kit for preparing the compositions described herein, the kit comprising instructions for preparing the composition. The disclosure also provides for a kit for administering the compositions described herein, the kit comprising instructions for administering the composition.

Compositions Comprising Epitopes Selected from Survivin, HIF-1α, IGFBP-2, and IGF-1R The compositions described herein include a plasmid comprising at least one nucleotide sequence encoding a polypeptide comprising at least 70% sequence identity to an epitope sequence selected from SEQ ID NOs: 54, 73, 85, and 87; and an excipient. The composition may include a plasmid which comprises at least one nucleotide sequence encoding a polypeptide comprising at least 80% sequence identity to an epitope sequence selected from SEQ ID NOs: 54, 73, 85, and 87. The composition may include a plasmid which comprises at least one nucleotide sequence encoding a polypeptide comprising at least 90% sequence identity to an epitope sequence selected from SEQ ID NOs: 54, 73, 85, and 87. The composition may include a plasmid which comprises at least one nucleotide sequence encoding a polypeptide comprising at least 95% sequence identity to an epitope sequence selected from SEQ ID NOs: 54, 73, 85, and 87. The composition may include a plasmid which comprises at least one nucleotide sequence encoding a polypeptide comprising at least 99% sequence identity to an epitope sequence selected from SEQ ID NOs: 54, 73, 85, and 87. The composition may include a plasmid which comprises at least one nucleotide sequence encoding a polypeptide comprising 100% sequence identity to an epitope sequence selected from SEQ ID NOs: 54, 73, 85, and 87. The composition may include a plasmid which comprises at least one nucleotide sequence encoding a polypeptide consisting of 100% sequence identity to the full length of an epitope sequence selected from SEQ ID NOs: 54, 73, 85, and 87.

Sometimes, the at least one nucleotide sequence may encode a polypeptide comprising at least 70% sequence identity to at least 20 contiguous amino acids of SEQ ID NO: 85. The at least one nucleotide sequence may encode a polypeptide comprising at least 80% sequence identity to at least 20 contiguous amino acids of SEQ ID NO: 85. The at least one nucleotide sequence may encode a polypeptide comprising at least 90% sequence identity to at least 20 contiguous amino acids of SEQ ID NO: 85. The at least one nucleotide sequence may encode a polypeptide comprising at least 95% sequence identity to at least 20 contiguous amino acids of SEQ ID NO: 85. The at least one nucleotide sequence may encode a polypeptide comprising at least 99% sequence identity to at least 20 contiguous amino acids of SEQ ID NO: 85. The at least one nucleotide sequence may encode a polypeptide comprising at least 100% sequence identity to at least 20 contiguous amino acids of SEQ ID NO: 85.

Sometimes, the at least one nucleotide sequence may encode a polypeptide comprising at least 70% sequence identity to at least 60 contiguous amino acids of SEQ ID NO: 87. The at least one nucleotide sequence may encode a polypeptide comprising at least 80% sequence identity to at least 60 contiguous amino acids of SEQ ID NO: 87. The at least one nucleotide sequence may encode a polypeptide comprising at least 90% sequence identity to at least 60 contiguous amino acids of SEQ ID NO: 87. The at least one nucleotide sequence may encode a polypeptide comprising at least 95% sequence identity to at least 60 contiguous amino acids of SEQ ID NO: 87. The at least one nucleotide sequence may encode a polypeptide comprising at least 99% sequence identity to at least 60 contiguous amino acids of SEQ ID NO: 87. The at least one nucleotide sequence may encode a polypeptide comprising at least 100% sequence identity to at least 60 contiguous amino acids of SEQ ID NO: 87.

In some instances, the composition comprises an isolated plasmid which comprises at least four nucleotide sequences. Sometimes, each of the at least four nucleotide sequences independently encodes a polypeptide comprising at least 60%, 70%, 80%, 90%, 95%, 99%, or 100% sequence identity to an epitope sequence selected from SEQ ID NOs: 54, 73, 85, and 87. Sometimes, the isolated plasmid may comprise four nucleotide sequences. Sometimes, each of the four nucleotide sequences may independently encode a polypeptide comprising at least 60%, 70%, 80%, 90%, 95%, 99%, or 100% sequence identity to an epitope sequence selected from SEQ ID NOs: 54, 73, 85, and 87. Other times, each of the four nucleotide sequences may encode a different polypeptide. Sometimes, each of the different polypeptide may comprise at least 60%, 70%, 80%, 90%, 95%, 99%, or 100% sequence identity to an epitope sequence selected from SEQ ID NOs: 54, 73, 85, and 87.

Sometimes, one of the four nucleotide sequences may encode a polypeptide comprising at least 70% sequence identity to at least 20 contiguous amino acids of SEQ ID NO: 85. One of the four nucleotide sequences may encode a polypeptide comprising at least 80% sequence identity to at least 20 contiguous amino acids of SEQ ID NO: 85. One of the four nucleotide sequences may encode a polypeptide comprising at least 90% sequence identity to at least 20 contiguous amino acids of SEQ ID NO: 85. One of the four nucleotide sequences may encode a polypeptide comprising at least 95% sequence identity to at least 20 contiguous amino acids of SEQ ID NO: 85. One of the four nucleotide sequences may encode a polypeptide comprising at least 100% sequence identity to at least 20 contiguous amino acids of SEQ ID NO: 85.

Sometimes, one of the four nucleotide sequences may encode a polypeptide comprising at least 70% sequence identity to at least 60 contiguous amino acids of SEQ ID NO: 87. One of the four nucleotide sequences may encode a polypeptide comprising at least 80% sequence identity to at least 60 contiguous amino acids of SEQ ID NO: 87. One of the four nucleotide sequences may encode a polypeptide comprising at least 90% sequence identity to at least 60 contiguous amino acids of SEQ ID NO: 87. One of the four nucleotide sequences may encode a polypeptide comprising at least 95% sequence identity to at least 60 contiguous amino acids of SEQ ID NO: 87. One of the four nucleotide sequences may encode a polypeptide comprising at least 100% sequence identity to at least 60 contiguous amino acids of SEQ ID NO: 87.

In some cases, the four nucleotide sequences are positioned in tandem within the plasmid. The four nucleotide sequences may be separated by a sequence of linker nucleic acids. The sequence of linker nucleic acids may be from about 1 to about 150, from about 5 to about 100, or from about 10 to about 50 nucleic acids in length. In some instances, the nucleic acids may encode one or more amino acid residues. Sometimes, the amino acid sequence of the linker may be from about 1 to about 50, or from about 5 to about 25 amino acid residues in length. Sometimes the linker may include a linker (SEQ ID NO: 14) as shown as underlined in FIG. 14.

Sometimes, the composition may further comprise at least one additional isolated plasmid. Sometimes, the composition may further comprise at least 2, 3, 4, 5, 6, 7, 8, 9, 10, 11, 12, 13, 14, 15, 16, 17, 18, 19, 20, 21, 22, 23, 24, 25, 30, 35, 40, 45, 50, or more additional isolated plasmid.

In some cases, the at least one additional isolated plasmid comprises a nucleotide sequence encoding a polypeptide comprising at least 70% sequence identity to an epitope sequence selected from SEQ ID NOs: 54, 73, 85, and 87. The at least one additional isolated plasmid may comprise a nucleotide sequence encoding a polypeptide comprising at least 80% sequence identity to an epitope sequence selected from SEQ ID NOs: 54, 73, 85, and 87. The at least one additional isolated plasmid may comprise a nucleotide sequence encoding a polypeptide comprising at least 90% sequence identity to an epitope sequence selected from SEQ ID NOs: 54, 73, 85, and 87. The at least one additional isolated plasmid may comprise a nucleotide sequence encoding a polypeptide comprising at least 95% sequence identity to an epitope sequence selected from SEQ ID NOs: 54, 73, 85, and 87. The at least one additional isolated plasmid may comprise a nucleotide sequence encoding a polypeptide comprising at least 99% sequence identity to an epitope sequence selected from SEQ ID NOs: 54, 73, 85, and 87. The at least one additional isolated plasmid may comprise a nucleotide sequence encoding a polypeptide comprising 100% sequence identity to an epitope sequence selected from SEQ ID NOs: 54, 73, 85, and 87.

A composition described herein may include a composition comprising: a plasmid comprising a nucleotide sequence encoding a polypeptide comprising at least 80% sequence identity to SEQ ID NO: 89; and an excipient. The composition may include a plasmid which comprises a nucleotide sequence encoding a polypeptide comprising at least 90% sequence identity to SEQ ID NO: 89. The composition may include a plasmid which comprises a nucleotide sequence encoding a polypeptide comprising at least 95% sequence identity to SEQ ID NO: 89. The composition may include a plasmid which comprises a nucleotide sequence encoding a polypeptide comprising 100% sequence identity to SEQ ID NO: 89. The composition may include a plasmid which comprises a nucleotide sequence encoding a polypeptide consisting of 100% sequence identity to SEQ ID NO: 89.

A composition described herein may include a composition that comprises a polypeptide comprising at least 80% sequence identity to SEQ ID NO: 89. The composition may include a polypeptide which comprises at least 90% sequence identity to SEQ ID NO: 89. The composition may include a polypeptide which comprises at least 95% sequence identity to SEQ ID NO: 89. The composition may include a polypeptide which comprises 100% sequence identity to SEQ ID NO: 89. The composition may include a polypeptide which consists of 100% sequence identity to SEQ ID NO: 89.

The composition may be formulated for the treatment of breast cancer or ovarian cancer in a subject. The breast cancer may be a relapsed or refractory breast cancer. The ovarian cancer may be a relapsed or refractory ovarian cancer. The breast cancer may be a metastasized breast cancer. The ovarian cancer may be a metastasized ovarian cancer.

The composition may elicits an immune response. The immune response may be characterized by a ratio of Type I cytokine production to Type II cytokine production that is greater than 1. The immune response may be characterized by a ratio of Type I cytokine production to Type II cytokine production that is less than 1. The immune response may be characterized by a ratio of IFN-γ production to IL-10 production that is greater than 1. The immune response may be characterized by a ratio of IFN-γ production to IL-10 production that is less than 1.

Sometimes the composition may further comprises an adjuvant. Sometimes, the adjuvant is GM-CSF.

The composition may further comprises an excipient. The excipient may be a pharmaceutically acceptable carrier.

Often times, the composition may be formulated for subcutaneous, intramuscular, or intradermal administration.

The disclosure also provides for a kit for preparing the compositions described herein, the kit comprising instructions for preparing the composition. The disclosure also provides for a kit for administering the compositions described herein, the kit comprising instructions for administering the composition.

Plasmids for Pharmaceutical Compositions

In some cases, the epitopes may be derived from human proteins that may be used directly in a peptide based vaccine. In other cases, the epitopes may be derived from human proteins and the encoding nucleic acid sequences encoding the epitopes may be incorporated into a nucleic acid construct designed to induce expression of the epitope in a subject following administration. For example, epitopes encoded from the nucleic acid construct may allow for the immune response to at least one epitope to be entrained, amplified, attenuated, suppressed, or eliminated to specific sets of proteins (e.g., self-proteins). In some cases, the peptide or the nucleic acid construct may be optimized into a protein or plasmid-based vaccination to induce, amplify or entrain a Th1 immune response. In some cases, the epitopes may be extended Th1 epitopes. In other cases, the peptide or the nucleic acid construct may be optimized into a protein or plasmid-based vaccination to suppress, attenuate or eliminate a pathological response, in a subject (e.g., human or animal) in need thereof.

The compositions described herein may include plasmids which contain nucleic acid sequences to express at least one epitope in a subject following administration of the composition (e.g., vaccine). Any plasmid backbones (e.g., vectors) known to one of ordinary skill in the art suitable for pharmaceutical use for expression of a nucleic sequence may be used in the compositions described herein. In some cases, commercially available plasmid backbones may be used. For example, the plasmid pUMVC3 may be used. In some cases, commercially available plasmid backbones may be modified, mutated, engineered or cloned prior to use. In other cases, non-commercially available plasmid backbones may be used.

Prior to inserting the nucleic acid sequence of at least one epitope, the plasmid backbone may be less than about 500 bp, about 1.0 kB, about 1.2 kB, about 1.4 kB, about 1.6 kB, about 1.8 kB, about 2.0 kB, about 2.2 kB, about 2.4 kB, about 2.6 kB, about 2.8 kB, about 3.0 kB, about 3.2 kB, about 3.4 kB, about 3.6 kB, about 3.8 kB, about 4.0 kB, about 4.2 kB, about 4.4 kB, about 4.6 kB, about 4.8 kB, about 5.0 kB, about 5.2 kB, about 5.4 kB, about 5.6 kB, about 5.8 kB, about 6.0 kB, about 6.2 kB, about 6.4 kB, about 6.6 kB, about 6.8 kB, about 7.0 kB, about 7.2 kB, about 7.4 kB, about 7.6 kB, about 7.8 kB, about 8.0 kB, about 8.2 kB, about 8.4 kB, about 8.6 kB, about 8.8 kB, about 9.0 kB, about 9.2 kB, about 9.4 kB, about 9.6 kB, about 9.8 kB, about 10.0 kB, about 10.2 kB, about 10.4 kB, about 10.6 kB, about 10.8 kB, about 11.0 kB, about 11.2 kB, about 11.4 kB, about 11.6 kB, about 11.8 kB, about 12.0 kB, about 12.2 kB, about 12.4 kB, about 12.6 kB, about 12.8 kB, about 13.0 kB, about 13.2 kB, about 13.4 kB, about 13.6 kB, about 13.8 kB, about 14 kB, about 14.5 kB, about 15 kB, about 15.5 kB, about 16 kB, about 16.5 kB, about 17 kB, about 17.5 kB, about 18 kB, about 18.5 kB, about 19 kB, about 19.5 kB, about 20 kB, about 30 kB, about 40 kB, about 50 kB, about 60 kB, about 70 kB, about 80 kB, about 90 kB, about 100 kB, about 110 kB, about 120 kB, about 130 kB, about 140 kB, about 150 kB, about 160 kB, about 170 kB, about 180 kB, about 190 kB or about 200 kB in length. In an exemplary case, the plasmid is about 4 kB in length prior to addition of the nucleic acid sequence encoding at least one epitope.

In some cases, the compositions described herein may include one plasmid. In other cases, the compositions described herein may include more than one plasmid. For example, the compositions described herein may include two plasmids, three plasmids, four plasmids, five plasmids, six plasmids, seven plasmids, eight plasmids, nine plasmids, ten plasmids, 11 plasmids, 12 plasmids, 13 plasmids, 14 plasmids, 15 plasmids, 16 plasmids, 17 plasmids, 18 plasmids 19 plasmids, 20 plasmids or more than 20 plasmids.

In some cases, the nucleic acids which encode at least one epitope of a plasmid may be deoxyribonucleic acids. For example, the deoxyribonucleic acids may be single stranded, double stranded or complementary. The deoxyribonucleic acids may be derived from genomic, mitochondrial or plasmid deoxyribonucleic acids. In other cases, the nucleic acids of a plasmid may be ribonucleic acids. For example, the ribonucleic acids may be single stranded or double stranded. In some cases, the ribonucleic acids may be micro, antisense, short hairpin, small interfering, messenger, transfer, ribosomal, or the like. In some cases, the nucleic acids of the plasmids may be a portion of deoxyribonucleic acids and a portion of ribonucleic acids.

The nucleic acids which encode at least one epitope of a plasmid may be derived from any species such that the epitope expressed from the nucleic acids results in an immune response in a subject. In some cases, the subject may be a rodent, a non-human primate or a human. The nucleic acids encoding the epitope of the plasmid may be isolated from any source of nucleic acids using methods and techniques known to one of ordinary skill in the art. The nucleic acids encoding the epitope of the plasmid may be cloned into the plasmid backbone using methods and techniques known to one of ordinary skill in the art.

In some cases, the nucleic acid sequence encoding the epitope may be an endogenous nucleic acid sequence to the subject. For example, the nucleic acid sequence for CD105 from a human may be used to express CD105 in a human. In other cases, the nucleic acid sequence for the antigenic epitope may be an exogenous nucleic acid sequence to the subject. For example, the nucleic acid sequence for CD105 from a non-human may be used to express CD105 in a human.

In some cases, the nucleic acid sequences to express the antigenic epitope may be wild-type nucleic acid sequences. For example, the naturally occurring nucleic acid sequence for CD105 in the genome of a species may be used to express CD105 in a subject. In other cases, the nucleic acid sequences encoding the epitope may be synthetic nucleic acid sequences. For example, the naturally occurring nucleic acid sequence for CD105 in the genome of a species may be modified using molecular techniques known to one of ordinary skill in the art and may be used to express CD105 in a subject.

In some cases, the nucleic acid sequence encoding the epitope may be an endogenous nucleic acid sequence to the subject. For example, the nucleic acid sequence for CD105 from a human may be used to express CD105 in a human. In other cases, the nucleic acid sequence for the antigenic epitope may be an exogenous nucleic acid sequence to the subject. For example, the nucleic acid sequence for CD105 from a non-human may be used to express CD105 in a human.

In some cases, the nucleic acid sequences to express the antigenic epitope may be wild-type nucleic acid sequences. For example, the naturally occurring nucleic acid sequence for CD105 in the genome of a species may be used to express CD105 in a subject. In other cases, the nucleic acid sequences encoding the epitope may be synthetic nucleic acid sequences. For example, the naturally occurring nucleic acid sequence for CD105 in the genome of a species may be modified using molecular techniques known to one of ordinary skill in the art and may be used to express CD105 in a subject.

In some cases, the nucleic acid sequence encoding the epitope may be an endogenous nucleic acid sequence to the subject. For example, the nucleic acid sequence for HIF-1A from a human may be used to express HIF-1A in a human. In other cases, the nucleic acid sequence for the antigenic epitope may be an exogenous nucleic acid sequence to the subject. For example, the nucleic acid sequence for HIF-1A from a non-human may be used to express HIF-1A in a human.

In some cases, the nucleic acid sequences to express the antigenic epitope may be wild-type nucleic acid sequences. For example, the naturally occurring nucleic acid sequence for HIF-1A in the genome of a species may be used to express HIF-1A in a subject. In other cases, the nucleic acid sequences encoding the epitope may be synthetic nucleic acid sequences. For example, the naturally occurring nucleic acid sequence for HIF-1A in the genome of a species may be modified using molecular techniques known to one of ordinary skill in the art and may be used to express HIF-1A in a subject.

In some cases, the nucleic acid sequence encoding the epitope may be an endogenous nucleic acid sequence to the subject. For example, the nucleic acid sequence for HIF-1A from a human may be used to express HIF-1A in a human. In other cases, the nucleic acid sequence for the antigenic epitope may be an exogenous nucleic acid sequence to the subject. For example, the nucleic acid sequence for HIF-1A from a non-human may be used to express HIF-1A in a human.

In some cases, the nucleic acid sequences to express the antigenic epitope may be wild-type nucleic acid sequences. For example, the naturally occurring nucleic acid sequence for HIF-1A in the genome of a species may be used to express HIF-1A in a subject. In other cases, the nucleic acid sequences encoding the epitope may be synthetic nucleic acid sequences. For example, the naturally occurring nucleic acid sequence for HIF-1A in the genome of a species may be modified using molecular techniques known to one of ordinary skill in the art and may be used to express HIF-1A in a subject.

In some cases, the nucleic acid sequence encoding the epitope may be an endogenous nucleic acid sequence to the subject. For example, the nucleic acid sequence for MDM2 from a human may be used to express MDM2 in a human. In other cases, the nucleic acid sequence for the antigenic epitope may be an exogenous nucleic acid sequence to the subject. For example, the nucleic acid sequence for MDM2 from a non-human may be used to express MDM2 in a human.

In some cases, the nucleic acid sequences to express the antigenic epitope may be wild-type nucleic acid sequences. For example, the naturally occurring nucleic acid sequence for MDM2 in the genome of a species may be used to express MDM2 in a subject. In other cases, the nucleic acid sequences encoding the epitope may be synthetic nucleic acid sequences. For example, the naturally occurring nucleic acid sequence for MDM2 in the genome of a species may be modified using molecular techniques known to one of ordinary skill in the art and may be used to express MDM2 in a subject.

In some cases, the nucleic acid sequence encoding the epitope may be an endogenous nucleic acid sequence to the subject. For example, the nucleic acid sequence for MDM2 from a human may be used to express MDM2 in a human. In other cases, the nucleic acid sequence for the antigenic epitope may be an exogenous nucleic acid sequence to the subject. For example, the nucleic acid sequence for MDM2 from a non-human may be used to express MDM2 in a human.

In some cases, the nucleic acid sequences to express the antigenic epitope may be wild-type nucleic acid sequences. For example, the naturally occurring nucleic acid sequence for MDM2 in the genome of a species may be used to express MDM2 in a subject. In other cases, the nucleic acid sequences encoding the epitope may be synthetic nucleic acid sequences. For example, the naturally occurring nucleic acid sequence for MDM2 in the genome of a species may be modified using molecular techniques known to one of ordinary skill in the art and may be used to express MDM-2 in a subject.

In some cases, the nucleic acid sequence encoding the epitope may be an endogenous nucleic acid sequence to the subject. For example, the nucleic acid sequence for Yb-1 from a human may be used to express Yb-1 in a human. In other cases, the nucleic acid sequence for the antigenic epitope may be an exogenous nucleic acid sequence to the subject. For example, the nucleic acid sequence for Yb-1 from a non-human may be used to express Yb-1 in a human.

In some cases, the nucleic acid sequences to express the antigenic epitope may be wild-type nucleic acid sequences. For example, the naturally occurring nucleic acid sequence for Yb-1 in the genome of a species may be used to express Yb-1 in a subject. In other cases, the nucleic acid sequences encoding the epitope may be synthetic nucleic acid sequences. For example, the naturally occurring nucleic acid sequence for Yb-1 in the genome of a species may be modified using molecular techniques known to one of ordinary skill in the art and may be used to express Yb-1 in a subject.

In some cases, the nucleic acid sequence encoding the epitope may be an endogenous nucleic acid sequence to the subject. For example, the nucleic acid sequence for Yb-1 from a human may be used to express Yb-1 in a human. In other cases, the nucleic acid sequence for the antigenic epitope may be an exogenous nucleic acid sequence to the subject. For example, the nucleic acid sequence for Yb-1 from a non-human may be used to express Yb-1 in a human.

In some cases, the nucleic acid sequences to express the antigenic epitope may be wild-type nucleic acid sequences. For example, the naturally occurring nucleic acid sequence for Yb-1 in the genome of a species may be used to express Yb-1 in a subject. In other cases, the nucleic acid sequences encoding the epitope may be synthetic nucleic acid sequences. For example, the naturally occurring nucleic acid sequence for Yb-1 in the genome of a species may be modified using molecular techniques known to one of ordinary skill in the art and may be used to express Yb-1 in a subject.

In some cases, the nucleic acid sequence encoding the epitope may be an endogenous nucleic acid sequence to the subject. For example, the nucleic acid sequence for SOX-2 from a human may be used to express SOX-2 in a human. In other cases, the nucleic acid sequence for the antigenic epitope may be an exogenous nucleic acid sequence to the subject. For example, the nucleic acid sequence for SOX-2 from a non-human may be used to express SOX-2 in a human.

In some cases, the nucleic acid sequences to express the antigenic epitope may be wild-type nucleic acid sequences. For example, the naturally occurring nucleic acid sequence for SOX-2 in the genome of a species may be used to express SOX-2 in a subject. In other cases, the nucleic acid sequences encoding the epitope may be synthetic nucleic acid sequences. For example, the naturally occurring nucleic acid sequence for SOX-2 in the genome of a species may be modified using molecular techniques known to one of ordinary skill in the art and may be used to express SOX-2 in a subject.

In some cases, the nucleic acid sequence encoding the epitope may be an endogenous nucleic acid sequence to the subject. For example, the nucleic acid sequence for SOX-2 from a human may be used to express SOX-2 in a human. In other cases, the nucleic acid sequence for the antigenic epitope may be an exogenous nucleic acid sequence to the subject. For example, the nucleic acid sequence for SOX-2 from a non-human may be used to express SOX-2 in a human.

In some cases, the nucleic acid sequences to express the antigenic epitope may be wild-type nucleic acid sequences. For example, the naturally occurring nucleic acid sequence for SOX-2 in the genome of a species may be used to express SOX-2 in a subject. In other cases, the nucleic acid sequences encoding the epitope may be synthetic nucleic acid sequences. For example, the naturally occurring nucleic acid sequence for SOX-2 in the genome of a species may be modified using molecular techniques known to one of ordinary skill in the art and may be used to express SOX-2 in a subject.

In some cases, the nucleic acid sequence encoding the epitope may be an endogenous nucleic acid sequence to the subject. For example, the nucleic acid sequence for HER-2 from a human may be used to express HER-2 in a human. In other cases, the nucleic acid sequence for the antigenic epitope may be an exogenous nucleic acid sequence to the subject. For example, the nucleic acid sequence for HER-2 from a non-human may be used to express HER-2 in a human.

In some cases, the nucleic acid sequences to express the antigenic epitope may be wild-type nucleic acid sequences. For example, the naturally occurring nucleic acid sequence for HER-2 in the genome of a species may be used to express HER-2 in a subject. In other cases, the nucleic acid sequences encoding the epitope may be synthetic nucleic acid sequences. For example, the naturally occurring nucleic acid sequence for HER-2 in the genome of a species may be modified using molecular techniques known to one of ordinary skill in the art and may be used to express HER-2 in a subject.

In some cases, the nucleic acid sequence encoding the epitope may be an endogenous nucleic acid sequence to the subject. For example, the nucleic acid sequence for HER-2 from a human may be used to express HER-2 in a human. In other cases, the nucleic acid sequence for the antigenic epitope may be an exogenous nucleic acid sequence to the subject. For example, the nucleic acid sequence for HER-2 from a non-human may be used to express HER-2 in a human.

In some cases, the nucleic acid sequences to express the antigenic epitope may be wild-type nucleic acid sequences. For example, the naturally occurring nucleic acid sequence for HER-2 in the genome of a species may be used to express HER-2 in a subject. In other cases, the nucleic acid sequences encoding the epitope may be synthetic nucleic acid sequences. For example, the naturally occurring nucleic acid sequence for HER-2 in the genome of a species may be modified using molecular techniques known to one of ordinary skill in the art and may be used to express HER-2 in a subject.

In some cases, the nucleic acid sequence encoding the epitope may be an endogenous nucleic acid sequence to the subject. For example, the nucleic acid sequence for IGFBP2 from a human may be used to express IGFBP2 in a human. In other cases, the nucleic acid sequence for the antigenic epitope may be an exogenous nucleic acid sequence to the subject. For example, the nucleic acid sequence for IGFBP2 from a non-human may be used to express IGFBP2 in a human.

In some cases, the nucleic acid sequences to express the antigenic epitope may be wild-type nucleic acid sequences. For example, the naturally occurring nucleic acid sequence for IGFBP2 in the genome of a species may be used to express IGFBP2 in a subject. In other cases, the nucleic acid sequences encoding the epitope may be synthetic nucleic acid sequences. For example, the naturally occurring nucleic acid sequence for IGFBP2 in the genome of a species may be modified using molecular techniques known to one of ordinary skill in the art and may be used to express IGFBP2 in a subject.

In some cases, the nucleic acid sequence encoding the epitope may be an endogenous nucleic acid sequence to the subject. For example, the nucleic acid sequence for IGFBP2 from a human may be used to express IGFBP2 in a human. In other cases, the nucleic acid sequence for the antigenic epitope may be an exogenous nucleic acid sequence to the subject. For example, the nucleic acid sequence for IGFBP2 from a non-human may be used to express IGFBP2 in a human.

In some cases, the nucleic acid sequences to express the antigenic epitope may be wild-type nucleic acid sequences. For example, the naturally occurring nucleic acid sequence for IGFBP2 in the genome of a species may be used to express IGFBP2 in a subject. In other cases, the nucleic acid sequences encoding the epitope may be synthetic nucleic acid sequences. For example, the naturally occurring nucleic acid sequence for IGFBP2 in the genome of a species may be modified using molecular techniques known to one of ordinary skill in the art and may be used to express IGFBP2 in a subject.

In some cases, the nucleic acid sequence encoding the epitope may be an endogenous nucleic acid sequence to the subject. For example, the nucleic acid sequence for IGF-1R from a human may be used to express IGF-1R in a human. In other cases, the nucleic acid sequence for the antigenic epitope may be an exogenous nucleic acid sequence to the subject. For example, the nucleic acid sequence for IGF-1R from a non-human may be used to express IGF-1R in a human.

In some cases, the nucleic acid sequences to express the antigenic epitope may be wild-type nucleic acid sequences. For example, the naturally occurring nucleic acid sequence for IGF-1R in the genome of a species may be used to express IGF-1R in a subject. In other cases, the nucleic acid sequences encoding the epitope may be synthetic nucleic acid sequences. For example, the naturally occurring nucleic acid sequence for IGF-1R in the genome of a species may be modified using molecular techniques known to one of ordinary skill in the art and may be used to express IGF-1R in a subject.

In some cases, the nucleic acid sequence encoding the epitope may be an endogenous nucleic acid sequence to the subject. For example, the nucleic acid sequence for IGF-1R from a human may be used to express IGF-1R in a human. In other cases, the nucleic acid sequence for the antigenic epitope may be an exogenous nucleic acid sequence to the subject. For example, the nucleic acid sequence for IGF-1R from a non-human may be used to express IGF-1R in a human.

In some cases, the nucleic acid sequences to express the antigenic epitope may be wild-type nucleic acid sequences.

For example, the naturally occurring nucleic acid sequence for IGF-1R in the genome of a species may be used to express IGF-1R in a subject. In other cases, the nucleic acid sequences encoding the epitope may be synthetic nucleic acid sequences. For example, the naturally occurring nucleic acid sequence for IGF-1R in the genome of a species may be modified using molecular techniques known to one of ordinary skill in the art and may be used to express IGF-1R in a subject.

In some cases, the nucleic acid sequence encoding the epitope may be an endogenous nucleic acid sequence to the subject. For example, the nucleic acid sequence for CDH3 from a human may be used to express CDH3 in a human. In other cases, the nucleic acid sequence for the antigenic epitope may be an exogenous nucleic acid sequence to the subject. For example, the nucleic acid sequence for CDH3 from a non-human may be used to express CDH3 in a human.

In some cases, the nucleic acid sequences to express the antigenic epitope may be wild-type nucleic acid sequences. For example, the naturally occurring nucleic acid sequence for CDH3 in the genome of a species may be used to express CDH3 in a subject. In other cases, the nucleic acid sequences encoding the epitope may be synthetic nucleic acid sequences. For example, the naturally occurring nucleic acid sequence for CDH3 in the genome of a species may be modified using molecular techniques known to one of ordinary skill in the art and may be used to express CDH3 in a subject.

In some cases, the nucleic acid sequence encoding the epitope may be an endogenous nucleic acid sequence to the subject. For example, the nucleic acid sequence for CDH3 from a human may be used to express CDH3 in a human. In other cases, the nucleic acid sequence for the antigenic epitope may be an exogenous nucleic acid sequence to the subject. For example, the nucleic acid sequence for CDH3 from a non-human may be used to express CDH3 in a human.

In some cases, the nucleic acid sequences to express the antigenic epitope may be wild-type nucleic acid sequences. For example, the naturally occurring nucleic acid sequence for CDH3 in the genome of a species may be used to express CDH3 in a subject. In other cases, the nucleic acid sequences encoding the epitope may be synthetic nucleic acid sequences. For example, the naturally occurring nucleic acid sequence for CDH3 in the genome of a species may be modified using molecular techniques known to one of ordinary skill in the art and may be used to express CDH3 in a subject.

The compositions described herein include a composition comprising: a first plasmid comprising a first nucleotide sequence, the first nucleotide sequence encoding a first epitope of a first antigen expressed by cells associated with breast cancer; and a second nucleotide sequence, the second nucleotide sequence encoding a second epitope of a second antigen expressed by cells associated with breast cancer, wherein the first nucleotide sequence and the second nucleotide sequence are located in one or more plasmids. In some cases, the composition may include nucleic acids which encode epitopes from the following proteins, CD105, HIF1α, MDM2, Yb-1, SOX-2, HER-2, IGFBP2, IGF-1R and CDH3.

In some cases, the compositions may include a composition comprising: a first plasmid comprising a first nucleotide sequence, the first nucleotide sequence encoding a first epitope of a first antigen, the first epitope is a portion of a peptide selected from: CD105, Yb-1, SOX-2, CDH3 or MDM2, wherein the first nucleotide sequence is located in a plasmid. In other cases, the composition may include a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CD105, Yb-1, SOX-2, CDH3 or MDM2, wherein the first nucleotide sequence and the second nucleotide sequence are located in one or more plasmids.

In some cases, the composition may include nucleic acids which encode epitopes from the following proteins, CD105, MDM2, Yb-1, SOX-2, and CDH3. In some cases, the composition may include a nucleic acid sequence encoding an epitope of the peptide CD105 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of CAGAACGGCACCTGGCCCCGCGAGGTGCTGCTGGTGCTGTCCGTGAACTCCTCCGT GTCCTGCACCTACAGGCCCTGGGCATCCCCCTGCACCTGGCCTACAACTCCTCCCT GGTGACCTTCCAGGAGCCCCCCGGCGTGAACACCACCGAGCTG (SEQ ID NO: 2); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACCGTGTTCATGCGCCTGAACAT-CATCTCCCCCGACCTGTCCGGCTGCACCTCCAAG GGCCTGGTGCTGCCCGCCGTGCTGGGCATCAC-CTICGGCGCCTTCCTGATCGGCGCC CTGCTGACCGCCGCCCTGTGGTACATCTACTCCCACAC-CCGCTCCCCCTCCAAGCGC GAGCCCGTGGTGGCCGTGGCCGCCCCCGCCTC-CTCCGAGTCCTCCTCCACCAACCAC TCCATCGGCTCCACCCAGTCCACCCCCTGCTCCACCTCCATGGCC (SEQ ID NO: 3); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACCGTGTCCATGCGCCTGAACATCGTGTCCCCCGACCTGTCCGGCAAGGGCCTGGTG CTGCCCTCCGTGCTGGGCATCACCTICGGCGCCTTCCTGATCGGCGCCCTGCTGACC GCCGCCCTGTGGTACATCTACTCCCACACCCGCGCCCCTCCAAGCGCGAGCCCGTG GTGGCCGTGGCCGCCCCCGCCTCCTCCGAGTCCTCCTCCACCAACCACTCCATCGGC TCCACCCAGTCCACCCCCTGCTCCACCTCCTCCATGGCC (SEQ ID NO: 4); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACCGTGTCCATGCGCCTGAACATCGTGTCCCCCGACCTGTCCGGCAAGGGCCTGGTG CTGCCCTCCGTGCTGGGCATCACCTTCGGCGCCTTCCTGATCGGCGCCCTGCTGACC GCCGCCCTGTGGTACATCTACTCCCACACCCGCGCCCCTCCAAGCGCGAGCCCGTG GTGGCCGTGGCCGCCCCCGCCTCCTCCGAGTCCTCCTCCACCAACCACTCCATCGGC TCCACCCAGTCCACCCCCTGCTCCACCTCCTCCATGGCC (SEQ ID NO: 5); a nucleotide sequence encoding an amino acid sequence, the amino acid sequence having at least 50%, 600%, 70%, 80%, 90%, 91%, 920, 93%, 94%, 95%, 96%, 97%, 98%, 99%, or 100% sequence identity to the amino acid sequence of EARMLNASIVASFVELPL (SEQ ID NO: 6); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of QNGTWPREVLLVLSVNSSVFL-HLQALGIPLHLAYNSSLVTFQEPPGVNTTEL (SEQ ID NO: 1); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TVFMRLNIISPDLSGCTSKGLVLPAVL-GITFGAFLIGALLTAALWYIYSHTRSPSKREPVV AVAAPASSESSSTNHSIGSTQSTPCSTSSMA (SEQ ID NO: 8); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TVSMRLNIVSPDLSGKGLVLPSVLGIT-FGAFLIGALLTAALWYIYSHTRGPSKREPVVAV AAPASSESSSTNHSIGSTQSTPCSTSSMA (SEQ ID NO: 9); or a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TVSMRLNIVSPDLSGKGLVLPSVLGIT-FGAFLIGALLTAALWYIYSHTRAPSKREPVVAV AAPASSESSSTNHSIGSTQSTPCSTSSMA (SEQ ID NO: 10). In some cases, the composition may include a nucleic acid sequence encoding an epitope of the peptide Yb-1 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of GGAGTGCCAGT-GCAGGGCTCCAAGTACGCTGCCGACCGCAACCAC-TACCGCCGCTA CCCACGCCGTCGCGGCCCAC-CCCGCAACTACCAGCAGAAC (SEQ ID NO: 11); a nucleotide sequence having at least 50%, 60%, 70%, 80%, 90%, 91%, 92%, 93%, 94%, 95%, 96%, 97%, 98%, 99%, or 100% sequence identity to the nucleotide sequence of GGCGTGCCCGT-GCAGGGCTCCAAGTACGCCGCCGACCGCAACCAC-TACCGCCGCTA CCCCCGCGCGCCGCGCCCCCCCGCAACTACCA-GCAGAAC (SEQ ID NO: 12); a nucleotide sequence having at least 50%, 60%, 70%, 80%, 90%, 91%, 92%, 93%, 94%, 95%, 96%, 97%, 98%, 99%, or 100% sequence identity to the nucleotide sequence of GGCGTGCCCGT-GCAGGGCTCCAAGTACGCCGCCGACCGCAACCAC-TACCGCCGCTA CCCCCGCCGCCGCGGC-CCCCCCCGCAACTACCAGCAGAAC (SEQ ID NO: 12); a nucleotide sequence encoding an amino acid sequence, the amino acid sequence having at least 50%, 60%, 70%, 80%, 90%, 910%, 92%, 93%, 94%, 95%, 96%, 97%, 98%, 99%, or 100% sequence identity to the amino acid sequence of EDVFVHQTAIKKNNPRK (SEQ ID NO: 14); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of YRRNF-NYRRRRPEN (SEQ ID NO: 15), or a nucleotide sequence encoding an amino acid sequence, the amino acid sequence having at least 50%, 60%, 70%, 809%, 90%, 91%, 92%0, 93%, 94%, 95%, 96%, 97%, 98%, 99%, or 100% sequence identity to the amino acid sequence of GVPVQG-SKYAADRNHYRRYPRRRGPPRNYQQN (SEQ ID NO: 16). In some cases, the composition may include a nucleic acid sequence encoding an epitope of the peptide SOX-2 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of GGCCTCAATGCG-CACGGCGCAGCGCAGATGCAGCCCATGCACCGC-TACGACGTGAG CGCCCTGCAGTACAACTCCAT-GACCAGCTCGCAGACCTACATGAACGGCTCGCCCA CCTACAGCATGTCCTACTCGCAGCAGGGCAC-CCCTGGCATGGCTCTTGGCTCCATGG GITCGGTG (SEQ ID NO: 17); a nucleotide sequence having at least 50%, 60%, 70%, 80%, 90%, 91%, 92%, 93%, 94%, 95%, 96%, 97%, 98%, 99%, or 100% sequence identity to the nucleotide sequence of GGCCTGAACGCCCACGGCGC-CGCCCAGATGCAGCCCATGCACCGCTACGACGT-GTC CGCCCTGCAGTACAACTCCATGACCTCCTC-CCAGACCTACATGAACGGCTCCCCCAC CTACTCCATGTCCTACTCCCAGCAGGGCACCCCCG-GCATGGCCCTGGGCTCCATGG CTCCGTG (SEQ ID NO: 18); a nucleotide sequence having at least 50%, 60%, 70%, 80%, 90%9, 91%, 92%, 93%, 94%, 95%, 96%, 97%, 98%, 99%, or 100% sequence identity to the nucleotide sequence of GGCCTGAACGCCCACGGCGCCGCCCA-GATGCAGCCCATGCACCGCTACGACGTGTC CGC-CCTGCAGTACAACTCCATGACCTCCTCCCAGAC-CTACATGAACGGCTCCCCCAC CTACTCCATGTCCTACTCCCAGCAGGGCACCCCCG-GCATGGCCCTGGGCTCCATGG CTCCGTG (SEQ ID NO: 18); or a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of GLNAHGAAQMQPMHRYD-VSALQYNSMTSSQTYMNGSPTYSMSYSQQGTPG-MALGSM GSV (SEQ ID NO: 20). In some cases, the composition may include, a nucleic acid sequence encoding an epitope of the peptide CDH3 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of AGGTCACTGAAGGAAAGGAATCCAT-TGAAAATCTTCCCATCCAAACGTATCTTACG AAGA-CACAAGAGAGATTGGGTGGTTGCTCCAATATCTGT-CCCTGAAAATGGCAAGG GTCCCTTCCCACAGA-GACTGAATCAGCTCAAGTCTAATAAAGATAGAGA-CACCAAG ATITTCTACAGCATCACGGGGCCGGGT-GCAGACAGCCCACCTGAGGGTGTCTTCGCT GTAGAGAAGGAGACA (SEQ ID NO: 21); a nucleotide sequence having at least 50%, 60%, 70%, 80%, 90%, 91%, 92%, 93%, 94%, 95%, 96%, 97%, 98%, 99%, or 100% sequence identity to the nucleotide sequence of TTGAAAATCTTCCCATCCAAACGTATCTTAC-GAAGACACAAGAGAGATTGGGTGGT TGCTC-CAATATCTGTCCCTGAAAATGGCAAGGGTCCCTTC-CCACAGAGACTGAATCA GCTCAAGTCTAATAAAGATAGAGACAC-CAAGATTTTCTACAGCATCACGGGGCCGG GTGCA-GACAGCCCACCTGAGGGTGTCTTCGCTGTAGA-GAAGGAGACA (SEQ ID NO: 22); a nucleotide sequence having at least 50%, 60%, 70%, 80%, 90%, 91%, 92%, 93%, 94%, 95%, 96%, 97%, 98%, 99%, or 100% sequence identity to the nucleotide sequence of GCCATGCACTC-CCCCCCCACCCGCATCCTGCGCCGCCGCAAGCGC-GAGTGGGTGAT GCCCCCCATCTTCGTGCCCGA-GAACGGCAAGGGCCCCTTCCCCCAGCGCCTGAACC AGCTGAAGTCCAACAAGGACCGCGGCAC-CAAGATCTCTACTCCATCACCGGCCCC GGCGC-CGACTCCCCCCCCGAGGGCGTGTTCACCATCGA-GAAGGAGTCC (SEQ ID NO: 23); a nucleotide sequence having at least 50%, 60%, 70%, 80%, 90%, 91%, 92%, 93%, 94%, 95%, 96%, 97%, 98%, 99%, or 100% sequence identity to the nucleotide sequence of GTGATGAACTC-CCCCCCCTCCCGCATCCTGCGCCGCCGCAAGCGC-GAGTGGGTGAT GCCCCCCATCTCCGTGCCCGA-GAACGGCAAGGGCCCCTTCCCCCAGCGCCTGAACC AGCTGAAGTCCAACAAGGACCGCGGCACCAAGCT-GTTCTACTCCATCACCGGCCCC GGCGCCGACTC-CCCCCCCGAGGGCGTGTTCACCATCGAGAAGGA-GACC (SEQ ID NO: 24); a nucleotide sequence encoding an amino acid sequence, the amino acid sequence having at least 50%6, 60%, 70%, 80%, 90%, 91%, 92%, 93%, 94%, 95%, 96%, 97%, 98%, 99%, or 100% sequence identity to the amino acid sequence of RSLKERNPLKIFPSKRILR-RHKRDWVVAPISVPENGKGPFPQRLNQLK-SNKDRDTKIFYSI TGPGADSPPEGVFAVEKET (SEQ ID NO: 25); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LKIFPSKRILRRHKRDWV-VAPISVPENGKGPFPQRLNQLKSNKDRDTKIFYSITG-PGADSP PEGVFAVEKET (SEQ ID NO: 26); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of AMHSPP-TRILRRRKREWVMPPIFVPENGKGPFPQRLNQLK-SNKDRGTKIFYSITGPGADS PPEGVFTIEKES (SEQ ID NO: 27); or a nucleotide sequence encoding an amino acid sequence, the amino acid sequence having at least 50%, 60%, 70%, 80%, 90%, 91%, 92%, 93%, 94%, 95%, 96%, 97%, 97%, 98%, 99%, or 100% sequence identity to the amino acid sequence of VMNSPPSRILRRRKREWVMP-PISVPENGKGPFPQRLNQLKSNKDRGTKLFYSITGP-GADS PPEGVFTIEKET (SEQ ID NO: 28). In some cases, the composition may include, a nucleic acid sequence encoding an epitope of the peptide MDM2 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACCTACACCATGAAGGAG-GTGCTGTTCTACCTGGGCCAGTACATCATGAC-CAAGCG CCTGTACGACGAGAAGCAGCAGCA-CATCGTGTACTGCTCCAACGACCTGCTGGGCG ACCTGTTCGGCGTGCCCTCCTTCTCCGTGAAGGAG-CACCGCAAaATCTACCATGA TCTACCGCAACCTG-GTGGTGGTGAACCAGCAGGAGTCCTCCGACTCCG-GCACCTCC GTGTCC (SEQ ID NO: 29); a nucleotide sequence having at least 50%, 60%, 70%, 80%, 90% 91%, 92%, 93%, 94%, 95%, 96%, 97%, 98%, 99%, or 100% sequence identity to the nucleotide sequence of ACCTA-CACCATGAAGGAGATCATCTTCTACATCGGCCAG-TACATCATGACCAAGCG CCTGTACGACGA-GAAGCAGCAGCACATCGTGTACTGCTCCAACGAC-CTGCTGGGCG ACGTGTTCGGCGTGCCCTCCTTCTC-CGTGAAGGAGCACCGCAAGATCTACGCCATGA TCTACCGCAACCTGGTGGCCGTGTCCCAGCAG-GACTCCGGCACCTCCCTGTCC (SEQ ID NO: 30); a nucleotide sequence having at least 50%, 60%, 70%, 801%, 90%, 91%, 92%, 93%, 94%, 95%, 96%, 97%, 97%, 98%, 99%, or 100% sequence identity to the nucleotide sequence of ATCTACACCATGAAGGAGATCATCTTCTACATCG-GCCAGTACATCATGACCAAGCG CCTGTACGACGA-GAAGCAGCAGCACATCGTGTACTGCTCCAACGAC-CTGCTGGGCG ACGTGTTCGGCGTGCCCTCCTTCTCCGTGAAGGAG-CACCGCAAGATCTACGCCATGA TCTACCGCAAC-CTGGTGGTGGTGTCCCAGCAGGACTCCGGCAC-CTCCCCCTCC (SEQ ID NO: 31); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TYTMKEVLFYL-GQYIMTKRLYDEKQQHIVYCSNDLLGDLF-GVPSFSVKEHRKIYTMIYR NLVVVNQQESSDSGTSV (SEQ ID NO: 32); a nucleotide sequence encoding an amino acid sequence, the amino acid sequence having at least 506, 60%, 70%, 80%, 90%, 91%, 92%, 93%, 94%, 95%, 96%, 97%, 98%, 99%, or 100% sequence identity to the amino acid sequence of TYTMKEIIFYIGQYIMT-KRLYDEKQQHIVYCSNDLLGDVFGVPSFSVKEHRKI-YAMIYRN LVAVSQQDSGTSLS (SEQ ID NO: 33); or a nucleotide sequence encoding an amino acid sequence, the amino acid sequence having at least 50%, 60%, 70%, 80%, 90%, 91%, 92%, 93%, 94%, 95%, 96%, 97%, 97%, 98%, 99%, or 100% sequence identity to the amino acid sequence of IYTMKEIIFYIGQYIMTKRLYDEKQQHIVYC-SNDLLGDVFGVPSFSVKEHRKIYAMIYRN LVVVSQQDSGTSPS (SEQ ID NO: 34).

In an exemplary case, the compositions may include a nucleic acid sequence encoding a fusion peptide of five epitopes is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATGGCG-GTACCCATGCAACTGTCCTGCTCTAGACAGAACG-GCACCTGGCCCCGCGA GGTGCTGCTGGTGCTGTC-CGTGAACTCCTCCGTGTTCCTGCACCTACAGGCC-CTGGG CATCCCCCTGCACCTGGCCTACAACTCCTC-CCTGGTGACCTTCCAGGAGCCCCCGG CGT-GAACACCACCGAGCTGAGATCCACCGGTGGAGT-GCCAGTGCAGGGCTCCAAGT ACGCTGCCGACCGCAACCACTACCGCCGCTAC-CCACGCCGTCGCGGCCCACCCCGC AACTACCA-GCAGAACACGCGTGGCCTCAATGCGCACGGCGCA-GCGCAGATGCAGCC CATGCACCGCTACGACGTGAGCGCCCTGCAGTA-CAACTCCATGACCAGCTCGCAGA CCTACAT-GAACGGCTCGCCCACCTACAGCATGTC-CTACTCGCAGCAGGGCACCCCT GGCATGGCTCTTGGCTCCATGGGGTTCGGTGAGATC-CCAATTGAGGTCACTGAAGGA AAGGAATCCATT-GAAAATCTTCCCATCCAAACGTATCTTACGAAGA-CACAAGAGAG ATTGGGTGGTTGCTCCAATATCTGTCCCT-GAAAATGGCAAGGGTCCCTTCCCACAGA GACT-GAATCAGCTCAAGTCTAATAAAGATAGAGACAC-CAAGATTTCTACAGCATC ACGGGGCCGGGTGCAGACAGCCCACCTGAGGGT-GTCTFCGCTGTAGAGAAGGAGAC AAGATCCGCCG-GCGAAACCTACACCATGAAGGAGGTGCTGTCTAC-CTGGGCCAGT ACATCATGACCAAGCGCCTGTACGACGAGAAGCA-GCAGCACATCGTGTACTGCTCC AACGACCT-GCTGGGCGACCTGTTCGGCGTGCCCTCCTTCTC-CGTGAAGGAGCACCGC AAAATCTACACCATGATCTACCGCAACCTGGTG-GTGGTGAACCAGCAGGAGTCCTC CGACTCCG-GCACCTCCGTGTCCAGATCTAG (SEQ ID NO: 35); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATG-GCGGTACCCATGACCGTGTTCATGCGCCTGAACAT-CATCTCCCCCGACCTGTCC GGCTGCACCTC-CAAGGGCCTGGTGCTGCCCGCCGTGCTGGGCATC- ACCTCGGCGCC TTCCTGATCGGCGCCCTGCTGAC-CGCCGCCCTGTGGTACATCTACTCCCACACCCGC TCCCCCTCCAAGCGCGAGCCCGTGGTGGCCGTG-GCCGCCCCCGCCTCCTCCGAGTCC TCCTCCAC-CAACCACTCCATCGGCTCCACCCAGTCCACCCCCT-GCTCCACCTCCTCC
ATGGCCACCGGTGGAGTGCCAGTGCAGGGCTC-CAAGTACGCTGCCGACCGCAACCA CTACCGCCGC-TACCCACGCCGTCGCGGCCCACCCCGCAACTAC-CAGCAGAACACGC
GTGGCCTCAATGCGCACGGCGCAGCGCAGATGCA-GCCCATGCACCGCTACGACGTG AGCGCCCTGCAG-TACAACTCCATGACCAGCTCGCAGACCTACAT-GAACGGCTCGCC
CACCTACAGCATGTCCTACTCGCAGCAGGGCAC-CCCTGGCATGGCTCTTGGCTCCAT GGTCGGT-GAGATCCCAATTGTGAAAATCTTCCCATCCAAACG-TATCTACGAAG
ACACAAGAGAGATGGGTGGTGCTCCAATATCTGTC-CCTGAAAATGGCAAGGGTC CCTCCCACAGAGACT-GAATCAGCTCAAGTCAATAAAGATAGAGACAC-CAAGAT
TCTACAGCATCACGGGGCCGGGTGCAGACAGC-CCACCTGAGGGTGTCTTCGCTGT AGAGAAGGAGA-CAAGATCCGCCGGCGAAACCTACACCAT-GAAGGAGGTGCTGTTC
TACCTGGGCCAGTACATCATGACCAAGCGCCTG-TACGACGAGAAGCAGCAGCACAT CGTGTACT-GCTCCAACGACCTGCTGGGCGACCTGTTCGGCGT-GCCCTCCTTCTCCGT
GAAGGAGCACCGCAAAATCTACACCATGATCTAC-CGCAACCTGGTGGTGGTGAACC AGCAGGAGTC-CTCCGACTCCGGCACCTCCGTGTCCAGATCTTAG (SEQ ID NO: 36); a nucleotide sequence having at least 50%, 60%, 70%, 80%, 90%, 91%, 92%, 93%, 94%, 95%, 96%, 97%, 98%, 99%, or 100% sequence identity to the nucleo tide sequence of ATGGCGGTACCCATGACCGT-GTCCATGCGCCTGAACATCGTGTCCCCCGACCT-GTCC GGCAAGGGCCTGGTGCTGCCCTCCGT-GCTGGGCATCACCTTCGGCGCCTCCTGA-TC GGCGCCCTGCTGACCGCCGCCCTGTGGTA-CATCTACTCCCACACCCGCGGCCCCTCC AAGCGC-GAGCCCGTGGTGGCCGTGGCCGCCCCCGCCTC-CTCCGAGTCCTCCTCCACC
AACCACTCCATCGGCTCCACCCAGTCCACCCCCT-GCTCCACCTCCTCCATGGCCACC GGTGGCGTGC-CCGTGCAGGGCTCCAAGTACGCCGCCGACCG-CAACCACTACCGCCG
CTACCCCGCCGCCGCGGCCCCCCCCGCAACTAC-CAGCAGAACACGCGTGGCCTGA ACGCCCACG-GCGCCGCCCAGATGCAGCCCATGCACCGCTAC-GACGTGTCCGCCCTG
CAGTACAACTCCATGACCTCCTCCCAGACCTACAT-GAACGGCTCCCCCACCTACTCC ATGTCCTACTC-CCAGCAGGGCACCCCCGGCATGGCCCTGGGCTC-CATGGGCTCCGTG
AGATCCCAATGGCCATGCACTCCCCCCCCACCCG-CATCCTGCGCCGCCGCAAGCGC GAGTGGGTGAT-GCCCCCCATCTCGTGCCCGAGAACGGCAAGGGC-CCCTTCCCCCA
GCGCCTGAACCAGCTGAAGTCCAACAAGGAC-CGCGGCACCAAGATCTTCTACTCCA TCACCGGC-CCCGGCGCCGACTCCCCCCCCGAGGGCGTGT-TCACCATCGAGAAGGAG
TCCAGATCCGCCGGCGAAACCTACACCAT-GAAGGAGATCATCTTCTACATCGGCCA GTACAT-CATGACCAAGCGCCTGTACGACGAGAAGCAGCAG-CACATCGTGTACTGCT
CCAACGACCTGCTGGGCGACGTGTTCGGCGTGC-CCTCCTTCTCCGTGAAGGAGCACC GCAAGATC-TACGCCATGATCTACCGCAACCTGGTGGCCGTGTC-CCAGCAGGACTCC
GGCACCTCCCTGTCCAGATCTAG (SEQ ID NO: 37); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATG-GCGGTACCCATGACCGTGTCCATGCGCCT-GAACATCGTGTCCCCCGACCTGTCC GGCAAGGGC-CTGGTGCTGCCCTCCGTGCTGGGCATCACCTCGGC-GCCTTCCTGATC GGCGCCCTGCTGACCGCCGCCCT-GTGGTACATCTACTCCCACACCCGCGCCCCCTCC
AAGCGCGAGCCCGTGGTGGCCGTGGCCGC-CCCCGCCTCCTCCGAGTCCTCCTCCACC AAC-CACTCCATCGGCTCCACCCAGTCCACCCCCTGCTC-CACCTCCTCCATGGCCACC
GGTGGCGTGCCCGTGCAGGGCTCCAAGTACGC-CGCCGACCGCAACCACTACCGCCG CTACCCCGC-CGCCGCGGCCCCCCCCGCAACTACCAGCA-GAACACGCGTGGCCTGA
ACGCCCACGGCGCCGCCCAGATGCAGCCCATG-CACCGCTACGACGTGTCCGCCCTG CAGTA-CAACTCCATGACCTCCTCCCAGACCTACATGAACG-GCTCCCCCACCTACTCC
ATGTCCTACTCCCAGCAGGGCACCCCCGGCATGGC-CCTGGGCTCCATGGGCTCCGTG AGATCCCAATTG-GTGATGAACTCCCCCCCCTCCCGCATCCTGCGC-CGCCGCAAGCGC
GAGTGGGTGATGCCCCCCATCTCCGTGCCCGA-GAACGGCAAGGGCCCCTCCCCCA GCGCCTGAAC-CAGCTGAAGTCCAACAAGGACCGCGGCAC-CAAGCTGTTCTACTCCA
TCACCGGCCCCGGCGCCGACTC-CCCCCCCGAGGGCGTGTCACCATCGAGAAGGAG ACCAGATCCGCCGGCGAAATCTACACCAT-GAAGGAGATCATCTTCTACATCGGCCA GTACAT-CATGACCAAGCGCCTGTACGACGAGAAGCAGCAG-CACATCGTGTACTGCT
CCAACGACCTGCTGGGCGACGTGTTCGGCGTGC-CCTCCTTCTCCGTGAAGGAGCACC GCAAGATC-TACGCCATGATCTACCGCAACCTGGTGGTGGTGTC-CCAGCAGGACTCC
GGCACCTCCCCTCCAGATCTTAG (SEQ ID NO: 38); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMQLSCSRQNGTWPREVLLVLSVNSSVFL-HLQALGIPLHLAYNSSLVTFQEPPGVN TTELRSTG-GVPVQGSKYAADRNHYRRYPRRRGPPRNYQQN-TRGLNAHGAAQMQPMH RYDVSALQYNSMTSSQTYMNGSPTYSMSYSQQGT-PGMALGSMGSVRSQLRSLKERNP LKIFPSKRILRRH-KRDWVVAPISVPENGKGPFPQRLNQLKSNKDRDTKI-FYSITGPGADSP PEGVFAVEKETRSAGETYTMKEVLFYLGQYIMT-KRLYDEKQQHIVYCSNDLLGDLFGV PSFSVKEHRKI-YTMIYRNLVVVNQQESSDSGTSVSRS (SEQ ID NO: 39); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMTVFMRLNIISPDLSGCTSK-GLVLPAVLGITFGAFLIGALLTAALWYIYSHTRSPS KREPVVAVAAPASSESSSTNHSIGSTQSTPCSTSS- MATGGVPVQGSKYAADRNHYRRYP RRRGPPRNYQQNTRGLNAHGAAQMQPMHRYDVSALQYNSMTSSQTYMNGSPTYSMSYSQQGTPGMALGSMGSVRSQLLKIFPSKRILRRHKRDWVVAPISVPENGKGPFPQRLNQ LKSNKDRDTKIFYSITGPGADSPPEGVFAVEKETRSAGETYTMKEVLFYLGQYIMTKRL YDEKQQHIVYCSNDLLGDLFGVPSFSVKEHRKIYTMIYRNLVVVNQQESSDSGTSVSRS (SEQ ID NO: 40); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMTVSMRLNIVSPDLSGKGLVLPSVLGITFGAFLIGALLTAALWYIYSHTRGPSKRE PVVAVAAPASSESSSTNHSIGSTQSTPCSTSSMATGGVPVQGSKYAADRNHYRRYPRRR GPPRNYQQNTRGLNAHGAAQMQPMHRYDVSALQYNSMTSSQTYMNGSPTYSMSYSQ QGTPGMALGSMGSVRSQLAMHSPPTRILRRRKREWVMPPIFVPENGKGPFPQRLNQLK SNKDRGTKIFYSITGPGADSPPEGVFTIEKESRSAGETYTMKEIIFYIGQYIMTKRLYDEK QQHIVYCSNDLLGDVFGVPSFSVKEHRKIYAMIYRNLVAVSQQDSGTSLSRS (SEQ ID NO: 41); or a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMTVSMRLNIVSPDLSGKGLVLPSVLGITFGAFLIGALLTAALWYIYSHTRAPSKRE PVVAVAAPASSESSSTNHSIGSTQSTPCSTSSMATGGVPVQGSKYAADRNHYRRYPRRR GPPRNYQQNTRGLNAHGAAQMQPMHRYDVSALQYNSMTSSQTYMNGSPTYSMSYSQ QGTPGMALGSMGSVRSQLVMNSPPSRILRRRKREWVMPPISVPENGKGPFPQRLNQLKS NKDRGTKLFYSITGPGADSPPEGVFTIEKETRSAGEIYTMKEIIFYIGQYIMTKRLYDEKQ QHIVYCSNDLLGDVFGVPSFSVKEHRKIYAMIYRNLVVVSQQDSGTSPSRS (SEQ ID NO: 42).

In some cases, the composition may include nucleic acids which encode epitopes from the following proteins, HER-2, IGFBP2 and IGF-1R. In some cases, the composition may comprise a first plasmid comprising a first nucleotide sequence, the first nucleotide sequence encoding a first epitope of a first antigen, the first epitope is a portion of a peptide selected from: IGFBP-2, HER-2, IGF-1R, wherein the first nucleotide sequence is located in a plasmid. In some cases, the composition may comprise: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: IGFBP-2, HER-2 or IGF-1R, wherein the first nucleotide sequence and the second nucleotide sequence are located in one or more plasmids. In some cases, the compositions may comprise a nucleic acid sequence encoding an epitope of the peptide IGFBP-2 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATGCTGCCGAGAGTGGGCTGCCCCGCGCTGCCGCTGCCGCCGCCGCCGCTGCTGCCGCTGCTGCCGCTGCTGCTGCTGCTACTGGGCGCGAGTGGCGGCGGCGGCGGGGCGC GCGCGGAGGTGCTGTTCCGCTGCCCGCCCTGCACACCCGAGCGCCTGGCCGCCTGC GGGCCCCCGCCGGTTGCGCCGCCCGCCGCGGTGGCCGCAGTGGCCGGAGGCGCCCG CATGCCATGCGCGGAGCTCGTCCGGGAGCCGGGCTGCGGCTGCTGCTCGGTGTGCG CCCGGCTGGAGGGCGAGGCGTGCGGCGTCTACACCCCGCGCTGCGGCCAGGGGCTG CGCTGCTATCCCCACCCGGGCTCCGAGCTGCCCCTGCAGGCGCTGGTCATGGGCGA GGGCACTGTGAGAAGCGCCGGGACGCCGAGTATGGCGCCAGCCCGGAGCAGGTT GCAGACAATGGCGATGACCACTCAGAAGGAGGCCTGGTGGAG (SEQ ID NO: 43), a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATGCTGCCCCGCCTGGCCCCGCGCCCCGCCCCTGCCCTCCCTGCTGCTG CTGCTGCTGGGCGCCGGCGGCTGCGGCCCCGGCGTGCGCGCCGAGGTGCTGTT CCGCTGCCCCCCTGCACCCCCGAGCGCCTGGCCGCCTGCGGCCCCCCCCCGACGC CCCCTGCGCCAGCTGGTGCGCGAGCCCGCTGCGGCTGCTGCTCCGTGTGCGCCC GCCAGGAGGGCGAGGCCTGCGGCGTGTACATCCCCCGCTGCGCCCAGACCCTGCGC TGCTACCCCAACCCCGGCTCCGAGCTGCCCCTGAAGGCCCTGGTGACCGGCGCCGG CACCTGCGAGAAGCGCCGCGTGGGCACCACCCCCAGCAGGTGGCCGACTCCGACG ACGACCACTCCGAGGGCGGCCTGGTGGAG (SEQ ID NO: 44); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATGCTGCCCCGCCTGGGCGGCCCCGCCCTGCCCTGCTGCTGCCCTCCCTGCTGCTG CTGCTGCTGGGCGCCGGCGGCTGCGGCCCCGGCGTGCGCGCCGAGGTGCTGTT CCGCTGCCCCCCTGCACCCCCGAGCGCCTGGCCGCCTGCGGCCCCCCCCCGACGC CCCCTGCGCCGAGCTGGTGCGCGAGCCCGCTGCGCTGCGTCCGTGTGCGCCC GCCAGGAGGGCGAGGCCTGCGGCGTGTACATCCCCCGCTGCGCCCAGACCCTGCGC TGCTACCCCAACCCCGGCTCCGAGCTGCCCCTGAAGGCCCTGGTGACCGGCGCCGG CACCTGCGAGAAGCGCCGCGTGGGCACCACCCCCCAGCAGGTGGCCGACTCCGAGG ACGACCACTCCGAGGGCGGCCTGGTGGAG (SEQ ID NO: 45); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of NHVDSTMNMLGGGGS (SEQ ID NO: 46); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of ELAVFREKVTEQHRQ (SEQ ID NO: 47), a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LGLEEPKKLRPPPAR (SEQ ID NO: 48); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of DQVLERISTMRLPDE (SEQ ID NO: 49); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of GPLE-HLYSLHIPNCD (SEQ ID NO: 50); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of KHGLYN-LKQCKMSLN (SEQ ID NO: 51); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of PNTGKLIQGAP-TIRG (SEQ ID NO: 52); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of PECHLFYNEQQEARG (SEQ ID NO: 53); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MLPRVGCPALPLPPPPLLPLL-PLLLLLLGASGGGGARAEVLFRCPPCTPERLAACG-PPP VAPPAAVAAVAGGARMPCAELVREPGCGCCSV-CARLEGEACGVYTPRCGQGLRCYPH PGSELPLQALVMGEGTCEKRRDAEYGASPEQ-VADNGDDHSEGGLVE (SEQ ID NO: 54); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MLPRLG-GPALPLLLPSLLLLLLLGAGGCGPGVRAEVLFRCP-PCTPERLAACGPPPDAPCA ELVREPGCGCCSVCAR-QEGEACGVYIPRCAQTLRCYPNPGSELPLKALVTGA-GTCEKRR VGTTPQQVADSDDDHSEGGLVE (SEQ ID NO: 55); and a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MLPRLGGPALPLLLPSLLLLLLLGAG-GCGPGVRAEVLFRCPPCTPERLAACGPPPDAPCA ELVREPGCGCCSVCARQEGEACGVYIPRCAQTLRCY-PNPGSELPLKALVTGAGTCEKRR VGATPQQ-VADSEDDHSEGGLVE (SEQ ID NO: 56). In some cases, the compositions may comprise a nucleic acid sequence encoding an epitope of the peptide HER-2 is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACGATGCGGAGACTGCT-GCAGGAAACGGAGCTGGTGGAGCCGCTGACAC-CTAGCG GAGCGATGCCCAACCAGGCGCAGATGCG-GATCCTGAAAGAGACGGAGCTGAGGAA GGTGAAGGTGCTFGGATCTGGCGCTTFUGGCACA-GTCTACAAGGGCATCTGGATCCC TGATGGGGA-GAATGTGAAAATTCCAGTGGCCATCAAAGTGT-GAGGGAAAACACAT CCCCCAAAGCCAACAAAGAAATCTAGAC-GAAGCATACGTGATGGCTGGTGTGGGC TCCCCATATGTCTCCCGCCTCTGGGCATCTGCCT-GACATCCACGGTGCAGCTGGTG ACACAGCTATGC-CCTATGGCTGCCTCTTAGACCATGTCCGGGAAAAC-CGCGGACG CCTGGGCTCCCAGGACCTGCTGAACTGGTGTAT-GCAGATGCCAAGGGGATGAGCT ACCTGGAGGAT-GTGCGGCTCGTACACAGGGACTTGGCCGCTCG-GAACGTGCTGGTC AAGAGTCCCAACCATGTCAAAATACA-GACTCGGGCTGGCTCGGCTGCTGGACAT TGACGA-GACAGAGTACCATGCAGATGGGGGJCAAGGTGC-CCATCAAGTGGATGGCG CTGGAGTCCATTCTCCGCCGGCGGTTTCACCCAC-CAGAGTGATGTGTGGAGTTATGGT GTGACTGT-GTGGGAGCTGATGACTTTTGGGGCCAAACCTAC-GATGGGATCCCAGC CCGGGAGATCCCTGACCTGCTG-GAAAAGGGGGAGCGGCTGCCCCAGCCCCCCATCT GCACCATGATGTCTACATGATCATGGTCAAATGTTG-GATGATFGACTCTGAATGTC GGCCAAGATTC-CGGGAGTGGTGTCTGAATTCTCCCGCATGGCCA-GGGACCCCCAG CGCTITGTGGTCATCCAGAATGAGGACTTGGCTC-CCGGAGCTGGCGGCATGGTGCA CCACAGGCAC-CGCAGCTCATCTCCTCTGCCTGCTGCCCGACCT-GCTGGTGCC ACTCT GGAAAGGCCCAAGACTCTCTCCCCA-GGGAAGAATGGGGTCGTCAAAGACGTTTTTG CCT-TGGGGGTGCCGTGGAGAACCCCGAGTACTG (SEQ ID NO: 57); a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACCATGCGCCGCCTGCTGCAGGA-GACCGAGCTGGTGGAGCCCCTGACCCCCTCCGG CGCCGTGCCCAACCAGGCCCAGATGCGCATCCT-GAAGGAGACCGAGCTGCGCAAGC TGAAGGT-GCTGGGCTCCGGCGCCTTCGGCACCGTGTA-CAAGGGCATCTGGATCCCC GACGGCGAGAACGTGAAGATCCCCGTGGCCAT-CAAGGTGCTGCGCGAGAACACCTC CCCCAAGGC-CAACAAGGAGATCCTGGACGAGGCCTACGTGATG-GCCGGCGTGGGCT CCCCCTACGTGTCCCGCCTGCTGGGCATCTGCCT-GACCTCCACCGTGCAGCTGGTGA CCCAGCTGAT-GCCCTACGGCTGCCTGCTGGACCACGTGCGCGAG-CACCGCGGCCGC CTGGGCTCCCAGGACCTGCTGAACTGGTGCGT-GCAGATCGCCAAGGGCATGTCCTA CCTGGAGGAG-GTGCGCCTGGTGCACCGCGACCTGGCCGCCCG-CAACGTGCTGGTGA AGTCCCCCAACCACGTGAAGATCACCGACTTCG-GCCTGGCCCGCCTGCTGGACATC GACGAGAC-CGAGTACCACGCCGACGGCGGCAAGGTGCCCAT-CAAGTGGATGGCCCT GGAGTCCATCCTGCGCCGCCGCTTCACCCACCA-GTCCGACGTGTGGTCCTACGGCGT GACCGT-GTGGGAGCTGATGACCTTCGGCGCCAAGCCCTAC-GACGGJCATCCCCGCCC GCGAGATCCCCGACCTGCTGGAGAAGGGC-GAGCGCCTGCCCCAGCCCCCCATCTGC ACCATC-GACGTGTACATGATCATGGTGAAGTGCTGGAT-GATCGACTCCGAGTGCCG CCCCCGCTTCCGCGAGCTGGTGTCCGAGTTCTC-CCGCATGGCCCGCGACCCCCAGCG CTCGTGGT-GATCCAGAACGAGGACCTGGCCCTGGGCACCG-GCTCCACCGCCCACC GCCGCCACCGCTCCTCCTCCCCCCCCCCCCCCATC-CGCCCCGCCGGCGCCACCCTGG AGCGC-CCCAAGACCCTGTCCCCCGGCAAGAACGGCGTG-GTGAAGGACGTGTTCGCC TITCGGCGGCGCCGTGGAGAACCCCGAGTACCTG (SEQ ID NO: 58), a nucleotide sequence having at least 50%, 60%, 70%, 80%, 90%, 91%, 92%, 93%, 94%, 95%, 96%, 97%, 98%, 99%, or 100% sequence identity to the nucleotide sequence of ACCATGCGCCGCCTGCTGCAGGAGACCGAGCTGGTGGAGCCCCTGACCCCCTCCGG CGCCATGCCCAACCAGGCCCAGATGCGCATCCTGAAGGAGACCGAGCTGCGCAAGG TGAAGGTGCTGGGCTCCGGCGCCTTCGGCACCGTGTACAAGGGCATCTGGATCCCC GACGGCGAGAACGTGAAGATCCCCGTGGCCATCAAGGTGCTGCGCGAGAACACCTC CCCCAAGGCCAACAAGGAGATCCTGGACGAGGCCTACGTGATGGCCGGCGTGGGCT CCCCCTACGTGTCCCGCCTGCTGGGCATCTGCCTGACCTCCACCGTGCAGCTGGTGA CCCAGCTGATGCCCTACGGCTGCCTGCTGGACCACGTGCGCGAGCACCGCGGCCGC CTGGGCTCCCAGGACCTGCTGAACTGGTGCGTGCAGATCGCCAAGGGCATGTCCTA CCTGGAGGACGTGCGCCTGGTGCACCGCGACCTGGCCGCCCGCAACGTGCTGGTGA AGTCCCCCAACCACGTGAAGATCACCGACTCGGCCTGGCCCGCCTGCTGGACATC GACGAGACCGAGTACCACGCCGACGGCGGCAAGGTGCCCATCAAGTGGATGGCCCT GGAGTCCATCCTGCGCCGCCGCTTTCACCCACCAGTCCGACGTGTGGTCCTACGGCGT GACCGTGTGGGAGCTGATGACCTTCGGCGCCAAGCCCTACGACGGCATCCCCGCCC GCGAGATCCCCGACCTGCTGGAGAAGGGCGAGCGCCTGCCCCAGCCCCCATCTGC ACCATCGACGTGTACATGATCATGGTGAAGTGCTGGATGATCGACTCCGAGTGCCG CCCCCGCTTCCGCGAGCTGGTGTCCGAGTTCTCCCGCATGGCCCGCGACCCCCAGCG CTTCGTGGTGATCCAGAACGAGGACCTGACCCCCGGCACCGGCTCCACCGCCCACC GCCGCCACCGCTCCTCCTCCCCCTGCCCCCGTGCGCCCCGCCGGCGCCACCCTGG AGCGCCCCAAGACCCTGTCCCCCGGCAAGAACGGCGTGGTGAAGGACGTGTTCGCC TCGGCGGCGCCGTGGAGAACCCCGAGTACCTG (SEQ ID NO: 59); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TMRRLLQETELVEPLTPSGAMPNQAQMRILKETELRKVKVLGSGAFGTVYKGIWIPDGE NVKIPVAIKVLRENTSPKANKEILDEAYVMAGVGSPYVSRLLGICLTSTVQLVTQLMPY GCLLDHVRENRGRLGSQDLLNWCMQIAKGMSYLEDVRLVHRDLAARNVLVKSPNHV KITDFGLARLLDIDETEYHADGGKVPIKWMALESILRRRFTHQSDVWSYGVTVWELMT FGAKPYDGIPAREIPDLLEKGERLPQPPICTIDVYMIMVKCWMIDSECRPRFRELVSEFSR MARDPQRFVVIQNEDLAPGAGGMVHHRHRSSSPLPAARPAGATLERPKTLSPGKNGVV KDVFAFGGAVENPEYL (SEQ ID NO: 60); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TMRRLLQETELVEPLTPSGAVPNQAQMRILKETELRKLKVLGSGAFGTVYKGIWIPDGE NVKIPVAIKVLRENTSPKANKEILDEAYVMAGVGSPYVSRLLGICLTSTVQLVTQLMPY GCLLDHVREHRGRLGSQDLLNWCVQIAKGMSYLEEVRLVHRDLAARNVLVKSPNHVK ITDFGLARLLDIDETEYHADGGKVPIKWMALESILRRRFTHQSDVWSYGVTVWELMTF GAKPYDGIPAREIPDLLEKGERLPQPPICTIDVYMIMVKCWMIDSECRPRFRELVSEFSR MARDPQRFVVIQNEDLALGTGSTAHRRHRSSSPPPPIRPAGATLERPKTLSPGKNGVVK DVFAFGGAVENPEYL (SEQ ID NO: 61); and a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TMRRLLQETELVEPLTPSGAMPNQAQMRILKETELRKVKVLGSGAFGTVYKGIWIPDGE NVKIPVAIKVLRENTSPKANKEILDEAYVMAGVGSPYVSRLLGICLTSTVQLVTQLMPY GCLLDHVREHRGRLGSQDLLNWCVQIAKGMSYLEDVRLVHRDLAARNVLVKSPNHV KITDFGLARLLDIDETEYHADGGKVPIKWMALESILRRRFTHQSDVWSYGVTVWELMT FGAKPYDGIPAREIPDLLEKGERLPQPPICTIDVYMIMVKCWMIDSECRPRFRELVSEFSR MARDPQRFVVIQNEDLTPGTGSTAHRRHRSSSPLPPVRPAGATLERPKTLSPGKNGVVK DVFAFGGAVENPEYL (SEQ ID NO: 62). In some cases, the compositions may comprise a nucleic acid sequence encoding an epitope of the peptide IGF-1R is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of TGGTCCTTCGGCGTGGTGCTGTGGGAGATCGCCACCCTGGCCGAGCAGCCCTACCA GGGCCTGTCCAACGAGCAGGTGCTGCGCTTCGTGATGGAGGGCGGCCTGCTGGACA AGCCCGACAACTGCCCCGACATGCTGTTCGAGCTGATGCGCATGTGCTGGCAGTAC AACCCCAAGATGCGCCCTCCTTCCTGGAGCACAAGGCCGAGAACGGCCCCGGCCC CGGCGTGCTGGTGCTGCGCGCCTCCTTCGACGAGCGCCAGCCCTACGCCCACATGA ACGGAGGCCGCAAGAACGAGCGCGCCCTGCCC (SEQ ID NO: 63); a nucleotide sequence having at least 50%, 60%, 70%, 80%, 90%, 91%, 92%, 93%, 94%, 95%, 96%, 97%, 98%, 99%, or 100% sequence identity to the nucleotide sequence of TGGTCCTTCGGCGTGGTGCTGTGGGAGATCGCCACCCTGGCCGAGCAGCCCTACCA GGGCCTGTCCAACGAGCAGGTGCTGCGCTTCGTGATGGAGGGCGGCCTGCTGGACA AGCCCGACAACTGCCCCGACATGCTGTTCGAGCTGATGCGCATGTGCTGGCAGTAC AACCCCAAGATGCGCCCCTCCTCCTGGAGCACAAGGCCGAGAACGGCCCCGGCCC CGGCGTGCTGGTGCTGCGCGCCTCCTTCGACGAGCGCCAGCCCTACGCCCACATGA ACGGCGGCCGCGCCAACGAGCGCGCCCTGCCC (SEQ ID NO: 64); a nucleotide sequence having at least 50%, 60%, 70%, 80%, 90%, 91%, 92%, 93%, 94%, 95%, 96%, 97%, 98%, 99%, or 100% sequence identity to the nucleotide sequence of TGGTCCTTCGGCGTGGTGCTGTGGGAGATCGCCACCCTGGCCGAGCAGCCCTACCA GGGCCTGTCCAACGAGCAGGTGCTGCGCTTCGTGATGGAGGGCGGCCTGCTGGACA AGCCCGACAACTGCCCCGACATGCTGTGTCGAGCTGATGCGCATGTGCTGGCAGTAC AACCCCAAGATGCGCCCCTCCTfCCTGGAGCACAAGGCCGAGAACGGCCCCGGCGT GCTGGTGCTGCGCGCCTCCTTCGACGAGCGCCAGCCCTACGCCCACATGAACGGCG GCCGCGCCAACGAGCGCGCCCTGCCC (SEQ ID NO: 65); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of DYRSYRFPKLTVITE (SEQ ID NO: 66); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of IRGWKLFYNYALVIF (SEQ ID NO: 67); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of VVTGYVKIRHSHALV (SEQ ID NO: 68); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of FFYVQAKTGYENFIH (SEQ ID NO: 69); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LIIALPVAVLLIVGG (SEQ ID NO: 70); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LVIMLYVFHRKRNNS (SEQ ID NO: 71); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of NCHHVVRLLGVVSQG (SEQ ID NO: 72), a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of WSFGVVLWEIATLAEQPYQGLSNEQVLRFVMEGGLLDKPDNCPDMLFELMRMCWQY NPKMRPSFLEHKAENGPGPGVLVLRASFDERQPYAHMNGGRKNERALP (SEQ ID NO: 73); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of WSFGVVLWEIATLAEQPYQGLSNEQVLRFVMEGGLLDKPDNCPDMLFELMRMCWQY NPKMRPSFLEHKAENGPGPGVLVLRASFDERQPYAHMNGGRANERALP (SEQ ID NO: 74); and a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of WSFGVVLWEIATLAEQPYQGLSNEQVLRFVMEGGLLDKPDNCPDMLFELMRMCWQY NPKMRPSFLEHKAENGPGVLVLRASFDERQPYAHMNGGRANERALP (SEQ ID NO: 75). In some cases, the compositions may comprise a nucleic acid sequence encoding a fusion protein of three epitopes is selected from the group consisting of: a nucleotide sequence having at least 50%, 60%, 70%, 80%, 90%, 91%, 92%, 93%, 94%, 95%, 96%, 97%, 98%, 99%, or 100% sequence identity to the nucleotide sequence of ATGGCGGTACCAATGCTGCCGAGAGTGGCTGCCCCGCGCTGCCCCGCGCC GCCGCTGCTGCCGCTGCTGCCGCTGCTGCTGCTGCTACTGGGCGGCAGTGOCGGCG GCGGCGGGGCGCGCGGAGGTGCTGTTCCGCTGCCCGCCCTGCACACCCGAGCGC CTGGCCGCCTGCGGGCCCCCGCCGGTTGCCGCCCGCCCGCCGCGGTGGCCGCAGTGGC CGGAGGCGCCCGCATGCCATGCGCGGAGTCTCCCGGGGAGCCGGGCTGCGGCTGCT GCTCGGTGTGCGCCCGGCTGGAGGGCGAGGCGTGCGGCGTCTACACCCCGCGCTGC GGCCAGGGGCTGCGCTGCTATCCCCACCCGGGCTCCGAGCTGCCCCTGCAGGCGCT GGTCATGGGCGAGGGCACTTGTGAGAAGCGCCGGGACGCCGAGTATGGCGCCAGC CCGGAGCAGGTTIGCAGACAATGGCGATGACCACTCAGAAGGAGGCCTGGTGGAGC AATTGACGATGCGGAGACTGCTGCAGGAAACGGAGCTGGTGGAGCCGCTGACACCT AGCGGAGCGATGCCCAACCAGGCGCAGATGCGGATCCTGAAAGAGACGGAGCTGA GGAAGGTGAAGGTGCTTGGATCTGGCGCTTTTGGCACAGTCTACAAGGGCATCTGG ATCCCTGATGGGGAGAATGTGAAAATCCAGTGGCCATCAAAGTGTGAGGGAAAA CACATCCCCCAAAGCCAACAAAGAAATCTTAGACGAAGCATACGTGATGGCTGGTG TGGGCTCCCCATATGTCTCCCGCCTCTGGGCATCTGCCTGACATCCACGGTGCAGC TGGTGACACAGCTTATGCCCTATGGCTGCCTCTAGACCATGTCCGGGAAAACCGCG GACGCCTGGGCTCCCAGGACCTGCTGAACTGGTGTATGCAGATTGCCAAGGGGATG AGCTACCTGGAGGATGTGCGGCTCGTACACAGGGACTTGGCCGCTCGGAACGTGCT GGTCAAGAGTCCCAACCATGTCAAAATTACAGACTTCGGGCTGGCTCGGCTGCTGG ACATTGACGAGACAGAGTACCATGCAGATGGGGGCAAGGTGCCCATCAAGTGGAT GGCGCTGGAGTCCATCTCCGCCGGCGGTTCACCCACCAGAGTGATGTGTGGAGT ATGGTGTGACTGTGTGGGAGCTGATGACTTGGGGCCAAACCTACGATGGGATC CCAGCCCGGGAGATCCCTGACCTGCTGGAAAAGGGGAGCGGCTGCCCCAGCCCCC CATCTGCACCATTGATGTCTACATGATCATGGTCAAATGTTGGATGATTGACTCTGA ATGTCGGCCAAGATCCGGGAGTGGTGTCTGAATCTCCCGCATGGCCAGGGACC CCCAGCGCTTTTGTGGTCATCCAGAATGAGGACTTGGCTCCCGGAGCTGGCGGCATG GTGCACCACAGGCACCGCAGCTCATCTCCTCTGCCTGCTGCCCGACCTGCTGGTGCC ACTCTGGAAAGGCCCAAGACTCTCTCCCCAGGGAAGAATGGGGTCGTCAAAGACGT TTTTGCCTTTGGGGGTGCCGTGGAGAACCCCGAGTACTTGGGCCGGCCGGTACCTG GTCCTTCGGCGTGGTGCTGTGGGAGATCGCCACCCTGGCCGAGCAGCCCTACCAGG GCCTGTCCAACGAGCAGGTGCTGCGCTTCGTGATGGAGGGCGGCCTGCTGGACAAG CCCGACAACTGCCCCGACATGCTGTCGAGCTGATGCGCATGTGCTGGCAGTACAA CCCCAAGATGCGCCCCTCCTTCCTGGAGCACAAGGCCGAGAACGGCCCCGGCCCCG GCGTGCTGGTGCTGCGCGCCTCCTTCGACGAGCGCCAGCCCTACGCCCACATGAAC GGAGCCGCAAGAACGAGCGCGCCCTGCCCGCGGCCGCATAG (SEQ ID NO: 76); a nucleotide sequence having at least 50%, 60%, 71%, 80%, 90%, 91%, 92%, 93%, 94%, 95%, 96%, 97%, 98%, 99%, or 100% sequence identity to the nucleotide sequence of ATGGCGGTACCAATGCTGCCCCGCCTGGGCGGCCCCGCCCTGCCCTGCTGCTGCCC TCCCTGCTGCTGCTGCTGCT GCTGGGCGCCGGCGGCTGCGGCCCCGGCGTGCGCGCC GAGGTGCTGTTCCGCTGCCCCCCTGCACCCCGAGCGCCTGGCCGCCTGCGGCCCCCCCCCCGACGCCCCTGCGCCGAGCTGGTGCGCGAGCCCGGCTGCGGCTGCTGCTC CGTGTGCGCCGCCAGGAGGGCGAGGCCTGCGGCGTGTACATCCCCCGCTGCGCCCAGACCCTGCGCTGCTACCCCAACCCCGGCTCCGAGCTGCCCCTGAAGGCCCTGGTG ACCGGCGCCGGCACCTGCGAGAAGCGCCGCGTGGGCACCACCCCCCAGCAGGTGGCCGACTCCGACGACGACCACTCCGAGGGCGGCCTGGTGGAGCAATTGACCATGCGCC GCCTGCTGCAGGAGACCGAGCTGGTGGAGCCCCTGACCCCCTCCGGCGCCGTGCCCAACCAGGCCCAGATGCGCATCCTGAAGGAGACCGAGCTGCGCAAGCTGAAGGTGCT GGGCTCCGGCGCCTFCGGCACCGTGTACAAGGGCATCTGGATCCCCGACGGCGAGAACGTGAAGATCCCCGTGGCCATCAAGGTGCTGCGCGAGAACACCTCCCCAAGGCC AACAAGGAGATCCTGGACGAGGCCTACGTGATGGCCGGCGTGGGCTCCCCCTACGTGTCCCGCCTGCTGGGCATCTGCCTGACCTCCACCGTGCAGCTGGTGACCCAGCTGAT GCCCTACGGCTGCCTGCTGGACCACGTGCGCGAGCACCGCGGCCGCCTGGGCTCCCAGGACCTGCTGAACTGGTGCGTGCAGATCGCCAAGGGCATGTCCTACCTGGAGGAG GTGCGCCTGGTGCACCGCGACCTGGCCGCCCGCAACGTGCTGGTGAAGTCCCCCAACCACGTGAAGATCACCGACTTCGGCCTGGCCCGCCTGCTGGACATCGACGAGACCG AGTACCACGCCGACGGCGGCAAGGTGCCCATCAAGTGGATGGCCCTGGAGTCCATCCTGCGCCGCCGCTTCACCCACCAGTCCGACGTGTGGTCCTACGGCGTGACCGTGTGG GAGCTGATGACCTTCGGCGCCAAGCCCTACGACGGCATCCCCGCCCGCGAGATCCCCGACCTGCTGGAGAAGGGCGAGCGCCTGCCCCAGCCCCCCATCTGCACCATCGACG TGTACATGATCATGGTGAAGTGCTGGATGATCGACTCCGAGTGCCGCCCCCGCTTCCGCGAGCTGGTGTCCGAGTTCTCCCGCATGGCCCGCGACCCCCAGCGCTCGTGGTGA TCCAGAACGAGGACCTGGCCCTGGGCACCGGCTCCACCGCCCACCGCCGCCACCGCTCCTCCTCCCCCCCCCCCCCATCCGCCCCGCCGGCGCCACCCTGGAGCGCCCCAAG ACCCTGTCCCCCGGCAAGAACGGCGTGGTGAAGGACGTGTCGCCTTCGGCGGCGCCGTGGAGAACCCCGAGTACCTGGGCCGGCCGGTACCTFGGTCCTTCGGCGTGGTGC TGTGGGAGATCGCCACCCTGGCCGAGCAGCCCTACCAGGGCCTGTCCAACGAGCAGGTGCTGCGCTCGTGATGGAGGiCGGCCTGCTGGACAAGCCCGACAACTGCCCCGA CATGCTGTTCGAGCTGATGCGCATGTGCTGGCAGTACAACCCCAAGATGCGCCCTCCTTCCTGGAGCACAAGGCCGAGAACGGCCCCGGCCCCGGCGTGCTGGTGCTGCGCG CCTCCTCGACGAGCGCCAGCCCTACGCCCACATGAACGGiCGGCCGCGCCAACGAGCGCGCCCTGCCCGCGGCCGCATAG (SEQ ID NO: 77); a nucleotide sequence having at least 50%, 60%, 70%, 80%, 90%, 91%, 92%, 93%, 94%, 95%, 96%, 97%, 98%, 99%, or 100%, sequence identity to the nucleotide sequence of ATGGCGGTACCAATGCTGCCCCGCCTGGGCGGCCCCGCCCTGCCCCTGCTGCTGCCC TCCCTGCTGCTGCTGCTGCTGGGCGCCGGCGGCTGCGGCCCCGGCGTGCGCGCC GAGGTGCTGTCCGCTGCCCCCCTGCACCCCGAGCGCCTGGCCGCCTGCGGCCCCCCCCCCGACGCCCCCTGCGCCGAGCTGGTGCGCGAGCCCGGCTGCGGCTGCTGCTC CGTGTGCGCCGCCAGGAGGGCGAGGCCTGCGGCGTGTACATCCCCCGCTGCGCCCAGACCCTGCGCTGCTACCCCAACCCCGGCTCCGAGCTGCCCCTGAAGGCCCTGGTG ACCGGCGCCGGCACCTGCGAGAAGCGCCGCGTGGGCGCCACCCCCCAGCAGGTGGCCGACTCCGAGGACGACCACTCCGAGGGCGGCCTGGTGGAGCAATGACCATGCGCC GCCTGCTGCAGGAGACCGAGCTGGTGGAGCCCCTGACCCCCTCCGGCGCCATGCCCAACCAGGCCCAGATGCGCATCCTGAAGGAGACCGAGCTGCGCAAGGTGAAGGTGC TGGGCTCCGGCGCCTTCGGCACCGTGTACAAGGGCATCTGGATCCCCGACGGCGAGAACGTGAAGATCCCCGTGGCCATCAAGGTGCTGCGCGAGAACACCTCCCCAAGGC CAACAAGGAGATCCTGGACGAGGCCTACGTGATGGCCGGCGTGGGCTCCCCCTACGTGTCCCGCCTGCTGGGCATCTGCCTGACCTCCACCGTGCAGCTGGTGACCCAGCTGA TGCCCTACGGCTGCCTGCTGGACCACGTGCGCGAGCACCGCGGCCGCCTGGGCTCCCAGGACCTGCTGAACTGGTGCGTGCAGATCGCCAAGGGCATGTCCTACCTGGAGGA CGTGCGCCTGGTGCACCGCGACCTGGCCGCCCGCAACGTGCTGGTGAAGTCCCCCAACCACGTGAAGATCACCGACTCGGCCTGGCCCGCCTGCTGGACATCGACGAGACC GAGTACCACGCCGACGGCGGCAAGGTGCCCATCAAGTGGATGGCCCTGGAGTCCATCCTGCGCCGCCGCTTCACCCACCAGTCCGACGTGTGGTCCTACGGCGTGACCGTGTG GGAGCTGATGACCTCGGCGCCAAGCCCTACGACGGCATCCCCGCCCGCGAGATCCCCGACCTGCTGGAGAAGGGCGAGCGCCTGCCCCAGCCCCCCATCTGCACCATCGAC GTGTACATGATCATGGTGAAGTGCTGGATGATCGACTCCGAGTGCCGCCCCCGCTFCCGCGAGCTGGTGTCCGAGTTCTCCCGCATGGCCCGCGACCCCCAGCGCTTCGTGGTG ATCCAGAACGAGGACCTGACCCCCGGCACCGGCTCCACCGCCCACCGCCGCCACCGCTCCTCCTCCCCCCTGCCCCCGTGCGCCCCGCCGGCGCCACCCTGGAGCGCCCCAA GACCCTGTCCCCCGGCAAGAACGGCGTGGTGAAGGACGTGTCGCCTCGGCGGCGCCGTGGAGAACCCCGAGTACCTGGGCCGGCCGGTACCTTGGTCCTCGGCGTGGTG CTGTGGGAGATCGCCACCCTGGCCGAGCAGCCCTACCAGGGCCTGTCCAACGAGCAGGTGCTGCGCTTCGTGATGGAGGGCGGCCTGCTGGACAAGCCCGACAACTGCCCCG ACATGCTGTTCGAGCTGATGCGCATGTGCTGGCAGTACAACCCCAAGATGCGCCCCTCCTCCTGGAGCACAAGGCCGAGAACGGCCCCGGCGTGCTGGTGCTGCGCGCCTC CTCGACGAGCGCCAGCCCTACGCCCACATGAACGGCGGCCGCGCCAACGAGCGCG CCCTGCCCGCGGCCGCATAG (SEQ ID NO: 78); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMLPRVGCPALPLPPPPLLPLL-PLLLLLLGASGGGGGARAEVLFRCPPCTPERLAAC GPPPVAPPAAV AAVAGGARMPCAELVREPGCGCCSV-CARLEGEACGVYTPRCGQGLR CYPHPGSEL-PLQALVMGEGTCEKRRDAEYGASPEQVADNGDDH-SEGGLVEQLTMRRL LQETELVEPLTPSGAMPNQAQMRILKETELRKVKV-LGSGAFGTVYKGIWIPDGENVKIP VAIKVLRENTSP-KANKEILDEAYVMAGVGSPYVSRLLGICLTST-VQLVTQLMPYGCLLD HVRENRGRLGSQDLLNWCMQIAKGMSYLEDVR-LVHRDLAARNVLVKSPNHVKITDFG LARLLDIDE-TEYHADGGKVPIKWMALESILRRRFTHQSD-VWSYGVTVWELMTFGAKPY DGIPAREIPDLLEKGERLPQPPICTIDVYMIMVKCW-MIDSECRPRFRELVSEFSRMARDP QRFVVIQNED-LAPGAGGMVHHRHRSSSPLPAARPAGATLERPKTL-SPGKNGVVKDVFA FGGAVENPEYLGRPVPWSFGVVLWEIATLAEQPY-QGLSNEQVLRFVMEGGLLDKPDNC PDMLFELMRM-CWQYNPKMRPSFLEHKAENGPGPGVLVLRASFDER-QPYAHMNGGRK NERALPAAA (SEQ ID NO: 79); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMLPRLGGPALPLLLPSLLLLLLLGAGGCG-PGVRAEVLFRCPPCTPERLAACGPPP DAPCAEL-VREPGCGCCSVCARQEGEACGVYIPRCAQTLRCYP-NPGSELPLKALVTGAGT CEKRRVGTTPQQVADSDDDHSEGGLVEQLTMR-RLLQETELVEPLTPSGAVPNQAQMRI LKETELRKLK-VLGSGAFGTVYKGIWIPDGENVKIPVAIKVLRENTSP-KANKEILDEAYV MAGVGSPYVSRLLGICLTSTVQLVTQLMPYGCLLD-HVREHRGRLGSQDLLNWCVQIAK GMSYLEEVR-LVHRDLAARNVLVKSPNHVKITDFGLARLLDIDE-TEYHADGGKVPIKWM ALESILRRRFTHQSDVWSYGVTVWELMTFGAKPYD-GIPAREIPDLLEKGERLPQPPICTI DVYMIMVKCW-MIDSECRPRFRELVSEFSRMARDPQRFVVIQNEDLA-LGTGSTAHRRHR SSSPPPPIRPAGATLERPKTLSPGKNGVVKDVFAFG-GAVENPEYLGRPVPWSFGVVLWEI ATLAEQPYQGL-SNEQVLRFVMEGGLLDKPDNCPDMLFELMRM-CWQYNPKMRPSFLEH KAENGPGPGVLVLRASFDERQPYAHMNGGRANER-ALPAAA (SEQ ID NO: 80); and a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMLPRLGG-PALPLLLPSLLLLLLLGAGGCGPGVRAEVLFRCPPCT-PERLAACGPPP DAPCAELVREPGCGCCSVCARQEGE-ACGVYIPRCAQTLRCYPNPGSELPLKALVTGAGT CEKRRVGATPQQVADSEDDHSEGGLVEQLTMR-RLLQETELVEPLTPSGAMPNQAQMRI LKETELRKVK-VLGSGAFGTVYKGIWIPDGENVKIPVAIKVLRENTSP-KANKEILDEAYV MAGVGSPYVSRLLGICLTSTVQLVTQLMPYGCLLD-HVREHRGRLGSQDLLNWCVQIAK GMSYLEDVR-LVHRDLAARNVLVKSPNHVKITDFGLARLLDIDE-TEYHADGGKVPIKW MALESILRRRFTHQSDVWSYGVTVWELMTFGAKPY-DGIPAREIPDLLEKGERLPQPPICT IDVYMIMVKCW-MIDSECRPRFRELVSEFSRMARDPQRFVVIQNEDLT-PGTGSTAHRRHR SSSPLPPVRPAGATLERPKTLSPGKNGVVKDVFAFG-GAVENPEYLGRPVPWSFGVVLW EIATLAEQPYQGL-SNEQVLRFVMEGGLLDKPDNCPDMLFELMRM-CWQYNPKMRPSFL EHKAENGPGVLVLRASFDERQPYAHMNGGRANER-ALPAAA (SEQ ID NO: 81).

In some cases, the compositions may comprise a first and a second epitope independently selected from: CD105, Yb-1, SOX-2, CDH3 or MDM2. In some cases, the compositions may comprise a Third epitope, the first, second and Third epitopes independently selected from: CD105, Yb-1, SOX-2, CDH3 or MDM2. In some cases, the compositions may comprise a Third and a fourth epitope, the first, second, Third and fourth epitopes independently selected from: CD105, Yb-1, SOX-2, CDH3 or MDM2. In some cases, the compositions may comprise a Third, a fourth and a fifth epitope, the first, second, Third, fourth and fifth epitopes independently selected from: CD105, Yb-1, SOX-2, CDH3 or MDM2.

In some cases, the compositions may comprise a first and a second epitope independently selected from: IGFBP2, HER-2 or IGF-1R. In some cases, the compositions may comprise a Third epitope, the first, second and Third epitopes independently selected from: IGFBP2, HER-2 or IGF-1R.

In some cases, the compositions may be capable of being administered to a subject. In some cases, the subject is in need of administration of the composition. In some cases, the composition is effective to elicit an immune response in a subject. In some cases, the composition is effective to eliminate a number of cells associated with breast cancer in a subject. In some cases, the composition can be used to prevent the growth of cells associated with breast cancer in a subject.

In some cases, the first and the second nucleic acid sequences are located on the first plasmid. In some cases, the second nucleic acid sequence is located on a second plasmid.

In some cases, the cells associated with breast cancer are selected from: breast cells expressing atypical features, pre-neoplastic breast cells, breast cancer cells, pre-invasive breast cancer cells, breast cancer stem cells, epithelial cells, mesenchymal cells, stromal cells, or a combination thereof.

In some cases, the first and the second nucleic acid sequences are purified to at least 70% purity. In some cases, the first and the second nucleic acid sequences are located on the first plasmid and are separated by a sequence of linker nucleic acids. In some cases, the first nucleic acid sequence is adjacent to the second nucleic acid sequence on the first plasmid.

In some cases, at least the first plasmid is contained within a pharmaceutical composition. In some cases, at least the first plasmid is contained within a pharmaceutical composition further comprising a pharmaceutical carrier. In some cases, at least the first plasmid is contained within a pharmaceutical composition further comprising a pharmaceutical carrier and an adjuvant. In some cases, at least the first plasmid is contained within a pharmaceutical composition further comprising an adjuvant. In some cases, the composition further comprises an adjuvant and a pharmaceutically acceptable carrier. In some cases, the adjuvant is GM-CSF.

In some cases, a subject is selected from: a human with breast cancer, a mouse with breast cancer or a rat with breast cancer. In some cases, a subject is selected from: a human without breast cancer, a mouse without breast cancer or a rat without breast cancer.

In some cases, the immune response is a Type 1 immune response. In some cases, the first nucleic acid sequence is a species selected from: human, mouse or rat. In some cases, the second nucleic acid sequence is a species selected from: human, mouse or rat. In some cases, the immune response is characterized by a ratio of Type I cytokine production to Type II cytokine production that is greater than 1. In some cases, the immune response is characterized by a ratio of Type I cytokine production to Type II cytokine production that is less than 1. In some cases, the immune response is characterized by a ratio of IFNγ production to IL-10 production that is greater than 1. In some cases, the immune response is characterized by a ratio of IFNγ production to IL-10 production that is less than 1.

In some cases, the compositions include a composition comprising: a first plasmid comprising a first nucleotide sequence, the first nucleotide sequence encoding a first epitope of a first antigen, the first epitope is a portion of an HIF-1α peptide, wherein the first nucleotide sequence is located in a plasmid. In other cases, the compositions include a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are portions of an HIF-1α peptide, wherein the first nucleotide sequence and the second nucleotide sequence are located in one or more plasmids.

The nucleic acid sequences which encode epitopes from the following proteins, CD105, HIF1α, MDM2, Yb-1, SOX-2, HER-2, IGFBP2, IGF-1R and CDH3 may differ from those listed herein. In some cases, nucleic acid sequences which are greater than 50%, 60%, 70%, 80%, 90%, 91%, 92%, 93%, 94%, 95%, 96%, 97%, 98%, 99%, or 100%, or greater than 50% homologous to those disclosed herein may be used in the compositions described herein.

The compositions described herein, in some cases, may include a composition comprising: a first epitope of a first antigen expressed by cells associated with breast cancer; and a second epitope of a second antigen expressed by cells associated with breast cancer.

In some cases, the composition may comprise: at least a first epitope of a first antigen, the first epitope is a portion of a peptide selected from: CD105, Yb-1, SOX-2, CDH3 or MDM2. In some cases, the composition may comprise: at least a first epitope of a first antigen, at least a second epitope of a second antigen, the first and the second epitopes are independently selected from: CD105, Yb-1, SOX-2, CDH3 or MDM2. In some cases, at least a first epitope of the peptide CD105 is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of EARMLNASIVASFVELPL (SEQ ID NO: 6); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of QNGTWPREVLLVLSVNSSVFLHLQALGIPLHLAYNS-SLVTFQEPPGVNTTEL (SEQ ID NO: 1); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TVFMRLNIISPDLSGCTSKGLVLPAVL-GITFGAFLIGALLTAALWYIYSHTRSPSKREPVV AVAAPASSESSSTNHSIGSTQSTPCSTSSMA (SEQ ID NO: 8); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TVSMRLNIVSP-DLSGKGLVLPSVLGITFGAFLIGALLTAALWYIYSH-TRGPSKREPVVAV AAPASSESSSTNHSIGSTQSTPCST-SSMA (SEQ ID NO: 9); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TVSMRLNIVSPDLSGKGLVLPSVLGITFGAFLIGALL-TAALWYIYSHTRAPSKREPVVAV AAPASSESSST-NHSIGSTQSTPCSTSSMA (SEQ ID NO: 10). In some cases, at least a first epitope of the peptide Yb-1 is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of EDVFVHQTAIKKNNPRK (SEQ ID NO: 14); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of YRRNFNYRRRRPEN (SEQ ID NO: 15); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of GVPVQGSKYAADRNHYR-RYPRRRGPPRNYQQN (SEQ ID NO: 16). In some cases, at least a first epitope of the peptide SOX-2 is selected from the group consisting of an amino acid sequence, the amino acid sequence having at least 50%, 60%, 70%, 80%, 90%, 91%, 92%6, 93%, 94%, 95%, 96%, 97%, 98%, 99° %, or 100° % sequence identity to the amino acid sequence of GLNAHGAAQMQPMHRYDVSALQYNSMTSSQ-TYMNGSPTYSMSYSQQGTPGMALGSM GSV (SEQ ID NO: 20). In some cases, at least a first epitope of the peptide CDH3 is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of RSLKERNPLKIFPSKRILRRHKRDWV-VAPISVPENGKGPFPQRLNQLKSNKDRDTKIFYSI TGPGADSPPEGVFAVEKET (SEQ ID NO: 25); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LKIFPSKRILRRHKRDWV-VAPISVPENGKGPFPQRLNQLKSNKDRDTKIFYSITG-PGADSP PEGVFAVEKET (SEQ ID NO: 26); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of AMHSPPTRILRRRKREWVMP-PIFVPENGKGPFPQRLNQLKSNKDRGTKIFYSITGP-GADS PPEGVFTIEKES (SEQ ID NO: 27); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of VMNSPPSRILRRRKREWVMPPIS-VPENGKGPFPQRLNQLKSNKDRGTKLFYSITGP-GADS PPEGVFTIEKET (SEQ ID NO: 28). In some cases, at least a first epitope of the peptide MDM-2 is selected from the group consisting of an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TYTM-KEVLFYLGQYIMTKRLYDEKQQHIVYCSNDLL-GDLFGVPSFSVKEHRKIYTMIYR NLVVVNQQESSDS-GTSV (SEQ ID NO: 32); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TYTM-KEIIFYIGQYIMTKRLYDEKQQHIVYCSNDLLGDVF-GVPSFSVKEHRKIYAMIYRN LVAVSQQDSGTSLS (SEQ ID NO: 33); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of IYTMKEII-FYIGQYIMTKRLYDEKQQHIVYCSNDLLGDVF-GVPSFSVKEHRKIYAMIYRN LVVVSQQDSGTSPS (SEQ ID NO: 34).

In some cases, the compositions described herein include an amino acid sequence of a fusion peptide of five epitopes is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMQLSCSRQNGTWPREVLLVLS-VNSSVFLHLQALGIPLHLAYNSSLVTFQEPPGVN TITELRSTGGVPVQGSKYAADRNHYRRYPRRRGP-PRNYQQNTRGLNAHGAAQMQPMH RYD-VSALQYNSMTSSQTYMNGSPTYSMSYSQQGTPG-MALGSMGSVRSQLRSLKERNP LKIFPSKRILRRHKRDWVVAPISVPENGKGPFPQRLN-QLKSNKDRDTKIFYSITGPGADSP PEGV-FAVEKETRSAGETYTMKEVLFYLGQYIMT-KRLYDEKQQHIVYCSNDLLGDLFGV PSFSVKEHRKIYTMIYRNLVVVNQQESSDSGTSVSRS (SEQ ID NO: 39); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMT-VFMRLNIISPDLSGCTSKGLVLPAVLGITFGAFLI-GALLTAALWYIYSHTRSPS KREPVVA-VAAPASSESSSTNHSIGSTQSTPCSTSSMATGGVPVQ-GSKYAADRNHYRRYP RRRGPPRNYQQNTRGLNAH-GAAQMQPMHRYDVSALQYNSMTSSQTYMNGSP-TYSMS YSQQGTPGMALGSMGSVRSQLLKIFPSKRIL-RRHKRDWVVAPISVPENGKGPFPQRLNQ LKSNKDRDTKIFYSITGPGADSPPEGV-FAVEKETRSAGETYTMKEVLFYLGQYIMTKRL YDEKQQHIVYCSNDLLGDLFGVPSFSVKEHRKIYT-MIYRNLVVVNQQESSDSGTSVSRS (SEQ ID NO: 40); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMTVSMRLNIVSPDLS-GKGLVLPSVLGITFGAFLIGALLTAALWYIYSH-TRGPSKRE PVVAVAAPASSESSSTNHSIGSTQSTPCST-SSMATGGVPVQGSKYAADRNHYRRYPRRR GPPRNYQQNTRGLNAHGAAQMQPMHRYD-VSALQYNSMTSSQTYMNGSPTYSMSYSQ QGTPG-MALGSMGSVRSQLAMHSPPTRILRRRKREWVMP-PIFVPENGKGPFPQRLNQLK SNKDRGTKIFYSITGPGADSPPEGVFTIEKESRSAG-ETYTMKEIIFYIGQYIMTKRLYDEK QQHIVYC-SNDLLGDVFGVPSFSVKEHRKIYAMIYRNLVA-VSQQDSGTSLSRS (SEQ ID NO: 41); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMTVSMRLNIVSPDLSGKGLV-LPSVLGITFGAFLIGALLTAALWYIYSHTRAPSKRE PVVAVAAPASSESSSTNHSIGSTQSTPCSTSSMATG-GVPVQGSKYAADRNHYRRYPRRR GPPRNYQQN-TRGLNAHGAAQMQPMHRYDVSALQYNSMTSSQ-TYMNGSPTYSMSYSQ QGTPGMALGSMGSVRSQLVMNSPPSRILR-RRKREWVMPPISVPENGKGPFPQRLNQLKS NKDRGTKLFYSITGPGADSPPEGVFTIEKETRSAGEI-YTMKEIIFYIGQYIMTKRLYDEKQ QHIVYCSNDLL-GDVFGVPSFSVKEHRKIYAMIYRNLVVVSQQDS-GTSPSRS (SEQ ID NO: 42).

The compositions described herein may further include a composition comprising: a first plasmid comprising a first nucleotide sequence, the first nucleotide sequence encoding a first epitope of a first antigen, the first epitope is a portion of a peptide selected from: IGFBP-2, HER-2 or IGF-1R, wherein the first nucleotide sequence is located in a plasmid. In some cases, the composition may comprise: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: IGFBP-2, HER-2 or IGF-1R, wherein the first nucleotide sequence and the second nucleotide sequence are located in one or more plasmids. In some cases, at least a first epitope of the peptide IGFBP-2 is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of NHVDST-MNMLGGGGS (SEQ ID NO: 46); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of ELAVFREKVTEQHRQ (SEQ ID NO: 47); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LGLEEPKKLRPPPAR (SEQ ID NO: 48); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of DQVLERISTMRLPDE (SEQ ID NO: 49); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of GPLE-HLYSLHIPNCD (SEQ ID NO: 50); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of KHGLYNLKQCKMSLN (SEQ ID NO: 51); an amino acid sequence, the amino acid sequence having at least 50%, 60%, 70%, 80%, 90%, 91%6, 92%, 93%, 94%, 95%, 96%, 97%, 98%, 99%, or 100% sequence identity to the amino acid sequence of PECHL-FYNEQQEARG (SEQ ID NO: 53); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MLPRVGCPALPLPPPPLLPLL-PLLLLLLGASGGGGGARAEVLFRCPPCTPERLAACG-PPP VAPPAAVAAVAGGARMPCAELVREPGCGCCSV-CARLEGEACGVYTPRCGQGLRCYPH PGSELPLQALVMGEGTCEKRRDAEYGASPEQ-VADNGDDHSEGGLVE (SEQ ID NO: 54); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MLPRLGGPALPLLLPSLLLLLLLGAG-GCGPGVRAEVLFRCPPCTPERLAACGPPPDAPCA ELVREPGCGCCSVCARQEGEACGVYIPRCAQTLRCY-PNPGSELPLKALVTGAGTCEKRR VGTTPQQ-VADSDDDHSEGGLVE (SEQ ID NO: 55); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MLPRLGGPALPLLLPSLLLLLLLGAG-GCGPGVRAEVLFRCPPCTPERLAACGPPPDAPCA ELVREPGCGCCSVCARQEGEACGVYIPRCAQTLRCY-PNPGSELPLKALVTGAGTCEKRR VGATPQQ-VADSEDDHSEGGLVE (SEQ ID NO: 56). In some cases, at least a first epitope of the peptide HER-2 is selected from the group consisting of: a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TMRRLLQETELVEPLTPS-GAMPNQAQMRILKETELRKVKVLGSGAFGTVYKGI-WIPDGE NVKIPVAIKVLRENTSPKANKEILDEAY-VMAGVGSPYVSRLLGICLTSTVQLVTQLMPY GCLLDHVRENRGRLGSQDLLNWCMQIAKGM-SYLEDVRLVHRDLAARNVLVKSPNHV KITDF-GLARLLDIDETEYHADGGKVPIKWMALESILR-RRFTHQSDVWSYGVTVWELMT FGAKPYDGIPAREIPDLLEKGERLPQPPICTIDVYMIM-VKCWMIDSECRPRFRELVSEFSR MARDPQRFV-VIQNEDLAPGAGGMVHHRHRSSSPLPAARPA-GATLERPKTLSPGKNGVV KDVFAFGGAVENPEYL (SEQ ID NO: 60); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TMRRLLQETELVEPLTPSGAVPN-QAQMRILKETELRKLKVLGSGAFGTVYKGIWIPDGE NVKIPVAIKVLRENTSPKANKEILDEAYVMAGVG-SPYVSRLLGICLTSTVQLVTQLMPY GCLLDHVREH-RGRLGSQDLLNWCVQIAKGMSYLEEVRLVHRD-LAARNVLVKSPNHVK ITDFGLARLLDIDETEYHADGGKVPIKWMALESILR-RRFTHQSDVWSYGVTVWELMTF GAKPYDGIPA-REIPDLLEKGERLPQPPICTIDVYMIMVKCWMIDSE-CRPRFRELVSEFSR MARDPQRFVVIQNEDLALGTGSTAHRRHRSSSPPP-PIRPAGATLERPKTLSPGKNGVVK DVFAFGGAVEN-PEYL (SEQ ID NO: 61); or a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of TMRRLLQETELVEPLTPS-GAMPNQAQMRILKETELRKVKVLGSGAFGTVYKGI-WIPDGE NVKIPVAIKVLRENTSPKANKEILDEAY-VMAGVGSPYVSRLLGICLTSTVQLVTQLMPY GCLLDHVREHRGRLGSQDLLNWCVQIAKGM-SYLEDVRLVHRDLAARNVLVKSPNHV KITDF-GLARLLDIDETEYHADGGKVPIKWMALESILR-RRFTHQSDVWSYGVTVWELMT FGAKPYDGIPAREIPDLLEKGERLPQPPICTIDVYMIM-VKCWMIDSECRPRFRELVSEFSR MARDPQRFV-VIQNEDLTPGTGSTAHRRHRSSSPLPPVRPAGATLER-PKTLSPGKNGVVK DVFAFGGAVENPEYL (SEQ ID NO: 62). In some cases, a nucleic acid sequence encoding an epitope of the peptide IGF-1R is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of DYRSYR-FPKLTVITE (SEQ ID NO: 66); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of IRGWKLFYNYALVIF (SEQ ID NO: 67); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of VVTGYVKIRHSHALV (SEQ ID NO: 68); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of FFYVQAKTGYEN-FIH (SEQ ID NO: 69); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LIIALPVA-VLLIVGG (SEQ ID NO: 70); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of LVIMLYVFHRKRNNS (SEQ ID NO: 71); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of NCHHVVRLLGVVSQG (SEQ ID NO: 72); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of WSFGVVLWEIAT-LAEQPYQGLSNEQVLRFVMEGGLLDKPDNCPDM-LFELMRMCWQY NPKMRPSFLEHKAENGPGPGVLV-LRASFDERQPYAHMNGGRKNERALP (SEQ ID NO: 73); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of WSFGVVLWEIAT-LAEQPYQGLSNEQVLRFVMEGGLLDKPDNCPDM-LFELMRMCWQY NPKMRPSFLEHKAENGPGPGVLV-LRASFDERQPYAHMNGGRANERALP (SEQ ID NO: 74); or an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of WSFGVVLWEIAT-LAEQPYQGLSNEQVLRFVMEGGLLDKPDNCPDM-LFELMRMCWQY NPKMRPSFLEHKAENGPGVLVL-RASFDERQPYAHMNGGRANERALP (SEQ ID NO: 75).

The compositions described herein may further include a nucleic acid sequence encoding a fusion protein of three epitopes is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMLPRVGCPALPLPPPPLLPLL-PLLLLLLGASGGGGGARAEVLFRCPPCTPERLAAC GPPPVAPPAAVAAVAGGARMPCAELVREPGCGCCSV-CARLEGEACGVYTPRCGQGLR CYPHPGSEL-PLQALVMGEGTCEKRRDAEYGASPEQVADNGDDH-SEGGLVEQLTMRRL LQETELVEPLTPSGAMPNQAQMRILKETELRKVKV-LGSGAFGTVYKGIWIPDGENVKIP VAIKVLRENTSP-KANKEILDEAYVMAGVGSPYVSRLLGICLTST-VQLVTQLMPYGCLLD HVRENRGRLGSQDLLNWCMQIAKGMSYLEDVRLVHRDLAARNVLVKSPNHVKITDFG LARLLDIDETEYHADGGKVPIKWMALESILRRRFTHQSDVWSYGVTVWELMTFGAKPY DGIPAREIPDLLEKGERLPQPPICTIDVYMIMVKCWMIDSECRPRFRELVSEFSRMARDP QRFVVIQNEDLAPGAGGMVHHRHRSSSPLPAARPAGATLERPKTLSPGKNGVVKDVFA FGGAVENPEYLGRPVPWSFGVVLWEIATLAEQPYQGLSNEQVLRFVMEGGLLDKPDNC PDMLFELMRMCWQYNPKMRPSFLEHKAENGPGPGVLVLRASFDERQPYAHMNGGRK NERALPAAA (SEQ ID NO: 79), an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of MAVPMLPRLGGPALPLLLPSLLLLLLLGAGGCGPGVRAEVLFRCPPCTPERLAACGPPP DAPCAELVREPGCGCCSVCARQEGEACGVYIPRCAQTLRCYPNPGSELPLKALVTGAGT CEKRRVGTTPQQVADSDDDHSEGGLVEQLTMRRLLQETELVEPLTPSGAVPNQAQMRI LKETELRKLKVLGSGAFGTVYKGIWIPDGENVKIPVAIKVLRENTSPKANKEILDEAYV MAGVGSPYVSRLLGICLTSTVQLVTQLMPYGCLLDHVREHRGRLGSQDLLNWCVQIAK GMSYLEEVRLVHRDLAARNVLVKSPNHVKITDFGLARLLDIDETEYHADGGKVPIKWM ALESILRRRFTHQSDVWSYGVTVWELMTFGAKPYDGIPAREIPDLLEKGERLPQPPICTI DVYMIMVKCWMIDSECRPRFRELVSEFSRMARDPQRFVVIQNEDLALGTGSTAHRRHR SSSPPPPIRPAGATLERPKTLSPGKNGVVKDVFAFGGAVENPEYLGRPVPWSFGVVLWEI ATLAEQPYQGLSNEQVLRFVMEGGLLDKPDNCPDMLFELMRMCWQYNPKMRPSFLEH KAENGPGPGVLVLRASFDERQPYAHMNGGRANERALPAAA (SEQ ID NO: 80); or an amino acid sequence, the amino acid sequence having at least 50%, 60%, 70%, 80%, 90%, 91% 92%, 93%, 94%, 95%, 96%, 97%, 98%, 99%, or 100% sequence identity to the amino acid sequence of MAVPMLPRLGGPALPLLLPSLLLLLLLGAGGCGPGVRAEVLFRCPPCTPERLAACGPPP DAPCAELVREPGCGCCSVCARQEGEACGVYIPRCAQTLRCYPNPGSELPLKALVTGAGT CEKRRVGATPQQVADSEDDHSEGGLVEQLTMRRLLQETELVEPLTPSGAMPNQAQMRI LKETELRKVKVLGSGAFGTVYKGIWIPDGENVKIPVAIKVLRENTSPKANKEILDEAYV MAGVGSPYVSRLLGICLTSTVQLVTQLMPYGCLLDHVREHRGRLGSQDLLNWCVQIAK GMSYLEDVRLVHRDLAARNVLVKSPNHVKITDFGLARLLDIDETEYHADGGKVPIKW MALESILRRRFTHQSDVWSYGVTVWELMTFGAKPYDGIPAREIPDLLEKGERLPQPPICT IDVYMIMVKCWMIDSECRPRFRELVSEFSRMARDPQRFVVIQNEDLTPGTGSTAHRRHR SSSPLPPVRPAGATLERPKTLSPGKNGVVKDVFAFGGAVENPEYLGRPVPWSFGVVLW EIATLAEQPYQGLSNEQVLRFVMEGGLLDKPDNCPDMLFELMRMCWQYNPKMRPSFL EHKAENGPGVLVLRASFDERQPYAHMNGGRANERALPAAA (SEQ ID NO: 81).

In some cases, the composition comprises a first and a second epitope independently selected from: CD105, Yb-1, SOX-2, CDH3 or MDM2. In some cases, the composition further comprises a Third epitope, the first, second and Third epitopes independently selected from: CD105, Yb-1, SOX-2, CDH3 or MDM2. In some cases, the composition further comprises a Third and a fourth epitope, the first, second, Third and fourth epitopes independently selected from: CD105, Yb-1, SOX-2, CDH3 or MDM2. In some cases, the composition further comprises a Third, a fourth and a fifth epitope, the first, second, Third, fourth and fifth epitopes independently selected from: CD105, Yb-1, SOX-2, CDH3 or MDM2.

In some cases, the composition comprises a first and a second epitope independently selected from: IGFBP2, HER-2 or IGF-1R. In some cases, the composition further comprises a Third epitope, the first, second and Third epitopes independently selected from IGFBP2, HER-2 or IGF-1R.

In some cases, a composition may comprise: at least a first epitope of a first antigen, the first epitope is a portion of a peptide from HIF-1α. In some cases, a composition may comprise: at least a first epitope of a first antigen, at least a second epitope of a second antigen, the first and the second epitopes are from HIF-1α.

In some cases, the compositions may include a nucleic acid sequence encoding an epitope of the peptide HIF-1α is selected from the group consisting of: a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of DSKTFLSRHSLDMKFSYCDERITELMGYEPEELLGRSIYEYYHALDSDHLTKTHHDMFT KGQVTTGQYRMLAKRGGYVWVETQATVIYN (SEQ ID NO: 82); a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of SDNVNKYMGLTQFELTGHSVFDFTHP (SEQ ID NO: 83); and a nucleotide sequence encoding an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of GGYVWVETQATVIYNTKNSQ (SEQ ID NO: 84).

In some cases, the composition may include at least a first epitope of the peptide HIF-1α is selected from the group consisting of: an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of DSKTFLSRHSLDMKFSYCDERITELMGYEPEELLGRSIYEYYHALDSDHLTKTHHDMFT KGQVTTGQYRMLAKRGGYVWVETQATVIYN (SEQ ID NO: 82); an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of SDNVNKYMGLTQFELTGHSVFDFTHP (SEQ ID NO: 83); and an amino acid sequence, the amino acid sequence having at least 50%, 60%, 70%, 80%, 90%, 91%, 92%, 93%, 94%, 95%, 96%, 97%, 98%, 99%, or 100% sequence identity to the amino acid sequence of GGYVWVETQATVIYNTKNSQ (SEQ ID NO: 84).

The compositions described herein may contain short epitopes encoded on a single plasmid backbone. In some cases, the plasmid backbone may encode one short epitope. In other cases, the plasmids described herein may encode more than one short epitope. For example, the compositions described herein may encode two short epitopes, three short epitopes, four short epitopes, five short epitopes, six short epitopes, seven short epitopes, eight short epitopes, nine short epitopes, ten short epitopes, 11 short epitopes, 12 short epitopes, 13 short epitopes, 14 short epitopes, 15 short epitopes, 16 short epitopes, 17 short epitopes, 18 short epitopes 19 short epitopes, 20 short epitopes or more than 20 short epitopes. In an exemplary case, the plasmid encodes no more than six short epitopes.

The compositions described herein may contain extended epitopes encoded on a single plasmid backbone. In some cases, the plasmid may encode one extended epitope. In other cases, the compositions may encode more than one extended epitope. For example, the plasmids may encode two extended epitopes, three extended epitopes, four extended epitopes, five extended epitopes, six extended epitopes, seven extended epitopes, eight extended epitopes, nine extended epitopes, ten extended epitopes, 11 extended epitopes, 12 extended epitopes, 13 extended epitopes, 14 extended epitopes, 15 extended epitopes, 16 extended epitopes, 17 extended epitopes, 18 extended epitopes 19 extended epitopes, 20 extended epitopes or more than 20 extended epitopes. In an exemplary case, the plasmid encodes no more than four extended epitopes.

The compositions of breast cancer vaccines described herein may contain short epitopes and extended epitopes on a single plasmid backbone. In some cases, the plasmid may include one short epitope. In other cases, the compositions of plasmids described herein may include more than one short epitope. For example, the compositions of plasmids described herein may include two short epitopes, three short epitopes, four short epitopes, five short epitopes, six short epitopes, seven short epitopes, eight short epitopes, nine short epitopes, ten short epitopes, 11 short epitopes, 12 short epitopes, 13 short epitopes, 14 short epitopes, 15 short epitopes, 16 short epitopes, 17 short epitopes, 18 short epitopes 19 short epitopes, 20 short epitopes or more than 20 short epitopes.

In some cases, the plasmid may encode one extended epitope. In other cases, the compositions described herein may encode more than one extended epitope. For example, the compositions described herein may encode two extended epitopes, three extended epitopes, four extended epitopes, five extended epitopes, six extended epitopes, seven extended epitopes, eight extended epitopes, nine extended epitopes, ten extended epitopes, 11 extended epitopes, 12 extended epitopes, 13 extended epitopes, 14 extended epitopes, 15 extended epitopes, 16 extended epitopes, 17 extended epitopes, 18 extended epitopes 19 extended epitopes, 20 extended epitopes or more than 20 extended epitopes.

Plasmids for the compositions containing more than one sequence encoding an epitope may contain spacers between each epitope sequence. In some cases, sequences of short epitopes may be encoded in tandem without the use of spacers. In some cases, sequences of extended epitopes may be encoded in tandem without the use of spacers. In some cases, sequences of short epitopes may be encoded in tandem with the use of spacers. In some cases, sequences of extended epitopes may be encoded in tandem with the use of spacers.

In an exemplary case, a composition may be a plasmid-based vaccine containing short and extended antigenic epitopes. The plasmid, or plasmids, of the vaccine may be constructed using a 4 kB plasmid backbone (e.g., pUMVC3 or pNGVL3). Often, the plasmid may contain an antibiotic resistance gene. For example, pUMVC3 contains the kanamycin resistance gene in addition to an origin of replication for selection and propagation in bacteria. In some cases, the multiple cloning site in pUMVC3 may be flanked by eukaryotic transcriptional control elements to promote the expression of inserted sequences (e.g., gene cassettes) in eukaryotic cells. For example, the inserted sequences may be epitopes.

In an exemplary case, the nucleic acid coding sequence of the antigenic epitope peptides may be assembled with the Kozak consensus translation initiation sequence, a termination codon, and cloning sites in the plasmid backbone. Standard molecular techniques known to one of ordinary skill in the art which include synthetic oligonucleotides, polymerase chain reaction amplification, restriction endonucleases, and nucleic acid ligase (e.g., DNA ligase) may be used to generate nucleic acid (e.g., DNA fragments) and insert the nucleic acid fragments into the plasmid vector backbone.

In some cases, the plasmid may contain a nucleic acid sequence coding for at least one tag. In some cases, the tag may be translated into a peptide. Any nucleic acid sequence for a tag known to one of ordinary skill in the art may be used with the plasmids described herein. For example, the tag may be a histidine tag with three histidine residues, a histidine tag with four histidine residues, a histidine tag with five histidine residues, or a histidine tag with six histidine residues, or the like. Expression of the tag in a subject may be determined using any suitable technique known to one of ordinary skill in the art.

In some cases, plasmids may be sequenced using any sequencing technique known to one of ordinary skill in the art such that the results of the sequencing technique provides nucleotide level resolution of the entire plasmid.

In some aspects, the composition may be a multiantigen breast cancer vaccine. For example, the multiantigen breast cancer vaccine may contain a plurality of antigens. In some cases, expression of one antigen may impact expression of a different antigen. In some cases, expression of more than one antigen may impact expression of a different antigen. In some cases, expression of one antigen may impact expression of more than one different antigen. In some cases, expression of one antigen may not impact expression of a different antigen. In some cases, expression of more than one antigen may not impact expression of a different antigen. In some cases, expression of one antigen may not impact expression of more than one different antigen. For example, antigenic competition may limit the immunogenicity of multiantigen vaccines. Any techniques known to one of ordinary skill in the art may be used to determine if an immune response elicited following administration of a multiple antigen vaccine is of comparable magnitude to each antigen as a single antigen vaccine. For example, ELISPOT (e.g., for secretion of IFNγ) may determine the magnitude of the immune response. In some cases, the ELISPOT may detect rodent, non-human primate or human peptides.

Plasmids—Survivin, HIF-1A, IGF-1R, and/or IGFBP2

A composition described herein may include a nucleic acid-based vaccine which comprises a plasmid encoding one or more epitopes selected from Survivin, HIF-1A, IGF-1R, or IGFBP2. Sometimes, the epitopes may be derived from human proteins and the encoding nucleic acid sequences encoding the epitopes may be incorporated into a nucleic acid construct designed to induce expression of the epitope in a subject following administration. For example, epitopes encoded from the nucleic acid construct may allow for the immune response to at least one epitope to be entrained, amplified, attenuated, suppressed, or eliminated to specific sets of proteins (e.g., self-proteins).

In some instances, the vaccine described herein is a peptide based vaccine. The peptide based vaccine can comprise a plasmid which encodes one or more epitopes selected from Survivin, HIF-1A, IGF-1R, or IGFBP2. The epitopes may be derived from human proteins that may be used directly in a peptide based vaccine.

In some cases, the peptide or the nucleic acid construct may be optimized into a protein or plasmid-based vaccination to induce, amplify or entrain a TH1 immune response. In some cases, the epitopes may be extended TH1 epitopes. In other cases, the peptide or the nucleic acid construct may be optimized into a protein or plasmid-based vaccination to suppress, attenuate or eliminate a pathological response, in a subject (e.g., human or animal) in need thereof.

The compositions described herein may include plasmids which contain nucleic acid sequences to express at least one epitope in a subject following administration of the composition (e.g., vaccine).

Any plasmid backbones (e.g., vectors) known to one of ordinary skill in the art suitable for pharmaceutical use for expression of a nucleic sequence may be used in the compositions described herein.

The vector can be a circular plasmid or a linear nucleic acid. The circular plasmid or linear nucleic acid can be capable of directing expression of a particular nucleotide sequence in an appropriate subject cell. The vector can have a promoter operably linked to the polypeptide-encoding nucleotide sequence, which can be operably linked to termination signals. The vector can also contain sequences required for proper translation of the nucleotide sequence. The vector comprising the nucleotide sequence of interest can be chimeric, meaning that at least one of its components is heterologous with respect to at least one of its other components. The expression of the nucleotide sequence in the expression cassette can be under the control of a constitutive promoter or of an inducible promoter, which can initiate transcription only when the host cell is exposed to some particular external stimulus.

The vector can be a plasmid. The plasmid can be useful for transfecting cells with nucleic acid encoding the polypeptide, which the transformed host cells can be cultured and maintained under conditions wherein expression of the polypeptide takes place.

The plasmid can comprise a nucleic acid sequence that encodes one or more of the various polypeptide disclosed herein. A single plasmid can contain coding sequence for a single polypeptide, or coding sequence for more than one polypeptide. Sometimes, the plasmid can further comprise coding sequence that encodes an adjuvant, such as an immune stimulating molecule, such as a cytokine.

The plasmid can further comprise an initiation codon, which can be upstream of the coding sequence, and a stop codon, which can be downstream of the coding sequence. The initiation and termination codon can be in frame with the coding sequence. The plasmid can also comprise a promoter that is operably linked to the coding sequence, and an enhancer upstream of the coding sequence. The enhancer can be human actin, human myosin, human hemoglobin, human muscle creatine or a viral enhancer such as one from CMV, FMDV. RSV or EBV. Polynucleotide function enhances are described in U.S. Pat. Nos. 5,593,972, 5,962, 428, and WO94/016737.

The plasmid can also comprise a mammalian origin of replication in order to maintain the plasmid extrachromosomally and produce multiple copies of the plasmid in a cell. The plasmid can be pVAXI, pCEP4 or pREP4 from Invitrogen (San Diego, Calif.).

The plasmid can also comprise a regulatory sequence, which may be well suited for gene expression in a cell into which the plasmid is administered. The coding sequence can comprise a codon that can allow more efficient transcription of the coding sequence in the host cell.

In some cases, commercially available plasmid backbones may be used. For example, the plasmid pUMVC3 may be used. In some cases, commercially available plasmid backbones may be modified, mutated, engineered or cloned prior to use. In other cases, non-commercially available plasmid backbones may be used.

Additional plasmids can include pSE420 (Invitrogen, San Diego, Calif.), which can be used for protein production in *Escherichia coli* (*E. coli*). The plasmid can also be pYES2 (Invitrogen, San Diego, Calif.), which can be used for protein production in *Saccharomyces cerevisiae* strains of yeast. The plasmid can also be of the MAXBAC™ complete baculovirus expression system (Invitrogen, San Diego, Calif.), which can be used for protein production in insect cells. The plasmid can also be pcDNA I or pcDNA3 (Invitrogen San Diego, Calif.), which can be used for protein production in mammalian cells such as Chinese hamster ovary (CHO) cells.

The vector can be circular plasmid, which can transform a target cell by integration into the cellular genome or exist extrachromosomally (e.g., autonomous replicating plasmid with an origin of replication). Exemplary vectors include pVAX, pcDNA3.0, or provax, or any other expression vector capable of expressing DNA encoding the antigen and enabling a cell to translate the sequence to an antigen that is recognized by the immune system.

The nucleic acid based vaccine can also be a linear nucleic acid vaccine, or linear expression cassette ("LEC"), that is capable of being efficiently delivered to a subject via electroporation and expressing one or more polypeptides disclosed herein. The LEC can be any linear DNA devoid of any phosphate backbone. The DNA can encode one or more polypeptides disclosed herein. The LEC can contain a promoter, an intron, a stop codon, and/or a polyadenylation signal. The expression of the polypeptide may be controlled by the promoter. The LEC can not contain any antibiotic resistance genes and/or a phosphate backbone. The LEC can not contain other nucleic acid sequences unrelated to the polypeptide expression.

The LEC can be derived from any plasmid capable of being linearized. The plasmid can express the polypeptide. Exemplary plasmids include: pNP (Puerto Rico/34), pM2 (New Caledonia/99), WLV009, pVAX, pcDNA3.0, provax, or any other expression vector capable of expressing DNA encoding the antigen and enabling a cell to translate the sequence to an antigen that is recognized by the immune system.

Prior to inserting the nucleic acid sequence of at least one epitope, the plasmid backbone may be less than about 500 bp, about 1.0 kB, about 1.2 kB, about 1.4 kB, about 1.6 kB, about 1.8 kB, about 2.0 kB, about 2.2 kB, about 2.4 kB, about 2.6 kB, about 2.8 kB, about 3.0 kB, about 3.2 kB, about 3.4 kB, about 3.6 kB, about 3.8 kB, about 4.0 kB, about 4.2 kB, about 4.4 kB, about 4.6 kB, about 4.8 kB, about 5.0 kB, about 5.2 kB, about 5.4 kB, about 5.6 kB, about 5.8 kB, about 6.0 kB, about 6.2 kB, about 6.4 kB, about 6.6 kB, about 6.8 kB, about 7.0 kB, about 7.2 kB, about 7.4 kB, about 7.6 kB, about 7.8 kB, about 8.0 kB, about 8.2 kB, about 8.4 kB, about 8.6 kB, about 8.8 kB, about 9.0 kB, about 9.2 kB, about 9.4 kB, about 9.6 kB, about 9.8 kB, about 10.0 kB, about 10.2 kB, about 10.4 kB, about 10.6 kB, about 10.8 kB, about 11.0 kB, about 11.2 kB, about 11.4 kB, about 11.6 kB, about 11.8 kB, about 12.0 kB, about 12.2 kB, about 12.4 kB, about 12.6 kB, about 12.8 kB, about 13.0 kB, about 13.2 kB, about 13.4 kB, about 13.6 kB, about 13.8 kB, about 14 kB, about 14.5 kB, about 15 kB, about 15.5 kB, about 16 kB, about 16.5 kB, about 17 kB, about 17.5 kB, about 18 kB, about 18.5 kB, about 19 kB, about 19.5 kB, about 20 kB, about 30 kB, about 40 kB, about 50 kB, about 60 kB, about 70 kB, about 80 kB, about 90 kB, about 100 kB, about 110 kB, about 120 kB, about 130 kB, about 140 kB, about 150 kB, about 160 kB, about 170 kB, about 180 kB, about 190 kB or about 200 kB in length. In an exemplary case, the plasmid is about 4 kB in length prior to addition of the nucleic acid sequence encoding at least one epitope.

In some cases, the compositions described herein may include one plasmid. In other cases, the compositions described herein may include more than one plasmid. For example, the compositions described herein may include two plasmids, three plasmids, four plasmids, five plasmids, six plasmids, seven plasmids, eight plasmids, nine plasmids, ten plasmids, 11 plasmids, 12 plasmids, 13 plasmids, 14 plasmids, 15 plasmids, 16 plasmids, 17 plasmids, 18 plasmids 19 plasmids, 20 plasmids or more than 20 plasmids.

The nucleic acids which encode at least one epitope of a plasmid may be derived from any species such that the epitope expressed from the nucleic acids results in an immune response in a subject. In some cases, the subject may be a rodent, a non-human primate or a human. The nucleic acids encoding the epitope of the plasmid may be isolated from any source of nucleic acids using methods and techniques known to one of ordinary skill in the art. The nucleic acids encoding the epitope of the plasmid may be cloned into the plasmid backbone using methods and techniques known to one of ordinary skill in the art.

In some cases, the nucleic acid sequence encoding the epitope may be an endogenous nucleic acid sequence to the subject. For example, the nucleic acid sequence for Survivin from a human may be used to express Survivin in a human. In other cases, the nucleic acid sequence for the antigenic epitope may be an exogenous nucleic acid sequence to the subject. For example, the nucleic acid sequence for Survivin from a non-human may be used to express Survivin in a human.

In some cases, the nucleic acid sequences to express the antigenic epitope may be wild-type nucleic acid sequences. For example, the naturally occurring nucleic acid sequence for Survivin in the genome of a species may be used to express Survivin in a subject. In other cases, the nucleic acid sequences encoding the epitope may be synthetic nucleic acid sequences. For example, the naturally occurring nucleic acid sequence for Survivin in the genome of a species may be modified using molecular techniques known to one of ordinary skill in the art and may be used to express Survivin in a subject.

In some cases, the nucleic acid sequence encoding the epitope may be an endogenous nucleic acid sequence to the subject. For example, the nucleic acid sequence for HIF-1A from a human may be used to express HIF-1A in a human. In other cases, the nucleic acid sequence for the antigenic epitope may be an exogenous nucleic acid sequence to the subject. For example, the nucleic acid sequence for HIF-1A from a non-human may be used to express HIF-1A in a human.

In some cases, the nucleic acid sequences to express the antigenic epitope may be wild-type nucleic acid sequences. For example, the naturally occurring nucleic acid sequence for HIF-1A in the genome of a species may be used to express HIF-1A in a subject. In other cases, the nucleic acid sequences encoding the epitope may be synthetic nucleic acid sequences. For example, the naturally occurring nucleic acid sequence for HIF-1A in the genome of a species may be modified using molecular techniques known to one of ordinary skill in the art and may be used to express HIF-1A in a subject.

In some cases, the nucleic acid sequence encoding the epitope may be an endogenous nucleic acid sequence to the subject. For example, the nucleic acid sequence for IGFBP2 from a human may be used to express IGFBP2 in a human. In other cases, the nucleic acid sequence for the antigenic epitope may be an exogenous nucleic acid sequence to the subject. For example, the nucleic acid sequence for IGFBP2 from a non-human may be used to express IGFBP2 in a human.

In some cases, the nucleic acid sequences to express the antigenic epitope may be wild-type nucleic acid sequences. For example, the naturally occurring nucleic acid sequence for IGFBP2 in the genome of a species may be used to express IGFBP2 in a subject. In other cases, the nucleic acid sequences encoding the epitope may be synthetic nucleic acid sequences. For example, the naturally occurring nucleic acid sequence for IGFBP2 in the genome of a species may be modified using molecular techniques known to one of ordinary skill in the art and may be used to express IGFBP2 in a subject.

In some cases, the nucleic acid sequence encoding the epitope may be an endogenous nucleic acid sequence to the subject. For example, the nucleic acid sequence for IGF-1R from a human may be used to express IGF-1R in a human. In other cases, the nucleic acid sequence for the antigenic epitope may be an exogenous nucleic acid sequence to the subject. For example, the nucleic acid sequence for IGF-1R from a non-human may be used to express IGF-1R in a human.

In some cases, the nucleic acid sequences to express the antigenic epitope may be wild-type nucleic acid sequences. For example, the naturally occurring nucleic acid sequence for IGF-1R in the genome of a species may be used to express IGF-1R in a subject. In other cases, the nucleic acid sequences encoding the epitope may be synthetic nucleic acid sequences. For example, the naturally occurring nucleic acid sequence for IGF-1R in the genome of a species may be modified using molecular techniques known to one of ordinary skill in the art and may be used to express IGF-1R in a subject.

In some cases, the composition may include nucleic acids which encode one or more epitopes from the proteins Survivin, HIF-1A, IGFBP2, and IGF-1R. In some instances, the plasmid may comprise a nucleic acid sequence encoding a polypeptide that comprises at least 70% sequence identity to IGFBP-2 (SEQ ID NO: 54). In some instances, the plasmid may include a nucleic acid sequence encoding a polypeptide that comprises at least 75%, 80%, 85%, 90%, 91%, 92%, 93%, 94%, 95%, 96%, 97%, 98%, 99%, or 100% sequence identity to IGFBP-2 (SEQ ID NO: 54). In some cases, the plasmid may include a nucleic acid sequence encoding a polypeptide that comprises at least 80% sequence identity to IGFBP-2 (SEQ ID NO: 54). In some cases, the plasmid may include a nucleic acid sequence encoding a polypeptide that comprises at least 90% sequence identity to IGFBP-2 (SEQ ID NO: 54). Sometimes, the plasmid may include a nucleic acid sequence encoding a polypeptide that comprises at least 95% sequence identity to IGFBP-2 (SEQ ID NO: 54). Sometimes, the plasmid may include a nucleic acid sequence encoding a polypeptide that comprises at least 99% sequence identity to IGFBP-2 (SEQ ID NO: 54). In some instances, the plasmid may include a nucleic acid sequence encoding a polypeptide that comprises 100% sequence identity to IGFBP-2 (SEQ ID NO: 54). In some instances, the plasmid may include a nucleic acid sequence encoding a polypeptide that consists of 100% sequence identity to IGFBP-2 (SEQ ID NO: 54).

In some cases, the plasmid may comprise a nucleic acid sequence encoding a polypeptide that comprises at least 70% sequence identity to at least 100 to at least 163 contiguous amino acids of IGFBP-2 (SEQ ID NO:54). In some cases, the plasmid may comprise a nucleic acid sequence encoding a polypeptide that comprises at least 70% sequence identity to at least 105 to at least 160, at least 110 to at least 155, or at least 120 to at least 145 contiguous amino acids of IGFBP-2 (SEQ ID NO:54).

In some cases, the plasmid may comprise a nucleic acid sequence encoding a polypeptide that comprises at least 80% sequence identity to at least 100 to at least 163 contiguous amino acids of IGFBP-2 (SEQ ID NO:54). In some cases, the plasmid may comprise a nucleic acid sequence encoding a polypeptide that comprises at least 80% sequence identity to at least 105 to at least 160, at least 110 to at least 155, or at least 120 to at least 145 contiguous amino acids of IGFBP-2 (SEQ ID NO:54).

In some cases, the plasmid may comprise a nucleic acid sequence encoding a polypeptide that comprises at least 90% sequence identity to at least 100 to at least 163 contiguous amino acids of IGFBP-2 (SEQ ID NO:54). In some cases, the plasmid may comprise a nucleic acid sequence encoding a polypeptide that comprises at least 90% sequence identity to at least 105 to at least 160, at least 110 to at least 155, or at least 120 to at least 145 contiguous amino acids of IGFBP-2 (SEQ ID NO:54).

In some cases, the plasmid may comprise a nucleic acid sequence encoding a polypeptide that comprises at least 95% sequence identity to at least 100 to at least 163 contiguous amino acids of IGFBP-2 (SEQ ID NO:54). In some cases, the plasmid may comprise a nucleic acid sequence encoding a polypeptide that comprises at least 95% sequence identity to at least 105 to at least 160, at least 110 to at least 155, or at least 120 to at least 145 contiguous amino acids of IGFBP-2 (SEQ ID NO:54).

In some cases, the plasmid may comprise a nucleic acid sequence encoding a polypeptide that comprises 100% sequence identity to at least 100 to at least 163 contiguous amino acids of IGFBP-2 (SEQ ID NO:54). In some cases, the plasmid may comprise a nucleic acid sequence encoding a polypeptide that comprises 100% sequence identity to at least 105 to at least 160, at least 110 to at least 155, or at least 120 to at least 145 contiguous amino acids of IGFBP-2 (SEQ ID NO:54).

In some cases, the plasmid may comprise a nucleic acid sequence encoding a polypeptide that consists of 100% sequence identity to at least 100 to at least 163 contiguous amino acids of IGFBP-2 (SEQ ID NO:54). In some cases, the plasmid may comprise a nucleic acid sequence encoding a polypeptide that consists of 100% sequence identity to at least 105 to at least 160, at least 110 to at least 155, or at least 120 to at least 145 contiguous amino acids of IGFBP-2 (SEQ ID NO:54).

In some instances, the plasmid may comprise a nucleic acid sequence that comprises at least 50% sequence identity to IGFBP-2 (SEQ ID NO: 43). In some instances, the plasmid may include a nucleic acid sequence that comprises at least 55%, 60%, 65%, 70%, 75%, 80%, 85%, 90%, 95%, 96%, 97%, 98%, 99%, or 100% sequence identity to IGFBP-2 (SEQ ID NO: 43). In some cases, the plasmid may include a nucleic acid sequence that comprises at least 70% sequence identity to IGFBP-2 (SEQ ID NO: 43). In some cases, the plasmid may include a nucleic acid sequence that comprises at least 80% sequence identity to IGFBP-2 (SEQ ID NO: 43). In some cases, the plasmid may include a nucleic acid sequence that comprises at least 90% sequence identity to IGFBP-2 (SEQ ID NO: 43). Sometimes, the plasmid may include a nucleic acid sequence that comprises at least 95% sequence identity to IGFBP-2 (SEQ ID NO: 43). Sometimes, the plasmid may include a nucleic acid sequence that comprises at least 99% sequence identity to IGFBP-2 (SEQ ID NO: 43). In some instances, the plasmid may include a nucleic acid sequence that comprises 100% sequence identity to IGFBP-2 (SEQ ID NO: 43). In some instances, the plasmid may include a nucleic acid sequence that consists of 100% sequence identity to IGFBP-2 (SEQ ID NO: 43).

In some instances, the plasmid may comprise a nucleic acid sequence encoding a polypeptide that comprises at least 70% sequence identity to Survivin (SEQ ID NO: 85). In some instances, the plasmid may include a nucleic acid sequence encoding a polypeptide that comprises at least 75%, 80%, 85%, 90%, 91%, 92%, 93%, 94%, 95%, 96%, 97%, 98%, 99%, or 100% sequence identity to Survivin (SEQ ID NO: 85). In some cases, the plasmid may include a nucleic acid sequence encoding a polypeptide that comprises at least 80% sequence identity to Survivin (SEQ ID NO: 85). In some cases, the plasmid may include a nucleic acid sequence encoding a polypeptide that comprises at least 90% sequence identity to Survivin (SEQ ID NO: 85). Sometimes, the plasmid may include a nucleic acid sequence encoding a polypeptide that comprises at least 95% sequence identity to Survivin (SEQ ID NO: 85). Sometimes, the plasmid may include a nucleic acid sequence encoding a polypeptide that comprises at least 99% sequence identity to Survivin (SEQ ID NO: 85). In some instances, the plasmid may include a nucleic acid sequence encoding a polypeptide that comprises 100% sequence identity to Survivin (SEQ ID NO: 85). In some instances, the plasmid may include a nucleic acid sequence encoding a polypeptide that consists of 100% sequence identity to Survivin (SEQ ID NO: 85).

In some cases, the plasmid may comprise a nucleic acid sequence encoding a polypeptide that comprises at least 70% sequence identity to at least 10 to at least 38 contiguous amino acids of Survivin (SEQ ID NO: 85). In some cases, the plasmid may comprise a nucleic acid sequence encoding a polypeptide that comprises at least 70% sequence identity to at least 12 to at least 35, at least 15 to at least 30, or at least 20 to at least 25 contiguous amino acids of Survivin (SEQ ID NO: 85). In some cases, the plasmid may comprise a nucleic acid sequence encoding a polypeptide that comprises at least 70% sequence identity to at least 13, 14, 15, 16, 17, 18, 19, 20, 21, 22, 23, 24, 25, 26, 27, 28, 29, 30, 32, 34, or 36 contiguous amino acids of Survivin (SEQ ID NO: 85).

In some cases, the plasmid may comprise a nucleic acid sequence encoding a polypeptide that comprises at least 80% sequence identity to at least 10 to at least 38 contiguous amino acids of Survivin (SEQ ID NO: 85). In some cases, the plasmid may comprise a nucleic acid sequence encoding a polypeptide that comprises at least 80% sequence identity to at least 12 to at least 35, at least 15 to at least 30, or at least 20 to at least 25 contiguous amino acids of Survivin (SEQ ID NO: 85). In some cases, the plasmid may comprise a nucleic acid sequence encoding a polypeptide that comprises at least 80% sequence identity to at least 13, 14, 15, 16, 17, 18, 19, 20, 21, 22, 23, 24, 25, 26, 27, 28, 29, 30, 32, 34, or 36 contiguous amino acids of Survivin (SEQ ID NO: 85).

In some cases, the plasmid may comprise a nucleic acid sequence encoding a polypeptide that comprises at least 90% sequence identity to at least 10 to at least 38 contiguous amino acids of Survivin (SEQ ID NO: 85). In some cases, the plasmid may comprise a nucleic acid sequence encoding a polypeptide that comprises at least 90% sequence identity to at least 12 to at least 35, at least 15 to at least 30, or at least 20 to at least 25 contiguous amino acids of Survivin (SEQ ID NO: 85). In some cases, the plasmid may comprise a nucleic acid sequence encoding a polypeptide that comprises at least 90% sequence identity to at least 13, 14, 15, 16, 17, 18, 19, 20, 21, 22, 23, 24, 25, 26, 27, 28, 29, 30, 32, 34, or 36 contiguous amino acids of Survivin (SEQ ID NO: 85).

In some cases, the plasmid may comprise a nucleic acid sequence encoding a polypeptide that comprises at least 95% sequence identity to at least 10 to at least 38 contiguous amino acids of Survivin (SEQ ID NO: 85). In some cases, the plasmid may comprise a nucleic acid sequence encoding a polypeptide that comprises at least 95% sequence identity to at least 12 to at least 35, at least 15 to at least 30, or at least 20 to at least 25 contiguous amino acids of Survivin (SEQ ID NO: 85). In some cases, the plasmid may comprise a nucleic acid sequence encoding a polypeptide that comprises at least 95% sequence identity to at least 13, 14, 15, 16, 17, 18, 19, 20, 21, 22, 23, 24, 25, 26, 27, 28, 29, 30, 32, 34, or 36 contiguous amino acids of Survivin (SEQ ID NO: 85).

In some cases, the plasmid may comprise a nucleic acid sequence encoding a polypeptide that comprises 100% sequence identity to at least 10 to at least 38 contiguous amino acids of Survivin (SEQ ID NO: 85). In some cases, the plasmid may comprise a nucleic acid sequence encoding a polypeptide that comprises 100% sequence identity to at least 12 to at least 35, at least 15 to at least 30, or at least 20 to at least 25 contiguous amino acids of Survivin (SEQ ID NO: 85). In some cases, the plasmid may comprise a nucleic acid sequence encoding a polypeptide that comprises 100% sequence identity to at least 13, 14, 15, 16, 17, 18, 19, 20, 21, 22, 23, 24, 25, 26, 27, 28, 29, 30, 32, 34, or 36 contiguous amino acids of Survivin (SEQ ID NO: 85).

In some cases, the plasmid may comprise a nucleic acid sequence encoding a polypeptide that consists of 100% sequence identity to at least 10 to at least 38 contiguous amino acids of Survivin (SEQ ID NO: 85). In some cases, the plasmid may comprise a nucleic acid sequence encoding a polypeptide that consists of 100% sequence identity to at least 12 to at least 35, at least 15 to at least 30, or at least 20 to at least 25 contiguous amino acids of Survivin (SEQ ID NO: 85). In some cases, the plasmid may comprise a nucleic acid sequence encoding a polypeptide that consists of 100% sequence identity to at least 13, 14, 15, 16, 17, 18, 19, 20, 21, 22, 23, 24, 25, 26, 27, 28, 29, 30, 32, 34, or 36 contiguous amino acids of Survivin (SEQ ID NO: 85).

In some instances, the plasmid may comprise a nucleic acid sequence that comprises at least 50% sequence identity to Survivin (SEQ ID NO: 86). In some instances, the plasmid may include a nucleic acid sequence that comprises at least 55%, 60%, 65%, 70%, 75%, 80%, 85%, 90%, 95%, 96%, 97%, 98%, 99%, or 100% sequence identity to Survivin (SEQ ID NO: 86). In some cases, the plasmid may include a nucleic acid sequence that comprises at least 70% sequence identity to Survivin (SEQ ID NO: 86). In some cases, the plasmid may include a nucleic acid sequence that comprises at least 80% sequence identity to Survivin (SEQ ID NO: 86). In some cases, the plasmid may include a nucleic acid sequence that comprises at least 90% sequence identity to Survivin (SEQ ID NO: 86). Sometimes, the plasmid may include a nucleic acid sequence that comprises at least 95% sequence identity to Survivin (SEQ ID NO: 86). Sometimes, the plasmid may include a nucleic acid sequence that comprises at least 99% sequence identity to Survivin (SEQ ID NO: 86). In some instances, the plasmid may include a nucleic acid sequence that comprises 100% sequence identity to Survivin (SEQ ID NO: 86). In some instances, the plasmid may include a nucleic acid sequence that consists of 100% sequence identity to Survivin (SEQ ID NO: 86).

In some instances, the plasmid may comprise a nucleic acid sequence encoding a polypeptide that comprises at least 70% sequence identity to HIF-1A (SEQ ID NO: 87). In some instances, the plasmid may include a nucleic acid sequence encoding a polypeptide that comprises at least 75%, 80%, 85%, 90%, 91%, 92%, 93%, 94%, 95%, 96%, 97%, 98%, 99%, or 100%6 sequence identity to HIF-1A (SEQ ID NO: 87). In some cases, the plasmid may include a nucleic acid sequence encoding a polypeptide that comprises at least 80% sequence identity to HIF-1A (SEQ ID NO: 87). In some cases, the plasmid may include a nucleic acid sequence encoding a polypeptide that comprises at least 90% sequence identity to HIF-1A (SEQ ID NO: 87). Sometimes, the plasmid may include a nucleic acid sequence encoding a polypeptide that comprises at least 95% sequence identity to HIF-1A (SEQ ID NO: 87). Sometimes, the plasmid may include a nucleic acid sequence encoding a polypeptide that comprises at least 99% sequence identity to HIF-1A (SEQ ID NO: 87). In some instances, the plasmid may include a nucleic acid sequence encoding a polypeptide that comprises 100% sequence identity to HIF-1A (SEQ ID NO: 87). In some instances, the plasmid may include a nucleic acid sequence encoding a polypeptide that consists of 100% sequence identity to HIF-1A (SEQ ID NO: 87).

In some cases, the plasmid may comprise a nucleic acid sequence encoding a polypeptide that comprises at least 70% sequence identity to at least 40 to at least 89 contiguous amino acids of HIF-1A (SEQ ID NO: 87). In some cases, the plasmid may comprise a nucleic acid sequence encoding a polypeptide that comprises at least 70% sequence identity to at least 40 to at least 85, at least 50 to at least 80, at least 55 to at least 75, or at least 60 to at least 70 contiguous amino acids of HIF-1A (SEQ ID NO: 87). In some cases, the plasmid may comprise a nucleic acid sequence encoding a polypeptide that comprises at least 70% sequence identity to at least 61, 62, 63, 64, 65, 66, 67, 68, 69, 70, 71, 72, 73, 74, 75, 76, 77, 78, 79, 80, 81, 82, 83, 84, 85, 86, 87, or 88 contiguous amino acids of HIF-1A (SEQ ID NO: 87).

In some cases, the plasmid may comprise a nucleic acid sequence encoding a polypeptide that comprises at least 80% sequence identity to at least 40 to at least 89 contiguous amino acids of HIF-1A (SEQ ID NO: 87). In some cases, the plasmid may comprise a nucleic acid sequence encoding a polypeptide that comprises at least 80% sequence identity to at least 40 to at least 85, at least 50 to at least 80, at least 55 to at least 75, or at least 60 to at least 70 contiguous amino acids of HIF-1A (SEQ ID NO: 87). In some cases, the plasmid may comprise a nucleic acid sequence encoding a polypeptide that comprises at least 80% sequence identity to at least 61, 62, 63, 64, 65, 66, 67, 68, 69, 70, 71, 72, 73, 74, 75, 76, 77, 78, 79, 80, 81, 82, 83, 84, 85, 86, 87, or 88 contiguous amino acids of HIF-1A (SEQ ID NO: 87).

In some cases, the plasmid may comprise a nucleic acid sequence encoding a polypeptide that comprises at least 90% sequence identity to at least 40 to at least 89 contiguous amino acids of HIF-1A (SEQ ID NO: 87). In some cases, the plasmid may comprise a nucleic acid sequence encoding a polypeptide that comprises at least 90% sequence identity to at least 40 to at least 85, at least 50 to at least 80, at least 55 to at least 75, or at least 60 to at least 70 contiguous amino acids of HIF-1A (SEQ ID NO: 87). In some cases, the plasmid may comprise a nucleic acid sequence encoding a polypeptide that comprises at least 90% sequence identity to at least 61, 62, 63, 64, 65, 66, 67, 68, 69, 70, 71, 72, 73, 74, 75, 76, 77, 78, 79, 80, 81, 82, 83, 84, 85, 86, 87, or 88 contiguous amino acids of HIF-1A (SEQ ID NO: 87).

In some cases, the plasmid may comprise a nucleic acid sequence encoding a polypeptide that comprises at least 95% sequence identity to at least 40 to at least 89 contiguous amino acids of HIF-1A (SEQ ID NO: 87). In some cases, the plasmid may comprise a nucleic acid sequence encoding a polypeptide that comprises at least 95% sequence identity to at least 40 to at least 85, at least 50 to at least 80, at least 55 to at least 75, or at least 60 to at least 70 contiguous amino acids of HIF-1A (SEQ ID NO: 87). In some cases, the plasmid may comprise a nucleic acid sequence encoding a polypeptide that comprises at least 95% sequence identity to at least 61, 62, 63, 64, 65, 66, 67, 68, 69, 70, 71, 72, 73, 74, 75, 76, 77, 78, 79, 80, 81, 82, 83, 84, 85, 86, 87, or 88 contiguous amino acids of HIF-1A (SEQ ID NO: 87).

In some cases, the plasmid may comprise a nucleic acid sequence encoding a polypeptide that comprises 100% sequence identity to at least 40 to at least 89 contiguous amino acids of HIF-1A (SEQ ID NO: 87). In some cases, the plasmid may comprise a nucleic acid sequence encoding a polypeptide that comprises 100% sequence identity to at least 40 to at least 85, at least 50 to at least 80, at least 55 to at least 75, or at least 60 to at least 70 contiguous amino acids of HIF-1A (SEQ ID NO: 87). In some cases, the plasmid may comprise a nucleic acid sequence encoding a polypeptide that comprises 100% sequence identity to at least 61, 62, 63, 64, 65, 66, 67, 68, 69, 70, 71, 72, 73, 74, 75, 76, 77, 78, 79, 80, 81, 82, 83, 84, 85, 86, 87, or 88 contiguous amino acids of HIF-1A (SEQ ID NO: 87).

In some cases, the plasmid may comprise a nucleic acid sequence encoding a polypeptide that consists of 100% sequence identity to at least 40 to at least 89 contiguous amino acids of HIF-1A (SEQ ID NO: 87). In some cases, the plasmid may comprise a nucleic acid sequence encoding a polypeptide that consists of 100% sequence identity to at least 40 to at least 85, at least 50 to at least 80, at least 55 to at least 75, or at least 60 to at least 70 contiguous amino acids of HIF-1A (SEQ ID NO: 87). In some cases, the plasmid may comprise a nucleic acid sequence encoding a polypeptide that consists of 100% sequence identity to at least 61, 62, 63, 64, 65, 66, 67, 68, 69, 70, 71, 72, 73, 74, 75, 76, 77, 78, 79, 80, 81, 82, 83, 84, 85, 86, 87, or 88 contiguous amino acids of HIF-1A (SEQ ID NO: 87).

In some instances, the plasmid may comprise a nucleic acid sequence that comprises at least 50% sequence identity to HIF-1A (SEQ ID NO: 88). In some instances, the plasmid may include a nucleic acid sequence that comprises at least 55%, 60%, 65%, 70%, 75%, 80%, 85%, 90%, 95%, 96%, 97%, 98%, 99%, or 100% sequence identity to HIF-1A (SEQ ID NO: 88). In some cases, the plasmid may include a nucleic acid sequence that comprises at least 70% sequence identity to HIF-1A (SEQ ID NO: 88). In some cases, the plasmid may include a nucleic acid sequence that comprises at least 80% sequence identity to HIF-1A (SEQ ID NO: 88). In some cases, the plasmid may include a nucleic acid sequence that comprises at least 90% sequence identity to HIF-1A (SEQ ID NO: 88). Sometimes, the plasmid may include a nucleic acid sequence that comprises at least 95% sequence identity to HIF-1A (SEQ ID NO: 88). Sometimes, the plasmid may include a nucleic acid sequence that comprises at least 99% sequence identity to HIF-1A (SEQ ID NO: 88). In some instances, the plasmid may include a nucleic acid sequence that comprises 100% sequence identity to HIF-1A (SEQ ID NO: 88). In some instances, the plasmid may include a nucleic acid sequence that consists of 100% sequence identity to HIF-1A (SEQ ID NO: 88).

In some instances, the plasmid may comprise a nucleic acid sequence encoding a polypeptide that comprises at least 70% sequence identity to IGF-1R (SEQ ID NO: 73). In some instances, the plasmid may include a nucleic acid sequence encoding a polypeptide that comprises at least 75%, 80%, 85%, 90%, 91%, 92%, 93%, 94%, 95%, 96, 97%, 98%, 99%, or 100% sequence identity to IGF-1R (SEQ ID NO: 73). In some cases, the plasmid may include a nucleic acid sequence encoding a polypeptide that comprises at least 80% sequence identity to IGF-1R (SEQ ID NO: 73). In some cases, the plasmid may include a nucleic acid sequence encoding a polypeptide that comprises at least 90% sequence identity to IGF-1R (SEQ ID NO: 73). Sometimes, the plasmid may include a nucleic acid sequence encoding a polypeptide that comprises at least 95% sequence identity to IGF-1R (SEQ ID NO: 73). Sometimes, the plasmid may include a nucleic acid sequence encoding a polypeptide that comprises at least 99% sequence identity to IGF-1R (SEQ ID NO: 73). In some instances, the plasmid may include a nucleic acid sequence encoding a polypeptide that comprises 100% sequence identity to IGF-1R (SEQ ID NO: 73). In some instances, the plasmid may include a nucleic acid sequence encoding a polypeptide that consists of 100% sequence identity to IGF-1R (SEQ ID NO: 73).

In some cases, the plasmid may comprise a nucleic acid sequence encoding a polypeptide that comprises at least 70% sequence identity to at least 50 to at least 104 contiguous amino acids of IGF-1R (SEQ ID NO:73). In some cases, the plasmid may comprise a nucleic acid sequence encoding a polypeptide that comprises at least 70% sequence identity to at least 55 to at least 100, at least 60 to at least 90, or at least 70 to at least 80 contiguous amino acids of IGF-1R (SEQ ID NO:73).

In some cases, the plasmid may comprise a nucleic acid sequence encoding a polypeptide that comprises at least 80% sequence identity to at least 50 to at least 104 contiguous amino acids of IGF-1R (SEQ ID NO:73). In some cases, the plasmid may comprise a nucleic acid sequence encoding a polypeptide that comprises at least 80% sequence identity to at least 55 to at least 100, at least 60 to at least 90, or at least 70 to at least 80 contiguous amino acids of IGF-1R (SEQ ID NO:73).

In some cases, the plasmid may comprise a nucleic acid sequence encoding a polypeptide that comprises at least 90% sequence identity to at least 50 to at least 104 contiguous amino acids of IGF-1R (SEQ ID NO:73). In some cases, the plasmid may comprise a nucleic acid sequence encoding a polypeptide that comprises at least 90% sequence identity to at least 55 to at least 100, at least 60 to at least 90, or at least 70 to at least 80 contiguous amino acids of IGF-1R (SEQ ID NO:73).

In some cases, the plasmid may comprise a nucleic acid sequence encoding a polypeptide that comprises at least 95% sequence identity to at least 50 to at least 104 contiguous amino acids of IGF-1R (SEQ ID NO:73). In some cases, the plasmid may comprise a nucleic acid sequence encoding a polypeptide that comprises at least 95% sequence identity to at least 55 to at least 100, at least 60 to at least 90, or at least 70 to at least 80 contiguous amino acids of IGF-1R (SEQ ID NO:73).

In some cases, the plasmid may comprise a nucleic acid sequence encoding a polypeptide that comprises 100% sequence identity to at least 50 to at least 104 contiguous amino acids of IGF-1R (SEQ ID NO:73). In some cases, the plasmid may comprise a nucleic acid sequence encoding a polypeptide that comprises 100% sequence identity to at least 55 to at least 100, at least 60 to at least 90, or at least 70 to at least 80 contiguous amino acids of IGF-1R (SEQ ID NO:73).

In some cases, the plasmid may comprise a nucleic acid sequence encoding a polypeptide that consists of 100% sequence identity to at least 50 to at least 104 contiguous amino acids of IGF-1R (SEQ ID NO:73). In some cases, the plasmid may comprise a nucleic acid sequence encoding a polypeptide that consists of 100% sequence identity to at least 55 to at least 100, at least 60 to at least 90, or at least 70 to at least 80 contiguous amino acids of IGF-1R (SEQ ID NO:73).

In some instances, the plasmid may comprise a nucleic acid sequence that comprises at least 50% sequence identity to IGF-1R (SEQ ID NO: 63). In some instances, the plasmid may include a nucleic acid sequence that comprises at least 55%, 60%, 65%, 70%, 75%, 80%, 85%, 90%, 95%, 96%, 97%, 98%, 99%, or 100% sequence identity to IGF-1R (SEQ ID NO: 63). In some cases, the plasmid may include a nucleic acid sequence that comprises at least 70% sequence identity to IGF-1R (SEQ ID NO: 63). In some cases, the plasmid may include a nucleic acid sequence that comprises at least 80% sequence identity to IGF-1R (SEQ ID NO: 63). In some cases, the plasmid may include a nucleic acid sequence that comprises at least 90% sequence identity to IGF-1R (SEQ ID NO: 63). Sometimes, the plasmid may include a nucleic acid sequence that comprises at least 95% sequence identity to IGF-1R (SEQ ID NO: 63). Sometimes, the plasmid may include a nucleic acid sequence that comprises at least 99% sequence identity to IGF-1R (SEQ ID NO: 63). In some instances, the plasmid may include a nucleic acid sequence that comprises 100% sequence identity to IGF-1R (SEQ ID NO: 63). In some instances, the plasmid may include a nucleic acid sequence that consists of 100% sequence identity to IGF-1R (SEQ ID NO: 63).

Sometimes, an isolated and purified plasmid may comprise at least one nucleic acid sequence encoding a polypeptide comprising at least 70% sequence identity to an epitope sequence selected from SEQ ID NOs: 54, 73, 85, and 87. The plasmid may comprise at least one nucleic acid sequence encoding a polypeptide comprising at least 75%, 80%, 85%, 90%, 91%, 92%, 93%, 94%, 95%, 96%, 97%, 98%, 99%, or 100% sequence identity to an epitope sequence selected from SEQ ID NOs: 54, 73, 85, and 87. The plasmid may comprise at least one nucleic acid sequence encoding a polypeptide comprising at least 80% sequence identity to an epitope sequence selected from SEQ ID NOs: 54, 73, 85, and 87. The plasmid may comprise at least one nucleic acid sequence encoding a polypeptide comprising at least 90% sequence identity to an epitope sequence selected from SEQ ID NOs: 54, 73, 85, and 87. The plasmid may comprise at least one nucleic acid sequence encoding a polypeptide comprising at least 95% sequence identity to an epitope sequence selected from SEQ ID NOs: 54, 73, 85, and 87. The plasmid may comprise at least one nucleic acid sequence encoding a polypeptide comprising at least 99% sequence identity to an epitope sequence selected from SEQ ID NOs: 54, 73, 85, and 87. The plasmid may comprise at least one nucleic acid sequence encoding a polypeptide comprising 100% sequence identity to an epitope sequence selected from SEQ ID NOs: 54, 73, 85, and 87. The plasmid may comprise at least one nucleic acid sequence encoding a polypeptide consisting of 100% sequence identity to an epitope sequence selected from SEQ ID NOs: 54, 73, 85, and 87.

Sometimes, an isolated and purified plasmid may comprise at least four nucleic acid sequences in which each of the four nucleic acid sequences encodes a polypeptide comprising at least 70% sequence identity to an epitope sequence selected from SEQ ID NOs: 54, 73, 85, and 87. The plasmid may comprise at least four nucleic acid sequences in which each of the four nucleic acid sequences encodes a polypeptide comprising at least 75%, 80%, 85%, 90%, 91%, 92%, 93%, 94%, 95%, 96%, 97%, 98%, 99%, or 100% sequence identity to an epitope sequence selected from SEQ ID NOs: 54, 73, 85, and 87. The plasmid may comprise at least four nucleic acid sequences in which each of the four nucleic acid sequences encodes a polypeptide comprising at least 80% sequence identity to an epitope sequence selected from SEQ ID NOs: 54, 73, 85, and 87. The plasmid may comprise at least four nucleic acid sequences in which each of the four nucleic acid sequences encodes a polypeptide comprising at least 90% sequence identity to an epitope sequence selected from SEQ ID NOs: 54, 73, 85, and 87. The plasmid may comprise at least four nucleic acid sequences in which each of the four nucleic acid sequences encodes a polypeptide comprising at least 95% sequence identity to an epitope sequence selected from SEQ ID NOs: 54, 73, 85, and 87. The plasmid may comprise at least four nucleic acid sequences in which each of the four nucleic acid sequences encodes a polypeptide comprising at least 99% sequence identity to an epitope sequence selected from SEQ ID NOs: 54, 73, 85, and 87. The plasmid may comprise at least four nucleic acid sequences in which each of the four nucleic acid sequences encodes a polypeptide comprising 100% sequence identity to an epitope sequence selected from SEQ ID NOs: 54, 73, 85, and 87. The plasmid may comprise at least four nucleic acid sequences in which each of the four nucleic acid sequences encodes a polypeptide consisting of 100% sequence identity to an epitope sequence selected from SEQ ID NOs: 54, 73, 85, and 87. In some instances, the at least four nucleic acid sequences independently encodes a polypeptide to an epitope sequence selected from SEQ ID NOs: 54, 73, 85, and 87. In other instances, the at least four nucleic acid sequences encodes different polypeptides to the epitope sequences selected from SEQ ID NOs: 54, 73, 85, and 87.

Sometimes, the plasmid may comprise four nucleic acid sequences in which each of the four nucleic acid sequences encodes a polypeptide comprising at least 70% sequence identity to an epitope sequence selected from SEQ ID NOs: 54, 73, 85, and 87. The plasmid may comprise four nucleic acid sequences in which each of the four nucleic acid sequences encodes a polypeptide comprising at least 75%, 80%, 85%, 90%, 91%, 92%, 93%, 94%, 95%, 96%, 97%, 98%, 99%, or 100% sequence identity to an epitope sequence selected from SEQ ID NOs: 54, 73, 85, and 87. The plasmid may comprise four nucleic acid sequences in which each of the four nucleic acid sequences encodes a polypeptide comprising at least 80% sequence identity to an epitope sequence selected from SEQ ID NOs: 54, 73, 85, and 87. The plasmid may comprise four nucleic acid sequences in which each of the four nucleic acid sequences encodes a polypeptide comprising at least 90% sequence identity to an epitope sequence selected from SEQ ID NOs: 54, 73, 85, and 87. The plasmid may comprise four nucleic acid sequences in which each of the four nucleic acid sequences encodes a polypeptide comprising at least 95% sequence identity to an epitope sequence selected from SEQ ID NOs: 54, 73, 85, and 87. The plasmid may comprise four nucleic acid sequences in which each of the four nucleic acid sequences encodes a polypeptide comprising at least 99% sequence identity to an epitope sequence selected from SEQ ID NOs: 54, 73, 85, and 87. The plasmid may comprise four nucleic acid sequences in which each of the four nucleic acid sequences encodes a polypeptide comprising 100% sequence identity to an epitope sequence selected from SEQ ID NOs: 54, 73, 85, and 87. The plasmid may comprise four nucleic acid sequences in which each of the four nucleic acid sequences encodes a polypeptide consisting of 100% sequence identity to an epitope sequence selected from SEQ ID NOs: 54, 73, 85, and 87. In some instances, the four nucleic acid sequences independently encodes a polypeptide to an epitope sequence selected from SEQ ID NOs: 54, 73, 85, and 87. In other instances, the four nucleic acid sequences encodes different polypeptides to the epitope sequences selected from SEQ ID NOs: 54, 73, 85, and 87.

In some instances, a plasmid may comprise a nucleic acid sequence encoding a polypeptide comprising at least 70% sequence identity to SEQ ID NO: 89. In some cases, a plasmid may comprise a nucleic acid sequence encoding a polypeptide comprising at least 75%, 80%, 85%, 90%, 91%, 92%, 93%, 94%, 95%, 96%, 97%, 98%, 99%, or 100% sequence identity to SEQ ID NO: 89. A plasmid may comprise a nucleic acid sequence encoding a polypeptide comprising at least 80% sequence identity to SEQ ID NO: 89. A plasmid may comprise a nucleic acid sequence encoding a polypeptide comprising at least 90% sequence identity to SEQ ID NO: 89. A plasmid may comprise a nucleic acid sequence encoding a polypeptide comprising at least 95% sequence identity to SEQ ID NO: 89. A plasmid may comprise a nucleic acid sequence encoding a polypeptide comprising at least 99% sequence identity to SEQ ID NO: 89. A plasmid may comprise a nucleic acid sequence encoding a polypeptide comprising 100% sequence identity to SEQ ID NO: 89. A plasmid may comprise a nucleic acid sequence encoding a polypeptide consisting of 100% sequence identity to SEQ ID NO: 89.

In some instances, a plasmid may comprise a nucleic acid sequence comprising at least 70% sequence identity to SEQ ID NO: 90. In some cases, a plasmid may comprise a nucleic acid sequence comprising at least 75%, 80%, 85%, 90%, 91%, 92%, 93%, 94%, 95%, 96%, 97%, 98%, 99%, or 100% sequence identity to SEQ ID NO: 90. A plasmid may comprise a nucleic acid sequence comprising at least 80% sequence identity to SEQ ID NO: 90. A plasmid may comprise a nucleic acid sequence comprising at least 90% sequence identity to SEQ ID NO: 90. A plasmid may comprise a nucleic acid sequence comprising at least 95% sequence identity to SEQ ID NO: 90. A plasmid may comprise a nucleic acid sequence comprising at least 99% sequence identity to SEQ ID NO: 90. A plasmid may comprise a nucleic acid sequence comprising 100% sequence identity to SEQ ID NO: 90. A plasmid may comprise a nucleic acid sequence consisting of 100% sequence identity to SEQ ID NO: 90.

In some instances, a plasmid may comprise a nucleic acid sequence comprising at least 70% sequence identity to SEQ ID NO: 91. In some cases, a plasmid may comprise a nucleic acid sequence comprising at least 75%, 80%, 85%, 90%, 91%, 92%, 93%, 94%, 95%, 96%, 97%, 98%, 99%, or 100% sequence identity to SEQ ID NO: 91. A plasmid may comprise a nucleic acid sequence comprising at least 80% sequence identity to SEQ ID NO: 91. A plasmid may comprise a nucleic acid sequence comprising at least 90% sequence identity to SEQ ID NO: 91. A plasmid may comprise a nucleic acid sequence comprising at least 95% sequence identity to SEQ ID NO: 91. A plasmid may comprise a nucleic acid sequence comprising at least 99% sequence identity to SEQ ID NO: 91. A plasmid may comprise a nucleic acid sequence comprising 100% sequence identity to SEQ ID NO: 91. A plasmid may comprise a nucleic acid sequence consisting of 100% sequence identity to SEQ ID NO: 91.

Sometimes, plasmids comprising more than one epitope sequences may comprise spacers between each epitope sequence. In some cases, sequences of the epitopes may be encoded in tandem without the use of spacers. In some cases, sequences of epitopes may be encoded in tandem with the use of spacers. In some cases, the spacers may comprise sequences encoding from about 1 to about 50, about 3 to about 40, about 5 to about 35, or about 10 to about 30 amino acid residues. In some instances, the spacers may comprise sequences encoding about 1, 2, 3, 4, 5, 6, 7, 8, 9, 10, 11, 12, 13, 14, 15, 16, 17, 18, 19, 20, 25, or 30 amino acid residues.

In some cases, the plasmid may contain a nucleic acid sequence coding for at least one tag. In some cases, the tag may be translated into a peptide. Any nucleic acid sequence for a tag known to one of ordinary skill in the art may be used with the plasmids described herein. For example, the tag may be a histidine tag with three histidine residues, a histidine tag with four histidine residues, a histidine tag with five histidine residues, or a histidine tag with six histidine residues, or the like. Expression of the tag in a subject may be determined using any suitable technique known to one of ordinary skill in the art.

In some cases, plasmids may be sequenced using any sequencing technique known to one of ordinary skill in the art such that the results of the sequencing technique provides nucleotide level resolution of the entire plasmid.

In some aspects, the composition may be a multiantigen breast cancer vaccine or a multiantigen ovarian cancer vaccine. For example, the multiantigen breast cancer vaccine or multiantigen ovarian cancer vaccine may contain a plurality of antigens. In some cases, expression of one antigen may impact expression of a different antigen. In some cases, expression of more than one antigen may impact expression of a different antigen. In some cases, expression of one antigen may impact expression of more than one different antigen. In some cases, expression of one antigen may not impact expression of a different antigen. In some cases, expression of more than one antigen may not impact expression of a different antigen. In some cases, expression of one antigen may not impact expression of more than one different antigen. For example, antigenic competition may limit the immunogenicity of multiantigen vaccines. Any techniques known to one of ordinary skill in the art may be used to determine if an immune response elicited following administration of a multiple antigen vaccine is of comparable magnitude to each antigen as a single antigen vaccine. For example, ELISPOT (e.g., for secretion of IFNγ) may determine the magnitude of the immune response. In some cases, the ELISPOT may detect rodent, non-human primate or human peptides. In some instances, the multiantigen breast cancer or ovarian cancer vaccine may comprise a plurality of epitopes derived from a plurality of antigens selected from Survivin, HIF-1α, IGF-1R, and/or IGFBP-2.

Nucleic Acids

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences).

Isolated nucleic acid molecule can include DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Nucleic acid molecules may refer to at least two nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984). Letsinger et al, J. Am. Chem. Soc. 110:4470 (1988); and Pauwels et al., Chemica Scripta 26:141 (1986)), phosphorothioate (Mag et al., Nucleic Acids Res. 19:1437 (1991); and U.S. Pat. No. 5,644,048), phosphorodithioate (Briu et al., J. Am. Chem. Soc. 111.2321 (1989)), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am Chem. Soc. 114:1895 (1992). Meier et al., Chem. Int. Ed. Engl 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"). Koshkin et al., J. Am. Chem. Soc. 120.13252 3 (1998); positive backbones (Denpcy et al., Proc. Natl. Acad. Sci. USA 92:6097 (1995)): non-ionic backbones (U.S. Pat. Nos. 5,386,023, 5,637,684, 5,602,240, 5,216,141 and 4,469,863; Kiedrowski et al., Angew. Chenm. Intl. Ed English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed Y. S. Sanghui and P. Dan Cook; Mesmaeker et al., Bloorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7. ASC Symposium Series 580. "Carbohydrate Modifications in Antisense Research". Ed. Y S Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. "Locked nucleic acids" are also included within the definition of nucleic acid analogs LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

Pharmaceutical Compositions

The immunogenic compositions of the disclosure are preferably formulated as a vaccine for in vivo administration to the subject, such that they confer an antibody titer superior to the criterion for seroprotection for each antigenic component for an acceptable percentage of subjects. Antigens with an associated antibody titer above which a subject is considered to be seroconverted against the antigen are well known, and such titers are published by organizations such as WHO. Preferably more than 80% of a statistically significant sample of subjects is seroconverted, more preferably more than 90%, still more preferably more than 93% and most preferably 96-100%.

Adjuvants

The immunogenic compositions of the disclosure are preferably adjuvanted. An adjuvant can be used to enhance the immune response (humoral and/or cellular) elicited in a patient receiving the vaccine. Sometimes, adjuvants can elicit a TH1-type response. Other times, adjuvants can elicit a TH2-type response. A TH1-type response can be characterized by the production of cytokines such as IFN-γ as opposed to a TH2-type response which can be characterized by the production of cytokines such as IL-4, IL-5 and IL-10.

Adjuvant can comprise stimulatory molecules such as cytokines. Non-limiting examples of cytokines include: CCL20, a-interferon (IFN-a), β-interferon (IFN-β), γ-interferon, platelet derived growth factor (PDGF), TNFa, TNFp, granulocyte macrophage colony-stimulating factor (GM-CSF), epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2. In some instances, the adjuvant is GM-CSF.

Additional adjuvants include: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In some aspects, an adjuvant can be a modulator of a toll like receptor. Examples of modulators of toll-like receptors include TLR-9 agonists and are not limited to small molecule modulators of toll-like receptors such as Imiquimod. Other examples of adjuvants that are used in combination with a vaccine described herein can include and are not limited to saponin, CpG ODN and the like.

Sometimes, adjuvants may include an aluminum salt such as aluminum hydroxide gel (alum), aluminum phosphate, a salt of calcium, iron or zinc, or may be an insoluble suspension of acylated tyrosine, or acylated sugars, cationically or anionically derivatized polysaccharides, or polyphosphazenes.

Sometimes, suitable adjuvant systems which promote a predominantly Th1 response include, Monophosphoryl lipid A or a derivative thereof, particularly 3-de-O-acylated monophosphoryl lipid A, and a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. The vaccine may additionally comprise a saponin, more preferably QS21. The formulation may also comprises an oil in water emulsion and tocopherol (WO 95/17210). Unmethylated CpG containing oligonucleotides (WO 96/02555) are also preferential inducers of a Th1 response and are suitable for use in the present disclosure.

In some instances, aluminum salts are used. Sometimes in order to minimize the levels of adjuvant (particularly aluminum salts) in the compositions of the disclosure, the polysaccharide conjugates may be unadjuvanted.

Sometimes, a suitable adjuvant system may include an adjuvant or immunostimulant such as but not limited to detoxified lipid A from any source and non-toxic derivatives of lipid A, saponins and other reagents capable of stimulating a TH1 type response. It has been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., N.Y., p407-419).

A further detoxified version of MPL results from the removal of the acyl chain from the 3-position of the disaccharide backbone, and is called 3-O-Deacylated monophosphoryl Lipid A (3D-MPL). It can be purified and prepared by the methods taught in GB 2122204B, which reference also discloses the preparation of diphosphoryl lipid A, and 3-O-deacylated variants thereof.

In some instances, 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2. The bacterial lipopolysaccharide derived adjuvants to be formulated in the compositions of the present disclosure may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al, 1986, Int. ArchAllergy. Immunol, 79(4):392-6; Hilgers et al, 1987, Immunology, 60(1): 141-6; and EP 0 549 074 B1). A particularly preferred bacterial lipopolysaccharide adjuvant is 3D-MPL.

Accordingly, the LPS derivatives that may be used in the present disclosure are those immunostimulants that are similar in structure to that of LPS or MPL or 3D-MPL. In another aspect of the present disclosure the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., CritRev TherDrug Carrier Syst, 1996, 12 (1-2):1-55; and EP 0362 279 B1.

Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0362279 B1. Other saponins which have been used in systemic vaccination studies include those derived from other plant species such as *Gypsophila* and *Saponaria* (Bomford et al., Vaccine, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739.

Sometimes, an adjuvant is selected from bacteria toxoids, polyoxypropylene-polyoxyethylene block polymers, aluminum salts, liposomes, CpG polymers, oil-in-water emulsions, or a combination thereof.

Sometimes, an adjuvant is an oil-in-water emulsion. The oil-in-water emulsion can include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The oils used can include such as those from an animal (such as fish) or vegetable source. Sources for vegetable oils can include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil, etc. The grain group can include: corn oil and oils of other cereal grains such as wheat, oats, rye, rice, teff, triticale, and the like. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk can be metabolizable and can therefore be used in with the vaccines described herein. The procedures for separation, purification, saponification and other means necessary for obtaining pure oils from animal sources are well known in the art. Fish can contain metabolizable oils which can be readily recovered. For example, cod liver oil shark liver oils, and whale oil such as spermaceti can exemplify several of the fish oils which can be used herein. A number of branched chain oils can be synthesized biochemically in 5-carbon isoprene units and can be generally referred to as terpenoids. Shark liver oil contains a branched, unsaturated terpenoid known as squalene, 2,6,10,15,19,23-hexamethyl-2,6,10,14,18,22-tetracosahexaene. Squalane, the saturated analog to squalene, can also be used. Fish oils, including squalene and squalane, can be readily available from commercial sources or can be obtained by methods known in the art.

Other useful oils include tocopherols, can included in vaccines for use in elderly patients (e.g. aged 60 years or older) due to vitamin E been reported to have a positive effect on the immune response in this patient group. Further, tocopherols have antioxidant properties that can help to stabilize the emulsions. Various tocopherols exist ($\alpha$, $\beta$, $\gamma$, $\delta$, $\epsilon$ or $\zeta$) but $\alpha$ is usually used. An example of $\alpha$-tocopherol is DL-$\alpha$-tocopherol. $\alpha$-tocopherol succinate can be compatible with cancer vaccines and can be a useful preservative as an alternative to mercurial compounds.

Mixtures of oils can be used e.g. squalene and $\alpha$-tocopherol. An oil content in the range of 2-20% (by volume) can be used.

Surfactants can be classified by their 'HLB' (hydrophile/lipophile balance). In some cases, surfactants have a HLB of at least 10, at least 15, and/or at least 16. Surfactants can include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers: octoxynols, which can vary in the number of repeating ethoxy (oxy-1,2-ethanediyl) groups, with octoxynol-9 (Triton X-100, or t-octylphenoxypolyethoxyethanol) being of particular interest: (octylphenoxy)polyethoxyethanol (IGEPAL CA-630/NP-40); phospholipids such as phosphatidylcholine (lecithin), nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants can be used herein.

Mixtures of surfactants can be used e.g. Tween 80/Span 85 mixtures. A combination of a polyoxyethylene sorbitan ester and an octoxynol can also be suitable. Another combination can comprise laureth 9 plus a polyoxyethylene sorbitan ester and/or an octoxynol.

The amounts of surfactants (% by weight) can be: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants include, but are not limited to:

A submicron emulsion of squalene, polysorbate 80, and sorbitan trioleate. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59'. The MF59 emulsion advantageously includes citrate ions e.g. 10 mM sodium citrate buffer.

A submicron emulsion of squalene, a tocopherol, and polysorbate 80. These emulsions can have from 2 to 10% squalene, from 2 to 10% tocopherol and from 0.3 to 3% polysorbate 80, and the weight ratio of squalene:tocopherol is preferably ≤1 (e.g. 0.90) as this can provide a more stable emulsion. Squalene and polysorbate 80 may be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion has submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80.

An emulsion of squalene, a tocopherol, and a Triton detergent (e.g. Triton X-100). The emulsion can also include a 3d-MPL (see below). The emulsion can contain a phosphate buffer.

An emulsion comprising a polysorbate (e.g. polysorbate 80), a Triton detergent (e.g. Triton X-100) and a tocopherol (e.g. an α-tocopherol succinate). The emulsion can include these three components at a mass ratio of about 75:11:10 (e.g. 750 µml polysorbate 80, 110 µml Triton X-100 and 100 µ/ml α-tocopherol succinate), and these concentrations should include any contribution of these components from antigens. The emulsion can also include squalene. The emulsion may also include a 3d-MPL. The aqueous phase can contain a phosphate buffer.

An emulsion of squalane, polysorbate 80 and poloxamer 401 ("Pluronic™ L121"). The emulsion can be formulated in phosphate buffered saline, pH 7.4. This emulsion can be a useful delivery vehicle for muramyl dipeptides, and can be used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80).

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion can be thermoreversible and/or has at least 90% of the oil droplets (by volume) with a size less than 200 nm. The emulsion can also include one or more of: alditol; a cryoprotective agent (e.g. a sugar, such as dodecylmaltoside and/or sucrose); and/or an alkylpolyglycoside. The emulsion can include a TLR4 agonist. Such emulsions can be lyophilized.

An emulsion of squalene, poloxamer 105 and Abil-Care. The final concentration (weight) of these components in adjuvanted vaccines can be 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. Phospholipid components can include phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives can include. QuilA saponin, cholesterol, a saponin-lipophile conjugate (such as GPI-0100, produced by addition of aliphatic amine to desacylsaponin via the carboxyl group of glucuronic acid), dimethyldioctadecylammonium bromide and/or N,N-dioctadecyl-N,N-bis (2-hydroxyethyl)propanediamine.

Carriers and Excipients

In some instances, a composition described herein may further comprise carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH-buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another instances, the pharmaceutical preparation is substantially free of preservatives. In other instances, the pharmaceutical preparation can contain at least one preservative. General methodology on pharmaceutical dosage forms is found in Ansel et al., Pharmaceutical Dosage Forms and Drug Delivery Systems (Lippencott Williams & Wilkins, Baltimore Md. (1999)). It will be recognized that, while any suitable carrier known to those of ordinary skill in the art can be employed to administer the pharmaceutical compositions described herein, the type of carrier will vary depending on the mode of administration.

In some instances, the composition may include a surfactant. Exemplary surfactants may include octylphenoxy polyoxyethanols and polyoxyethylene sorbitan esters, as described in "Surfactant Systems" Eds: Attwood and Florence (1983, Chapman and Hall). Octylphenoxy polyoxyethanols (the octoxynols), including t-octylphenoxypolyethoxvethanol (Triton X-100™) are also described in Merck Index Entry 6858 (Page 1162, 12th Edition, Merck & Co. Inc., Whitehouse Station, N.J., USA; ISBN 0911910-12-3). The polyoxyethylene sorbitan esters, including polyoxyethylene sorbitan monooleate (Tween 80™) are described in Merck Index Entry 7742 (Page 1308, 12th Edition, Merck & Co. Inc., Whitehouse Station, N.J., USA; ISBN 0911910-12-3). Both may be manufactured using methods described therein, or purchased from commercial sources such as Sigma Inc.

Exemplary non-ionic surfactants may include Triton X-45, t-octylphenoxy polyethoxyethanol (Triton X-100), Triton X-102, Triton X-114, Triton X-165, Triton X-205, Triton X-305, Trito-57, Triton-101, Trito-128, Breij 35, polyoxyethylene-9-lauryl ether (laureth 9) and polyoxyethylene-9-stearyl ether (steareth 9). Polyoxyethylene ethers may include polyoxyethylene-8-stearyl ether, polyoxyethylene-4-lauryl ether, polyoxyethylene-35-lauryl ether, and polyoxyethylene-23-lauryl ether.

Alternative terms or names for polyoxyethylene lauryl ether are disclosed in the CAS registry. The CAS registry number of polyoxyethylene-9 lauryl ether is: 9002-92-0. Polyoxyethylene ethers such as polyoxyethylene lauryl ether are described in the Merck index (12th ed: entry 7717, Merck & Co. Inc., Whitehouse Station, N.J., USA; ISBN 0911910-12-3). Laureth 9 is formed by reacting ethylene oxide with dodecyl alcohol and has an average of nine ethylene oxide units.

The ratio of the length of the polyoxyethylene section to the length of the alkyl chain in the surfactant (i.e., the ratio of n: alkyl chain length), affects the solubility of this class of surfactant in an aqueous medium. Thus, the surfactants of the present disclosure may be in solution or may form particulate structures such as micelles or vesicles. As a solution, the surfactants of the present disclosure are safe, easily sterilisable, simple to administer, and maybe manufactured in a simple fashion without the GMP and QC issues associated with the formation of uniform particulate structures. Some polyoxyethylene ethers, such as laureth 9, are capable of forming non-vesicular solutions. However, polyoxyethylene-8 palmitoyl ether (C18E8) is capable of forming vesicles. Accordingly, vesicles of polyoxyethylene-8 palmitoyl ether in combination with at least one additional non-ionic surfactant, can be employed in the formulations of the present disclosure.

Within the inherent experimental variability of such a biological assay, the polyoxyethylene ethers, or surfactants of general formula (I), of the present disclosure preferably have a haemolytic activity, of approximately between 0.5-0.0001%, more preferably between 0.05-0.0001%, even more preferably between 0.005-0.0001%, and most preferably between 0.003-0.0004%. Ideally, said polyoxyethylene ethers or esters should have a haemolytic activity similar (i.e., within a ten-fold difference) to that of either polyoxyethylene-9 lauryl ether or polyoxyethylene-8 stearyl ether.

Two or more non-ionic surfactants from the different groups of surfactants described may be present in the vaccine formulation described herein. In particular, a combination of a polyoxyethylene sorbitan ester such as polyoxyethylene sorbitan monooleate (Tween 80™) and an octoxynol such as t-octylphenoxypolyethoxyethanol (Triton) X-100™ is preferred. Another particularly preferred combination of non-ionic surfactants comprises laureth 9 plus a polyoxyethylene sorbitan ester or an octoxynol or both.

Preferably each non-ionic surfactant is present in the final vaccine formulation at a concentration of between 0.001 to 20%, more preferably 0.01 to 10%, and most preferably up to about 2% (w/v). Where one or two surfactants are present, these are generally present in the final formulation at a concentration of up to about 2% each, typically at a concentration of up to about 0.6% each. One or more additional surfactants may be present, generally up to a concentration of about 1% each and typically in traces up to about 0.2% or 0.1% each. Any mixture of surfactants may be present in the vaccine formulations according to the disclosure. Non-ionic surfactants such as those discussed above have preferred concentrations in the final vaccine composition as follows: polyoxyethylene sorbitan esters such as Tween 80™: 0.01 to 1%, most preferably about 0.1% (w/v); octyl- or nonylphenoxy polyoxyethanols such as Triton X-100™ or other detergents in the Triton series: 0.001 to 0.1%, most preferably 0.005 to 0.02% (w/v); polyoxyethylene ethers of general formula (1) such as laureth 9:0.1 to 20%, preferably 0.1 to 10% and most preferably 0.1 to 1% or about 0.5% (w/v).

A composition may be encapsulated within liposomes using well-known technology Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The composition may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup 87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

A composition may include preservatives such as thiomersal or 2-phenoxyethanol. In some instances, the vaccine is substantially free from (e.g. <10 μg/ml) mercurial material e.g. thiomersal-free. α-Tocopherol succinate may be used as an alternative to mercurial compounds.

For controlling the tonicity, a physiological salt such as sodium salt can be included in the vaccine. Other salts can include potassium chloride, potassium dihydrogen phosphate, disodium phosphate, and/or magnesium chloride, or the like.

A composition may have an osmolality of between 200 mOsm/kg and 400 mOsm/kg, between 240-360 mOsm/kg, or within the range of 290-310 mOsm/kg.

A composition may comprise one or more buffers, such as a Tris buffer; a borate buffer; a succinate buffer; a histidine buffer (particularly with an aluminum hydroxide adjuvant); or a citrate buffer. Buffers, in some cases, are included in the 5-20 mM range.

The pH of the composition may be between about 5.0 and about 8.5, between about 6.0 and about 8.0, between about 6.5 and about 7.5, or between about 7.0 and about 7.8.

A composition may be sterile. The vaccine can be non-pyrogenic e.g. containing <1 EU (endotoxin unit, a standard measure) per dose, and can be <0.1 EU per dose. The composition can be gluten free.

A composition may include detergent e.g. a polyoxyethylene sorbitan ester surfactant (known as 'Tweens'), an octoxynol (such as octoxynol-9 (Triton X-100) or t-octyl-phenoxypolyethoxyethanol), a cetyl trimethyl ammonium bromide ('CTAB'), or sodium deoxycholate, particularly for a split or surface antigen vaccine. The detergent can be present only at trace amounts. Thus the vaccine can include less than 1 mg/ml of each of octoxynol-10 and polysorbate 80. Other residual components in trace amounts can be antibiotics (e.g. neomycin, kanamycin, polymyxin B).

A composition may be formulated as a sterile solution or suspension, in suitable vehicles, well known in the art. The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

A composition may be formulated with one or more pharmaceutically acceptable salts. Pharmaceutically acceptable salts can include those of the inorganic ions, such as, for example, sodium, potassium, calcium, magnesium ions, and the like. Such salts can include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

Additional salts may comprise a bile acid or a derivative thereof. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particularly preferred example is sodium deoxycholate (NaDOC) which may be present in the final vaccine dose.

A composition comprising an active agent such as a peptide or a nucleic acid described herein, in combination with one or more adjuvants may be formulated in conventional manner using one or more physiologically acceptable carriers, comprising excipients, diluents, and/or auxiliaries, e.g., which facilitate processing of the active agents into preparations that can be administered. Proper formulation may depend at least in part upon the route of administration chosen. The agent(s) described herein may be delivered to a patient using a number of routes or modes of administration, including oral, buccal, topical, rectal, transdermal, transmucosal, subcutaneous, intravenous, and intramuscular applications, as well as by inhalation.

The active agents may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol.

For injectable formulations, the vehicle may be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation may also comprise polymer compositions which are biocompatible, biodegradable, such as poly(lactic-co-glycolic)acid. These materials may be made into micro or nanospheres, loaded with drug and further coated or derivative to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some instances, a composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it may be dispensed with an infusion bottle containing sterile pharmaceutical grade water or saline. Where the composition is administered by injection, an ampoule of sterile water for injection or saline can be provided so that the ingredients may be mixed prior to administration.

When administration is by injection, the active agent may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the active compound may be in powder form for constitution with a suitable vehicle, e.g., sterile pyrogen-free water, before use. In another embodiment, the pharmaceutical composition does not comprise an adjuvant or any other substance added to enhance the immune response stimulated by the peptide. In another embodiment, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In addition to the formulations described above, the active agents may also be formulated as a depot preparation. Such long acting formulations may be administered by implantation or transcutaneous delivery (for example subcutaneously or intramuscularly), intramuscular injection or use of a transdermal patch. Thus, for example, the agents may be formulated with suitable polymeric or hydrophobic materials (for example as an emulsion in an acceptable oil) or ion exchange resins, or as sparingly soluble derivatives, for example, as a sparingly soluble salt.

In some cases, compositions comprising one or more agents exert local and regional effects when administered topically or injected at or near particular sites of infection Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another embodiment, local/topical formulations comprising a transporter, carrier, or ion channel inhibitor are used to treat epidermal or mucosal viral infections.

Compositions may contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents can be formulated in an oleaginous hydrocarbon base, an anhydrous absorption base, a water-in-oil absorption base, an oil-in-water water-removable base and/or a water-soluble base Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Lubricants which may be used to form pharmaceutical compositions and dosage forms can include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

The compositions may be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions may be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions can also consist of solid preparations constituting soaps or cleansing bars.

Compositions may contain adjuvants such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

For oral administration, the active agent(s) may be formulated readily by combining the active agent(s) with pharmaceutically acceptable carriers well known in the art. Such carriers enable the agents of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier may be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the active agents may be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use may contain active agent(s) with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Oils or non-aqueous solvents can be required to bring the active agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al, Proc. Natl. Acad. Sci. USA 75: 4194-4198 (1978), incorporated herein by reference. Ligands can also be attached to the liposomes to direct these compositions to particular sites of action.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores may be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that may be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers can be added. All formulations for oral administration may be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or can contain emulsifying agents, for example, such as lecithin, sorbitan monooleate, or acacia. Aqueous solutions may be prepared by dissolving the active component in water and adding suitable colorants, flavors, stabilizers, and thickening agents. Aqueous suspensions may be prepared by dispersing the finely divided active component in water with viscous material, such as natural or synthetic gums, resins, methylcellulose, sodium carboxymethylcellulose, and other well known suspending agents. Suitable fillers or carriers with which the compositions may be administered include agar, alcohol, fats, lactose, starch, cellulose derivatives, polysaccharides, polyvinylpyrrolidone, silica, sterile saline and the like, or mixtures thereof used in suitable amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension may be made by adding the active compound to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

When formulating compounds for oral administration, it may be desirable to utilize gastroretentive formulations to enhance absorption from the gastrointestinal (GI) tract. A formulation which is retained in the stomach for several hours may release compounds of the invention slowly and provide a sustained release that can be used herein. Disclosure of such gastro-retentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm Res. 20, 1466-73, Hoffman, A.; Stepensky, D.; Law, E.; Eyal, S. Klausner. E.; Friedman, M. 2004 "Pharmacokinetic and pharmacodynamic aspects of gastroretentive dosage forms" Int. J. Pharm. 11, 141-53, Streubel, A.; Siepmann, J; Bodmeier, R.; 2006 "Gastroretentive drug delivery systems" Expert Opin. Drug Deliver. 3, 217-3, and Chavanpatil, M.D.; Jain. P.; Chaudhari, S.; Shear, R.; Vavia, P. R. "Novel sustained release, swellable and bioadhesive gastroretentive drug delivery system for ofloxacin" Int. J. Pharm. 2006 Mar. 24. Expandable, floating and bioadhesive techniques can be utilized to maximize absorption of the compounds of the invention.

The solubility of the components of the compositions may be enhanced by a surfactant or other appropriate co-solvent m the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions may be packaged in multidose form. Preservatives may be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g. from 0.001% to 0.008%, preferably about 0.005% by weight. It has been found that a concentration of benzalkonium chloride of 0.005% can be sufficient to preserve the compositions of the present invention from microbial attack.

In instances relating to topical/local application, the compositions may include one or more penetration enhancers. For example, the formulations may comprise suitable solid or gel phase carriers or excipients that increase penetration or help delivery of agents or combinations of agents of the invention across a permeability barrier, e.g., the skin Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In another embodiment, the compositions may include one or more such penetration enhancers.

The compositions for local/topical application may include one or more antimicrobial preservatives such as quaternary ammonium compounds, organic mercurials, p-hydroxy benzoates, aromatic alcohols, chlorobutanol, and the like.

The compositions may be formulated into aerosol solutions, suspensions or dry powders. The aerosol can be adminstered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a transporter, carrier, or ion channel inhibitor can be dissolved, suspended or emulsified in a propellant or a mixture of solvent and propellant, e.g., for administration as a nasal spray or inhalant, Aerosol formulations can contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages m drops or sprays. Nasal solutions can be similar to nasal secretions in that they are generally isotonic and slightly buffered to maintain a pH of about 5.5 to about 6.5, although pH values outside of this range may additionally be used. Antimicrobial agents or preservatives may also be included in the formulation.

An aerosol formulation for inhalations and inhalants may be designed so that the agent or combination of agents is carried into the respiratory tree of the subject when administered by the nasal or oral respiratory route Inhalation solutions may be administered, for example, by a nebulizer. Inhalations or insufflations, comprising finely powdered or liquid drugs, may be delivered to the respiratory system as a pharmaceutical aerosol of a solution or suspension of the agent or combination of agents in a propellant, e.g., to aid in disbursement. Propellants may be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants may include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson. U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998; Hydrocarbon propellants useful in the invention include, for example, propane, isobutane, n-butane, pentane, isopentane and neopentane. A blend of hydrocarbons may also be used as a propellant. Ether propellants include, for example, dimethyl ether as well as the ethers. An aerosol formulation of the invention may also comprise more than one propellant. For example, the aerosol formulation may comprise more than one propellant from the same class, such as two or more fluorocarbons; or more than one, more than two, more than three propellants from different classes, such as a fluorohydrocarbon and a hydrocarbon. Pharmaceutical compositions of the present invention may also be dispensed with a compressed gas, e.g., an inert gas such as carbon dioxide, nitrous oxide or nitrogen.

Aerosol formulations may also include other components, for example, ethanol, isopropanol propylene glycol, as well as surfactants or other components such as oils and detergents. These components may serve to stabilize the formulation and/or lubricate valve components.

The aerosol formulation may be packaged under pressure and can be formulated as an aerosol using solutions, suspensions, emulsions, powders and semisolid preparations. For example, a solution aerosol formulation may comprise a solution of an agent of the invention such as a transporter, carrier, or ion channel inhibitor in (substantially) pure propellant or as a mixture of propellant and solvent. The solvent may be used to dissolve the agent and/or retard the evaporation of the propellant. Solvents may include, for example, water, ethanol and glycols. Any combination of suitable solvents may be use, optionally combined with preservatives, antioxidants, and/or other aerosol components.

An aerosol formulation may be a dispersion or suspension. A suspension aerosol formulation may comprise a suspension of an agent or combination of agents of the instant invention, e.g., a transporter, carrier, or ion channel inhibitor, and a dispersing agent. Dispersing agents may include, for example, sorbitan trioleate, oleyl alcohol oleic acid, lecithin and corn oil. A suspension aerosol formulation may also include lubricants, preservatives, antioxidant, and/or other aerosol components.

An aerosol formulation may similarly be formulated as an emulsion. An emulsion aerosol formulation may include, for example, an alcohol such as ethanol a surfactant, water and a propellant, as well as an agent or combination of agents of the invention, e.g., a transporter, carrier, or ion channel. The surfactant used may be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

The compounds may be formulated for administration as suppositories. A low melting wax, such as a mixture of triglycerides, fatty acid glycerides, Witepsol S55 (trademark of Dynamite Nobel Chemical, Germany), or cocoa butter is first melted and the active component is dispersed homogeneously, for example, by stirring. The molten homogeneous mixture is then poured into convenient sized molds, allowed to cool, and to solidify.

The compounds may be formulated for vaginal administration. Pessaries, tampons, creams, gels, pastes, foams or sprays containing in addition to the active ingredient such carriers as are known in the art to be appropriate.

The compounds may be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, may be utilized in a formulation suitable for intra ocular implantation or injection for sustained release administration, as well. Any suitable biodegradable and biocompatible polymer may be used.

Dosages, Routes of Administration, and Therapeutic Regimens

The compositions and methods described herein may elicit an immune response to an epitope of an antigenic peptide in a subject. In some cases, the compositions may be breast cancer vaccines or ovarian cancer vaccines. In some cases, the breast cancer vaccine may be a multiantigen breast cancer vaccine. In some cases, the ovarian cancer vaccine may be a multiantigen ovarian cancer vaccine.

In some cases, the subject may be tumor bearing prior to administration of the vaccine. In other cases, the subject may not be tumor bearing prior to administration of the vaccine. In other cases, the subject may not be tumor bearing prior to administration of the vaccine but become tumor bearing after administration of the vaccine. In other cases, the subject may not be tumor bearing prior to administration of the vaccine and may not become tumor bearing after administration of the vaccine. In some instances, the tumors may be breast cancer tumors. In some cases, the breast cancer tumors in rodents are DMBA-induced tumors. For example, the breast cancer tumors in rodents may be derived from M6 or MMC cells. Often, the breast cancer tumors in humans are triple negative tumors in humans.

The compositions described herein may be administered to a subject in need thereof as a vaccine. In some cases, the subject may be immunized with the multiantigen breast cancer vaccine or multiantigen ovarian cancer vaccine. For example, the vaccine may be a breast cancer vaccine (e.g., multiantigen vaccine), or ovarian cancer vaccine (e.g., multiantigen vaccine).

The vaccine described herein may be delivered via a variety of routes. Delivery routes may include oral (including buccal and sub-lingual), rectal, nasal, topical, transdermal patch, pulmonary, vaginal, suppository, or parenteral (including intramuscular, intraarterial, intrathecal intradermal, intraperitoneal, subcutaneous and intravenous) administration or in a form suitable for administration by aerosolization, inhalation or insufflation. General information on drug delivery systems can be found in Ansel et al, Pharmaceutical Dosage Forms and Drug Delivery Systems (Lippencott Williams & Wilkins, Baltimore Md. (1999). The vaccine described herein can be administered to muscle, or can be administered via intradermal or subcutaneous injections, or transdermally, such as by iontophoresis. Epidermal administration of the vaccine can be employed.

In some instances, the vaccine may also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine may be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine may include material for a single immunization, or may include material for multiple immunizations (i.e. a 'multidose' kit). The inclusion of a preservative is preferred in multidose arrangements. As an alternative (or in addition) to including a preservative in multidose compositions, the compositions can be contained in a container having an aseptic adaptor for removal of material.

The vaccine may be administered in a dosage volume of about 0.1, 0.2, 0.3, 0.4, 0.5, 0.6, 0.7, 0.8, 0.9, or 1.0 mL. Sometimes the vaccine can be administered in a higher dose e.g. of more than 1 ml.

In some cases, the subject may be immunized with one dose of the vaccine. In other cases, the subject may be immunized with more than one dose of the vaccine. For example, the subject may be immunized with more than one, more than two, more than three, more than four, more than five, more than six, more than seven, more than eight, more than nine, more than ten, more than 11, more than 12, more than 13, more than 14, more than 15, more than 16, more than 17, more than 18, more than 19 or more than 20 doses of the vaccine. In an exemplary case, the subject is immunized with three doses of the vaccine.

In the cases that a subject receives more than one dose of the vaccine, time may elapse between the first dose and each subsequent dose of the vaccine. In some cases, the time that elapses between the first dose an each subsequent dose of the vaccine may be seconds, minutes, hours, days, weeks, months or years. For example, more than one dose may be administered to the subject by intervals. In some cases, the intervals may occur over seconds, minutes, hours, days, weeks, months or years. In some cases, subjects may receive a booster dose. For example, the booster may be administered to the subject more than one, more than two, more than three, more than four, more than five, more than six, more than seven, more than eight, more than nine, more than ten, more than 11, more than 12, more than 13, more than 14, more than 15, more than 16, more than 17, more than 18, more than 19 or more than 20 booster doses of the vaccine. In an exemplary case, the subject may receive up to three boosters of the vaccine.

In some cases, intervals may be the same between each dose of the vaccine. In some cases, intervals may be the same between each booster of the vaccine. In some cases, intervals may be different between each dose of the vaccine. In some cases, intervals may be different between each booster of the vaccine.

In an exemplary case, more than one dose is administered to the subject over an interval of at least one day. In some cases, the interval may be a one day, two day, three day, four day, five day, six day, seven day, eight day, nine day, ten day, 11 day, 12 day, 13 day, 14 day, 15 day, 16 day, 17 day, 18 day, 19 day, 20 day, 21 day, 22 day, 23 day, 24 day, 25 day, 26 day, 27 day, 28 day, 29 day or 30 day interval. In other cases, the interval may be a range of days, for example, the range of days may be 1-5 days, 1-7 days, 1-10 days, 3-15 days, 5-10 days, 5-15 days, 5-20 days, 7-10 days, 7-15 days, 7-20 days, 7-25 days, 10-15 days, 10-20 days, 10-25 days, 15-20 days, 15-25 days, 15-30 days, 20-30 days, 20-35 days, 20-40 days, 20-50 days, 25-50 days, 30-50 days, 35-50 days, or 40-50 days.

Subjects may be evaluated after administration of the vaccine. In some cases, the subject may be evaluated within one month (e.g., short term) of the final administration of the vaccine. For example, short term may be one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the final administration of the vaccine. In some cases, the subject may be evaluated within four month (e.g., long term) of the final administration of the vaccine. For example, short term may be one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or 31 weeks after the final administration of the vaccine.

In some cases, the subject may receive at least one booster dose of the vaccine after the final administration of the vaccine doses. For example, at least one booster dose may be administered to the subject one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or 31 weeks after the final administration of the vaccine doses. In some cases, the subject may receive one booster, two boosters, three boosters, four boosters, five boosters, six boosters, seven boosters, eight boosters, nine boosters, ten boosters, 11 boosters, 12 boosters, 13 boosters, 14 boosters, 15 boosters, 16 boosters, 17 boosters, 18 boosters, 19 boosters, 20 boosters, 21 boosters, 22 boosters, 23 boosters, 24 boosters, 25 boosters, 26 boosters, 27 boosters, 28 boosters, 29 boosters or 30 booster doses.

The disclosure provides in a further aspect a pharmaceutical kit comprising an intradermal administration device and a vaccine formulation as described herein. The device is preferably supplied already filled with the vaccine. Preferably the vaccine is in a liquid volume smaller than for conventional intramuscular vaccines as described herein, particularly a volume of between about 0.05 ml and 0.2 ml. Preferably the device is a short needle delivery device for administering the vaccine to the dermis.

Suitable devices for use with the intradermal vaccines described herein include short needle devices such as those described in U.S. Pat. Nos. 4,886,499, 5,190,521, 5,328,483, 5,527,288, 4,270,537, 5,015,235, 5,141,496, 5,417,662. Intradermal vaccines may also be administered by devices which limit the effective penetration length of a needle into the skin, such as those described in WO99/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration. However, the use of conventional syringes requires highly skilled operators and thus devices which are capable of accurate delivery without a highly skilled user are preferred.

Another case of the disclosure relates to a method to immunize a subject or population of subjects against a disease in order to prevent a disease, and/or reduce the severity of disease in the subject or population of subjects. The method includes the step of administering to a subject or population of subjects that is not infected with the disease (or believed not to be infected with the disease), a composition of the disclosure.

The composition of one case of the disclosure may be administered using techniques well known to those in the art. Preferably, compounds are formulated and administered by genetic immunization. Techniques for formulation and administration may be found in "Remington's Pharmaceutical Sciences", 18th ed., 1990, Mack Publishing Co., Easton, Pa. Suitable routes may include parenteral delivery, such as intramuscular, intradermal, subcutaneous, intramedullary injections, as well as, intrathecal direct intraventricular, intravenous, intraperitoneal, intranasal, or intraocular injections, just to name a few. Other routes include oral or transdermal delivery. For injection, the composition of one case of the disclosure may be formulated in aqueous solutions, preferably in physiologically compatible buffers such as Hanks' solution, Ringer's solution, or physiological saline buffer.

For parenteral application, which includes intramuscular, intradermal, subcutaneous, intranasal, intracapsular, intraspinal, intrasternal, and intravenous injection, particularly suitable are injectable, sterile solutions, preferably oily or aqueous solutions, as well as suspensions, emulsions, or implants, including suppositories. Formulations fix injection may be presented in unit dosage form, e.g., in ampoules or in multi-dose containers, with an added preservative. The compositions may take such forms as suspensions, solutions or emulsions in oily or aqueous vehicles, and may contain formulator agents such as suspending, stabilizing and/or dispersing agents. Alternatively, the active ingredient may be in powder form for constitution with a suitable vehicle, e.g., sterile pyrogen-free water, before use.

For enteral application, particularly suitable are tablets, dragees, liquids, drops, suppositories, or capsules. The pharmaceutical compositions may be prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze dry the new compounds and use the lyophilizates obtained, for example, for the preparation of products for injection.

For administration by inhalation, the compounds for use according to one case of the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. For topical, or transdermal, application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient; preferably in combination with a solid or liquid inert carrier material, is packaged in a squeeze bottle or in admixture with a pressurized volatile, normally gaseous propellant, e.g., a freon. The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In accordance with one case of the present disclosure the compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, intramucosal (e.g., gut), intranasal, intramuscular, or intraperitoneal routes.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

Immunogenicity of Compositions

The immunogenicity of the compositions described herein may be evaluated in a subject. In some cases, the epitope encoded by the composition (e.g., plasmid-based vaccines) may be evaluated in a recipient subject. For example, the recipient subject may be a rodent, a non-human primate or a human. In some cases, the rodent is a mouse. For example, the mouse may be a neu-TG mouse, a C3 mouse or an FVB mouse.

The compositions and methods described herein may elicit an immune response to an epitope of an antigenic peptide in a subject. In some instances, the compositions may be a breast cancer vaccine or ovarian cancer vaccine. In some cases, the breast cancer vaccine may be a multiantigen breast cancer vaccine. In some cases, the ovarian cancer vaccine may be a multiantigen ovarian cancer vaccine.

The immune response may be a Type I immune response, a Type II immune response or both Type I and Type II immune responses. In some cases, a Type I immune response may result in the secretion of inflammatory cytokines (e.g., IFNγ, TNFα) by antigen specific T-cells. The inflammatory cytokines (e.g., Type I cytokines) may activate cytotoxic T-cells which, for example, may kill cells which express at least one epitope encoded for (e.g., nucleic acids, plasmids) or delivered (e.g., peptide, protein) by the vaccine. In some cases, the Th1 cytokines may activate additional immune cells. In some cases, a Type II immune response may result in the secretion of immunosuppressive cytokines (e.g., IL-10, IL-4 and IL-5) by regulatory T-cells. The immunosuppressive cytokines (e.g., Type II cytokines) may activate regulatory T-cells which, for example, may not kill cells which express at least one antigenic epitope encoded for (e.g., nucleic acids, plasmids) or delivered (e.g., peptide, protein) by the vaccine but rather suppress the Th1 immune response.

Whether a Th1 or a Th2 immune response, or both, may occur in a subject may be the result of the affinity between the epitope and the MHC-T cell receptor interaction. In some cases, the affinity of the binding peptides for MHC molecules may be high. In other cases, the affinity of the binding peptides for MHC molecules may be low. In some cases, low affinity binding peptides may induce a Th2 response. In other cases, high affinity binding peptides may induce a Th1 response. The affinity of candidate binding peptides for MHC molecules may be screened. For example, IFNγ and IL-10 secretion induced by a candidate binding peptide may be determined as described herein or using techniques known to one of ordinary skill in the art.

The immunogenicity of the vaccine may be analyzed in the subject using any of the plurality of methods known to one of ordinary skill in the art. In some cases, immunogenicity may be analyzed by detecting expression of peptides in the subject encoded by the vaccine administered to the subject. For example, detection methods may include ELISPOT, ELISA. Western blotting, flow cytometry, histology, chromatography, mass spectrometry and the like. Often, immunogenicity to isolated peptides produced in the subject in response to the vaccine may be analyzed. In some cases, a sample of tumor cells, cancer cells, spleen cells or normal cells taken from the subject may be analyzed.

In some cases, lymphocytes may be isolated from the subject for analysis of immunogenicity. For example, lymphocytes may be isolated from the spleen, from the lymph nodes and/or from the draining lymph nodes. In some cases, the lymphocytes may be isolated after administration of the single dose of the vaccine. In other cases, the lymphocytes may be isolated after administration of the last dose of a plurality of doses of the vaccine. For example, lymphocytes may be isolated one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days or 30 days after administration of either the single dose of the vaccine.

In some cases, the lymphocytes may be isolated after administration of the last dose of a plurality of doses of the vaccine. In other cases, the lymphocytes may be isolated after administration of the last dose of a plurality of doses of the vaccine. For example, lymphocytes may be isolated one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days or 30 days after administration of the last dose of a plurality of doses of the vaccine.

In some cases, a protein detection method may be used to determine the amount of each peptide encoded for by the nucleic acids of the composition (e.g., the plasmid-based vaccine) produced by the subject. For example, an ELISPOT may be performed and the ELISPOT may detect IFNγ. For another example, a different ELISPOT may be performed and the ELISPOT may detect Granzyme B. In some cases, a protein detection method may be used to determine the presence of protein specific T-cells in response to the composition (e.g., plasmid-based vaccine) produced by the subject. For example, an ELISPOT may be performed and the ELISPOT may detect IFNγ. For another example, a different ELISPOT may be performed and the ELISPOT may detect Granzyme B.

Immunogenicity of the peptides encoded by the vaccine may be determined by comparing the results from subjects after administration of the composition (e.g., vaccine) to the results of the methods described herein from subjects after administration of a control composition (e.g., nothing encoded by the plasmids or no peptides). In some cases, the control may be the adjuvant alone. In other cases, the control may be a negative control (e.g., blank plasmids lacking antigenic peptide epitopes). Immunogenicity may be determined by an increase in the amount of IFNγ produced (e.g., IFNγ positive spots on an ELISPOT) or increase in the amount of tumor specific Granzyme B produced (Granzyme B positive spots on an ELISPOT). The increase may be observed in subjects after administration of the composition (e.g., vaccine) compared to subjects administered a control composition. In some cases, the increase may be statistically different than the control as indicated by a P value (e.g., p<0.05). Often, statistically different at p<0.05 is statistically significant.

For example, the statistical significance of immunogenicity may be determined by comparing two groups (n=10 subjects per group) for a 98% power where at least the two-sided level may be 0.05 and the true effect size may be 2.0. In some cases, the effect size may be defined as the difference in mean specific T-cell response level divided by the common standard deviation. A true effect size of about 1.5 or less would not be significant.

Additional parameters may be analyzed after administration of at least one dose of the vaccine. In some cases, blood may be isolated from a subject and a plurality of tests performed on the blood known to one of ordinary skill in the art. For example, a basic metabolic panel and/or a complete blood count performed. In some cases, additional tissues may be examined. For example, the spleen, skin, skeletal muscle, lymph node, bone, bone marrow, ovary, oviduct, uterus, peripheral nerve, brain, heart, thymus, lung, kidney, liver and/or pancreas may be examined after administration of at least one dose of the vaccine.

Efficacy of the Compositions Using Model Systems

The compositions described herein may be utilized with a plurality of mouse model systems. In some cases, the mouse models may include genetically diverse mouse models. In some cases, the mouse model may be a tumor implant model. For example, the mice may include, TgMMTV-neu (neu-TG) and TgC3(I)-Tag (C3). In some cases, a genetically similar mouse model may be used. For example, the neu-TG mouse model system may have a genotype similar to two different types of human cancers, (1) human luminal cancer and is estrogen receptor negative (ER−), and (2) HER2+ human breast cancer and overexpresses the neu oncogene. In other cases, the C3 mouse may have a genotype that may be similar to basal breast cancer and/or triple negative breast cancer. The mouse model of DMBA induced breast cancers in FVB mice may be heterogeneic and may have tumors comparable to multiple subtypes of human breast cancers. For example, a mouse model of genetically similar may be Medroxyprogesterone-DMBA-induced tumors in FVB mice (DMBA).

Figure 35:
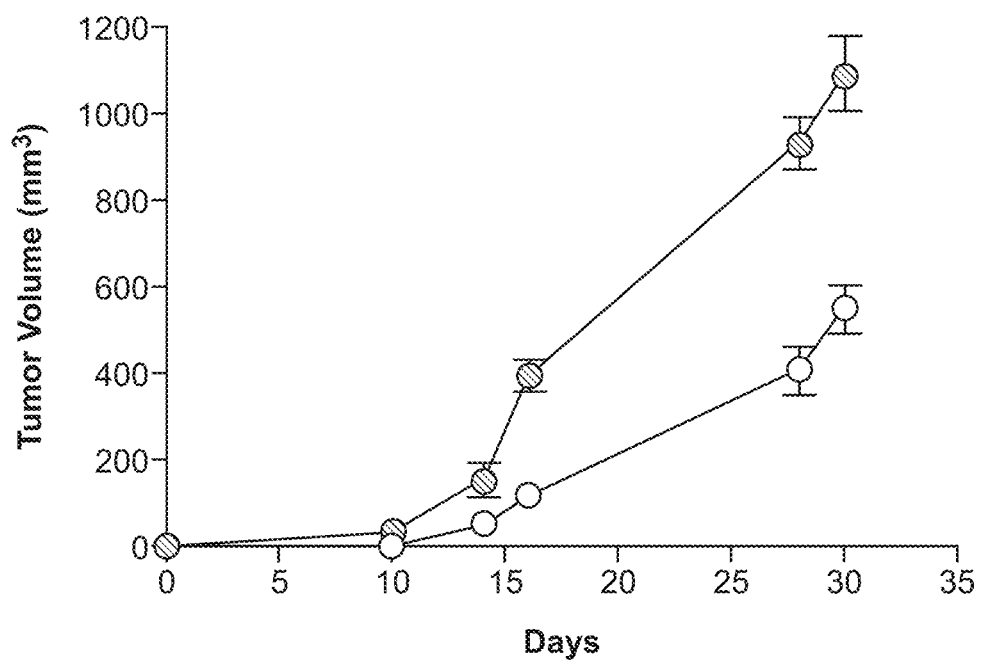
FIG. 35 demonstrates that multi-epitope IGF-1R vaccine inhibits the growth of implanted breast cancer.

In some cases, the mouse model may be a tumor implant model. For example, a tumor implant model, as shown in FIG. 35, may be used to analyze the therapeutic efficacy of the compositions described herein. For example, the composition may be a breast cancer vaccine. In some cases, tumor cells may be implanted subcutaneously in the mouse. For example, at least 1,000, 2,500, 5,000, 7,500, 10,000, 12,500, 15,000, 17,500, 20,000, 22,500, 25,000, 27,500, 30,000, 35,000, 40,000, 45,000, 50,000, 75,000, 100,000, 125,000, 150,000, 175,000, 200,000, 225,000, 250,000, 275,000, 300,000, 350,000, 400,000, 450,000, 500,000, 750,000, 1,000,000, 1,250,000, 1,500,000, 1,750,000, 2,000,000, 2,500,000, 3,000,000, 3,500,000, 4,000,000, 4,500,000, 5,000,000, 5,500,000, 6,000,000, 6,500,000, 7,000,000, 7,500,000, 8,000,000, 8,500,000, 9,000,000, 9,500,000 or at least 1,000,000,000 tumor cells may be implanted subcutaneously in the mouse. In some cases, the tumor cells may be MMA cells.

Tumor growth may be measured using methods known to one of ordinary skill in the art. For example, methods of measurement may include tumor diameter, tumor volume, tumor mass and the like. In some cases, imaging, extraction or histologic techniques may be used. For example, any of the techniques may include use of a contrast agent.

In some cases, the efficacy of the vaccine may be determined by the size of tumor growth relative to a control (e.g., unvaccinated mouse or a mouse treated with a control vaccine). For example, in the absence of vaccination, greater than 90% of the mice may develop tumors and in the presence of vaccination, a 60% inhibition of tumor growth may be observed. In some cases, vaccination may inhibit at least 2%, 5%, 7%, 10%, 15%, 20%, 25%, 30%, 35%, 40%, 45%, 50%, 55%, 60%, 65%, 70%, 75%, 80%, 85%, 90%, 95% or at least 99% of tumor growth.

After administration of the vaccine, the subject may be 100% tumor free. In other cases, the subject may be less than 100% tumor free after administration of the vaccine. For example, the subject may be less than 99%, 95%, 90%, 85%, 80%, 75%, 70%, 65%, 60%, 55%, 50%, 45%, 40%, 35%, 30%, 25%, 20%, 15% or less than 10% tumor free after administration of the vaccine. In some cases, the subject may become tumor free hours after administration of the vaccine. For example, the subject may become tumor free one hour, two hours, three hours, four hours, five hours, six hours, seven hours, eight hours, nine hours, ten hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours or more after administration of the vaccine. In other cases, the subject may become tumor free days after administration of the vaccine. For example, the subject may become tumor free one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days or more after administration of the vaccine. In other cases, the subject may become tumor free weeks after administration of the vaccine. For example, the subject may become tumor free one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks or more after administration of the vaccine. In other cases, the subject may become tumor free months after administration of the vaccine. For example, the subject may become tumor free one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months or more after administration of the vaccine. In other cases, the subject may become tumor free years after administration of the vaccine. For example, the subject may become tumor free one year, two years, three years, four years, five years, six years, seven years, eight years, nine years, ten years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years or more after administration of the vaccine.

In some cases, the efficacy of the vaccine may be determined by the amount of IFNγ produced in a vaccinated subject (e.g., mouse) relative to a control (e.g., unvaccinated mouse). In some cases, the efficacy of the vaccine may be determined by the amount of IL-10 produced in a vaccinated subject (e.g., mouse) relative to a control (e.g., unvaccinated mouse).

In some aspects, polyclonality of the epitope-specific immune response may be evaluated. In some cases, an evaluation of polyclonality may be performed by assessing the production of IgG antibodies in response to epitopes of the administered vaccine. In some cases, IgGs may be elicted to one antigen. In other cases. IgGs may be elicted to multiple antigens. In some cases, a lysate may be prepared from a sample taken from a subject and evaluated from the pre-immunization and post-immunization serum of the subject. For example, a subject may be a mouse of the neu-TG mouse model and IgGs detected using a method of peptide detection, such as ELISA or ELISPOT.

In some cases, the response to each antigen between pre-vaccination subjects (e.g., mice) and post-vaccination subjects (e.g., mice) may be analyzed using statistical methods. For example, statistical methods may include analysis using single factor ANOVA. In some cases, an analysis of the number of antigens to which subjects (e.g., mice) developed immunity during the course of vaccination may be performed.

Toxicity and Safety Profile of Compositions

The compositions described herein may be assessed for toxicity and safety. Methods to assess toxicity and safety known to one of ordinary skill in the art may be used with the compositions described herein. In some cases, a dose escalation study may be performed. In some cases, toxicity and safety studies may screen for the development of diseases in the subject, damage to organs in the subject, damage to tissues in the subject, damage to cells in the subject, blood disorders and the like. For example, diseases may include autoimmune diseases.

Manufacture and Quality Control of Compositions

Manufacture and testing of the compositions described herein (e.g., plasmid-based vaccines) may be performed in compliance with current standards of cGMP Biologics Production Facilities (BPF). Process development may include the transfer of the candidate cells (e.g., cell line(s)) each containing the appropriate plasmid constructs with the kanamycin selection marker to the cGMP BPF. In some cases, a research bank may be generated from the bacterial stock. For example, a scaled pilot production that may match a later cGMP manufacture may be utilized to asses plasmid yield and purity. In some cases, the preliminary manufacturing batch records and quality control testing schedules may be established. For example, the master cell bank(s) may be generated from each bacterial stock. In some cases, quality control testing may be performed inclusive of: plasmid and host cell identity, plasmid copy number, purity, viability, and retention of antibiotic resistance (plasmid retention).

In some cases, finalized and approved manufacturing batch records and standard operating procedures may be followed for cGMP production and purification of the vaccine plasmid(s) and lot release criteria may be developed. In some cases, the final bulk/pooled purified product may be quality control tested in accordance with current regulatory guidelines and then may be vialed as single dose units following validated fill and finish standard operating procedures. In compliance with cGMP regulations, the vialed product may undergo quality control testing prior to final product release.

Clinical Trials for Ovarian Cancer

The compositions and methods described herein may be administered to human subjects in need thereof. While standard practices are followed in accordance with rules and regulations set forth by the Federal Department of Agriculture (FDA) and any other relevant governing bodies, administration of the compositions and methods described herein to human subjects may follow established guidelines. In some cases, a pre-investigational new drug (IND) packet may be prepared. In some cases, a standard operating procedure (SOP) for production of the plasmids described herein may be used for manufacturing purposes. For example, manufacturing may occur in a good manufacturing practice (GMP) facility. In some cases, the GMP facility may include a master cell bank.

A clinical trial may be performed to evaluate the safety and determine the most immunogenic dose of the multi-antigen DNA plasmid-based vaccine. In some instances, the clinical trial may be performed to determine the safety of administration (e.g., intradermal) of a multi-antigen vaccine (e.g., three doses) in subjects (e.g., patients) that may have an ovarian cancer and to determine the immunogenic dose of the compositions (e.g., a multi-antigen vaccine) in subjects. In some cases, the clinical trial may be performed to determine the safety of administration (e.g., intradermal) of a multi-antigen vaccine (e.g., three doses) in subjects (e.g., patients) that may have ovarian cancer and to determine the immunogenic dose of the compositions (e.g., a multi-antigen vaccine) in subjects.

The clinical trial may be a Phase I trial of the safety and immunogenicity of the compositions described herein (e.g., vaccines). In some cases, subjects with non-metastatic ovarian cancer may be enrolled. In some cases, the patient may have been treated to complete remission. In some cases, patients may have been treated with primary or salvage therapy. In some cases, patients may have completed chemotherapy, radiotherapy and/or use of systemic steroids prior to enrolling in the clinical trial. For example, patients may be at least one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days or more from last cytotoxic chemotherapy and/or radiotherapy and any use of systemic steroids. In an exemplary case, patients may be 28 days from last cytotoxic chemotherapy and/or radiotherapy and any use of systemic steroids.

In some cases, Phase I may evaluate 3 dose levels of the compositions (e.g., vaccines). For example, subjects may be assigned to one of three doses: Arm 1 (150 mcg), Arm 2 (300 mcg), and Arm 3 (600 mcg). In some cases, no more than ten subjects may be enrolled in each arm. For example, three doses of the vaccine may be administered to each subject such that one month elapses between each dose. In some cases, booster doses may be administered to the subject following the third dose of the vaccine. For example, the booster may be administered such that one booster is administered two months following the third dose of the vaccine and one booster administered four months after the booster.

In some cases, the Arm 2 cohort of 10 subjects may be enrolled in Phase I of the trial if the doses in Arm 1 are safe. In some cases, if the Arm 2 dose is safe then the immunologic efficacy of both Arm 1 and Arm 2 may be examined. For example, if the Arm 1 dose is more efficacious, the trial may terminate. In some cases, if the efficacy is greater in the Arm 2 dose compared to the Arm 1 does, then subjects may be enrolled into the Arm 3 dose schema. In some cases, if the Arm 3 dose appears safe, the immunologic efficacy between Arm 2 and 3 will be examined. For example, safety may be assessed per CTEP CTCAE v. 4.0. In some cases, benchmarks for safety to move to the next arm may be a grade 3 toxicity rate of ≤15% and a grade 4 toxicity rate of ≤15%.

Immunologic efficacy of the three doses may be evaluated via an assessment of the generation of T cells. In some cases, immunologic efficacy may be defined as achievement of augmented IFN-g T-cell immunity to the antigens in the vaccine.

Figure 5:
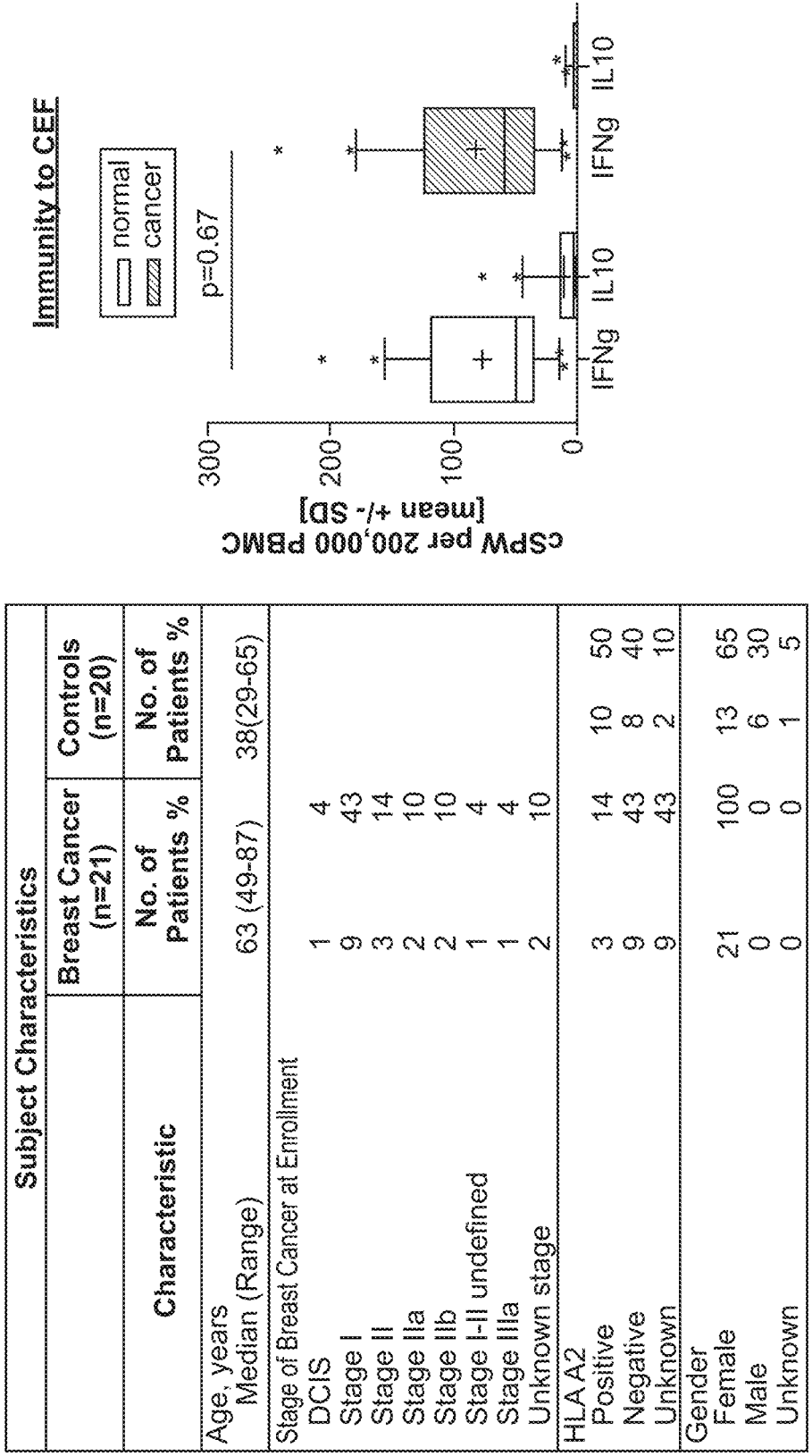
FIG. 5 demonstrates characteristics of breast cancer subjects.

Design and Recruitment Plan. The two endpoints of the Phase I clinical trial may be to, (1) determine the safety of intradermal administration of the vaccine given with GM-CSF as an adjuvant and, (2) determine the immunogenicity of the vaccine. In some cases, subjects may be immunized with the plasmid based vaccine (e.g., 100 ug of total plasmid per subject). In some cases, subjects may receive three vaccines administered across intervals (30-days). For example, the vaccines may be administered to the subject at the deltoid region in a draining lymph node site (FIG. 5).

Subjects with Stage IIb, III, and IV ovarian cancer who have been treated to complete remission may be enrolled in the trial. In some cases, the trial may accrue a target number of subjects (e.g., 22 subjects). Subjects may undergo leukapheresis (e.g., for baseline immunologic assessment) and blood draw (e.g., for baseline toxicity assessment) at beginning of the study and an 180 cc blood draw at one, six, and 12 months after the final vaccination. In some cases, blood may be analyzed for changes in serum chemistries as an assessment of potential toxicity. Peripheral blood mononuclear cells and sera collected at these time points may be evaluated for the development of tumor specific immunity as described herein. A leukapheresis product may be obtained after the final vaccination (e.g., 3 months) for additional studies.

Safety. In some cases, the vaccine may elicit an immediate allergic reaction. In some cases, the vaccine may cause side effects due to immunologic consequences of the vaccination targeting other, unrelated tissues. In some cases, after evaluation of these toxicities, criteria for stopping treatment or removing subjects from the study may be established.

During Phase I, more than 200 subjects may receive the ovarian cancer vaccine. In some cases, the composition may include GM-CSF (100-150 ug) admixed with the ovarian cancer vaccine. In some cases, the composition may be administered using the method of intradermal injection monthly for 3-6 months. For example, intradermal administration may result in allergic reaction to the skin. In some cases, subjects may be monitored following immunizations (e.g., for one hour).

Subjects may be examined at a routine visit following administration of the vaccine. In some cases, subjects may be evaluated at each visit based on the modified National Cancer Institute toxicity criteria. In some cases, subjects may undergo a complete physical examination. In addition, serum chemistries, including renal function tests, uric acid, blood counts, serum glucose, and liver function tests for each subject may be evaluated. In some cases, the development of connective tissue disorders and laboratory autoantibody responses may be assessed as a potential immunologic toxicity associated with the use of DNA vaccination. In some cases, the development of anti-DNA antibodies may be assessed, for example, anti-ANA, anti-C3, anti-thyroid and ds-DNA antibodies. In some cases, assessments may be performed at the end of the vaccination regimen, and at 12 months of follow-up.

A sample size of 22 subjects may be enrolled into each arm of the trial. In some cases, if no toxicities occur, the probability of a toxicity occurring may be at least 90% if the true toxicity rate, i.e., any Grade 3 or 4 toxicity, is 10% or less. For example, a toxicity occurrence may indicate that the toxicity rate is less than 10%. In some cases, the trial may continue and may be deemed sufficiently safe as long as the observed toxicity rate is consistent with a true grade 3 rate of 15% or less and a true grade 4 rate of 5% or less. In some cases, stopping rules may be utilized such that if sufficient evidence suggests the true toxicity rates exceed these thresholds, the study may be stopped. For example, sufficient evidence may be taken to be a lower one-sided confidence limit in excess of the appropriate threshold. For grade 3, such a limit may be reached if this level of toxicity occurred in 2 of the first 3 or fewer, 3 of the first 7 or fewer, 4 of the first 12 or fewer, 5 of the first 17 or fewer, or 6 of the first 22 or fewer enrolled subjects. For grade 4, one of the following may result in stopping the trial: 2 of the first 10 or fewer, 3 of the first 22 or fewer enrolled subjects experience grade 4 toxicity. For example, if the true probability of grade 3 toxicity is 10% or 30%, then the probability of stopping the study may be approximately 0.06 and 0.76, respectively. If the true probability of grade 4 toxicity is 3% or 23%, then the probability of stopping may be roughly 0.05 and 0.93, respectively (probabilities estimated from 5,000 simulations).

Immunogenicity. The vaccine may elicit an immunogenic response in the subject. In some cases, the type of immune response elicited after immunization may be determined. For example, the compositions described herein may elicit a Th1 immune response when administered to a subject. In some cases, the Th1 immune response may include formation of and persistence of antigen specific T cells that recognize at least one peptide of the vaccine. For example, a peptide may be a stem cell and/or an EMT antigen.

The type of immune response may be determined through an assessment of the types of cytokine secreted by antigen specific T cells. In some cases, the types of cytokines may be identified using an ELISPOT assay. For example, an ELISPOT method may include analysis of sample supernatants after antigen stimulation (e.g., 72 hours). In some cases, the sample supernatants may be evaluated for a panel of cytokines. In some cases, the evaluation may be a multiplex analysis. For example, the multiplex analysis of cytokines may include the cytokines for Th1 (e.g., IFN-g, IL-2, TNF-$\alpha$, IL-1b, GM-CSF), Th17 (IL-17), and Th2 (e.g., IL-6, IL-4, IL-10, IL-13). An exemplary data set is depicted in FIG. 37. In some cases, the presence of TGF-$\beta$ in sample supernatants may also be analyzed. For example, TGF-$\beta$ may be analyzed using an ELISA method. In some cases, the magnitude of or pattern of secretion may serve as a biomarker of clinical outcome after vaccination.

Heat maps may be generated from multiplexed cytokine data. In some cases, the heat maps are color coded as to the magnitude of antigen specific cytokine increase or decrease with vaccination. In some cases, the heat maps may depict specific patterns of the type of and magnitude of the immune response to the at least one immunizing antigen.

In some cases, a subject may be classified as immunized by development of protein specific precursor frequencies that are more robust than 1:20,000 PBMC to the majority of the immunizing antigens. In some cases, if subjects have pre-existent immunity to any of the antigens, then the responses may augment more than twice the baseline response.

In some cases, the analysis of immunogenicity may determine the magnitude of the Th1 antigen specific immune response. For example, the Th1 response may be determined by performing an IFN-g ELISPOT, which is linear and precise between 2.0 and $3.5 \times 10^5$. PBMC/well, has a detection limit of 1:60,000, and has a detection efficiency of 93%. In some cases, pre-vaccine and post-vaccine samples may be analyzed simultaneously to correct for variability. For example, a cryopreservation method that preserves antigen specific T cell responses in frozen cells when compared to freshly isolated PBMC may be used. In some cases, the samples may include 1 ug/ml protein antigens (e.g., recombinant proteins are available on all of the proposed candidate antigens, human myoglobin (negative control)) or 1 ug/ml CMV lysate and 0.5 U/ml tt (positive controls) and peptide antigens encompassed within the vaccine at 10 ug/ml).

The ovarian cancer vaccine may exhibit immunologic success that may be analyzed using statistical methods. Often immunologic success of the vaccine may be the occurrence of an immune response (e.g., Th1) to greater than 50% of the antigens expressed by the plasmids within the vaccine. In some cases, the vaccine may be administered to a group of subjects (e.g. 22 subjects) such that the probability of an observed success rate in excess of 50% may be less than 0.1 if the true success rate is 40%. For example, the observed success rate may be 0.06. In some cases, the vaccine may be administered to a group of subjects (e.g. 22 subjects) such that the probability of an observed success rate in excess of 50% may be greater than 0.7 if the true success rate is 70%.

For example, use of a group of 22 patients may demonstrate, with at least 80% confidence, that an estimated immunologic response rate may be within at least 0.14 of the true response rate. In some cases, if half of the subjects elicit an immunogenic response, then the power may be at least 91% for statistical significance (at the two-sided level of 0.05) and the difference in continuous measures if the true effect size is 1.5. For example, Spearman's correlation coefficient may be used to estimate the correlation between two continuous measures. In some cases, the data may estimate an expected response rate in a larger population.

For another example, 25% of subjects may elicit a good response to the vaccine. In some cases, 25% of subjects with a good response may be the baseline to evaluate the effectiveness of a vaccine. In some cases, the true response rate may be 60% where use of a group of 22 subjects may provide a power of 97% for a statistically significant response rate compared to the fixed rate of 25% (one-sided level of significance of 0.05).

Clinical Trials for Breast Cancer

In some instances, the clinical trial may be a Phase I trial of the safety and immunogenicity of the compositions described herein (e.g., vaccines) for subjects with non-metastatic breast cancer. In some cases, the breast cancer may be node positive triple negative (ER(−) PR(−) HER2/neu(−)) breast cancer (TNBC). In some cases, the patient may have been treated to complete remission. In some cases, patients may have been treated with primary or salvage therapy. In some cases, patients may have completed chemotherapy, radiotherapy and/or use of systemic steroids prior to enrolling in the clinical trial. For example, patients may be at least one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days or more from last cytotoxic chemotherapy and/or radiotherapy and any use of systemic steroids. In an exemplary case, patients may be 28 days from last cytotoxic chemotherapy and/or radiotherapy and any use of systemic steroids.

In some cases, as descried above Phase I may evaluate 3 dose levels of the compositions (e.g., vaccines), such as for example Arm 1 (150 mcg), Arm 2 (300 mcg), and Arm 3 (600 mcg). In some cases, no more than ten subjects may be enrolled in each arm. For example, three doses of the vaccine may be administered to each subject such that one month elapses between each dose. In some cases, booster doses may be administered to the subject following the third dose of the vaccine. For example, the booster may be administered such that one booster is administered two months following the third dose of the vaccine and one booster administered four months after the booster.

In some cases, the Arm 2 cohort of 10 subjects may be enrolled in Phase I of the trial if the doses in Arm 1 are safe. In some cases, if the Arm 2 dose is safe then the immunologic efficacy of both Arm 1 and Arm 2 may be examined. For example, if the Arm 1 dose is more efficacious, the trial may terminate. In some cases, if the efficacy is greater in the Arm 2 dose compared to the Arm 1 does, then subjects may be enrolled into the Arm 3 dose schema. In some cases, if the Arm 3 dose appears safe, the immunologic efficacy between Arm 2 and 3 will be examined. For example, safety may be assessed per CTEP CTCAE v. 4.0. In some cases, benchmarks for safety to move to the next arm may be a grade 3 toxicity rate of ≤15% and a grade 4 toxicity rate of ≤15%.

Immunologic efficacy of the three doses may be evaluated via an assessment of the generation of T-cells. In some cases, immunologic efficacy may be defined as achievement of augmented IFNγ T-cell immunity to the antigens in the vaccine.

Design and Recruitment Plan. The two endpoints of the Phase I clinical trial may be to, (1) determine the safety of intradermal administration of the vaccine given with GM-CSF as an adjuvant and, (2) determine the immunogenicity of the vaccine. In some cases, subjects may be immunized with the plasmid based vaccine (e.g., 100 µg of total plasmid per subject). In some cases, subjects may receive three vaccines administered across intervals (30-days). For example, the vaccines may be administered to the subject at the deltoid region in a draining lymph node site (FIG. 5).

Subjects with Stage IIb, III, and IV breast cancer (e.g., triple negative) who have been treated to complete remission may be enrolled in the trial. In some cases, the trial may accrue a target number of subjects (e.g., 22 subjects). Subjects may undergo leukapheresis (e.g., for baseline immunologic assessment) and blood draw (e.g., for baseline toxicity assessment) at beginning of the study and an 180 cc blood draw at one, six, and 12 months after the final vaccination. In some cases, blood may be analyzed for changes in serum chemistries as an assessment of potential toxicity. Peripheral blood mononuclear cells and sera collected at these time points may be evaluated for the development of tumor specific immunity as described herein. A leukapheresis product may be obtained after the final vaccination (e.g., 3 months) for additional studies.

Safety. In some cases, the vaccine may elicit an immediate allergic reaction. In some cases, the vaccine may cause side effects due to immunologic consequences of the vaccination targeting other, unrelated tissues. In some cases, after evaluation of these toxicities, criteria for stopping treatment or removing subjects from the study may be established.

During Phase I, more than 200 subjects may receive the breast cancer vaccine. In some cases, the composition may include GM-CSF (100-150 ug) admixed with HER2 peptide/protein/or DNA-based vaccines. In some cases, the composition may be administered using the method of intradermal injection monthly for 3-6 months. For example, intradermal administration may result in allergic reaction to the skin. In some cases, subjects may be monitored following immunizations (e.g., for one hour).

Subjects may be examined at a routine visit following administration of the vaccine. In some cases, subjects may be evaluated at each visit based on the modified National Cancer Institute toxicity criteria. In some cases, subjects may undergo a complete physical examination. In addition, serum chemistries, including renal function tests, uric acid, blood counts, serum glucose, and liver function tests for each subject may be evaluated. In some cases, the development of connective tissue disorders and laboratory autoantibody responses may be assessed as a potential immunologic toxicity associated with the use of DNA vaccination. In some cases, the development of anti-DNA antibodies may be assessed, for example, anti-ANA, anti-C3, anti-thyroid and ds-DNA antibodies. In some cases, assessments may be performed at the end of the vaccination regimen, and at 12 months of follow-up.

A sample size of 22 subjects may be enrolled into each arm of the trial. In some cases, if no toxicities occur, the probability of a toxicity occurring may be at least 90% if the true toxicity rate, i.e., any Grade 3 or 4 toxicity, is 10% or less. For example, a toxicity occurrence may indicate that the toxicity rate is less than 10%. In some cases, the trial may continue and may be deemed sufficiently safe as long as the observed toxicity rate is consistent with a true grade 3 rate of 15% or less and a true grade 4 rate of 5% or less. In some cases, stopping rules may be utilized such that if sufficient evidence suggests the true toxicity rates exceed these thresholds, the study may be stopped. For example, sufficient evidence may be taken to be a lower one-sided confidence limit in excess of the appropriate threshold. For grade 3, such a limit may be reached if this level of toxicity occurred in 2 of the first 3 or fewer, 3 of the first 7 or fewer, 4 of the first 12 or fewer, 5 of the first 17 or fewer, or 6 of the first 22 or fewer enrolled subjects. For grade 4, one of the following may result in stopping the trial: 2 of the first 10 or fewer, 3 of the first 22 or fewer enrolled subjects experience grade 4 toxicity. For example, if the true probability of grade 3 toxicity is 10% or 30%, then the probability of stopping the study may be approximately 0.06 and 0.76, respectively. If the true probability of grade 4 toxicity is 3% or 23%, then the probability of stopping may be roughly 0.05 and 0.93, respectively (probabilities estimated from 5,000 simulations).

Immunogenicity. The vaccine may elicit an immunogenic response in the subject. In some cases, the type of immune response elicited after immunization may be determined. For example, the compositions described herein may elicit a Th1 immune response when administered to a subject. In some cases, the Th1 immune response may include formation of and persistence of antigen specific T-cells that recognize at least one peptide of the vaccine. For example, a peptide may be a stem cell and/or an EMT antigen.

The type of immune response may be determined through an assessment of the types of cytokine secreted by antigen specific T-cells. In some cases, the types of cytokines may be identified using an ELISPOT assay. For example, an ELISPOT method may include analysis of sample supernatants after antigen stimulation (e.g., 72 hours). In some cases, the sample supernatants may be evaluated for a panel of cytokines. In some cases, the evaluation may be a multiplex analysis. For example, the multiplex analysis of cytokines may include the cytokines for Th1 (e.g., IFNγ, IL-2, TNFα, IL-1b, GM-CSF), Th17 (IL-17), and Th2 (e.g., IL-6, IL-4, IL-10, IL-13). An exemplary data set is depicted in FIG. 37. In some cases, the presence of TGF-β in sample supernatants may also be analyzed. For example, TGF-β may be analyzed using an ELISA method. In some cases, the magnitude of or pattern of secretion may serve as a biomarker of clinical outcome after vaccination.

Heat maps may be generated from multiplexed cytokine data. In some cases, the heat maps are color coded as to the magnitude of antigen specific cytokine increase (e.g., red, see FIG. 37) or decrease (e.g., blue, see FIG. 37) with vaccination. For example, the intensity of the colors may symbolize the lowest (e.g., pale, see FIG. 37) to highest (e.g., vivid, see FIG. 37) quartile of response. In some cases, the heat maps may depict specific patterns of the type of and magnitude of the immune response to the at least one immunizing antigen. For example, the magnitude of cytokine secretion.

In some cases, a subject may be classified as immunized by development of protein specific precursor frequencies that are more robust than 1:20,000 PBMC to the majority of the immunizing antigens. In some cases, if subjects have pre-existent immunity to any of the antigens, then the responses may augment more than twice the baseline response.

In some cases, the analysis of immunogenicity may determine the magnitude of the Th1 antigen specific immune response. For example, the Th1 response may be determined by performing an IFNγ ELISPOT, which is linear and precise between 2.0 and $3.5 \times 10^5$ PBMC/well, has a detection limit of 1:60,000, and has a detection efficiency of 93%. In some cases, pre-vaccine and post-vaccine samples may be analyzed simultaneously to correct for variability. For example, a cryopreservation method that preserves antigen specific T-cell responses in frozen cells when compared to freshly isolated PBMC may be used. In some cases, the samples may include 1 ug/ml protein antigens (e.g., recombinant proteins are available on all of the proposed candidate antigens, human myoglobin (negative control)) or 1 ug/ml CMV lysate and 0.5 U/ml tt (positive controls) and peptide antigens encompassed within the vaccine at 10 ug/ml).

The breast cancer vaccine may exhibit immunologic success that may be analyzed using statistical methods. Often immunologic success of the vaccine may be the occurrence of an immune response (e.g., Th1) to greater than 50% of the antigens expressed by the plasmids within the vaccine. In some cases, the vaccine may be administered to a group of 22 subjects such that the probability of an observed success rate in excess of 50% may be less than 0.1 if the true success rate is 40%. For example, the observed success rate may be 0.06. In some cases, the vaccine may be administered to a group of 22 subjects such that the probability of an observed success rate in excess of 50% may be greater than 0.7 if the true success rate is 70%.

For example, use of a group of 22 patients may demonstrate, with at least 80% confidence, that an estimated immunologic response rate may be within at least 0.14 of the true response rate. In some cases, if half of the subjects elicit an immunogenic response, then the power may be at least 91% for statistical significance (at the two-sided level of 0.05) and the difference in continuous measures if the true effect size is 1.5. For example, Spearman's correlation coefficient may be used to estimate the correlation between two continuous measures. In some cases, the data may estimate an expected response rate in a larger population.

For another example, 25% of subjects may elicit a good response to the vaccine. In some cases, 25% of subjects with a good response may be the baseline to evaluate the effectiveness of a vaccine. In some cases, the true response rate may be 60% where use of a group of 22 subjects may provide a power of 97% for a statistically significant response rate compared to the fixed rate of 25% (one-sided level of significance of 0.05).

Applications

The compositions described herein may be administered to a subject in need of a vaccine for preventing breast cancer or ovarian cancer. In some instances, the cancer is breast cancer. In some cases, the cancer is ovarian cancer. The methods described herein may be combined with the compositions described herein for administration to a subject in need of a vaccine for preventing breast cancer or ovarian cancer. In some cases, administration of the vaccine may initiate the elimination of cells as the cells begin to express increased levels proteins that are components of the vaccine. In some cases, the proteins may be stem cell/EMT associated. For example, increased levels of proteins may be expressed during the malignant transformation of normal cells into cancer cells, such as for example breast cancer cells or ovarian cancer cells. In some instances, elimination of the breast cancer or ovarian cancer cells before the disease becomes clinically evident may prevent the occurrence of cancer in a subject. In some cases, elimination of the breast or ovarian cancer cells before the disease becomes clinically evident may prevent the occurrence of breast or ovarian cancer in a subject.

The vaccine for preventing breast cancer or ovarian cancer may be administered in a single dose administered to the subject, the dose of at least 10 µg, 15 µg, 20 µg, 25 µg, 30 µg, 35 µg, 40 µg, 45 µg, 50 µg, 55 µg, 60 µg, 651 µg, 70 µg, 75 µg, 80 µg, 85 µg, 86 µg, 87 µg, 88 µg, 89 µg, 90 µg, 91 µg, 92 µg, 93 µg, 4 µg, 95 µg, 96 µg, 97 µg, 98 µg, 99 µg, 100 µg, 101 µg, 102 µg, 103 µg, 104 µg, 105 µg, 106 µg, 107 µg, 108 µg, 109 µg, 110 µg, 111 µg, 112 µg, 113 µg, 114 µg, 115 µg, 116 µg, 117 µg, 118 µg, 119 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, or at least 200 µg/plasmid. In an exemplary case, the single dose administered to the subject is 100 µg/plasmid.

The vaccine for preventing breast cancer or ovarian cancer may be administered in more than one dose administered to the subject, each dose of at least 10 µg, 15 µg, 20 µg, 25 µg, 30 µg, 35 µg, 40 µg, 45 µg, 50 µg, 551 µg, 60 µg, 65 µg, 70 µg, 75 µg, 80 µg, 85 µg, 86 µg, 87 µg, 88 µg, 89 µg, 90 µg, 91 µg, 92 µg, 93 µg, 4 µg, 95 µg, 96 µg, 97 µg, 98 µg, 99 µg, 100 µg, 101 µg, 102 µg, 103 µg, 104 µg, 105 µg, 106 µg, 107 µg, 108 µg, 109 µg, 110 µg, 111 µg, 112 µg, 113 µg, 114 µg, 115 µg, 116 µg, 117 µg, 118 µg, 119 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, or at least 200 µg/plasmid. In some cases, each dose administered to the subject may be greater than or less than the previous dose administered to the subject.

The compositions described herein may be administered to a subject in need thereof of a vaccine for treating breast cancer or ovarian cancer. The methods described herein may be combined with the compositions described herein for administration to a subject in need thereof of a vaccine for treating breast cancer or ovarian cancer. In some cases, administration of the vaccine may initiate the elimination of cells that express increased levels proteins that are components of the vaccine. In some cases, the proteins may be stem cell/EMT associated. For example, increased levels of proteins may be expressed by cancer cells, such as for example breast cancer cells or ovarian cancer cells. In some cases, elimination of cancer cells after the disease becomes clinically evident may prevent the persistence and propogation of breast cancer or ovarian cancer in a subject. In some cases, elimination of the breast or ovarian cancer cells after the disease becomes clinically evident may prevent the persistence and propogation of breast or ovarian cancer in a subject.

Subjects

The compositions described herein may be administered to a subject in need of a vaccine for breast cancer or ovarian cancer. The methods described herein may be combined with the compositions described herein for administration to a subject in need of a vaccine for breast cancer or ovarian cancer. In some cases, the vaccine may be administered to a subject who does not have breast cancer or ovarian cancer. In other cases, the vaccine may be administered to a subject who has had breast cancer or ovarian cancer. In yet other cases, the vaccine may be administered to a subject who has breast cancer or ovarian cancer.

In some cases, the subject may be a healthy individual. In some cases, the subject may be an individual with breast cancer or ovarian cancer. For example, the individual may be a patient. In some cases, the subject is a human individual. In other cases, the subject is a non-human individual. For example, non-human individuals may be a non-human primate, including such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term "subject" does not denote a particular age. Thus, both adult and newborn individuals are intended to be covered.

Breast Cancer and Ovarian Cancer

Disclosed herein, in certain embodiments, is a vaccine for treating a breast cancer or an ovarian cancer. In some instances, the breast cancer is a relapsed or refractory breast cancer. In some cases, the ovarian cancer is a relapsed or refractory ovarian cancer. In some instances, the breast cancer is a metastasized breast cancer. In some instances, the ovarian cancer is a metastasized ovarian cancer.

Types of Breast Cancer

The compositions described herein may be administered to a subject in need of a vaccine for cancer, often the cancer is breast cancer. The methods described herein may be combined with the compositions described herein for administration to a subject in need of a vaccine for cancer. Often, the breast cancer may be any type of breast cancer, for example, the breast cancer may be ductal carcinoma in situ, lobular carcinoma in situ, invasive ductal carcinoma, infiltrating ductal carcinoma, inflammatory breast cancer, triple-negative breast cancer, paget disease of the nipple, phyllodes tumor, angiosarcoma, adenoid cystic carcinoma, adenocystic carcinoma, low-grade adenosquamous carcinoma, medullary carcinoma, mucinous carcinoma, colloid carcinoma, papillary carcinoma, tubular carcinoma, metaplastic carcinoma, spindle cell carcinoma, squamous carcinoma, micropapillary carcinoma and mixed carcinoma.

In some cases, the subject may be classified with a particular grade of breast cancer. For example, the grades of breast cancer may be Grade X, Grade 1, Grade 2, Grade 3 or Grade 4. For another example, breast cancers may be indicated by a category of tubule formation, nuclear grade and/or the mitotic rate. Each category may also be assigned a specific score between one and three. In some cases, the subject may have a particular stage of breast cancer. In some cases, the stages may be assigned based on the tumor, the regional lymph nodes and/or distant metastasis. For example, the stages assigned to the tumor may be TX, T0, Tis, T1, T2, T3 or T4. For example, the stages assigned to the regional lymph nodes may be NX, N0, N1, N2 or N3. For example, the stages assigned to the distant metastasis may be MX, M0 or M1. In some cases, the stages may be stage 0, stage I, stage II, stage III or stage IV. Often the breast cancer is classified as more than one grade, or stage of cancer.

Additional Therapeutic Agents

In some instances, the breast or ovarian cancer vaccine described herein is administered to a patient in combination with an additional therapeutic agent. In some instances, the additional therapeutic agent is a chemotherapeutic agent, a steroid, an immunotherapeutic agent, a targeted therapy, or a combination thereof.

In some embodiments, the additional therapeutic agent is selected from: Adriamycin. Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide;

verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In some embodiments, the additional therapeutic agent is selected from: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphorvl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators, nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenvlacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulminosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurprin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy;

velaresol; veramine; verdins; verteporfin; vinorelbine; vinxaltine; vitaxin; vorozole; zanoterone; zeniplatin; zilascorb; and zinostatin stimalamer.

In some embodiments, the additional therapeutic agent is selected from: agents which act by arresting cells in the G2-M phases due to stabilized microtubules, e.g., Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2. Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A. Epothilone B. Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651). SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin, CanadensoL Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University). H16 (Kansas State University), Oncocidin A1 (also known as BTO-956 and DIME), DDE-313 (Parker Hughes Institute), Fijianolide B, Laulimalide. SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In some embodiments, the additional therapeutic agent is selected from: agents that affect the tumor micro-environment such as cellular signaling network (e.g. phosphatidylinositol 3-kinase (PI3K) signaling pathway, signaling from the B-cell receptor and the IgE receptor). Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG900, AP24534, Arry-614, AT7519, AT9283, AV-951, axitinib, AZD152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TK1258, TLN-232, TTP607, XL147, XL228, XL281RO5126766, XL418, XL765.

In some embodiments, the additional therapeutic agent is selected from: inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In some embodiments, the additional therapeutic agent is selected from: interferons, interleukins, Tumor Necrosis Factors, Growth Factors, or the like.

In some embodiments, the additional therapeutic agent is selected from: ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

In some embodiments, the additional therapeutic agent is selected from: Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

In some embodiments, the additional therapeutic agent is selected front Monoclonal Antibodies such as for example alemtuzumab, bevacizumab, catumaxomab, cetuximab, edrecolomab, gemtuzumab, panitumumab, rituximab, trastuzumab; Immunosuppressants, eculizumab, efalizumab, muromab-CD3, natalizumab; TNF alpha Inhibitors such as for example adalimumab, afelimomab, certolizumab pegol, golimumab, infliximab; Interleukin Inhibitors, basiliximab, canakinumab, daclizumab, mepolizumab, tocilizumab, ustekinumab; Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, clauduximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

In some embodiments, the additional therapeutic agent is selected from: Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

In some embodiments, the additional therapeutic agent is selected from a checkpoint inhibitor. Exemplary checkpoint inhibitors include:

PD-L1 inhibitors such as Genentech's MPDL3280A (RG7446), Anti-mouse PD-L1 antibody Clone 10F.9G2 (Cat # BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, and AstraZeneca's MEDI4736;

PD-L2 inhibitors such as GlaxoSmithKline's AMP-224 (Amplimmune), and rHIgM12B7;

PD-1 inhibitors such as anti-mouse PD-1 antibody Clone J43 (Cat # BE0033-2) from BioXcell, anti-mouse PD-1 antibody Clone RMP1-14 (Cat # BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG4 monoclonal antibody nivolumab (Opdivo®, BMS-936558, MDX 1106), AstraZeneca's AMP-514 and AMP-224, and Pidilizumab (CT-011) from CureTech Ltd;

CTLA-4 inhibitors such as Bristol Meyers Squibb's anti-CTLA-4 antibody ipilimumab (also known as Yervoy®, MDX-010, BMS-734016 and MDX-101), anti-CTLA4 Antibody, clone 9H10 from Millipore, Pfizer's tremelimumab (CP-675,206, ticilimumab), and anti-CTLA4 antibody clone BNI3 from Abcam;

LAG3 inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12:

B7-H3 inhibitors such as MGA271;

KIR inhibitors such as Lirilumab (IPH2101);

CD137 inhibitors such as urelumab (BMS-663513, Bristol-Myers Squibb), PF-05082566 (anti-4-1BB, PF-2566, Pfizer), or XmAb-5592 (Xencor);

PS inhibitors such as Bavituximab;

and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

Samples

A sample for analysis of the immunogenicity, safety and/or toxicity may be isolated from an individual. In some cases, the sample may be selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and genitourinary tracts. In some cases, the sample may be tissue, often a biopsy sample. For example, the biopsy may contain skin tissue, breast tissue, glandular tissue, skeletal muscle tissue and/or adipose tissue.

Kits

Kits and articles of manufacture are also provided herein for use with one or more methods described herein. The kits can contain one or more of the polypeptides and/or one or more of the nucleic acid molecules described herein, such as the polypeptides and nucleic acid molecules identified as SEQ ID NOs: 1-91, or polypeptides and/or nucleic acid molecules having a sequence at least 40%, 50%, 60%, 70%, 80%, 90%, 95%, or more sequence homology with a polypeptide or nucleic acid molecule selected from the group consisting of SEQ ID NOs: 1-91. The kits can also contain nucleic acids that encode one or more of the polypeptides described herein. The kits can further contain adjuvants, reagents, and buffers necessary for the makeup and delivery of the vaccines.

The kits can also include a carrier, package, or container that is compartmentalized to receive one or more containers such as vials, tubes, and the like, each of the container(s) comprising one of the separate elements, such as the polypeptides and adjuvants, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1

Identification of Breast Cancer Antigens and Determination of Epitopes that Elicit a Th1 CD4+ T-Cell Response An antibody analysis has been performed using 224 individuals' sera. One hundred and twenty four Stage I/II breast cancer (BrCA) patients; 78 ER+ (63%), 31 HER2+ (25%), and 15 TNBC (12%), were evaluated for antibody responses against each candidate protein. The control population consisted of 100 age-matched women. The candidate proteins analyzed for immunogenicity as exemplified in the FIGS, described below using mouse models. Additionally, candidate proteins analyzed for immunogenicity are listed in FIGS. 19 and 23.

Indirect ELISA Assays Using Recombinant Proteins. Recombinant proteins were available for all proposed candidate antigens. Subject sera were analyzed at titrations of 1:100 and 1:200 in duplicates or triplicates. Western blot analysis demonstrated that sensitivity and specificity of the ELISA assays were 70% or greater with the exception of CD105 which could not be validated by Western Blot.

Figure 3:
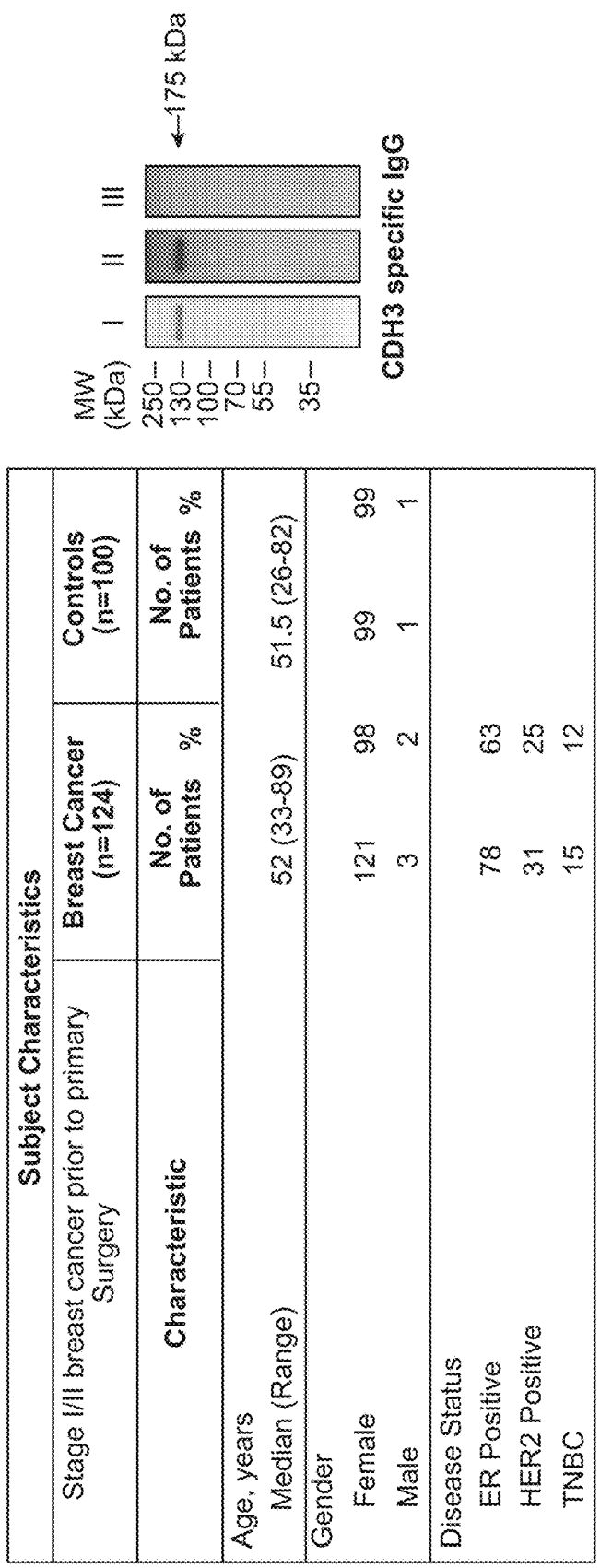
FIG. 3 depicts antigen specific IgG immunity.
Figure 4:
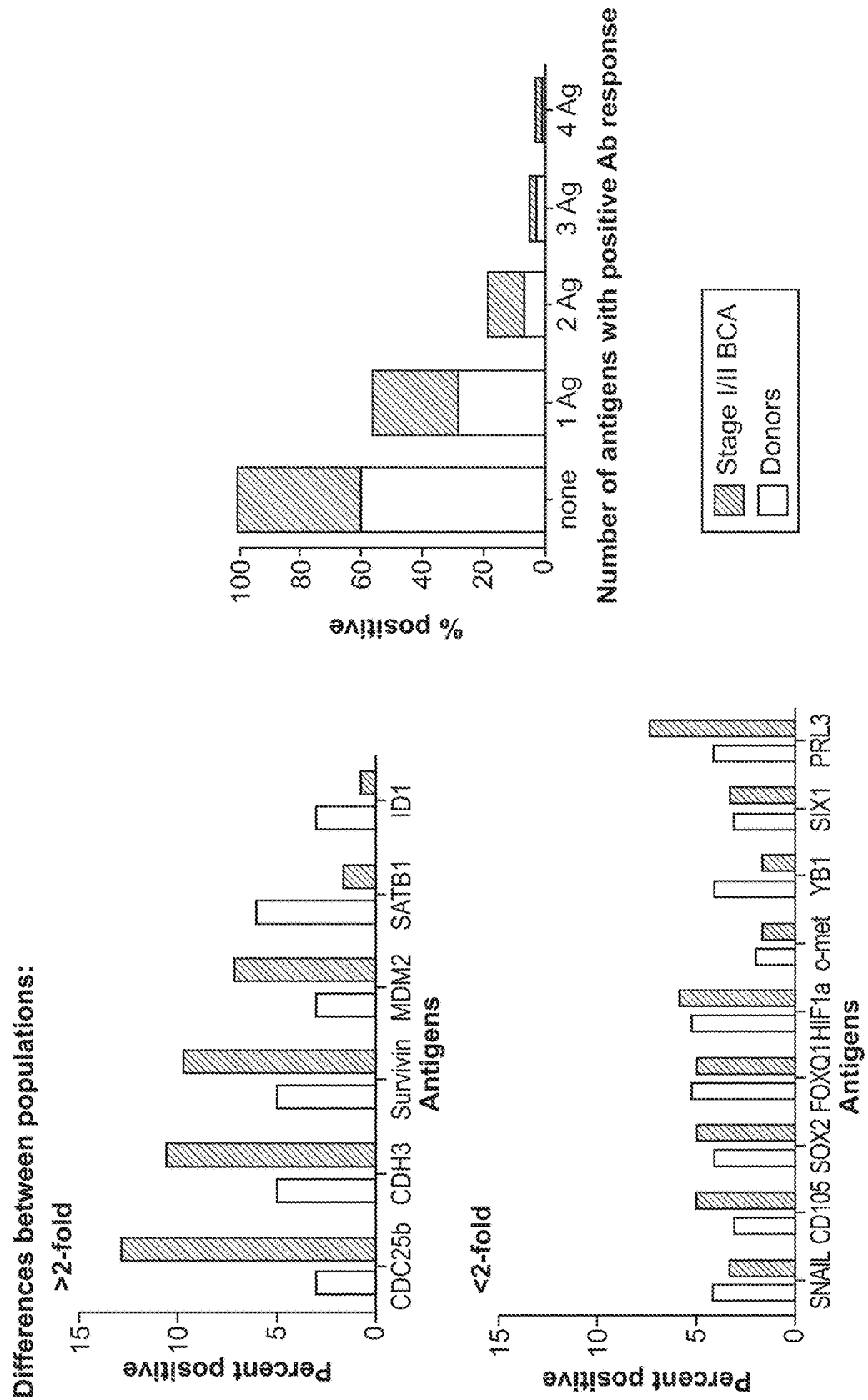
FIG. 4 shows population based epitope screening.

Screen Breast Cancer Cases and Controls. All proteins tested were immunogenic, i.e., there was at least one individual analyzed who demonstrated detectable IgG antibody immunity directed against the specific antigen that could be documented by western blot with appropriate specificity controls (example for CDH3 in FIG. 3). Antibody responses could be identified in both volunteer controls as well as cancer patients. To describe the incidence of immunity to a particular antigen, the mean ug/ml and two standard deviations of the control population was used to determine a cutoff value above which a response was considered positive with 95% confidence. The incidence of antibody immunity for the tested antigens ranged from 2% (BrCA patients to Yb-1) to 13% (BrCA patients to CDC25b) positive. Six antigens demonstrated a greater than 2-fold difference in incidence of response between BrCA patients and donors; CDC25b, CDH3, Survivin, MDM2, SATB1, and ID1. Of note, SATB1 and ID1 responses were found in a greater number of volunteer donors as compared to cancer patients. FIG. 4, Panel B shows results from the 9 antigens where there was 2-fold or less difference in incidence between BrCA patients and donors.

Statistical Analysis for Cancer-Specificity of Immune Responses. Four of the antigens demonstrated statistically significant differences in immunity between cancer patients and controls using unpaired T-tests with Welch's correction. BrCA patients had a higher level of antibody immunity to CDC25B (p=0.02), CDH3 (p=0.0002), Survivin (p=0.09) than volunteer controls.

Identification of Candidate Antigens for Epitope Mapping. 15 immunogenic proteins associated with stem cell/EMT were identified to move forward to epitope mapping.

Figure 28:
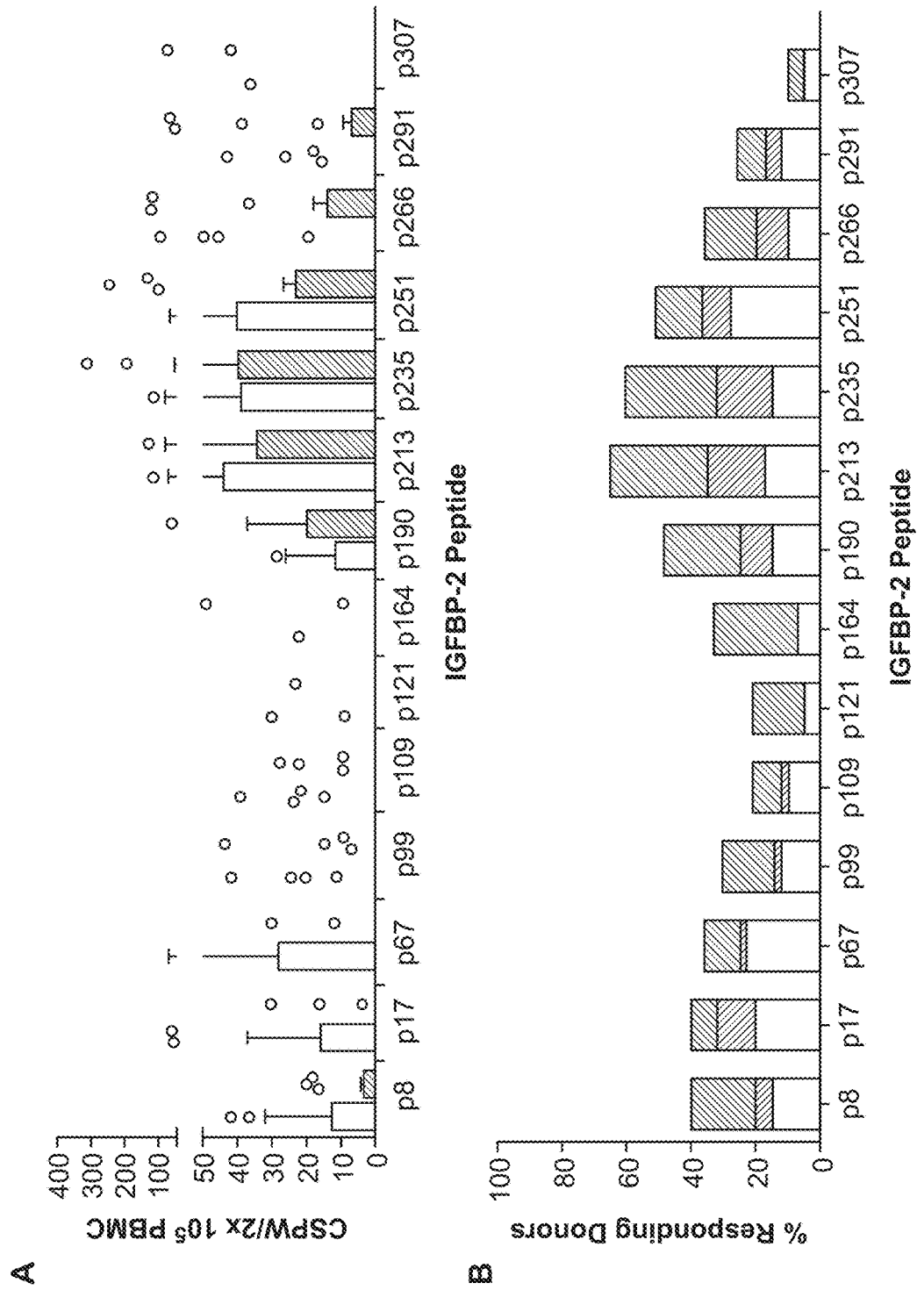
FIG. 28 demonstrates that the IGFBP-2 C-terminus is enriched for epitopes that induce IL-10-secreting T-cells as compared to the N-terminus.

For example, see FIG. 28 which depicts IFNγ and IL-10 secretion by T-cells in response to epitopes from the C terminus of IGFBP-2. In particular, FIG. 28 at part (A) shows an ELISPOT for IFNγ (white) and IL-10 (black) in breast cancer patient PBMC for IGFBP-2 peptides presented as interquartile box plots with Turkey whiskers (n=20).

Median corrected spots per well (CSPW) are indicated by the horizontal bar. At part (B), the percent of PBMC stimulated with IGFBP-2 peptides induced an IFNγ (white bars) response, an IL-10 (black bars) response, or both (gray bars) in ELISPOT.

Figure 29:
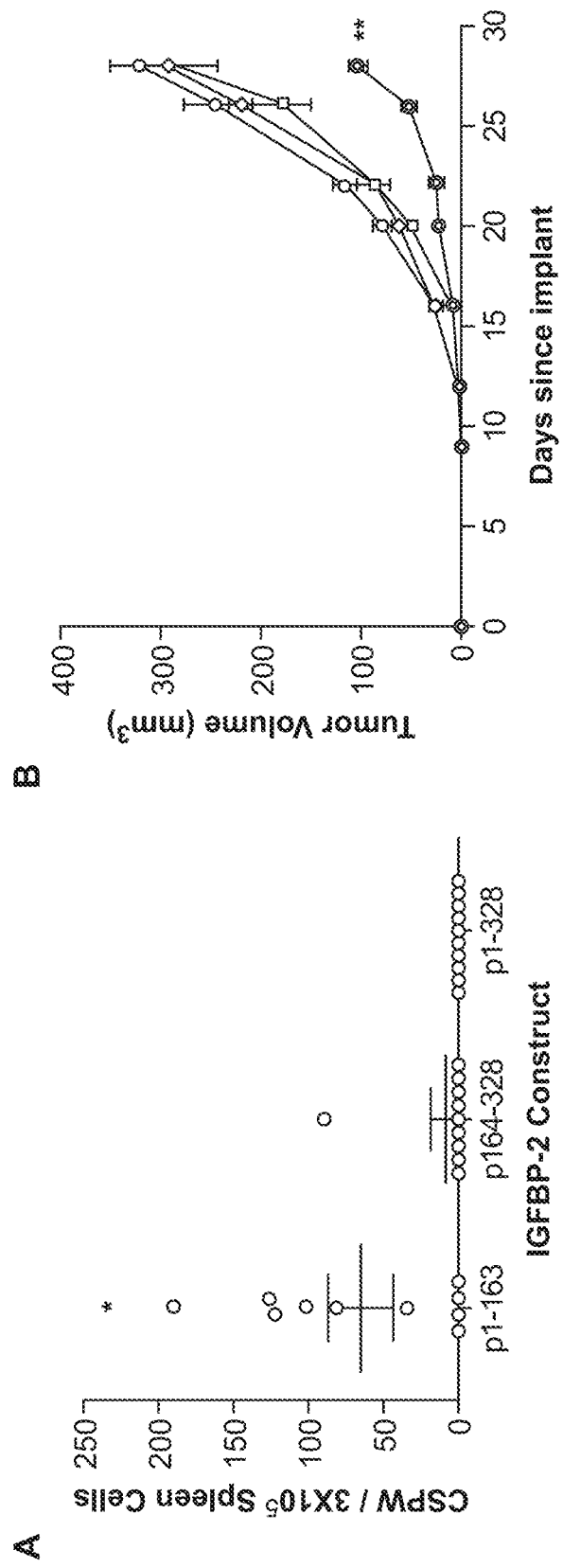
FIG. 29 shows that the N-terminus, but not C-terminus, IGFBP-2 vaccine both stimulates Type I immunity and inhibits tumor growth.

In another example, see FIG. 29, which depicts Th1 immune response and inhibition of tumor growth to the N-terminus, but not C-terminus of IGFBP-2. (A) IFNγ ELISPOT in splenocytes from mice immunized with the indicated vaccine. The data are presented as corrected spots per well (CSPW). The horizontal bar indicates the mean CSPW±SEM, n=10 mice/group. *p<0.01. (B) Mean tumor volume (mm³±SEM) from mice injected with pUMVC3 alone (●), pUMVC3-hIGFBP2 (1-328) (■), pUMVC3-hIGFBP2 (164-328) (▲) or pUMVC3-hIGFBP2 (1-163) (o), n=5 mice/group; **p<0.001.

Figure 30:
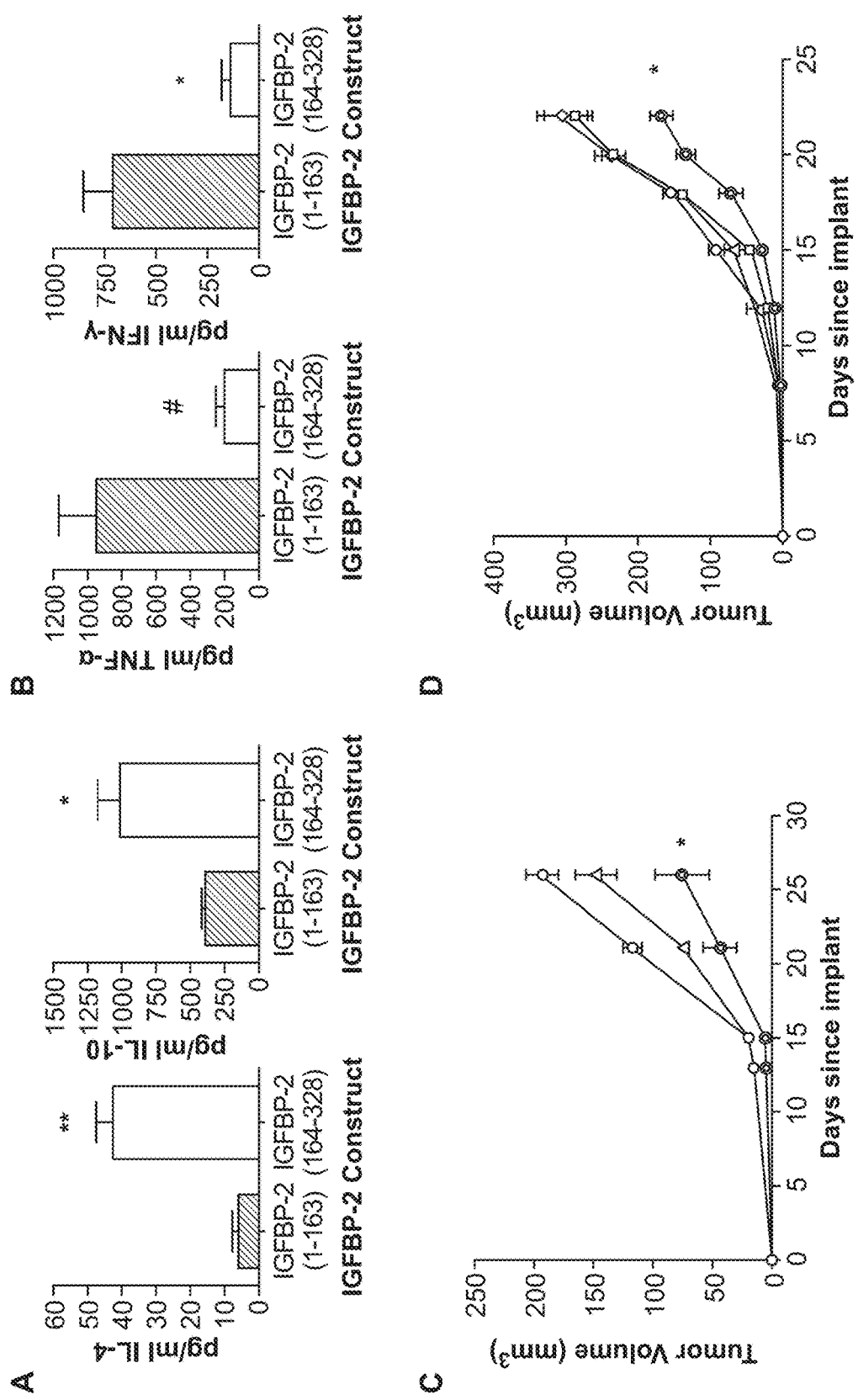
FIG. 30 shows that the IGFBP-2 vaccine-induced Th2 abrogates the anti-tumor effect of IGFBP-2-specific Th1.

In yet another example, see FIG. 30, which depicts IGFBP-2 vaccine-induced Th2 abrogated the anti-tumor effect of IGFBP-2-specific Th1. Type II cytokines IL-4 and IL-10 (A) and Type I cytokines TNFα and IFNγ (B) secretion from T-cell lines expanded with peptides in IGFBP2 (1-163) or IGFBP2 (164-328) (mean ng/ml±SD); **p<0.001. *p<0.01 and #p<0.05. (C) Mean tumor volume (mm³±SEM) from mice infused with CD3+ T-cells expanded from mice vaccinated with pUMVC3-hIGFBP2 (1-163) (o), pUMVC3-hIGFBP2 (164-328) (▲) or naïve T-cells (●). n=4 mice/group; *p<0.01. (D) Mean tumor volume (mm³±SEM) from mice injected with pUMVC3 alone (●), pUMVC3-hIGFBP2 (164-328) (▲), pUMVC3-hIGFBP2 (1-163) (o) or pUMVC3-hIGFBP2 (1-163)+ pUMVC3-hIGFBP2 (164-328) (▼). n=5 mice/group; *p<0.01. FIG. 1 Th1 and Th2 epitopes vary in functional avidity.

Figure 16:
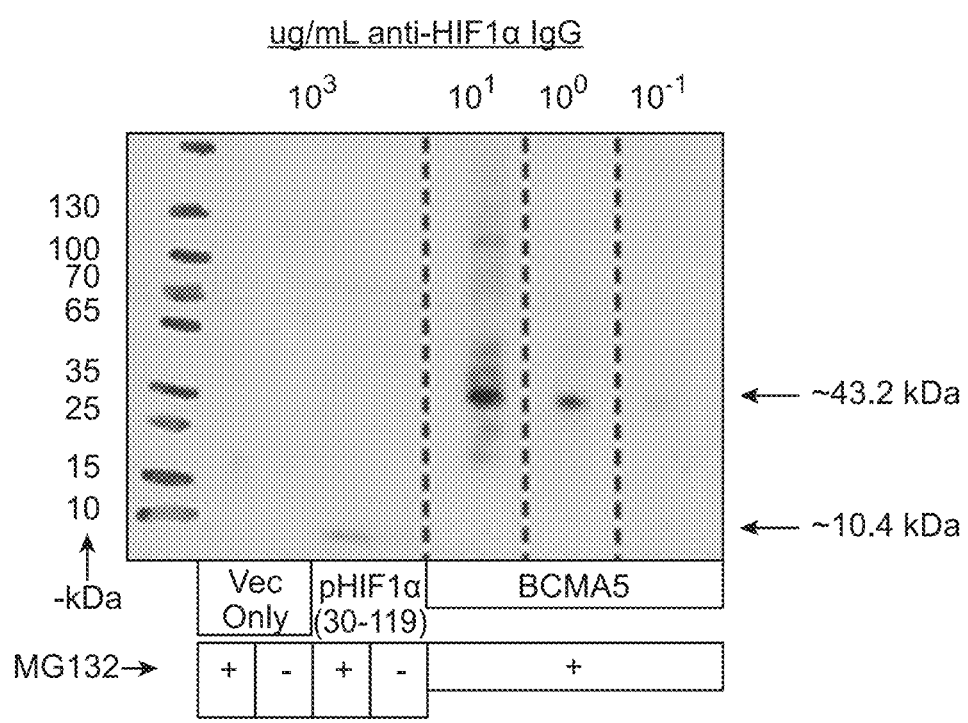
FIG. 16 shows a Western blot analysis of HIF1α expression in a single plasmid, pHIF1α and a plasmid encoding 5 antigens, BCMA5.
Figure 17:
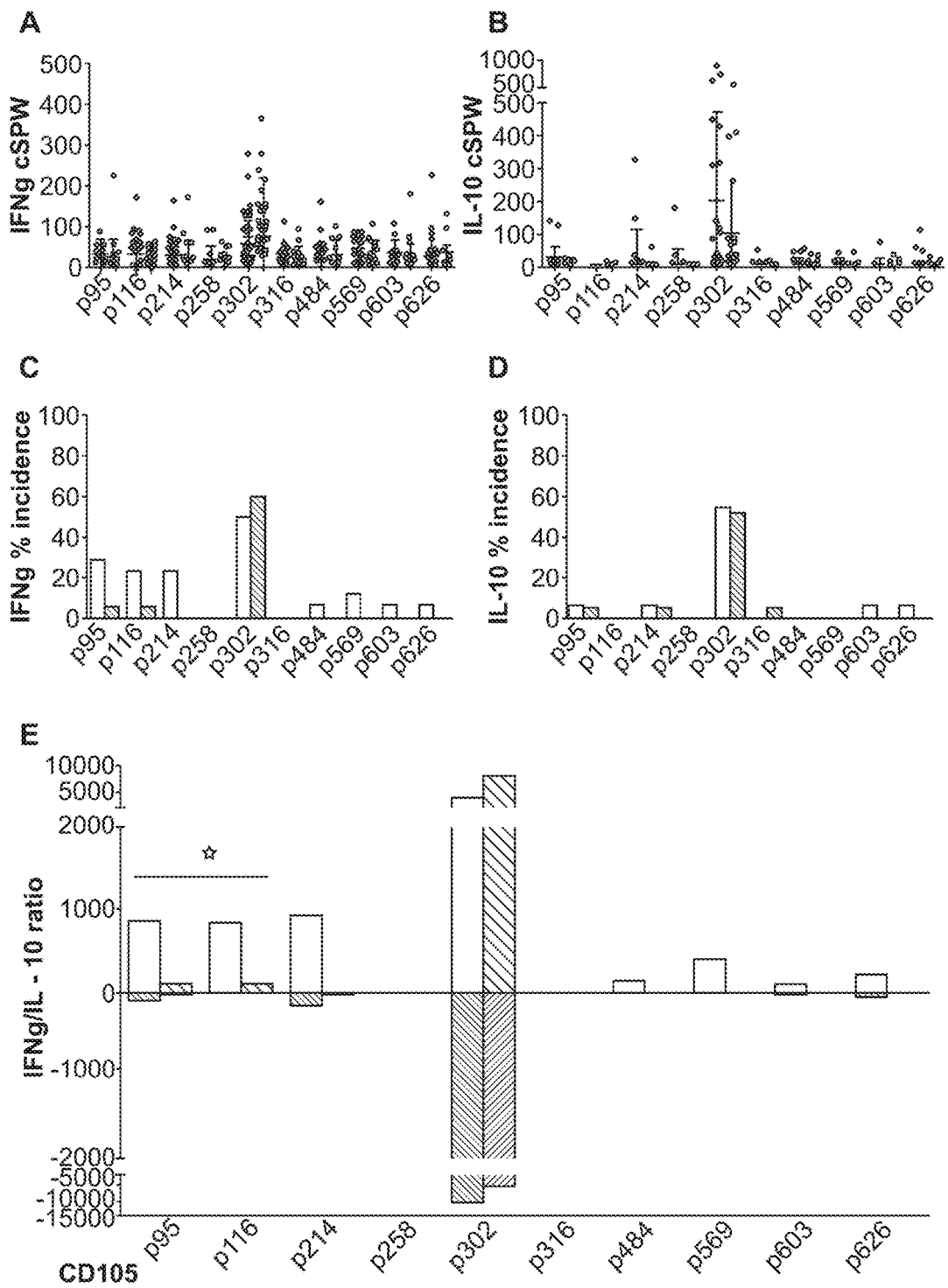
FIG. 17 shows magnitude and incidence of IFNγ predominant. IFNγ/IL-10 activity ratios for the CD105 antigen.
Figure 18:
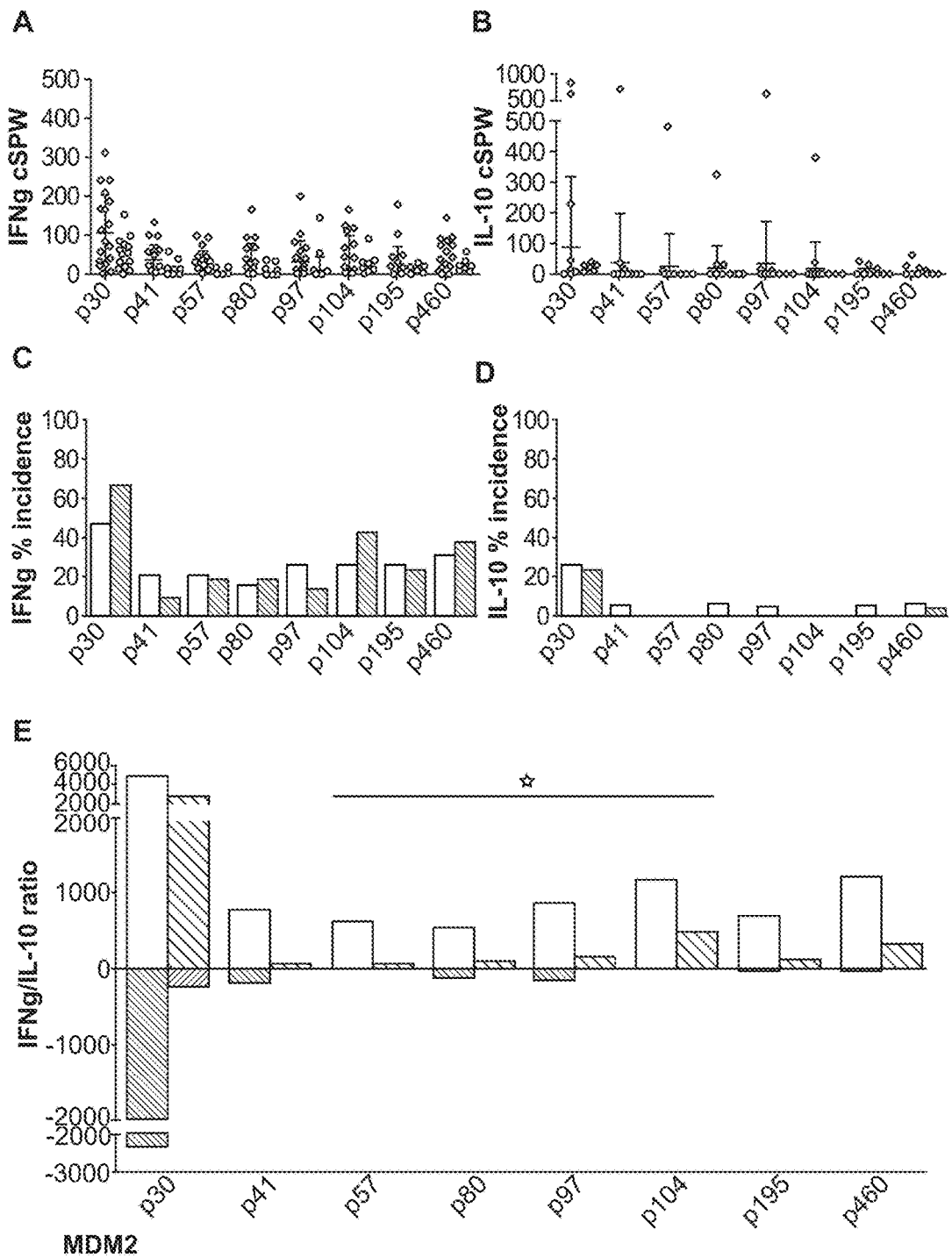
FIG. 18 shows magnitude and incidence of IFNγ predominant. IFNγ/IL-10 activity ratios for the MDM-2 antigen.

For another example, see FIG. 16, which depicts Western blot analysis of HIF1α expression in a single plasmid, pHIF1α and a plasmid encoding 5 antigens, BCMA5. 10-fold dilutions of anti-HIFα 0.1-10 μg/μL) were used to probe the blot after cuts were made along the dashed lines indicated. Only one lysate-loaded lane was used per antibody titration.

Example 2

Identification of Promiscuous High Affinity Binding Class II Epitopes Derived from Stem Cell/EMT Antigens Archived leukapheresis from 20 BrCA patients and 20 control donors was used. The mean age of the BRCA patients was 63 (range 49-87) and the mean age of the controls was 38 (range 29-65). Of the BrCA patients 81% were Stage I or II at the time of diagnosis, 10% were of unknown stage and the remainder were Stage III.

Constructed Peptides Per in Silico Mapping. Class II epitopes for the first 6 immunogenic BCS/EMT proteins were predicted using an algorithm method. Briefly, protein sequences of the candidate antigens were screened for potential MHC II epitopes using 3 publically available web based algorithms. Each protein was screened across the most common 14 HLA-DR alleles. A maximum of 20 epitopes were chosen/allele based on an estimated binding affinity. Each amino acid (aa) in each predicted epitope was given a score (sum score) dependent on the number of times the aa appeared in a predicted high binding epitope. The Sum Score was multiplied by the number of alleles with epitopes that included that specific amino acid, thus, each amino acid was thus assigned a multi-score which is the product of the frequency of increased binding affinity and the promiscuity of predicted responses across a broad population range. Forty-nine peptides derived from all 6 candidate proteins, chosen based on the multi-score of each epitope, were constructed for screening. Peptides that allowed at least 25% coverage of the full length protein were selected. The median peptide coverage for the candidate proteins was 28% of the total sequence (range 26-45%).

Figure 6:
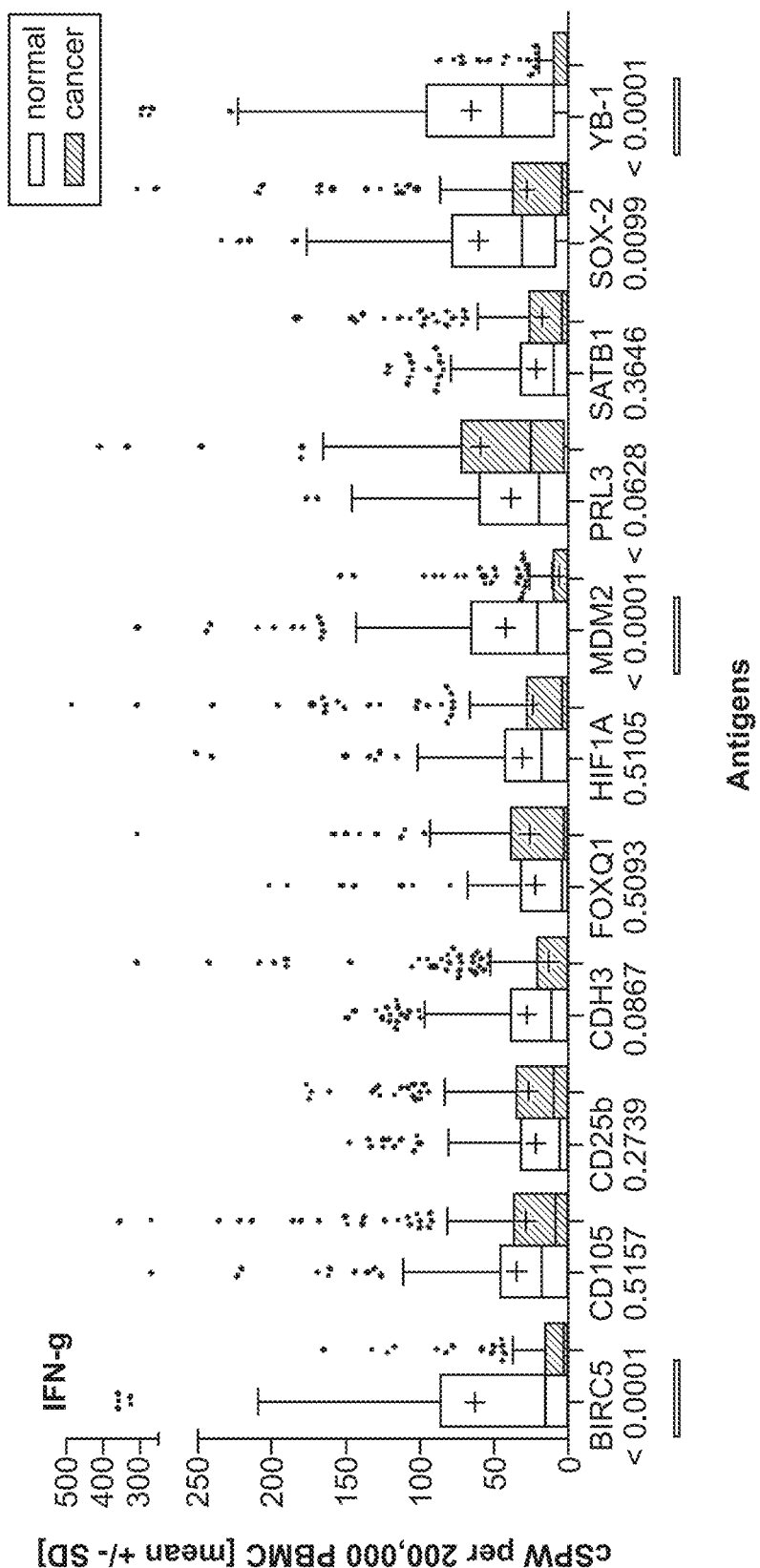
FIG. 6 depicts antigen specific IFNγ responses for stem cell/EMT proteins.

Samples Screened by IFNγ ELISPOT. FIG. 6 shows cumulative data on all donors for IFNγ responses to all peptides/antigen for representative antigens. In general, IFNγ responses were higher in volunteer donors as compared to BrCA patients and were statistically higher for survivin (BIRC5); p<0.001, MDM2; p<0.001, SOX-2; p=0.01, and Yb-1; p<0.001.

A positive response was defined as a mean value of experimental replicates statistically greater (p<0.05) than the mean replicates of the no antigen wells. The percent incidence was similar across donor type with 24-38% of subjects responding to a particular antigen above the median of responses. A two-way ANOVA to detect differences between experimental groups or peptides attributes 2.82% of the variation in response to donor type (p=0.0265) and 71.33% of the variation to the specific peptide tested (p=0.003) for IFNγ responses. Although donor type was weakly significant, the attributable variation is small.

Identification and Screening of Peptides from Each of the Candidate Antigens. Four epitopes were identified from each of the candidate antigens for IFNγ responses.

Example 3

Figure 7:
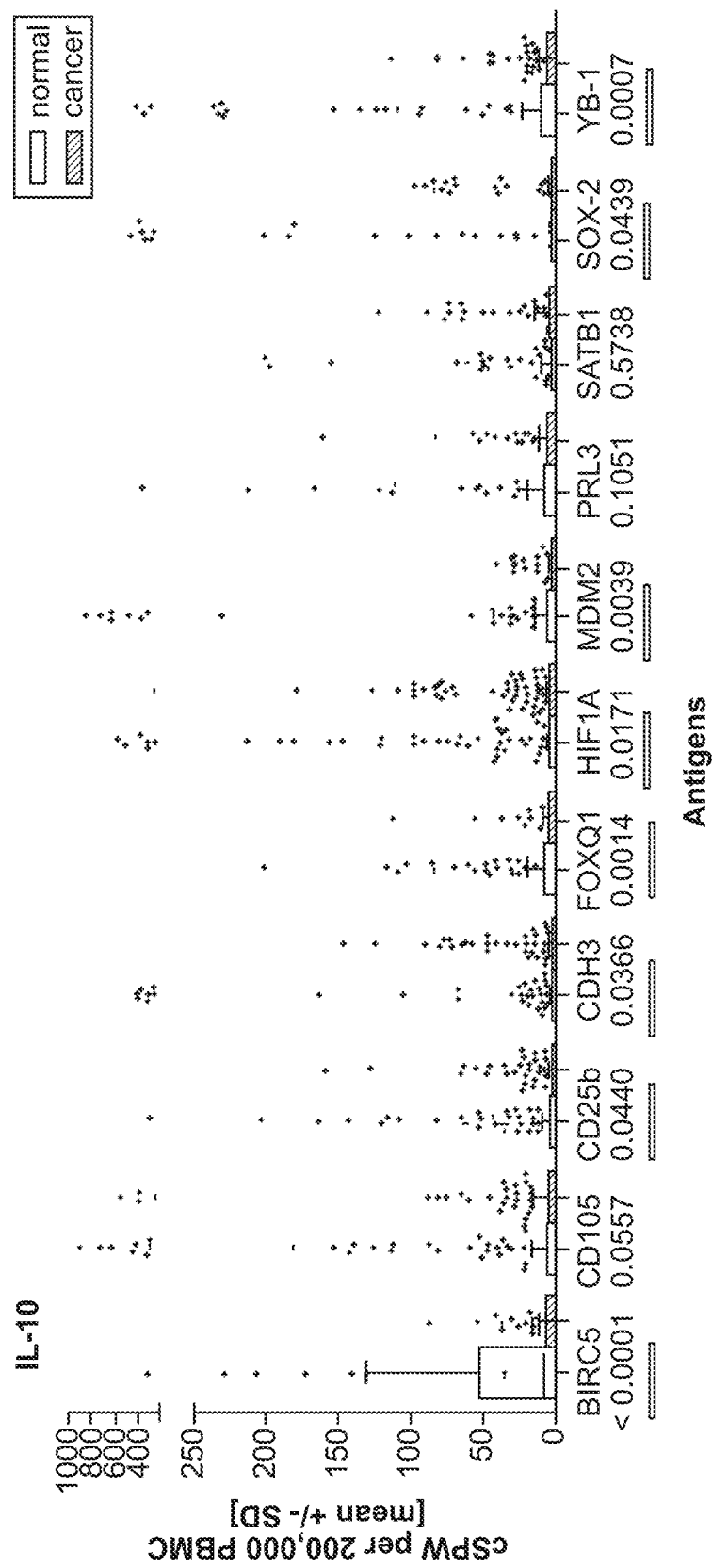
FIG. 7 depicts antigen specific IL-10 responses for stem cell/EMT proteins

Evaluation of Stem Cell/EMT Antigen-Derived Epitopes Preferentially Elicit T-Cells that Secrete IFNγ or IL-10 and Selection of Peptides as Candidate Vaccine Epitopes with Low Immune Suppressive Potential Samples Screened by IL-10 ELISPOT FIG. 7 shows cumulative data on all donors for IL-10 responses to all peptides/antigen for representative antigens. In general, IL-10 responses were of lower magnitude than IFNγ responses and volunteer donors demonstrated statistically significant higher median responses for most antigens- survivin (birc5); p<0.0001, CDC25b; p=0.044, CDH3; p=0.037, FOXQ1; p=0.0014, HIF1α; p=0.017, MDM2; p=0.0039, SOX-2; p=0.044, and Yb-1; p=0.0007.

Similar to IFNγ data, for IL-10, the donor type accounts for less than 0.01% of the variation between antigens (p=0.911) while the individual peptide accounts for 90.51% (p<0.0001).

Identification of Peptides that Induced Antigen Specific IFNγ Secreting T-Cells Compared to IL-10 Secreting T-Cells. A matrix scoring system that prioritized antigens for in vivo evaluation of extended epitopes that demonstrated IFNγ specific activity in the absence of IL-10 activity across the populations was used. Extended epitopes were superior to shorter class 11 epitopes in that the longer epitopes elicited a diverse immune response consisting of both T and B-cells and anti-tumor responses were dependent on both CD4 and CD8 T-cells. Regions in a candidate antigen that contained multiple epitopes that preferentially induced a greater magnitude and incidence of IFNγ responses and little or no IL-10 inducing activity were identified. A ratio (IFNγ/ IL-10 activity ratio) of the incidence X magnitude of antigen specific IFNγ induction/the incidence X magnitude of antigen specific IL-10 induction was evaluated (see FIGS. 10 and 11).

Figure 10:
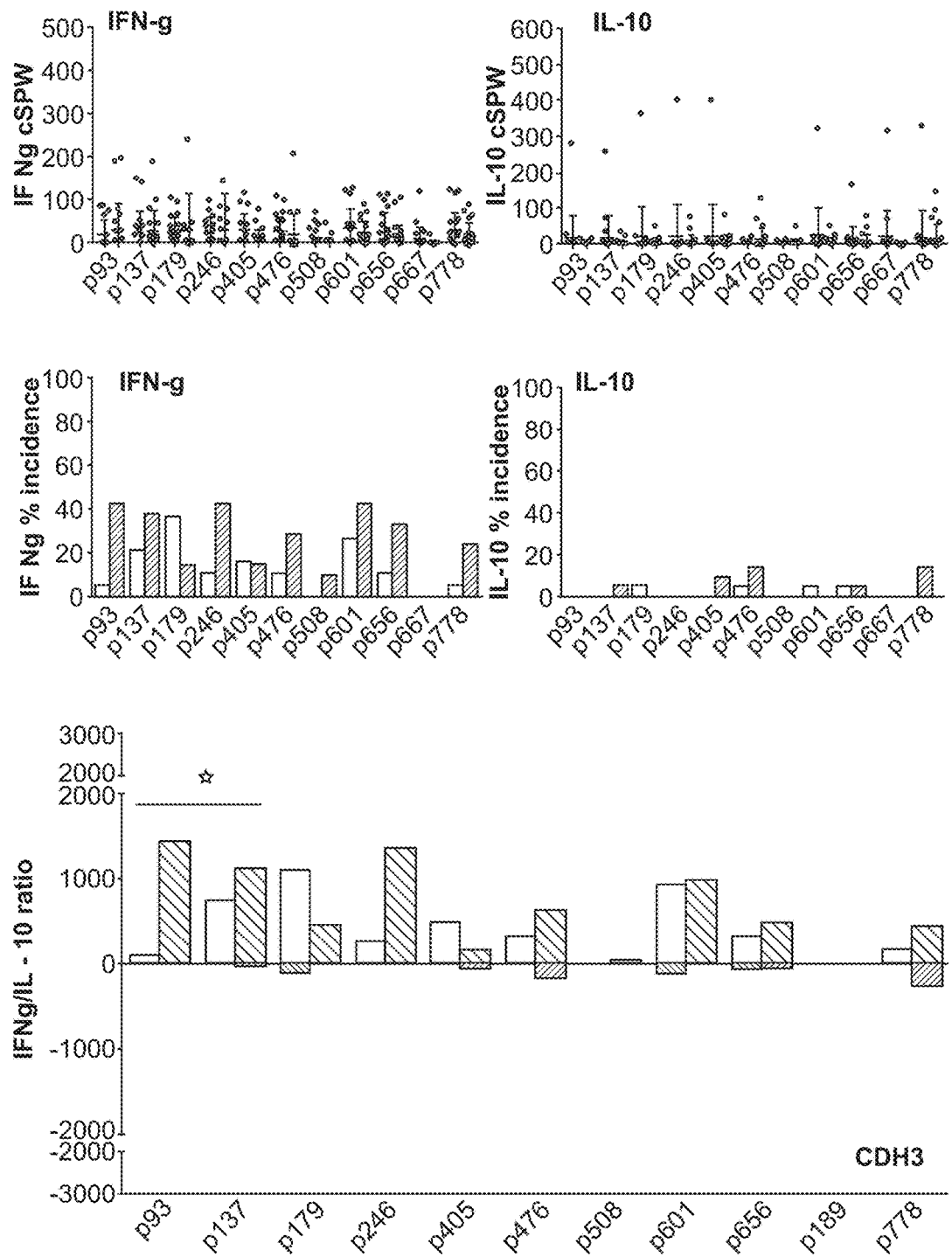
FIG. 10 shows magnitude and incidence of IFNγ predominant. IFNγ/IL-10 activity ratios for the CDH3 antigen.

For example, FIG. 10 depicts a higher magnitude and incidence of IFNγ predominance. IFNγ/IL-10 activity ratios for selected antigens. IFNγ/IL-10 ratio, defined as the mean cSPW×incidence per peptide, shown by donor type. IFNγ cSPW×incidence shown on the positive y-axis for volunteer donors, shown in white bars, and cancer donors, shown in white bars with black pattern. IL-10 cSPW×incidence shown on the negative y-axis for volunteer donors, shown in black bars, and cancer donors, shown in black bars with white pattern. (A) CDH3, (B) HIF1α, (C) survivin, and (D) FOXQ1.

Figure 11:
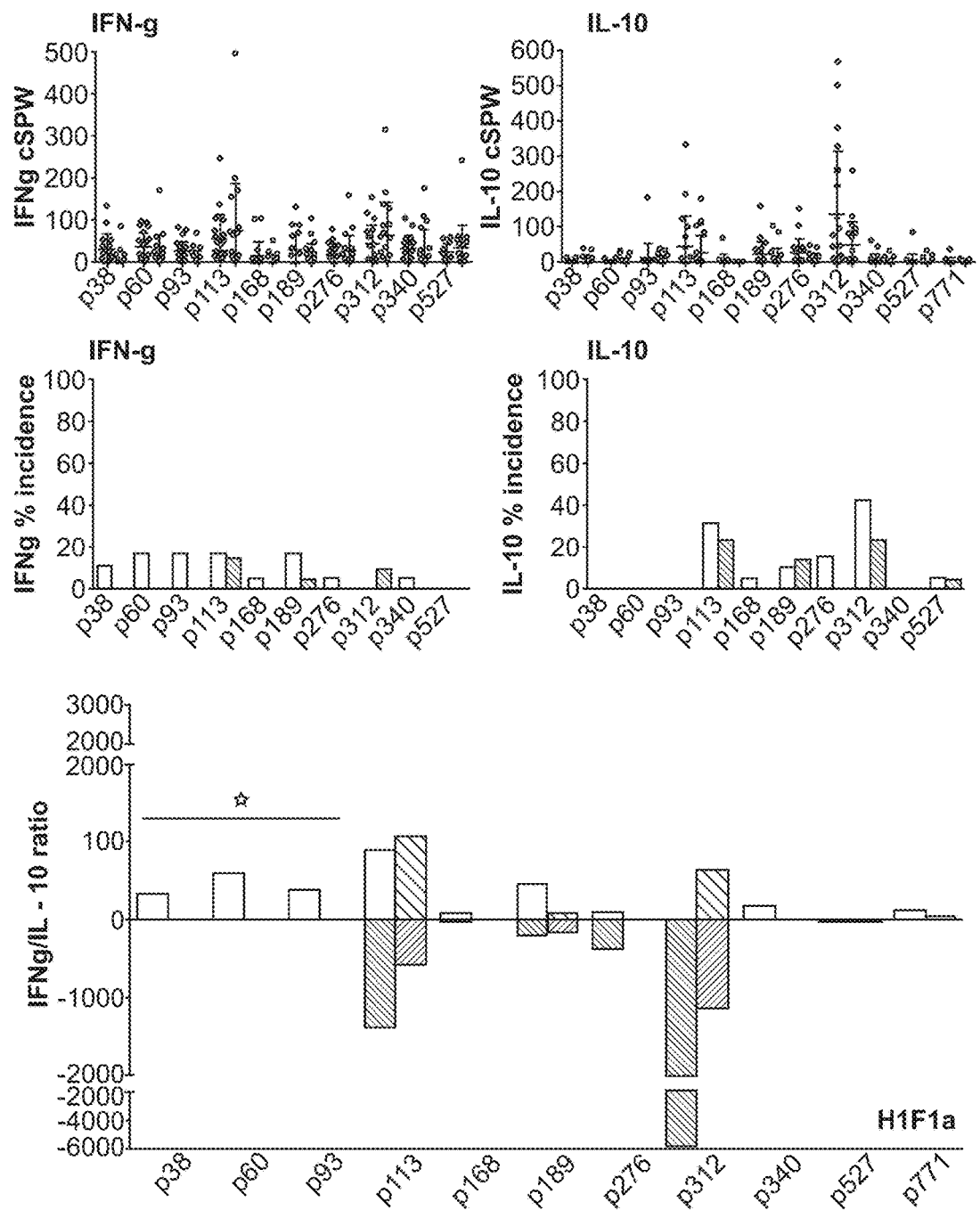
FIG. 11 shows magnitude and incidence of IFNγ predominant. IFNγ/IL-10 activity ratios for the HIF1α antigen.

For example, FIG. 11, shows the lower magnitude and incidence IFNγ predominance. IFNγ/IL-10 activity ratios for selected antigens. IFNγ/IL-10 ratio, defined as the mean cSPW×incidence per peptide, shown by donor type. IFNγ cSPW×incidence shown on the positive y-axis for volunteer donors, shown in white bars, and cancer donors, shown in white bars with black pattern. IL-10 cSPW×incidence shown on the negative y-axis for volunteer donors, shown in black bars, and cancer donors, shown in black bars with white pattern. (A) CDH3, (B) HIF1x, (C) survivin, and (D) FOXQ1.

The evaluated antigens were categorized into 4 major groups based on the IFNγ/IL-10 activity ratio. The first group, exemplified by CDH3 (FIG. 10) displayed a high incidence/magnitude IFNγ response with very little IL-10 activity. This pattern indicated a top tier antigen and included CDH3, SOX2, MDM2, and Yb-1. The second tier antigens demonstrated a similar predominant IFNγ response with minimal to no IL-10 induction in regions of selected extended epitopes, however the magnitude of the immune response was greater than a log lower than the top tier candidates. FIG. 11, HIF1α, exemplifies This category which also includes CD105, CDC25B, and SATB1. Vaccine candidates were derived from these categories (see FIGS. 10 and 11).

Figure 9:
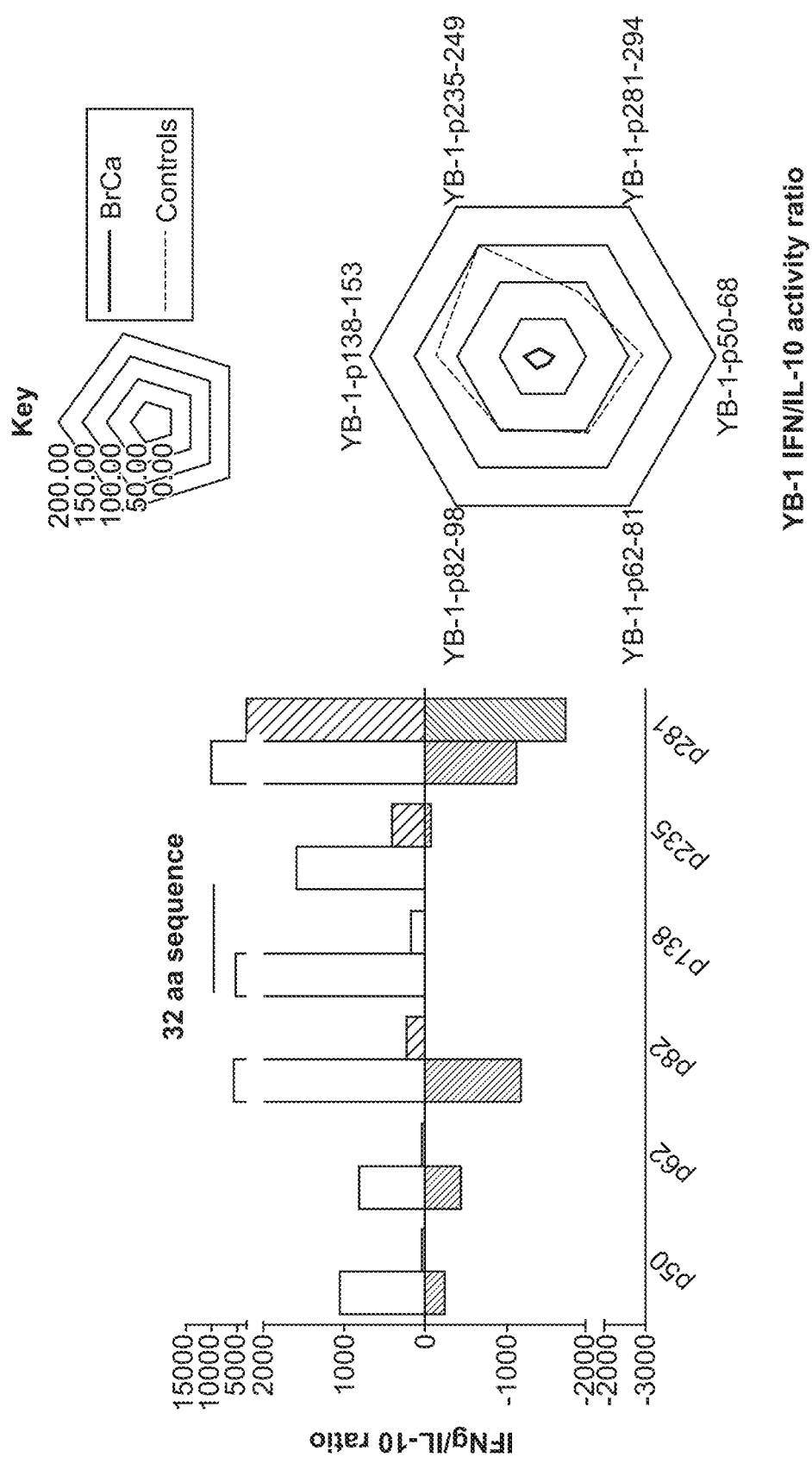
FIG. 9 shows extended epitopes for Yb-1 based on IFNγ/IL-10 activity ratio.
Figure 19:
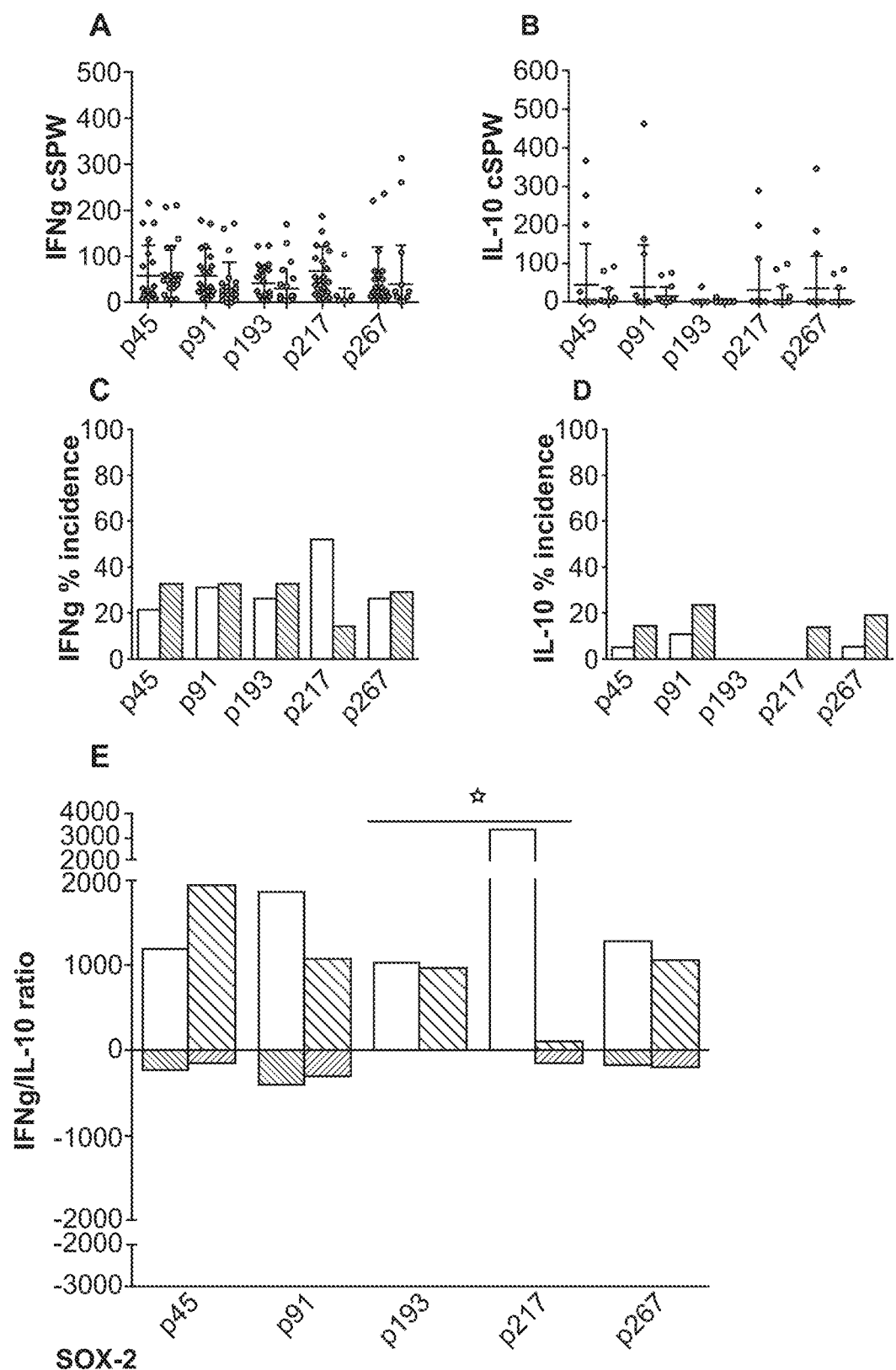
FIG. 19 shows magnitude and incidence of IFNγ predominant. IFNγ/IL-10 activity ratios for the SOX-2 antigen.
Figure 20:
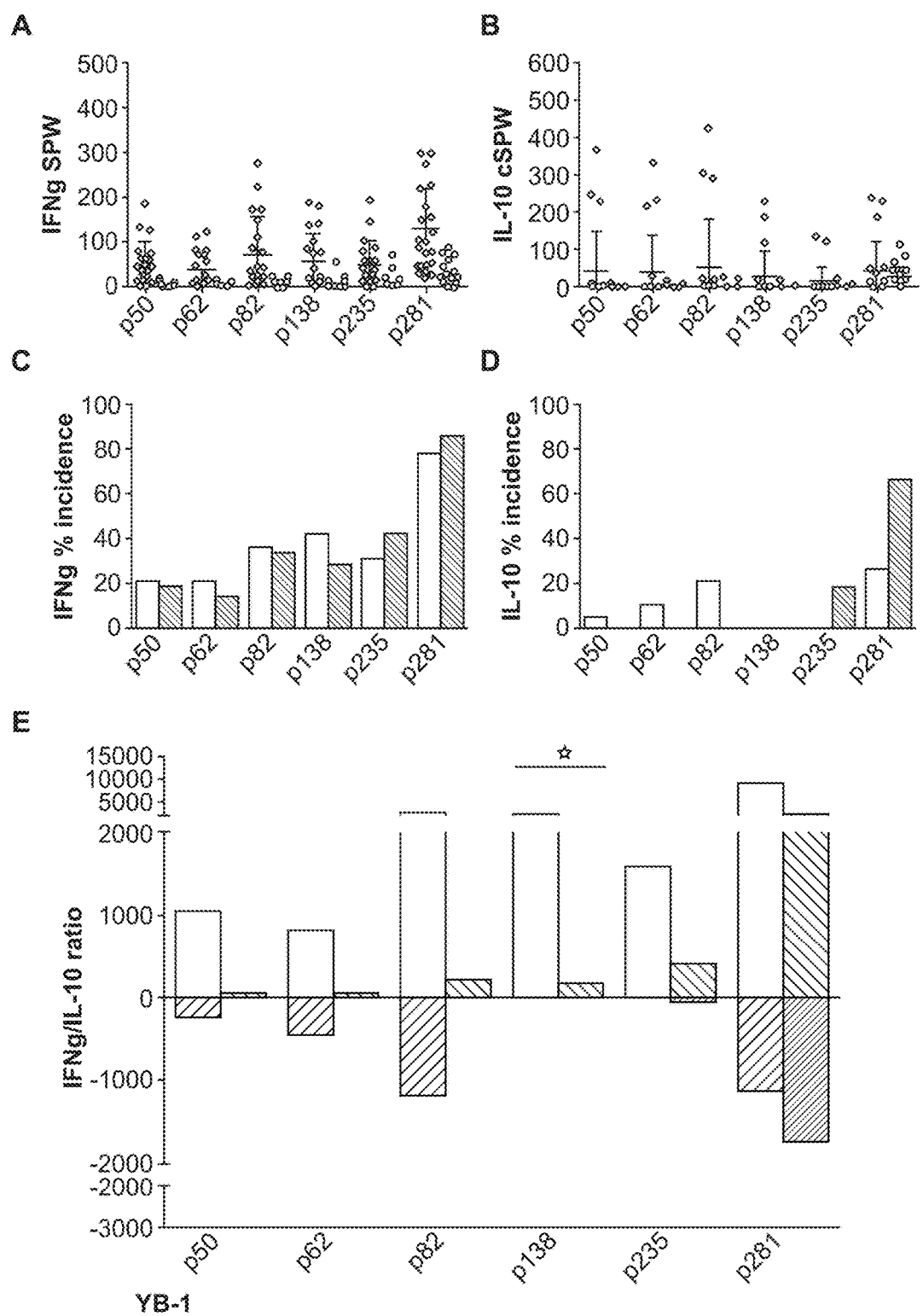
FIG. 20 shows magnitude and incidence of IFNγ predominant. IFNγ/IL-10 activity ratios for the Yb-1 antigen.

The other two groups had characteristics which were much less desirable for a vaccine immunogen. Although there are epitopes that stimulate a high magnitude and incidence IFNγ response, these sequences equally induce high magnitude IL-10 immunity at an equal incidence in tested individuals. Antigens such as c-met, IGF-1R, PRL3, and SIX1 are grouped into this category. Finally, some candidate antigens were not immunogenic as demonstrated by both a low incidence as well as low magnitude of any immune response, as shown in FIG. 19 for FOXQ1. ID1 and SNAIL also were associated with very low incidence and magnitude of immune response. Immunogenic and inducing high magnitude and incidence IL-10 responses or weakly immunogenic, these latter two categories of antigens will be excluded from further consideration for the final vaccine formulation. In FIG. 9, a list of extended epitopes based on IFNγ/IL-10 activity ratio is shown. See also FIGS. 17-20.

Example 4

Identification of the Response of Peptide Specific Th1 Cells to Protein Presented on Endogenous APC T-Cell Lines Generated Against Candidate Epitopes. PBMC derived from 3 donors who have demonstrated positive responses in the ELISPOT assay were stimulated with 10 ug/ml of the antigenic peptide. IL-12 (10 ng/ml) and IL-2 (10 u/ml) were added into the culture on Day 5. The peptide stimulation and cytokine addition was repeated twice at 7-10 day intervals. The cultures were subsequently expanded with CD3/CD28 beads. IL-2 (30 u/ml) was added into the culture every 2-3 days for 10-11 days. The established peptide specific T-cell lines were then evaluated using a 3-day IFNγ ELISPOT assay. The cultured T-cells were stimulated with different concentrations of the peptide and commercially available recombinant protein loaded on autologous APC. Irrelevant peptides and proteins were used as negative controls. The response to peptide and protein antigens which was significantly (p<0.05) increased compared with no antigen control, in at least one donor, was defined as positive response. MHC II and MHC I blocking antibodies (10 μg/ml) were added into some of the antigen stimulated wells to validate whether the epitope was MHC restricted. In addition, a portion of the T-cells were stained with CD3 FITC, CD4 PE-Cy7, CD45RO APC, and CD62L PE or CCR7 PE to evaluate the central memory cell population in the T-cell lines as compared with the cells before antigen stimulation (PBMC).

Figure 15A:
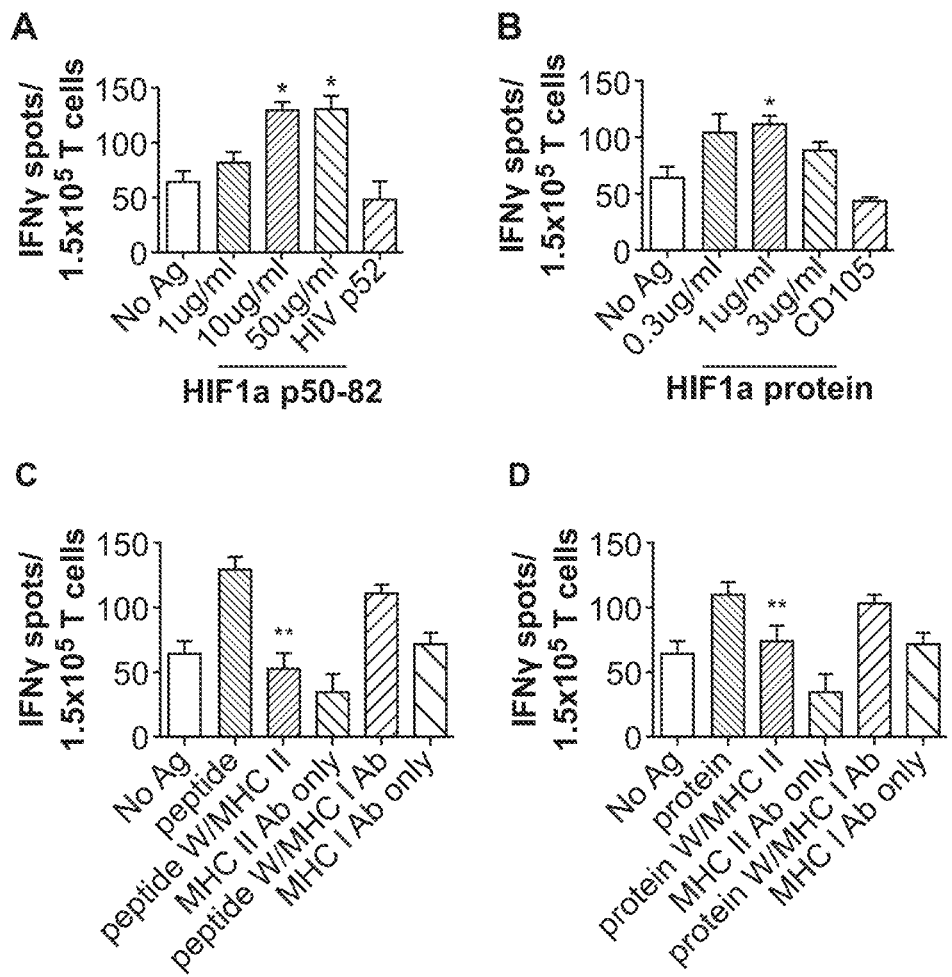
FIG. 15A shows an exemplary validation of peptide specific T-cells as native epitopes.
Figure 15B:
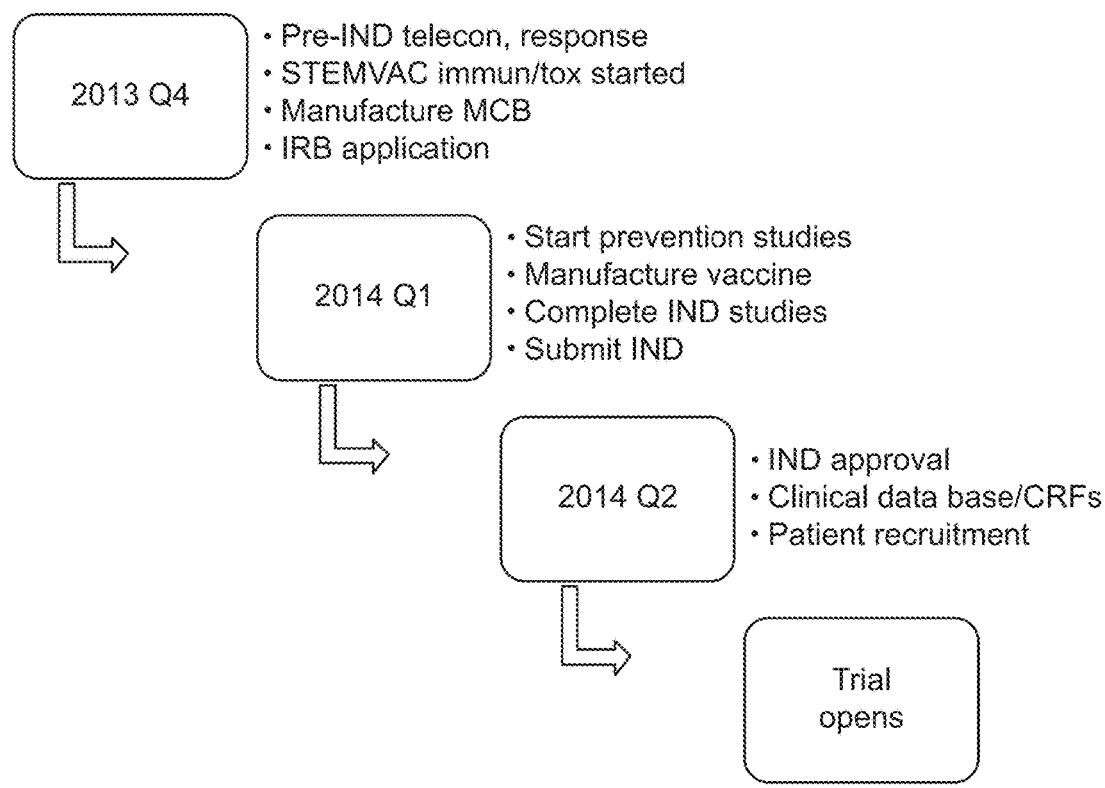
FIG. 15B depicts a timeline for a clinical trial using a composition described herein.
Figure 15C:
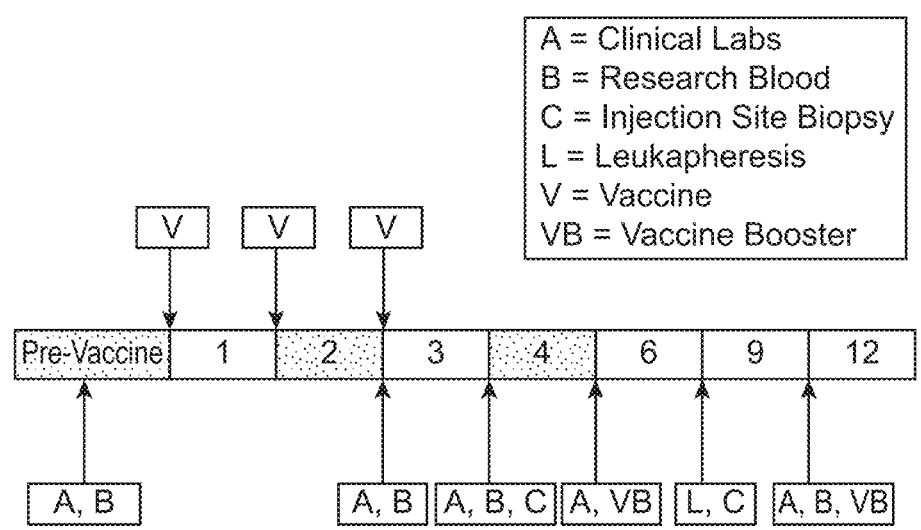
FIG. 15C depicts a study schema for Phase I of a clinical trial using a composition described herein.

T-Cell Lines Screened Against Positive and Negative Controls for Specificity to Both Peptide and Recombinant Protein. FIG. 29 shows validation data for HIF1α peptide p60-82 as a representative example. A HIF1α p60-82 specific T-cell line responded to the peptide and recombinant HIF1α protein presented on endogenous APC. Both the peptide (10 ug/ml and 50 ug/ml) and protein (1 ug/ml) significantly stimulated IFNγ response from the peptide specific T-cell line. Irrelevant peptide (HIV p52-68) and protein (CD105) did not (FIG. 15A). MHC II antibody significantly inhibited both peptide and protein induced IFNγ responses, but MHC I antibody did not (FIG. 15A). The CD45RO+CD62L+CD4+ central memory cells proliferated in the cultured T-cell line (73%) as compared to the basal level in PBMC before culture (9%).

Figure 8:
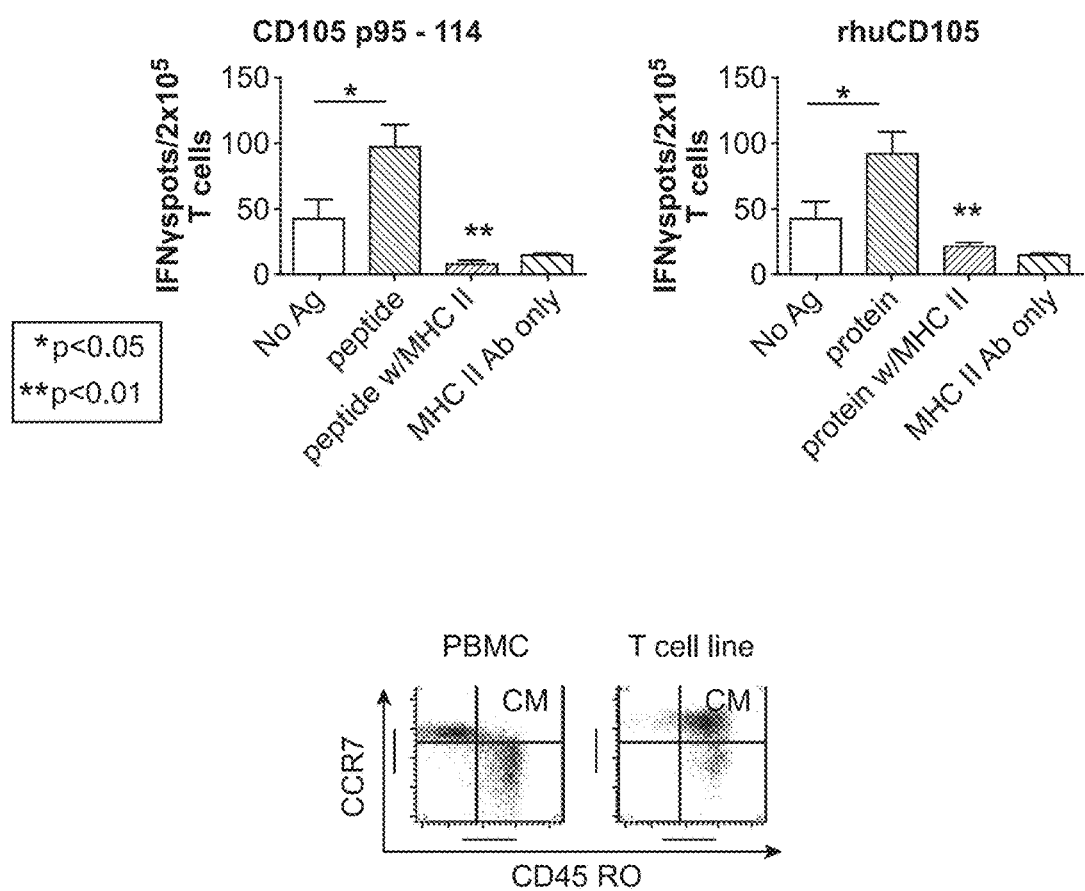
FIG. 8 shows that peptides in extended sequences validate as native epitopes with the CD105 extended epitope (52aa) QNGTWPREVLLVLSVNS SVFLHL QALGI PLHLAYNSSLVTFQEPPGVNTTEL (SEQ ID NO: 1).

For example, see FIG. 8, which shows peptides in extended sequences validate as native epitopes. CD105 extended epitope (52aa) QNGTWPREVLLVLSVNS SVFLHL QALGI PLHLAYNSSLVTFQEPPGVNTTEL (SEQ ID NO: 1) (one of 2 epitopes in the sequence).

Similarly, validated peptides were identified and derived from CD105, SATB1, CDH3, SOX2, YB1, and MDM2. Of the peptides validated, all peptide specific T-cell lines demonstrated statistically positive peptide responses. MHC II antibody inhibited more than 70% of the peptide specific responses in 75% of peptide specific lines evaluated, and MHC I antibody inhibited more than 70% of the peptide responses in 20% of the lines. MHC II antibody inhibited >70% of the protein specific responses among all the positive protein responders (90%). Central memory T-cell populations were significantly increased after culture.

For the 6 antigens in the top and second tier groups, CDH3, SOX2, MDM2, YB1, HIF1α and CD105, areas of extended epitopes suitable for vaccination with high to moderately high IFNγ ratio and low to minimal IL-10 ratio were identified. Each sequence encompassed 2 or more shorter (15-22-aa) validated Class II epitopes. The extended sequences range from 32-aa to 90-aa in length (see Table 6).

Linked together, the sequences derived from CDH3, Yb-1, MDM2, SOX2, and CD105, encode a unique fusion protein termed "STEMVAC" (see Supplemental Table 5).

Identification of Candidate Epitopes for Inclusion in a Multi-Antigen Vaccine from Each of the Candidate Antigens. Five extended epitopes were derived from 5 of the 15 candidate antigens suitable for a vaccine that preferentially induced IFNγ secretion with little Th2 (IL-10) were identified. These sequences were combined into a unique fusion protein, STEMVAC, which is the basis of a breast cancer vaccine.

Example 5

Construction of a Multiantigen Th1 Polyepitope Plasmid Based Vaccine Targeting Stem Cell/EMT Antigens and Determination of Safety and Immunogenicity Determination of Immunogenicity and Effectiveness of Plasmid Based Vaccine Constructs Containing Either or Both Short Th Epitopes or Extended Th Epitopes Using the TgMMTVneu Mouse Model with the IGF-1R Antigen. In order to directly compare the ability of the short and extended epitope plasmid vaccines to control tumor growth, a syngeneic tumor implant model was employed. Mice (TgMMTVneu) were separated into 4 vaccination groups (pIGF-IRexep, pIGF-IRshep, vector, and IGF-IR peptides) and implanted with syngeneic breast cancer cells (MMC) 7 days after the 3rd vaccination. Dosages were as stated above. The ability of MMC cells to form a tumor, and the tumor growth rate was measured. The IGF-IR peptide vaccine, the short epitope plasmid vaccine, and the extended epitope plasmid vaccine all significantly controlled tumor growth compared to the group that was vaccinated with vector alone ($p<0.0001$, from 14-31 days). The mice vaccinated with pIGF-IRexep had the slowest growing tumors, but they were not significantly different from tumor growth in animals vaccinated with pIGF-IRshep, $p>0.05$.

Figure 2:
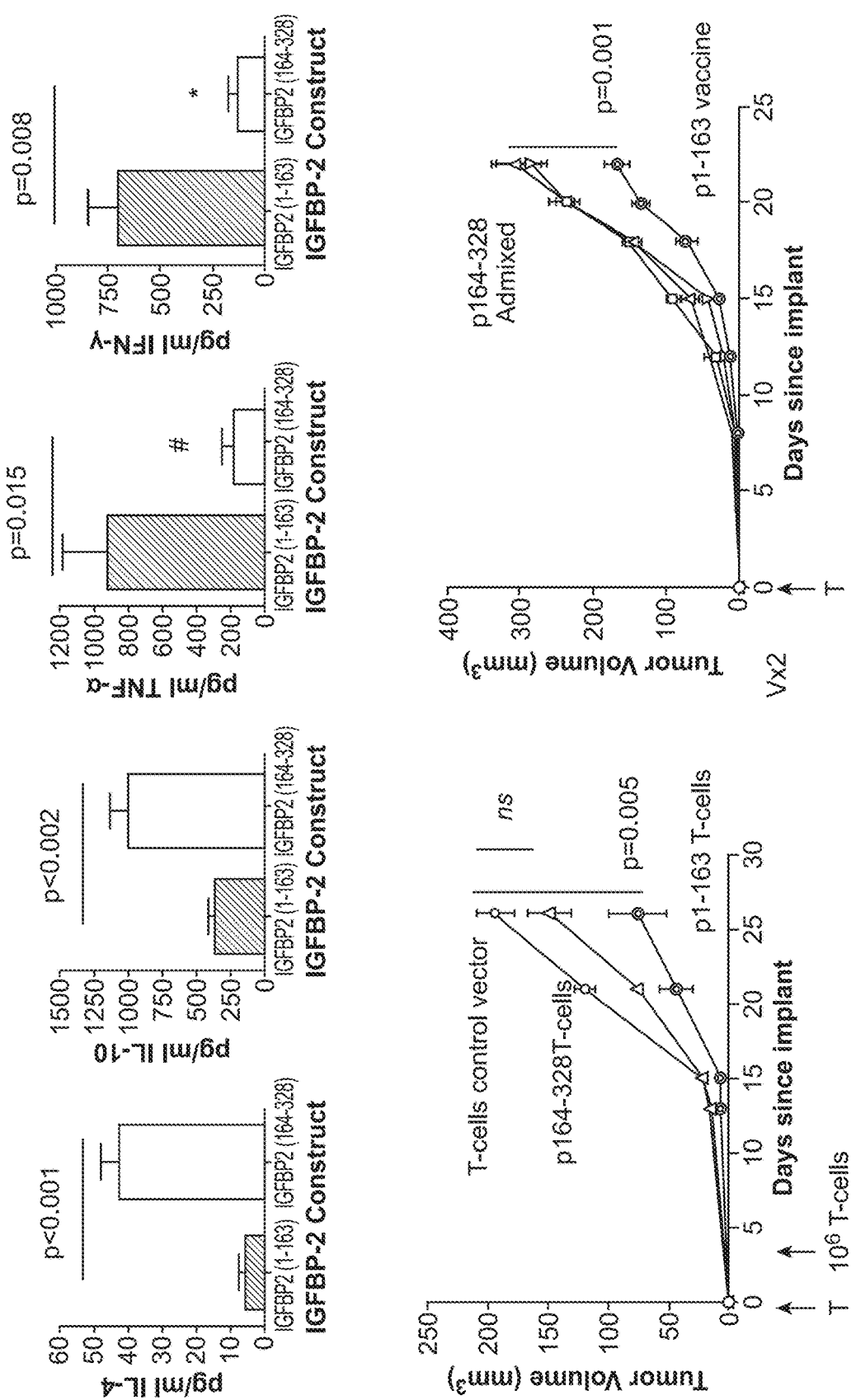
FIG. 2 shows that Th2 abrogates the anti-tumor efficacy of Th1.

For example, FIG. 2 Th2 immune responses abrogate the anti-tumor efficacy of Th1 immune responses.

Figure 21:
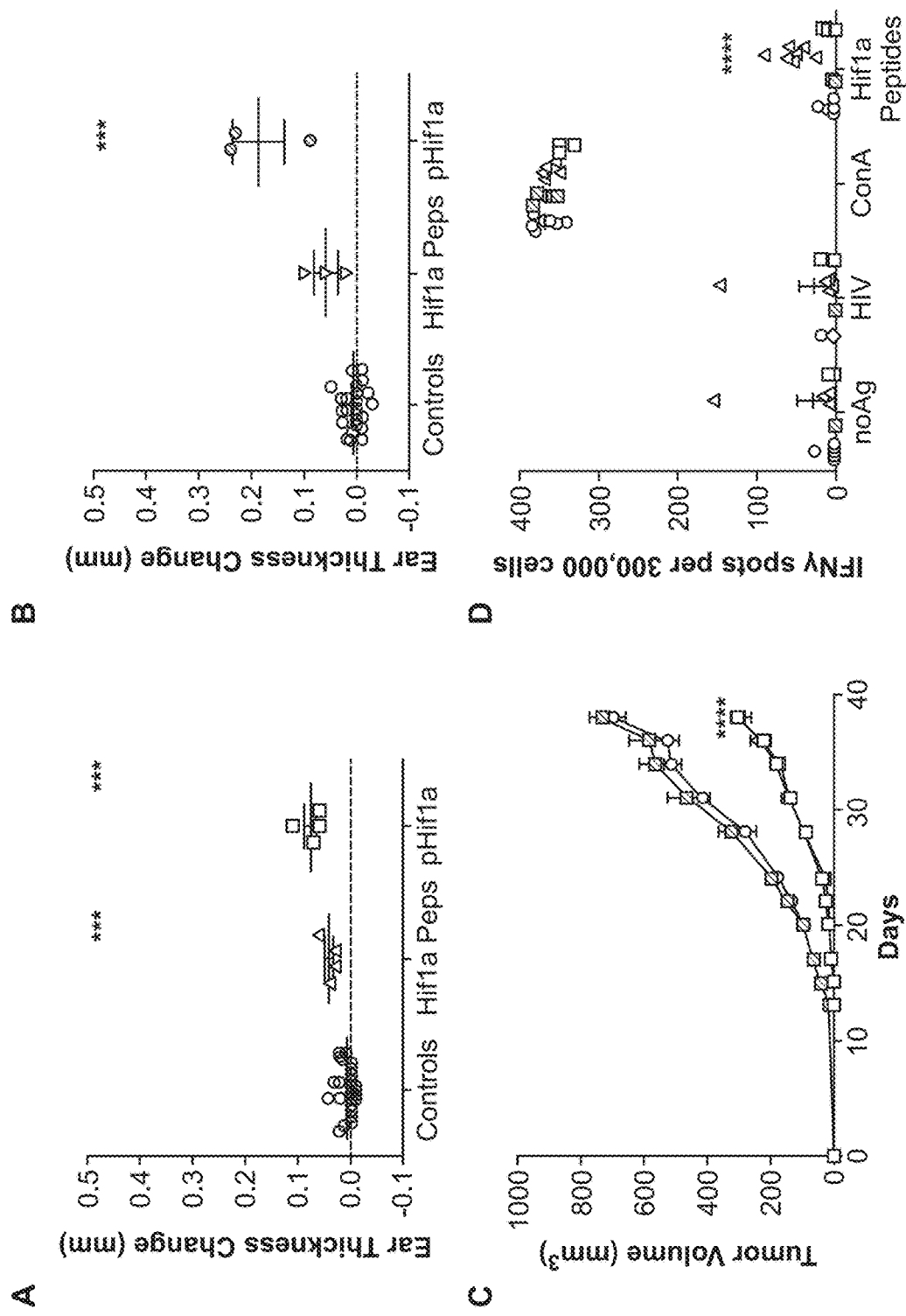
FIG. 21 depicts HIF1α peptide and plasmid vaccine immunogenicity and efficacy in mice.

For example, FIG. 21 HIF1α peptide and plasmid vaccine immunogenicity and efficacy were determined in mice. (A) DTH responses were measured by change in ear thickness (mm) 24 hours after application of HIF1α peptide mix in 50% DMSO. Plotted are responses of individual FVB/NJ mice from the different vaccination cohorts: Controls (both adjuvant only and vector groups, see Methods), HIF1α Peps (peptide vaccine), and pHif1a (plasmid vaccine). Dotted line represents 0.0 mm change in earthickness from baseline. * $p<0.001$ vs. controls. (B) DTH responses measured 24 hours after application of HIF1α peptide mix in 50% DMSO. Plotted are responses of individual MMTV-C3(1)-Tag transgenic mice from the different vaccination cohorts as listed above. * $p<0.001$ vs. controls. (C) Efficacy of vaccines to control M6 tumor growth was assessed by measuring tumor volume (mm3) over time post-implant (days) in MMTV-C3(1)-Tag transgenic mice. Vaccination groups were adjuvant only (○), Vector (□), HIF1α Peptides (▲), or pHIF1α (■). Error bars show SEM for each group. HIFla peptide vaccinated mice and HIF1α DNA vaccinated mice had significantly smaller tumor burden vs. control mice as early as 24 days after implant. **$p<0.0001$ vs. adjuvant only group. (D) IFNγ ELISPOT assessed T-cell responses to peptide or control stimulations. Each plotted point represents the spots per well of individual FVB/NJ mice in vaccination groups treated with adjuvant only (○), Vector (□), HIF1α Peptides (▲), or pHif1a (■). Lines show Mean & SEM of responses. * $p<0.001$ HIF1α peptides vs. No Ag response. Although HIF1α plasmid generated DTH responses, IFNγ ELISPOT are low level.

Figure 22:
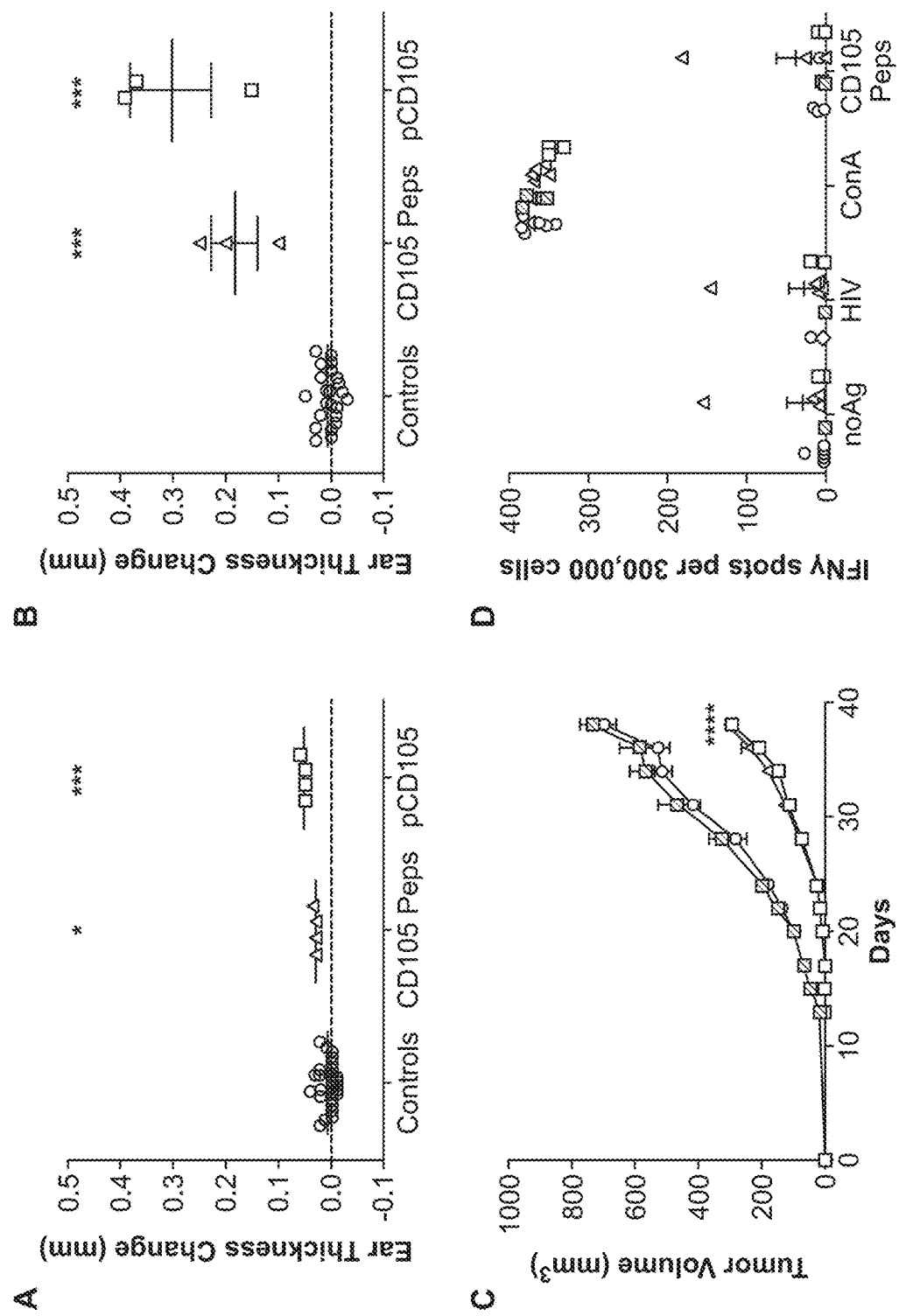
FIG. 22 depicts CD105 peptide and plasmid vaccine immunogenicity and efficacy in mice.

For another example, FIG. 22 CD105 peptide and plasmid vaccine immunogenicity and efficacy were determined in mice. (A) DTH responses were measured by change in ear thickness (mm) 24 hours after application of CD105 peptide mix in 50% DMSO. Plotted are responses of individual FVB/NJ mice from the different vaccination cohorts: Controls (both adjuvant only and vector groups, see Methods), CD105 Peps (peptide vaccine), and pCD105 (plasmid vaccine). Dotted line represents 0.0 mm change in ear thickness from baseline. * $p<0.05$, * $p<0.001$ vs. controls. (B) DTH responses measured 24 hours after application of CD105 peptide mix in 50% DMSO. Plotted are responses of individual MMTV-C3(1)-Tag transgenic mice from the different vaccination cohorts as listed above. * $p<0.001$ vs. controls. (C) Efficacy of vaccines to control M6 tumor growth was assessed by measuring tumor volume (mm3) over time post-implant (days) in MMTV-C3(1)-Tag transgenic mice. Vaccination groups were adjuvant only (○), Vector (□), CD105 Peptides (▲), or pCD105 (■). Error bars show SEM for each group. CD105 peptide vaccinated mice and CD105 DNA vaccinated mice had significantly smaller tumor burden vs. control mice as early as 24 days after implant. ****$p<0.0001$ vs. adjuvant only group. (D) IFNγ ELISPOT assessed T-cell responses to peptide or control stimulations. Each plotted point represents the spots per well of individual FVB/NJ mice in vaccination groups treated with adjuvant only (○), Vector (□), CD105 Peptides (▲), or pCD105 (■). Lines show Mean & SEM of responses. No significance found for CD105 peptide responses in any group.

Figure 23:
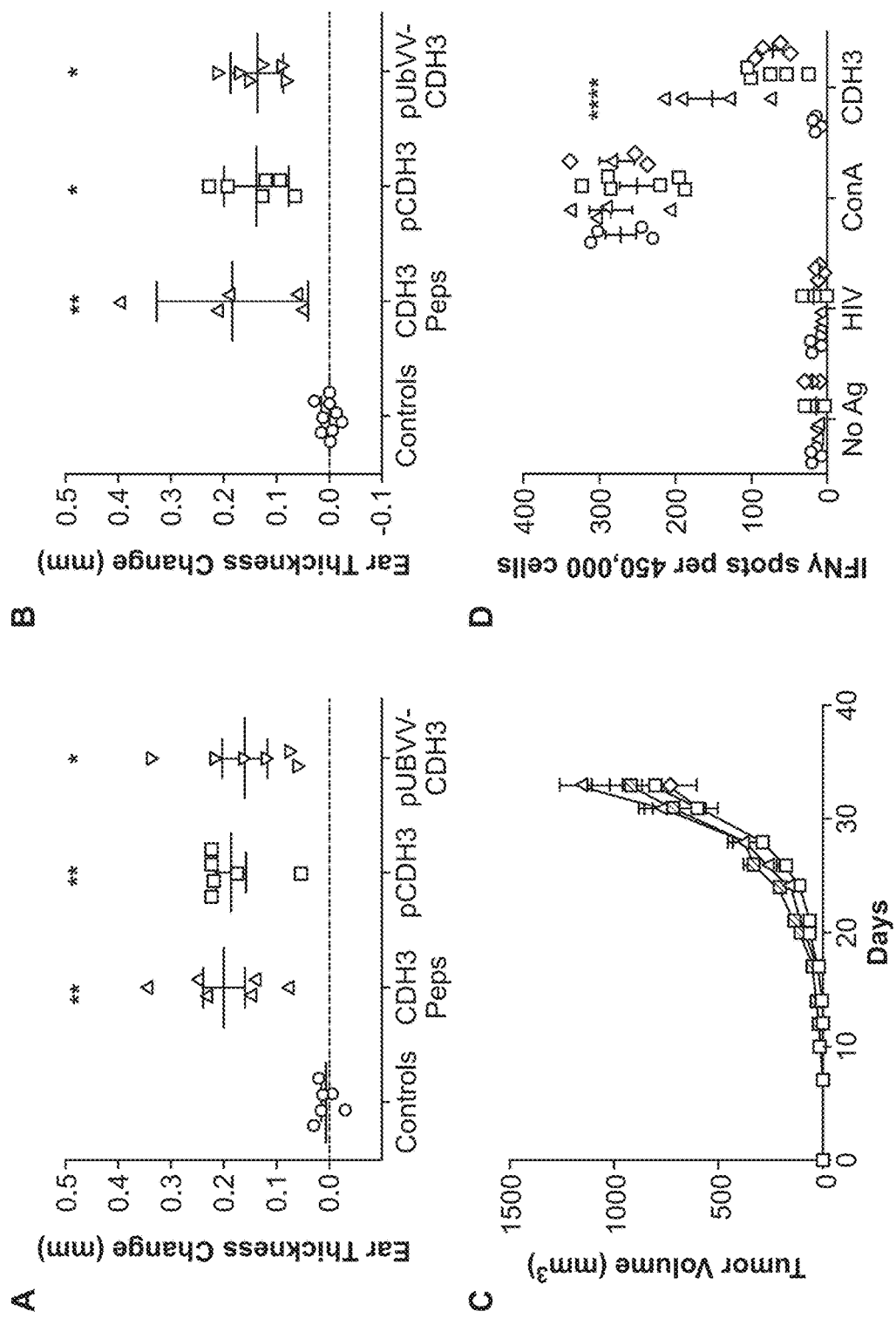
FIG. 23 depicts CDH3 peptide and plasmid vaccine immunogenicity and efficacy in mice.

For another example, FIG. 23 CDH3 peptide and plasmid vaccine immunogenicity and efficacy were determined in mice. (A) DTH responses were measured by change in ear thickness (mm) 24 hours after application of CDH3 peptide mix in 50% DMSO. Plotted are responses of individual FVB/NJ mice from the different vaccination cohorts: Controls (see Methods), CDH3 Peps (peptide vaccine), pCDH3 (plasmid vaccine) and pUbVV-CDH3. Dotted line represents 0.0 mm change in ear thickness from baseline. * $p<0.05$, ** $p<0.01$ vs. controls. (B) DTH responses measured 24 hours after application of CDH3 peptide mix in 50% DMSO. Plotted are responses of individual FVB/N/Tg-neu transgenic mice from the different vaccination cohorts as listed above. * $p<0.05$,  $p<0.01$ vs. controls. (C) Efficacy of vaccines to control MMC tumor growth was assessed by measuring tumor volume (mm3) over time post-implant (days) in FVB/N/Tg-neu transgenic mice. Vaccination groups were adjuvant only (○), Vector (□), CDH3 Peptides (▲), pCDH3 (■), or pUBVV-CDH3 (♦). Error bars show SEM for each group. Neither CDH3 peptide or DNA vaccinated mice had significantly smaller tumor burden vs. control mice. (D) IFNγ ELISPOT assessed T-cell responses to peptide or control stimulations. Each plotted point represents the spots per well of individual FVB/NJ mice in vaccination groups treated with adjuvant only (○), CDH3 Peptides (▲), pCDH3 (■), or pUBVV-CDH3 (♦). Lines show Mean & SEM of responses. ** $p<0.0001$ CDH3 peptides vs. No Ag response.

Figure 24:
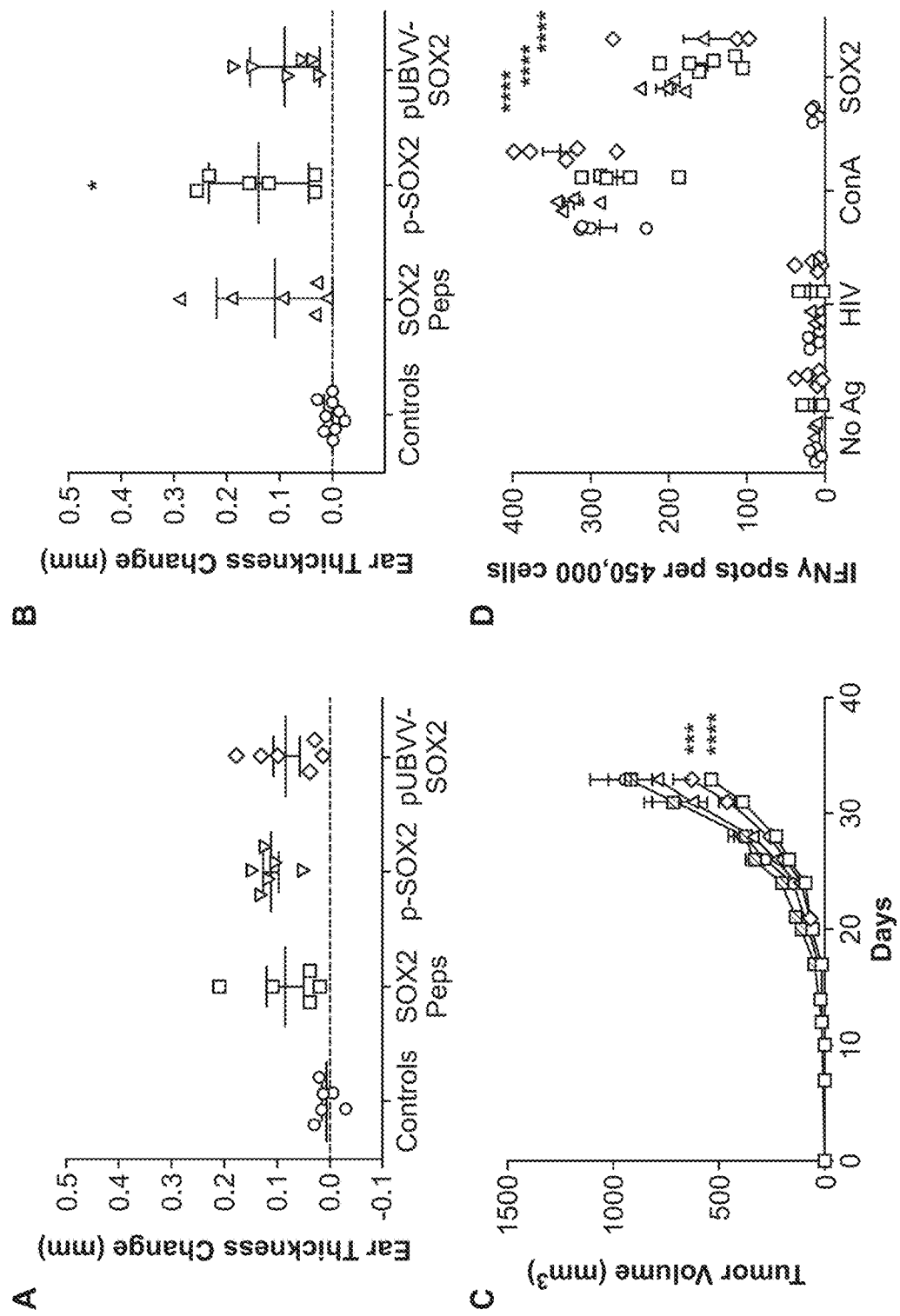
FIG. 24 depicts SOX2 peptide and plasmid vaccine immunogenicity and efficacy in mice.

For another example, FIG. 24, SOX2 peptide and plasmid vaccine immunogenicity and efficacy were determined in mice. (A) DTH responses were measured by change in ear Thickness (mm) 24 hours after application of SOX2 peptide mix in 50% DMSO. Plotted are responses of individual FVB/NJ mice from the different vaccination cohorts: Controls (see Methods), SOX2 Peps (peptide vaccine), pSOX2 (plasmid vaccine) and pUbVV-SOX2. Dotted line represents 0.0 mm change in ear Thickness from baseline. No significance found versus controls. (B) DTH responses measured 24 hours after application of SOX2 peptide mix in 50% DMSO. Plotted are responses of individual FVB/N/Tg-neu transgenic mice from the different vaccination cohorts as listed above. * $p<0.05$ vs. controls. (C) Efficacy of vaccines to control MMC tumor growth was assessed by measuring tumor volume (mm3) over time post-implant (days) in FVB/N/Tg-neu transgenic mice. Vaccination groups were adjuvant only (○), Vector (□), SOX2 Peptides (▲), pSOX2 (■), or pUBVV-SOX2 (♦). Error bars show SEM for each group. *p<0.001, p<0.0001 vs. adjuvant only group. (D) IFNγ ELISPOT assessed T-cell responses to peptide or control stimulations. Each plotted point represents the spots per well of individual FVB/NJ mice in vaccination groups treated with adjuvant only (j), SOX2 Peptides (▲), pSOX2 (■), or pUBVV-SOX2 (♦). Lines show Mean & SEM of responses. * p<0.001 SOX2 peptides, ** p<0.0001 pSOX2, ** p<0.0001 pUbVV-SOX2 vs. No Ag response. Although SOX2 peptide and plasmid generated IFNγ ELISPOT responses, DTH responses are low level or not significant in plasmid and peptide.

Figure 25:
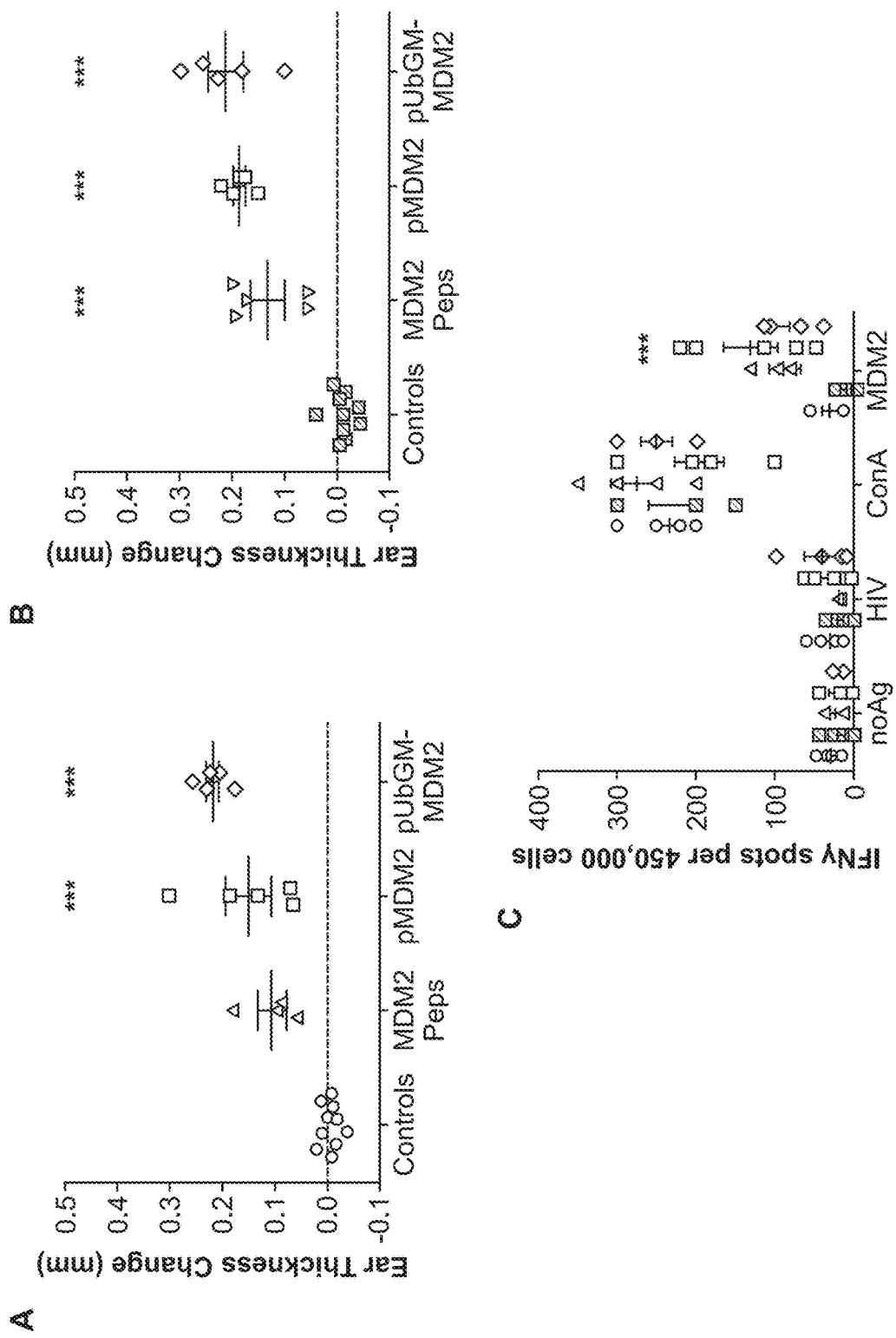
FIG. 25 depicts MDM2 peptide and plasmid vaccine immunogenicity and efficacy in mice.

For another example, FIG. 25 MDM2 peptide and plasmid vaccine immunogenicity and efficacy were determined in mice. (A) DTH responses were measured by change in ear Thickness (mm) 24 hours after application of MDM2 peptide mix in 50% DMSO. Plotted are responses of individual FVB/NJ mice from the different vaccination cohorts: Controls (see Methods). MDM2 Peps (peptide vaccine), pMDM2 (plasmid vaccine) and pUbVV-MDM2. Dotted line represents 0.0 mm change in ear Thickness from baseline. * p<0.001 vs. controls. (B) DTH responses measured 24 hours after application of MDM2 peptide mix in 50% DMSO. Plotted are responses of individual FVB/N/Tg-neu transgenic mice from the different vaccination cohorts as listed above. * p<0.001 vs. controls. (C) IFNγ ELISPOT assessed T-cell responses to peptide or control stimulations. Each plotted point represents the spots per well of individual FVB/NJ mice in vaccination groups treated with adjuvant only (○), Vector (□), MDM2 Peptides (▲), pMDM2 (■), or pUBVV-MDM2 (♦). Lines show Mean & SEM of responses. *** p<0.001 pMDM2 vs. No Ag response.

Figure 26:
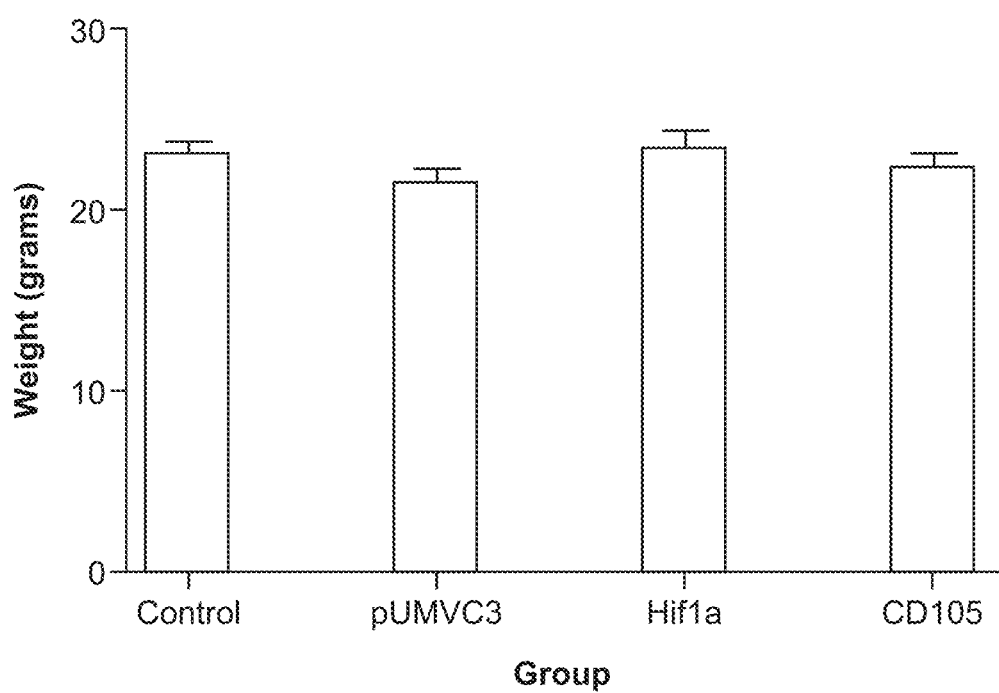
FIG. 26 shows the mass of mice three months after the last vaccine.
Figure 27:
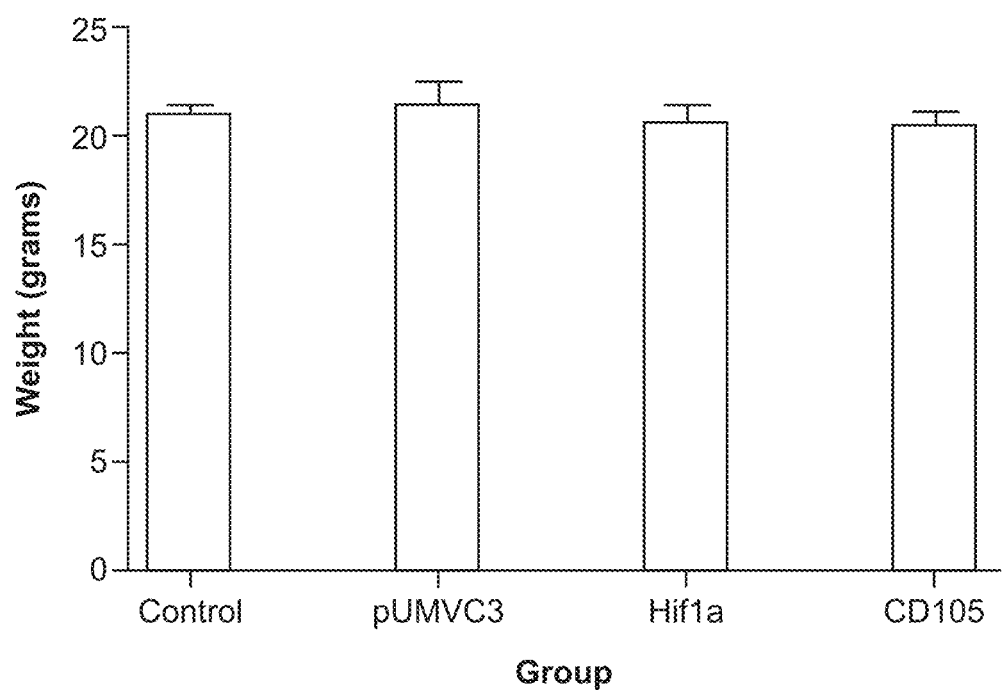
FIG. 27 shows the mass of mice ten days after the last vaccine.

Following vaccination, the masses of mice were determined. For example, at FIG. 26 the mass of mice three months after the last vaccine. Mice (n=5) were left untreated, immunized with pUMVC3 alone, pUMVC3-hHif1a (30-119), or pUMVC3-hCD105 (87-138), x axis, with CFA/IFA as an adjuvant. The mass of each mouse, y axis, (mean±SEM) was recorded three months after the last vaccine. The mass of mice was also determined ten days after the last vaccine. See FIG. 27 Mice (n=5) were left untreated, immunized with pUMVC3 alone, pUMVC3-hHif1a (30-119), or pUMVC3-hCD105 (87-138), x axis, with CFA/IFA as an adjuvant. The mass of each mouse, y axis, (mean±SEM) was recorded ten days after the last vaccine.

Determination and Construction of Sequences for Short and Extended Epitopes from IGF-1R. Two plasmids were constructed, the DNA sequences verified, and used for vaccination experiments. The short epitope plasmid, pIGF-IRshep, expressed a protein with tandemly linked MHC II epitopes corresponding to human IGF-1R. Additionally, there are four amino acids at the N-terminus (MAVP) and three amino acids at the C-terminus (AAA) that are not related to the IGF-IR sequence. The extended epitope plasmid, pIGF-IRexep, expresses a protein with two 1360. Additionally, there are four amino acids at the N-terminus (MAVP) and three amino acids at the C-terminus (AAA) that are not related to the IGF-IR sequence. The vector backbone of each plasmid is pUMVC3, which contains the CMV promoter, directing constitutive expression of the genes in mammalian cells. This vector is qualified for clinical use. The chosen epitopes in the C-terminal region of IGF-IR were assayed with synthetic peptides and demonstrated a propensity to induce greater stimulation of Th1 (IFNγ) compared to Th2 (IL-10) cells in ELISPOT assays of human PBMC samples (described in original proposal).

Evaluation of the Immunogenicity of Short and Extended IGF-1R Epitopes Via IFNγ ELISPOT in TgMMTVneu Mice. Vaccination experiments were designed to test the immunogenicity of the short and extended IGF-1R epitope plasmids in an adoptive cell transfer assay in TgMMTVneu mice. Eight mice per group were vaccinated five times at 2 week intervals with either pIGF-IRexep, pIGF-IRshep, IGF-IR peptides (p196-1210, p1242-1256, p1332-1351, and p1341-1355) or pUMVC3 (vector only). Plasmids and peptides were dosed at 50 ug/injection with CFA/IFA adjuvant. Two weeks after the last vaccination, splenocytes of each vaccination group were isolated and separated into CD3+ T-cell and CD3-negative fractions using magnetic beads that negatively select for mouse T-cells (MACS). Each cell fraction was monitored by flow cytometry to ascertain the percent of T and B cells in each fraction. The CD3+ fractions contained >96% T-cells and <3.3% B cells for all groups. The CD3-negative fractions contained 71-75% B cells and 2.4-6% T-cells for all groups. The splenocyte fractions were then injected into the tail vein ($10^6$ cells/mouse) of unvaccinated TgMMTVneu mice that had MMC tumor cells implanted 5 days previous ($2 \times 10^5$ MMC/mouse). Tumor volumes were measured. CD3+ T-cells from peptide vaccinated mice significantly inhibited tumor growth (p<0.001) compared to vector control, but CD3+ T-cells from either of the IGF-IR plasmid vaccine groups did not promote significant tumor protection. CD3-negative splenocytes (majority B cells) from pIGF-IRexep vaccinated animals did inhibit tumor growth significantly (p<0.001) compared to vector control. Neither CD3-negative cells from pIFG-IRshep nor peptide vaccinated mice controlled tumor growth.

As T-cell immunity is required for the generation of anti-tumor antibodies, a delayed type hypersensitivity (DTH) assay to show that antigen-specific reactive T-cells were generated by pIGF-IRexep vaccination was performed. FVB mice were received three injections, at two week intervals, with either pIGF-IRexep, pUMVC3 vector, IGF-IR peptides, or adjuvant alone (plasmids and peptides were dosed at 50 ug/injection with CFA/IFA adjuvant). Two weeks after the 3rd vaccination the DTH assay was performed by vigorously rubbing either PBS or the IGF-IR peptide mix on to the mouse ears, and ear swelling was monitored for three days. The results demonstrate that significant DTH responses to IGF-IR peptides occurred in peptide-vaccinated and pIGF-IRexep-vaccinated mice compared to vector and adjuvant controls compared to ears treated with PBS (p<0.05, 4-48 hrs by one way ANOVA). Neither vector nor adjuvant controls had significant DTH reactions compared to PBS treatments.

Evaluation of the Clinical Efficacy of Short Vs. Extended IGF-1R Epitopes in TgMMTVneu Mice. In order to directly compare the ability of the short and extended epitope plasmid vaccines to control tumor growth, a syngeneic tumor implant model was employed. Mice (TgMMTVneu) were separated into 4 vaccination groups (pIGF-IRexep, pIGF-IRshep, vector, and IGF-IR peptides) and implanted with syngeneic breast cancer cells (MMC) 7 days after the 3rd vaccination. Dosages were as stated above. The ability of MMC cells to form a tumor, and the tumor growth rate was measured. The IGF-IR peptide vaccine, the short epitope plasmid vaccine, and the extended epitope plasmid vaccine all significantly controlled tumor growth compared to the group that was vaccinated with vector alone (p<0.0001, from 14-31 days). The mice vaccinated with pIGF-IRexep had the slowest growing tumors, but they were not significantly different from tumor growth in animals vaccinated with pIGF-IRshep, p>0.05.

Determination of the Mechanism of Action of the Therapeutic Efficacy Via Blocking Studies. In order to further delineate the role of B and T-cells in the tumor protection mediated by the pIGF-IRexep and IGF-1R peptide vaccines, critical effectors were blocked using depleting antibodies specific for T and B cells, Mice were depleted of lymphocyte classes with specific antibodies following vaccination. MMC tumor growth was measured after vaccination in animals depleted for T or B cells. The pIGF-IRexep vaccine was tumor protective compared to vector-vaccinated animals (p<0.01), except in the groups where B or T-cells had been depleted, this result indicates a role for both lymphocyte classes in the protective immune response. The IGF-IR peptide vaccine was tumor protective compared to vector-vaccinated animals (p<0.01), except in the group where T-cells had been depleted. Depletion of B cells had no significant effect on tumor protection by the peptide vaccine. The extended epitope plasmid vaccine can induce tumor protective immunity through both B and T-cells, but the short epitope peptides induce only tumor protective T-cell immunity.

Example 6

Determination of the Safety and Immunogenicity of Individual Antigen Vaccines

Stem cell/EMT associated proteins elicit IgG antibody immunity. FIG. 4 shows the incidence of antibody immunity stem cell/EMT antigens in BrCA patients and volunteer donors. % of volunteer donors positive is shown as white bars and BrCA patient positive as black bars. (A) Antigens with greater than 2-fold difference in incidence between the two populations, (B) 2fold or less incidence in positively between the two populations. Y-axis, % positive, X-axis, antigens.

At FIG. 5, the results of a population based epitope screening experiment are shown. In greater detail, at FIG. 6, antigen specific IFNγ responses for stem cell/EMT proteins. IFNγ ELISPOT responses to stem cell/EMT antigens. Y-axis shows corrected spots/well (corrected for background) and X-axis shows the antigen tested for both volunteer donors (white bars) and BrCA patients (gray bars). Data is presented as interquartile box plots with Tukey whiskers. Median CSPW are indicated by the horizontal bar.

Further at FIG. 7, antigen specific IL-10 responses for stem cell/EMT proteins. IL-10 ELISPOT responses to stem cell/EMT antigens. Y-axis shows corrected spots/well (corrected for background) and X-axis shows the antigen tested for both volunteer donors (white bars) and BrCA patients (gray bars). Data is presented as interquartile box plots with Tukey whiskers. Median CSPW are indicated by the horizontal bar.

All rodent experiments were performed from the same standard operating procedures (SOP) consistent with what is required for the submission of an Investigational New Drug (IND) application with the FDA. For immunology studies. FVB/NJ mice (n=7/group) were vaccinated four times, intradermally in the ear, every 7-10 days with either CFA/IFA+PBS (control), CFA/IFA+50 µg pUMVC3 (vector control), CFA/IFA+50 µg each of validated peptides derived from the individual antigens in a mix, or CFA/IFA+50 µg pUMVC3 encoding the extended epitope from an individual antigen. Three days after the fourth vaccination, a delayed type hypersensitivity test (DTH) was performed. Peptide and DNA vaccinated mice were given 50 µg of each antigenic peptide in an equal volume DMSO rubbed onto their unvaccinated ear. The CFA/IFA and CFA/IFA+50 µg pUMVC3 control mice were either treated with vaccinating peptides (n=4), control peptides (n=4), or DMSO+PBS (n=6) rubbed onto the unvaccinated ear. Experimental groups were tested with a mix of antigen specific peptides in DSMO. Ears were measured prior to treatment (0 hours) and at 24 hours, and the overall change in ear Thickness between the two time points compared. Significance was measured at the p=0.05 level by a one-way ANOVA with Tukey's post-hoc test to determine differences between each pair of treatment group. Ten days after DTH, mice were sacrificed and spleens processed for use in an IFNγ ELISPOT assay with 300,000 cells/well in a 2-day culture with antigenic stimulants or controls. Significant differences in IFNγ responses were measured at the p=0.05 level by two-Way ANOVA with Bonferroni's post-hoc test to determine differences within each treatment group comparing no antigen stimulation (NoAg) with each of the other stimulations.

For clinical efficacy studies, MMTV-neuTG (neuTG) or MMTV-C3(1)Tg (C3T) transgenic mice (n=6/group) were vaccinated four times, intradermally in the ear, every 7 to 10 days with either CFA/IFA+PBS, CFA/IFA+50 µg pUMVC3, CFA/IFA+50 µg each of identified short peptide epitopes as a mix, or CFA/IFA+50 µgPUMVC3 encoding the chosen extended epitope sequence. 7 to 10 days after the fourth vaccination, 5×10 syngeneic tumor cells for the particular model were implanted subcutaneously. After tumors developed, they were measured 2-3×/week. A significant difference in tumor volume was considered at the p=0.05 level by two-way ANOVA with Bonferroni's post-hoc test to determine differences between each pair of treatment groups at measurement time points. 28 days after tumor implant a DTH was performed. Peptide and DNA vaccinated mice were given 50 µg of each immunizing peptide+equal volume DMSO rubbed onto their unvaccinated ear. The CFA/IFA and CFA/IFA+50 µg pUMVC3 control mice were either treated with immunizing peptides (n=3), control peptides (n=3), or DMSO+PBS (n=5) rubbed onto the unvaccinated ear. Ears were measured prior to treatment (0 hours) and at 24 hours, and the overall change in ear Thickness between the two time points compared. Significance was measured at the p=0.05 level by one-way ANOVA with Tukey's post-hoc test to determine differences between each pair of treatment groups.

An IFNγ ELISPOT was performed on murine cryopreserved cells and a validated DTH response correlated with IFNγ ELISPOT. In matched analysis of DTH and IFNγ ELISPOT, 97 matched assays and analysis of 7 different antigens, there was a statistically significant correlation between the two tests, p<0.0001.

Safety studies were performed in mice. FIG. 35 shows that a multi-epitope IGF-1R vaccine inhibits the growth of implanted breast cancer. Mice were vaccinated with the IGF-1R peptides twice one week apart and then 1×10⁶ MMC cells were injected sq. Data shows the mean implanted tumor measurement from 8 mice±SEM (PBS alone (■); IGF-1R vaccine (○)).

Figure 13:
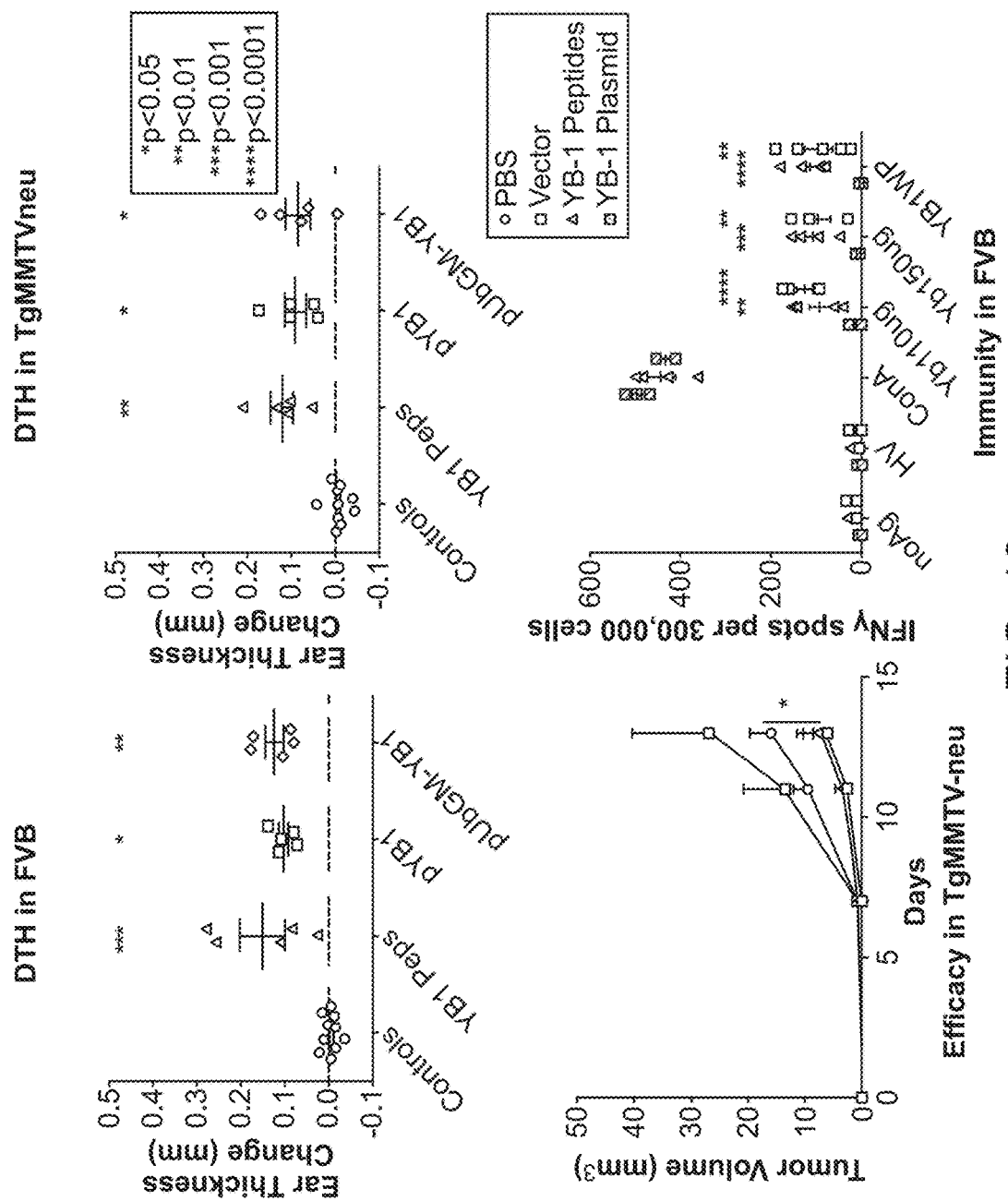
FIG. 13 shows immunogenicity and efficacy of an exemplary Yb-1 plasmid based vaccine in mice.

Additionally, FIG. 13 shows immunogenicity and efficacy of a Yb-1 plasmid based vaccine. Yb-1 peptide and plasmid vaccine immunogenicity and efficacy in mice. (A) DTH responses were measured by change in ear Thickness (mm) 24 hours after application of Yb1 peptide mix in 50% DMSO. Plotted are responses of individual FVB/NJ mice from the different vaccination cohorts: Controls (see Methods), YB1 Peps (peptide vaccine), pYB1 (plasmid vaccine) and pUbVV-YB1. Dotted line represents 0.0 mm change in ear Thickness from baseline. * p<0.05,  p<0.01, * p<0.001 vs. controls. (B) DTH responses measured 24 hours after application of YB1 peptide mix in 50% DMSO. Plotted are responses of individual FVB/N/Tg-neu transgenic mice from the different vaccination cohorts as listed above. * p<0.05, ** p<0.01 vs. controls. (C) IFNγ ELISPOT assessed T-cell responses to peptide or control stimulations. Each plotted point represents the spots per well of individual FVB/NJ mice in vaccination groups treated with adjuvant only (○), Vector (□), YB1 Peptides (▲), pYB1 (■), or pUBVV-YB1 (♦). Lines show Mean & SEM of responses. No significance found for YB1 peptide responses in any group.

Figure 12:
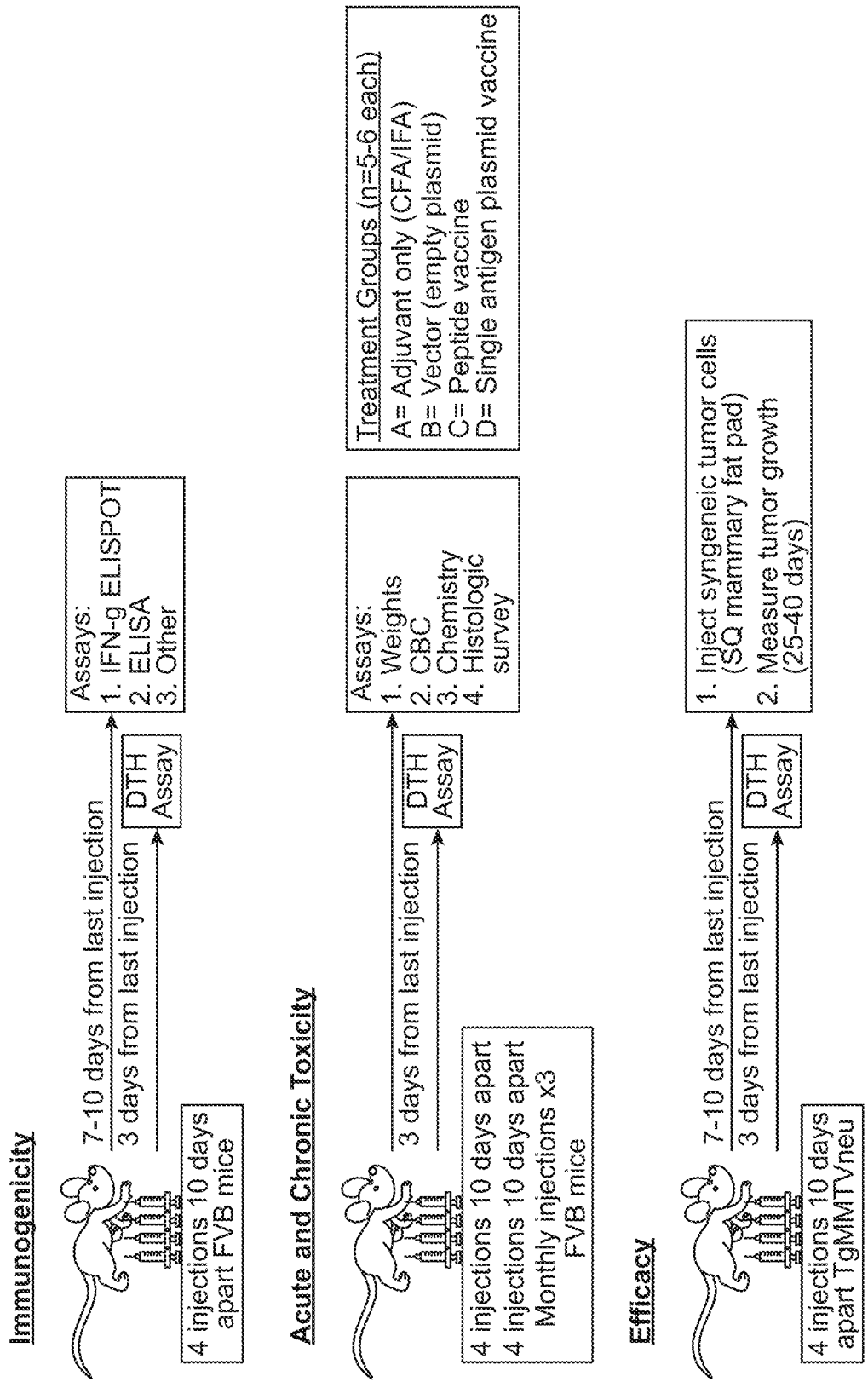
FIG. 12 depicts a chart of simultaneous in vivo evaluation in mice.

A simultaneous in vivo evaluation was also performed in TgMMTNneu mice (see FIG. 12).

Construction of Vaccines. The plasmid constructs created to date are shown in Supplemental Table 25. Each extended epitope was encoded in pUMVC3. Several constructs with multiple antigens were generated in preparation for testing once single antigen toxicity studies were complete.

All constructs were tested for expression by transfection into HEK293 cells and evaluating resultant cell lysates for antigen expression in the presence or absence of the proteosome inhibitor MG132. Expressed protein of transfected extended epitopes in all constructs generated has been detected. Primary antibodies directed against extended epitopes were either affinity-purified from rabbit antisera obtained from rabbits inoculated with the extended epitope as a long peptide or as commercially available antibodies. Expressed protein of the individual antigens in HEK293 cells was significantly increased when multiple epitopes were encoded in a single plasmid compared to single antigen constructs (see FIG. 16). Western blot analysis of HIF1α extended epitope expression demonstrated in plasmid-transfected HEK293 cell lysates. Each plasmid directed the expression of the expected size proteins, which were absent in the vector transfection control. Expression of HIF1α peptide (10.4 kDa) and HIF1α fragment of BCMA5 fusion protein (43.2 kDa) were verified in pHIF1α (single antigen vaccine) and pBCMA5 (a five antigen vaccine)-transfected HEK293 lysates, respectively.

To address the issue of the therapeutic efficacy of several antigens encoded in one vector or 3 individual antigen encoding plasmids, neuTG mice were immunized at 18 weeks with vaccines against neu, IGF-IR and IGFBP-2. An adjuvant control only group, a group with peptides derived from the antigens, a group with 3 plasmids encoding epitopes from each single antigen (50 ug % each), and a group with a single plasmid encoding epitopes linked together from the 3 antigens were treated. All the vaccines significantly delayed the development of breast tumors in the transgenic animals as compared to controls, peptides; p=0.0004, 3 plasmids; p, 0.0001, and the single plasmid with 3 antigens; p=0.0003. There was no statistical difference in efficacy between each of the 3 vaccine approaches.

All antigens tested to date have shown immunogenicity in rodent models either by DTH and ELIPOST and antitumor effect, with the exception of CDH3. For example, FIG. 3 demonstrates antigen specific IgG immunity. Western blot validation of IgG antibody response to CDH3. Western blot probing recombinant human CDH3 with (I) polyclonal anti CDH3 Ab, a representative ELISA positive BrCA patients sample (II) and an ELISA negative subject sample (III). Molecular weight marker (far left). Size of CDH3 is marked at 175 kDa.

Determination of the Toxicity of the Vaccination Via Blood Chemistry and Histology Studies. There were no untoward effects to vaccination observed in any of the mice immunized with any of the antigens. The mice experienced no mass loss or decrease in grooming prior to final analysis. Acute and chronic toxicity studies on the individual antigen vaccines have seen no toxicity; hematologic, chemical or histological. An acute and chronic toxicity report (for SATB1 and CDC25B). Acute toxicity studies 1 week after $4^{th}$ vaccination and chronic toxicity studies 3 months after $4^{th}$ vaccination.

Figure 36:
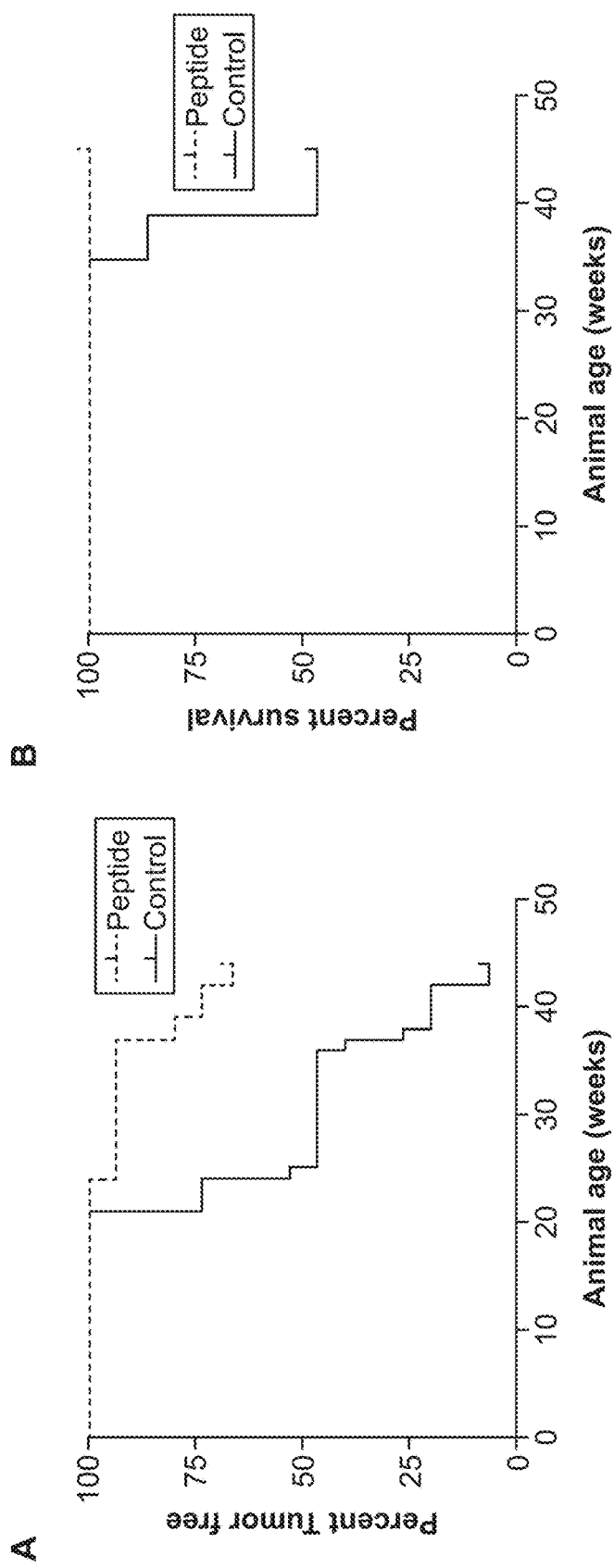
FIG. 36 shows that multiantigen ployepitope vaccines prevent the development of breast cancer in mice.

As shown in FIG. 36, multiantigen ployepitope vaccines prevent the development of breast cancer in neu-TG mice. (A) Disease free survival (B) Overall survival (n=15/group). SATB1 and CDC25B Toxicity Results Chronic Toxicity Study. Mice were injected with 100 mcg pUMVC3 alone, pUMVC3-hSATB1 (387-450) or pUMVC3-hCDC25B (124-164) four times, 7-10 days apart, using CFA/IFA. Control mice were not treated (see Tables 1 and 3).

TABLE 1

Timeline for Vaccinations and Tissue/Blood Collections

| Chronic Toxicity Study Design | | day −30 CFA Vac#1 | day −20 IFA Vac#2 | day −10 IFA Vac#3 | day 0 IFA Vac#4 | 3 months |
|---|---|---|---|---|---|---|
| Control | n = 5 | N/A | N/A | N/A | N/A | Collect |
| pUMVC3 | n = 5 | 100 μg | 100 μg | 100 μg | 100 μg | organs and |
| pUMVC3-hSATB1 (387-450) | n = 5 | 100 μg | 100 μg | 100 μg | 100 μg | sera, weigh mice |
| pUMVC3-hCDC25B (124-164) | n = 5 | 100 μg | 100 μg | 100 μg | 100 μg | |

Serum Chemistries and CBC.

All serum chemistry and complete blood count values for all groups were not significantly different from control (untreated) mice except HCT in the CDC25B group, MCH in the SATB1 group, and Polys in both pUMVC3 and SATB1 groups (see Tables 5 and 6). Of note, the HCT values of all groups is within the limits of the established ranges. Additionally, although the MCH values of the SATB1 group is significantly different, although it is closer to the established range of values available from Jackson Laboratory (15.2-15.6 pg) than that of the control group. The pUMVC3 vehicle also achieved significance in % Polys which indicates that the difference may be a vehicle effect and not a direct result of the SATB1 insert (see Tables 5-16).

Pathology. There were no treatment related lesions, which could be considered consistent with a toxic response that distinguished one group from another (see Tables 13-16).

Mass. Three months following the vaccination, the mass of animals receiving pUMVC3-hSATB1 (387-450) was 23.4±2.3 grams (g), those receiving pUMVC3-hCDC25B (124-164) was 23.4±1.3 g, those receiving pUMVC3 was 23.6±1.4 g and healthy untreated controls was 21.5±1.1. There were no statistically significant differences between any of the groups (see Tables 17-24).

Acute Toxicity Study. Mice were injected with 100 mcg pUMVC3 alone, pUMVC3-hSATB1 (387-450) or pUMVC3-hCDC25B (124-164) four times, 7-10 days apart, using CFAJIFA. Control mice were not treated (see Table 2).

TABLE 2

Timeline for Vaccinations and Tissue/Blood Collections

| Acute Toxicity Study Design | | day −30 CFA Vac#1 | day −20 IFA Vac#2 | day −10 IFA Vac#3 | day 0 IFA Vac#4 | 10 days |
|---|---|---|---|---|---|---|
| Control | n = 5 | N/A | N/A | N/A | N/A | Collect |
| pUMVC3 | n = 5 | 100 µg | 100 µg | 100 µg | 100 µg | organs and |
| pUMVC3-hSATB1 (387-450) | n = 5 | 100 µg | 100 µg | 100 µg | 100 µg | sera, weigh mice |
| pUMVC3-hCDC25B (124-164) | n = 5 | 100 µg | 100 µg | 100 µg | 100 µg | |

Serum Chemistries and CBC. All serum chemistry and complete blood count values for all groups were not significantly different from control (untreated) mice except Chloride in the SATB1 and CDC25B group, Calcium, Osm, ALT, Polys in the CDC25B group, and Lymph in the pUMVC3 groups (Table 7 and 8). Of note, Chloride in the SATB1 and CDC25B group is closer to the established ranges (110-204 meq/l) than that of the control group. Similarly, Osm in the CDC25B group is closer to the established range (321-330 arbitrary units) than that of the control group. ALT for all groups is within the limits of the established ranges (see Tables 5-16).

Pathology. There were no treatment related lesions, which could be considered consistent with a toxic response that distinguished one group from another (Tables 17-24).

Mass. Ten days following the vaccination, the mass of animals receiving pUMVC3-hSATB1 (387-450) was 20.9±0.7 grams (g), those receiving pUMVC3-hCDC25B (124-164) was 21±1.2 g, those receiving pUMVC3 was 21.3±1.0 g and healthy untreated controls was 21.4±1.5 g. There were no statistically significant differences between any of the groups.

Hif1a and CD105 Toxicity Results

Chronic Toxicity Study. Mice were injected with 100 mcg pUMVC3 alone, pUMVC3-hHif1a (30-119) or pUMVC3-hCD105 (87-138) four times, 7-10 days apart, using CFA/IFA. Control mice were not treated (see Table 3).

TABLE 3

Timeline for Vaccinations and Tissue/Blood Collections

| Chronic Toxicity Study Design | | day −30 CFA Vac#1 | day −20 IFA Vac#2 | day −10 IFA Vac#3 | day 0 IFA Vac#4 | 3 months |
|---|---|---|---|---|---|---|
| Control | n = 5 | N/A | N/A | N/A | N/A | Collect |
| pUMVC3 | n = 5 | 100 µg | 100 µg | 100 µg | 100 µg | organs and |
| pUMVC3-hHif1a (30-119) | n = 5 | 100 µg | 100 µg | 100 µg | 100 µg | sera, weigh mice |
| pUMVC3-hCD105 (87-138) | n = 5 | 100 µg | 100 µg | 100 µg | 100 µg | |

Serum Chemistries and CBC. All serum chemistry and complete blood count values for all groups were not significantly different from control (untreated) mice except BUN in the pUMVC3 and Hif1a groups, Anion Gap in all groups, Osmolality in the pUMVC3 group, and Cholesterol in the Hif1a and CD105 groups (Table 9 and 10). Of note, BUN and Anion Gap in the significantly different groups is closer to the established ranges (18-28 mg/dl and 23.3-27 arbitrary units, respectively) than that of the control group. The established ranges of Osmolality is 321-330, but none of the groups was in this range, and the treatment groups were not significantly different than the untreated mice. Although Cholesterol is significantly different in treatment groups as compared to control groups, the values of all groups is within the limits of the established range of 50-138 (see Tables 5-16).

Pathology. Organs were collected for this study but have not yet been analyzed by the pathologist (see Tables 17-24).

Mass. Three months following the vaccination, the mass of animals receiving pUMVC3-hHif1a (30-119) was 23.4±2.4 grams (g), those receiving pUMVC3-hCD105 (87-138) was 22.3±1.6 g, those receiving pUMVC3 was 21.5±1.4 g and healthy untreated controls was 23.1±1.7 g. There were no statistically significant differences between any of the groups.

Acute Toxicity Study. Mice were injected with 100 mcg pUMVC3 alone, pUMVC3-hHif1a (30-119) or pUMVC3-hCD105 (87-138) four times, 7-10 days apart, using CFA/IFA. Control mice were not treated (see Table 4).

TABLE 4

Timeline for Vaccinations and Tissue/Blood Collections

| Acute Toxicity Study Design | | day −30 CFA Vac#1 | day −20 IFA Vac#2 | day −10 IFA Vac#3 | day 0 IFA Vac#4 | 10 days |
|---|---|---|---|---|---|---|
| Control | n = 5 | N/A | N/A | N/A | N/A | Collect |
| pUMVC3 | n = 5 | 100 µg | 100 µg | 100 µg | 100 µg | organs and |
| pUMVC3-hHif1a (30-119) | n = 5 | 100 µg | 100 µg | 100 µg | 100 µg | sera, weigh mice |
| pUMVC3-hCD105 (87-138) | n = 5 | 100 µg | 100 µg | 100 µg | 100 µg | |

Serum Chemistries and CBC. All serum chemistry and complete blood count values for all groups were not significantly different from control (untreated) mice except Cholesterol & Globulin in the Hif1a group, Phosphorous for all groups, Calcium in the pUMVC3 group, Chloride in the CD105 group, and Lymph & White Blood Cells in the pUMVC3 and Hif1a groups (see Tables 5-16). Although Cholesterol, White Blood Cells, and Calcium is significantly different in the Hif1a group as compared to control groups, the values of all groups is within the limits of the established range of 50-138 mg/dl, 2-15 K/µL & 8-14 meq/1, respectively. Of note, the Globulin, Chloride, and Phosphorous in the treatment groups are closer to the established ranges (1.9-2.4 g/dL, 110-204 meq/l, & 4.6-10.8 mg/dl, respectively) than that of the control group (see Tables 5-16).

Pathology. There were no treatment related lesions, which could be considered consistent with a toxic response that distinguished one group from another (Tables 17-24).

Mass. Ten days following the vaccination, the mass of animals receiving pUMVC3-hHif1a (30-119) was 20.8±1.6 grams (g), those receiving pUMVC3-hCD105 (87-138) was 20.5±1.4 g, those receiving pUMVC3 was 21.5±2.2 g and healthy untreated controls was 21.1±1.1 g. There were no statistically significant differences between any of the groups (see Tables 5-16).

TABLE 5

Summary of (Chronic) Serum Chemistries for All Groups (Median and Range)

| Parameter (units) | Control/Untreated Median | Control/Untreated Range | pUMVC3 Median | pUMVC3 Range | pUMVC3-hSATB1 (387-450) Median | pUMVC3-hSATB1 (387-450) Range | pUMVC3-hCDC25B(124-164) Median | pUMVC3-hCDC25B(124-164) Range |
|---|---|---|---|---|---|---|---|---|
| Glucose Serum (mg/dl) | 123.5 | 52-159 | 128 | 52-162 | 135 | 46-208 | 67 | 47-102 |
| BUN (mg/dl) | 27 | 22-33 | 25 | 21-33 | 31 | 27-36 | 26.5 | 25-30 |
| Creatinine (mg/dl) | 0.25 | 0.2-0.3 | 0.2 | 0.2-0.3 | 0.2 | 0.2-0.3 | 0.2 | 0.2-0.2 |
| Sodium (meq/l) | 151.5 | 150-155 | 151 | 149-153 | 150 | 147-152 | 152.5 | 152-153 |
| Potassium (meq/l) | 9.55 | 9-10.2 | 8.1 | 7.8-9.3 | 8.7 | 6.5-9.7 | 8.7 | 8.1-8.8 |
| Na/K Ratio | 15.5 | 15-17 | 19 | 16-19 | 17 | 16-23 | 17.5 | 17-19 |
| Chloride (meq/l) | 107 | 105-110 | 108 | 107-108 | 106 | 105-108 | 110 | 105-113 |
| Carbon Dioxide (meq/l) | 18.5 | 15-23 | 19 | 16-25 | 19 | 16-29 | 23 | 17-31 |
| Anion Gap | 35.5 | 32-39 | 32 | 26-37 | 30 | 24-37 | 28 | 25-32 |
| Calcium (meq/l) | 10.05 | 9.6-10.6 | 9.7 | 9.3-10.4 | 9.7 | 9.1-10 | 9.8 | 9.3-9.8 |
| Phosphorus (meq/l) | 18.9 | 17-22.3 | 18 | 14.9-19.7 | 18 | 15.7-21 | 15.45 | 13.9-18.9 |
| Osm | 314.5 | 312-326 | 313 | 310-316 | 313 | 307-316 | 313 | 311-316 |
| Total Protein (g/dl) | 5.25 | 4.6-5.4 | 5.2 | 4.8-5.6 | 5.2 | 4.7-5.9 | 5.45 | 4.9-5.5 |
| Albumin (g/dl) | 3.1 | 2.8-3.2 | 3 | 2.8-3.1 | 2.9 | 2.6-3.3 | 3.1 | 2.7-3.2 |
| Globulin (g/dl) | 2.15 | 1.8-2.2 | 2.1 | 2-2.5 | 2.3 | 2.1-2.6 | 2.3 | 2.2-2.4 |
| Alb/Glob Ratio | 1.5 | 1.4-1.6 | 1.4 | 1.2-1.5 | 1.3 | 1.2-1.3 | 1.3 | 1.2-1.4 |
| Bilirubin Total (mg/dl) | 0.1 | 0.1-0.2 | 0.1 | 0.1-0.2 | 0.1 | 0.1-0.1 | 0.1 | 0.1-0.1 |
| ALP (U/L) | 99.5 | 90-108 | 107 | 75-148 | 100 | 82-149 | 101 | 88-114 |
| GGT (U/L) | 1 | 0-2 | 1 | 0-1 | 1 | 0-1 | 1 | 1-1 |
| ALT (U/L) | 56 | 32-61 | 48 | 41-59 | 43 | 39-57 | 58 | 51-65 |
| AST (U/L) | 140 | 73-207 | 172 | 104-210 | 98 | 78-181 | 139 | 126-145 |
| Cholesterol (mg/dl) | 125 | 98-133 | 138 | 131-150 | 129 | 118-150 | 129 | 119-133 |

* $p < 0.05$ compared to control (untreated)

TABLE 6

Summary of (Chronic) CBC for All Groups (Median and Range)

| Parameter (units) | Control/Untreated Median | Control/Untreated Range | pUMVC3 Median | pUMVC3 Range | pUMVC3-hSATB1 (387-450) Median | pUMVC3-hSATB1 (387-450) Range | pUMVC3-hCDC25B(124-164) Median | pUMVC3-hCDC25B(124-164) Range |
|---|---|---|---|---|---|---|---|---|
| WBC (K/μL) | 2.65 | 2.4-3.7 | 1.7 | 0.6-3.9 | 1.7 | 1.4-2.5 | 1.2 | 1.1-2.7 |
| RBC (M/μL) | 9.66 | 8.56-11.2 | 9.28 | 8.78-9.54 | 9.52 | 9.06-10.84 | 8.95 | 7.32-9.2 |
| HGB (g/dl) | 13.2 | 11-13.6 | 12.8 | 12-14.6 | 14 | 13.6-15.6 | 12.3 | 10-13.2 |
| HCT (%) | 50 | 46-56.4 | 46.8 | 44.6-48.8 | 48.4 | 46.2-55.6 | 44.6 * | 37.6-44.8 |
| MCV (fL) | 51.65 | 50.5-53.9 | 51.1 | 49.7-51.2 | 50.9 | 49.6-51.7 | 50 | 48.9-51.3 |
| MCH (pg) | 13.3 | 12.2-13.9 | 14 | 13.3-15.4 | 14.5 * | 14.2-15.1 | 13.95 | 13.5-14.4 |
| MCHC (%) | 25.35 | 24-26.9 | 28.1 | 25.9-30 | 28.1 | 19-29.7 | 27.75 | 26.8-29.3 |
| Platelet Count (K/μL) | 860 | 540-1072 | 734 | 672-952 | 768 | 568-1104 | 478 | 320-1006 |
| Polys(/μL) | 475 | 180-540 | 130 * | 0-340 | 90 * | 10-280 | 115 | 50-380 |
| Lymph(/μL) | 2140 | 1750-2960 | 1260 | 0-3550 | 1460 | 1260-2330 | 1050 | 990-2240 |
| Monos(/μL) | 125 | 80-260 | 70 | 0-200 | 30 | 30-120 | 50 | 20-80 |
| Eos(/μL) | 35 | 0-80 | 0 | 0-40 | 30 | 0-60 | 0 | 0-10 |
| Baso(/μL) | 0 | 0-0 | 0 | 0-0 | 0 | 0-0 | 0 | 0-0 |

* $p < 0.05$ compared to control (untreated)

TABLE 7

Summary of (Acute) Serum Chemistries for All Groups (Median and Range)

| Parameter (units) | Control/Untreated Median | Control/Untreated Range | pUMVC3 Median | pUMVC3 Range | pUMVC3-hSATB1 (387-450) Median | pUMVC3-hSATB1 (387-450) Range | pUMVC3-hCDC25B(124-164) Median | pUMVC3-hCDC25B(124-164) Range |
|---|---|---|---|---|---|---|---|---|
| Glucose Serum (mg/dl) | 226 | 111-267 | 198 | 93-266 | 259 | 67-356 | 258 | 57-343 |
| BUN (mg/dl) | 26 | 25-28 | 30 | 24-33 | 26 | 23-28 | 25 | 24-32 |
| Creatinine (mg/dl) | 0.2 | 0.2-0.2 | 0.2 | 0.2-0.2 | 0.3 | 0.2-0.3 | 0.2 | 0.2-0.3 |
| Sodium (meq/l) | 147 | 145-150 | 148 | 146-149 | 148 | 147-150 | 149 | 146-151 |
| Potassium (meq/l) | 7.2 | 6.9-8.4 | 8 | 6.6-9 | 8.2 | 7.4-9 | 8.2 | 7.6-9 |
| Na/K Ratio | 21 | 18-21 | 19 | 17-22 | 18 | 17-20 | 3.8 | 17-20 |

TABLE 7-continued

Summary of (Acute) Serum Chemistries for All Groups (Median and Range)

| Parameter (units) | Control/Untreated Median | Range | pUMVC3 Median | Range | pUMVC3-hSATB1 (387-450) Median | Range | pUMVC3-hCDC25B(124-164) Median | Range |
|---|---|---|---|---|---|---|---|---|
| Chloride (meq/l) | 105 | 102-108 | 109 | 105-110 | 109 * | 107-113 | 109 * | 108-111 |
| Carbon Dioxide (meq/l) | 19 | 16-22 | 17 | 14-22 | 20 | 14-24 | 22 | 17-23 |
| Anion Gap | 29 | 28-35 | 30 | 27-34 | 25 | 23-32 | 26 | 25-29 |
| Calcium (meq/l) | 9.2 | 9-9.7 | 9.1 | 8.6-9.7 | 9.5 | 9.3-10.3 | 10.2 * | 9.6-10.9 |
| Phosphorus (meq/l) | 18.6 | 12.9-21 | 13.9 | 12-19.3 | 19.6 | 17.9-21.6 | 18 | 15.8-19.7 |
| Osm | 308 | 306-312 | 310 | 307-312 | 314 | 308-317 | 316 * | 310-317 |
| Total Protein (g/dl) | 4.9 | 4.3-5.4 | 4.8 | 4.5-5.4 | 4.6 | 4.3-5.6 | 4.6 | 4.4-5.4 |
| Albumin (g/dl) | 3 | 2.7-3.3 | 3 | 2.7-3.1 | 2.7 | 2.5-3.2 | 2.7 | 2.6-3.2 |
| Globulin (g/dl) | 1.8 | 1.6-2.1 | 2 | 1.8-2.3 | 1.9 | 1.7-2.4 | 1.9 | 1.8-2.2 |
| Alb/Glob Ratio | 1.6 | 1.6-1.7 | 1.4 | 1.3-1.7 | 1.4 | 1.2-1.5 | 1.4 | 1.4-1.5 |
| Bilirubin Total (mg/dl) | 0.1 | 0.1-0.2 | 0.1 | 0.1-0.2 | 0.1 | 0.1-0.2 | 0.1 | 0.1-0.2 |
| ALP (U/L) | 95 | 92-107 | 103 | 83-118 | 97 | 81-109 | 97 | 89-107 |
| GGT (U/L) | 0 | 0-1 | 0 | 0-1 | 0 | 0-1 | 0 | 0-1 |
| ALT (U/L) | 36 | 28-38 | 70 | 45-77 | 69 | 46-71 | 62 * | 56-143 |
| AST (U/L) | 100 | 65-235 | 133 | 104-196 | 108 | 90-174 | 124 | 117-130 |
| Cholesterol (mg/dl) | 136 | 113-155 | 121 | 108-134 | 104 | 89-121 | 97 | 86-124 |

* $p < 0.05$ compared to control (untreated)

TABLE 8

Summary of (Acute) CBC for All Groups (Median and Range)

| Parameter (units) | Control/Untreated Median | Range | pUMVC3 Median | Range | pUMVC3-hSATB1 (387-450) Median | Range | pUMVC3-hCDC25B(124-164) Median | Range |
|---|---|---|---|---|---|---|---|---|
| WBC (K/μL) | 4 | 3.2-4.6 | 2.8 | 1.6-3.8 | 2.5 | 1.9-4.2 | 3.6 | 3.1-4.4 |
| RBC (M/μL) | 9.2 | 8.12-9.58 | 9.2 | 8.16-9.34 | 8.64 | 7.92-9.6 | 8.36 | 7.96-9.16 |
| HGB (g/dl) | 13.6 | 12.4-14 | 13.2 | 12-14 | 12.4 | 11.6-14 | 12 | 11.2-14 |
| HCT (%) | 44.8 | 41-46.8 | 44 | 38.8-45.8 | 41.6 | 39.2-47 | 40.4 | 38.8-45.4 |
| MCV (fL) | 48.7 | 48.3-50.5 | 48.2 | 47.3-49.1 | 49.4 | 48.1-50 | 49 | 48.1-49.7 |
| MCH (pg) | 14.5 | 13.6-15.3 | 14.7 | 14.3-14.9 | 14.6 | 13.8-14.9 | 14.5 | 14.3-15.3 |
| MCHC (%) | 29.9 | 27.8-30.9 | 30.4 | 29.7-31.5 | 29.9 | 28.7-30 | 29.8 | 29.3-30.9 |
| Platelet Count (K/μL) | 816 | 598-968 | 844 | 52.8-896 | 978 | 728-1130 | 1080 | 508-1100 |
| Polys(/μL) | 310 | 70-340 | 230 | 120-340 | 270 | 190-460 | 510 * | 310-640 |
| Lymph(/μL) | 3800 | 3070-4190 | 2600 * | 1310-3380 | 2230 | 1500-3600 | 2810 | 2530-3960 |
| Monos(/μL) | 60 | 0-140 | 80 | 0-190 | 100 | 80-150 | 160 | 120-180 |
| Eos(/μL) | 0 | 0-50 | 30 | 0-30 | 0 | 0-40 | 0 | 0-40 |
| Baso(/μL) | 0 | 0-0 | 0 | 0-0 | 0 | 0-0 | 0 | 0-0 |

* $p < 0.05$ compared to control (untreated)

TABLE 9

Summary of (Chronic) Serum Chemistries for All Groups (Median and Range)

| Parameter (units) | Control/Untreated Median | Range | pUMVC3 Median | Range | pUMVC3-hHif1a(30-119) Median | Range | pUMVC3-hCD105(87-138) Median | Range |
|---|---|---|---|---|---|---|---|---|
| Glucose (mg/dl) | 211 | 58-242 | 177 | 89-341 | 227 | 75-333 | 239 | 86-301 |
| BUN (mg/dl) | 32 | 25-34 | 26 | 25-29 | 26 ** | 21-27 | 24 ** | 20-28 |
| Creatinine (mg/dl) | 0.3 | 0.3-0.3 | 0.3 | 0.2-0.3 | 0.3 | 0.3-0.4 | 0.3 | 0.2-0.3 |
| Sodium (meq/l) | 152 | 151-153 | 150 | 149-151 | 152 | 149-153 | 150 | 148-154 |
| Potassium (meq/l) | 9 | 7.8-9.4 | 7.4 | 7.3-9 | 8.5 | 7.7-9.4 | 7.3 | 7-9.7 |
| Na/K Ratio | 17 | 16-20 | 20 | 17-20 | 18 | 16-19 | 21 | 16-21 |
| Chloride (meq/l) | 110 | 106-112 | 109 | 106-111 | 111 | 110-114 | 111 | 110-112 |
| Carbon Dioxide (meq/l) | 17 | 15-24 | 22 | 20-22 | 21 | 19-22 | 19 | 19-22 |
| Anion Gap | 34 | 29-36 | 27 * | 27-29 | 27 * | 26-30 | 25 ** | 24-33 |
| Calcium (meq/l) | 9.8 | 9.4-10 | 9.2 | 9.1-10.1 | 9.7 | 9.5-9.8 | 9.4 | 8.9-9.8 |
| Phosphorus (meq/l) | 19.3 | 14.8-21 | 17.2 | 11.6-17.3 | 18.5 | 16.2-19.5 | 15.5 | 13.4-16.8 |
| Osm | 321 | 315-321 | 314 * | 308-320 | 318 | 314-322 | 315 | 312-316 |
| Total Protein (g/dl) | 4.7 | 4.7-5.1 | 4.7 | 4.5-6.6 | 4.5 | 4.3-5.5 | 4.5 | 4.3-5.4 |

TABLE 9-continued

Summary of (Chronic) Serum Chemistries for All Groups (Median and Range)

| Parameter (units) | Control/ Untreated | | pUMVC3 | | pUMVC3- hHif1a(30-119) | | pUMVC3- hCD105(87-138) | |
|---|---|---|---|---|---|---|---|---|
| | Median | Range | Median | Range | Median | Range | Median | Range |
| Albumin (g/dl) | 2.8 | 2.8-3 | 2.6 | 2.5-3.5 | 2.5 | 2.4-3.2 | 2.5 | 2.5-3.1 |
| Globulin (g/dl) | 1.9 | 1.9-2.1 | 2.1 | 2-3.1 | 2 | 1.9-2.3 | 1.9 | 1.8-2.3 |
| Alb/Glob Ratio | 1.5 | 1.4-1.5 | 1.3 | 1.1-1.3 | 1.3 | 1.2-1.4 | 1.3 | 1.3-1.4 |
| Bilirubin Total (mg/dl) | 0.1 | 0.1-0.2 | 0.1 | 0.1-0.2 | 0.1 | 0.1-0.2 | 0.1 | 0.1-0.2 |
| ALP (U/L) | 90 | 79-103 | 88 | 50-96 | 92 | 80-97 | 87 | 81-96 |
| GGT (U/L) | 0 | 0-1 | 0 | 0-0 | 0 | 0-1 | 0 | 0-1 |
| ALT (U/L) | 44 | 43-60 | 55 | 41-59 | 50 | 45-56 | 51 | 39-60 |
| AST (U/L) | 100 | 75-102 | 111 | 110-228 | 98 | 83-142 | 107 | 79-184 |
| Cholesterol (mg/dl) | 135 | 106-144 | 106 | 88-124 | 99 * | 88-117 | 94 ** | 83-118 |

** $p < 0.01$ compared to control (untreated)
* $p < 0.05$ compared to control (untreated)

TABLE 10

Summary of (Chronic) Serum Chemistries for All Groups (Median and Range)

| Parameter (units) | Control/ Untreated | | pUMVC3 | | pUMVC3- hHif1a(30-119) | | pUMVC3- hCD105(87-138) | |
|---|---|---|---|---|---|---|---|---|
| | Median | Range | Median | Range | Median | Range | Median | Range |
| WBC (K/μL) | 3.8 | 2.3-5.6 | 3.8 | 2.2-5 | 3.4 | 3-5.2 | 4.4 | 2.8-6.4 |
| RBC (M/μL) | 9.96 | 7.2-10.32 | 9.24 | 8.62-9.68 | 8.8 | 8.2-10.02 | 8.9 | 8.14-9.72 |
| HGB (g/dl) | 14.8 | 10.4-15.4 | 13.4 | 12.6-14 | 13.2 | 11.6-15 | 13 | 12.2-14.2 |
| HCT (%) | 47.2 | 34.4-50.8 | 43.2 | 41.2-49.2 | 42.4 | 39.2-47.4 | 41.4 | 38-45.8 |
| MCV (fL) | 48.9 | 47.3-49.3 | 47.4 | 46.3-50.9 | 48 | 47.2-48.6 | 46.7 | 45.8-47.4 |
| MCH (pg) | 15 | 14.4-15.1 | 14.5 | 14.3-14.7 | 15 | 14.2-15 | 14.7 | 14.6-15.1 |
| MCHC (%) | 30.7 | 30.2-31.3 | 30.7 | 28.1-31 | 30.9 | 29.5-31.7 | 31.8 | 31.1-32.5 |
| Platelet Count (K/μL) | 908 | 598-1080 | 950 | 630-1112 | 908 | 842-1210 | 910 | 722-972 |
| Polys (/μL) | 230 | 50-340 | 390 | 180-2600 | 410 | 170-680 | 490 | 260-560 |
| Lymph (/μL) | 3570 | 2160-5260 | 2390 | 1740-3910 | 2960 | 2400-4470 | 4000 | 2210-5890 |
| Monos (/μL) | 0 | 0-0 | 0 | 0-150 | 0 | 0-40 | 30 | 0-40 |
| Eos (/μL) | 0 | 0-40 | 0 | 0-30 | 30 | 0-80 | 0 | 0-90 |
| Baso (/μL) | 0 | 0-0 | 0 | 0-0 | 0 | 0-0 | 0 | 0-0 |

TABLE 11

Summary of (Acute) Serum Chemistries for All Groups (Median and Range)

| Parameter (units) | Control/ Untreated | | pUMVC3 | | pUMVC3- hHif1a(30-119) | | pUMVC3- hCD105(87-138) | |
|---|---|---|---|---|---|---|---|---|
| | Median | Range | Median | Range | Median | Range | Median | Range |
| WBC (K/μL) | 4.3 | 3.6-5.1 | 2.6 | 2-2.8 | 2.9 | 1.5-3.9 | 3.4 | 2.3-4.6 |
| RBC (M/μL) | 9.2 | 8.5-9.9 | 9.2 | 8.2-9.5 | 9.1 | 7.4-9.78 | 9.66 | 9.18-10.77 |
| HGB (g/dl) | 12.9 | 12.3-14.4 | 13.2 | 11.4-13.8 | 12.9 | 9.6-14.1 | 13.8 | 13.5-15.6 |
| HCT (%) | 44.4 | 42-50.4 | 43.8 | 38.4-45.9 | 43.8 | 36.3-46.5 | 46.8 | 44.4-51.9 |
| MCV (fL) | 48.5 | 19.6-51 | 48.3 | 46.9-48.8 | 47.7 | 47.4-48.9 | 48.3 | 48-49.1 |
| MCH (pg) | 14.6 | 13.4-15 | 14.4 | 13.9-14.5 | 14.3 | 12.8-14.5 | 14.5 | 14.2-14.8 |
| MCHC (%) | 29.8 | 27.7-30.3 | 29.7 | 29-30.1 | 29.8 | 26.1-30.5 | 30.1 | 29.4-30.2 |
| Platelet Count (K/μL) | 687 | 414-894 | 843 | 450-1227 | 825 | 474-1032 | 825 | 597-1011 |
| Polys (/μL) | 140 | 40-330 | 200 | 20-350 | 480 | 100-630 | 360 | 90-480 |
| Lymph (/μL) | 4130 | 3460-4540 | 2160 | 1580-2460 | 2470 | 1200-3240 | 2750 | 2120-4050 |
| Monos (/μL) | 130 | 40-150 | 140 | 80-140 | 70 | 0-120 | 140 | 90-210 |
| Eos (/μL) | 40 | 0-150 | 30 | 0-80 | 0 | 0-30 | 40 | 0-60 |
| Baso (/μL) | 0 | 0-0 | 0 | 0-0 | 0 | 0-0 | 0 | 0-0 |

* $p < 0.05$ compared to control (untreated)

TABLE 12

Summary of (Acute) Serum Chemistries for All Groups (Median and Range)

| Parameter (units) | Control/Untreated Median | Control/Untreated Range | pUMVC3 Median | pUMVC3 Range | pUMVC3-hHif1a(30-119) Median | pUMVC3-hHif1a(30-119) Range | pUMVC3-hCD105(87-138) Median | pUMVC3-hCD105(87-138) Range |
|---|---|---|---|---|---|---|---|---|
| Glucose Serum (mg/dl) | 122 | 60-192 | 66 | 54-162 | 83 | 70-84 | 85 | 75-113 |
| BUN (mg/dl) | 27 | 24-30 | 26 | 20-28 | 25 | 23-28 | 25 | 19-25 |
| Creatinine (mg/dl) | 0.3 | 0.2-0.3 | 0.2 | 0.2-0.3 | 0.3 | 0.2-0.3 | 0.2 | 0.2-0.3 |
| Sodium (meq/l) | 150 | 148-153 | 151 | 149-152 | 150 | 149-153 | 152 | 151-153 |
| Potassium (meq/l) | 8.9 | 8.1-9.5 | 9.3 | 8.4-9.8 | 8.9 | 8.1-9.5 | 9.2 | 8.9-9.4 |
| Na/K Ratio | 17 | 16-19 | 16 | 15-18 | 17 | 16-19 | 17 | 16-17 |
| Chloride (meq/l) | 105 | 102-108 | 108 | 107-108 | 109 | 104-109 | 108 | 107-111 |
| Carbon Dioxide (meq/l) | 17 | 12-22 | 19 | 16-23 | 20 | 19-22 | 20 | 19-22 |
| Anion Gap | 36 | 33-43 | 34 | 26-37 | 31 | 30-34 | 32 | 30-34 |
| Calcium (meq/l) | 9.7 | 9.4-10.4 | 9.4 | 9-9.6 | 9.5 | 9.4-9.8 | 9.6 | 9.5-9.7 |
| Phosphorus (meq/l) | 18.8 | 17.6-21.1 | 14.9 | 14.1-15.7 | 15 | 11.2-15.8 | 13.3 | 12.3-14.7 |
| Osm | 312 | 310-315 | 311 | 309-314 | 309 | 307-317 | 311 | 311-317 |
| Total Protein (g/dl) | 4.8 | 4.4-5 | 4.9 | 4.4-5.1 | 5 | 4.7-5.2 | 5 | 4.9-5.1 |
| Albumin (g/dl) | 3 | 2.8-3.2 | 3.1 | 2.7-3.3 | 3 | 2.9-3.2 | 3 | 3-3.2 |
| Globulin (g/dl) | 1.8 | 1.6-1.8 | 1.8 | 1.7-2 | 1.9 | 1.8-2.2 | 1.9 | 1.9-2 |
| Alb/Glob Ratio | 1.8 | 1.7-1.8 | 1.7 | 1.6-1.8 | 1.6 | 1.4-1.8 | 1.6 | 1.5-1.7 |
| Bilirubin Total (mg/dl) | 0.2 | 0.2-0.3 | 0.2 | 0.2-0.3 | 0.2 | 0.2-0.2 | 0.2 | 0.2-0.2 |
| ALP (U/L) | 124 | 106-140 | 108 | 88-120 | 114 | 97-119 | 115 | 106-117 |
| GGT (U/L) | 0 | 0-0 | 0 | 0-1 | 0 | 0-0 | 0 | 0-0 |
| ALT (U/L) | 44 | 41-46 | 42 | 34-51 | 54 | 47-105 | 41 | 38-52 |
| AST (U/L) | 122 | 88-135 | 95 | 76-149 | 109 | 89-161 | 113 | 87-147 |
| Cholesterol (mg/dl) | 129 | 111-143 | 114 | 94-126 | 105 | 101-107 | 113 | 106-128 |

* p < 0.05 compared to control (untreated)

TABLE 13

Histology of Control (Untreated) Mice (Chronic)

| Organ | Mouse 1 | Mouse 2 | Mouse 3 | Mouse 4 | Mouse 5 |
|---|---|---|---|---|---|
| Bone Marrow | NSL | NSL | NSL | N/A | NSL |
| Brain | NSL | NSL | NSL | N/A | NSL |
| Heart | NSL | NSL | NSL | N/A | NSL |
| Kidney | NSL | NSL | Mild tubular ectasia | N/A | NSL |
| Lung | NSL | NSL | NSL | N/A | NSL |
| Adrenal | NSL | NSL | NSL | N/A | NSL |
| Liver | Mild MF random MG, focal mild acute hepatic necrosis | Mild MF random MG, focal mild acute hepatic necrosis | mild MF MG | N/A | mild MF MG |
| Thymus | NSL | NSL | NSL | N/A | N/A |
| Spleen | NSL | NSL | mild hemosiderosis | N/A | NSL |
| Pancreas | NSL | NSL | NSL | N/A | NSL |
| Ear | NSL | Focal mild neutrophilic dermatitis & folliculitis (incidental) | NSL | N/A | N/A |
| Ovary | NSL | NSL | NSL | N/A | NSL |
| Uterus | NSL | NSL | NSL | N/A | NSL |
| Salivary Gland | NSL | NSL | NSL | N/A | NSL |
| Lymphnodes | small fragments | NSL | NSL | N/A | NSL |
| Brown Fat | NSL | N/A | NSL | N/A | N/A |
| Comment | There is no evidence of any test-article related lesions in any of the tissues examined | There is no evidence of any test-article related lesions in any of the tissues examined | There is no evidence of any test-article related lesions in any of the tissues examined | N/A | There is no evidence of any test-article related lesions in any of the tissues examined |

NSL: no significant lesions
MF: multifocal
MG: microgranuloma
NA: tissue not available

TABLE 14

Histology of pUMVC3 Immunized Mice (Chronic)

| Organ | Mouse 1 | Mouse 2 | Mouse 3 | Mouse 4 | Mouse 5 |
|---|---|---|---|---|---|
| Bone Marrow | NSL | NSL | NSL | NSL | NSL |
| Brain | NSL | NSL | NSL | NSL | NSL |
| Heart | NSL | NSL | NSL | NSL | NSL |
| Kidney | NSL | NSL | NSL | NSL | NSL |
| Lung | NSL | mild PV PB LA | mild PV LA | NSL | NSL |
| Adrenal | mild x zone lipidosis | NSL | mild x zone lipidosis | NSL | mild x zone lipidosis |
| Liver | MF random MG | mild MF random MG | mild MF random MG | mild MF random MG | Moderate random MG & EMH |
| Thymus | NSL | NSL | NSL | NSL | N/A |
| Spleen | NSL | NSL | Mild hemosiderosis & MZ expansion | Mild hemosiderosis & MZ expansion | Mild hemosiderosis & MZ expansion |
| Pancreas | mild islet enlargement | mild islet enlargement | mild islet enlargement | NSL | mild islet enlargement |
| Ear | FE moderate granulomatous & focal pyogranulomatous auricular chondritis & dermatitis/cellulitis with lipid laden macrophages & free lipid, multifocal to coalescing, with epidermal hyperplasia chronic active | FE moderate granulomatous & focal pyogranulomatous auricular chondritis & dermatitis/cellulitis with lipid laden macrophages & free lipid, multifocal to coalescing, with epidermal hyperplasia chronic active | FE severe granulomatous & focal pyogranulomatous auricular chondritis & dermatitis/cellulitis with lipid laden macrophages & free lipid, multifocal to coalescing, with epidermal hyperplasia chronic active | FE moderate granulomatous & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active |
| Ovary | N/A | NSL | NSL | NSL | NSL |
| Uterus | N/A | NSL | NSL | NSL | NSL |
| Salivary Gland | N/A | NSL | NSL | NSL | NSL |
| Lymphnodes | Extracellular lipid & foamy macs in sinuses, marked germinal centers, focal acute necrosis in subcapsular sinus | Mild extracellular lipid | Extracellular lipid & foamy macs in sinuses, marked germinal centers, focal acute necrosis in subcapsular sinus; tiny | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus |
| Brown Fat | N/A | N/A | N/A | N/A | N/A |
| Comment | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined |

FE: Focally extensive
LH: lymphoid hyperplasia
MZ: Marginal zone
EMH: extramedullary hematopoiesis
PV: Paravascular
PB: Parabronchial
LA: Lymphoid aggregates

TABLE 15

Histology of pUMVC3-hSATB1 (387-450) Immunized Mice (Chronic)

| Organ | Mouse 1 | Mouse 2 | Mouse 3 | Mouse 4 | Mouse 5 |
|---|---|---|---|---|---|
| Bone Marrow | granulocytic hyperplasia | granulocytic hyperplasia | granulocytic hyperplasia | granulocytic hyperplasia | granluocytic hyperplasia |
| Brain | NSL | NSL | NSL | NSL | NSL |
| Kidney | NSL | NSL | NSL | NSL | NSL |
| Lung | NSL | NSL | Mild PV PB LA | minimal PV PB LA | moderate PV PB LA |
| Adrenal | mild x zone lipidosis | Mild x zone lipidosis | NSL | mild x zone lipofuscinosis | NSL |
| Liver | mild random MG & EMH | mild random MG & EMH | mild random MG | mild mf random MG | mild random MG |

TABLE 15-continued

Histology of pUMVC3-hSATB1 (387-450) Immunized Mice (Chronic)

| Organ | Mouse 1 | Mouse 2 | Mouse 3 | Mouse 4 | Mouse 5 |
|---|---|---|---|---|---|
| Thymus | NSL | NSL | Tiny | N/A | NSL |
| Spleen | NSL | NSL | NSL | NSL | NSL |
| Pancreas | NSL | NSL | NSL | NSL | NSL |
| Ear | FE moderate & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active | FE severe & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active |
| Ovary | NSL | NSL | NSL | NSL | NSL |
| Uterus | NSL | NSL | NSL | NSL | NSL |
| Salivary Gland | NSL | NSL | NSL | NSL | NSL |
| Skeletal Muscle | NSL | NSL | NSL | NSL | NSL |
| Lymphnodes | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus; Moderate sinuoisald hemosiderosis & acute hemorrhage | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus |
| Brown Fat | N/A | N/A | N/A | N/A | N/A |
| Comment | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined |

TABLE 16

Histology of pUMVC3-hCDC25B (124-164) Immunized Mice (Chronic)

| Organ | Mouse 1 | Mouse 2 | Mouse 3 | Mouse 4 | Mouse 5 |
|---|---|---|---|---|---|
| Bone Marrow | granluocytic hyperplasia | NSL | NSL | NSL | NSL |
| Brain | NSL | NSL | NSL | NSL | NSL |
| Kidney | NSL | NSL | NSL | NSL | NSL |
| Lung | moderate PV PB LA | NSL | mild PV PB LA | moderate PV PB LA | mild PV PB LA |
| Adrenal | mild x zone lipofuscinosis | NSL | mild x zone lipofuscinosis | NSL | NSL |
| Liver | mild random MG | mild random MG | mild random MG | moderate PV PB LA & mild MF acute necrosis | Mild random MG |
| Thymus | NSL | NSL | NSL | NSL | NSL |
| Spleen | NSL | NSL | NSL | NSL | NSL |
| Pancreas | NSL | NSL | NSL | NSL | NSL |
| Ear | FE moderate & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active | FE moderate & focal pyogranulomatous auricular chondritis & dermatitis/cellulitis with lipid laden macrophages & free lipid, multifocal to coalescing, with epidermal hyperplasia chronic active |

TABLE 16-continued

Histology of pUMVC3-hCDC25B (124-164) Immunized Mice (Chronic)

| Organ | Mouse 1 | Mouse 2 | Mouse 3 | Mouse 4 | Mouse 5 |
|---|---|---|---|---|---|
| Ovary | NSL | NSL | NSL | NSL | NSL |
| Uterus | NSL | NSL | NSL | NSL | NSL |
| Salivary Gland | NSL | NSL | NSL | NSL | NSL |
| Skeletal Muscle | NSL | NSL | NSL | NSL | NSL |
| Lymphnodes | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus | Extracellular lipid & foamy macs in sinuses, marked germinal centers, focal acute necrosis in subcapsular sinus |
| Brown Fat | N/A | NSL | N/A | N/A | N/A |
| Comment | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined |

TABLE 17

Histology of control (untreated) mice

| Organ | Mouse 1 | Mouse 2 | Mouse 3 | Mouse 4 | Mouse 5 |
|---|---|---|---|---|---|
| Bone Marrow | NSL | NSL | NSL | NSL | NSL |
| Brain | NSL | NSL | NSL | NSL | NSL |
| Kidney | NSL | NSL | NSL | NSL | NSL |
| Adrenal | NSL | NSL | NSL | NSL | NSL |
| Liver | NSL | NSL | NSL | NSL | mild random EMH |
| Thymus | NSL | NSL | NSL | NSL | NSL |
| Spleen | Moderate marginal zone hypercellularity & germinal centers | Moderate marginal zone hypercellularity & germinal centers | Moderate marginal zone hypercellularity & germinal centers | Moderate marginal zone hypercellularity & germinal centers | Moderate marginal zone hypercellularity & germinal centers |
| Pancreas | Mild islet enlargement | N/A | Mild islet enlargement | NSL | NSL |
| Ear | NSL | NSL | NSL | NSL | NSL |
| Ovary | NSL | NSL | NSL | small sample-CL only | small sample-CL only |
| Uterus | NSL | NSL | NSL | NSL | NSL |
| Salivary Gland | NSL | NSL | NSL | NSL | NSL |
| Draining and/or Distal LN | NSL | NSL | moderate sinusoidal increased mast cells. | Few germinal centers | N/A |
| Brown Fat | NSL | NSL | NSL | NSL | NSL |
| Comment | There is no evidence of any test-article related lesions in any of the tissues examined | There is no evidence of any test-article related lesions in any of the tissues examined | There is no evidence of any test- article related lesions in any of the tissues examined | There is no evidence of any test-article related lesions in any of the tissues examined | There is no evidence of any test-article related lesions in any of the tissues examined |

TABLE 18

Histology of pUMVC3 Immunized Mice

| Organ | Mouse 1 | Mouse 2 | Mouse 3 | Mouse 4 | Mouse 5 |
|---|---|---|---|---|---|
| Bone Marrow | NSL | NSL | NSL | NSL | NSL |
| Brain | NSL | NSL | NSL | NSL | NSL |
| Kidney | NSL | NSL | Mild MF lymphocytes in interstitium | NSL | NSL |
| Adrenal | NSL | NSL | NSL | NSL | mild multifocal spindle cell hyperplasia |

TABLE 18-continued

Histology of pUMVC3 Immunized Mice

| Organ | Mouse 1 | Mouse 2 | Mouse 3 | Mouse 4 | Mouse 5 |
|---|---|---|---|---|---|
| Liver | mild random EMH & microgranulomas | Focal mild fibrosis & neutrophils | mild MF EMH | mild MF EMH & random MG | mild MF EMH & random MG |
| Thymus | NSL | NSL | NSL | NSL | NSL |
| Spleen | Moderate marginal zone hypercellularity & germinal centers | Mild marginal zone hypercellularity | Mild marginal zone hypercellularity & germinal centers | Mild marginal zone hypercellularity & germinal centers | Moderate marginal zone hypercellularity & germinal centers |
| Pancreas | NSL | NSL | NSL | NSL | NSL |
| Ear | FE moderate to severe granulomatous & focal pyogranulomatous auricular chondritis & dermatitis/cellulitis with lipid laden macrophages & free lipid, multifocal to coalescing, with epidermal hyperplasia chronic active (injection site) | FE mild granulomatous & focal pyogranulomatous auricular chondritis & dermatitis/cellulitis with lipid laden macrophages & free lipid, multifocal to coalescing, with epidermal hyperplasia chronic active (injection site) | FE moderate to severe granulomatous & focal pyogranulomatous auricular chondritis & dermatitis/cellulitis with lipid laden macrophages & free lipid, multifocal to coalescing, with epidermal hyperplasia chronic active (injection site) | FE moderate granulomatous & focal pyogranulomatous auricular chondritis & dermatitis/cellulitis with lipid laden macrophages & free lipid, multifocal to coalescing, with epidermal hyperplasia chronic active (injection site) | severe histiocytic to granulomatous & pyogranulomatous auricular chondritis & dermatitis/cellulitis/myo sitis with lipid laden macrophages & free lipid, multifocal to coalescing, with epidermal & cartilagenous hyperplasia & hemorrhage & cytic degenertaion, chronic active (injection site) |
| Ovary | NSL | NSL | NSL | NSL | NSL |
| Uterus | NSL | NSL | NSL | NSL | NSL |
| Salivary Gland | NSL | NSL | NSL | NSL | NSL |
| Skeletal Muscle | NSL | Mullifocal mild to moderate granulomatous to fibrosis myositis & cellulitis | Multifocal mild to moderate granulomatous to fibrosis myositis & cellulitis | Multifocal mild to moderate granulomatous to fibrosis myositis & cellulitis | NSL |
| Draining and/or Distal LN | Extracellular lipid & foamy macs in sinuses | Extracellular lipid & foamy macs in sinuses | Extracellular lipid & foamy macs in sinuses | Extracellular lipid & foamy macs in sinuses | Extracellular lipid & foamy macs in sinuses; mild red blood cells within sinuses |
| Brown Fat | N/A | NSL | NSL | NSL | NSL |
| Comment | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined |

TABLE 19

Histology of pUMVC3-hSATB1 (387-450) Immunized Mice

| Organ | Mouse 1 | Mouse 2 | Mouse 3 | Mouse 4 | Mouse 5 |
|---|---|---|---|---|---|
| Bone Marrow | NSL | NSL | NSL | NSL | NSL |
| Brain | NSL | NSL | NSL | NSL | NSL |
| Kidney | Mild MF tubular ectasia | Mild MF tubular ectasia | Mild MF tubular ectasia | Mild MF tubular ectasia | Mild MF tubular ectasia |
| Adrenal | NSL | NSL | NSL | NSL | NSL |
| Liver | mild MF EMH & random MG | moderate MF EMH & random MG; focal mild fibrosis & neutrophils | Mild EMH | Moderate EMH & random MG | Moderate EMH & random MG; focal mild acute coagulative necrosis |
| Thymus | NSL | NSL | NSL | NSL | NSL |
| Spleen | Moderate marginal zone hypercellularity & germinal centers | Moderate marginal zone hypercellularity & germinal centers | Moderate marginal zone hypercellularity & germinal centers | Moderate marginal zone hypercellularity & germinal centers | Moderate marginal zone hypercellularity & germinal centers |

TABLE 19-continued

Histology of pUMVC3-hSATB1 (387-450) Immunized Mice

| Organ | Mouse 1 | Mouse 2 | Mouse 3 | Mouse 4 | Mouse 5 |
|---|---|---|---|---|---|
| Pancreas | NSL | NSL | NSL | NSL | NSL |
| Ear | severe histiocytic to granulomatous & pyogranulomatous auricular chondritis & dermatitis/cellulitis/myositis with lipid laden macrophages & free lipid, MF to coalescing, w/ epidermal & cartilagenous hyperplasia, chronic active (injection site) | severe histiocytic to granulomatous & pyogranulomatous auricular chondritis & dermatitis/cellulitis/my ositis with lipid laden macrophages & free lipid, MF to coalescing, with epidermal & cartilagenous hyperplasia, chronic active (injection site) | moderate granulomatous & pyogranulomatous auricular chondritis & dermatitis/cellulitis/my ositis with lipid laden macrophages & free lipid, MF to coalescing, with epidermal & cartilagenous hyperplasia, chronic active (injection site) | moderate to severe histiocytic to granulomatous & pyogranulomatous auricular chondritis & dermatitis/cellulitis/my ositis with lipid laden macrophages & free lipid, MF to coalescing, with epidermal & cartilagenous hyperplasia, chronic active (injection site) | severe histiocytic to granulomatous & pyogranulomatous auricular chondritis & dermatitis/cellulitis/my ositis with lipid laden macrophages & free lipid, MF to coalescing, with epidermal & cartilagenous & enlarged & prominent nerves, chronic active (injection site) |
| Ovary | NSL | NSL | NSL | NSL | NSL |
| Uterus | NSL | NSL | NSL | NSL | NSL |
| Salivary Gland | NSL | NSL | N/A | NSL | NSL |
| Skeletal Muscle | NSL | NSL | NSL | NSL | NSL |
| Draining and/or Distal LN | Extracellular lipid & foamy macs in sinuses marked with pyogranulomatous lymphadentitis | Extracellular lipid & foamy macs in sinuses | Extracellular lipid & foamy macs in sinuses; Red blood cells, histiocytes & hemosiderin in sinusoids | Lipid & lipid laden macs in sinusoids with mild pernodal granulomatous cellultis; minimal lipid & lipid-laden macs in sinusoids | Lipid & lipid laden macs in sinusoids; Histiocytes in sinusoids |
| Brown Fat | NSL | NSL | NSL | NSL | NSL |
| Comment | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined | Mammary Fat Pad - ducts mild hyperplasia. There is no evidence of any test-article related lesions in any tissues examined |

TABLE 20

Histology of pUMVC3-hCDC25B (124-164) Immunized Mice

| Organ | Mouse 1 | Mouse 2 | Mouse 3 | Mouse 4 | Mouse 5 |
|---|---|---|---|---|---|
| Bone Marrow | NSL | NSL | NSL | NSL | NSL |
| Brain | NSL | NSL | NSL | NSL | NSL |
| Kidney | NSL | NSL | Mild MF tubular ectasia | Mild MF tubular ectasia | Mild MF tubular ectasia, multifocal mild tubular hyperplasia & cysts |
| Adrenal | NSL | NSL | NSL | NSL | NSL |
| Liver | mild EMH | mild focal fibrosis & neutrophils, mild EMH | Mild EMH | Mild EMH | Mild EMH & MG with ISCH |
| Thymus | NSL | NSL | NSL | NSL | NSL |
| Spleen | Moderate marginal zone hypercellularity & germinal centers | Moderate marginal zone hypercellularity & germinal centers | Moderate marginal zone hypercellularity & germinal centers | Moderate marginal zone hypercellularity & germinal centers | Moderate marginal zone hypercellularity & germinal centers |
| Pancreas | NSL | NSL | NSL | NSL | NSL |
| Ear | severe histiocytic to granulomatous & pyogranulomatous auricular chondritis & dermatitis/cellulitis/ myositis with lipid laden macrophages & free lipid, MF to | severe histiocytic to granulomatous & pyogranulomatous auricular chondritis & dermatitis/cellulitis/ myositis with lipid laden macrophages & free lipid, MF to | severe histiocytic to granulomatous & pyogranulomatous auricular chondritis & dermatitis/cellulitis/ myositis with lipid laden macrophages & free lipid, MF to | moderate granulomatous & pyogranulomatous auricular chondritis & dermatitis/cellulitis/ myositis with lipid laden macrophages & free lipid, MF to | severegranulomatous & pyogranulomatous auricular chondritis & dermatitis/cellulitis/ myositis with lipid laden macrophages & free lipid, MF to coalescing, with |

TABLE 20-continued

Histology of pUMVC3-hCDC25B (124-164) Immunized Mice

| Organ | Mouse 1 | Mouse 2 | Mouse 3 | Mouse 4 | Mouse 5 |
|---|---|---|---|---|---|
| | coalescing, with epidermal & cartilagenous &, chronic active | coalescing, with epidermal & cartilagenous & squamous retention cyst, chronic active | coalescing, with epidermal & cartilagenous hyperplasia, chronic active | coalescing, with epidermal hyperplasia, chronic active | epidermal hyperplasia, chronic active |
| Ovary | NSL | NSL | NSL | NSL | NSL |
| Uterus | NSL | NSL | NSL | NSL | NSL |
| Salivary Gland | NSL | NSL | NSL | NSL | NSL |
| Skeletal Muscle | NSL | NSL | NSL | NSL | NSL |
| Draining and/or Distal LN | Marked lipid & lipid laden macs in sinusoids; multifocal mild granulomatous lymphadenitis; Histiocytes in sinusoids | Marked lipid & lipid laden macs in sinusoids; multifocal mild granulomatous lymphadenitis; Histiocytes in sinusoids | Marked lipid & lipid laden macs in sinusoids; multifocal mild granulomatous lymphadenitis; Histiocytes in sinusoids | Marked lipid & lipid laden macs in sinusoids; multifocal mild granulomatous lymphadenitis; Histiocytes in sinusoids | Marked lipid & lipid laden macs in sinusoids; multifocal mild granulomatous lymphadenitis; Histiocytes in sinusoids |
| Brown Fat | NSL | NSL | NSL | NSL | NSL |
| Comment | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined | There is no evidence of any test-article related lesions in any of the tissues examined |

ISCH: intrasinusoidal cell hypercellularity

TABLE 21

Histology of Untreated (control) Mice

| Organ | Mouse 1 | Mouse 2 | Mouse 3 | Mouse 4 | Mouse 5 |
|---|---|---|---|---|---|
| Bone Marrow | NSL | NSL | NSL | N/A | NSL |
| Brain | NSL | NSL | NSL | N/A | NSL |
| Kidney | NSL | Mild multifocal tubular ectasia | Mild multifocal tubular ectasia | N/A | NSL |
| Adrenal | NSL | NSL | NSL | N/A | NSL |
| Liver | Mild MF EMH | Mild MF EMH | Mild MF EMH | N/A | Minimal EMH |
| Thymus | NSL | NSL | Mild medullary hypercellularity | N/A | NSL |
| Spleen | NSL | NSL | NSL | N/A | Mild marginal zone hypercellularity |
| Pancreas | NSL | NSL | NSL | N/A | NSL |
| Ear | Minimal lymphocytic focal dermatitis | NSL | NSL | N/A | NSL |
| Ovary | NSL | NSL | N/A | N/A | NSL |
| Oviduct | NSL | NSL | NSL | N/A | NSL |
| DLN | Minimal germinal center | N/A | NSL | N/A | NSL |
| Distal LN | NSL | N/A | NSL | N/A | NSL |
| Comment | There is no histologic evidence of any test-article related lesions in any of the tissues examined. | There is no histologic evidence of any test-article related lesions in any of the tissues examined. | There is no histologic evidence of any test-article related lesions in any of the tissues examined. | N/A | There is no histologic evidence of any test-article related lesions in any of the tissues examined. |

TABLE 22

Histology of pUMVC3 Immunized Mice

| Organ | Mouse 1 | Mouse 2 | Mouse 3 | Mouse 4 | Mouse 5 |
|---|---|---|---|---|---|
| Bone Marrow | NSL | NSL | NSL | NSL | NSL |
| Brain | NSL | NSL | NSL | NSL | NSL |
| Kidney | Mild tubular ectasia & multifocal mild tubular hyperplasia | Mild tubular ectasia & multifocal mild tubular hyperplasia | Mild tubular ectasia & multifocal mild tubular hyperplasia | NSL | NSL |

TABLE 22-continued

Histology of pUMVC3 Immunized Mice

| Organ | Mouse 1 | Mouse 2 | Mouse 3 | Mouse 4 | Mouse 5 |
|---|---|---|---|---|---|
| Adrenal | NSL | NSL | NSL | NSL | NSL |
| Liver | Mild MF EMH | Mild MF EMH | Mild MF EMH | Mild MF EMH | Mild MF EMH |
| Thymus | NSL | NSL | NSL | NSL | NSL |
| Spleen | Mild marginal zone hyperplasia | Mild marginal zone hyperplasia, mild free lipid | Mild marginal zone hypercellularity | Moderate marginal zone hyperplasia | Moderate marginal zone hyperplasia |
| Pancreas | NSL | NSL | NSL | NSL | NSL |
| Ear | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active |
| Ovary | N/A | N/A | N/A | N/A | N/A |
| Oviduct | NSL | NSL | NSL | NSL | NSL |
| DLN | LH moderate with MF lipidosis | Multifocal mild granulomatous & lymphocytic adenitis with lipid laden macrophages & free lipid. Moderate LH. | Multifocal mild granulomatous & lymphocytic adenitis with lipid laden macrophages & free lipid. Moderate LH. | Multifocal mild granulomatous & lymphocytic adenitis with lipid laden macrophages & free lipid. Moderate LH. | Multifocal mild granulomatous & lymphocytic adenitis with lipid laden macrophages & free lipid. Moderate LH. |
| Distal LN | NSL | NSL | NSL | NSL | NSL |
| Comment | There is no evidence of any test-article related lesions in any of the tissues examined other than the injection site & This is likely related to adjuvant. | There is no evidence of any test-article related lesions in any of the tissues examined other than the injection site & DLN which are likely due to adjuvant | There is no evidence of any test-article related lesions in any of the tissues examined other than the injection site & This is likely related to adjuvant. | There is no evidence of any test-article related lesions in any of the tissues examined other than the injection site & This is likely related to adjuvant. | There is no evidence of any test-article related lesions in any of the tissues examined other than the injection site & This is likely related to adjuvant. |

TABLE 23

Histology of pUMVC3-hHif1a (30-119) Immunized Mice

| Organ | Mouse 1 | Mouse 2 | Mouse 3 | Mouse 4 | Mouse 5 |
|---|---|---|---|---|---|
| Bone Marrow | NSL | NSL | NSL | NSL | |
| Brain | NSL | NSL | NSL | NSL | |
| Kidney | Focal mild tubular hyperplasia | NSL | Moderate unilateral hydronephrosis | NSL | Minimal tubular ectasia |
| Adrenal | NSL | NSL | NSL | NSL | NSL |
| Liver | Mild MF EMH | Mild MF EMH | Moderate MF EMH | Moderate EMH | Mild MF EMH |
| Thymus | NSL | NSL | NSL | NSL | NSL |
| Spleen | Moderate marginal zone hyperplasia | Moderate marginal zone hyperplasia | Moderate marginal zone hyperplasia | Moderate marginal zone hyperplasia | Mild marginal zone hyperplasia |
| Pancreas | NSL | NSL | NSL | NSL | |
| Ear | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active |
| Ovary | N/A | N/A | NSL | NSL | NSL |
| Oviduct | NSL | NSL | NSL | NSL | NSL |

TABLE 23-continued

Histology of pUMVC3-hHif1a (30-119) Immunized Mice

| Organ | Mouse 1 | Mouse 2 | Mouse 3 | Mouse 4 | Mouse 5 |
|---|---|---|---|---|---|
| DLN | Multifocal moderate granulomatous & lymphocytic adenitis with lipid laden macrophages & free lipid. Moderate LH. | Multifocal moderate granulomatous & lymphocytic adenitis with lipid laden macrophages & free lipid. Moderate LH. | Multifocal moderate granulomatous & lymphocytic adenitis with lipid laden macrophages & free lipid. Moderate LH. | Multifocal moderate granulomatous & lymphocytic adenitis with lipid laden macrophages & free lipid. Moderate LH. | Multifocal moderate granulomatous & lymphocytic adenitis with lipid laden macrophages & free lipid. Moderate LH. |
| Distal LN | NSL | NSL | NSL | NSL | NSL |
| Comment | There is no evidence of any test-article related lesions in any of the tissues examined other than the injection site & DLN which are likely due to adjuvant. | There is no evidence of any test-article related lesions in any of the tissues examined other than the injection site & DLN which are likely due to adjuvant. | There is no evidence of any test-article related lesions in any of the tissues examined other than the injection site & DLN which are likely due to adjuvant. | There is no evidence of any test-article related lesions in any of the tissues examined other than the injection site & DLN which are likely due to adjuvant. | There is no evidence of any test-article related lesions in any of the tissues examined other than the injection site & DLN which are likely due to adjuvant. |

TABLE 24

Histology of pUMVC3-hHif1a (87-138) Immunized Mice

| Organ | Mouse 1 | Mouse 2 | Mouse 3 | Mouse 4 | Mouse 5 |
|---|---|---|---|---|---|
| Bone Marrow | Granulocytic hyperplasia | NSL | NSL | NSL | NSL |
| Brain | NSL | NSL | NSL | NSL | NSL |
| Kidney | NSL | NSL | NSL | NSL | NSL |
| Adrenal | NSL | NSL | NSL | NSL | NSL |
| Liver | Mild MF EMH | Mild focal acute coagulative necrosis | Mild focal acute coagulative necrosis with neutrophils; mild EMH | Mild MF EMH | Mild MF EMH |
| Thymus | NSL | NSL | NSL | NSL | NSL |
| Spleen | NSL | Moderate marginal zone hypercellularity | Moderate marginal zone hypercellularity | NSL | Moderate marginal zone hypercellularity |
| Pancreas | NSL | NSL | NSL | NSL | NSL |
| Ear | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active | FE moderate granulomatous & lymphocytic auricular chondritis & dermatitis/cellulitis with lipid laden macrophages & free lipid, multifocal to coalescing, chronic active |
| Ovary | N/A | NSL | NSL | NSL | NSL |
| Oviduct | NSL | NSL | NSL | NSL | NSL |
| DLN | Multifocal mild granulomatous & lymphocytic adenitis with lipid laden macrophages & free lipid. Moderate LH. | Multifocal minimal granulomatous & lymphocytic adenitis with lipid laden macrophages & free lipid. Moderate LH. | Multifocal moderate granulomatous & lymphocytic adenitis with lipid laden macrophages & free lipid. Moderate LH. | Multifocal moderate granulomatous & lymphocytic adenitis with lipid laden macrophages & free lipid. Moderate LH. | Multifocal mild granulomatous & lymphocytic adenitis with lipid laden macrophages & free lipid. Moderate LH. |
| Distal LN | NSL | NSL | NSL | NSL | NSL |
| Comment | There is no evidence of any test-article related lesions in any of | There is no evidence of any test-article related lesions in any of | There is no evidence of any test-article related lesions in any of | There is no evidence of any test-article related lesions in any of | There is no evidence of any test-article related lesions in any of |

TABLE 24-continued

Histology of pUMVC3-hHif1a (87-138) Immunized Mice

| Organ | Mouse 1 | Mouse 2 | Mouse 3 | Mouse 4 | Mouse 5 |
|---|---|---|---|---|---|
| | the tissues examined other than the injection site & DLN which are likely due to adjuvant. | the tissues examined other than the injection site & DLN which are likely due to adjuvant. | the tissues examined other than the injection site & DLN which are likely due to adjuvant. | the tissues examined other than the injection site & DLN which are likely due to adjuvant. | the tissues examined other than the injection site & DLN which are likely due to adjuvant. |

DLN: Draining Lymph Nodes

An exemplary list of plasmid based vaccines, some of which were administered to subjects as described herein is provided in Table 25.

TABLE 25

Plasmid Based Vaccines Constructed to Date

| Plasmid Name | Size (bp) | Antigen(s) Expressed | Epitope Region (a.a. numbers) | Plasmid Type |
|---|---|---|---|---|
| pCD105 (87-138) | 4210 | CD105/Endoglin | 87-138 | Single Ag |
| pCDC25B (124-164) | 4177 | CDC25B | 124-164 | Single Ag |
| pCDH3 (85-164) | 4294 | CDH3/P-cadherin | 85-164 | Single Ag |
| pHIF1α (30-119) | 4324 | HIF1α | 30-119 | Single Ag |
| pMDM2 (53-129) | 4288 | MDM2/HDM2 | 53-129 | Single Ag |
| pSATB1 (387-450) | 4246 | SATB1 | 387-450 | Single Ag |
| pSOX2 (185-243) | 4231 | SOX2 | 185-243 | Single Ag |
| pYB1 (130-161) | 4153 | Yb-1 | 130-161 | Single Ag |
| pUbGM-CD105 | 4424 | CD105/Endoglin | 87-138 | Ubiquitin-fusion 1 |
| pUbGM-CDC25B | 4391 | CDC25B | 124-164 | Ubiquitin-fusion 1 |
| pUbGM-CDH3 | 4508 | CDH3/P-cadherin | 85-164 | Ubiquitin-fusion 1 |
| pUbGM-HIF1α | 4538 | HIF1α | 30-119 | Ubiquitin-fusion 1 |
| pUbGM-MDM2 | 4502 | MDM2/HDM2 | 53-129 | Ubiquitin-fusion 1 |
| pUbGM-SATB1 | 4460 | SATB1 | 387-450 | Ubiquitin-fusion 1 |
| pUbGM-SOX2 | 4445 | SOX2 | 185-243 | Ubiquitin-fusion 1 |
| pUbGM-YB1 | 4367 | Yb-1 | 130-161 | Ubiquitin-fusion 1 |
| pUbVV-CD105 | 4421 | CD105/Endoglin | 87-138 | Ubiquitin-fusion 2 |
| pUbVV-CDC25B | 4388 | CDC25B | 124-164 | Ubiquitin-fusion 2 |
| pUbVV-CDH3 | 4505 | CDH3/P-cadherin | 85-164 | Ubiquitin-fusion 2 |
| pUbVV-HIF1α | 4535 | HIF1α | 30-119 | Ubiquitin-fusion 2 |
| pUbVV-MDM2 | 4499 | MDM2/HDM2 | 53-129 | Ubiquitin-fusion 2 |
| pUbVV-SATB1 | 4457 | SATB1 | 387-450 | Ubiquitin-fusion 2 |
| pUbVV-SOX2 | 4442 | SOX2 | 185-243 | Ubiquitin-fusion 2 |
| pUbVV-YB1 | 4364 | Yb-1 | 130-161 | Ubiquitin-fusion 2 |
| pBCMA2-IC | 4507 | IGF-IR, CDC25B | As listed for single Ags | Two Ag |
| pBCMA3-ICH | 4789 | IGF-IR, CDC25B, HIF1α | As listed for single Ags | Three Ag |
| pBCMA4-ICHC | 4957 | IGF-IR, CDC25B, HIF1α, CD105 | As listed for single Ags | Four Ag |
| pBCMA5-ICHCS | 5161 | IGF-IR, CDC25B. HIF1α, CD105, SATB1 | As listed for single Ags | Five Ag |
| pBCMA6-ICHCSS | 5350 | IGF-IR, CDC25B, HIF1α, CD105, SATB1, SOX2 | As listed for single Ags | Six Ag |
| pBCMA7-ICHCSSC | 5602 | IGF-IR, CDC25B, HIF1α, CD105, SATB1, SOX2, CDH3 | As listed for single Ags | Seven Ag |
| pBCMA8-ICHCSSCM | 5848 | IGF-IR, CDC25B, HIF1α, CD105, SATB1, SOX2, CDH3, MDM2 | As listed for single Ags | Eight Ag |
| pSTEMVAC-6(HCYSCM) | 5290 | HIF1α, CD105, Yb-1, SOX2, CDH3, MDM2 | As listed for single Ags | Six Ag |
| pSTEMVAC-5(CYSCM) | 5008 | CD105, Yb-1, SOX2, CDH3, MDM2 | As listed for single Ags | Five Ag |
| pSTEMVAC-4(CSCM) | 4927 | CD105, SOX2, CDH3, MDM2 | As listed for single Ags | Four Ag |
| pUbGM-BCMA5 | 5375 | IGF-IR, CDC25B, HIF1α, CD105, SATB1 | As listed for single Ags | Ubiquitin-fusion 1, Five Ag |
| pUbVV-BCMA5 | 5372 | IGF-IR, CDC25B, HIF1α, CD105, SATB1 | As listed for single Ags | Ubiquitin-fusion 2, Five Ag |
| pIGF1Rexep-ss | 4372 | IGF-IR | 1196-1261, 1323-1360 | Single Ag |

Example 7

Figure 14:
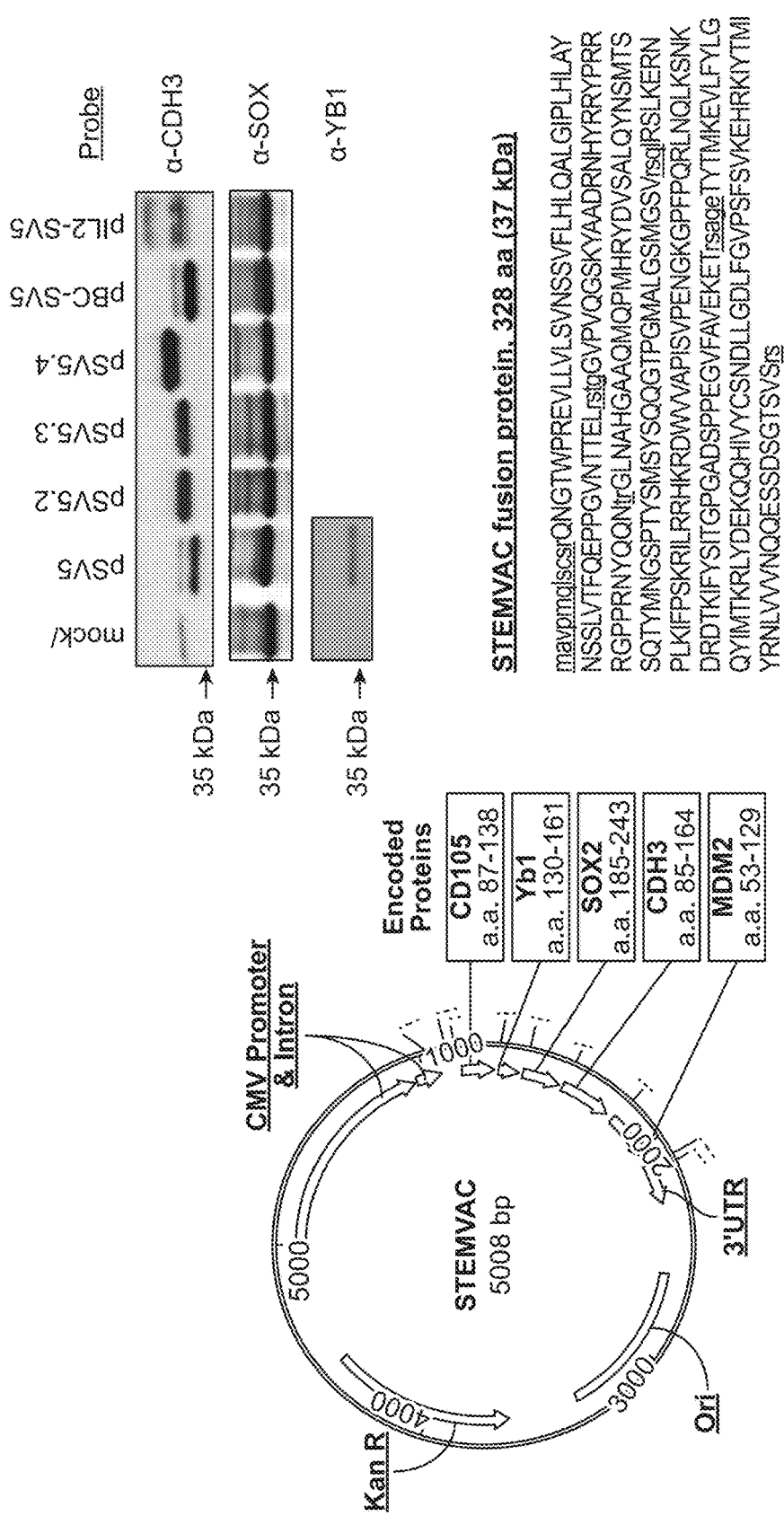
FIG. 14 depicts a map, immunogenicity and exemplary sequence of a composition described herein. SEQ ID NO: 39 is illustrated in FIG. 14.

Determine the Safety and Immunogenicity of Multiepitope Antigen Vaccines in Humans An exemplary composition is show in FIG. 14, the composition is a vaccine and termed STEMVAC.

FIG. 15A shows a validation of peptide specific T-cells as native epitopes for HIF1a. The peptide (A) and HIF1α protein (B) induced IFNγ responses. *indicates p<0.05 vs. no-Ag (white columns). C-D, The peptide (10 ug/ml; C) and protein (1 ug/ml; D) (black columns) induced responses inhibited by MHC II Ab, not by MHC 1 Ab (dark grey). **indicates p<0.05 vs. peptide or protein. Light grey, MHC II and MHC I Ab only.

Figure 31:
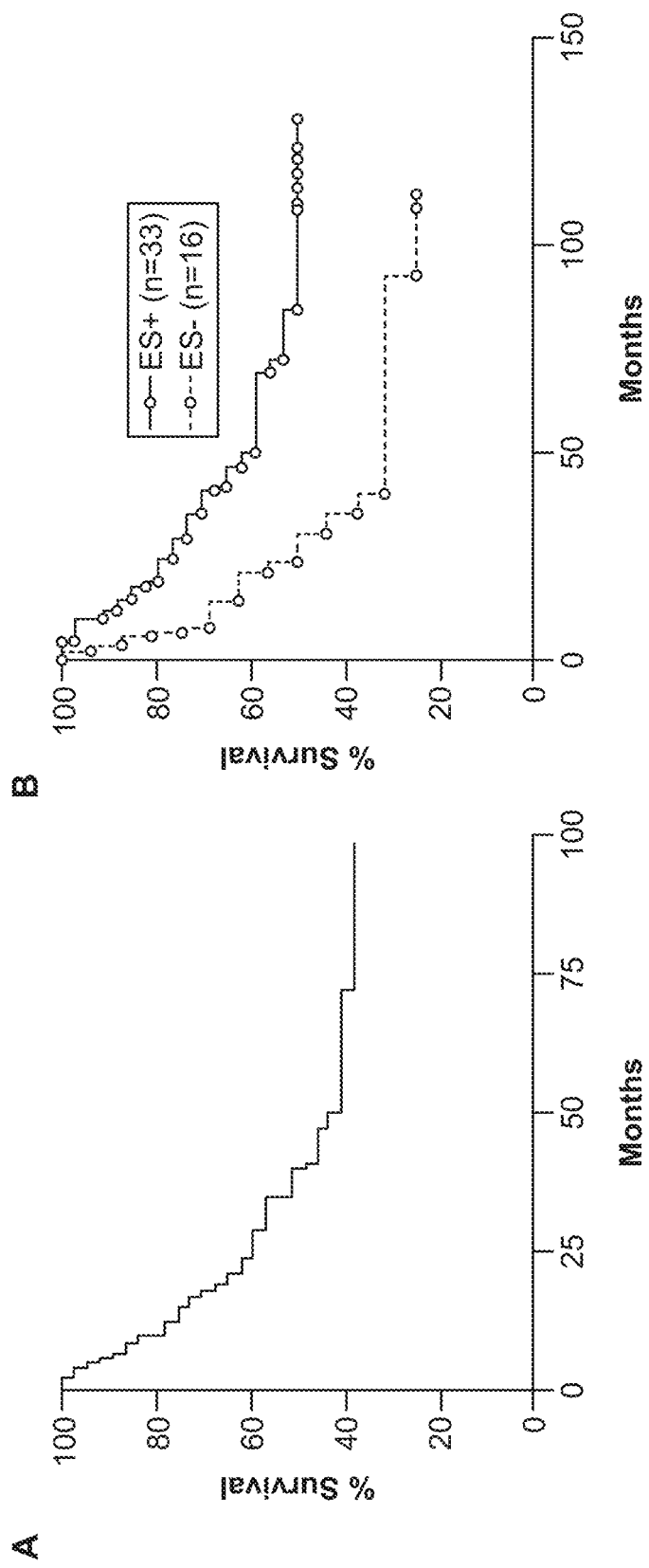
FIG. 31 demonstrates that HER2 Th1 epitope based vaccines may increase survival which is associated with epitope spreading in advanced stage HER2+ breast cancer patients.

Another exemplary composition is a vaccine comprising a HER2 epitope. FIG. 31 shows that HER2 Th1 epitope based vaccines may increase survival which is associated with epitope spreading in advanced stage HER2+ breast cancer patients. (A) Overall survival of 37 stage IV breast cancer patients after HER2 Th1 vaccination is 38% at a median follow-up of 8.5 years. Time 0 indicates the start of vaccination. (B) Kaplan-Meier curves in vaccinated patients; overall survival between epitope spreading-positive (ES+, solid line) (median 84 mo) and negative (ES−, dotted line) patients (median 24 mo).

Figure 32:
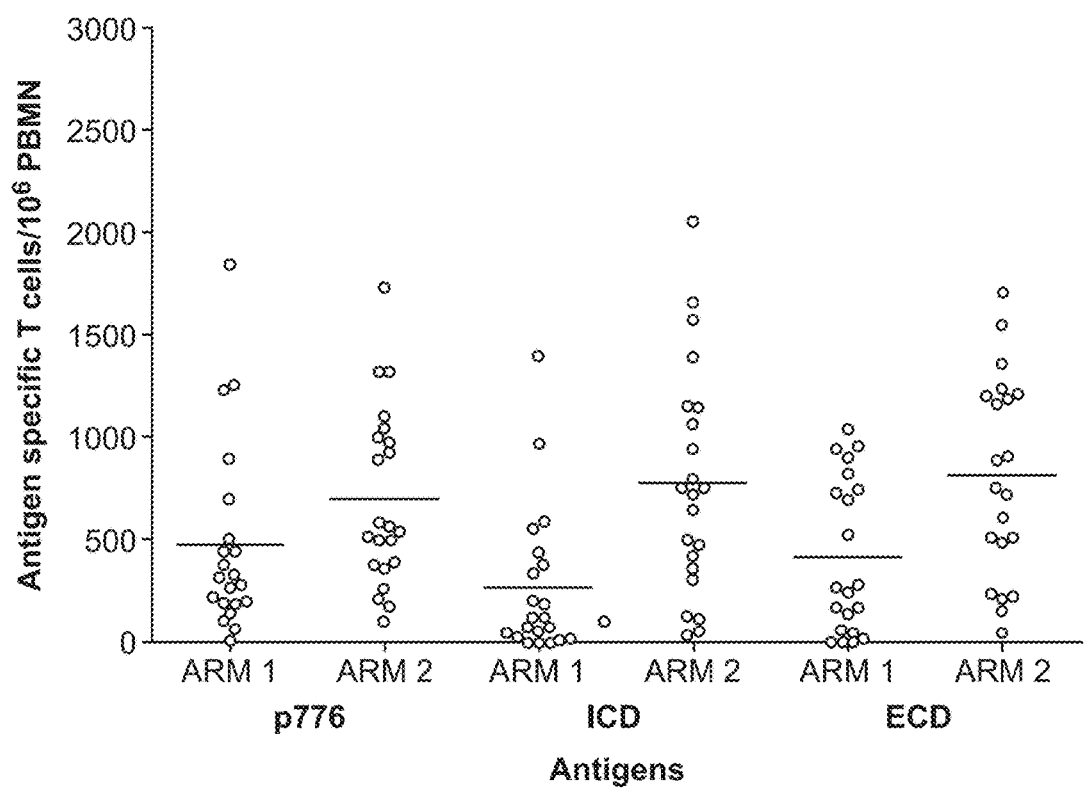
FIG. 32 demonstrates that extended Th plasmid based vaccines are more effective than peptide based vaccine in generating tumor antigen specific Th1 immunity.

At FIG. 32, the results comparing plasmid and peptide based vaccines are shown. Extended Th plasmid based vaccines are more effective than peptide based vaccine in generating tumor antigen specific Th1 immunity. Post-vaccination ELISPOT responses are shown for ARM 1 (○) and ARM 2 (●). ELISPOT responses to HER2 ICD Th peptide 776 and for HER2 ICD or ECD protein domains are reported as antigen specific T-cells/$10^6$ PBMC with each circle representing an individual patient response; and bold bars indicate the median in all panels.

Figure 33:
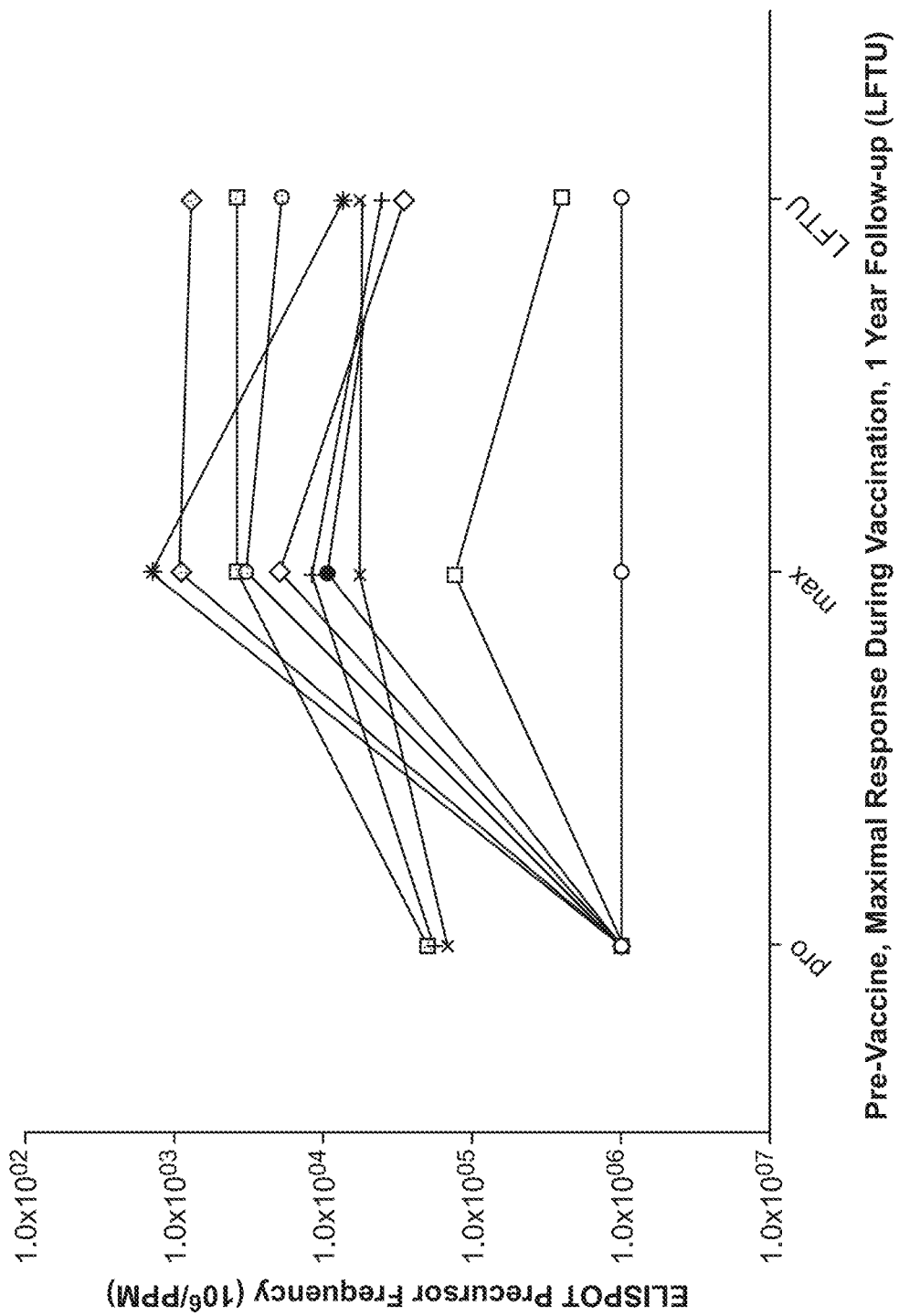
FIG. 33 shows that persistent HER2 ICD specific immunity >1 year after plasmid DNA based vaccination has ended.
Figure 34:
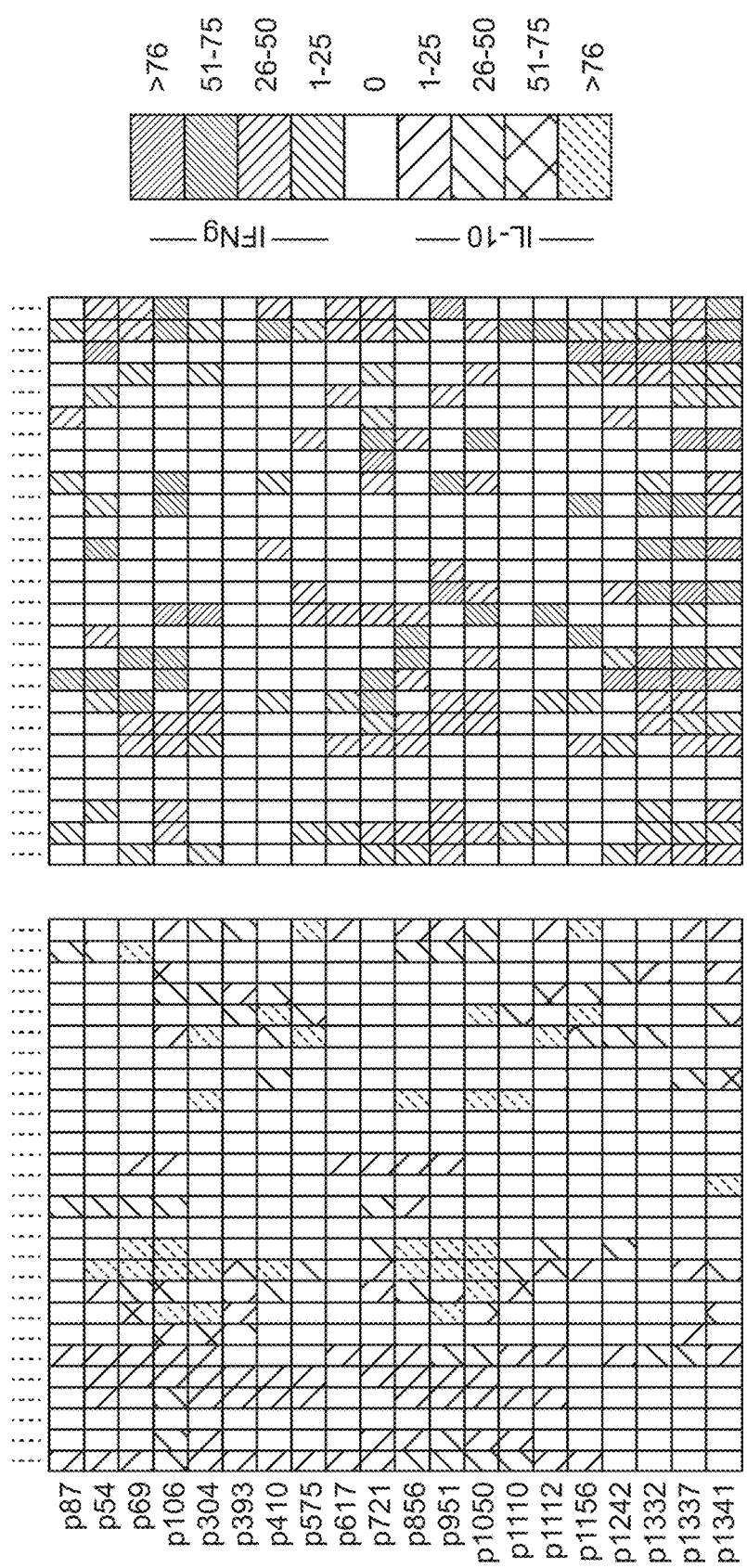
FIG. 34 shows IGF-1R epitopes screened for IFNγ and IL-10 T-cell secretion by ELISPOT.

Persistent HER2 ICD specific immunity >1 year after plasmid DNA based vaccination has ended, HER2 ICD specific IFNγ ELISPOT response to HER2 ICD is shown for 10 patients. See FIG. 33. Values plotted for each subject are pre-immunization (pre), maximal response during vaccination (max) and response after 1 year (LTFU).

Using supernatants from ELISPOT assays during the conduct of a Phase II study of a HER2 peptide vaccine from eight advanced stage HER2+ breast cancer patients receiving vaccinations. At FIG. 37, the values collected via cytokine multiplexing are color coded as to the magnitude of antigen specific cytokine increase (red) or decrease (blue) with vaccination (displayed as a cytokine "heat map"). The intensity of the colors symbolizes lowest (pale) to highest (vivid) quartile of response. The data suggest specific patterns of Th response to the HER2 ICD protein (immunizing antigen). Th1/17, Th2, and "mixed". Patient 12 and 17 increased HER2 specific Type 1 cytokine and IL-17 secretion with vaccination. This type of response is similar to what would be expected after immunization with a vaccine designed to elicit Th1 immunity. Patient 16 decreased both HER2 specific Th1 and Th17 cytokine production. This phenotype may limit the development or retention of tumor antigen specific immunity. Data is expressed as post-vaccine minus pre-vaccine cytokine level (1 month after last vaccine). Dark red: $4^{th}$ (highest) quartile increase in cytokine level with descending red colors reflecting the $3^{rd}$, $2^{nd}$, and $1^{st}$ quartile increase respectively. Dark blue: $4^{th}$ (highest) quartile decrease in cytokine level with descending blue colors reflecting the $3^{rd}$, $2^{nd}$, and $1^{st}$ quartile decrease respectively.

Example 8

TABLE 26

Epitopes and Construct Sequences

| Name | Sequence | SEQ ID NO |
|---|---|---|
| IGFBP-2 | MLPRVGCPALPLPPPPLLPLLPLLLLLLGASGGGGGARAEVLFRCPPCTPER LAACGPPPVAPPAAVAAVAGGARMPCAELVREPGCGCCSVCARLEGEACG VYTPRCGQGLRCYPHPGSELPLQALVMGEGTCEKRRDAEYGASPEQVADN GDDHSEGGLVE | 54 |
| | ATGCTGCCGAGAGTGGGCTGCCCCGCGCTGCCGCTGCCGCCGCCGCCGC TGCTGCCGCTGCTGCCGCTGCTGCTGCTGCTACTGGGCGCGAGTGGCGG CGGCGGCGGGGCGCGCGCGGAGGTGCTGTTCCGCTGCCCGCCCTGCAC ACCCGAGCGCCTGGCCGCCTGCCTGGCCCCCGCCGGTTGCGCCGCCCGCC GCGGTGGCCGCAGTGGCCGGAGGCGCCCGCATGCCATGCGCGGAGCTC GTCCGGGAGCCGGGCTGCGGCTGCTGCTCGGTGTGCGCCCGGCTGGAG GGCGAGGCGTGCGGCGTCTACACCCCGCGCTGCGGCCAGGGGCTGCGC TGCTATCCCCACCCGGGCTCCGAGCTGCCCCTGCAGGCGCTGGTCATGG GCGAGGGCACTTGTGAGAAGCGCCGGGACGCCGAGTATGGCGCCAGCC CGGAGCAGGTTGCAGACAATGGCGATGACCACTCAGAAGGAGGCCTGG TGGAG | 43 |
| Survivin | GCAFLSVKKQFEELTLGEFLKLDRERAKNKIAKETNNK | 85 |
| | GGCTGCGCCTTCCTGTCCGTGAAGAAGCAGTTCGAGGAGCTGACCCTGG GCGAGTTCCTGAAGCTGGACCGCGAGCGCGCCAAGAACAAGATCGCCA AGGAGACCAACAACAAG | 86 |
| HIF-1A | RSKESEVFYELAHQLPLPHNVSSHLDKASVMRLTISYLRVRKLLDAGDLDI EDDMKAQMNCFYLKALDGFVMLTDDGDMIYISDNVNK | 87 |
| | CGCTCCAAGGAGTCCGAGGTGTTCTACGAGCTGGCCCACCAGCTGCCCC TGCCCCACAACGTGTCCTCCCACCTGGACAAGGCCTCCGTGATGCGCCT GACCATCTCCTACCTGCGCGTGCGCAAGCTGCTGGACGCtGGCGACCTG GACATCGAGGACGACATGAAGGCCCAGATGAACTGCTTCTACCTGAAG | 88 |

TABLE 26-continued

Epitopes and Construct Sequences

| Name | Sequence | SEQ ID NO |
|---|---|---|
| | GCCCTGGACGGCTTCGTGATGGTGCTGACCGACGACGGCGACATGATCT ACATCTCCGACAACGTGAACAAG | |
| IGF-1R | WSFGVVLWEIATLAEQPYQGLSNEQVLRFVMEGGLLDKPDNCPDMLFEL MRMCWQYNPKMRPSFLEHKAENGPGPGVLVLRASFDERQPYAHMNGGR KNERALP | 73 |
| | TGGTCCTTCGGCGTGGTGCTGTGGGAGATCGCCACCCTGGCCGAGCAGC CCTACCAGGGCCTGTCCAACGAGCAGGTGCTGCGCTTCGTGATGGAGGG CGGCCTGCTGGACAAGCCCGACAACTGCCCCGACATGCTGTTCGAGCTG ATGCGCATGTGCTGGCAGTACAACCCCAAGATGCGCCCCTCCTTCCTGG AGCACAAGGCCGAGAACGGCCCCGGCCCCGGCGTGCTGGTGCTGCGCG CCTCCTTCGACGAGCGCCAGCCCTACGCCCACATGAACGGaGGCCGCAA GAACGAGCGCGCCCTGCCC | 63 |
| IG-FBP2- Survivin- HIF1A- IGF1R | MAVPMLPRVGCPALPLPPPPLLPLLPLLLLLLGASGGGGGARAEVLFRCPPC TPERLAACGPPPVAPPAAVAAVAGGARMPCAELVREPGCGCCSVCARLEG EACGVYTPRCGQGLRCYPHPGSELPLQALVMGEGTCEKRRDAEYGASPEQ VADNGDDHSEGGLVEQLGCAFLSVKKQFEELTLGEFLKLDRERAKNKIAK ETNNKGSEFRSKESEVFYELAHQLPLPHNVSSHLDKASVMRLTISYLRVRK LLDAGDLDIEDDMKAQMNCFYLKALDGFVMVLTDDGDMIYISDNVNKYR SGRPVPWSFGVVLWEIATLAEQPYQGLSNEQVLRFVMEGGLLDKPDNCPD MLFELMRMCWQYNPKMRPSFLEHKAENGPGPGVLVLRASTDERQPYAHM NGGRKNERALPAAA | 89 |
| | ATGGCGGTACCaTGCTGCCGAGAGTGGGCTGCCCCGCGCTGCCGCTGC CGCCGCCGCCGCTGCTGCCGCTGCTGCCGCTGCTGCTGCTGCTACTGGG CGCGAGTGGCGGCGGCGGCGGGGCGCGCGCGGAGGTGCTGTTCCGCTG CCCGCCCTGCACACCCGAGCGCCTGGCCGCCTGCGGGCCCCCGCCGGTT GCGCCGCCCGCCGCGGTGGCCGCAGTGGCCGGAGGCGCCCGCATGCCA TGCGCGGAGCTCGTCCGGGAGCCGGGCTGCGGCTGCTGCTCGGTGTGCG CCCGGCTGGAGGGCGAGGCGTGCGGCGTCTACACCCCGCGCTGCGGCC AGGGGCTGCGCTGCTATCCCCACCCGGGCTCCGAGCTGCCCCTGCAGGC GCTGGTCATGGGCGAGGGCACTTGTGAGAAGCGCCGGGACGCCGAGTA TGGCGCCAGCCCGGAGCAGGTTGCAGACAATGGCGATGACCACTCAGA AGGAGGCCTGGTGGAGCaattgGGCTGCGCCTTCCTGTCCGTGAAGAAGCA GTTCGAGGAGCTGACCCTGGGCGAGTTCCTGAAGCTGGACCGCGAGCG CGCCAAGAACAAGATCGCCAAGGAGACCAACAACAAGgGATCCGAATT CCGCTCCAAGGAGTCCGAGGTGTTCTACGAGCTGGCCCACCAGCTGCCC CTGCCCCACAACGTGTCCTCCCACCTGGACAAGGCCTCCGTGATGCGCC TGACCATCTCCTACCTGCGCGTGCGCAAGCTGCTGGACGCtGGCGACCT GGACATCGAGGACGACATGAAGGCCCAGATGAACTGCTTCTACCTGAA GGCCCTGGACGGCTTCGTGATGGTGCTGACCGACGACGGCGACATGATC TACATCTCCGACAACGTGAACAAGTACagatccggccggCCGGTACCtTGGTC CTTCGGCGTGGTGCTGTGGGAGATCGCCACCCTGGCCGAGCAGCCCTAC CAGGGCCTGTCCAACGAGCAGGTGCTGCGCTTCGTGATGGAGGGCGGC CTGCTGGACAAGCCCGCAACTGCCCCGACATGCTGTTCGAGCTGATGC GCATGTGCTGGCAGTACAACCCCAAGATGCGCCCCTCCTTCCTGGAGCA CAAGGCCGAGAACGGCCCCGGCCCCGGCGTGCTGGTGCTGCGCGCCTC CTTCGACGAGCGCCAGCCCTACGCCCACATGAACGGaGGCCGCAAGAAC GAGCGCGCCCTGCCCGCGGCCGCATAG | 90 |
| pUMCV3- IGFBP2- Survivin- HIF1A- IGF1R | TGGCCATTGCATACGTTGTATCCATATCATAATATGTACATTTATATTGG CTCATGTCCAACATTACCGCCATGTTGACATTGATTATTGACTAGTTATT AATAGTAATCAATTACGGGGTCATTAGTTCATAGCCCATATATGGAGTT CCGCGTTACATAACTTACGGTAAATGGCCCGCCTGGCTGACCGCCCAAC GACCCCGCCCATTGACGTCAATAATGACGTATGTTCCCATAGTAACGC CAATAGGGACTTTCCATTGACGTCAATGGGTGGAGTATTTACGGTAAAC TGCCCACTTGGCAGTACATCAAGTGTATCATATGCCAAGTACGCCCCCT ATTGACGTCAATGACGGTAAATGGCCCGCCTGGCATTATGCCCAGTACA TGACCTTATGGGACTTTCCTACTTGGCAGTACATCTACGTATTAGTCATC GCTATTACCATGGTGATGCGGTTTTGGCAGTACATCAATGGGCGTGGAT AGCGGTTTGACTCACGGGGATTTCCAAGTCTCCACCCCATTGACGTCAA TGGGAGTTTGTTTTGGCACCAAAATCAACGGGACTTTCCAAAATGTCGT AACAACTCCGCCCCATTGACGCAAATGGGCGGTAGGCGTGTACGGTGG GAGGTCTATATAAGCAGAGCTCGTTTAGTGAACCGTCAGATCGCCTGGA GACGCCATCCACGCTGTTTTGACCTCCATAGAAGACACCGGGACCGATC CAGCCTCCGCGCCGGGAACGGTGCATTGGAACGCGGATTCCCCGTGCC AAGAGTGACGTAAGTACCGCCTATAGACTCTATAGGCACACCCCTTTGG CTCTTATGCATGCTATACTGTTTTTGGCTTGGGGCCTATACACCCCCGCT TCCTTATGCTATAGGTGATGGTATAGCTTAGCCTATAGGTGTGGGTTATT GACCATTATTGACCACTCCAACGGTGGAGGGCAGTGTAGTCTGAGCAGT ACTCGTTGCTGCCGCGCGCGCCACCAGACATAATAGCTGACAGACTAAC AGACTGTTCCTTTCCATGGGTCTTTTCTGCAGTCACCGTCGTCGACGGTA | 91 |

TABLE 26-continued

Epitopes and Construct Sequences

| Name | Sequence | SEQ ID NO |
|---|---|---|
| | TCGATAAGCTTGATATCGAATTGCCGCCACCATGGCGGTACCaATGCTG | |
| | CCGAGAGTGGGCTGCCCCGCGCTGCCGCTGCCGCCGCCGCTGCTGC | |
| | CGCTGCTGCCGCTGCTGCTGCTGCTACTGGGCGCGAGTGGCGGCGGCGG | |
| | CGGGGCGCGCGCGGAGGTGCTGTTCCGCTGCCCGCCCTGCACACCCGAG | |
| | CGCCTGGCCGCCTGCGGGCCCCCGCCGGTTGCGCCGCCCGCCGCGGTGG | |
| | CCGCAGTGGCCGGAGGCGCCCGCATGCCATGCGCGGAGCTCGTCCGGG | |
| | AGCCGGGCTGCGGCTGCTGCTCGGTGTGCGCCCGGCTGGAGGGCGAGG | |
| | CGTGCGGCGTCTACACCCCGCCGCTGCGGCCAGGGGCTGCGCTGCTATCC | |
| | CCACCCGGGCTCCGAGCTGCCCCTGCAGGCGCTGGTCATGGGCGAGGG | |
| | CACTTGTGAGAAGCGCCGGGACGCCGAGTATGGCGCCAGCCCGGAGCA | |
| | GGTTGCAGACAATGGCGATGACCACTCAGAAGGAGGCCTGGTGGAGCaa | |
| | ttgGGCTGCGCCTTCCTGTCCGTGAAGAAGCAGTTCGAGGAGCTGACCCT | |
| | GGGCGAGTTCCTGAAGCTGGACCGCGAGCGCGCCAAGAACAAGATCGC | |
| | CAAGGAGACCAACAACAAGgGATCCGAATTCCGCTCCAAGGAGTCCGA | |
| | GGTGTTCTACGAGCTGGCCCACCAGCTGCCCCTGCCCCACAACGTGTCC | |
| | TCCCACCTGGACAAGGCCTCCGTGATGCGCCTGACCATCTCCTACCTGC | |
| | GCGTGCGCAAGCTGCTGGACGCtGGCGACCTGGACATCGAGGACGACAT | |
| | GAAGGCCCAGATGAACTGCTTCTACCTGAAGGCCCTGGACGGCTTCGTG | |
| | ATGGTGCTGACCGACGACGGCGACATGATCTACATCTCCGACAACGTGA | |
| | ACAAGTACagatccggccggCCGGTACCtTGGTCCTTCGGCGTGGTGCTGTGGG | |
| | AGATCGCCACCCTGGCCGAGCAGCCCTACCAGGGCCTGTCCAACGAGC | |
| | AGGTGCTGCGCTTCGTGATGGAGGGCGGCCTGCTGGACAAGCCCGACA | |
| | ACTGCCCCGACATGCTGTTCGAGCTGATGCGCATGTGCTGGCAGTACAA | |
| | CCCCAAGATGCGCCCCTCCTTCCTGGAGCACAAGGCCGAGAACGGCCCC | |
| | GGCCCCGGCGTGCTGGTGCTGCGCGCCTCCTTCGACGAGCGCCAGCCCT | |
| | ACGCCCACATGAACGGaGGCCGCAAGAACGAGCGCGCCCTGCCCGCGG | |
| | CCGCATAGTGATAGATCTTTTTCCCTCTGCCAAAAATTATGGGGACATC | |
| | ATGAAGCCCCTTGAGCATCTGACTTCTGGCTAATAAAGGAAATTTATTT | |
| | TCATTGCAATAGTGTGTTGGAATTTTTTGTGTCTCTCACTCGGAAGGACA | |
| | TATGGGAGGGCAAATCATTTAAAACATCAGAATGAGTATTTGGTTTAGA | |
| | GTTTGGCAACATATGCCCATTCTTCCGCTTCCTCGCTCACTGACTCGCTG | |
| | CGCTCGGTCGTTCGGCTGCGGCGAGCGGTATCAGCTCACTCAAAGGCGG | |
| | TAATACGGTTATCCACAGAATCAGGGGATAACGCAGGAAAGAACATGT | |
| | GAGCAAAAGGCCAGCAAAAGGCCAGGAACCGTAAAAAGGCCGCGTTG | |
| | CTGGCGTTTTTCCATAGGCTCCGCCCCCCTGACGAGCATCACAAAAATC | |
| | GACGCTCAAGTCAGAGGTGGCGAAACCCGACAGGACTATAAAGATACC | |
| | AGGCGTTTCCCCCTGGAAGCTCCCTCGTGCGCTCTCCTGTTCCGACCCTG | |
| | CCGCTTACCGGATACCTGTCCGCCTTTCTCCCTTCGGGAAGCGTGGCGCT | |
| | TTCTCATAGCTCACGCTGTAGGTATCTCAGTTCGGTGTAGGTCGTTCGCT | |
| | CCAAGCTGGGCTGTGTGCACGAACCCCCCGTTCAGCCCGACCGCTGCGC | |
| | CTTATCCGGTAACTATCGTCTTGAGTCCAACCCGGTAAGACACGACTTA | |
| | TCGCCACTGGCAGCAGCCACTGGTAACAGGATTAGCAGAGCGAGGTAT | |
| | GTAGGCGGTGCTACAGAGTTCTTGAAGTGGTGGCCTAACTACGGCTACA | |
| | CTAGAAGAACAGTATTTGGTATCTGCGCTCTGCTGAAGCCAGTTACCTT | |
| | CGGAAAAAGAGTTGGTAGCTCTTGATCCGGCAAACAAACCACCGCTGG | |
| | TAGCGGTGGTTTTTTTGTTTGCAAGCAGCAGATTACGCGCAGAAAAAAA | |
| | GGATCTCAAGAAGATCCTTTGATCTTTTCTACGGGGTCTGACGCTCAGT | |
| | GGAACGAAAACTCACGTTAAGGGATTTTGGTCATGAGATTATCAAAAA | |
| | GGATCTTCACCTAGATCCTTTTAAATTAAAAATGAAGTTTTAAATCAAT | |
| | CTAAAGTATATATGAGTAAACTTGGTCTGACAGTTACCAATGCTTAATC | |
| | AGTGAGGCACCTATCTCAGCGATCTGTCTATTTCGTTCATCCATAGTTGC | |
| | CTGACTCGGGGGGGGGGGCGCTGAGGTCTGCCTCGTGAAGAAGGTGT | |
| | TGCTGACTCATACCAGGCCTGAATCGCCCCATCATCCAGCCAGAAAGTG | |
| | AGGGAGCCACGGTTGATGAGAGCTTTGTTGTAGGTGGACCAGTTGGTGA | |
| | TTTTGAACTTTTGCTTTGCCACGGAACGGTCTGCGTTGTCGGGAAGATG | |
| | CGTGATCTGATCCTTCAACTCAGCAAAAGTTCGATTTATTCAACAAAGC | |
| | CGCCGTCCCGTCAAGTCAGCGTAATGCTCTGCCAGTGTTACAACCAATT | |
| | AACCAATTCTGATTAGAAAAACTCATCGAGCATCAAATGAAACTGCAAT | |
| | TTATTCATATCAGGATTATCAATACCATATTTTTGAAAAAGCCGTTTCTG | |
| | TAATGAAGGAGAAAACTCACCGAGGCAGTTCCATAGGATGGCAAGATC | |
| | CTGGTATCGGTCTGCGATTCCGACTCGTCCAACATCAATACAACCTATT | |
| | ATTTCCCCTCGTCAAAAATAAGGTTATCAAGTGAGAAATCACCATGAG | |
| | TGACGACTGAATCCGGTGAGAATGGCAAAAGCTTATGCATTTCTTTCCA | |
| | GACTTGTTCAACAGGCCAGCCATTACGCTCGTCATCAAAATCACTCGCA | |
| | TCAACCAAACCGTTATTCATTCGTGATTGCGCCTGAGCGAGACGAAATA | |
| | CGCGATCGCTGTTAAAAGGACAATTACAAACAGGAATCGAATGCAACC | |
| | GGCGCAGGAACACTGCCAGCGCATCAACAATATTTTCACCTGAATCAGG | |
| | ATATTCTTCTAATACCTGGAATGCTGTTTTCCCGGGGATCGCAGTGGTG | |
| | AGTAACCATGCATCATCAGGAGTACGGATAAAATGCTTGATGGTCGGA | |
| | AGAGGCATAAATTCCGTCAGCCAGTTTAGTCTGACCATCTCATCTGTAA | |
| | CATCATTGGCAACGCTACCTTTGCCATGTTTCAGAAACAACTCTGGCGC | |
| | ATCGGGCTTCCCATACAATCGATAGATTGTCGCACCTGATTGCCCGACA | |
| | TTATCGCGAGCCCATTTATACCCATATAAATCAGCATCCATGTTGGAAT | |
| | TTAATCGCGGCCTCGAGCAAGACGTTTCCCGTTGAATATGGCTCATAAC | |

TABLE 26-continued

Epitopes and Construct Sequences

| Name | Sequence | SEQ ID NO |
|---|---|---|
| | ACCCCTTGTATTACTGTTTATGTAAGCAGACAGTTTTATTGTTCATGATG ATATATTTTTATCTTGTGCAATGTAACATCAGAGATTTTGAGACACACAAC GTGGCTTTCCCCCCCCCCCCATTATTGAAGCATTTATCAGGGTTATTGTC TCATGAGCGGATACATATTTGAATGTATTTAGAAAAATAAACAAATAGG GGTTCCGCGCACATTTCCCCGAAAAGTGCCACCTGACGTCTAAGAAACC ATTATTATCATGACATTAACCTATAAAAATAGGCGTATCACGAGGCCCT TTCGTCTCGCGCGTTTCGGTGATGACGGTGAAACCTCTGACACATGCA GCTCCCGGAGACGGTCACAGCTTGTCTGTAAGCGGATGCCGGGAGCAG ACAAGCCCGTCAGGGCGCGTCAGCGGGTGTTGGCGGGTGTCGGGGCTG GCTTAACTATGCGGCATCAGAGCAGATTGTACTGAGAGTGCACCATATG CGGTGTGAAATACCGCACAGATGCGTAAGGAGAAAATACCGCATCAGA TTGGCTAT | |

Example 9

Multi-Antigen Construct Design and Expression

Figure 40:
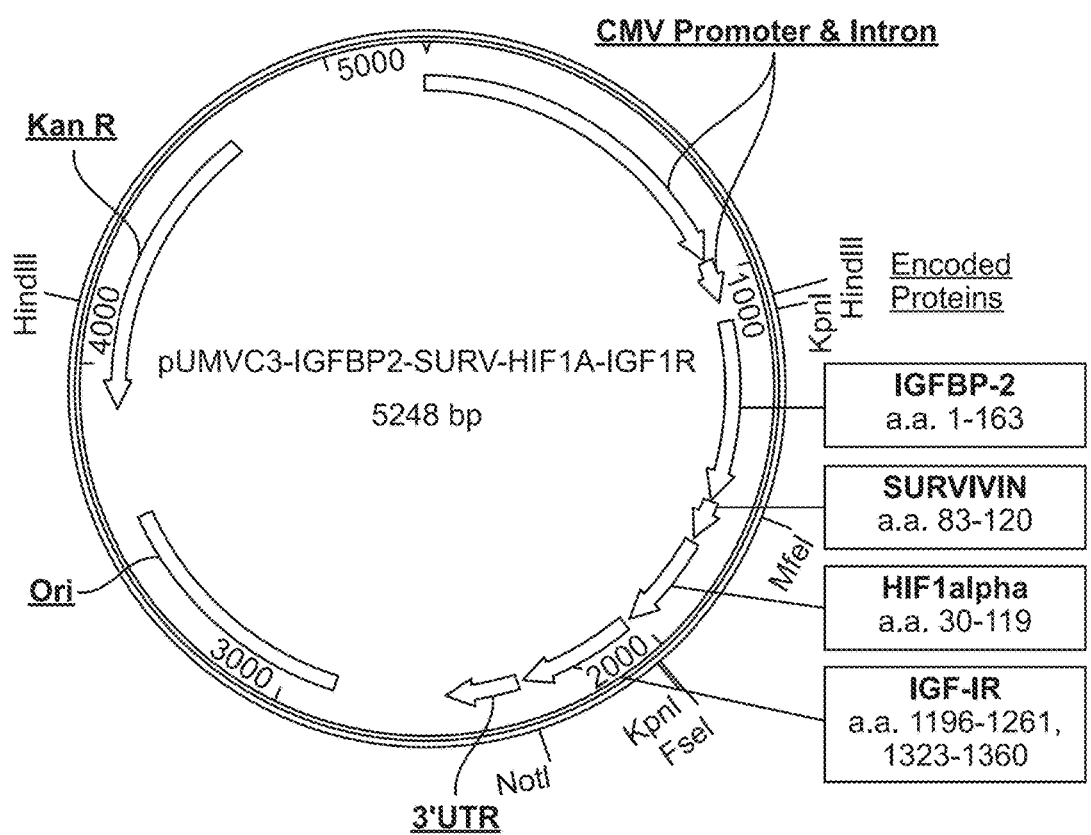
FIG. 40 illustrates a cartoon representation of a construct described herein.
Figure 41:
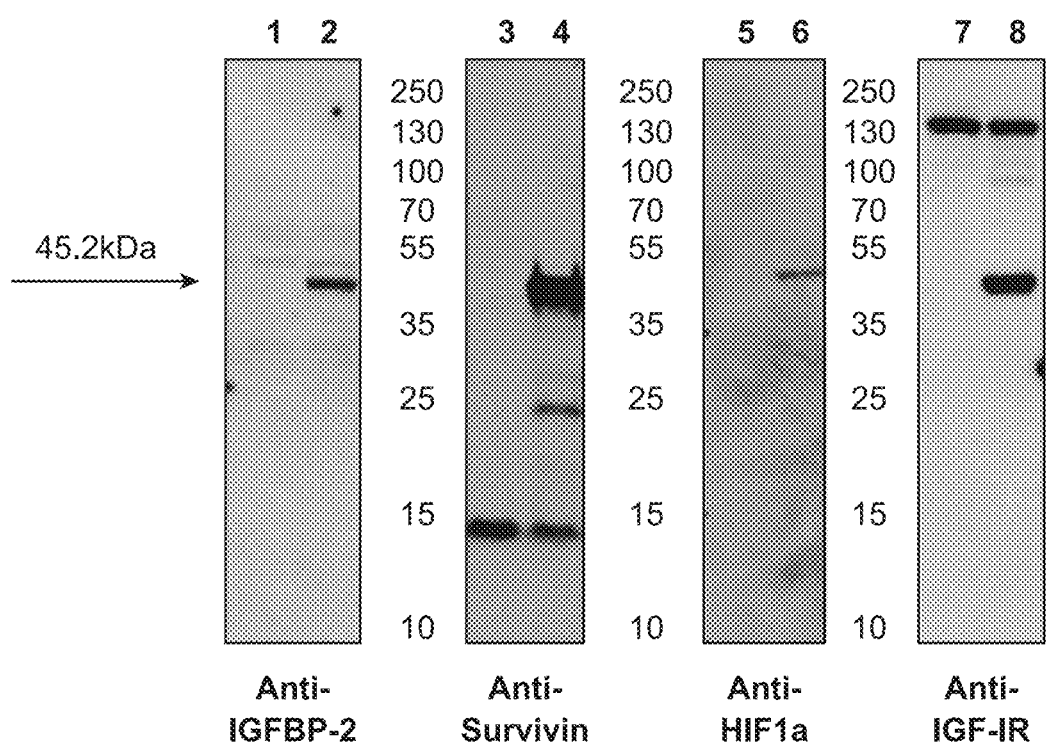
FIG. 41 shows a Western Blot image of IGFBP-2, Survivin, HIF-1A, and IGF-1R expression.

The pUMVC3-IGFBP2-Survivin-HIF1a-IGF1R fusion construct is according to FIG. 40 and Table 27. The fusion protein was expressed in HEK-293 cells and protein expression was checked by western blot analysis. The protein expression bands were further quantified using the NIH Image J software. FIG. 41 illustrates the protein expression of IGFBP-2, Survivin, HIF-1A, and IGF-1R

TABLE 27

| Tumor Antigen | RefSeq Number | Amino Acids | Mouse Homology |
|---|---|---|---|
| IGFBP-2 | NP_000588 | 1-163 | 72% |
| Survivin | NP_001159 | 83-120 | 87% |
| HIF1a | NP_001521 | 30-119 | 94% |
| IGF-IR | NP_000866 | 1196-1261 | 100% |
| | | 1323-1360 | 97% |

Example 10

Lentiviral Infection of ID8 with Luciferase Vector and Cell Line Selection

ID8 cells, ovarian surface epithelial cells derived from the C57B6 mice were infected with 2 mL/well pLentiIII-Luc2 viral vector supernatant (Applied Biological Materials Inc.) in the presence of 8 µg/ml polybrene (EMD Millipore Corporation). After overnight incubation at 37° C./5% $CO_2$, the viral supernatant and media with polybrene were removed and the plate was washed with PBS prior to the addition of warmed media. Cells were cultured in growth media for 72 hours and then placed under drug selection with 1 µg/mL puromycin, added daily (Invitrogen). One hundred µl of cells were added per well in a white 96-well plate (EMD Millipore Corporation) and equal volume of 3000 µg/ml d-luciferin was added immediately before reading. Lines were selected based maximal relative light units after addition of substrate as a measure of functional luciferase expression.

In Vivo Propagation of ID8-Luc2 Tumors.

Albino C57/BL/6/BrdCsHsd-Tyr$^c$ (Harlan Laboratories) were given a 200 µL intraperitoneal injection of 5×10$^6$ ID8 cells. With the mouse in the supine position, half the dose was injected using a 25 gauge needle in the lower left quadrant and the other half in the lower right quadrant. At designated intervals after tumor implant, the mice were weighed, bled, and imaged to monitor tumor progression.

Bioluminescence/Imaging.

Figure 42A:
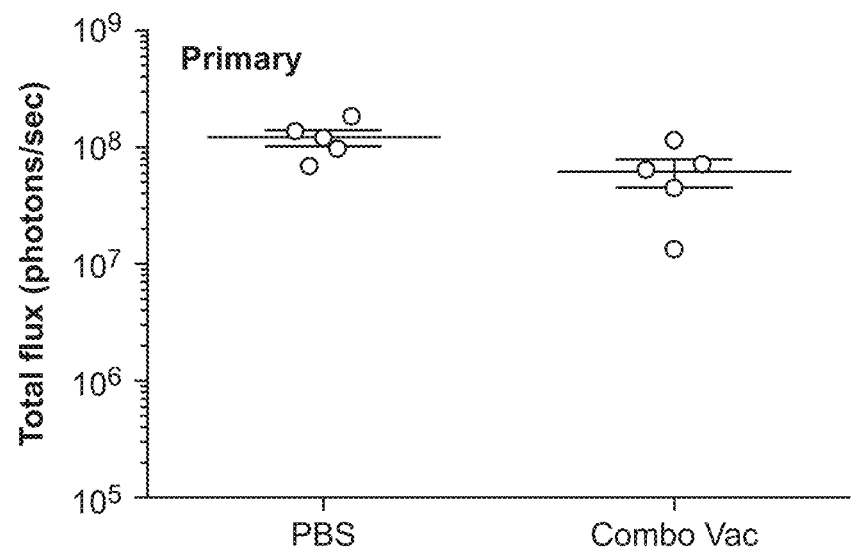
FIG. 42A-FIG. 42D show the anti-tumor effects of a multi-antigen vaccine in ID8 ovarian cancer implant model. Mice were imaged on an IVIS Bioluminescent Imager three weeks after implant of ID8-Luc. Total flux (photons/second) were measure in Primary implant (FIG. 42A) and metastatic sites (FIG. 42B). Representative animals are shown as adjuvant alone (FIG. 42C), and Tri-antigen vaccinated (FIG. 42D).
Figure 42B:
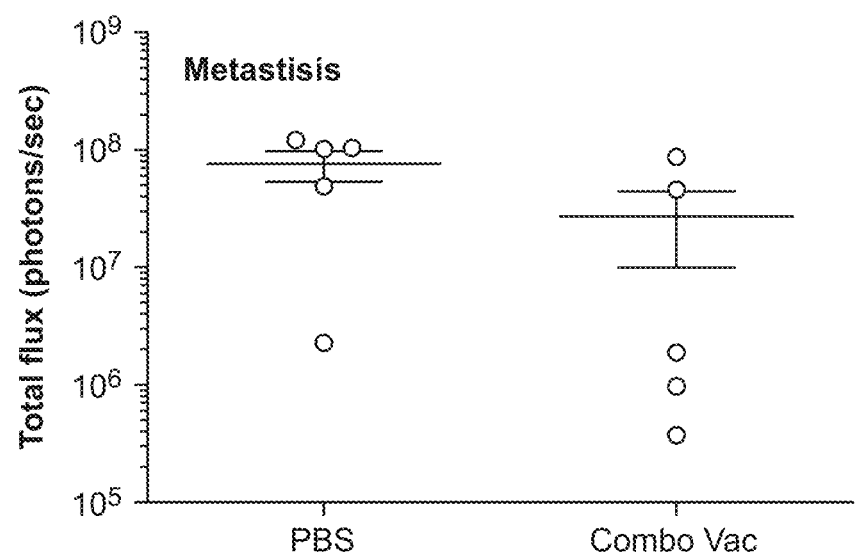

Bioluminescent images were taken with Xenogen IVIS using D-luciferin, (In Vivo Imaging Solutions) (FIG. 42A-FIG. 42B). Images were normalized using Living Image software (PerkinElmer). Maximum luminescent intensity and total flux in photons per second were calculated and reported for each mouse's upper abdominal (metastasis) or lower abdominal (primary) region.

Figure 42C:
Figure 42D:
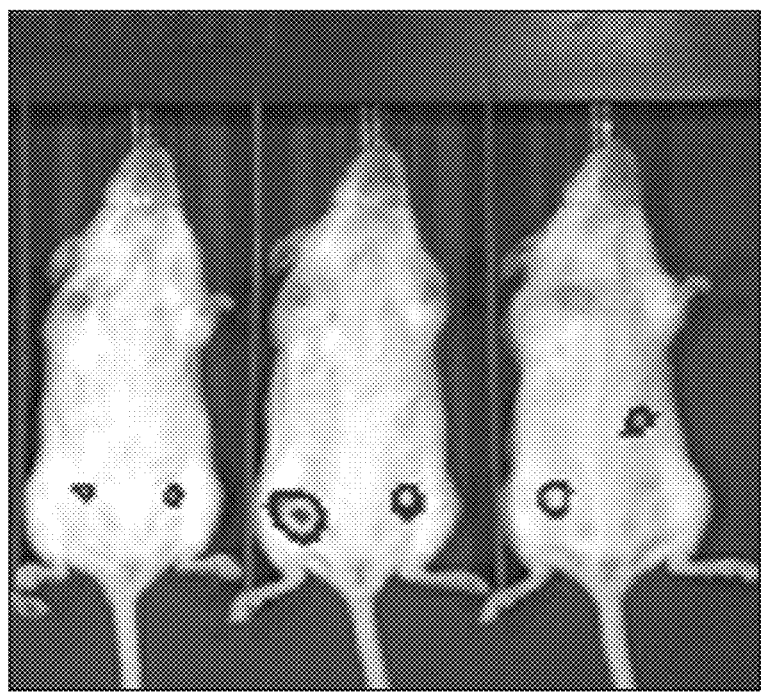

FIG. 42A shows the total flux (photons/second) in Primary implant and FIG. 3B shows the total flux at the metastatic sites. In addition, representative animals are shown as adjuvant alone (FIG. 42C), and Tri-antigen vaccinated (FIG. 42D).

Example 11

Method of Identifying Promiscuous MHC Class II Epitopes for Development of Human Vaccines Predicted MHCII epitopes to 14 of the frequent HLA-DR proteins were identified using compiled results from three different publicly available algorithms. The algorithm-generated epitope binding scores were used to map epitopes within protein sequences predicted to contain epitopes that interact with multiple HLA-DR proteins, referred to as "promiscuous epitopes". The 14 HLA-DR proteins screened by the algorithms were: HLA-DRB1*0101, HLA-DRB1*0301, HLA-DRB1*0401, HLA-DRB1*0404, HLA-DRB1*0405, HLA-DRB1*0701, HLA-DRB1*0802, HLA-DRB1*0901, HLA-DRB1*1101, HLA-DRB1*1201, HLA-DRB1*1302, HLA-DRB1*1501, HLA-DRB4*0101, and HLA-DRB5*0101. The web-based algorithms employed were SYFPEITHI (http://www.syfpeithi.de/Scripts/MHC-Server.dll/EpitopePrediction.htm), PROPRED (http://www.imtech.res.in/raghava/propred/), and RANKPEP (http://imed.med.ucmes,Tools/rankpep.html). The number of HLA-DR proteins available for screening varied for each website (6, 11, or 13 of the 14 listed above). Query protein sequences were obtained from the NCBI database and copied in the FASTA format for entry into the algorithm search engines and the top twenty scoring epitopes for each HLA-DR protein were used to create the "MHCII heatmap" of the query protein. For compiling and analyzing the epitope prediction data a MS Excel-based workbook was developed, referred to as the "MHCII Heatmap Template". Because each of the three algorithms has a different numerical scoring system for identified epitopes, the epitope scores were first normalized before compiling results from the different search methods. To normalize epitope scores, all scores were divided by the top score obtained by each algorithm, such that the epitope with the highest predicted affinity would have a normalized score of 1.0. The normalized scores were then pasted in to the MHCII Heatmap Template, which, with several embedded equations and functions, performed the following tasks: (i) each amino acid of a particular epitope was assigned the normalized score of the epitope, (ii) the number of different HLA-DR proteins/alleles that had epitopes at each amino acid position was calculated and graphed, (iii) the sum of the normalized scores from every epitope was calculated and graphed at every amino acid position, and (iv) a "Multiple Score" was calculated and graphed, which was the product of the normalized score sum and the number of HLA-DR alleles. The Multiple Score represents both the epitope binding strength and the epitope promiscuity, and this value was used to create the MHCII heatmap of the query protein. The graph of amino acid position (x axis) versus Multiple Score (y axis) allows easy visualization of protein regions predicted to contain promiscuous epitopes. Additionally, an MS Access application was created to simplify the input of FASTA protein sequences into vertical columns of the MHCII Heatmap Template. Once protein sequence has been entered, MHCII heatmap figures can be created by color-coding the amino acids based on Multiple Score values to aid in peptide selection for immunological assays. Generally, color-coding indicates Multiple Scores of 75-100%, 50-75%, 25-50%, and 10-25%.

Peptides were constructed based on composite scores. Peripheral blood mononuclear cells (PBMC) from 40 human donors were evaluated by ELISPOT for antigen-specific IFN-gamma (g) and IL-10 production induced by the predicted epitopes covering a minimum of 25% of the protein. For the IFN-g ELISPOT, cells were plated at 2×105 per well (96-well plate) in medium with 10 ug/mL of the various peptides or HIVp17, PHA (1 ug/ml), CEF (2.5 ug/mL) or medium alone for 7 days at 37° C. in 5% CO2. On day 5, recombinant human IL-2 (10 U/ml) was added. A second in vitro stimulation (IVS) was performed on day 8 by adding 2×105 peptide-loaded (same concentrations as listed above) autologous irradiated (3000 rads) human PBMC to the original culture, and incubated for 24 h. 96-well nitrocellulose plates were coated with 10 ug/ml anti-human IFN-g. The washed nitrocellulose plates were blocked with 2% bovine serum albumin in DPBS followed by a 24 h incubation with the PBMC culture. After extensive washing, biotinylated anti-human IFN-g was added for 2 h. For the IL-10 ELISPOT, an anti-human IL-10-coated (2 ug/ml) nitrocellulose 96-well plate was blocked as described above. PBMC concentration and peptide stimulations were as described above, except that PHA was used at 20 ug/ml. After extensive washing, biotinylated anti-human IL-10 was added for 2 h. After extensive washing, 1 ug/mL Streptavidin-AP was added for 45 minutes. Spots were visualized by incubating the plate with BCIP and NBT solutions spots were counted on the C.T.L. ELISPOT plate reader. The raw data was imported into the TVG database ELISPOT tool and positive responses were defined by a statistically significant difference ($p<0.05$) between the mean number of spots from five replicates in the experimental wells and the mean number from no antigen control wells. A TH1/TH2 ratio was created that analyzed both the magnitude and frequency of ELISPOT responses for each of the predicted class II-specific peptides using the following algorithm: (corrected mean spots per well)×(percent of responding donors). TH1/TH2 activity ratios are also derived from ELISA assays for the Type I and II cytokines using antigen specific T-cell stimulated media as well as by multi-plex assay for complex TH1TH2 phenotypes. Incidence and magnitude are incorporated into those analyses in a similar fashion.

Figure 43A:
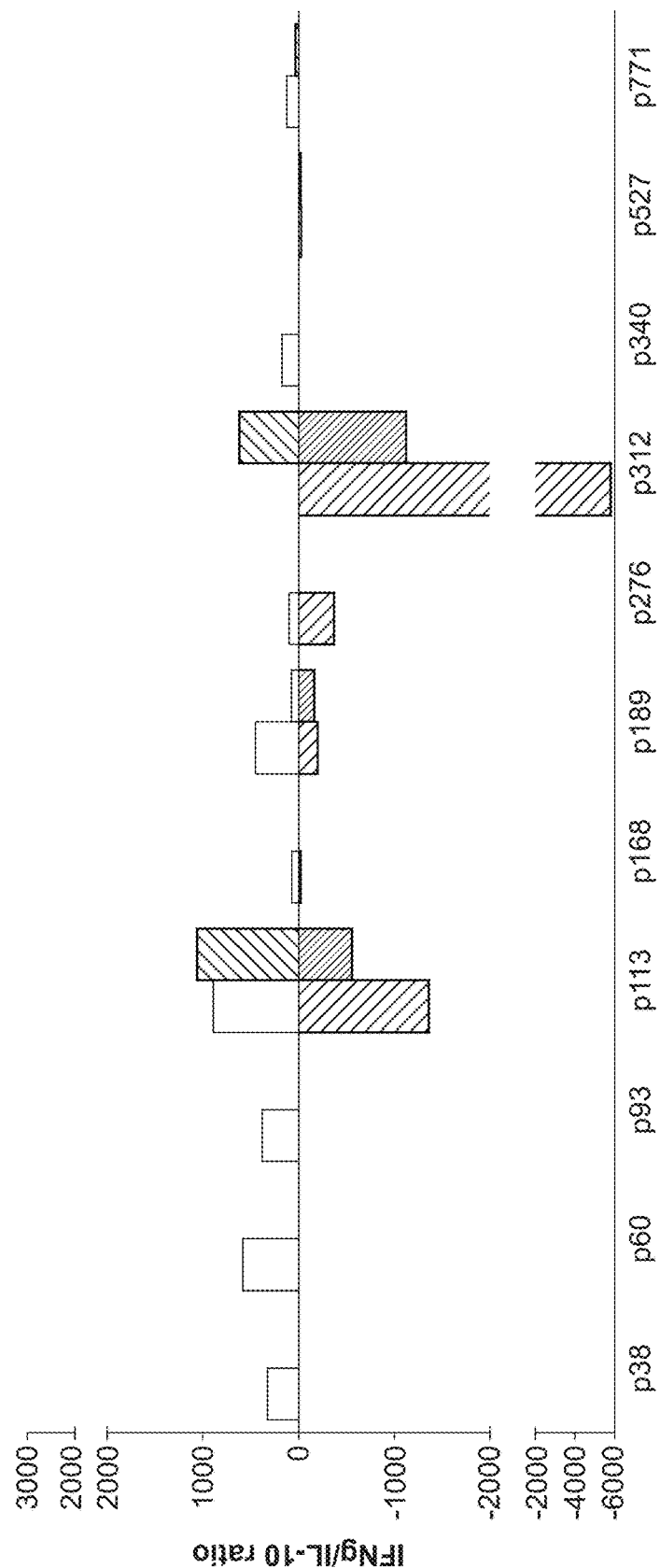
FIG. 43A and FIG. 43B illustrate TH1 response as a function of protein sequences. Selective TH1 inducing sequences were identified in the N-terminus of HIF1α and the C-terminus of survivin. The mean cSPW×incidence per peptide is shown by donor type. IFN-g cSPW×incidence is shown on the positive y-axis for volunteer donors (n=20) (white) and cancer donors (n=20) (gray). IL-10 cSPW× incidence is shown on the negative y-axis for volunteer donors (solid black) and cancer donors (dotted black).
Figure 43B:
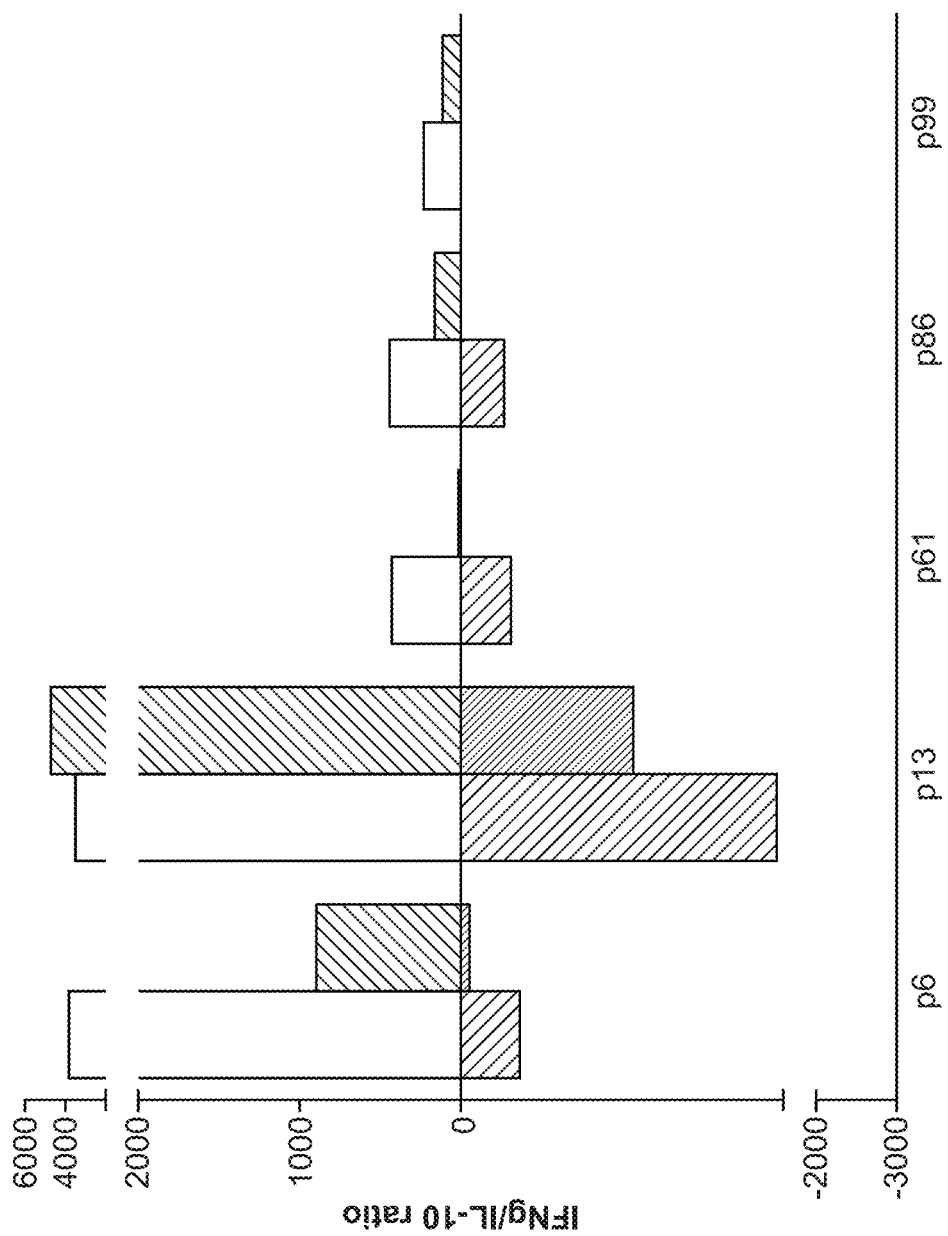

FIG. 43A and FIG. 43B illustrate TH1 response as a function of protein sequences. Selective TH1 inducing sequences were identified in the N-terminus of HIF1a and the C-terminus of Survivin. The mean cSPW×incidence per peptide is shown by donor type. IFN-g cSPW×incidence is shown on the positive y-axis for volunteer donors (n=20) (white) and cancer donors (n=20) (gray). IL-10 cSPW×incidence is shown on the negative y-axis for volunteer donors (solid black) and cancer donors (dotted black). FIG. 43A shows the TH1 response with respect to HIF-1A peptides. FIG. 43B shows the TH1 response with respect to Survivin peptides. Vertical lines show the selected sequences.

Example 12

Studies of antibody immunity show that IGF-IR, HIF1a and Survivin are also ovarian cancer antigens (FIG. 44). It was previously demonstrated that IGFBP-2 is immunogenic in ovarian cancer patients. Serum samples were taken at the time of primary surgery from 120 patients with ovarian cancer and analyzed by indirect ELISA using commercially available recombinant proteins. 100 age-matched volunteer control sera were analyzed in a similar fashion. IgG antibodies were assessed as an indicator of cellular immunity as cognate CD4+ T-cells are needed for immunoglobulin class switching from IgM to IgG. Results were confirmed by Western blot. Ovarian cancer patients had significantly higher levels of antibodies to the antigenic proteins than controls (FIG. 44). Patients also demonstrated a significantly higher incidence of antibodies ranging from 8-25% positively (median 15%) compared to controls (range 1-6%).

What is claimed is:

1. A composition comprising an amino acid sequence having at least 95% sequence identity to the amino acid sequence of SEQ ID NO: 39 or a fragment thereof, wherein SEQ ID NO: 39 or the fragment thereof is a fusion protein, and wherein SEQ ID NO: 39 or the fragment thereof comprise a plurality of epitopes, wherein the plurality of epitopes comprises all the amino acid sequences of SEQ ID NO: 1, SEQ ID NO: 16, SEQ ID NO: 20, SEQ ID NO: 25, and SEQ ID NO: 32.

2. The composition of claim 1, wherein the amino acid sequence has at least 99% sequence identity to the amino acid sequence of SEQ ID NO: 39 or the fragment thereof.

3. The composition of claim 1, wherein the amino acid sequence consists of the amino acid sequence of SEQ ID NO: 39.

4. The composition of claim 1, wherein the composition further comprises a pharmaceutical carrier, an adjuvant, or a combination thereof.

5. The composition of claim 4, wherein the adjuvant is GM-CSF.

6. The composition of claim 1, wherein the plurality of epitopes comprises a plurality of contiguous epitopes.

7. The composition of claim 1, wherein the plurality of epitopes comprises one or more linkers between one or more epitopes.

8. A method of treating a breast or ovarian cancer in a subject in need thereof, the method comprising:
    a) administering the composition of claim 1 to the subject; and
    b) eliciting an immune response to a breast or ovarian cancer cell in the subject.

9. A method of treating a breast or ovarian cancer in a subject in need thereof, the method comprising:
    a) administering the composition of claim 1 to the subject; and
    b) eliminating a number of breast or ovarian cancer cells in the subject.

10. The method of claim 8, wherein the immune response is a Type I immune response.

11. The method of claim 8, wherein the immune response is characterized by a ratio of Type I cytokine production to Type II cytokine production that is greater than 1.

12. The method of claim 8, wherein the immune response is characterized by a ratio of IFNg production to IL-10 production that is greater than 1.

* * * * *

UNITED STATES PATENT AND TRADEMARK OFFICE
CERTIFICATE OF CORRECTION

PATENT NO. : 10,293,035 B2
APPLICATION NO. : 15/300208
DATED : May 21, 2019
INVENTOR(S) : Disis et al.

Page 1 of 1

It is certified that error appears in the above-identified patent and that said Letters Patent is hereby corrected as shown below:

In the Specification

In Column 1, Lines 16-20, delete "This invention was made with the support of the United States government under grant number W81XWH-11-1-0760 by the Department of Defense, grant number P50CA083636 by the National Cancer Institute and grant number R01CA098761 by the National Cancer Institute." and insert:

-- This invention was made with Government support under Grant W81XWH-11-1-0760 awarded by the Department of Defense and Grants P50CA083636 and R01CA098761 awarded by the National Cancer Institute. The Government has certain rights in the invention. --

Signed and Sealed this
Twenty-fourth Day of January, 2023

Katherine Kelly Vidal
*Director of the United States Patent and Trademark Office*

SEQUENCE LISTING

```
<160> NUMBER OF SEQ ID NOS: 91

<210> SEQ ID NO 1
<211> LENGTH: 52
<212> TYPE: PRT
<213> ORGANISM: Artificial Sequence
<220> FEATURE:
<223> OTHER INFORMATION: Synthetic polynucleotide or polypeptide

<400> SEQUENCE: 1

Gln Asn Gly Thr Trp Pro Arg Glu Val Leu Leu Val Leu Ser Val Asn
1               5                   10                  15

Ser Ser Val Phe Leu His Leu Gln Ala Leu Gly Ile Pro Leu His Leu
            20                  25                  30
```

```
Ala Tyr Asn Ser Ser Leu Val Thr Phe Gln Glu Pro Pro Gly Val Asn
         35                  40                  45

Thr Thr Glu Leu
    50

<210> SEQ ID NO 2
<211> LENGTH: 156
<212> TYPE: DNA
<213> ORGANISM: Artificial Sequence
<220> FEATURE:
<223> OTHER INFORMATION: Synthetic polynucleotide or polypeptide

<400> SEQUENCE: 2
cagaacggca cctggccccg cgaggtgctg ctggtgctgt ccgtgaactc ctccgtgttc      60
ctgcacctac aggccctggg catcccctg cacctggcct acaactcctc cctggtgacc     120
ttccaggagc ccccggcgt gaacaccacc gagctg                                156

<210> SEQ ID NO 3
<211> LENGTH: 276
<212> TYPE: DNA
<213> ORGANISM: Artificial Sequence
<220> FEATURE:
<223> OTHER INFORMATION: Synthetic polynucleotide or polypeptide

<400> SEQUENCE: 3
accgtgttca tgcgcctgaa catcatctcc cccgacctgt ccggctgcac ctccaagggc      60
ctggtgctgc cgccgtgct gggcatcacc ttcggcgcct tcctgatcgg cgccctgctg     120
accgccgccc tgtggtacat ctactcccac acccgctccc cctccaagcg cgagcccgtg     180
gtggccgtgg ccgcccccgc ctcctccgag tcctcctcca ccaaccactc catcggctcc     240
acccagtcca cccctgctc cacctcctcc atggcc                                276

<210> SEQ ID NO 4
<211> LENGTH: 267
<212> TYPE: DNA
<213> ORGANISM: Artificial Sequence
<220> FEATURE:
<223> OTHER INFORMATION: Synthetic polynucleotide or polypeptide

<400> SEQUENCE: 4
accgtgtcca tgcgcctgaa catcgtgtcc cccgacctgt ccggcaaggg cctggtgctg      60
ccctccgtgc tgggcatcac cttcggcgcc ttcctgatcg gcgccctgct gaccgccgcc     120
ctgtggtaca tctactccca cacccgcggc cctccaagc gcgagcccgt ggtggccgtg     180 gccgccccg cctcctccga gtcctcctcc accaaccact ccatcggctc cacccagtcc     240
accccctgct ccacctcctc catggcc                                         267

<210> SEQ ID NO 5
<211> LENGTH: 267
<212> TYPE: DNA
<213> ORGANISM: Artificial Sequence
<220> FEATURE:
<223> OTHER INFORMATION: Synthetic polynucleotide or polypeptide

<400> SEQUENCE: 5
accgtgtcca tgcgcctgaa catcgtgtcc cccgacctgt ccggcaaggg cctggtgctg      60
ccctccgtgc tgggcatcac cttcggcgcc ttcctgatcg gcgccctgct gaccgccgcc     120
ctgtggtaca tctactccca cacccgcgcc cctccaagc gcgagcccgt ggtggccgtg     180
```

```
gccgccccecg cctcctccga gtcctcctcc accaaccact ccatcggctc cacccagtcc    240
accccctgct ccacctcctc catggcc                                         267
```

```
<210> SEQ ID NO 6
<211> LENGTH: 18
<212> TYPE: PRT
<213> ORGANISM: Artificial Sequence
<220> FEATURE:
<223> OTHER INFORMATION: Synthetic polynucleotide or polypeptide

<400> SEQUENCE: 6

Glu Ala Arg Met Leu Asn Ala Ser Ile Val Ala Ser Phe Val Glu Leu
1               5                   10                  15

Pro Leu

<210> SEQ ID NO 7
<211> LENGTH: 52
<212> TYPE: PRT
<213> ORGANISM: Artificial Sequence
<220> FEATURE:
<223> OTHER INFORMATION: Synthetic polynucleotide or polypeptide

<400> SEQUENCE: 7

Gln Asn Gly Thr Trp Pro Arg Glu Val Leu Leu Val Leu Ser Val Asn
1               5                   10                  15

Ser Ser Val Phe Leu His Leu Gln Ala Leu Gly Ile Pro Leu His Leu
            20                  25                  30

Ala Tyr Asn Ser Ser Leu Val Thr Phe Gln Glu Pro Pro Gly Val Asn
        35                  40                  45

Thr Thr Glu Leu
    50

<210> SEQ ID NO 8
<211> LENGTH: 92
<212> TYPE: PRT
<213> ORGANISM: Artificial Sequence
<220> FEATURE:
<223> OTHER INFORMATION: Synthetic polynucleotide or polypeptide

<400> SEQUENCE: 8

Thr Val Phe Met Arg Leu Asn Ile Ile Ser Pro Asp Leu Ser Gly Cys
1               5                   10                  15

Thr Ser Lys Gly Leu Val Leu Pro Ala Val Leu Gly Ile Thr Phe Gly
            20                  25                  30

Ala Phe Leu Ile Gly Ala Leu Leu Thr Ala Ala Leu Trp Tyr Ile Tyr
        35                  40                  45

Ser His Thr Arg Ser Pro Ser Lys Arg Glu Pro Val Val Ala Val Ala
    50                  55                  60

Ala Pro Ala Ser Ser Glu Ser Ser Thr Asn His Ser Ile Gly Ser
65                  70                  75                  80

Thr Gln Ser Thr Pro Cys Ser Thr Ser Ser Met Ala
                85                  90

<210> SEQ ID NO 9
<211> LENGTH: 89
<212> TYPE: PRT
<213> ORGANISM: Artificial Sequence
<220> FEATURE:
<223> OTHER INFORMATION: Synthetic polynucleotide or polypeptide
```

<400> SEQUENCE: 9

Thr Val Ser Met Arg Leu Asn Ile Val Ser Pro Asp Leu Ser Gly Lys
1               5                   10                  15

Gly Leu Val Leu Pro Ser Val Leu Gly Ile Thr Phe Gly Ala Phe Leu
            20                  25                  30

Ile Gly Ala Leu Leu Thr Ala Ala Leu Trp Tyr Ile Tyr Ser His Thr
        35                  40                  45

Arg Gly Pro Ser Lys Arg Glu Pro Val Val Ala Val Ala Ala Pro Ala
    50                  55                  60

Ser Ser Glu Ser Ser Thr Asn His Ser Ile Gly Ser Thr Gln Ser
65                  70                  75                  80

Thr Pro Cys Ser Thr Ser Ser Met Ala
                85

<210> SEQ ID NO 10
<211> LENGTH: 89
<212> TYPE: PRT
<213> ORGANISM: Artificial Sequence
<220> FEATURE:
<223> OTHER INFORMATION: Synthetic polynucleotide or polypeptide

<400> SEQUENCE: 10

Thr Val Ser Met Arg Leu Asn Ile Val Ser Pro Asp Leu Ser Gly Lys
1               5                   10                  15

Gly Leu Val Leu Pro Ser Val Leu Gly Ile Thr Phe Gly Ala Phe Leu
            20                  25                  30

Ile Gly Ala Leu Leu Thr Ala Ala Leu Trp Tyr Ile Tyr Ser His Thr
        35                  40                  45

Arg Ala Pro Ser Lys Arg Glu Pro Val Val Ala Val Ala Ala Pro Ala
    50                  55                  60

Ser Ser Glu Ser Ser Thr Asn His Ser Ile Gly Ser Thr Gln Ser
65                  70                  75                  80

Thr Pro Cys Ser Thr Ser Ser Met Ala
                85

<210> SEQ ID NO 11
<211> LENGTH: 96
<212> TYPE: DNA
<213> ORGANISM: Artificial Sequence
<220> FEATURE:
<223> OTHER INFORMATION: Synthetic polynucleotide or polypeptide

<400> SEQUENCE: 11
ggagtgccag tgcagggctc caagtacgct gccgaccgca accactaccg ccgctaccca      60
cgccgtcgcg gcccaccccg caactaccag cagaac                                96

<210> SEQ ID NO 12
<211> LENGTH: 96
<212> TYPE: DNA
<213> ORGANISM: Artificial Sequence
<220> FEATURE:
<223> OTHER INFORMATION: Synthetic polynucleotide or polypeptide

<400> SEQUENCE: 12
ggcgtgcccg tgcagggctc caagtacgcc gccgaccgca accactaccg ccgctacccc      60
cgccgccgcg gccccccccg caactaccag cagaac                                96

<210> SEQ ID NO 13
<211> LENGTH: 96

<212> TYPE: DNA
<213> ORGANISM: Artificial Sequence
<220> FEATURE:
<223> OTHER INFORMATION: Synthetic polynucleotide or polypeptide

<400> SEQUENCE: 13

```
ggcgtgcccg tgcagggctc caagtacgcc gccgaccgca accactaccg ccgctacccc    60
cgccgccgcg gccccccccg caactaccag cagaac                              96
```

<210> SEQ ID NO 14
<211> LENGTH: 17
<212> TYPE: PRT
<213> ORGANISM: Artificial Sequence
<220> FEATURE:
<223> OTHER INFORMATION: Synthetic polynucleotide or polypeptide

<400> SEQUENCE: 14

```
Glu Asp Val Phe Val His Gln Thr Ala Ile Lys Lys Asn Asn Pro Arg
1               5                   10                  15

Lys
```

<210> SEQ ID NO 15
<211> LENGTH: 14
<212> TYPE: PRT
<213> ORGANISM: Artificial Sequence
<220> FEATURE:
<223> OTHER INFORMATION: Synthetic polynucleotide or polypeptide

<400> SEQUENCE: 15

```
Tyr Arg Arg Asn Phe Asn Tyr Arg Arg Arg Arg Pro Glu Asn
1               5                   10
```

<210> SEQ ID NO 16
<211> LENGTH: 32
<212> TYPE: PRT
<213> ORGANISM: Artificial Sequence
<220> FEATURE:
<223> OTHER INFORMATION: Synthetic polynucleotide or polypeptide

<400> SEQUENCE: 16

```
Gly Val Pro Val Gln Gly Ser Lys Tyr Ala Ala Asp Arg Asn His Tyr
1               5                   10                  15

Arg Arg Tyr Pro Arg Arg Gly Pro Pro Arg Asn Tyr Gln Gln Asn
            20                  25                  30
```

<210> SEQ ID NO 17
<211> LENGTH: 177
<212> TYPE: DNA
<213> ORGANISM: Artificial Sequence
<220> FEATURE:
<223> OTHER INFORMATION: Synthetic polynucleotide or polypeptide

<400> SEQUENCE: 17

```
ggcctcaatg cgcacggcgc agcgcagatg cagcccatgc accgctacga cgtgagcgcc    60
ctgcagtaca actccatgac cagctcgcag acctacatga acggctcgcc cacctacagc   120
atgtcctact cgcagcaggg caccccctggc atggctcttg gctccatggg ttcggtg     177
```

<210> SEQ ID NO 18
<211> LENGTH: 177
<212> TYPE: DNA
<213> ORGANISM: Artificial Sequence
<220> FEATURE:
<223> OTHER INFORMATION: Synthetic polynucleotide or polypeptide

<400> SEQUENCE: 18
ggcctgaacg cccacggcgc cgcccagatg cagcccatgc accgctacga cgtgtccgcc      60
ctgcagtaca actccatgac ctcctcccag acctacatga acggctcccc cacctactcc     120
atgtcctact cccagcaggg caccccggc atggccctgg ctccatgggc tccgtg          177

<210> SEQ ID NO 19
<211> LENGTH: 177
<212> TYPE: DNA
<213> ORGANISM: Artificial Sequence
<220> FEATURE:
<223> OTHER INFORMATION: Synthetic polynucleotide or polypeptide

<400> SEQUENCE: 19
ggcctgaacg cccacggcgc cgcccagatg cagcccatgc accgctacga cgtgtccgcc      60
ctgcagtaca actccatgac ctcctcccag acctacatga acggctcccc cacctactcc     120
atgtcctact cccagcaggg caccccggc atggccctgg ctccatgggc tccgtg          177

<210> SEQ ID NO 20
<211> LENGTH: 59
<212> TYPE: PRT
<213> ORGANISM: Artificial Sequence
<220> FEATURE:
<223> OTHER INFORMATION: Synthetic polynucleotide or polypeptide

<400> SEQUENCE: 20

Gly Leu Asn Ala His Gly Ala Ala Gln Met Gln Pro Met His Arg Tyr
1               5                   10                  15

Asp Val Ser Ala Leu Gln Tyr Asn Ser Met Thr Ser Ser Gln Thr Tyr
                20                  25                  30

Met Asn Gly Ser Pro Thr Tyr Ser Met Ser Tyr Ser Gln Gln Gly Thr
            35                  40                  45

Pro Gly Met Ala Leu Gly Ser Met Gly Ser Val
        50                  55

<210> SEQ ID NO 21
<211> LENGTH: 240
<212> TYPE: DNA
<213> ORGANISM: Artificial Sequence
<220> FEATURE:
<223> OTHER INFORMATION: Synthetic polynucleotide or polypeptide

<400> SEQUENCE: 21
aggtcactga aggaaaggaa tccattgaaa atcttcccat ccaaacgtat cttacgaaga      60
cacaagagag attgggtggt tgctccaata tctgtccctg aaaatggcaa gggtcccttc     120
ccacagagac tgaatcagct caagtctaat aaagatagag acaccaagat tttctacagc     180
atcacggggc cgggtgcaga cagcccacct gagggtgtct tcgctgtaga aaggagaca     240

<210> SEQ ID NO 22
<211> LENGTH: 216
<212> TYPE: DNA
<213> ORGANISM: Artificial Sequence
<220> FEATURE:
<223> OTHER INFORMATION: Synthetic polynucleotide or polypeptide

<400> SEQUENCE: 22
ttgaaaatct tcccatccaa acgtatctta cgaagacaca agagagattg gtggttgct      60 ccaatatctg tccctgaaaa tggcaagggt cccttcccac agagactgaa tcagctcaag    120
tctaataaag atagagacac caagattttc tacagcatca cggggccggg tgcagacagc    180

```
ccacctgagg gtgtcttcgc tgtagagaag gagaca                                216
```

<210> SEQ ID NO 23
<211> LENGTH: 216
<212> TYPE: DNA
<213> ORGANISM: Artificial Sequence
<220> FEATURE:
<223> OTHER INFORMATION: Synthetic polynucleotide or polypeptide

<400> SEQUENCE: 23

```
ttgaaaatct tcccatccaa acgtatctta cgaagacaca agagagattg ggtggttgct       60
ccaatatctg tccctgaaaa tggcaagggt cccttcccac agagactgaa tcagctcaag      120
tctaataaag atagagacac caagattttc tacagcatca cggggccggg tgcagacagc      180
ccacctgagg gtgtcttcgc tgtagagaag gagaca                                216
```

<210> SEQ ID NO 24
<211> LENGTH: 216
<212> TYPE: DNA
<213> ORGANISM: Artificial Sequence
<220> FEATURE:
<223> OTHER INFORMATION: Synthetic polynucleotide or polypeptide

<400> SEQUENCE: 24

```
gtgatgaact ccccccccctc ccgcatcctg cgccgccgca agcgcgagtg ggtgatgccc      60
cccatctccg tgcccgagaa cggcaagggc cccttccccc agcgcctgaa ccagctgaag     120
tccaacaagg accgcggcac caagctgttc tactccatca ccggccccgg cgccgactcc     180 cccccgagg gcgtgttcac catcgagaag gagacc                                 216
```

<210> SEQ ID NO 25
<211> LENGTH: 80
<212> TYPE: PRT
<213> ORGANISM: Artificial Sequence
<220> FEATURE:
<223> OTHER INFORMATION: Synthetic polynucleotide or polypeptide

<400> SEQUENCE: 25

```
Arg Ser Leu Lys Glu Arg Asn Pro Leu Lys Ile Phe Pro Ser Lys Arg
1               5                   10                  15

Ile Leu Arg Arg His Lys Arg Asp Trp Val Val Ala Pro Ile Ser Val
            20                  25                  30

Pro Glu Asn Gly Lys Gly Pro Phe Pro Gln Arg Leu Asn Gln Leu Lys
        35                  40                  45

Ser Asn Lys Asp Arg Asp Thr Lys Ile Phe Tyr Ser Ile Thr Gly Pro
    50                  55                  60

Gly Ala Asp Ser Pro Pro Glu Gly Val Phe Ala Val Glu Lys Glu Thr
65                  70                  75                  80
```

<210> SEQ ID NO 26
<211> LENGTH: 72
<212> TYPE: PRT
<213> ORGANISM: Artificial Sequence
<220> FEATURE:
<223> OTHER INFORMATION: Synthetic polynucleotide or polypeptide

<400> SEQUENCE: 26

```
Leu Lys Ile Phe Pro Ser Lys Arg Ile Leu Arg Arg His Lys Arg Asp
1               5                   10                  15

Trp Val Val Ala Pro Ile Ser Val Pro Glu Asn Gly Lys Gly Pro Phe
            20                  25                  30
```

Pro Gln Arg Leu Asn Gln Leu Lys Ser Asn Lys Asp Arg Asp Thr Lys
            35                  40                  45

Ile Phe Tyr Ser Ile Thr Gly Pro Gly Ala Asp Ser Pro Pro Glu Gly
        50                  55                  60

Val Phe Ala Val Glu Lys Glu Thr
65                  70

<210> SEQ ID NO 27
<211> LENGTH: 72
<212> TYPE: PRT
<213> ORGANISM: Artificial Sequence
<220> FEATURE:
<223> OTHER INFORMATION: Synthetic polynucleotide or polypeptide

<400> SEQUENCE: 27

Ala Met His Ser Pro Pro Thr Arg Ile Leu Arg Arg Arg Lys Arg Glu
1               5                   10                  15

Trp Val Met Pro Pro Ile Phe Val Pro Glu Asn Gly Lys Gly Pro Phe
            20                  25                  30

Pro Gln Arg Leu Asn Gln Leu Lys Ser Asn Lys Asp Arg Gly Thr Lys
            35                  40                  45

Ile Phe Tyr Ser Ile Thr Gly Pro Gly Ala Asp Ser Pro Pro Glu Gly
        50                  55                  60

Val Phe Thr Ile Glu Lys Glu Ser
65                  70

<210> SEQ ID NO 28
<211> LENGTH: 72
<212> TYPE: PRT
<213> ORGANISM: Artificial Sequence
<220> FEATURE:
<223> OTHER INFORMATION: Synthetic polynucleotide or polypeptide

<400> SEQUENCE: 28

Val Met Asn Ser Pro Pro Ser Arg Ile Leu Arg Arg Arg Lys Arg Glu
1               5                   10                  15

Trp Val Met Pro Pro Ile Ser Val Pro Glu Asn Gly Lys Gly Pro Phe
            20                  25                  30

Pro Gln Arg Leu Asn Gln Leu Lys Ser Asn Lys Asp Arg Gly Thr Lys
            35                  40                  45

Leu Phe Tyr Ser Ile Thr Gly Pro Gly Ala Asp Ser Pro Pro Glu Gly
        50                  55                  60

Val Phe Thr Ile Glu Lys Glu Thr
65                  70

<210> SEQ ID NO 29
<211> LENGTH: 231
<212> TYPE: DNA
<213> ORGANISM: Artificial Sequence
<220> FEATURE:
<223> OTHER INFORMATION: Synthetic polynucleotide or polypeptide

<400> SEQUENCE: 29
acctacacca tgaaggaggt gctgttctac ctgggccagt acatcatgac caagcgcctg      60
tacgacgaga agcagcagca catcgtgtac tgctccaacg acctgctggg cgacctgttc     120
ggcgtgccct ccttctccgt gaaggagcac cgcaaaatct acaccatgat ctaccgcaac     180
ctggtggtgg tgaaccagca ggagtcctcc gactccggca cctccgtgtc c             231

<210> SEQ ID NO 30
<211> LENGTH: 222
<212> TYPE: DNA
<213> ORGANISM: Artificial Sequence
<220> FEATURE:
<223> OTHER INFORMATION: Synthetic polynucleotide or polypeptide

<400> SEQUENCE: 30

```
acctacacca tgaaggagat catcttctac atcggccagt acatcatgac caagcgcctg    60
tacgacgaga agcagcagca catcgtgtac tgctccaacg acctgctggg cgacgtgttc   120
ggcgtgccct ccttctccgt gaaggagcac cgcaagatct acgccatgat ctaccgcaac   180
ctggtggccg tgtcccagca ggactccggc acctccctgt cc                      222
```

<210> SEQ ID NO 31
<211> LENGTH: 222
<212> TYPE: DNA
<213> ORGANISM: Artificial Sequence
<220> FEATURE:
<223> OTHER INFORMATION: Synthetic polynucleotide or polypeptide

<400> SEQUENCE: 31

```
atctacacca tgaaggagat catcttctac atcggccagt acatcatgac caagcgcctg    60
tacgacgaga agcagcagca catcgtgtac tgctccaacg acctgctggg cgacgtgttc   120
ggcgtgccct ccttctccgt gaaggagcac cgcaagatct acgccatgat ctaccgcaac   180
ctggtggtgg tgtcccagca ggactccggc acctccccct cc                      222
```

<210> SEQ ID NO 32
<211> LENGTH: 76
<212> TYPE: PRT
<213> ORGANISM: Artificial Sequence
<220> FEATURE:
<223> OTHER INFORMATION: Synthetic polynucleotide or polypeptide

<400> SEQUENCE: 32

```
Thr Tyr Thr Met Lys Glu Val Leu Phe Tyr Leu Gly Gln Tyr Ile Met
1               5                   10                  15

Thr Lys Arg Leu Tyr Asp Glu Lys Gln Gln His Ile Val Tyr Cys Ser
            20                  25                  30

Asn Asp Leu Leu Gly Asp Leu Phe Gly Val Pro Ser Phe Ser Val Lys
        35                  40                  45

Glu His Arg Lys Ile Tyr Thr Met Ile Tyr Arg Asn Leu Val Val Val
    50                  55                  60

Asn Gln Gln Glu Ser Ser Asp Ser Gly Thr Ser Val
65                  70                  75
```

<210> SEQ ID NO 33
<211> LENGTH: 74
<212> TYPE: PRT
<213> ORGANISM: Artificial Sequence
<220> FEATURE:
<223> OTHER INFORMATION: Synthetic polynucleotide or polypeptide

<400> SEQUENCE: 33

```
Thr Tyr Thr Met Lys Glu Ile Ile Phe Tyr Ile Gly Gln Tyr Ile Met
1               5                   10                  15

Thr Lys Arg Leu Tyr Asp Glu Lys Gln Gln His Ile Val Tyr Cys Ser
            20                  25                  30

Asn Asp Leu Leu Gly Asp Val Phe Gly Val Pro Ser Phe Ser Val Lys
        35                  40                  45
```

```
Glu His Arg Lys Ile Tyr Ala Met Ile Tyr Arg Asn Leu Val Ala Val
        50                  55                  60

Ser Gln Gln Asp Ser Gly Thr Ser Leu Ser
65                  70
```

<210> SEQ ID NO 34
<211> LENGTH: 74
<212> TYPE: PRT
<213> ORGANISM: Artificial Sequence
<220> FEATURE:
<223> OTHER INFORMATION: Synthetic polynucleotide or polypeptide

<400> SEQUENCE: 34

```
Ile Tyr Thr Met Lys Glu Ile Ile Phe Tyr Ile Gly Gln Tyr Ile Met
1               5                   10                  15

Thr Lys Arg Leu Tyr Asp Glu Lys Gln Gln His Ile Val Tyr Cys Ser
            20                  25                  30

Asn Asp Leu Leu Gly Asp Val Phe Gly Val Pro Ser Phe Ser Val Lys
        35                  40                  45

Glu His Arg Lys Ile Tyr Ala Met Ile Tyr Arg Asn Leu Val Val Val
    50                  55                  60

Ser Gln Gln Asp Ser Gly Thr Ser Pro Ser
65                  70
```

<210> SEQ ID NO 35
<211> LENGTH: 987
<212> TYPE: DNA
<213> ORGANISM: Artificial Sequence
<220> FEATURE:
<223> OTHER INFORMATION: Synthetic polynucleotide or polypeptide

<400> SEQUENCE: 35

| | | |
|---|---|---|
| atggcggtac ccatgcaact gtcctgctct agacagaacg gcacctggcc ccgcgaggtg | 60 |
| ctgctggtgc tgtccgtgaa ctcctccgtg ttcctgcacc tacaggccct gggcatcccc | 120 |
| ctgcacctgg cctacaactc ctccctggtg accttccagg agcccccggg cgtgaacacc | 180 |
| accgagctga gatccaccgg tggagtgcca gtgcagggct ccaagtacgc tgccgaccgc | 240 |
| aaccactacc gccgctaccc acgccgtcgc ggcccacccc gcaactacca gcagaacacg | 300 |
| cgtggcctca tgcgcacgg cgcagcgcag atgcagccca tgcaccgcta cgacgtgagc | 360 |
| gccctgcagt acaactccat gaccagctcg cagacctaca tgaacggctc gcccacctac | 420 |
| agcatgtcct actcgcagca gggcacccct ggcatggctc ttggctccat gggttcggtg | 480 |
| agatcccaat tgaggtcact gaaggaaagg aatccattga aatcttccc atccaaacgt | 540 |
| atcttacgaa gacacaagag agattgggtg gttgctccaa tatctgtccc tgaaaatggc | 600 |
| aagggtccct tcccacagag actgaatcag ctcaagtcta taaagatag agacaccaag | 660 |
| atttctacaa gcatcacggg gccgggtgca gacagcccac tgagggtgt cttcgctgta | 720 |
| gagaaggaga caagatccgc cggcgaaacc tacaccatga aggaggtgct gttctacctg | 780 |
| ggccagtaca tcatgaccaa cgccctgtac gacgagaagc agcagcacat cgtgtactgc | 840 |
| tccaacgacc tgctgggcga cctgttcggc gtgccctcct ctccgtgaa ggagcaccgc | 900 |
| aaaatctaca ccatgatcta ccgcaacctg gtggtggtga accagcagga gtcctccgac | 960 |
| tccggcacct ccgtgtccag atcttag | 987 |

<210> SEQ ID NO 36
<211> LENGTH: 1059
<212> TYPE: DNA

<213> ORGANISM: Artificial Sequence
<220> FEATURE:
<223> OTHER INFORMATION: Synthetic polynucleotide or polypeptide

<400> SEQUENCE: 36

| | | | | | |
|---|---|---|---|---|---|
| atggcggtac | ccatgaccgt | gttcatgcgc | ctgaacatca | tctcccccga | cctgtccggc | 60 |
| tgcacctcca | agggcctggt | gctgcccgcc | gtgctgggca | tcaccttcgg | cgccttcctg | 120 |
| atcggcgccc | tgctgaccgc | cgccctgtgg | tacatctact | cccacacccg | ctcccccctcc | 180 |
| aagcgcgagc | ccgtggtggc | cgtggccgcc | cccgcctcct | ccgagtcctc | ctccaccaac | 240 |
| cactccatcg | ctccacccca | gtccacccccc | tgctccacct | cctccatggc | caccggtgga | 300 |
| gtgccagtgc | agggctccaa | gtacgctgcc | gaccgcaacc | actaccgccg | ctacccacgc | 360 |
| cgtcgcggcc | cacccccgcaa | ctaccagcag | aacacgcgtg | gcctcaatgc | gcacggcgca | 420 |
| gcgcagatgc | agcccatgca | ccgctacgac | gtgagcgccc | tgcagtacaa | ctccatgacc | 480 |
| agctcgcaga | cctacatgaa | cggctcgccc | acctacagca | tgtcctactc | gcagcagggc | 540 |
| acccctggca | tggctcttgg | ctccatgggt | tcggtgagat | cccaattgtt | gaaaatcttc | 600 |
| ccatccaaac | gtatcttacg | aagacacaag | agagattggg | tggttgctcc | aatatctgtc | 660 |
| cctgaaaatg | gcaagggtcc | cttcccacag | agactgaatc | agctcaagtc | taataaagat | 720 |
| agagacacca | agattttcta | cagcatcacg | gggccgggtg | cagacagccc | acctgagggt | 780 |
| gtcttcgctg | tagagaagga | gacaagatcc | gccggcgaaa | cctacaccat | gaaggaggtg | 840 |
| ctgttctacc | tgggccagta | catcatgacc | aagcgcctgt | acgacgagaa | gcagcagcac | 900 |
| atcgtgtact | gctccaacga | cctgctgggc | gacctgttcg | gcgtgccctc | cttctccgtg | 960 |
| aaggagcacc | gcaaaatcta | caccatgatc | taccgcaacc | tggtggtggt | gaaccagcag | 1020 |
| gagtcctccg | actccggcac | ctccgtgtcc | agatcttag | | | 1059 |

<210> SEQ ID NO 37
<211> LENGTH: 1041
<212> TYPE: DNA
<213> ORGANISM: Artificial Sequence
<220> FEATURE:
<223> OTHER INFORMATION: Synthetic polynucleotide or polypeptide

<400> SEQUENCE: 37

| | | | | | |
|---|---|---|---|---|---|
| atggcggtac | ccatgaccgt | gtccatgcgc | ctgaacatcg | tgtcccccga | cctgtccggc | 60 |
| aagggcctgg | tgctgccctc | cgtgctgggc | atcaccttcg | gcgccttcct | gatcggcgcc | 120 |
| ctgctgaccg | ccgccctgtg | gtacatctac | tcccacaccc | gcggcccctc | caagcgcgag | 180 |
| cccgtggtgg | ccgtggccgc | ccccgcctcc | tccgagtcct | cctccaccaa | ccactccatc | 240 |
| ggctccaccc | agtccacccc | ctgctccacc | tcctccatgg | ccaccggtgg | cgtgcccgtg | 300 |
| cagggctcca | gtacgccgcc | gaccgcaac | cactaccgcc | gctaccccg | ccgccgcggc | 360 |
| cccccccgca | actaccagca | gaacacgcgt | ggcctgaacg | cccacggcgc | cgcccagatg | 420 |
| cagcccatgc | accgctacga | cgtgtccgcc | ctgcagtaca | actccatgac | ctcctcccag | 480 |
| acctacatga | acggctcccc | cacctactcc | atgtcctact | cccagcaggg | cacccccggc | 540 |
| atggccctgg | gctccatggg | ctccgtgaga | tcccaattgg | ccatgcactc | ccccccccacc | 600 |
| cgcatcctgc | gccgccgcaa | gcgcgagtgg | gtgatgcccc | ccatcttcgt | gcccgagaac | 660 |
| ggcaagggcc | ccttcccccca | gcgcctgaac | cagctgaagt | ccaacaagga | ccgcggcacc | 720 |
| aagatcttct | actccatcac | cggccccggc | gccgactccc | cccccgaggg | cgtgttcacc | 780 |
| atcgagaagg | agtccagatc | cgccggcgaa | acctacacca | tgaaggagat | catcttctac | 840 |

```
atcggccagt acatcatgac caagcgcctg tacgacgaga agcagcagca catcgtgtac    900
tgctccaacg acctgctggg cgacgtgttc ggcgtgccct ccttctccgt gaaggagcac    960
cgcaagatct acgccatgat ctaccgcaac ctggtggccg tgtcccagca ggactccggc   1020
acctccctgt ccagatctta g                                             1041
```

<210> SEQ ID NO 38
<211> LENGTH: 1041
<212> TYPE: DNA
<213> ORGANISM: Artificial Sequence
<220> FEATURE:
<223> OTHER INFORMATION: Synthetic polynucleotide or polypeptide

<400> SEQUENCE: 38

```
atggcggtac ccatgaccgt gtccatgcgc ctgaacatcg tgccccccga cctgtccggc     60
aagggcctgg tgctgccctc cgtgctgggc atcaccttcg gcgccttcct gatcggcgcc    120
ctgctgaccg ccgccctgtg gtacatctac tcccacaccc gcgcccccctc caagcgcgag    180 cccgtggtgg ccgtggccgc ccccgcctcc tccgagtcct cctccaccaa ccactccatc    240
ggctccaccc agtccacccc ctgctccacc tcctccatgg ccaccggtgg cgtgcccgtg    300
cagggctcca gtacgccgc cgaccgcaac cactaccgcc gctaccccccg ccgccgcggc    360 ccccccccgca actaccagca gaacacgcgt ggcctgaacg cccacggcgc cgcccagatg    420
cagcccatgc accgctacga cgtgtccgcc ctgcagtaca actccatgac ctcctcccag    480
acctacatga acggctcccc cacctactcc atgtcctact cccagcaggg cacccccggc    540
atggccctgg gctccatggg ctccgtgaga tcccaattgg tgatgaactc cccccccctcc    600 cgcatcctgc cgccgcgcaa gcgcgagtgg gtgatgcccc catctccgt gcccgagaac    660 ggcaagggcc ccttccccca cgcctgaac cagctgaagt ccaacaagga ccgcggcacc    720
aagctgttct actccatcac cggccccggc gccgactccc ccccccgaggg cgtgttcacc    780 atcgagaagg agaccagatc cgccggcgaa atctacacca tgaaggagat catcttctac    840
atcggccagt acatcatgac caagcgcctg tacgacgaga agcagcagca catcgtgtac    900
tgctccaacg acctgctggg cgacgtgttc ggcgtgccct ccttctccgt gaaggagcac    960
cgcaagatct acgccatgat ctaccgcaac ctggtggtgg tgtcccagca ggactccggc   1020
acctccccct ccagatctta g                                             1041
```

<210> SEQ ID NO 39
<211> LENGTH: 328
<212> TYPE: PRT
<213> ORGANISM: Artificial Sequence
<220> FEATURE:
<223> OTHER INFORMATION: Synthetic polynucleotide or polypeptide

<400> SEQUENCE: 39

```
Met Ala Val Pro Met Gln Leu Ser Cys Ser Arg Gln Asn Gly Thr Trp
1               5                   10                  15

Pro Arg Glu Val Leu Leu Val Leu Ser Val Asn Ser Ser Val Phe Leu
                20                  25                  30

His Leu Gln Ala Leu Gly Ile Pro Leu His Leu Ala Tyr Asn Ser Ser
            35                  40                  45

Leu Val Thr Phe Gln Glu Pro Pro Gly Val Asn Thr Thr Glu Leu Arg
        50                  55                  60

Ser Thr Gly Gly Val Pro Val Gln Gly Ser Lys Tyr Ala Ala Asp Arg
65                  70                  75                  80
```

```
Asn His Tyr Arg Arg Tyr Pro Arg Arg Gly Pro Pro Arg Asn Tyr
                 85                  90                  95

Gln Gln Asn Thr Arg Gly Leu Asn Ala His Gly Ala Ala Gln Met Gln
            100                 105                 110

Pro Met His Arg Tyr Asp Val Ser Ala Leu Gln Tyr Asn Ser Met Thr
            115                 120                 125

Ser Ser Gln Thr Tyr Met Asn Gly Ser Pro Thr Tyr Ser Met Ser Tyr
            130                 135                 140

Ser Gln Gln Gly Thr Pro Gly Met Ala Leu Gly Ser Met Gly Ser Val
145                 150                 155                 160

Arg Ser Gln Leu Arg Ser Leu Lys Glu Arg Asn Pro Leu Lys Ile Phe
                165                 170                 175

Pro Ser Lys Arg Ile Leu Arg Arg His Lys Arg Asp Trp Val Val Ala
                180                 185                 190

Pro Ile Ser Val Pro Glu Asn Gly Lys Gly Pro Phe Pro Gln Arg Leu
                195                 200                 205

Asn Gln Leu Lys Ser Asn Lys Asp Arg Asp Thr Lys Ile Phe Tyr Ser
                210                 215                 220

Ile Thr Gly Pro Gly Ala Asp Ser Pro Pro Glu Gly Val Phe Ala Val
225                 230                 235                 240

Glu Lys Glu Thr Arg Ser Ala Gly Glu Thr Tyr Thr Met Lys Glu Val
                245                 250                 255

Leu Phe Tyr Leu Gly Gln Tyr Ile Met Thr Lys Arg Leu Tyr Asp Glu
                260                 265                 270

Lys Gln Gln His Ile Val Tyr Cys Ser Asn Asp Leu Leu Gly Asp Leu
                275                 280                 285

Phe Gly Val Pro Ser Phe Ser Val Lys Glu His Arg Lys Ile Tyr Thr
                290                 295                 300

Met Ile Tyr Arg Asn Leu Val Val Asn Gln Gln Glu Ser Ser Asp
305                 310                 315                 320

Ser Gly Thr Ser Val Ser Arg Ser
                325

<210> SEQ ID NO 40
<211> LENGTH: 352
<212> TYPE: PRT
<213> ORGANISM: Artificial Sequence
<220> FEATURE:
<223> OTHER INFORMATION: Synthetic polynucleotide or polypeptide

<400> SEQUENCE: 40

Met Ala Val Pro Met Thr Val Phe Met Arg Leu Asn Ile Ile Ser Pro
1               5                   10                  15

Asp Leu Ser Gly Cys Thr Ser Lys Gly Leu Val Leu Pro Ala Val Leu
            20                  25                  30

Gly Ile Thr Phe Gly Ala Phe Leu Ile Gly Ala Leu Leu Thr Ala Ala
            35                  40                  45

Leu Trp Tyr Ile Tyr Ser His Thr Arg Ser Pro Ser Lys Arg Glu Pro
    50                  55                  60

Val Val Ala Val Ala Ala Pro Ala Ser Ser Glu Ser Ser Ser Thr Asn
65                  70                  75                  80

His Ser Ile Gly Ser Thr Gln Ser Thr Pro Cys Ser Thr Ser Ser Met
                85                  90                  95

Ala Thr Gly Gly Val Pro Val Gln Gly Ser Lys Tyr Ala Ala Asp Arg
            100                 105                 110
```

```
Asn His Tyr Arg Arg Tyr Pro Arg Arg Gly Pro Pro Arg Asn Tyr
        115                 120                 125

Gln Gln Asn Thr Arg Gly Leu Asn Ala His Gly Ala Ala Gln Met Gln
130                 135                 140

Pro Met His Arg Tyr Asp Val Ser Ala Leu Gln Tyr Asn Ser Met Thr
145                 150                 155                 160

Ser Ser Gln Thr Tyr Met Asn Gly Ser Pro Thr Tyr Ser Met Ser Tyr
                165                 170                 175

Ser Gln Gln Gly Thr Pro Gly Met Ala Leu Gly Ser Met Gly Ser Val
                180                 185                 190

Arg Ser Gln Leu Leu Lys Ile Phe Pro Ser Lys Arg Ile Leu Arg Arg
                195                 200                 205

His Lys Arg Asp Trp Val Val Ala Pro Ile Ser Val Pro Glu Asn Gly
        210                 215                 220

Lys Gly Pro Phe Pro Gln Arg Leu Asn Gln Leu Lys Ser Asn Lys Asp
225                 230                 235                 240

Arg Asp Thr Lys Ile Phe Tyr Ser Ile Thr Gly Pro Gly Ala Asp Ser
                245                 250                 255

Pro Pro Glu Gly Val Phe Ala Val Glu Lys Glu Thr Arg Ser Ala Gly
                260                 265                 270

Glu Thr Tyr Thr Met Lys Glu Val Leu Phe Tyr Leu Gly Gln Tyr Ile
                275                 280                 285

Met Thr Lys Arg Leu Tyr Asp Glu Lys Gln Gln His Ile Val Tyr Cys
        290                 295                 300

Ser Asn Asp Leu Leu Gly Asp Leu Phe Gly Val Pro Ser Phe Ser Val
305                 310                 315                 320

Lys Glu His Arg Lys Ile Tyr Thr Met Ile Tyr Arg Asn Leu Val Val
                325                 330                 335

Val Asn Gln Gln Glu Ser Ser Asp Ser Gly Thr Ser Val Ser Arg Ser
                340                 345                 350

<210> SEQ ID NO 41
<211> LENGTH: 346
<212> TYPE: PRT
<213> ORGANISM: Artificial Sequence
<220> FEATURE:
<223> OTHER INFORMATION: Synthetic polynucleotide or polypeptide

<400> SEQUENCE: 41

Met Ala Val Pro Met Thr Val Ser Met Arg Leu Asn Ile Val Ser Pro
1               5                   10                  15

Asp Leu Ser Gly Lys Gly Leu Val Leu Pro Ser Val Leu Gly Ile Thr
                20                  25                  30

Phe Gly Ala Phe Leu Ile Gly Leu Leu Thr Ala Ala Leu Trp Tyr
                35                  40                  45

Ile Tyr Ser His Thr Arg Gly Pro Ser Lys Arg Glu Pro Val Val Ala
        50                  55                  60

Val Ala Ala Pro Ala Ser Ser Glu Ser Ser Thr Asn His Ser Ile
65                  70                  75                  80

Gly Ser Thr Gln Ser Thr Pro Cys Ser Thr Ser Met Ala Thr Gly
                85                  90                  95

Gly Val Pro Val Gln Gly Ser Lys Tyr Ala Ala Asp Arg Asn His Tyr
                100                 105                 110

Arg Arg Tyr Pro Arg Arg Gly Pro Pro Arg Asn Tyr Gln Gln Asn
                115                 120                 125
```

```
Thr Arg Gly Leu Asn Ala His Gly Ala Ala Gln Met Gln Pro Met His
        130                 135                 140

Arg Tyr Asp Val Ser Ala Leu Gln Tyr Asn Ser Met Thr Ser Ser Gln
145                 150                 155                 160

Thr Tyr Met Asn Gly Ser Pro Thr Tyr Ser Met Ser Tyr Ser Gln Gln
                165                 170                 175

Gly Thr Pro Gly Met Ala Leu Gly Ser Met Gly Ser Val Arg Ser Gln
                180                 185                 190

Leu Ala Met His Ser Pro Pro Thr Arg Ile Leu Arg Arg Lys Arg
                195                 200                 205

Glu Trp Val Met Pro Pro Ile Phe Val Pro Glu Asn Gly Lys Gly Pro
        210                 215                 220

Phe Pro Gln Arg Leu Asn Gln Leu Lys Ser Asn Lys Asp Arg Gly Thr
225                 230                 235                 240

Lys Ile Phe Tyr Ser Ile Thr Gly Pro Gly Ala Asp Ser Pro Pro Glu
                245                 250                 255

Gly Val Phe Thr Ile Glu Lys Glu Ser Arg Ser Ala Gly Glu Thr Tyr
                260                 265                 270

Thr Met Lys Glu Ile Ile Phe Tyr Ile Gly Gln Tyr Ile Met Thr Lys
        275                 280                 285

Arg Leu Tyr Asp Glu Lys Gln Gln His Ile Val Tyr Cys Ser Asn Asp
290                 295                 300

Leu Leu Gly Asp Val Phe Gly Val Pro Ser Phe Ser Val Lys Glu His
305                 310                 315                 320

Arg Lys Ile Tyr Ala Met Ile Tyr Arg Asn Leu Val Ala Val Ser Gln
                325                 330                 335

Gln Asp Ser Gly Thr Ser Leu Ser Arg Ser
                340                 345

<210> SEQ ID NO 42
<211> LENGTH: 346
<212> TYPE: PRT
<213> ORGANISM: Artificial Sequence
<220> FEATURE:
<223> OTHER INFORMATION: Synthetic polynucleotide or polypeptide

<400> SEQUENCE: 42

Met Ala Val Pro Met Thr Val Ser Met Arg Leu Asn Ile Val Ser Pro
1               5                   10                  15

Asp Leu Ser Gly Lys Gly Leu Val Leu Pro Ser Val Leu Gly Ile Thr
                20                  25                  30

Phe Gly Ala Phe Leu Ile Gly Ala Leu Leu Thr Ala Ala Leu Trp Tyr
            35                  40                  45

Ile Tyr Ser His Thr Arg Ala Pro Ser Lys Arg Glu Pro Val Val Ala
        50                  55                  60

Val Ala Ala Pro Ala Ser Ser Glu Ser Ser Thr Asn His Ser Ile
65                  70                  75                  80

Gly Ser Thr Gln Ser Thr Pro Cys Ser Thr Ser Ser Met Ala Thr Gly
                85                  90                  95

Gly Val Pro Val Gln Gly Ser Lys Tyr Ala Ala Asp Arg Asn His Tyr
                100                 105                 110

Arg Arg Tyr Pro Arg Arg Arg Gly Pro Pro Arg Asn Tyr Gln Gln Asn
            115                 120                 125

Thr Arg Gly Leu Asn Ala His Gly Ala Ala Gln Met Gln Pro Met His
        130                 135                 140
```

Arg Tyr Asp Val Ser Ala Leu Gln Tyr Asn Ser Met Thr Ser Ser Gln
145                 150                 155                 160

Thr Tyr Met Asn Gly Ser Pro Thr Tyr Ser Met Ser Tyr Gln Gln
            165                 170                 175

Gly Thr Pro Gly Met Ala Leu Gly Ser Met Gly Ser Val Arg Ser Gln
            180                 185                 190

Leu Val Met Asn Ser Pro Pro Ser Arg Ile Leu Arg Arg Lys Arg
            195                 200                 205

Glu Trp Val Met Pro Pro Ile Ser Val Pro Glu Asn Gly Lys Gly Pro
        210                 215                 220

Phe Pro Gln Arg Leu Asn Gln Leu Lys Ser Asn Lys Asp Arg Gly Thr
225                 230                 235                 240

Lys Leu Phe Tyr Ser Ile Thr Gly Pro Gly Ala Asp Ser Pro Pro Glu
                245                 250                 255

Gly Val Phe Thr Ile Glu Lys Glu Thr Arg Ser Ala Gly Glu Ile Tyr
            260                 265                 270

Thr Met Lys Glu Ile Ile Phe Tyr Ile Gly Gln Tyr Ile Met Thr Lys
        275                 280                 285

Arg Leu Tyr Asp Glu Lys Gln Gln His Ile Val Tyr Cys Ser Asn Asp
    290                 295                 300

Leu Leu Gly Asp Val Phe Gly Val Pro Ser Phe Ser Val Lys Glu His
305                 310                 315                 320

Arg Lys Ile Tyr Ala Met Ile Tyr Arg Asn Leu Val Val Ser Gln
                325                 330                 335

Gln Asp Ser Gly Thr Ser Pro Ser Arg Ser
            340                 345

<210> SEQ ID NO 43
<211> LENGTH: 489
<212> TYPE: DNA
<213> ORGANISM: Artificial Sequence
<220> FEATURE:
<223> OTHER INFORMATION: Synthetic polynucleotide or polypeptide

<400> SEQUENCE: 43
atgctgccga gagtgggctg ccccgcgctg ccgctgccgc cgccgccgct gctgccgctg      60
ctgccgctgc tgctgctgct actgggcgcg agtggcggcg gcggcggggc gcgcgcggag     120
gtgctgttcc gctgcccgcc ctgcacaccc gagcgcctgg ccgcctgcgg gccccgccg      180 gttgcgccgc cgccgcgt ggccgcagtg gccggaggcg cccgcatgcc atgcgcggag      240
ctcgtccggg agccgggctg cggctgctgc tcggtgtgcg cccggctgga gggcgaggcg      300
tgcggcgtct acaccccgcg ctgccggcca gggctgcgct gctatcccca cccgggctcc      360
gagctgcccc tgcaggcgct ggtcatgggc gagggcactt gtgagaagcg ccgggacgcc      420
gagtatggcg ccagcccgga gcaggttgca gacaatggcg atgaccactc agaaggaggc      480
ctggtggag                                                             489

<210> SEQ ID NO 44
<211> LENGTH: 423
<212> TYPE: DNA
<213> ORGANISM: Artificial Sequence
<220> FEATURE:
<223> OTHER INFORMATION: Synthetic polynucleotide or polypeptide

<400> SEQUENCE: 44
atgctgcccc gcctgggcgg cccccgccctg cccctgctgc tgccctccct gctgctgctg      60

```
ctgctgctgg gcgccggcgg ctgcggcccc ggcgtgcgcg ccgaggtgct gttccgctgc    120 ccccctgca cccccgagcg cctggccgcc tgcggccccc ccccgacgc ccctgcgcc      180 gagctggtgc gcgagcccgg ctgcggctgc tgctccgtgt gcgcccgcca ggagggcgag    240
gcctgcggcg tgtacatccc ccgctgcgcc cagaccctgc gctgctaccc caaccccggc    300
tccgagctgc ccctgaaggc cctggtgacc ggcgccggca cctgcgagaa cgccgcgtg     360 ggcaccaccc cccagcaggt ggccgactcc gacgacgacc actccgaggg cggcctggtg    420
gag                                                                  423

<210> SEQ ID NO 45
<211> LENGTH: 423
<212> TYPE: DNA
<213> ORGANISM: Artificial Sequence
<220> FEATURE:
<223> OTHER INFORMATION: Synthetic polynucleotide or polypeptide

<400> SEQUENCE: 45
atgctgcccc gcctgggcgg ccccgccctg cccctgctgc tgccctccct gctgctgctg    60
ctgctgctgg gcgccggcgg ctgcggcccc ggcgtgcgcg ccgaggtgct gttccgctgc    120 ccccctgca cccccgagcg cctggccgcc tgcggccccc ccccgacgc ccctgcgcc      180 gagctggtgc gcgagcccgg ctgcggctgc tgctccgtgt gcgcccgcca ggagggcgag    240
gcctgcggcg tgtacatccc ccgctgcgcc cagaccctgc gctgctaccc caaccccggc    300
tccgagctgc ccctgaaggc cctggtgacc ggcgccggca cctgcgagaa cgccgcgtg     360 ggcaccaccc cccagcaggt ggccgactcc gaggacgacc actccgaggg cggcctggtg    420
gag                                                                  423

<210> SEQ ID NO 46
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 46

Asn His Val Asp Ser Thr Met Asn Met Leu Gly Gly Gly Gly Ser
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 47

Glu Leu Ala Val Phe Arg Glu Lys Val Thr Glu Gln His Arg Gln
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 48

Leu Gly Leu Glu Glu Pro Lys Lys Leu Arg Pro Pro Pro Ala Arg
1               5                   10                  15
```

```
<210> SEQ ID NO 49
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 49

Asp Gln Val Leu Glu Arg Ile Ser Thr Met Arg Leu Pro Asp Glu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 50

Gly Pro Leu Glu His Leu Tyr Ser Leu His Ile Pro Asn Cys Asp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 51

Lys His Gly Leu Tyr Asn Leu Lys Gln Cys Lys Met Ser Leu Asn
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 52

Pro Asn Thr Gly Lys Leu Ile Gln Gly Ala Pro Thr Ile Arg Gly
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 53

Pro Glu Cys His Leu Phe Tyr Asn Glu Gln Gln Glu Ala Arg Gly
1               5                   10                  15

<210> SEQ ID NO 54
<211> LENGTH: 163
<212> TYPE: PRT
<213> ORGANISM: Artificial Sequence
<220> FEATURE:
<223> OTHER INFORMATION: Synthetic polynucleotide or polypeptide

<400> SEQUENCE: 54

Met Leu Pro Arg Val Gly Cys Pro Ala Leu Pro Leu Pro Pro Pro
1               5                   10                  15
```

```
Leu Leu Pro Leu Pro Leu Leu Leu Leu Gly Ala Ser Gly
            20              25              30

Gly Gly Gly Gly Ala Arg Ala Glu Val Leu Phe Arg Cys Pro Pro Cys
        35                  40                  45

Thr Pro Glu Arg Leu Ala Ala Cys Gly Pro Pro Val Ala Pro Pro
    50                  55                  60

Ala Ala Val Ala Ala Val Ala Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
    130                 135                 140

Ser Pro Glu Gln Val Ala Asp Asn Gly Asp His Ser Glu Gly Gly
145                 150                 155                 160

Leu Val Glu

<210> SEQ ID NO 55
<211> LENGTH: 141
<212> TYPE: PRT
<213> ORGANISM: Artificial Sequence
<220> FEATURE:
<223> OTHER INFORMATION: Synthetic polynucleotide or polypeptide

<400> SEQUENCE: 55

Met Leu Pro Arg Leu Gly Gly Pro Ala Leu Pro Leu Leu Leu Pro Ser
1               5                   10                  15

Leu Leu Leu Leu Leu Leu Gly Ala Gly Gly Cys Gly Pro Gly Val
            20                  25                  30

Arg Ala Glu Val Leu Phe Arg Cys Pro Pro Cys Thr Pro Glu Arg Leu
        35                  40                  45

Ala Ala Cys Gly Pro Pro Asp Ala Pro Cys Ala Glu Leu Val Arg
    50                  55                  60

Glu Pro Gly Cys Gly Cys Cys Ser Val Cys Ala Arg Gln Glu Gly Glu
65                  70                  75                  80

Ala Cys Gly Val Tyr Ile Pro Arg Cys Ala Gln Thr Leu Arg Cys Tyr
                85                  90                  95

Pro Asn Pro Gly Ser Glu Leu Pro Leu Lys Ala Leu Val Thr Gly Ala
            100                 105                 110

Gly Thr Cys Glu Lys Arg Arg Val Gly Thr Thr Pro Gln Gln Val Ala
        115                 120                 125

Asp Ser Asp Asp Asp His Ser Glu Gly Gly Leu Val Glu
    130                 135                 140

<210> SEQ ID NO 56
<211> LENGTH: 141
<212> TYPE: PRT
<213> ORGANISM: Artificial Sequence
<220> FEATURE:
<223> OTHER INFORMATION: Synthetic polynucleotide or polypeptide

<400> SEQUENCE: 56

Met Leu Pro Arg Leu Gly Gly Pro Ala Leu Pro Leu Leu Leu Pro Ser
1               5                   10                  15
```

Leu Leu Leu Leu Leu Leu Gly Ala Gly Gly Cys Gly Pro Gly Val
            20                  25                  30

Arg Ala Glu Val Leu Phe Arg Cys Pro Pro Cys Thr Pro Glu Arg Leu
        35                  40                  45

Ala Ala Cys Gly Pro Pro Asp Ala Pro Cys Ala Glu Leu Val Arg
50                  55                  60

Glu Pro Gly Cys Gly Cys Cys Ser Val Cys Ala Arg Gln Glu Gly Glu
65              70                  75                  80

Ala Cys Gly Val Tyr Ile Pro Arg Cys Ala Gln Thr Leu Arg Cys Tyr
                85                  90                  95

Pro Asn Pro Gly Ser Glu Leu Pro Leu Lys Ala Leu Val Thr Gly Ala
            100                 105                 110

Gly Thr Cys Glu Lys Arg Arg Val Gly Ala Thr Pro Gln Gln Val Ala
            115                 120                 125

Asp Ser Glu Asp Asp His Ser Glu Gly Gly Leu Val Glu
    130                 135                 140

<210> SEQ ID NO 57
<211> LENGTH: 1101
<212> TYPE: DNA
<213> ORGANISM: Artificial Sequence
<220> FEATURE:
<223> OTHER INFORMATION: Synthetic polynucleotide or polypeptide

<400> SEQUENCE: 57
acgatgcgga gactgctgca ggaaacggag ctggtggagc cgctgacacc tagcggagcg      60
atgcccaacc aggcgcagat gcggatcctg aaagagacgg agctgaggaa ggtgaaggtg     120
cttggatctg cgcttttgg cacagtctac aagggcatct ggatccctga tggggagaat     180
gtgaaaattc cagtggccat caaagtgttg agggaaaaca catcccccaa agccaacaaa     240
gaaatcttag acgaagcata cgtgatggct ggtgtgggct ccccatatgt ctcccgcctt     300
ctgggcatct gcctgacatc cacggtgcag ctggtgacac agcttatgcc ctatggctgc     360
ctcttagacc atgtccggga aaaccgcgga cgcctgggct cccaggacct gctgaactgg     420
tgtatgcaga ttgccaaggg gatgagctac ctggaggatg tgcggctcgt acacagggac     480
ttggccgctc ggaacgtgct ggtcaagagt cccaaccatg tcaaaattac agacttcggg     540
ctggctcggc tgctggacat tgacgagaca gagtaccatg cagatggggg caaggtgccc     600
atcaagtgga tggcgctgga gtccattctc cgccggcggt tcacccacca gagtgatgtg     660
tggagttatg gtgtgactgt gtgggagctg atgacttttg ggccaaaacc ttacgatggg     720
atcccagccc gggagatccc tgacctgctg gaaaagggg agcggctgcc ccagccccc       780
atctgcacca ttgatgtcta catgatcatg gtcaaatgtt ggatgattga ctctgaatgt     840
cggccaagat tccgggagtt ggtgtctgaa ttctcccgca tggccaggga ccccagcgc      900
tttgtggtca tccagaatga ggacttggct cccggagctg gcggcatggt gcaccacagg     960
caccgcagct catctcctct gcctgctgcc cgacctgctg gtgccactct ggaaaggccc    1020
aagactctct ccccagggaa gaatgggggtc gtcaaagacg ttttgccttg tgggggtgcc    1080
gtggagaacc ccgagtactt g                                              1101

<210> SEQ ID NO 58
<211> LENGTH: 1101
<212> TYPE: DNA
<213> ORGANISM: Artificial Sequence
<220> FEATURE:
<223> OTHER INFORMATION: Synthetic polynucleotide or polypeptide

<400> SEQUENCE: 58

```
accatgcgcc gcctgctgca ggagaccgag ctggtggagc ccctgacccc ctccggcgcc        60
gtgcccaacc aggcccagat gcgcatcctg aaggagaccg agctgcgcaa gctgaaggtg       120
ctgggctccg gcgccttcgg caccgtgtac aagggcatct ggatccccga cggcgagaac       180
gtgaagatcc ccgtggccat caaggtgctg cgcgagaaca cctcccccaa ggccaacaag       240
gagatcctgg acgaggccta cgtgatggcc ggcgtgggct cccccctacgt gtcccgcctg      300
ctgggcatct gcctgacctc caccgtgcag ctggtgaccc agctgatgcc ctacggctgc       360
ctgctggacc acgtgcgcga gcaccgcggc cgcctgggct cccaggacct gctgaactgg       420
tgcgtgcaga tcgccaaggg catgtcctac ctggaggagg tgcgcctggt gcaccgcgac       480
ctggccgccc gcaacgtgct ggtgaagtcc cccaaccacg tgaagatcac cgacttcggc       540
ctggcccgcc tgctggacat cgacgagacc gagtaccacg ccgacggcgg caaggtgccc       600
atcaagtgga tggccctgga gtccatcctg cgccgccgct tcacccacca gtccgacgtg       660
tggtcctacg gcgtgaccgt gtgggagctg atgaccttcg gcgccaagcc ctacgacggc       720
atccccgccc gcgagatccc cgacctgctg gagaagggcg agcgcctgcc ccagcccccc       780
atctgcacca tcgacgtgta catgatcatg gtgaagtgct ggatgatcga ctccgagtgc       840
cgccccgct tccgcgagct ggtgtccgag ttctcccgca tggcccgcga ccccagcgc        900
ttcgtggtga tccagaacga ggacctggcc ctgggcaccg gctccaccgc ccaccgccgc       960
caccgctcct cctcccccccc ccccccatc cgccccgccg cgccacccct ggagcgcccc      1020
aagaccctgt ccccccggcaa gaacggcgtg gtgaaggacg tgttcgcctt cggcggcgcc      1080
gtggagaacc ccgagtacct g                                               1101
```

<210> SEQ ID NO 59
<211> LENGTH: 1101
<212> TYPE: DNA
<213> ORGANISM: Artificial Sequence
<220> FEATURE:
<223> OTHER INFORMATION: Synthetic polynucleotide or polypeptide

<400> SEQUENCE: 59

```
accatgcgcc gcctgctgca ggagaccgag ctggtggagc ccctgacccc ctccggcgcc        60
atgcccaacc aggcccagat gcgcatcctg aaggagaccg agctgcgcaa ggtgaaggtg       120
ctgggctccg gcgccttcgg caccgtgtac aagggcatct ggatccccga cggcgagaac       180
gtgaagatcc ccgtggccat caaggtgctg cgcgagaaca cctcccccaa ggccaacaag       240
gagatcctgg acgaggccta cgtgatggcc ggcgtgggct cccccctacgt gtcccgcctg      300
ctgggcatct gcctgacctc caccgtgcag ctggtgaccc agctgatgcc ctacggctgc       360
ctgctggacc acgtgcgcga gcaccgcggc cgcctgggct cccaggacct gctgaactgg       420
tgcgtgcaga tcgccaaggg catgtcctac ctggaggacg tgcgcctggt gcaccgcgac       480
ctggccgccc gcaacgtgct ggtgaagtcc cccaaccacg tgaagatcac cgacttcggc       540
ctggcccgcc tgctggacat cgacgagacc gagtaccacg ccgacggcgg caaggtgccc       600
atcaagtgga tggccctgga gtccatcctg cgccgccgct tcacccacca gtccgacgtg       660
tggtcctacg gcgtgaccgt gtgggagctg atgaccttcg gcgccaagcc ctacgacggc       720
atccccgccc gcgagatccc cgacctgctg gagaagggcg agcgcctgcc ccagcccccc       780
atctgcacca tcgacgtgta catgatcatg gtgaagtgct ggatgatcga ctccgagtgc       840
```

```
cgcccccgct tccgcgagct ggtgtccgag ttctcccgca tggcccgcga ccccagcgc    900 ttcgtggtga tccagaacga ggacctgacc cccggcaccg gctccaccgc ccaccgccgc    960
caccgctcct cctccccccct gcccccgtg cgccccgccg gcgccaccct ggagcgcccc   1020
aagaccctgt cccccggcaa gaacggcgtg gtgaaggacg tgttcgcctt cggcggcgcc   1080
gtggagaacc ccgagtacct g                                             1101

<210> SEQ ID NO 60
<211> LENGTH: 367
<212> TYPE: PRT
<213> ORGANISM: Artificial Sequence
<220> FEATURE:
<223> OTHER INFORMATION: Synthetic polynucleotide or polypeptide

<400> SEQUENCE: 60

Thr Met Arg Arg Leu Leu Gln Glu Thr Glu Leu Val Glu Pro Leu Thr
1               5                   10                  15

Pro Ser Gly Ala Met Pro Asn Gln Ala Gln Met Arg Ile Leu Lys Glu
                20                  25                  30

Thr Glu Leu Arg Lys Val Lys Val Leu Gly Ser Gly Ala Phe Gly Thr
            35                  40                  45

Val Tyr Lys Gly Ile Trp Ile Pro Asp Gly Glu Asn Val Lys Ile Pro
        50                  55                  60

Val Ala Ile Lys Val Leu Arg Glu Asn Thr Ser Pro Lys Ala Asn Lys
65                  70                  75                  80

Glu Ile Leu Asp Glu Ala Tyr Val Met Ala Gly Val Gly Ser Pro Tyr
                85                  90                  95

Val Ser Arg Leu Leu Gly Ile Cys Leu Thr Ser Thr Val Gln Leu Val
            100                 105                 110

Thr Gln Leu Met Pro Tyr Gly Cys Leu Leu Asp His Val Arg Glu Asn
        115                 120                 125

Arg Gly Arg Leu Gly Ser Gln Asp Leu Leu Asn Trp Cys Met Gln Ile
    130                 135                 140

Ala Lys Gly Met Ser Tyr Leu Glu Asp Val Arg Leu Val His Arg Asp
145                 150                 155                 160

Leu Ala Ala Arg Asn Val Leu Val Lys Ser Pro Asn His Val Lys Ile
                165                 170                 175

Thr Asp Phe Gly Leu Ala Arg Leu Leu Asp Ile Asp Glu Thr Glu Tyr
            180                 185                 190

His Ala Asp Gly Gly Lys Val Pro Ile Lys Trp Met Ala Leu Glu Ser
        195                 200                 205

Ile Leu Arg Arg Arg Phe Thr His Gln Ser Asp Val Trp Ser Tyr Gly
    210                 215                 220

Val Thr Val Trp Glu Leu Met Thr Phe Gly Ala Lys Pro Tyr Asp Gly
225                 230                 235                 240

Ile Pro Ala Arg Glu Ile Pro Asp Leu Leu Glu Lys Gly Glu Arg Leu
                245                 250                 255

Pro Gln Pro Pro Ile Cys Thr Ile Asp Val Tyr Met Ile Met Val Lys
            260                 265                 270

Cys Trp Met Ile Asp Ser Glu Cys Arg Pro Arg Phe Arg Glu Leu Val
        275                 280                 285

Ser Glu Phe Ser Arg Met Ala Arg Asp Pro Gln Arg Phe Val Val Ile
    290                 295                 300

Gln Asn Glu Asp Leu Ala Pro Gly Ala Gly Gly Met Val His His Arg
305                 310                 315                 320
```

His Arg Ser Ser Ser Pro Leu Pro Ala Ala Arg Pro Ala Gly Ala Thr
            325                 330                 335

Leu Glu Arg Pro Lys Thr Leu Ser Pro Gly Lys Asn Gly Val Val Lys
            340                 345                 350

Asp Val Phe Ala Phe Gly Gly Ala Val Glu Asn Pro Gly Tyr Leu
            355                 360                 365

<210> SEQ ID NO 61
<211> LENGTH: 367
<212> TYPE: PRT
<213> ORGANISM: Artificial Sequence
<220> FEATURE:
<223> OTHER INFORMATION: Synthetic polynucleotide or polypeptide

<400> SEQUENCE: 61

Thr Met Arg Arg Leu Leu Gln Glu Thr Glu Leu Val Glu Pro Leu Thr
1               5                   10                  15

Pro Ser Gly Ala Val Pro Asn Gln Ala Gln Met Arg Ile Leu Lys Glu
            20                  25                  30

Thr Glu Leu Arg Lys Leu Lys Val Leu Gly Ser Gly Ala Phe Gly Thr
        35                  40                  45

Val Tyr Lys Gly Ile Trp Ile Pro Asp Gly Glu Asn Val Lys Ile Pro
    50                  55                  60

Val Ala Ile Lys Val Leu Arg Glu Asn Thr Ser Pro Lys Ala Asn Lys
65                  70                  75                  80

Glu Ile Leu Asp Glu Ala Tyr Val Met Ala Gly Val Gly Ser Pro Tyr
                85                  90                  95

Val Ser Arg Leu Leu Gly Ile Cys Leu Thr Ser Thr Val Gln Leu Val
            100                 105                 110

Thr Gln Leu Met Pro Tyr Gly Cys Leu Leu Asp His Val Arg Glu His
        115                 120                 125

Arg Gly Arg Leu Gly Ser Gln Asp Leu Leu Asn Trp Cys Val Gln Ile
    130                 135                 140

Ala Lys Gly Met Ser Tyr Leu Glu Glu Val Arg Leu Val His Arg Asp
145                 150                 155                 160

Leu Ala Ala Arg Asn Val Leu Val Lys Ser Pro Asn His Val Lys Ile
                165                 170                 175

Thr Asp Phe Gly Leu Ala Arg Leu Leu Asp Ile Asp Glu Thr Glu Tyr
            180                 185                 190

His Ala Asp Gly Gly Lys Val Pro Ile Lys Trp Met Ala Leu Glu Ser
        195                 200                 205

Ile Leu Arg Arg Arg Phe Thr His Gln Ser Asp Val Trp Ser Tyr Gly
    210                 215                 220

Val Thr Val Trp Glu Leu Met Thr Phe Gly Ala Lys Pro Tyr Asp Gly
225                 230                 235                 240

Ile Pro Ala Arg Glu Ile Pro Asp Leu Leu Glu Lys Gly Glu Arg Leu
                245                 250                 255

Pro Gln Pro Pro Ile Cys Thr Ile Asp Val Tyr Met Ile Met Val Lys
            260                 265                 270

Cys Trp Met Ile Asp Ser Glu Cys Arg Pro Arg Phe Arg Glu Leu Val
        275                 280                 285

Ser Glu Phe Ser Arg Met Ala Arg Asp Pro Gln Arg Phe Val Val Ile
    290                 295                 300

Gln Asn Glu Asp Leu Ala Leu Gly Thr Gly Ser Thr Ala His Arg Arg
305                 310                 315                 320

His Arg Ser Ser Pro Pro Pro Ile Arg Pro Ala Gly Ala Thr
                325                 330                 335

Leu Glu Arg Pro Lys Thr Leu Ser Pro Gly Lys Asn Gly Val Val Lys
            340                 345                 350

Asp Val Phe Ala Phe Gly Gly Ala Val Glu Asn Pro Gly Tyr Leu
        355                 360                 365

<210> SEQ ID NO 62
<211> LENGTH: 367
<212> TYPE: PRT
<213> ORGANISM: Artificial Sequence
<220> FEATURE:
<223> OTHER INFORMATION: Synthetic polynucleotide or polypeptide

<400> SEQUENCE: 62

Thr Met Arg Arg Leu Leu Gln Glu Thr Glu Leu Val Glu Pro Leu Thr
1               5                   10                  15

Pro Ser Gly Ala Met Pro Asn Gln Ala Gln Met Arg Ile Leu Lys Glu
            20                  25                  30

Thr Glu Leu Arg Lys Val Lys Val Leu Gly Ser Gly Ala Phe Gly Thr
        35                  40                  45

Val Tyr Lys Gly Ile Trp Ile Pro Asp Gly Glu Asn Val Lys Ile Pro
50                  55                  60

Val Ala Ile Lys Val Leu Arg Glu Asn Thr Ser Pro Lys Ala Asn Lys
65                  70                  75                  80

Glu Ile Leu Asp Glu Ala Tyr Val Met Ala Gly Val Gly Ser Pro Tyr
                85                  90                  95

Val Ser Arg Leu Leu Gly Ile Cys Leu Thr Ser Thr Val Gln Leu Val
            100                 105                 110

Thr Gln Leu Met Pro Tyr Gly Cys Leu Leu Asp His Val Arg Glu His
        115                 120                 125

Arg Gly Arg Leu Gly Ser Gln Asp Leu Leu Asn Trp Cys Val Gln Ile
130                 135                 140

Ala Lys Gly Met Ser Tyr Leu Glu Asp Val Arg Leu Val His Arg Asp
145                 150                 155                 160

Leu Ala Ala Arg Asn Val Leu Val Lys Ser Pro Asn His Val Lys Ile
                165                 170                 175

Thr Asp Phe Gly Leu Ala Arg Leu Leu Asp Ile Asp Glu Thr Glu Tyr
            180                 185                 190

His Ala Asp Gly Gly Lys Val Pro Ile Lys Trp Met Ala Leu Glu Ser
        195                 200                 205

Ile Leu Arg Arg Arg Phe Thr His Gln Ser Asp Val Trp Ser Tyr Gly
210                 215                 220

Val Thr Val Trp Glu Leu Met Thr Phe Gly Ala Lys Pro Tyr Asp Gly
225                 230                 235                 240

Ile Pro Ala Arg Glu Ile Pro Asp Leu Leu Glu Lys Gly Glu Arg Leu
                245                 250                 255

Pro Gln Pro Pro Ile Cys Thr Ile Asp Val Tyr Met Ile Met Val Lys
            260                 265                 270

Cys Trp Met Ile Asp Ser Glu Cys Arg Pro Arg Phe Arg Glu Leu Val
        275                 280                 285

Ser Glu Phe Ser Arg Met Ala Arg Asp Pro Gln Arg Phe Val Val Ile
    290                 295                 300

Gln Asn Glu Asp Leu Thr Pro Gly Thr Gly Ser Thr Ala His Arg Arg
305                 310                 315                 320

His Arg Ser Ser Pro Leu Pro Pro Val Arg Pro Ala Gly Ala Thr
            325                 330                 335

Leu Glu Arg Pro Lys Thr Leu Ser Pro Gly Lys Asn Gly Val Val Lys
        340                 345                 350

Asp Val Phe Ala Phe Gly Gly Ala Val Glu Asn Pro Glu Tyr Leu
            355                 360                 365

<210> SEQ ID NO 63
<211> LENGTH: 312
<212> TYPE: DNA
<213> ORGANISM: Artificial Sequence
<220> FEATURE:
<223> OTHER INFORMATION: Synthetic polynucleotide or polypeptide

<400> SEQUENCE: 63
tggtccttcg gcgtggtgct gtgggagatc gccaccctgg ccgagcagcc ctaccagggc    60
ctgtccaacg agcaggtgct gcgcttcgtg atggagggcg gcctgctgga caagcccgac   120
aactgccccg acatgctgtt cgagctgatg cgcatgtgct ggcagtacaa ccccaagatg   180
cgcccctcct tcctggagca caaggccgag aacggccccg ccccggcgt gctggtgctg    240 cgcgcctcct tcgacgagcg ccagccctac gcccacatga cggaggccg caagaacgag   300 cgcgccctgc cc                                                     312

<210> SEQ ID NO 64
<211> LENGTH: 312
<212> TYPE: DNA
<213> ORGANISM: Artificial Sequence
<220> FEATURE:
<223> OTHER INFORMATION: Synthetic polynucleotide or polypeptide

<400> SEQUENCE: 64
tggtccttcg gcgtggtgct gtgggagatc gccaccctgg ccgagcagcc ctaccagggc    60
ctgtccaacg agcaggtgct gcgcttcgtg atggagggcg gcctgctgga caagcccgac   120
aactgccccg acatgctgtt cgagctgatg cgcatgtgct ggcagtacaa ccccaagatg   180
cgcccctcct tcctggagca caaggccgag aacggccccg ccccggcgt gctggtgctg    240 cgcgcctcct tcgacgagcg ccagccctac gcccacatga cggcggccg cgccaacgag   300 cgcgccctgc cc                                                     312

<210> SEQ ID NO 65
<211> LENGTH: 306
<212> TYPE: DNA
<213> ORGANISM: Artificial Sequence
<220> FEATURE:
<223> OTHER INFORMATION: Synthetic polynucleotide or polypeptide

<400> SEQUENCE: 65
tggtccttcg gcgtggtgct gtgggagatc gccaccctgg ccgagcagcc ctaccagggc    60
ctgtccaacg agcaggtgct gcgcttcgtg atggagggcg gcctgctgga caagcccgac   120
aactgccccg acatgctgtt cgagctgatg cgcatgtgct ggcagtacaa ccccaagatg   180
cgcccctcct tcctggagca caaggccgag aacggccccg cgtgctggt gctgcgcgcc    240 tccttcgacg agcgccagcc ctacgcccac atgaacggcg gcgcgccaa cgagcgcgcc    300 ctgccc                                                            306

<210> SEQ ID NO 66
<211> LENGTH: 15

```
<212> TYPE: PRT
<213> ORGANISM: Artificial Sequence
<220> FEATURE:
<223> OTHER INFORMATION: Synthetic polynucleotide or polypeptide

<400> SEQUENCE: 66

Asp Tyr Arg Ser Tyr Arg Phe Pro Lys Leu Thr Val Ile Thr Glu
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 67

Ile Arg Gly Trp Lys Leu Phe Tyr Asn Tyr Ala Leu Val Ile Phe
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 68

Val Val Thr Gly Tyr Val Lys Ile Arg His Ser His Ala Leu Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 69

Phe Phe Tyr Val Gln Ala Lys Thr Gly Tyr Glu Asn Phe Ile His
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 70

Leu Ile Ile Ala Leu Pro Val Ala Val Leu Leu Ile Val Gly Gly
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic polynucleotide or polypeptide

<400> SEQUENCE: 71

Leu Val Ile Met Leu Tyr Val Phe His Arg Lys Arg Asn Asn Ser
1               5                   10                  15

<210> SEQ ID NO 72
<211> LENGTH: 15
<212> TYPE: PRT
```

<213> ORGANISM: Artificial Sequence
<220> FEATURE:
<223> OTHER INFORMATION: Synthetic polynucleotide or polypeptide

<400> SEQUENCE: 72

```
Asn Cys His His Val Val Arg Leu Leu Gly Val Val Ser Gln Gly
1               5                   10                  15
```

<210> SEQ ID NO 73
<211> LENGTH: 104
<212> TYPE: PRT
<213> ORGANISM: Artificial Sequence
<220> FEATURE:
<223> OTHER INFORMATION: Synthetic polynucleotide or polypeptide

<400> SEQUENCE: 73

```
Trp Ser Phe Gly Val Val Leu Trp Glu Ile Ala Thr Leu Ala Glu Gln
1               5                   10                  15

Pro Tyr Gln Gly Leu Ser Asn Glu Gln Val Leu Arg Phe Val Met Glu
                20                  25                  30

Gly Gly Leu Leu Asp Lys Pro Asp Asn Cys Pro Asp Met Leu Phe Glu
            35                  40                  45

Leu Met Arg Met Cys Trp Gln Tyr Asn Pro Lys Met Arg Pro Ser Phe
        50                  55                  60

Leu Glu His Lys Ala Glu Asn Gly Pro Gly Pro Gly Val Leu Val Leu
65                  70                  75                  80

Arg Ala Ser Phe Asp Glu Arg Gln Pro Tyr Ala His Met Asn Gly Gly
                    85                  90                  95

Arg Lys Asn Glu Arg Ala Leu Pro
                100
```

<210> SEQ ID NO 74
<211> LENGTH: 104
<212> TYPE: PRT
<213> ORGANISM: Artificial Sequence
<220> FEATURE:
<223> OTHER INFORMATION: Synthetic polynucleotide or polypeptide

<400> SEQUENCE: 74

```
Trp Ser Phe Gly Val Val Leu Trp Glu Ile Ala Thr Leu Ala Glu Gln
1               5                   10                  15

Pro Tyr Gln Gly Leu Ser Asn Glu Gln Val Leu Arg Phe Val Met Glu
                20                  25                  30

Gly Gly Leu Leu Asp Lys Pro Asp Asn Cys Pro Asp Met Leu Phe Glu
            35                  40                  45

Leu Met Arg Met Cys Trp Gln Tyr Asn Pro Lys Met Arg Pro Ser Phe
        50                  55                  60

Leu Glu His Lys Ala Glu Asn Gly Pro Gly Pro Gly Val Leu Val Leu
65                  70                  75                  80

Arg Ala Ser Phe Asp Glu Arg Gln Pro Tyr Ala His Met Asn Gly Gly
                    85                  90                  95

Arg Ala Asn Glu Arg Ala Leu Pro
                100
```

<210> SEQ ID NO 75
<211> LENGTH: 102
<212> TYPE: PRT
<213> ORGANISM: Artificial Sequence
<220> FEATURE:
<223> OTHER INFORMATION: Synthetic polynucleotide or polypeptide

<400> SEQUENCE: 75

Trp Ser Phe Gly Val Val Leu Trp Glu Ile Ala Thr Leu Ala Glu Gln
1               5                   10                  15

Pro Tyr Gln Gly Leu Ser Asn Glu Gln Val Leu Arg Phe Val Met Glu
            20                  25                  30

Gly Gly Leu Leu Asp Lys Pro Asp Asn Cys Pro Asp Met Leu Phe Glu
        35                  40                  45

Leu Met Arg Met Cys Trp Gln Tyr Asn Pro Lys Met Arg Pro Ser Phe
    50                  55                  60

Leu Glu His Lys Ala Glu Asn Gly Pro Gly Val Leu Val Leu Arg Ala
65                  70                  75                  80

Ser Phe Asp Glu Arg Gln Pro Tyr Ala His Met Asn Gly Gly Arg Ala
                85                  90                  95

Asn Glu Arg Ala Leu Pro
            100

<210> SEQ ID NO 76
<211> LENGTH: 1947
<212> TYPE: DNA
<213> ORGANISM: Artificial Sequence
<220> FEATURE:
<223> OTHER INFORMATION: Synthetic polynucleotide or polypeptide

<400> SEQUENCE: 76
atggcggtac caatgctgcc gagagtgggc tgccccgcgc tgccgctgcc gccgccgccg     60
ctgctgccgc tgctgccgct gctgctgctg ctactgggcg cgagtggcgg cggcggcggg    120
gcgcgcgcgg aggtgctgtt ccgctgcccg ccctgcacac ccgagcgcct ggccgcctgc    180
gggcccccgc cggttgcgcc gcccgccgcg gtggccgcag tggccggagg cgcccgcatg    240
ccatgcgcgg agctcgtccg ggagccgggc tgcggctgct gctcggtgtg cgcccggctg    300
gagggcgagg cgtgcggcgt ctacaccccg cgctgcggcc aggggctgcg ctgctatccc    360
cacccgggct ccgagctgcc cctgcaggcg ctggtcatgg gcgagggcac ttgtgagaag    420 cgccggacg ccgagtatgg cgccagcccg agcaggttg cagacaatgg cgatgaccac    480
tcagaaggag gcctggtgga gcaattgacg atgcggagac tgctgcagga aacggagctg    540
gtggagccgc tgacacctag cggagcgatg cccaaccagg cgcagatgcg gatcctgaaa    600
gagacggagc tgaggaaggt gaaggtgctt ggatctggcg cttttggcac agtctacaag    660
ggcatctgga tccctgatgg ggagaatgtg aaaattccag tggccatcaa gtgttgagg    720 gaaaacacat ccccaaagc caacaaagaa atcttagacg aagcatacgt gatggctggt    780
gtgggctccc catatgtctc ccgccttctg ggcatctgcc tgacatccac ggtgcagctg    840
gtgacacagc ttatgcccta tggctgcctc ttagaccatg tccgggaaaa ccgcggacgc    900
ctgggctccc aggacctgct gaactggtgt atgcagattg ccaaggggat gagctacctg    960
gaggatgtgc ggctcgtaca cagggacttg gccgctcgga acgtgctggt caagagtccc   1020
aaccatgtca aaattacaga cttcgggctg gctcggctgc tggacattga cgagacagag   1080
taccatgcag atgggggcaa ggtgcccatc aagtggatgg cgctggagtc cattctccgc   1140
cggcggttca cccaccagag tgatgtgtgg agttatggtg tgactgtgtg ggagctgatg   1200
acttttgggg ccaaaccttat cgatgggatc ccagcccggg agatccctga cctgctggaa   1260 aaggggagc ggctgcccca gccccccatc tgcaccattg atgtctacat gatcatggtc   1320
aaatgttgga tgattgactc tgaatgtcgg ccaagattcc gggagttggt gtctgaattc   1380

| | |
|---|---|
| tcccgcatgg ccagggaccc ccagcgcttt gtggtcatcc agaatgagga cttggctccc | 1440 |
| ggagctggcg gcatggtgca ccacaggcac cgcagctcat ctcctctgcc tgctgcccga | 1500 |
| cctgctggtg ccactctgga aaggcccaag actctctccc cagggaagaa tggggtcgtc | 1560 |
| aaagacgttt ttgcctttgg gggtgccgtg gagaacccccg agtacttggg ccggccggta | 1620 |
| ccttggtcct tcggcgtggt gctgtgggag atcgccaccc tggccgagca gccctaccag | 1680 |
| ggcctgtcca acgagcaggt gctgcgcttc gtgatggagg cgggcctgct ggacaagccc | 1740 |
| gacaactgcc ccgacatgct gttcgagctg atgcgcatgt gctggcagta caaccccaag | 1800 |
| atgcgcccct ccttcctgga gcacaaggcc gagaacggcc ccggcccccgg cgtgctggtg | 1860 |
| ctgcgcgcct ccttcgacga cgccagccc tacgcccaca tgaacggagg ccgcaagaac | 1920 |
| gagcgcgccc tgcccgcggc cgcatag | 1947 |

<210> SEQ ID NO 77
<211> LENGTH: 1881
<212> TYPE: DNA
<213> ORGANISM: Artificial Sequence
<220> FEATURE:
<223> OTHER INFORMATION: Synthetic polynucleotide or polypeptide

<400> SEQUENCE: 77

| | |
|---|---|
| atggcggtac caatgctgcc ccgcctgggc ggccccgccc tgcccctgct gctgccctcc | 60 |
| ctgctgctgc tgctgctgct gggcgccggc ggctgcggcc ccggcgtgcg cgccgaggtg | 120 |
| ctgttccgct gccccccctg caccccccgag cgcctggccg cctgcggccc cccccccgac | 180 |
| gccccctgcg ccgagctggt gcgcgagccc ggctgcggct gctgctccgt gtgcgcccgc | 240 |
| caggagggcg aggcctgcgg cgtgtacatc ccccgctgcg cccagaccct gcgctgctac | 300 |
| cccaaccccg gctccgagct gcccctgaag gccctggtga ccggcgccgg cacctgcgag | 360 |
| aagcgccgcg tgggcaccac ccccccagcag gtggccgact ccgacgacga ccactccgag | 420 |
| ggcggcctgg tggagcaatt gaccatgcgc gcctgctgc aggagaccga gctggtggag | 480 |
| cccctgaccc cctccggcgc cgtgcccaac caggcccaga tgcgcatcct gaaggagacc | 540 |
| gagctgcgca agctgaaggt gctgggctcc ggcgccttcg gcaccgtgta caagggcatc | 600 |
| tggatccccg acggcgagaa cgtgaagatc cccgtggcca tcaaggtgct gcgcgagaac | 660 |
| acctcccca aggccaacaa ggagatcctg gacgaggcc acgtgatggc cggcgtgggc | 720 |
| tcccccctacg tgtcccgcct gctgggcatc tgcctgacct ccaccgtgca gctggtgacc | 780 |
| cagctgatgc cctacggctg cctgctggac acgtgcgcg agcaccgcgg ccgcctgggc | 840 |
| tcccaggacc tgctgaactg gtgcgtgcag atcgccaagg gcatgtccta cctggaggag | 900 |
| gtgcgcctgg tgcaccgcga cctggccgcc gcaacgtgc tggtgaagtc ccccaaccac | 960 |
| gtgaagatca ccgacttcgg cctggcccgc ctgctggaca tcgacgagac cgagtaccac | 1020 |
| gccgacggcg gcaaggtgcc catcaagtgg atggccctgg agtccatcct cgccgccgc | 1080 |
| ttcacccacc agtccgacgt gtggtcctac ggcgtgaccg tgtgggagct gatgaccttc | 1140 |
| ggcgccaagc cctacgacgg catccccgcc cgcgagatcc ccgacctgct ggagaagggc | 1200 |
| gagcgcctgc cccagccccc catctgcacc atcgacgtgt acatgatcat ggtgaagtgc | 1260 |
| tggatgatcg actccgagtg ccgccccgc ttccgcgagc tggtgtccga gttctcccgc | 1320 |
| atggcccgcg accccagcg cttcgtggtg atccagaacg aggacctggc cctgggcacc | 1380 |
| ggctccaccg cccaccgccg ccaccgctcc tcctcccccc ccccccccat ccgccccgcc | 1440 |
| ggcgccaccc tggagcgccc caagaccctg tcccccggca agaacggcgt ggtgaaggac | 1500 |

```
gtgttcgcct tcggcggcgc cgtggagaac cccgagtacc tgggccggcc ggtaccttgg    1560
tccttcggcg tggtgctgtg ggagatcgcc accctggccg agcagcccta ccagggcctg    1620
tccaacgagc aggtgctgcg cttcgtgatg gagggcggcc tgctggacaa gcccgacaac    1680 tgcccccgaca tgctgttcga gctgatgcgc atgtgctgga gtacaaccc caagatgcgc    1740 ccctccttcc tggagcacaa ggccgagaac ggccccggcc ccggcgtgct ggtgctgcgc    1800
gcctccttcg acgagcgcca gccctacgcc cacatgaacg gcggccgcgc caacgagcgc    1860
gccctgcccg cggccgcata g                                              1881
```

<210> SEQ ID NO 78
<211> LENGTH: 1875
<212> TYPE: DNA
<213> ORGANISM: Artificial Sequence
<220> FEATURE:
<223> OTHER INFORMATION: Synthetic polynucleotide or polypeptide

<400> SEQUENCE: 78

```
atggcggtac caatgctgcc ccgcctgggc ggccccgccc tgccctgct gctgccctcc      60 ctgctgctgc tgctgctgct gggcgccggc ggctgcggcc ccggcgtgcg cgccgaggtg    120
ctgttccgct gcccccccctg caccccccgag cgcctggccg cctgcggccc ccccccgac    180 gccccctgcg ccgagctggt gcgcgagccc ggctgcggct gctgctccgt gtgcgcccgc    240
caggagggcg aggcctgcgg cgtgtacatc ccccgctgcg cccagaccct gcgctgctac    300
cccaaccccg gctccgagct gccccctgaag gccctggtga ccggcgccgg cacctgcgag    360
aagcgccgcg tgggcgccac ccccccagcag gtggccgact ccgaggacga ccactccgag    420
ggcggcctgg tggagcaatt gaccatgcgc gcctgctgc aggagaccga gctggtggag    480 ccctgaccc cctccggcgc catgcccaac caggcccaga tgcgcatcct gaaggagacc    540
gagctgcgca aggtgaaggt gctgggctcc ggcgccttcg gcaccgtgta caagggcatc    600
tggatccccg acggcgagaa cgtgaagatc cccgtggcca tcaaggtgct cgcgagaac    660 acctccccca aggccaacaa ggagatcctg gacgaggcct acgtgatggc cggcgtgggc    720 tcccccctacg tgtcccgcct gctgggcatc tgcctgacct ccaccgtgca gctggtgacc    780
cagctgatgc cctacggctg cctgctggac cacgtgcgcg agcaccgcgg ccgcctgggc    840
tcccaggacc tgctgaactg gtgcgtgcag atcgccaagg gcatgtccta cctggaggac    900
gtgcgcctgg tgcaccgcga cctggccgcc cgcaacgtgc tggtgaagtc ccccaaccac    960
gtgaagatca ccgacttcgg cctggcccgc ctgctggaca tcgacgagac cgagtaccac    1020
gccgacggcg gcaaggtgcc catcaagtgg atggccctgg agtccatcct cgccgccgc    1080 ttcacccacc agtccgacgt gtggtcctac ggcgtgaccg tgtgggagct gatgaccttc    1140
ggcgccaagc cctacgacgg catccccgcc cgcgagatcc ccgacctgct ggagaagggc    1200
gagcgcctgc cccagccccc catctgcacc atcgacgtgt acatgatcat ggtgaagtgc    1260
tggatgatcg actccgagtg ccgccccgc ttccgcgagc tggtgtccga gttctcccgc    1320
atggcccgcg accccagcg cttcgtggtg atccagaacg aggacctgac ccccggcacc    1380
ggctccaccg cccaccgccg ccaccgctcc tcctcccccc tgccccccgt gcgccccgcc    1440
ggcgccaccc tggagcgccc caagaccctg tccccggca agaacggcgt ggtgaaggac    1500
gtgttcgcct cggcggcgc cgtggagaac cccgagtacc tgggccggcc ggtaccttgg    1560
tccttcggcg tggtgctgtg ggagatcgcc accctggccg agcagcccta ccagggcctg    1620
```

```
tccaacgagc aggtgctgcg cttcgtgatg gagggcggcc tgctggacaa gcccgacaac    1680
tgccccgaca tgctgttcga gctgatgcgc atgtgctggc agtacaaccc caagatgcgc    1740
ccctccttcc tggagcacaa ggccgagaac ggccccggcg tgctggtgct gcgcgcctcc    1800
ttcgacgagc gccagcccta cgcccacatg aacggcggcc gcgccaacga gcgcgccctg    1860
cccgcggccg catag                                                    1875
```

<210> SEQ ID NO 79
<211> LENGTH: 648
<212> TYPE: PRT
<213> ORGANISM: Artificial Sequence
<220> FEATURE:
<223> OTHER INFORMATION: Synthetic polynucleotide or polypeptide

<400> SEQUENCE: 79

```
Met Ala Val Pro Met Leu Pro Arg Val Gly Cys Pro Ala Leu Pro Leu
1               5                   10                  15

Pro Pro Pro Pro Leu Leu Pro Leu Leu Pro Leu Leu Leu Leu Leu Leu
            20                  25                  30

Gly Ala Ser Gly Gly Gly Gly Ala Arg Ala Glu Val Leu Phe Arg
        35                  40                  45

Cys Pro Pro Cys Thr Pro Glu Arg Leu Ala Ala Cys Gly Pro Pro
    50                  55                  60

Val Ala Pro Pro Ala Ala Val Ala Ala Val Ala Gly Gly Ala Arg Met
65                  70                  75                  80

Pro Cys Ala Glu Leu Val Arg Glu Pro Gly Cys Gly Cys Cys Ser Val
                85                  90                  95

Cys Ala Arg Leu Glu Gly Glu Ala Cys Gly Val Tyr Thr Pro Arg Cys
                100                 105                 110

Gly Gln Gly Leu Arg Cys Tyr Pro His Pro Gly Ser Glu Leu Pro Leu
            115                 120                 125

Gln Ala Leu Val Met Gly Glu Gly Thr Cys Glu Lys Arg Arg Asp Ala
        130                 135                 140

Glu Tyr Gly Ala Ser Pro Glu Gln Val Ala Asp Asn Gly Asp Asp His
145                 150                 155                 160

Ser Glu Gly Gly Leu Val Glu Gln Leu Thr Met Arg Arg Leu Leu Gln
                165                 170                 175

Glu Thr Glu Leu Val Glu Pro Leu Thr Pro Ser Gly Ala Met Pro Asn
            180                 185                 190

Gln Ala Gln Met Arg Ile Leu Lys Glu Thr Glu Leu Arg Lys Val Lys
        195                 200                 205

Val Leu Gly Ser Gly Ala Phe Gly Thr Val Tyr Lys Gly Ile Trp Ile
210                 215                 220

Pro Asp Gly Glu Asn Val Lys Ile Pro Val Ala Ile Lys Val Leu Arg
225                 230                 235                 240

Glu Asn Thr Ser Pro Lys Ala Asn Lys Glu Ile Leu Asp Glu Ala Tyr
                245                 250                 255

Val Met Ala Gly Val Gly Ser Pro Tyr Val Ser Arg Leu Leu Gly Ile
            260                 265                 270

Cys Leu Thr Ser Thr Val Gln Leu Val Thr Gln Leu Met Pro Tyr Gly
        275                 280                 285

Cys Leu Leu Asp His Val Arg Glu Asn Arg Gly Arg Leu Gly Ser Gln
    290                 295                 300

Asp Leu Leu Asn Trp Cys Met Gln Ile Ala Lys Gly Met Ser Tyr Leu
305                 310                 315                 320
```

Glu Asp Val Arg Leu Val His Arg Asp Leu Ala Ala Arg Asn Val Leu
            325                 330                 335

Val Lys Ser Pro Asn His Val Lys Ile Thr Asp Phe Gly Leu Ala Arg
        340                 345                 350

Leu Leu Asp Ile Asp Glu Thr Glu Tyr His Ala Asp Gly Gly Lys Val
            355                 360                 365

Pro Ile Lys Trp Met Ala Leu Glu Ser Ile Leu Arg Arg Arg Phe Thr
370                 375                 380

His Gln Ser Asp Val Trp Ser Tyr Gly Val Thr Val Trp Glu Leu Met
385                 390                 395                 400

Thr Phe Gly Ala Lys Pro Tyr Asp Gly Ile Pro Ala Arg Glu Ile Pro
                405                 410                 415

Asp Leu Leu Glu Lys Gly Glu Arg Leu Pro Gln Pro Pro Ile Cys Thr
            420                 425                 430

Ile Asp Val Tyr Met Ile Met Val Lys Cys Trp Met Ile Asp Ser Glu
        435                 440                 445

Cys Arg Pro Arg Phe Arg Glu Leu Val Ser Glu Phe Ser Arg Met Ala
    450                 455                 460

Arg Asp Pro Gln Arg Phe Val Val Ile Gln Asn Glu Asp Leu Ala Pro
465                 470                 475                 480

Gly Ala Gly Gly Met Val His His Arg His Arg Ser Ser Ser Pro Leu
                485                 490                 495

Pro Ala Ala Arg Pro Ala Gly Ala Thr Leu Glu Arg Pro Lys Thr Leu
            500                 505                 510

Ser Pro Gly Lys Asn Gly Val Val Lys Asp Val Phe Ala Phe Gly Gly
        515                 520                 525

Ala Val Glu Asn Pro Glu Tyr Leu Gly Arg Pro Val Pro Trp Ser Phe
    530                 535                 540

Gly Val Val Leu Trp Glu Ile Ala Thr Leu Ala Glu Gln Pro Tyr Gln
545                 550                 555                 560

Gly Leu Ser Asn Glu Gln Val Leu Arg Phe Val Met Glu Gly Gly Leu
                565                 570                 575

Leu Asp Lys Pro Asp Asn Cys Pro Asp Met Leu Phe Glu Leu Met Arg
            580                 585                 590

Met Cys Trp Gln Tyr Asn Pro Lys Met Arg Pro Ser Phe Leu Glu His
        595                 600                 605

Lys Ala Glu Asn Gly Pro Gly Pro Gly Val Leu Val Leu Arg Ala Ser
    610                 615                 620

Phe Asp Glu Arg Gln Pro Tyr Ala His Met Asn Gly Gly Arg Lys Asn
625                 630                 635                 640

Glu Arg Ala Leu Pro Ala Ala Ala
                645

<210> SEQ ID NO 80
<211> LENGTH: 626
<212> TYPE: PRT
<213> ORGANISM: Artificial Sequence
<220> FEATURE:
<223> OTHER INFORMATION: Synthetic polynucleotide or polypeptide

<400> SEQUENCE: 80

Met Ala Val Pro Met Leu Pro Arg Leu Gly Gly Pro Ala Leu Pro Leu
1               5                   10                  15

Leu Leu Pro Ser Leu Leu Leu Leu Leu Leu Gly Ala Gly Gly Cys
            20                  25                  30

```
Gly Pro Gly Val Arg Ala Glu Val Leu Phe Arg Cys Pro Cys Thr
         35                  40                  45
Pro Glu Arg Leu Ala Ala Cys Gly Pro Pro Asp Ala Pro Cys Ala
 50                  55                  60
Glu Leu Val Arg Glu Pro Gly Cys Gly Cys Ser Val Cys Ala Arg
 65                  70                  75                  80
Gln Glu Gly Glu Ala Cys Gly Val Tyr Ile Pro Arg Cys Ala Gln Thr
                 85                  90                  95
Leu Arg Cys Tyr Pro Asn Pro Gly Ser Glu Leu Pro Leu Lys Ala Leu
                100                 105                 110
Val Thr Gly Ala Gly Thr Cys Glu Lys Arg Arg Val Gly Thr Thr Pro
                115                 120                 125
Gln Gln Val Ala Asp Ser Asp Asp His Ser Glu Gly Gly Leu Val
                130                 135                 140
Glu Gln Leu Thr Met Arg Arg Leu Leu Gln Glu Thr Glu Leu Val Glu
145                 150                 155                 160
Pro Leu Thr Pro Ser Gly Ala Val Pro Asn Gln Ala Gln Met Arg Ile
                165                 170                 175
Leu Lys Glu Thr Glu Leu Arg Lys Leu Lys Val Leu Gly Ser Gly Ala
                180                 185                 190
Phe Gly Thr Val Tyr Lys Gly Ile Trp Ile Pro Asp Gly Glu Asn Val
                195                 200                 205
Lys Ile Pro Val Ala Ile Lys Val Leu Arg Glu Asn Thr Ser Pro Lys
                210                 215                 220
Ala Asn Lys Glu Ile Leu Asp Glu Ala Tyr Val Met Ala Gly Val Gly
225                 230                 235                 240
Ser Pro Tyr Val Ser Arg Leu Leu Gly Ile Cys Leu Thr Ser Thr Val
                245                 250                 255
Gln Leu Val Thr Gln Leu Met Pro Tyr Gly Cys Leu Leu Asp His Val
                260                 265                 270
Arg Glu His Arg Gly Arg Leu Gly Ser Gln Asp Leu Leu Asn Trp Cys
                275                 280                 285
Val Gln Ile Ala Lys Gly Met Ser Tyr Leu Glu Glu Val Arg Leu Val
                290                 295                 300
His Arg Asp Leu Ala Ala Arg Asn Val Leu Val Lys Ser Pro Asn His
305                 310                 315                 320
Val Lys Ile Thr Asp Phe Gly Leu Ala Arg Leu Leu Asp Ile Asp Glu
                325                 330                 335
Thr Glu Tyr His Ala Asp Gly Gly Lys Val Pro Ile Lys Trp Met Ala
                340                 345                 350
Leu Glu Ser Ile Leu Arg Arg Arg Phe Thr His Gln Ser Asp Val Trp
                355                 360                 365
Ser Tyr Gly Val Thr Val Trp Glu Leu Met Thr Phe Gly Ala Lys Pro
                370                 375                 380
Tyr Asp Gly Ile Pro Ala Arg Glu Ile Pro Asp Leu Leu Glu Lys Gly
385                 390                 395                 400
Glu Arg Leu Pro Gln Pro Pro Ile Cys Thr Ile Asp Val Tyr Met Ile
                405                 410                 415
Met Val Lys Cys Trp Met Ile Asp Ser Glu Cys Arg Pro Arg Phe Arg
                420                 425                 430
Glu Leu Val Ser Glu Phe Ser Arg Met Ala Arg Asp Pro Gln Arg Phe
                435                 440                 445
```

```
Val Val Ile Gln Asn Glu Asp Leu Ala Leu Gly Thr Gly Ser Thr Ala
            450                 455                 460

His Arg Arg His Arg Ser Ser Pro Pro Pro Ile Arg Pro Ala
465                 470                 475                 480

Gly Ala Thr Leu Glu Arg Pro Lys Thr Leu Ser Pro Gly Lys Asn Gly
                485                 490                 495

Val Val Lys Asp Val Phe Ala Phe Gly Gly Ala Val Glu Asn Pro Glu
            500                 505                 510

Tyr Leu Gly Arg Pro Val Pro Trp Ser Phe Gly Val Val Leu Trp Glu
            515                 520                 525

Ile Ala Thr Leu Ala Glu Gln Pro Tyr Gln Gly Leu Ser Asn Glu Gln
530                 535                 540

Val Leu Arg Phe Val Met Glu Gly Gly Leu Leu Asp Lys Pro Asp Asn
545                 550                 555                 560

Cys Pro Asp Met Leu Phe Glu Leu Met Arg Met Cys Trp Gln Tyr Asn
                565                 570                 575

Pro Lys Met Arg Pro Ser Phe Leu Glu His Lys Ala Glu Asn Gly Pro
                580                 585                 590

Gly Pro Gly Val Leu Val Leu Arg Ala Ser Phe Asp Glu Arg Gln Pro
            595                 600                 605

Tyr Ala His Met Asn Gly Gly Arg Ala Asn Glu Arg Ala Leu Pro Ala
            610                 615                 620

Ala Ala
625

<210> SEQ ID NO 81
<211> LENGTH: 624
<212> TYPE: PRT
<213> ORGANISM: Artificial Sequence
<220> FEATURE:
<223> OTHER INFORMATION: Synthetic polynucleotide or polypeptide

<400> SEQUENCE: 81

Met Ala Val Pro Met Leu Pro Arg Leu Gly Gly Pro Ala Leu Pro Leu
1               5                   10                  15

Leu Leu Pro Ser Leu Leu Leu Leu Leu Leu Gly Ala Gly Gly Cys
                20                  25                  30

Gly Pro Gly Val Arg Ala Glu Val Leu Phe Arg Cys Pro Pro Cys Thr
            35                  40                  45

Pro Glu Arg Leu Ala Ala Cys Gly Pro Pro Asp Ala Pro Cys Ala
    50                  55                  60

Glu Leu Val Arg Glu Pro Gly Cys Gly Cys Cys Ser Val Cys Ala Arg
65                  70                  75                  80

Gln Glu Gly Glu Ala Cys Gly Val Tyr Ile Pro Arg Cys Ala Gln Thr
                85                  90                  95

Leu Arg Cys Tyr Pro Asn Pro Gly Ser Glu Leu Pro Leu Lys Ala Leu
            100                 105                 110

Val Thr Gly Ala Gly Thr Cys Glu Lys Arg Arg Val Gly Ala Thr Pro
        115                 120                 125

Gln Gln Val Ala Asp Ser Glu Asp His Ser Glu Gly Gly Leu Val
    130                 135                 140

Glu Gln Leu Thr Met Arg Arg Leu Leu Gln Glu Thr Glu Leu Val Glu
145                 150                 155                 160

Pro Leu Thr Pro Ser Gly Ala Met Pro Asn Gln Ala Gln Met Arg Ile
                165                 170                 175
```

```
Leu Lys Glu Thr Glu Leu Arg Lys Val Lys Val Leu Gly Ser Gly Ala
                180                 185                 190

Phe Gly Thr Val Tyr Lys Gly Ile Trp Ile Pro Asp Gly Glu Asn Val
            195                 200                 205

Lys Ile Pro Val Ala Ile Lys Val Leu Arg Glu Asn Thr Ser Pro Lys
        210                 215                 220

Ala Asn Lys Glu Ile Leu Asp Glu Ala Tyr Val Met Ala Gly Val Gly
225                 230                 235                 240

Ser Pro Tyr Val Ser Arg Leu Leu Gly Ile Cys Leu Thr Ser Thr Val
                245                 250                 255

Gln Leu Val Thr Gln Leu Met Pro Tyr Gly Cys Leu Leu Asp His Val
            260                 265                 270

Arg Glu His Arg Gly Arg Leu Gly Ser Gln Asp Leu Leu Asn Trp Cys
        275                 280                 285

Val Gln Ile Ala Lys Gly Met Ser Tyr Leu Glu Asp Val Arg Leu Val
        290                 295                 300

His Arg Asp Leu Ala Ala Arg Asn Val Leu Val Lys Ser Pro Asn His
305                 310                 315                 320

Val Lys Ile Thr Asp Phe Gly Leu Ala Arg Leu Leu Asp Ile Asp Glu
                325                 330                 335

Thr Glu Tyr His Ala Asp Gly Gly Lys Val Pro Ile Lys Trp Met Ala
            340                 345                 350

Leu Glu Ser Ile Leu Arg Arg Phe Thr His Gln Ser Asp Val Trp
        355                 360                 365

Ser Tyr Gly Val Thr Val Trp Glu Leu Met Thr Phe Gly Ala Lys Pro
    370                 375                 380

Tyr Asp Gly Ile Pro Ala Arg Glu Ile Pro Asp Leu Leu Glu Lys Gly
385                 390                 395                 400

Glu Arg Leu Pro Gln Pro Pro Ile Cys Thr Ile Asp Val Tyr Met Ile
                405                 410                 415

Met Val Lys Cys Trp Met Ile Asp Ser Glu Cys Arg Pro Arg Phe Arg
            420                 425                 430

Glu Leu Val Ser Glu Phe Ser Arg Met Ala Arg Asp Pro Gln Arg Phe
        435                 440                 445

Val Val Ile Gln Asn Glu Asp Leu Thr Pro Gly Thr Gly Ser Thr Ala
450                 455                 460

His Arg Arg His Arg Ser Ser Pro Leu Pro Pro Val Arg Pro Ala
465                 470                 475                 480

Gly Ala Thr Leu Glu Arg Pro Lys Thr Leu Ser Pro Gly Lys Asn Gly
                485                 490                 495

Val Val Lys Asp Val Phe Ala Phe Gly Ala Val Glu Asn Pro Glu
            500                 505                 510

Tyr Leu Gly Arg Pro Val Pro Trp Ser Phe Gly Val Val Leu Trp Glu
        515                 520                 525

Ile Ala Thr Leu Ala Glu Gln Pro Tyr Gln Gly Leu Ser Asn Glu Gln
        530                 535                 540

Val Leu Arg Phe Val Met Glu Gly Gly Leu Leu Asp Lys Pro Asp Asn
545                 550                 555                 560

Cys Pro Asp Met Leu Phe Glu Leu Met Arg Met Cys Trp Gln Tyr Asn
                565                 570                 575

Pro Lys Met Arg Pro Ser Phe Leu Glu His Lys Ala Glu Asn Gly Pro
            580                 585                 590
```

Gly Val Leu Val Leu Arg Ala Ser Phe Asp Glu Arg Gln Pro Tyr Ala
            595                 600                 605

His Met Asn Gly Gly Arg Ala Asn Glu Arg Ala Leu Pro Ala Ala Ala
    610                 615                 620

<210> SEQ ID NO 82
<211> LENGTH: 89
<212> TYPE: PRT
<213> ORGANISM: Artificial Sequence
<220> FEATURE:
<223> OTHER INFORMATION: Synthetic polynucleotide or polypeptide

<400> SEQUENCE: 82

Asp Ser Lys Thr Phe Leu Ser Arg His Ser Leu Asp Met Lys Phe Ser
1               5                   10                  15

Tyr Cys Asp Glu Arg Ile Thr Glu Leu Met Gly Tyr Glu Pro Glu Glu
            20                  25                  30

Leu Leu Gly Arg Ser Ile Tyr Glu Tyr Tyr His Ala Leu Asp Ser Asp
        35                  40                  45

His Leu Thr Lys Thr His His Asp Met Phe Thr Lys Gly Gln Val Thr
    50                  55                  60

Thr Gly Gln Tyr Arg Met Leu Ala Lys Arg Gly Gly Tyr Val Trp Val
65                  70                  75                  80

Glu Thr Gln Ala Thr Val Ile Tyr Asn
                85

<210> SEQ ID NO 83
<211> LENGTH: 26
<212> TYPE: PRT
<213> ORGANISM: Artificial Sequence
<220> FEATURE:
<223> OTHER INFORMATION: Synthetic polynucleotide or polypeptide

<400> SEQUENCE: 83

Ser Asp Asn Val Asn Lys Tyr Met Gly Leu Thr Gln Phe Glu Leu Thr
1               5                   10                  15

Gly His Ser Val Phe Asp Phe Thr His Pro
            20                  25

<210> SEQ ID NO 84
<211> LENGTH: 20
<212> TYPE: PRT
<213> ORGANISM: Artificial Sequence
<220> FEATURE:
<223> OTHER INFORMATION: Synthetic polynucleotide or polypeptide

<400> SEQUENCE: 84

Gly Gly Tyr Val Trp Val Glu Thr Gln Ala Thr Val Ile Tyr Asn Thr
1               5                   10                  15

Lys Asn Ser Gln
            20

<210> SEQ ID NO 85
<211> LENGTH: 38
<212> TYPE: PRT
<213> ORGANISM: Artificial Sequence
<220> FEATURE:
<223> OTHER INFORMATION: Synthetic polynucleotide or polypeptide

<400> SEQUENCE: 85

Gly Cys Ala Phe Leu Ser Val Lys Lys Gln Phe Glu Glu Leu Thr Leu
1               5                   10                  15

Gly Glu Phe Leu Lys Leu Asp Arg Glu Arg Ala Lys Asn Lys Ile Ala
            20                  25                  30

Lys Glu Thr Asn Asn Lys
        35

<210> SEQ ID NO 86
<211> LENGTH: 114
<212> TYPE: DNA
<213> ORGANISM: Artificial Sequence
<220> FEATURE:
<223> OTHER INFORMATION: Synthetic polynucleotide or polypeptide

<400> SEQUENCE: 86
ggctgcgcct tcctgtccgt gaagaagcag ttcgaggagc tgaccctggg cgagttcctg     60
aagctggacc gcgagcgcgc caagaacaag atcgccaagg agaccaacaa caag         114

<210> SEQ ID NO 87
<211> LENGTH: 88
<212> TYPE: PRT
<213> ORGANISM: Artificial Sequence
<220> FEATURE:
<223> OTHER INFORMATION: Synthetic polynucleotide or polypeptide

<400> SEQUENCE: 87

Arg Ser Lys Glu Ser Glu Val Phe Tyr Glu Leu Ala His Gln Leu Pro
1               5                   10                  15

Leu Pro His Asn Val Ser Ser His Leu Asp Lys Ala Ser Val Met Arg
            20                  25                  30

Leu Thr Ile Ser Tyr Leu Arg Val Arg Lys Leu Leu Asp Ala Gly Asp
        35                  40                  45

Leu Asp Ile Glu Asp Met Lys Ala Gln Met Asn Cys Phe Tyr Leu Lys
    50                  55                  60

Ala Leu Asp Gly Phe Val Met Val Leu Thr Asp Asp Gly Asp Met Ile
65                  70                  75                  80

Tyr Ile Ser Asp Asn Val Asn Lys
                85

<210> SEQ ID NO 88
<211> LENGTH: 267
<212> TYPE: DNA
<213> ORGANISM: Artificial Sequence
<220> FEATURE:
<223> OTHER INFORMATION: Synthetic polynucleotide or polypeptide

<400> SEQUENCE: 88
cgctccaagg agtccgaggt gttctacgag ctggcccacc agctgcccct gccccacaac     60
gtgtcctccc acctggacaa ggcctccgtg atgcgcctga ccatctccta cctgcgcgtg    120
cgcaagctgc tggacgctgg cgacctggac atcgaggacg acatgaaggc ccagatgaac    180
tgcttctacc tgaaggccct ggacggcttc gtgatggtgc tgaccgacga cggcgacatg    240
atctacatct ccgacaacgt gaacaag                                        267

<210> SEQ ID NO 89
<211> LENGTH: 415
<212> TYPE: PRT
<213> ORGANISM: Artificial Sequence
<220> FEATURE:
<223> OTHER INFORMATION: Synthetic polynucleotide or polypeptide

<400> SEQUENCE: 89

| | | | | | | | | | | | | | | | |
|---|---|---|---|---|---|---|---|---|---|---|---|---|---|---|---|
| Met | Ala | Val | Pro | Met | Leu | Pro | Arg | Val | Gly | Cys | Pro | Ala | Leu | Pro | Leu |
| 1 | | | | 5 | | | | | 10 | | | | | 15 | |
| Pro | Pro | Pro | Pro | Leu | Leu | Pro | Leu | Leu | Pro | Leu | Leu | Leu | Leu | Leu | Leu |
| | | | 20 | | | | | 25 | | | | | 30 | | |
| Gly | Ala | Ser | Gly | Gly | Gly | Gly | Ala | Arg | Ala | Glu | Val | Leu | Phe | Arg | |
| | | 35 | | | | | 40 | | | | | 45 | | | |
| Cys | Pro | Pro | Cys | Thr | Pro | Glu | Arg | Leu | Ala | Ala | Cys | Gly | Pro | Pro | Pro |
| | | 50 | | | | | 55 | | | | | 60 | | | |
| Val | Ala | Pro | Pro | Ala | Val | Ala | Ala | Val | Ala | Gly | Gly | Ala | Arg | Met | |
| 65 | | | | | 70 | | | | | 75 | | | | | 80 |
| Pro | Cys | Ala | Glu | Leu | Val | Arg | Glu | Pro | Gly | Cys | Gly | Cys | Cys | Ser | Val |
| | | | | 85 | | | | | 90 | | | | | 95 | |
| Cys | Ala | Arg | Leu | Glu | Gly | Glu | Ala | Cys | Gly | Val | Tyr | Thr | Pro | Arg | Cys |
| | | | 100 | | | | | 105 | | | | | 110 | | |
| Gly | Gln | Gly | Leu | Arg | Cys | Tyr | Pro | His | Pro | Gly | Ser | Glu | Leu | Pro | Leu |
| | | 115 | | | | | 120 | | | | | 125 | | | |
| Gln | Ala | Leu | Val | Met | Gly | Glu | Gly | Thr | Cys | Glu | Lys | Arg | Arg | Asp | Ala |
| | 130 | | | | | 135 | | | | | 140 | | | | |
| Glu | Tyr | Gly | Ala | Ser | Pro | Glu | Gln | Val | Ala | Asp | Asn | Gly | Asp | Asp | His |
| 145 | | | | | 150 | | | | | 155 | | | | | 160 |
| Ser | Glu | Gly | Gly | Leu | Val | Glu | Gln | Leu | Gly | Cys | Ala | Phe | Leu | Ser | Val |
| | | | | 165 | | | | | 170 | | | | | 175 | |
| Lys | Lys | Gln | Phe | Glu | Glu | Leu | Thr | Leu | Gly | Glu | Phe | Leu | Lys | Leu | Asp |
| | | | 180 | | | | | 185 | | | | | 190 | | |
| Arg | Glu | Arg | Ala | Lys | Asn | Lys | Ile | Ala | Lys | Glu | Thr | Asn | Asn | Lys | Gly |
| | | 195 | | | | | 200 | | | | | 205 | | | |
| Ser | Glu | Phe | Arg | Ser | Lys | Glu | Ser | Glu | Val | Phe | Tyr | Glu | Leu | Ala | His |
| | 210 | | | | | 215 | | | | | 220 | | | | |
| Gln | Leu | Pro | Leu | Pro | His | Asn | Val | Ser | Ser | His | Leu | Asp | Lys | Ala | Ser |
| 225 | | | | | 230 | | | | | 235 | | | | | 240 |
| Val | Met | Arg | Leu | Thr | Ile | Ser | Tyr | Leu | Arg | Val | Arg | Lys | Leu | Leu | Asp |
| | | | | 245 | | | | | 250 | | | | | 255 | |
| Ala | Gly | Asp | Leu | Asp | Ile | Glu | Asp | Asp | Met | Lys | Ala | Gln | Met | Asn | Cys |
| | | | 260 | | | | | 265 | | | | | 270 | | |
| Phe | Tyr | Leu | Lys | Ala | Leu | Asp | Gly | Phe | Val | Met | Val | Leu | Thr | Asp | Asp |
| | | 275 | | | | | 280 | | | | | 285 | | | |
| Gly | Asp | Met | Ile | Tyr | Ile | Ser | Asp | Asn | Val | Asn | Lys | Tyr | Arg | Ser | Gly |
| | 290 | | | | | 295 | | | | | 300 | | | | |
| Arg | Pro | Val | Pro | Trp | Ser | Phe | Gly | Val | Val | Leu | Trp | Glu | Ile | Ala | Thr |
| 305 | | | | | 310 | | | | | 315 | | | | | 320 |
| Leu | Ala | Glu | Gln | Pro | Tyr | Gln | Gly | Leu | Ser | Asn | Glu | Gln | Val | Leu | Arg |
| | | | | 325 | | | | | 330 | | | | | 335 | |
| Phe | Val | Met | Glu | Gly | Gly | Leu | Leu | Asp | Lys | Pro | Asp | Asn | Cys | Pro | Asp |
| | | | 340 | | | | | 345 | | | | | 350 | | |
| Met | Leu | Phe | Glu | Leu | Met | Arg | Met | Cys | Trp | Gln | Tyr | Asn | Pro | Lys | Met |
| | | 355 | | | | | 360 | | | | | 365 | | | |
| Arg | Pro | Ser | Phe | Leu | Glu | His | Lys | Ala | Glu | Asn | Gly | Pro | Gly | Pro | Gly |
| | 370 | | | | | 375 | | | | | 380 | | | | |

Val Leu Val Leu Arg Ala Ser Phe Asp Glu Arg Gln Pro Tyr Ala His
385                 390                 395                 400

Met Asn Gly Gly Arg Lys Asn Glu Arg Ala Leu Pro Ala Ala Ala
            405                 410                 415

<210> SEQ ID NO 90
<211> LENGTH: 1248
<212> TYPE: DNA
<213> ORGANISM: Artificial Sequence
<220> FEATURE:
<223> OTHER INFORMATION: Synthetic polynucleotide or polypeptide

<400> SEQUENCE: 90

| | | |
|---|---|---|
| atggcggtac caatgctgcc gagagtgggc tgccccgcgc tgccgctgcc gccgccgccg | 60 |
| ctgctgccgc tgctgccgct gctgctgctg ctactgggcg cgagtggcgg cggcggcggg | 120 |
| gcgcgcgcgg aggtgctgtt ccgctgcccg ccctgcacac ccgagcgcct ggccgcctgc | 180 |
| gggcccccgc cggttgcgcc gcccgccgcg gtggccgcag tggccggagg cgcccgcatg | 240 |
| ccatgcgcgg agctcgtccg ggagccgggc tgcggctgct gctcggtgtg cgcccggctg | 300 |
| gagggcgagg cgtgcggcgt ctacaccccg cgctgcggcc aggggctgcg ctgctatccc | 360 |
| cacccgggct ccgagctgcc cctgcaggcg ctggtcatgg cgagggcac ttgtgagaag | 420 |
| cgccgggacg ccgagtatgg cgccagcccg gagcaggttg cagacaatgg cgatgaccac | 480 |
| tcagaaggag gcctggtgga gcaattgggc tgcgccttcc tgtccgtgaa gagcagttc | 540 |
| gaggagctga ccctgggcga gttcctgaag ctggaccgcg agcgcgccaa gaacaagatc | 600 |
| gccaaggaga ccaacaacaa gggatccgaa ttccgctcca aggagtccga ggtgttctac | 660 |
| gagctggccc accagctgcc cctgccccac aacgtgtcct cccacctgga caaggcctcc | 720 |
| gtgatgcgcc tgaccatctc ctacctgcgc gtgcgcaagc tgctggacgc tggcgacctg | 780 |
| gacatcgagg acgacatgaa ggcccagatg aactgcttct acctgaaggc cctggacggc | 840 |
| ttcgtgatgg tgctgaccga cgacggcgac atgatctaca ctccgacaa cgtgaacaag | 900 |
| tacagatccg gccggccggt accttggtcc ttcggcgtgg tgctgtggga gatcgccacc | 960 |
| ctggccgagc agccctacca gggcctgtcc aacgagcagg tgctgcgctt cgtgatggag | 1020 |
| ggcggcctgc tggacaagcc cgacaactgc ccgacatgc tgttcgagct gatgcgcatg | 1080 |
| tgctggcagt acaaccccaa gatgcgcccc tccttcctgg agcacaaggc cgagaacggc | 1140 |
| cccggccccg cgtgctggt gctgcgcgcc tccttcgacg agcgccagcc ctacgcccac | 1200 |
| atgaacggag ccgcaagaa cgagcgcgcc ctgcccgcgg ccgcatag | 1248 |

<210> SEQ ID NO 91
<211> LENGTH: 5248
<212> TYPE: DNA
<213> ORGANISM: Artificial Sequence
<220> FEATURE:
<223> OTHER INFORMATION: Synthetic polynucleotide or polypeptide

<400> SEQUENCE: 91

| | | |
|---|---|---|
| tggccattgc atacgttgta tccatatcat aatatgtaca tttatattgg ctcatgtcca | 60 |
| acattaccgc catgttgaca ttgattattg actagttatt aatagtaatc aattacgggg | 120 |
| tcattagttc atagcccata tatggagttc cgcgttacat aacttacggt aaatggcccg | 180 |
| cctggctgac cgcccaacga cccccgccca ttgacgtcaa taatgacgta tgttcccata | 240 |
| gtaacgccaa tagggacttt ccattgacgt caatgggtgg agtatttacg gtaaactgcc | 300 |
| cacttggcag tacatcaagt gtatcatatg ccaagtacgc ccctattga cgtcaatgac | 360 |

```
ggtaaatggc ccgcctggca ttatgcccag tacatgacct tatgggactt tcctacttgg      420
cagtacatct acgtattagt catcgctatt accatggtga tgcggttttg cagtacatc       480 aatgggcgtg gatagcggtt tgactcacgg ggatttccaa gtctccaccc cattgacgtc      540
aatgggagtt tgttttggca ccaaaatcaa cgggactttc caaaatgtcg taacaactcc      600
gccccattga cgcaaatggg cggtaggcgt gtacggtggg aggtctatat aagcagagct      660
cgtttagtga accgtcagat cgcctggaga cgccatccac gctgttttga cctccataga      720
agacaccggg accgatccag cctccgcggc cgggaacggt gcattggaac gcggattccc      780
cgtgccaaga gtgacgtaag taccgcctat agactctata ggcacacccc tttggctctt      840
atgcatgcta tactgttttt ggcttgggc ctatacaccc ccgcttcctt atgctatagg      900
tgatggtata gcttagccta taggtgtggg ttattgacca ttattgacca ctccaacggt      960
ggagggcagt gtagtctgag cagtactcgt tgctgccgcg cgcgccacca gacataatag     1020
ctgacagact aacagactgt tcctttccat gggtcttttc tgcagtcacc gtcgtcgacg     1080
gtatcgataa gcttgatatc gaattgccgc caccatggcg gtaccaatgc tgccgagagt     1140
gggctgcccc gcgctgccgc tgccgccgcc gccgctgctg ccgctgctgc cgctgctgct     1200
gctgctactg ggcgcgagtg gcggcggcgg cggggcgcgc gcggaggtgc tgttccgctg     1260
cccgccctgc acacccgagc gcctggccgc ctgcgggccc ccgccggttg cgccgcccgc     1320
cgcggtggcc gcagtggccg gaggcgcccg catgccatgc gcggagctcg tccgggagcc     1380
gggctgcggc tgctgctcgg tgtgcgcccg gctggagggc gaggcgtgcg gcgtctacac     1440
cccgcgctgc ggccagggc tgcgctgcta tccccacccg ggctccgagc tgccctgca     1500 ggcgctggtc atgggcgagg gcacttgtga gaagcgccgg gacgccgagt atggcgccag     1560
cccggagcag gttgcagaca atggcgatga ccactcagaa ggaggcctgg tggagcaatt     1620
gggctgcgcc ttcctgtccg tgaagaagca gttcgaggag ctgacccgg gcgagttcct     1680 gaagctggac cgcgagcgcg ccaagaacaa gatcgccaag gagaccaaca acaagggatc     1740
cgaattccgc tccaaggagt ccgaggtgtt ctacgagctg gcccaccagc tgccccctgcc    1800 ccacaacgtg tcctcccacc tggacaaggc ctccgtgatg cgcctgacca tctcctacct     1860
gcgcgtgcgc aagctgctgg acgctggcga cctggacatc gaggacgaca tgaaggccca     1920
gatgaactgc ttctacctga aggccctgga cggcttcgtg atggtgctga ccgacgacgg     1980
cgacatgatc tacatctccg acaacgtgaa caagtacaga tccggccggc cggtaccttg     2040
gtccttcggc gtggtgctgt gggagatcgc caccctggcc gagcagccct accagggcct     2100
gtccaacgag caggtgctgc gcttcgtgat ggagggcggc ctgctggaca gcccgacaa      2160 ctgccccgac atgctgttcg agctgatgcg catgtgctgg cagtacaacc ccaagatgcg     2220
cccctccttc ctggagcaca aggccgagaa cggcccggc ccggcgtgc tggtgctgcg      2280 cgcctccttc gacgagcgcc agccctacgc ccacatgaac ggaggccgca gaacgagcg      2340 cgccctgccc gcggccgcat agtgatagat ctttttccct ctgccaaaaa ttatgggac      2400 atcatgaagc cccttgagca tctgacttct ggctaataaa ggaaatttat tttcattgca     2460
atagtgtgtt ggaatttttt gtgtctctca ctcggaagga catatgggag gcaaatcat      2520 ttaaaacatc agaatgagta tttggtttag agtttggcaa catatgccca ttcttccgct     2580
tcctcgctca ctgactcgct gcgctcggtc gttcggctgc ggcgagcggt atcagctcac     2640
tcaaaggcgg taatacggtt atccacagaa tcagggata acgcaggaaa gaacatgtga     2700
gcaaaaggcc agcaaaaggc caggaaccgt aaaaaggccg cgttgctggc gttttccat     2760
```

```
aggctccgcc cccctgacga gcatcacaaa aatcgacgct caagtcagag gtggcgaaac   2820
ccgacaggac tataaagata ccaggcgttt ccccctggaa gctccctcgt gcgctctcct   2880
gttccgaccc tgccgcttac cggatacctg tccgcctttc tcccttcggg aagcgtggcg   2940
ctttctcata gctcacgctg taggtatctc agttcggtgt aggtcgttcg ctccaagctg   3000
ggctgtgtgc acgaaccccc cgttcagccc gaccgctgcg ccttatccgg taactatcgt   3060
cttgagtcca acccggtaag acacgactta tcgccactgg cagcagccac tggtaacagg   3120
attagcagag cgaggtatgt aggcggtgct acagagttct tgaagtggtg cctaactac   3180 ggctacacta agaacagt atttggtatc tgcgctctgc tgaagccagt taccttcgga   3240
aaaagagttg gtagctcttg atccggcaaa caaaccaccg ctggtagcgg tggttttttt   3300
gtttgcaagc agcagattac gcgcagaaaa aaggatctc aagaagatcc tttgatcttt   3360
tctacggggt ctgacgctca gtggaacgaa aactcacgtt aagggatttt ggtcatgaga   3420
ttatcaaaaa ggatcttcac ctagatcctt ttaaattaaa aatgaagttt taaatcaatc   3480
taaagtatat atgagtaaac ttggtctgac agttaccaat gcttaatcag tgaggcacct   3540
atctcagcga tctgtctatt tcgttcatcc atagttgcct gactcggggg ggggggggcgc   3600 tgaggtctgc ctcgtgaaga aggtgttgct gactcatacc aggcctgaat cgccccatca   3660
tccagccaga aagtgaggga gccacggttg atgagagctt tgttgtaggt ggaccagttg   3720
gtgattttga acttttgctt tgccacggaa cggtctgcgt tgtcgggaag atgcgtgatc   3780
tgatccttca actcagcaaa agttcgattt attcaacaaa gccgccgtcc cgtcaagtca   3840
gcgtaatgct ctgccagtgt tacaaccaat taaccaattc tgattagaaa aactcatcga   3900
gcatcaaatg aaactgcaat ttattcatat caggattatc aataccatat ttttgaaaaa   3960
gccgtttctg taatgaagga gaaaactcac cgaggcagtt ccataggatg caagatcct   4020 ggtatcggtc tgcgattccg actcgtccaa catcaataca acctattaat ttccctcgt   4080 caaaataag gttatcaagt gagaaatcac catgagtgac gactgaatcc ggtgagaatg   4140
gcaaaagctt atgcatttct ttccagactt gttcaacagg ccagccatta cgctcgtcat   4200
caaaatcact cgcatcaacc aaaccgttat tcattcgtga ttgcgcctga gcgagacgaa   4260
atacgcgatc gctgttaaaa ggacaattac aaacaggaat cgaatgcaac cggcgcagga   4320
acactgccag cgcatcaaca atattttcac ctgaatcagg atattcttct aatacctgga   4380
atgctgtttt cccggggatc gcagtggtga gtaaccatgc atcatcagga gtacggataa   4440
aatgcttgat ggtcggaaga ggcataaatt ccgtcagcca gtttagtctg accatctcat   4500
ctgtaacatc attggcaacg ctacctttgc catgtttcag aaacaactct ggcgcatcgg   4560
gcttcccata caatcgatag attgtcgcac ctgattgccc gacattatcg cgagcccatt   4620
tatacccata taaatcagca tccatgttgg aatttaatcg cggcctcgag caagacgttt   4680
cccgttgaat atggctcata caccccttg tattactgtt tatgtaagca gacagtttta   4740
ttgttcatga tgatatattt ttatcttgtg caatgtaaca tcagagattt tgagacacaa   4800
cgtggctttc cccccccccc cattattgaa gcatttatca gggttattgt ctcatgagcg   4860
gatacatatt tgaatgtatt tagaaaaata aacaataggg gttccgcgc acatttcccc   4920 gaaaagtgcc acctgacgtc taagaaacca ttattatcat gacattaacc tataaaaata   4980
ggcgtatcac gaggcccttt cgtctcgcgc gtttcggtga tgacggtgaa aacctctgac   5040
acatgcagct cccggagacg gtcacagctt gtctgtaagc ggatgccggg agcagacaag   5100
cccgtcaggg cgcgtcagcg ggtgttggcg ggtgtcgggg ctggcttaac tatgcggcat   5160
```

```
cagagcagat tgtactgaga gtgcaccata tgcggtgtga aataccgcac agatgcgtaa    5220
ggagaaaata ccgcatcaga ttggctat                                       5248
```